US010669589B2

(12) United States Patent
Bell et al.

(10) Patent No.: US 10,669,589 B2
(45) Date of Patent: *Jun. 2, 2020

(54) METHOD TO DETERMINE RESPONSIVENESS OF CANCER TO EPIDERMAL GROWTH FACTOR RECEPTOR TARGETING TREATMENTS

(71) Applicants: The General Hospital Corporation, Boston, MA (US); Dana-Farber Cancer Institute, Inc., Boston, MA (US)

(72) Inventors: Daphne Winifred Bell, Chevy Chase, MD (US); Daniel A. Haber, Chesnut Hill, MA (US); Pasi Antero Janne, Newton, MA (US); Bruce E. Johnson, Brookline, MA (US); Thomas J. Lynch, Newton, MA (US); Matthew Meyerson, Concord, MA (US); Juan Guillermo Paez, Dean Funes (AR); William R. Sellers, Chestnut Hill, MA (US); Jeffrey E. Settleman, Newton, MA (US); Raffaella Sordella, Bedford, MA (US)

(73) Assignees: The General Hospital Corporation, Boston, MA (US); Dana-Farber Cancer Institute, Inc., Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/981,514

(22) Filed: May 16, 2018

(65) Prior Publication Data

US 2018/0251860 A1 Sep. 6, 2018

Related U.S. Application Data

(63) Continuation of application No. 14/638,779, filed on Mar. 4, 2015, now Pat. No. 10,000,815, which is a continuation of application No. 13/896,772, filed on May 17, 2013, now Pat. No. 9,035,036, which is a continuation of application No. 11/894,160, filed on Aug. 20, 2007, now Pat. No. 8,465,916, which is a continuation of application No. 11/294,621, filed on Dec. 5, 2005, now Pat. No. 7,294,468, which is a continuation of application No. PCT/US2005/010645, filed on Mar. 31, 2005.

(60) Provisional application No. 60/592,287, filed on Jul. 29, 2004, provisional application No. 60/577,916, filed on Jun. 7, 2004, provisional application No. 60/574,035, filed on May 25, 2004, provisional application No. 60/565,985, filed on Apr. 27, 2004, provisional application No. 60/565,753, filed on Apr. 27, 2004, provisional application No. 60/561,095, filed on Apr. 9, 2004, provisional application No. 60/558,218, filed on Mar. 31, 2004.

(51) Int. Cl.
| C12Q 1/68 | (2018.01) |
| C12Q 1/6886 | (2018.01) |
| C12Q 1/48 | (2006.01) |
| G01N 33/574 | (2006.01) |
| G01N 33/74 | (2006.01) |

(52) U.S. Cl.
CPC .......... *C12Q 1/6886* (2013.01); *C12Q 1/485* (2013.01); *G01N 33/574* (2013.01); *G01N 33/74* (2013.01); *C12Q 2600/106* (2013.01); *C12Q 2600/118* (2013.01); *C12Q 2600/136* (2013.01); *C12Q 2600/156* (2013.01); *C12Q 2600/158* (2013.01); *C12Q 2600/16* (2013.01); *G01N 2333/485* (2013.01); *G01N 2800/52* (2013.01)

(58) Field of Classification Search
None
See application file for complete search history.

(56) References Cited

U.S. PATENT DOCUMENTS

| 5,710,010 A | 1/1998 | Vogelstein et al. |
| 5,861,251 A | 1/1999 | Park et al. |
| 6,821,724 B1 | 11/2004 | Mittman et al. |
| 7,250,289 B2 | 7/2007 | Zhou |
| 7,294,468 B2 | 11/2007 | Bell et al. |
| 7,960,118 B2 | 6/2011 | Seshagiri |
| 7,964,349 B2 | 6/2011 | Bell et al. |
| 8,105,769 B2 | 1/2012 | Bell et al. |
| 8,232,062 B2 | 7/2012 | Seshagiri et al. |
| 2005/0272083 A1 | 12/2005 | Seshagiri |
| 2008/0207615 A1 | 8/2008 | Bell et al. |
| 2008/0234264 A1 | 9/2008 | Bell et al. |

FOREIGN PATENT DOCUMENTS

| AU | 25185/92 | 4/1993 |
| WO | 2002/0102976 A2 | 12/2002 |
| WO | 2005/079434 A2 | 9/2005 |

OTHER PUBLICATIONS

Frederick et al (Cancer Research, 2000, 60:1383-1387).*
Shintani et al (Cancer Research, 1999, 59:4142-4147).*
Reiter et al (Genomics, 2001, 71:1-20).*
Kramer et al (Current Protocols, 2001, 56:15.1.1-15.1.14).*
Tang et al., "Chip-based genotyping by mass spectrometry", Proc Natl Acad Sci USA 96(18) 10016-10020 (1999).
Tockman et al., Considerations in bringing a cancer biomarker to clinical application, Cancer Res 52(9 Suppl) 2711s-2718s (1992).
Tokumo et al., Lung Cancer, 53:117-121 (2006). "Double mutation and gene copy number of EGFR is gefitinib refractory non-small-cell lung cancer."

(Continued)

*Primary Examiner* — Laura B Goddard
(74) *Attorney, Agent, or Firm* — Nixon Peabody LLP; David S. Resnick; Shayne Y. Huff

(57) ABSTRACT

Disclosed herein are methods and reagents for determining the responsiveness of cancer to an epidermal growth factor receptor (EGFR) targeting treatment. The detection of these mutations will allow for the administration of gefitinib, erlotinib and other tyrosine kinase inhibitors to those patients most likely to respond to the drug.

13 Claims, 23 Drawing Sheets

Specification includes a Sequence Listing.

(56) References Cited

OTHER PUBLICATIONS

U.S. Appl. No. 11/294,621, filed Dec. 5, 2005, Office Action dated Feb. 7, 2007.
U.S. Appl. No. 11/294,621, filed Dec. 5, 2005, Office Action dated Jul. 13, 2006.
U.S. Appl. No. 11/894,135, filed Aug. 20, 2007, Office Action dated Nov. 30, 2009.
U.S. Appl. No. 11/894,135, filed Aug. 20, 2007, Office Action dated Feb. 9, 2009.
U.S. Appl. No. 11/894,159, filed Aug. 20, 2007, Office Action dated Oct. 27, 2009.
U.S. Appl. No. 11/894,160, filed Aug. 20, 2007, Office Action dated Jul. 20, 2010.
U.S. Appl. No. 11/894,160, filed Aug. 20, 2007, Office Action dated Feb. 18, 2010.
Vansteenkiste, Exprt Rev Anticancer Ther, 4(1):5-17 (2004). "Gefitinib(Iressa®): a novel treatment for non-small cell lung cancer."
Vogelstein et al., "Digital PCR", Proc Natl Acad Sci USA 96(16) 9236-9241 (1999).
Wabuyele et al., "Approaching real-time molecular diagnostics: single-pair fluorescence resonance energy transfer (spFRET) detection for the analysis of low abundant point mutations in K-ras oncogenes", J Am Chem Sco 125(23) 6937-6945 (2003).
Pandit et al., Journal of Biological Chemistry, 1996, 271:5850-5858.
Eskstrand et al., "Amplified and rearranged epidermal growth factor receptor genes in human glioblastomas reveal deletions of sequences encoding portions of the N- and/or C-terminal tails", Proc Natl Acad Sci USA 89(10) 4309-4313 (1992).
NCBI, Accession No. NP_005219, "Epidermal growth factor receptor isoform a precursor [*Homo sapiens*]", (2015).
Klinger-Hoffman et al., "Inhibition of phosphatidylinositol 3-kinase signaling negates the growth advantage imparted by a mutant epidermal growth factor receptor on human glioblastoma cells", Int J Cancer 105(3) 331-339 (2003).
Zembutsu et al., "Gene-expression profiles of human tumor xenografts in nude mice treated orally with the EGFR tyrosine kinase inhibitor ZD1839", Int J Oncol 23(1) 29-39 (2003).
*Esoterix Genetic Laboratories LLC* v. *Qiagen Inc.*, 133 F.Supp.3d 349 (2015).
Order Granting Motion to Vacate, *Esoterix Genetic Laboratories* v. *Quiagen*, No. 14-13228 (D. Mass. Jul. 13, 2017).
Lee et al., Int. J. Cancer, 113:510-511 (2005). "Absence of EGFR Mutation in the Kinase Domain in Common Human Cancers Besides Non-Small Cell Lung Cancer."
Ullrich et al., Nature, 309:418-425 (1984). "Human Epidermal growth factor receptor cDNA sequence and aberrant expression of the amplified gene in A431 epidermoid carcinoma cells."
Kris et al., JAMA, 290(16):2149-2158 (2003). "Efficacy of Gefitinib, an Inhibitor of the Epidermal Growth Factor Receptor Tyrosine Kinase, in Sympotomatic Patients with Non-Small Cell Lung Cancer."
Fukuoka et al., J. Clin. Oncol., 21(12):2237-2246 (2003). "Multi-Institutional Randomized Phase II Trial for Gefitinib for Previously Treated Patients with Advanced Non-Small-Cell Lung Cancer."
Pao et al., Seminars in Cancer Biology, 14:33-40 (2004). "'Targeting' the epidermal growth factor receptor tyrosine kinase with gefitinib (Iressa ©) in non-small cell lung cancer (NSCLC)."
Grundler et al., Blood, 102(2):646-651 (2003). "Sensitivity toward tyrosine kinase inhibitors varies between different activating mutations of the FLT3 receptor."
Liao et al., Blood, 100(2):585-593 (2002). "Inhibition of constitutively active forms of mutant kit by multitargeted indolinone tyrosine kinase inhibitors."
Rich et al., N. Engl. J. Med., 351(12):1260-1261 (2004). "EGFR Mutations and Sensitivity to Gefitinib."
Barber e al., N. Engl. J. Med., 351(27):2883 (2004). "Somatic Mutations of EGFR in Colorectal Cancers and Glioblastomas."

Gilbert et al., N. Engl. J. Med., 353(2):209-210 (2005). "Lack of Mutations in EGFR in Gastroenteropancreatic Neuroendocrine Tumors."
Aebersold et al., "Prevalence and clinical impact of Met Y1253D-activating point mutation in radiotherapy-treated squamous cell cancer of the oropharynx", Oncogene 22(52) 8519-8523 (2003).
Allan et al., "Genetic alterations in bronchial mucosa and plasma DNA from individuals at high risk of lung cancer", Int J Cancer 91(3) 359-365 (2001).
Arteaga et al., "Unliganded epidermal growth factor receptor dimerization induced by direct interaction of quinazolines with the ATP binding site", J Biol Chem 272(37) 23247-23254 (1997).
Blencke et al., "Mutation of threonine 766 in the epidermal growth factor receptor reveals a hotspot for resistance formation against selective tyrosine kinase inhibitors", J Biol Chem 278(17) 15435-15440 (2003).
Bowie et al., "Deciphering the message in protein sequences: tolerance to amino acid substitutions", Science 247(4948) 1306-1310 (1990).
Cappuzzo et al., "Gefitinib in pretreated non-small-cell lung cancer (NSCLC): analysis of efficacy and correlation with HER2 and epidermal growth factor receptor expression in locally advanced or metastatic NSCLC", J Clin Oncol 21(14) 2658-2663 (2003).
Choong et al., "Gefitinib response of erlotinib-refractory lung cancer involving meninges—role of EGFR mutation", Nat Clin Pract Oncol 3(1) 50-57 (2006).
Ciardiello et al., A novel approach in the treatment of cancer: targeting the epidermal growth factor receptor, Clin Cancer Res 7(10) 2958-2970 (2001).
Clayton et al., "K-ras point mutation detection in lung cancer: comparison of two approaches to somatic mutation detection using ARMS allele-specific amplification", Clin Chem 46(12) 1929-1938 (2000).
Cohen Et al., "Response of some head and neck cancers to epidermal growth factor receptor tyrosine kinase inhibitors may be linked to mutation of ERBB2 rather than EGFR", Clin Cancer Res 11(22) 8105-8108 (2005).
Dancey et al., "Predictive factors for epidermal growth factor receptor inhibitors—the bull's-eye hits the arrow", Cancer Cell 5(5) 411-415 (2004).
Esteller et al., "Detection of aberrant promoter hypermethylation of tumor suppressor genes in serum DNA from non-small cell lung cancer patients", Cancer Res 59(1) 67-70 (1999).
Fenstermaker et al., "Tandem duplication of the epidermal growth factor receptor tyrosine kinase and calcium internalization domains in A-172 glioma cells", Oncogene 16(26) 3435-3446 (1998).
Fitch et al., Gene & Development, 17:214-228 (2003). "Genetics of Dark Skin in Mice."
Frederick et al., Cancer Research, 60(5):1383-1387 (2000). "Diversity and frequency of epidermal growth factor receptor mutations in human glioblastomas."
Greulich et al., "Oncogenic transformation by inhibitor-sensitive and -resistant EGFR mutants", PLoS Med 2(11) e313 (2005).
Grunwald et al., "Developing inhibitors of the epidermal growth factor receptor for cancer treatment", J Natl Cancer Inst 95(12) 851-867 (2003).
Han et al., Cancer Research, 56(17):3859-3861 (1996). "Tyrphostin AG 1478 preferentially inhibits human glioma cells expressing truncated rather than wild-type epidermal growth factor receptors."
Han et al., Oncology Research, 9(11-12):581-587 (1997). "Preferential inhibition of glioblastoma cells with wild-type epidermal growth factor receptors by a novel tyrosine kinase inhibitor ethyl-2,5-dihydroxycinnamate."
Hirsch et al., Journal of Clinical Oncology, 21(20):3798-3807 (2003). "Epidermal growth factor receptor in non-small-cell lung carcinomas: correlation between gene copy number and protein expression and impact on prognosis."
Kersting et al., "Differential frequencies of p16(INK4a) promoter hypermethylation, p53 mutation, and K-ras mutation in exfoliative material mark the development of lung cancer in symptomatic chronic smokers", J Clin Oncol 18(18) 3221-3229 (2000).
Kobayashi et al., New England Journal of Medicine, 352:786-792 (2005). "EGFR mutation and resistance of non-small-cell lung cancer to Gifitinib."

(56) References Cited

OTHER PUBLICATIONS

Leon et al., "Free DNA in the serum of cancer patients and the effect of therapy", Cancer Res 37(3) 646-650 (1977).
Li et al., Cancer Res, 63:7443-7450 (2003). "Resistance to small molecule inhibitors of epidermal growth factor receptor in malignant gliomas."
Lynch et al., New England J of Medicine, 350:2129-2139 (2004). "Activating mutations in the Epidermal Growth Factor Receptor underlying responsiveness of non-small-cell lung cancer to Gefitinib."
Matyas et al., "Evaluation and application of denaturing HPLC for mutation detection in Marfan syndrome: Identification of 20 novel mutations and two novel polymorphisms in the FBN1 gene", Hum Mutat 19(4) 443-456 (2002).
Owshalimpur et al., Molecular and Cellular Probes, 13(3):169-173 (1999). "Genomic structure of the EPHA1 receptor tyrosine kinase gene."
Paez et al., Science, 304:1497-1500 (2004). "EGFR mutations in lung cancer: correlation with clinical response to Gefitinib therapy."
Palmisano et al., "Predicting lung cancer by detecting aberrant promoter methylation in sputum", Cancer Res 60(12) 5954-5958 (2000).
Pao et al., PNAS, 101:13306-13311 (2004). "EGF receptor gene mutations are common in lung cancers from never smokers and are associated with sensitivity of tumors to gefitinib and erlotinib."
Pao et al., "Acquired resistance of lung adenocarcinomas to gefitinib or erlotinib is associated with a second mutation in the EGFR kinase domain", PLoS Med 2(3) e73 (2005).
Pedersen, Int J of Cancer, 108(5):643-653 (2004). "Expression of a naturally occurring constitutively active variant of the epidermal growth factor receptor in mouse fibroblasts increases motility."
Riely et al., Clinical Cancer Research, 12:839-844 (2006). "Clinical course of patients with non-small cell lung cancer and epidermal growth factor receptor exon 19 and exon 21 mutations treated with gefitinib or erlotinib."
Sakurada et al., Clinical Lung Cancer, 7:S138-S144 (2006). "Epidermal growth factor receptor tyrosine kinase inhibitorsin lung cancer: impact of primary or secondary mutations."
Sanchez-Cespedes et al., "Detection of chromosome 3p alterations in serum DNA of non-small-cell lung cancer patients", Ann Oncol 9(1) 113-116 (1998).
Shu et al., PNAS USA, 87:9103-7 (1990). "Tissue specific transformation by epidermal growth factor receptor: a single point mutation within the ATP-binding pocket of the erbB product increases its intrinsic kinase activity and activates its sarcomagenic potential."
Sidransky et al., "Identification of p53 gene mutations in bladder cancers and urine samples", Science 252(5006) 706-709 (1991).
Sidransky et al., "Identification of ras oncogene mutations in the stool of patients with curable colorectal tumors", Science 256(50530 102-106 (1992).
Slamon et al., "Human breast cancer: correlation of relapse and survival with amplification of the HER-2/neu oncogene", Science 235(4785) 177-182 (1987).

\* cited by examiner

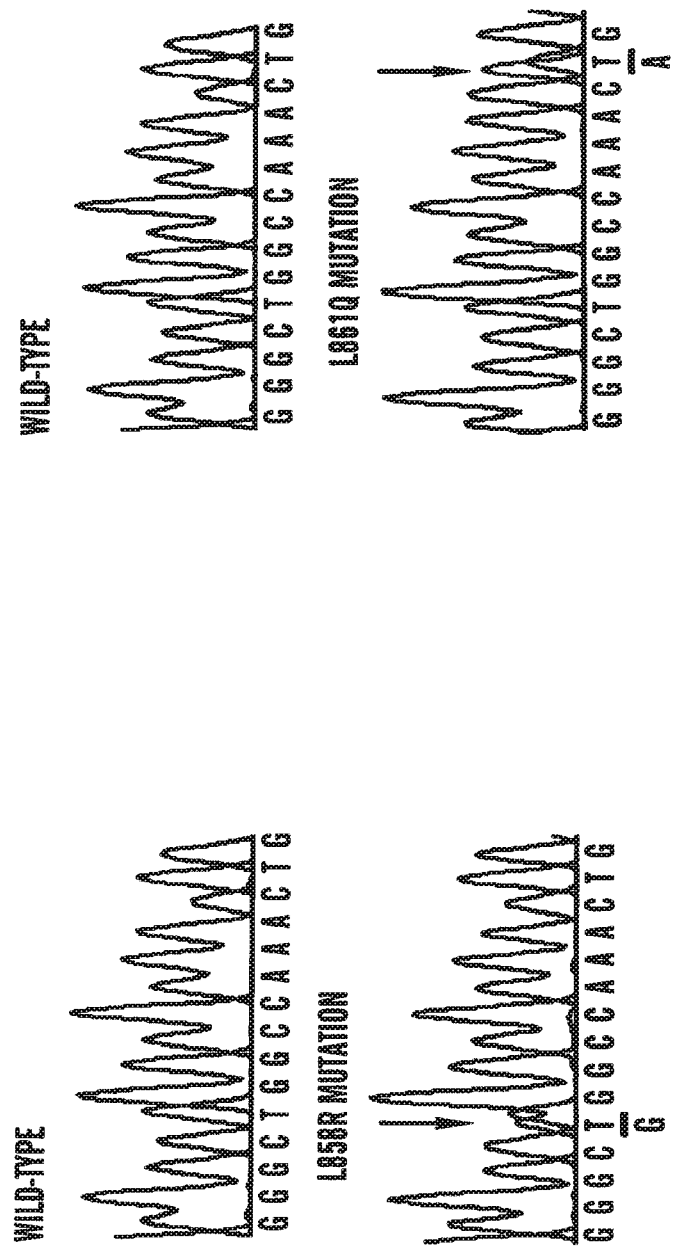

```
CCCGGCGCAGCGCGGCCGCAGCAGCCTCCGCCCCCCGCACGGTGTGAGCGCCCGACGCGG  -185
............................................................

CCGAGGCGGCCGGAGTCCCGAGCTAGCCCCGGCGGCCGCCGCCGCCCAGACCGGACGACA  -125
............................................................

GGCCACCTCGTCGGCGTCCGCCCGAGTCCCCGCCTCGCCGCCAACGCCACAACCACCGCG  -65
............................................................

CACGGCCCCCTGACTCCGTCCAGTATTGATCGGGAGAGCCGGAGCGAGCTCTTCGGGGAG  -5
............................................................

CAGCGATGCGACCCTCCGGGACGGCCGGGGCAGCGCTCCTGGCGCTGCTGGCTGCGCTCT  55
.....-M--R--P--S--G--T--A--G--A--A--L--L--A--L--A--A--L--    18

GCCCGGCGAGTCGGGCTCTGGAGGAAAAGAAAGTTTGCCAAGGCACGAGTAACAAGCTCA  115
C--P--A--S--R--A--L--E--E--K--K--V--C--Q--G--T--S--N--K--L--  38

CGCAGTTGGGCACTTTTGAAGATCATTTTCTCAGCCTCCAGAGGATGTTCAATAACTGTG  175
T--Q--L--G--T--F--E--D--H--F--L--S--L--Q--R--M--F--N--N--C--  58

AGGTGGTCCTTGGGAATTTGGAAATTACCTATGTGCAGAGGAATTATGATCTTTCCTTCT  235
E--V--V--L--G--N--L--E--I--T--Y--V--Q--R--N--Y--D--L--S--F--  78

TAAAGACCATCCAGGAGGTGGCTGGTTATGTCCTCATTGCCCTCAACACAGTGGAGCGAA  295
L--K--T--I--Q--E--V--A--G--Y--V--L--I--A--L--N--T--V--E--R--  98

TTCCTTTGGAAAACCTGCAGATCATCAGAGGAAATATGTACTACGAAAATTCCTATGCCT  355
I--P--L--E--N--L--Q--I--I--R--G--N--M--Y--Y--E--N--S--Y--A--  118

TAGCAGTCTTATCTAACTATGATGCAAATAAAACCGGACTGAAGGAGCTGCCCATGAGAA  415
L--A--V--L--S--N--Y--D--A--N--K--T--G--L--K--E--L--P--M--R--  138

ATTTACAGGAAATCCTGCATGGCGCCGTGCGGTTCAGCAACAACCCTGCCCTGTGCAACG  475
N--L--Q--E--I--L--H--G--A--V--R--F--S--N--N--P--A--L--C--N--  158

TGGAGAGCATCCAGTGGCGGGACATAGTCAGCAGTGACTTTCTCAGCAACATGTCGATGG  535
V--E--S--I--Q--W--R--D--I--V--S--S--D--F--L--S--N--M--S--M--  178

ACTTCCAGAACCACCTGGGCAGCTGCCAAAAGTGTGATCCAAGCTGTCCCAATGGGAGCT  595
D--F--Q--N--H--L--G--S--C--Q--K--C--D--P--S--C--P--N--G--S--  198

GCTGGGGTGCAGGAGAGGAGAACTGCCAGAAACTGACCAAAATCATCTGTGCCCAGCAGT  655
C--W--G--A--G--E--E--N--C--Q--K--L--T--K--I--I--C--A--Q--Q--  218

GCTCCGGGCGCTGCCGTGGCAAGTCCCCCAGTGACTGCTGCCACAACCAGTGTGCTGCAG  715
C--S--G--R--C--R--G--K--S--P--S--D--C--C--H--N--Q--C--A--A--  238

GCTGCACAGGCCCCCGGGAGAGCGACTGCCTGGTCTGCCGCAAATTCCGAGACGAAGCCA  775
G--C--T--G--P--R--E--S--D--C--L--V--C--R--K--F--R--D--E--A--  258

CGTGCAAGGACACCTGCCCCCCACTCATGCTCTACAACCCCACCACGTACCAGATGGATG  835
T--C--K--D--T--C--P--P--L--M--L--Y--N--P--T--T--Y--Q--M--D--  278

TGAACCCCGAGGGCAAATACAGCTTTGGTGCCACCTGCGTGAAGAAGTGTCCCCGTAATT  895
V--N--P--E--G--K--Y--S--F--G--A--T--C--V--K--K--C--P--R--N--  298
```

FIG. 5 (cont'd)

```
ATGTGGTGACAGATCACGGCTCGTGCGTCCGAGCCTGTGGGGCCGACAGCTATGAGATGG  955
Y--V--V--T--D--H--G--S--C--V--R--A--C--G--A--D--S--Y--E--M--  318

AGGAAGACGGCGTCCGCAAGTGTAAGAAGTGCGAAGGGCCTTGCCGCAAAGTGTGTAACG  1015
E--E--D--G--V--R--K--C--K--K--C--E--G--P--C--R--K--V--C--N--  338

GAATAGGTATTGGTGAATTTAAAGACTCACTCTCCATAAATGCTACGAATATTAAACACT  1075
G--I--G--I--G--E--F--K--D--S--L--S--I--N--A--T--N--I--K--H--  358

TCAAAAACTGCACCTCCATCAGTGGCGATCTCCACATCCTGCCGGTGGCATTTAGGGGTG  1135
F--K--N--C--T--S--I--S--G--D--L--H--I--L--P--V--A--F--R--G--  378

ACTCCTTCACACATACTCCTCCTCTGGATCCACAGGAACTGGATATTCTGAAAACCGTAA  1195
D--S--F--T--H--T--P--P--L--D--P--Q--E--L--D--I--L--K--T--V--  398

AGGAAATCACAGGGTTTTTGCTGATTCAGGCTTGGCCTGAAAACAGGACGGACCTCCATG  1255
K--E--I--T--G--F--L--L--I--Q--A--W--P--E--N--R--T--D--L--H--  418

CCTTTGAGAACCTAGAAATCATACGCGGCAGGACCAAGCAACATGGTCAGTTTTCTCTTG  1315
A--F--E--N--L--E--I--I--R--G--R--T--K--Q--H--G--Q--F--S--L--  438

CAGTCGTCAGCCTGAACATAACATCCTTGGGATTACGCTCCCTCAAGGAGATAAGTGATG  1375
A--V--V--S--L--N--I--T--S--L--G--L--R--S--L--K--E--I--S--D--  458

GAGATGTGATAATTTCAGGAAACAAAAATTTGTGCTATGCAAATACAATAAACTGGAAAA  1435
G--D--V--I--I--S--G--N--K--N--L--C--Y--A--N--T--I--N--W--K--  478

AACTGTTTGGGACCTCCGGTCAGAAAACCAAAATTATAAGCAACAGAGGTGAAAACAGCT  1495
K--L--F--G--T--S--G--Q--K--T--K--I--I--S--N--R--G--E--N--S--  498

GCAAGGCCACAGGCCAGGTCTGCCATGCCTTGTGCTCCCCCGAGGGCTGCTGGGGCCCGG  1555
C--K--A--T--G--Q--V--C--H--A--L--C--S--P--E--G--C--W--G--P--  518

AGCCCAGGGACTGCGTCTCTTGCCGGAATGTCAGCCGAGGCAGGGAATGCGTGGACAAGT  1615
E--P--R--D--C--V--S--C--R--N--V--S--R--G--R--E--C--V--D--K--  538

GCAACCTTCTGGAGGGTGAGCCAAGGGAGTTTGTGGAGAACTCTGAGTGCATACAGTGCC  1675
C--N--L--L--E--G--E--P--R--E--F--V--E--N--S--E--C--I--Q--C--  558

ACCCAGAGTGCCTGCCTCAGGCCATGAACATCACCTGCACAGGACGGGGACCAGACAACT  1735
H--P--E--C--L--P--Q--A--M--N--I--T--C--T--G--R--G--P--D--N--  578

GTATCCAGTGTGCCCACTACATTGACGGCCCCCACTGCGTCAAGACCTGCCCGGCAGGAG  1795
C--I--Q--C--A--H--Y--I--D--G--P--H--C--V--K--T--C--P--A--G--  598

TCATGGGAGAAAACAACACCCTGGTCTGGAAGTACGCAGACGCCGGCCATGTGTGCCACC  1855
V--M--G--E--N--N--T--L--V--W--K--Y--A--D--A--G--H--V--C--H--  618

TGTGCCATCCAAACTGCACCTACGGATGCACTGGGCCAGGTCTTGAAGGCTGTCCAACGA  1915
L--C--H--P--N--C--T--Y--G--C--T--G--P--G--L--E--G--C--P--T--  638

ATGGGCCTAAGATCCCGTCCATCGCCACTGGGATGGTGGGGGCCCTCCTCTTGCTGCTGG  1975
N--G--P--K--I--P--S--I--A--T--G--M--V--G--A--L--L--L--L--L--  658

TGGTGGCCCTGGGGATCGGCCTCTTCATGCGAAGGCGCCACATCGTTCGGAAGCGCACGC  2035
V--V--A--L--G--I--G--L--F--M--R--R--R--H--I--V--R--K--R--T--  678
```

FIG. 5 (cont'd)

```
TGCGGAGGCTGCTGCAGGAGAGGGAGCTTGTGGAGCCTCTTACACCCAGTGGAGAAGCTC  2095
L--R--R--L--L--Q--E--R--E--L--V--E--P--L--T--P--S--G--E--A--   698

CCAACCAAGCTCTCTTGAGGATCTTGAAGGAAACTGAATTCAAAAAGATCAAAGTGCTGG  2155
P--N--Q--A--L--L--R--I--L--K--E--T--E--F--K--K--I--K--V--L--   718

GCTCCGGTGCGTTCGGCACGGTGTATAAGGGACTCTGGATCCCAGAAGGTGAGAAAGTTA  2215
G--S--G--A--F--G--T--V--Y--K--G--L--W--I--P--E--G--E--K--V--   738

AAATTCCCGTCGCTATCAAGGAATTAAGAGAAGCAACATCTCCGAAAGCCAACAAGGAAA  2275
K--I--P--V--A--I--K--E--L--R--E--A--T--S--P--K--A--N--K--E--   758

TCCTCGATGAAGCCTACGTGATGGCCAGCGTGGACAACCCCCACGTGTGCCGCCTGCTGG  2335
I--L--D--E--A--Y--V--M--A--S--V--D--N--P--H--V--C--R--L--L--   778

GCATCTGCCTCACCTCCACCGTGCAGCTCATCACGCAGCTCATGCCCTTCGGCTGCCTCC  2395
G--I--C--L--T--S--T--V--Q--L--I--T--Q--L--M--P--F--G--C--L--   798

TGGACTATGTCCGGGAACACAAAGACAATATTGGCTCCCAGTACCTGCTCAACTGGTGTG  2455
L--D--Y--V--R--E--H--K--D--N--I--G--S--Q--Y--L--L--N--W--C--   818

TGCAGATCGCAAAGGGCATGAACTACTTGGAGGACCGTCGCTTGGTGCACCGCGACCTGG  2515
V--Q--I--A--K--G--M--N--Y--L--E--D--R--R--L--V--H--R--D--L--   838

CAGCCAGGAACGTACTGGTGAAAACACCGCAGCATGTCAAGATCACAGATTTTGGGCTGG  2575
A--A--R--N--V--L--V--K--T--P--Q--H--V--K--I--T--D--F--G--L--   858

CCAAACTGCTGGGTGCGGAAGAGAAAGAATACCATGCAGAAGGAGGCAAAGTGCCTATCA  2635
A--K--L--L--G--A--E--E--K--E--Y--H--A--E--G--G--K--V--P--I--   878

AGTGGATGGCATTGGAATCAATTTTACACAGAATCTATACCCACCAGAGTGATGTCTGGA  2695
K--W--M--A--L--E--S--I--L--H--R--I--Y--T--H--Q--S--D--V--W--   898

GCTACGGGGTGACTGTTTGGGAGTTGATGACCTTTGGATCCAAGCCATATGACGGAATCC  2755
S--Y--G--V--T--V--W--E--L--M--T--F--G--S--K--P--Y--D--G--I--   918

CTGCCAGCGAGATCTCCTCCATCCTGGAGAAAGGAGAACGCCTCCCTCAGCCACCCATAT  2815
P--A--S--E--I--S--S--I--L--E--K--G--E--R--L--P--Q--P--P--I--   938

GTACCATCGATGTCTACATGATCATGGTCAAGTGCTGGATGATAGACGCAGATAGTCGCC  2875
C--T--I--D--V--Y--M--I--M--V--K--C--W--M--I--D--A--D--S--R--   958

CAAAGTTCCGTGAGTTGATCATCGAATTCTCCAAAATGGCCCGAGACCCCCAGCGCTACC  2935
P--K--F--R--E--L--I--I--E--F--S--K--M--A--R--D--P--Q--R--Y--   978

TTGTCATTCAGGGGGATGAAAGAATGCATTTGCCAAGTCCTACAGACTCCAACTTCTACC  2995
L--V--I--Q--G--D--E--R--M--H--L--P--S--P--T--D--S--N--F--Y--   998

GTGCCCTGATGGATGAAGAAGACATGGACGACGTGGTGGATGCCGACGAGTACCTCATCC  3055
R--A--L--M--D--E--E--D--M--D--D--V--V--D--A--D--E--Y--L--I--  1018

CACAGCAGGGCTTCTTCAGCAGCCCCTCCACGTCACGGACTCCCCTCCTGAGCTCTCTGA  3115
P--Q--Q--G--F--F--S--S--P--S--T--S--R--T--P--L--L--S--S--L--  1038

GTGCAACCAGCAACAATTCCACCGTGGCTTGCATTGATAGAAATGGGCTGCAAAGCTGTC  3175
S--A--T--S--N--N--S--T--V--A--C--I--D--R--N--G--L--Q--S--C--  1058
```

FIG. 5 (cont'd)

```
CCATCAAGGAAGACAGCTTCTTGCAGCGATACAGCTCAGACCCCACAGGCGCCTTGACTG  3235
P--I--K--E--D--S--F--L--Q--R--Y--S--S--D--P--T--G--A--L--T--  1078

AGGACAGCATAGACGACACCTTCCTCCCAGTGCCTGAATACATAAACCAGTCCGTTCCCA  3295
E--D--S--I--D--D--T--F--L--P--V--P--E--Y--I--N--Q--S--V--P--  1098

AAAGGCCCGCTGGCTCTGTGCAGAATCCTGTCTATCACAATCAGCCTCTGAACCCCGCGC  3355
K--R--P--A--G--S--V--Q--N--P--V--Y--H--N--Q--P--L--N--P--A--  1118

CCAGCAGAGACCCACACTACCAGGACCCCCACAGCACTGCAGTGGGCAACCCCGAGTATC  3415
P--S--R--D--P--H--Y--Q--D--P--H--S--T--A--V--G--N--P--E--Y--  1138

TCAACACTGTCCAGCCCACCTGTGTCAACAGCACATTCGACAGCCCTGCCCACTGGGCCC  3475
L--N--T--V--Q--P--T--C--V--N--S--T--F--D--S--P--A--H--W--A--  1158

AGAAAGGCAGCCACCAAATTAGCCTGGACAACCCTGACTACCAGCAGGACTTCTTTCCCA  3535
Q--K--G--S--H--Q--I--S--L--D--N--P--D--Y--Q--Q--D--F--F--P--  1178

AGGAAGCCAAGCCAAATGGCATCTTTAAGGGCTCCACAGCTGAAAATGCAGAATACCTAA  3595
K--E--A--K--P--N--G--I--F--K--G--S--T--A--E--N--A--E--Y--L--  1198

GGGTCGCGCCACAAAGCAGTGAATTTATTGGAGCATGA  3633  (SEQ ID NO 511)
R--V--A--P--Q--S--S--E--F--I--G--A--*-  1210  (SEQ ID NO 512)
```

|  |  |  | SEQ ID NO |
|---|---|---|---|
| | | | |

```
                      activation loop
L858R     KTPQHVKITDFG AKLLGAEEKEYH        870      477
EGFR      KTPQHVKITDFGLAKLLGAEEKEYH        870      478
BRAF      H DLTVKIGD    AT KSRWSGSHQ       608      479
             ***  *****
```

FIG. 6A

```
                      P-loop                          SEQ ID NO
G719S     ETEFKKIKVL SGAFGTVYKGLWIP        733      480
EGFR      ETEFKKIKVLGSGAFGTVYKGLWIP        733      481
BRAF      DGQITVGQRI S SF TVYKGKWHG        477      482
             ***  ******* *
```

FIG. 6B

```
          742      |750|752                           SEQ ID NO
Del-1     VAIK     T-SPKANKEILDEAYV        765      483
Del-2     VAIKELREAT-         LDEAYV        765      484
Del-3     VAIKE    T-SPKANKEILDEAYV        765      485
Del-4     VAIKE    - KANKEILDEAYV          765      486
Del-5     VAIK     - PKANKEILDEAYV         765      487
EGFR      VAIKELREAT-SPKANKEILDEAYV        765      488
BRAF      VAVKMLNVTAPTPQQLQAFKNEVGV        503      489
          ** *                    * *
```

FIG. 6C

Alignment of Abl1 to EGFR

```
Abl1(242)  ITMKHKLGGGQYGEVYEGVWK----KYSLTVAVKTLKEDT---MEVEEFLKEAAVMKEIKHPNLVQLLGVCTREPPFYIIT  790
EGFR(712)  FKKIKVLGSGAFGTVYKGLWIPEGEKVKIPVAIKELREATSPKANKEILDEAYVMASVDNPHVCRLLGICLTS-TVQLIT
Consensus          LG G FG VY GLW     K  I VAIK LKE T     E L EA VM  I P L   LLGIC          IIT   869

Abl1(316)  EFMTYGNLLDYLRECNRQEVNAVVLLYMATQISSAMEYLEKKNFIHRDLAARNCLVGENHLVKVADFGLSRLMTGDTYTA
EGFR(791)  QLMPFGCLLDYVREHKDN-IGSQYLLNWCVQIAKGMNYLEDRRLVHRDLAARNVLVKTPQHVKITDFGLAKLLGAEEKEY
Consensus    M FG LLDYLRE    N I A LL     QIA AM YLE K  IHRDLAARN LV      VKI DFGLAKLL AD    949

Abl1(396)  HA-GAKFPIKWTAPESLAYNKFSIKSDVWAFGVLLWEIATYGMSPYPGIDLSQVYELLEKDYRMERPEGCPEKVYELMRA
EGFR(870)  HAEGGKVPIKWMALESILHRIYTHQSDVWSYGVTVWELMTFGSKPYDGIPASEISSILEKGERLPQPPICTIDVYMIMVK
Consensus  HA GAK PIKW A ESI H FS SDVWAFGV LWEI TFG  PY GI  S I ILEK RL  P  C   VY IM
                                                                            979

Abl1(475)  CWQWNPSDRPSFAEIHQAF-------  (SEQ ID NO 491)
EGFR(950)  CWMIDADSRPKFRELIIEFSKMARDPQRYL  (SEQ ID NO 492)
Consensus  CW       RP F EI  F
```

FIG. 9

SEQUENCE LISTING

<160> NUMBER OF SEQ ID NOS: 762

<210> SEQ ID NO 1
<211> LENGTH: 23
<212> TYPE: DNA
<213> ORGANISM: Homo sapiens

<400> SEQUENCE: 1
ggaaatatag ggaagggaag gaa          23

<210> SEQ ID NO 2
<211> LENGTH: 22
<212> TYPE: DNA
<213> ORGANISM: Homo sapiens

<400> SEQUENCE: 2
ttgacagggt accaggagat ga          22

<210> SEQ ID NO 3
<211> LENGTH: 20

```
<212> TYPE: DNA
<213> ORGANISM: Homo sapiens

<400> SEQUENCE: 3
ctgaaccgcc aaggactcat                                              20

<210> SEQ ID NO 4
<211> LENGTH: 23
<212> TYPE: DNA
<213> ORGANISM: Homo sapiens

<400> SEQUENCE: 4
ttttccctcc ctactaacac acg                                          23

<210> SEQ ID NO 5
<211> LENGTH: 20
<212> TYPE: DNA
<213> ORGANISM: Homo sapiens

<400> SEQUENCE: 5
actgatgccc tgaccctgtt                                              20

<210> SEQ ID NO 6
<211> LENGTH: 19
<212> TYPE: DNA
<213> ORGANISM: Homo sapiens

<400> SEQUENCE: 6
cccatggttc cccactctt                                               19

<210> SEQ ID NO 7
<211> LENGTH: 20
<212> TYPE: DNA
<213> ORGANISM: Homo sapiens

<400> SEQUENCE: 7
agggactcca aagccatgtg                                              20

<210> SEQ ID NO 8
<211> LENGTH: 19
<212> TYPE: DNA
<213> ORGANISM: Homo sapiens

<400> SEQUENCE: 8
ctctctgggg ccatccact                                               19

<210> SEQ ID NO 9
<211> LENGTH: 23
<212> TYPE: DNA
<213> ORGANISM: Homo sapiens

<400> SEQUENCE: 9
cattgtcaag ggcaatgtaa gtg                                          23

<210> SEQ ID NO 10
<211> LENGTH: 20
<212> TYPE: DNA
<213> ORGANISM: Homo sapiens

<400> SEQUENCE: 10
ctctcaccaa ccctcgctgt                                              20

<210> SEQ ID NO 11
```

```
<211> LENGTH: 20
<212> TYPE: DNA
<213> ORGANISM: Homo sapiens

<400> SEQUENCE: 11
acatggggag ccagagtgac                                              20

<210> SEQ ID NO 12
<211> LENGTH: 20
<212> TYPE: DNA
<213> ORGANISM: Homo sapiens

<400> SEQUENCE: 12
tgcaacccag agaaagtgtg                                              20

<210> SEQ ID NO 13
<211> LENGTH: 24
<212> TYPE: DNA
<213> ORGANISM: Homo sapiens

<400> SEQUENCE: 13
tgagctttca accctagttt gttg                                         24

<210> SEQ ID NO 14
<211> LENGTH: 20
<212> TYPE: DNA
<213> ORGANISM: Homo sapiens

<400> SEQUENCE: 14
gtttgcctcc tgctgtctca                                              20

<210> SEQ ID NO 15
<211> LENGTH: 24
<212> TYPE: DNA
<213> ORGANISM: Homo sapiens

<400> SEQUENCE: 15
tgtccttgtg tttttgaaga ttcc                                         24

<210> SEQ ID NO 16
<211> LENGTH: 23
<212> TYPE: DNA
<213> ORGANISM: Homo sapiens

<400> SEQUENCE: 16
tgcagacaga tgacaaacat gaa                                          23

<210> SEQ ID NO 17
<211> LENGTH: 21
<212> TYPE: DNA
<213> ORGANISM: Homo sapiens

<400> SEQUENCE: 17
tgggtgagtc tctgtgtgga g                                            21

<210> SEQ ID NO 18
<211> LENGTH: 25
<212> TYPE: DNA
<213> ORGANISM: Homo sapiens

<400> SEQUENCE: 18
cattgccata gcaaaaataa acaca                                        25
```

```
<210> SEQ ID NO 19
<211> LENGTH: 19
<212> TYPE: DNA
<213> ORGANISM: Homo sapiens

<400> SEQUENCE: 19
ggttcaactg ggcgtccta                                                    19

<210> SEQ ID NO 20
<211> LENGTH: 20
<212> TYPE: DNA
<213> ORGANISM: Homo sapiens

<400> SEQUENCE: 20
ccttctccga ggtggaattg                                                   20

<210> SEQ ID NO 21
<211> LENGTH: 20
<212> TYPE: DNA
<213> ORGANISM: Homo sapiens

<400> SEQUENCE: 21
cgcaccatgg catctcttta                                                   20

<210> SEQ ID NO 22
<211> LENGTH: 23
<212> TYPE: DNA
<213> ORGANISM: Homo sapiens

<400> SEQUENCE: 22
aaaacgatct ctatgtccgt ggt                                               23

<210> SEQ ID NO 23
<211> LENGTH: 20
<212> TYPE: DNA
<213> ORGANISM: Homo sapiens

<400> SEQUENCE: 23
cagccagcca aacaatcaga                                                   20

<210> SEQ ID NO 24
<211> LENGTH: 23
<212> TYPE: DNA
<213> ORGANISM: Homo sapiens

<400> SEQUENCE: 24
tctttggagt cttcagaggg aaa                                               23

<210> SEQ ID NO 25
<211> LENGTH: 20
<212> TYPE: DNA
<213> ORGANISM: Homo sapiens

<400> SEQUENCE: 25
tgtggtttcg ttggaagcaa                                                   20

<210> SEQ ID NO 26
<211> LENGTH: 20
<212> TYPE: DNA
<213> ORGANISM: Homo sapiens

<400> SEQUENCE: 26
aattgacagc tcccccacag                                                   20
```

<210> SEQ ID NO 27
<211> LENGTH: 20
<212> TYPE: DNA
<213> ORGANISM: Homo sapiens

<400> SEQUENCE: 27
ggctttctga cgggagtcaa					20

<210> SEQ ID NO 28
<211> LENGTH: 21
<212> TYPE: DNA
<213> ORGANISM: Homo sapiens

<400> SEQUENCE: 28
ccacccaaag actctccaag a					21

<210> SEQ ID NO 29
<211> LENGTH: 20
<212> TYPE: DNA
<213> ORGANISM: Homo sapiens

<400> SEQUENCE: 29
cctttccatc acccctcaag					20

<210> SEQ ID NO 30
<211> LENGTH: 20
<212> TYPE: DNA
<213> ORGANISM: Homo sapiens

<400> SEQUENCE: 30
agtgccttcc cattgcctaa					20

<210> SEQ ID NO 31
<211> LENGTH: 20
<212> TYPE: DNA
<213> ORGANISM: Homo sapiens

<400> SEQUENCE: 31
accggaattc cttcctgctt					20

<210> SEQ ID NO 32
<211> LENGTH: 23
<212> TYPE: DNA
<213> ORGANISM: Homo sapiens

<400> SEQUENCE: 32
cactgaaaca aacaacaggg tga				23

<210> SEQ ID NO 33
<211> LENGTH: 20
<212> TYPE: DNA
<213> ORGANISM: Homo sapiens

<400> SEQUENCE: 33 aggggggtgag tcacaggttc					20

<210> SEQ ID NO 34
<211> LENGTH: 26
<212> TYPE: DNA
<213> ORGANISM: Homo sapiens

<400> SEQUENCE: 34
tcagaagaaa tgttttttatt ccaagg				26

-continued

```
<210> SEQ ID NO 35
<211> LENGTH: 21
<212> TYPE: DNA
<213> ORGANISM: Homo sapiens

<400> SEQUENCE: 35
gcaaatccaa ttttcccact t                                             21

<210> SEQ ID NO 36
<211> LENGTH: 20
<212> TYPE: DNA
<213> ORGANISM: Homo sapiens

<400> SEQUENCE: 36
gcaggagctc tgtgccctat                                               20

<210> SEQ ID NO 37
<211> LENGTH: 20
<212> TYPE: DNA
<213> ORGANISM: Homo sapiens

<400> SEQUENCE: 37
tcccacagca tgacctacca                                               20

<210> SEQ ID NO 38
<211> LENGTH: 23
<212> TYPE: DNA
<213> ORGANISM: Homo sapiens

<400> SEQUENCE: 38
tttgcttctt aaggaactga aaa                                           23

<210> SEQ ID NO 39
<211> LENGTH: 20
<212> TYPE: DNA
<213> ORGANISM: Homo sapiens

<400> SEQUENCE: 39
tgtcacccaa ggtcatggag                                               20

<210> SEQ ID NO 40
<211> LENGTH: 20
<212> TYPE: DNA
<213> ORGANISM: Homo sapiens

<400> SEQUENCE: 40
caaaagccaa gggcaaagaa                                               20

<210> SEQ ID NO 41
<211> LENGTH: 20
<212> TYPE: DNA
<213> ORGANISM: Homo sapiens

<400> SEQUENCE: 41
ggagtcccaa ctccttgacc                                               20

<210> SEQ ID NO 42
<211> LENGTH: 19
<212> TYPE: DNA
<213> ORGANISM: Homo sapiens

<400> SEQUENCE: 42
```

```
gtcctgccca cacaggatg                                            19

<210> SEQ ID NO 43
<211> LENGTH: 20
<212> TYPE: DNA
<213> ORGANISM: Homo sapiens

<400> SEQUENCE: 43
gctttcccca ctcacacaca                                           20

<210> SEQ ID NO 44
<211> LENGTH: 20
<212> TYPE: DNA
<213> ORGANISM: Homo sapiens

<400> SEQUENCE: 44
caaacctcgg caatttgttg                                           20

<210> SEQ ID NO 45
<211> LENGTH: 20
<212> TYPE: DNA
<213> ORGANISM: Homo sapiens

<400> SEQUENCE: 45
ccaccaatcc aacatccaga                                           20

<210> SEQ ID NO 46
<211> LENGTH: 20
<212> TYPE: DNA
<213> ORGANISM: Homo sapiens

<400> SEQUENCE: 46
tggcccagag ccatagaaac                                           20

<210> SEQ ID NO 47
<211> LENGTH: 26
<212> TYPE: DNA
<213> ORGANISM: Homo sapiens

<400> SEQUENCE: 47
ttccaagatc attctacaag atgtca                                    26

<210> SEQ ID NO 48
<211> LENGTH: 23
<212> TYPE: DNA
<213> ORGANISM: Homo sapiens

<400> SEQUENCE: 48
gcacattcag agattctttc tgc                                       23

<210> SEQ ID NO 49
<211> LENGTH: 20
<212> TYPE: DNA
<213> ORGANISM: Homo sapiens

<400> SEQUENCE: 49
tccaaatgag ctggcaagtg                                           20

<210> SEQ ID NO 50
<211> LENGTH: 23
<212> TYPE: DNA
<213> ORGANISM: Homo sapiens

<400> SEQUENCE: 50
```
tcccaaacac tcagtgaaac aaa                                            23

<210> SEQ ID NO 51
<211> LENGTH: 20
<212> TYPE: DNA
<213> ORGANISM: Homo sapiens

<400> SEQUENCE: 51
gtgcatcgct ggtaacatcc                                                20

<210> SEQ ID NO 52
<211> LENGTH: 20
<212> TYPE: DNA
<213> ORGANISM: Homo sapiens

<400> SEQUENCE: 52
tgtggagatg agcagggtct                                                20

<210> SEQ ID NO 53
<211> LENGTH: 20
<212> TYPE: DNA
<213> ORGANISM: Homo sapiens

<400> SEQUENCE: 53
atcgcattca tgcgtcttca                                                20

<210> SEQ ID NO 54
<211> LENGTH: 20
<212> TYPE: DNA
<213> ORGANISM: Homo sapiens

<400> SEQUENCE: 54
atccccatgg caaactcttg                                                20

<210> SEQ ID NO 55
<211> LENGTH: 19
<212> TYPE: DNA
<213> ORGANISM: Homo sapiens

<400> SEQUENCE: 55
gctcagagcc tggcatgaa                                                 19

<210> SEQ ID NO 56
<211> LENGTH: 19
<212> TYPE: DNA
<213> ORGANISM: Homo sapiens

<400> SEQUENCE: 56
catcctcccc tgcatgtgt                                                 19

<210> SEQ ID NO 57
<211> LENGTH: 20
<212> TYPE: DNA
<213> ORGANISM: Homo sapiens

<400> SEQUENCE: 57
tggctcgtct gtgtgtgtca                                                20

<210> SEQ ID NO 58
<211> LENGTH: 25
<212> TYPE: DNA
<213> ORGANISM: Homo sapiens

<400> SEQUENCE: 58
cgaaagaaaa tacttgcatg tcaga                                     25

<210> SEQ ID NO 59
<211> LENGTH: 20
<212> TYPE: DNA
<213> ORGANISM: Homo sapiens

<400> SEQUENCE: 59
tgaagcaaat tgcccaagac                                           20

<210> SEQ ID NO 60
<211> LENGTH: 20
<212> TYPE: DNA
<213> ORGANISM: Homo sapiens

<400> SEQUENCE: 60
tgacatttct ccagggatgc                                           20

<210> SEQ ID NO 61
<211> LENGTH: 20
<212> TYPE: DNA
<213> ORGANISM: Homo sapiens

<400> SEQUENCE: 61
aagtgtcgca tcaccaatgc                                           20

<210> SEQ ID NO 62
<211> LENGTH: 19
<212> TYPE: DNA
<213> ORGANISM: Homo sapiens

<400> SEQUENCE: 62
atgcgatctg ggacacagg                                            19

<210> SEQ ID NO 63
<211> LENGTH: 20
<212> TYPE: DNA
<213> ORGANISM: Homo sapiens

<400> SEQUENCE: 63
ggcacctgct ggcaatagac                                           20

<210> SEQ ID NO 64
<211> LENGTH: 27
<212> TYPE: DNA
<213> ORGANISM: Homo sapiens

<400> SEQUENCE: 64
tgacttcata tccatgtgag tttcact                                   27

<210> SEQ ID NO 65
<211> LENGTH: 20
<212> TYPE: DNA
<213> ORGANISM: Homo sapiens

<400> SEQUENCE: 65
tataccctcc atgaggcaca                                           20

<210> SEQ ID NO 66
<211> LENGTH: 20
<212> TYPE: DNA
<213> ORGANISM: Homo sapiens

```
<400> SEQUENCE: 66
gggaaaaacc cacacaggaa                                               20

<210> SEQ ID NO 67
<211> LENGTH: 21
<212> TYPE: DNA
<213> ORGANISM: Homo sapiens

<400> SEQUENCE: 67
tcagaaccag catctcaagg a                                             21

<210> SEQ ID NO 68
<211> LENGTH: 19
<212> TYPE: DNA
<213> ORGANISM: Homo sapiens

<400> SEQUENCE: 68
gatgctggag ggagcacct                                                19

<210> SEQ ID NO 69
<211> LENGTH: 22
<212> TYPE: DNA
<213> ORGANISM: Homo sapiens

<400> SEQUENCE: 69
ccttgttgag gacattcaca gg                                            22

<210> SEQ ID NO 70
<211> LENGTH: 20
<212> TYPE: DNA
<213> ORGANISM: Homo sapiens

<400> SEQUENCE: 70
atgtgcccga ggtggaagta                                               20

<210> SEQ ID NO 71
<211> LENGTH: 20
<212> TYPE: DNA
<213> ORGANISM: Homo sapiens

<400> SEQUENCE: 71
ggagggcaga ggactagctg                                               20

<210> SEQ ID NO 72
<211> LENGTH: 20
<212> TYPE: DNA
<213> ORGANISM: Homo sapiens

<400> SEQUENCE: 72
gtgcctggcc aagtctttgt                                               20

<210> SEQ ID NO 73
<211> LENGTH: 20
<212> TYPE: DNA
<213> ORGANISM: Homo sapiens

<400> SEQUENCE: 73
ctgcagccta gcaacagagc                                               20

<210> SEQ ID NO 74
<211> LENGTH: 20
<212> TYPE: DNA
```

<213> ORGANISM: Homo sapiens

<400> SEQUENCE: 74
aagaaccaga ggagccagga                    20

<210> SEQ ID NO 75
<211> LENGTH: 20
<212> TYPE: DNA
<213> ORGANISM: Homo sapiens

<400> SEQUENCE: 75
cgggtaagga tgtgggttgt                    20

<210> SEQ ID NO 76
<211> LENGTH: 20
<212> TYPE: DNA
<213> ORGANISM: Homo sapiens

<400> SEQUENCE: 76
caggtgttct gcctcctgaa                    20

<210> SEQ ID NO 77
<211> LENGTH: 20
<212> TYPE: DNA
<213> ORGANISM: Homo sapiens

<400> SEQUENCE: 77
gcttcaggag gcagaacacc                    20

<210> SEQ ID NO 78
<211> LENGTH: 22
<212> TYPE: DNA
<213> ORGANISM: Homo sapiens

<400> SEQUENCE: 78
ggagcaagcc taagaaggtt ca                 22

<210> SEQ ID NO 79
<211> LENGTH: 21
<212> TYPE: DNA
<213> ORGANISM: Homo sapiens

<400> SEQUENCE: 79
gccttgtatc catttgccac a                  21

<210> SEQ ID NO 80
<211> LENGTH: 21
<212> TYPE: DNA
<213> ORGANISM: Homo sapiens

<400> SEQUENCE: 80
tgacaacacg ttttgggtca t                  21

<210> SEQ ID NO 81
<211> LENGTH: 23
<212> TYPE: DNA
<213> ORGANISM: Homo sapiens

<400> SEQUENCE: 81
tgcatattcc atttcagaac aga                23

<210> SEQ ID NO 82
<211> LENGTH: 23

<212> TYPE: DNA
<213> ORGANISM: Homo sapiens

<400> SEQUENCE: 82
aaacagtttc attgctgcta aat    23

<210> SEQ ID NO 83
<211> LENGTH: 23
<212> TYPE: DNA
<213> ORGANISM: Homo sapiens

<400> SEQUENCE: 83
ccggatacag atacccaaaa aga    23

<210> SEQ ID NO 84
<211> LENGTH: 20
<212> TYPE: DNA
<213> ORGANISM: Homo sapiens

<400> SEQUENCE: 84
ggaggcttca agggatgaga    20

<210> SEQ ID NO 85
<211> LENGTH: 20
<212> TYPE: DNA
<213> ORGANISM: Homo sapiens

<400> SEQUENCE: 85
gctgttgtcc tgcttggcta    20

<210> SEQ ID NO 86
<211> LENGTH: 25
<212> TYPE: DNA
<213> ORGANISM: Homo sapiens

<400> SEQUENCE: 86
tggttgtaat gttgaactag cttgc    25

<210> SEQ ID NO 87
<211> LENGTH: 24
<212> TYPE: DNA
<213> ORGANISM: Homo sapiens

<400> SEQUENCE: 87
tggctgtcag ctaaataagc atgt    24

<210> SEQ ID NO 88
<211> LENGTH: 24
<212> TYPE: DNA
<213> ORGANISM: Homo sapiens

<400> SEQUENCE: 88
tcaatttgct tcatttctcc tgtt    24

<210> SEQ ID NO 89
<211> LENGTH: 21
<212> TYPE: DNA
<213> ORGANISM: Homo sapiens

<400> SEQUENCE: 89
tgctgctgaa ctaccaacca a    21

<210> SEQ ID NO 90

```
<211> LENGTH: 24
<212> TYPE: DNA
<213> ORGANISM: Homo sapiens

<400> SEQUENCE: 90
tgtggtagta attgtggaaa actg                                          24

<210> SEQ ID NO 91
<211> LENGTH: 20
<212> TYPE: DNA
<213> ORGANISM: Homo sapiens

<400> SEQUENCE: 91
caaagcaccg tctcaactcg                                               20

<210> SEQ ID NO 92
<211> LENGTH: 20
<212> TYPE: DNA
<213> ORGANISM: Homo sapiens

<400> SEQUENCE: 92
cccgaaactg ccaacttcat                                               20

<210> SEQ ID NO 93
<211> LENGTH: 20
<212> TYPE: DNA
<213> ORGANISM: Homo sapiens

<400> SEQUENCE: 93
ggaaaacagg accccagtgt                                               20

<210> SEQ ID NO 94
<211> LENGTH: 20
<212> TYPE: DNA
<213> ORGANISM: Homo sapiens

<400> SEQUENCE: 94
ccctcctcca cagagctgat                                               20

<210> SEQ ID NO 95
<211> LENGTH: 21
<212> TYPE: DNA
<213> ORGANISM: Homo sapiens

<400> SEQUENCE: 95
gacagaagct gacaagcagc a                                             21

<210> SEQ ID NO 96
<211> LENGTH: 20
<212> TYPE: DNA
<213> ORGANISM: Homo sapiens

<400> SEQUENCE: 96
aggttccatt ccctcccagt                                               20

<210> SEQ ID NO 97
<211> LENGTH: 22
<212> TYPE: DNA
<213> ORGANISM: Homo sapiens

<400> SEQUENCE: 97
tgggagtgag agtttggaag aa                                            22
```

```
<210> SEQ ID NO 98
<211> LENGTH: 20
<212> TYPE: DNA
<213> ORGANISM: Homo sapiens

<400> SEQUENCE: 98
tatgaggccg tgagctgaaa                                               20

<210> SEQ ID NO 99
<211> LENGTH: 18
<212> TYPE: DNA
<213> ORGANISM: Homo sapiens

<400> SEQUENCE: 99
agggccctgc tctggttt                                                 18

<210> SEQ ID NO 100
<211> LENGTH: 20
<212> TYPE: DNA
<213> ORGANISM: Homo sapiens

<400> SEQUENCE: 100
ccaattgggc gttagtgaaa                                               20

<210> SEQ ID NO 101
<211> LENGTH: 20
<212> TYPE: DNA
<213> ORGANISM: Homo sapiens

<400> SEQUENCE: 101
ctcatgagat tggggcatca                                               20

<210> SEQ ID NO 102
<211> LENGTH: 20
<212> TYPE: DNA
<213> ORGANISM: Homo sapiens

<400> SEQUENCE: 102
aggcccatga tctcagaagc                                               20

<210> SEQ ID NO 103
<211> LENGTH: 20
<212> TYPE: DNA
<213> ORGANISM: Homo sapiens

<400> SEQUENCE: 103
ggttgcagga gagacgaggt                                               20

<210> SEQ ID NO 104
<211> LENGTH: 19
<212> TYPE: DNA
<213> ORGANISM: Homo sapiens

<400> SEQUENCE: 104
aggcccttca ccctgtgac                                                19

<210> SEQ ID NO 105
<211> LENGTH: 20
<212> TYPE: DNA
<213> ORGANISM: Homo sapiens

<400> SEQUENCE: 105
atgacccctc cgatcctacc                                               20
```

```
<210> SEQ ID NO 106
<211> LENGTH: 20
<212> TYPE: DNA
<213> ORGANISM: Homo sapiens

<400> SEQUENCE: 106
taatcctgct ccacggcatt                                              20

<210> SEQ ID NO 107
<211> LENGTH: 20
<212> TYPE: DNA
<213> ORGANISM: Homo sapiens

<400> SEQUENCE: 107
ggaaaaagca gaggcaggtg                                              20

<210> SEQ ID NO 108
<211> LENGTH: 20
<212> TYPE: DNA
<213> ORGANISM: Homo sapiens

<400> SEQUENCE: 108
tggtctcaag aacccagcag                                              20

<210> SEQ ID NO 109
<211> LENGTH: 19
<212> TYPE: DNA
<213> ORGANISM: Homo sapiens

<400> SEQUENCE: 109
gacaccctcc ccctctcat                                               19

<210> SEQ ID NO 110
<211> LENGTH: 20
<212> TYPE: DNA
<213> ORGANISM: Homo sapiens

<400> SEQUENCE: 110
actatgacac cccggctgag                                              20

<210> SEQ ID NO 111
<211> LENGTH: 21
<212> TYPE: DNA
<213> ORGANISM: Homo sapiens

<400> SEQUENCE: 111
tgcttgatgt aaaaccctctg g                                           21

<210> SEQ ID NO 112
<211> LENGTH: 20
<212> TYPE: DNA
<213> ORGANISM: Homo sapiens

<400> SEQUENCE: 112
gcaatccaac agccatgaga                                              20

<210> SEQ ID NO 113
<211> LENGTH: 20
<212> TYPE: DNA
<213> ORGANISM: Homo sapiens

<400> SEQUENCE: 113
ggagcaaacc cctatgtcca                                              20
```

<210> SEQ ID NO 114
<211> LENGTH: 21
<212> TYPE: DNA
<213> ORGANISM: Homo sapiens

<400> SEQUENCE: 114
tcctccaact gtgtgttgtg g                                              21

<210> SEQ ID NO 115
<211> LENGTH: 19
<212> TYPE: DNA
<213> ORGANISM: Homo sapiens

<400> SEQUENCE: 115
tggggaccac tgctgagag                                                 19

<210> SEQ ID NO 116
<211> LENGTH: 20
<212> TYPE: DNA
<213> ORGANISM: Homo sapiens

<400> SEQUENCE: 116
tgcagccttc tctccttgaa                                                20

<210> SEQ ID NO 117
<211> LENGTH: 20
<212> TYPE: DNA
<213> ORGANISM: Homo sapiens

<400> SEQUENCE: 117
gcagagcagt gtggcagaag                                                20

<210> SEQ ID NO 118
<211> LENGTH: 19
<212> TYPE: DNA
<213> ORGANISM: Homo sapiens

<400> SEQUENCE: 118
acaggtggga agggactgg                                                 19

<210> SEQ ID NO 119
<211> LENGTH: 19
<212> TYPE: DNA
<213> ORGANISM: Homo sapiens

<400> SEQUENCE: 119
agtggggtgg gctgagaac                                                 19

<210> SEQ ID NO 120
<211> LENGTH: 20
<212> TYPE: DNA
<213> ORGANISM: Homo sapiens

<400> SEQUENCE: 120
tctctggggc agaaagagga                                                20

<210> SEQ ID NO 121
<211> LENGTH: 20
<212> TYPE: DNA
<213> ORGANISM: Homo sapiens

<400> SEQUENCE: 121
acccggccac actgtatttc                                              20

<210> SEQ ID NO 122
<211> LENGTH: 20
<212> TYPE: DNA
<213> ORGANISM: Homo sapiens

<400> SEQUENCE: 122
catcccaccc agctctcaac                                              20

<210> SEQ ID NO 123
<211> LENGTH: 20
<212> TYPE: DNA
<213> ORGANISM: Homo sapiens

<400> SEQUENCE: 123
agggcatagc cctattgagc                                              20

<210> SEQ ID NO 124
<211> LENGTH: 20
<212> TYPE: DNA
<213> ORGANISM: Homo sapiens

<400> SEQUENCE: 124
cccaggaaaa agccagagaa                                              20

<210> SEQ ID NO 125
<211> LENGTH: 20
<212> TYPE: DNA
<213> ORGANISM: Homo sapiens

<400> SEQUENCE: 125
caggtgtggg tggagtaggc                                              20

<210> SEQ ID NO 126
<211> LENGTH: 18
<212> TYPE: DNA
<213> ORGANISM: Homo sapiens

<400> SEQUENCE: 126
ctcaggcgcc atccactt                                                18

<210> SEQ ID NO 127
<211> LENGTH: 21
<212> TYPE: DNA
<213> ORGANISM: Homo sapiens

<400> SEQUENCE: 127
aagaagacga ccaacgtgag c                                            21

<210> SEQ ID NO 128
<211> LENGTH: 18
<212> TYPE: DNA
<213> ORGANISM: Homo sapiens

<400> SEQUENCE: 128
aggagctcca gggcacag                                                18

<210> SEQ ID NO 129
<211> LENGTH: 22
<212> TYPE: DNA
<213> ORGANISM: Homo sapiens

<400> SEQUENCE: 129
cctcctctgt aaagtgggtg ga        22

<210> SEQ ID NO 130
<211> LENGTH: 20
<212> TYPE: DNA
<213> ORGANISM: Homo sapiens

<400> SEQUENCE: 130
agagggcctc agtgcagagt        20

<210> SEQ ID NO 131
<211> LENGTH: 20
<212> TYPE: DNA
<213> ORGANISM: Homo sapiens

<400> SEQUENCE: 131
agatggggca gaactggatg        20

<210> SEQ ID NO 132
<211> LENGTH: 20
<212> TYPE: DNA
<213> ORGANISM: Homo sapiens

<400> SEQUENCE: 132
gggtcccaga ccaaatctga        20

<210> SEQ ID NO 133
<211> LENGTH: 20
<212> TYPE: DNA
<213> ORGANISM: Homo sapiens

<400> SEQUENCE: 133
aggtgctccc ttcacagcat        20

<210> SEQ ID NO 134
<211> LENGTH: 22
<212> TYPE: DNA
<213> ORGANISM: Homo sapiens

<400> SEQUENCE: 134
ttcagggact acagctgagg aa        22

<210> SEQ ID NO 135
<211> LENGTH: 21
<212> TYPE: DNA
<213> ORGANISM: Homo sapiens

<400> SEQUENCE: 135
gccgtatgtt atctgggagg t        21

<210> SEQ ID NO 136
<211> LENGTH: 21
<212> TYPE: DNA
<213> ORGANISM: Homo sapiens

<400> SEQUENCE: 136
tgggcccatt acactttaag a        21

<210> SEQ ID NO 137
<211> LENGTH: 20
<212> TYPE: DNA
<213> ORGANISM: Homo sapiens

```
<400> SEQUENCE: 137
ttccatcacc ggtacctcct                                              20

<210> SEQ ID NO 138
<211> LENGTH: 23
<212> TYPE: DNA
<213> ORGANISM: Homo sapiens

<400> SEQUENCE: 138
ccataaatca aaaatgcacc aca                                          23

<210> SEQ ID NO 139
<211> LENGTH: 23
<212> TYPE: DNA
<213> ORGANISM: Homo sapiens

<400> SEQUENCE: 139
gagtggtctt aggaagatga tgc                                          23

<210> SEQ ID NO 140
<211> LENGTH: 22
<212> TYPE: DNA
<213> ORGANISM: Homo sapiens

<400> SEQUENCE: 140
aaagtcatgg gctgcaatac aa                                           22

<210> SEQ ID NO 141
<211> LENGTH: 18
<212> TYPE: DNA
<213> ORGANISM: Homo sapiens

<400> SEQUENCE: 141
atggtcccca ctgcttgg                                                18

<210> SEQ ID NO 142
<211> LENGTH: 20
<212> TYPE: DNA
<213> ORGANISM: Homo sapiens

<400> SEQUENCE: 142
aggagctcac ctcaccctgt                                              20

<210> SEQ ID NO 143
<211> LENGTH: 20
<212> TYPE: DNA
<213> ORGANISM: Homo sapiens

<400> SEQUENCE: 143
ccttgcgtct ctccacacat                                              20

<210> SEQ ID NO 144
<211> LENGTH: 20
<212> TYPE: DNA
<213> ORGANISM: Homo sapiens

<400> SEQUENCE: 144
tggcaacggg taacaatgaa                                              20

<210> SEQ ID NO 145
<211> LENGTH: 20
<212> TYPE: DNA
<213> ORGANISM: Homo sapiens
```

```
<400> SEQUENCE: 145
ggctgaggta agctgcttcg                                            20

<210> SEQ ID NO 146
<211> LENGTH: 23
<212> TYPE: DNA
<213> ORGANISM: Homo sapiens

<400> SEQUENCE: 146
aaaaagaagt atcttgcccc ttt                                        23

<210> SEQ ID NO 147
<211> LENGTH: 21
<212> TYPE: DNA
<213> ORGANISM: Homo sapiens

<400> SEQUENCE: 147 aaccctctt agggctctgt g                                           21

<210> SEQ ID NO 148
<211> LENGTH: 19
<212> TYPE: DNA
<213> ORGANISM: Homo sapiens

<400> SEQUENCE: 148
caggaggatg gcaggcttc                                             19

<210> SEQ ID NO 149
<211> LENGTH: 23
<212> TYPE: DNA
<213> ORGANISM: Homo sapiens

<400> SEQUENCE: 149
cgtagagagc ttcaggacct gtg                                        23

<210> SEQ ID NO 150
<211> LENGTH: 20
<212> TYPE: DNA
<213> ORGANISM: Homo sapiens

<400> SEQUENCE: 150
ttccgagaag ttttgcctga                                            20

<210> SEQ ID NO 151
<211> LENGTH: 22
<212> TYPE: DNA
<213> ORGANISM: Homo sapiens

<400> SEQUENCE: 151
tgtgaacatc attcaaggcg ta                                         22

<210> SEQ ID NO 152
<211> LENGTH: 25
<212> TYPE: DNA
<213> ORGANISM: Homo sapiens

<400> SEQUENCE: 152
aaaatgtgtg atatccctag acagg                                      25

<210> SEQ ID NO 153
<211> LENGTH: 20
<212> TYPE: DNA
```

<213> ORGANISM: Homo sapiens

<400> SEQUENCE: 153
tccacatttc agcaacagca                                              20

<210> SEQ ID NO 154
<211> LENGTH: 21
<212> TYPE: DNA
<213> ORGANISM: Homo sapiens

<400> SEQUENCE: 154
ggctgcttcc tgagacacag t                                            21

<210> SEQ ID NO 155
<211> LENGTH: 20
<212> TYPE: DNA
<213> ORGANISM: Homo sapiens

<400> SEQUENCE: 155
tatctaccgg tgcgggactt                                              20

<210> SEQ ID NO 156
<211> LENGTH: 20
<212> TYPE: DNA
<213> ORGANISM: Homo sapiens

<400> SEQUENCE: 156
aggtgtagcc tcccctcaca                                              20

<210> SEQ ID NO 157
<211> LENGTH: 20
<212> TYPE: DNA
<213> ORGANISM: Homo sapiens

<400> SEQUENCE: 157
aggctggtgg tgtctctgtg                                              20

<210> SEQ ID NO 158
<211> LENGTH: 20
<212> TYPE: DNA
<213> ORGANISM: Homo sapiens

<400> SEQUENCE: 158
caagctgcca accctcagtt                                              20

<210> SEQ ID NO 159
<211> LENGTH: 24
<212> TYPE: DNA
<213> ORGANISM: Homo sapiens

<400> SEQUENCE: 159
tggatttcaa atactgaagc cact                                         24

<210> SEQ ID NO 160
<211> LENGTH: 22
<212> TYPE: DNA
<213> ORGANISM: Homo sapiens

<400> SEQUENCE: 160
tggaattggt ggtgttgaat tt                                           22

<210> SEQ ID NO 161
<211> LENGTH: 23

<212> TYPE: DNA
<213> ORGANISM: Homo sapiens

<400> SEQUENCE: 161
gggcttcata tgttctgaca tgg                                    23

<210> SEQ ID NO 162
<211> LENGTH: 19
<212> TYPE: DNA
<213> ORGANISM: Homo sapiens

<400> SEQUENCE: 162
cagaggacca cgccatagg                                         19

<210> SEQ ID NO 163
<211> LENGTH: 20
<212> TYPE: DNA
<213> ORGANISM: Homo sapiens

<400> SEQUENCE: 163
ccgagattta gccaccagga                                        20

<210> SEQ ID NO 164
<211> LENGTH: 20
<212> TYPE: DNA
<213> ORGANISM: Homo sapiens

<400> SEQUENCE: 164
cctgggaagc aaacaacaca                                        20

<210> SEQ ID NO 165
<211> LENGTH: 20
<212> TYPE: DNA
<213> ORGANISM: Homo sapiens

<400> SEQUENCE: 165
aggtccccag tctcctctcc                                        20

<210> SEQ ID NO 166
<211> LENGTH: 20
<212> TYPE: DNA
<213> ORGANISM: Homo sapiens

<400> SEQUENCE: 166
agacccatgc agccatccta                                        20

<210> SEQ ID NO 167
<211> LENGTH: 19
<212> TYPE: DNA
<213> ORGANISM: Homo sapiens

<400> SEQUENCE: 167
cgtgaaccac cgagcttgt                                         19

<210> SEQ ID NO 168
<211> LENGTH: 19
<212> TYPE: DNA
<213> ORGANISM: Homo sapiens

<400> SEQUENCE: 168
agaggggcag aaggggaac                                         19

<210> SEQ ID NO 169

```
<211> LENGTH: 20
<212> TYPE: DNA
<213> ORGANISM: Homo sapiens

<400> SEQUENCE: 169 ggtggggtg aggagcttag                                              20

<210> SEQ ID NO 170
<211> LENGTH: 20
<212> TYPE: DNA
<213> ORGANISM: Homo sapiens

<400> SEQUENCE: 170
tcgtttaagc cacccagtca                                             20

<210> SEQ ID NO 171
<211> LENGTH: 21
<212> TYPE: DNA
<213> ORGANISM: Homo sapiens

<400> SEQUENCE: 171
tgcaaataag gaaagcaaac a                                           21

<210> SEQ ID NO 172
<211> LENGTH: 21
<212> TYPE: DNA
<213> ORGANISM: Homo sapiens

<400> SEQUENCE: 172
tcctgacatg gtcttccaac c                                           21

<210> SEQ ID NO 173
<211> LENGTH: 22
<212> TYPE: DNA
<213> ORGANISM: Homo sapiens

<400> SEQUENCE: 173
cagcatcttc acacacctct ga                                          22

<210> SEQ ID NO 174
<211> LENGTH: 20
<212> TYPE: DNA
<213> ORGANISM: Homo sapiens

<400> SEQUENCE: 174
gctggctcta atcccacct                                              20

<210> SEQ ID NO 175
<211> LENGTH: 20
<212> TYPE: DNA
<213> ORGANISM: Homo sapiens

<400> SEQUENCE: 175
ctaatccggg aagttgttgc                                             20

<210> SEQ ID NO 176
<211> LENGTH: 24
<212> TYPE: DNA
<213> ORGANISM: Homo sapiens

<400> SEQUENCE: 176
ttctgtatca gcagcttctc tgtg                                        24
```

```
<210> SEQ ID NO 177
<211> LENGTH: 19
<212> TYPE: DNA
<213> ORGANISM: Homo sapiens

<400> SEQUENCE: 177
caagtgccac catggatca                                               19

<210> SEQ ID NO 178
<211> LENGTH: 21
<212> TYPE: DNA
<213> ORGANISM: Homo sapiens

<400> SEQUENCE: 178
ggcagtgtac tgacccttg a                                             21

<210> SEQ ID NO 179
<211> LENGTH: 24
<212> TYPE: DNA
<213> ORGANISM: Homo sapiens

<400> SEQUENCE: 179
gcacaagtta ttaagagccc aagg                                         24

<210> SEQ ID NO 180
<211> LENGTH: 20
<212> TYPE: DNA
<213> ORGANISM: Homo sapiens

<400> SEQUENCE: 180
agcatactgg cctcacacca                                              20

<210> SEQ ID NO 181
<211> LENGTH: 22
<212> TYPE: DNA
<213> ORGANISM: Homo sapiens

<400> SEQUENCE: 181
gcacatgggc agtgttgtat tt                                           22

<210> SEQ ID NO 182
<211> LENGTH: 20
<212> TYPE: DNA
<213> ORGANISM: Homo sapiens

<400> SEQUENCE: 182
gagccccaca cagatttcct                                              20

<210> SEQ ID NO 183
<211> LENGTH: 20
<212> TYPE: DNA
<213> ORGANISM: Homo sapiens

<400> SEQUENCE: 183
atgggacgga gaagtggttg                                              20

<210> SEQ ID NO 184
<211> LENGTH: 20
<212> TYPE: DNA
<213> ORGANISM: Homo sapiens

<400> SEQUENCE: 184
tccctgtatc agggctcgtc                                              20
```

```
<210> SEQ ID NO 185
<211> LENGTH: 20
<212> TYPE: DNA
<213> ORGANISM: Homo sapiens

<400> SEQUENCE: 185
ttcctacgca gcacaccaat                                              20

<210> SEQ ID NO 186
<211> LENGTH: 20
<212> TYPE: DNA
<213> ORGANISM: Homo sapiens

<400> SEQUENCE: 186
gcaggcacta aaccctttcc                                              20

<210> SEQ ID NO 187
<211> LENGTH: 20
<212> TYPE: DNA
<213> ORGANISM: Homo sapiens

<400> SEQUENCE: 187
gcacgcatgt gaccaatttc                                              20

<210> SEQ ID NO 188
<211> LENGTH: 20
<212> TYPE: DNA
<213> ORGANISM: Homo sapiens

<400> SEQUENCE: 188
agccctgaga gggaggtagg                                              20

<210> SEQ ID NO 189
<211> LENGTH: 19
<212> TYPE: DNA
<213> ORGANISM: Homo sapiens

<400> SEQUENCE: 189
cacacaccac ccctctgct                                               19

<210> SEQ ID NO 190
<211> LENGTH: 21
<212> TYPE: DNA
<213> ORGANISM: Homo sapiens

<400> SEQUENCE: 190
aaagatttgg ggtgagggct a                                            21

<210> SEQ ID NO 191
<211> LENGTH: 20
<212> TYPE: DNA
<213> ORGANISM: Homo sapiens

<400> SEQUENCE: 191
ctgaaagctc agggataggg                                              20

<210> SEQ ID NO 192
<211> LENGTH: 18
<212> TYPE: DNA
<213> ORGANISM: Homo sapiens

<400> SEQUENCE: 192
ctggccaagc tgcacaga                                                18
```

```
<210> SEQ ID NO 193
<211> LENGTH: 20
<212> TYPE: DNA
<213> ORGANISM: Homo sapiens

<400> SEQUENCE: 193
tgcagccaac gatttgaaag                                               20

<210> SEQ ID NO 194
<211> LENGTH: 20
<212> TYPE: DNA
<213> ORGANISM: Homo sapiens

<400> SEQUENCE: 194
ggaaagcccc aagtctgaaa                                               20

<210> SEQ ID NO 195
<211> LENGTH: 21
<212> TYPE: DNA
<213> ORGANISM: Homo sapiens

<400> SEQUENCE: 195
tcatcatgag atccccacac t                                             21

<210> SEQ ID NO 196
<211> LENGTH: 20
<212> TYPE: DNA
<213> ORGANISM: Homo sapiens

<400> SEQUENCE: 196
gcatttcccc ctgaaggagt                                               20

<210> SEQ ID NO 197
<211> LENGTH: 23
<212> TYPE: DNA
<213> ORGANISM: Homo sapiens

<400> SEQUENCE: 197
tggattcagt aaccaggaag tga                                           23

<210> SEQ ID NO 198
<211> LENGTH: 20
<212> TYPE: DNA
<213> ORGANISM: Homo sapiens

<400> SEQUENCE: 198
cccattccac caggatgatt                                               20

<210> SEQ ID NO 199
<211> LENGTH: 20
<212> TYPE: DNA
<213> ORGANISM: Homo sapiens

<400> SEQUENCE: 199
gtttccagct gcccactacc                                               20

<210> SEQ ID NO 200
<211> LENGTH: 20
<212> TYPE: DNA
<213> ORGANISM: Homo sapiens

<400> SEQUENCE: 200
```
gctcgaaacc acatgttcca                                            20

<210> SEQ ID NO 201
<211> LENGTH: 20
<212> TYPE: DNA
<213> ORGANISM: Homo sapiens

<400> SEQUENCE: 201
ctggatttgg ggttctctgc                                            20

<210> SEQ ID NO 202
<211> LENGTH: 22
<212> TYPE: DNA
<213> ORGANISM: Homo sapiens

<400> SEQUENCE: 202
cgggaacagc tagcagattt tt                                         22

<210> SEQ ID NO 203
<211> LENGTH: 20
<212> TYPE: DNA
<213> ORGANISM: Homo sapiens

<400> SEQUENCE: 203
gggaattttg gagggggaact                                           20

<210> SEQ ID NO 204
<211> LENGTH: 20
<212> TYPE: DNA
<213> ORGANISM: Homo sapiens

<400> SEQUENCE: 204
gcttcagtca ccacagagca                                            20

<210> SEQ ID NO 205
<211> LENGTH: 23
<212> TYPE: DNA
<213> ORGANISM: Homo sapiens

<400> SEQUENCE: 205
tgagtctacc cagcaatcat ttg                                        23

<210> SEQ ID NO 206
<211> LENGTH: 20
<212> TYPE: DNA
<213> ORGANISM: Homo sapiens

<400> SEQUENCE: 206
ttcccgagag ctacaggaca                                            20

<210> SEQ ID NO 207
<211> LENGTH: 21
<212> TYPE: DNA
<213> ORGANISM: Homo sapiens

<400> SEQUENCE: 207
ggtaacaagg gtacccacga a                                          21

<210> SEQ ID NO 208
<211> LENGTH: 20
<212> TYPE: DNA
<213> ORGANISM: Homo sapiens

<400> SEQUENCE: 208

| | |
|---|---|
| gtttgagggg ctgagtgtgg | 20 |

<210> SEQ ID NO 209
<211> LENGTH: 20
<212> TYPE: DNA
<213> ORGANISM: Homo sapiens

<400> SEQUENCE: 209

| | |
|---|---|
| cctcaccctt agggcttgtg | 20 |

<210> SEQ ID NO 210
<211> LENGTH: 20
<212> TYPE: DNA
<213> ORGANISM: Homo sapiens

<400> SEQUENCE: 210

| | |
|---|---|
| agcccaggtc atgccttaga | 20 |

<210> SEQ ID NO 211
<211> LENGTH: 20
<212> TYPE: DNA
<213> ORGANISM: Homo sapiens

<400> SEQUENCE: 211

| | |
|---|---|
| gggtagcttg ggagcaaaga | 20 |

<210> SEQ ID NO 212
<211> LENGTH: 20
<212> TYPE: DNA
<213> ORGANISM: Homo sapiens

<400> SEQUENCE: 212

| | |
|---|---|
| ccaaacccca gagagcagac | 20 |

<210> SEQ ID NO 213
<211> LENGTH: 22
<212> TYPE: DNA
<213> ORGANISM: Homo sapiens

<400> SEQUENCE: 213

| | |
|---|---|
| catttcccct aatccttttc ca | 22 |

<210> SEQ ID NO 214
<211> LENGTH: 22
<212> TYPE: DNA
<213> ORGANISM: Homo sapiens

<400> SEQUENCE: 214

| | |
|---|---|
| gtgatcccag atttaggcct tc | 22 |

<210> SEQ ID NO 215
<211> LENGTH: 22
<212> TYPE: DNA
<213> ORGANISM: Homo sapiens

<400> SEQUENCE: 215

| | |
|---|---|
| gcctctcgtg gtttgttttg tc | 22 |

<210> SEQ ID NO 216
<211> LENGTH: 22
<212> TYPE: DNA
<213> ORGANISM: Homo sapiens

```
<400> SEQUENCE: 216
cccagggtag ggtccaataa tc                                          22

<210> SEQ ID NO 217
<211> LENGTH: 22
<212> TYPE: DNA
<213> ORGANISM: Homo sapiens

<400> SEQUENCE: 217
cttcctggtg gaggtgactg at                                          22

<210> SEQ ID NO 218
<211> LENGTH: 22
<212> TYPE: DNA
<213> ORGANISM: Homo sapiens

<400> SEQUENCE: 218
caggcatagt gtgtgatggt ca                                          22

<210> SEQ ID NO 219
<211> LENGTH: 23
<212> TYPE: DNA
<213> ORGANISM: Homo sapiens

<400> SEQUENCE: 219
tcacgataca cattctcaga tcc                                         23

<210> SEQ ID NO 220
<211> LENGTH: 22
<212> TYPE: DNA
<213> ORGANISM: Homo sapiens

<400> SEQUENCE: 220
gaagatctcc cagaggagga tg                                          22

<210> SEQ ID NO 221
<211> LENGTH: 21
<212> TYPE: DNA
<213> ORGANISM: Homo sapiens

<400> SEQUENCE: 221
cgtaacgtgc tgttgaccaa t                                           21

<210> SEQ ID NO 222
<211> LENGTH: 22
<212> TYPE: DNA
<213> ORGANISM: Homo sapiens

<400> SEQUENCE: 222
aaacgaggga agagccagaa ag                                          22

<210> SEQ ID NO 223
<211> LENGTH: 22
<212> TYPE: DNA
<213> ORGANISM: Homo sapiens

<400> SEQUENCE: 223
tggggagcac aataaaagaa ga                                          22

<210> SEQ ID NO 224
<211> LENGTH: 22
<212> TYPE: DNA
<213> ORGANISM: Homo sapiens
```

<400> SEQUENCE: 224
actcttggct cctggattct tg                                              22

<210> SEQ ID NO 225
<211> LENGTH: 22
<212> TYPE: DNA
<213> ORGANISM: Homo sapiens

<400> SEQUENCE: 225
ggaagtcagt gtgcagggaa ta                                              22

<210> SEQ ID NO 226
<211> LENGTH: 22
<212> TYPE: DNA
<213> ORGANISM: Homo sapiens

<400> SEQUENCE: 226
ttttagcaga aataggcaag ca                                              22

<210> SEQ ID NO 227
<211> LENGTH: 24
<212> TYPE: DNA
<213> ORGANISM: Homo sapiens

<400> SEQUENCE: 227
tggtaatcct aaacacaatg caga                                            24

<210> SEQ ID NO 228
<211> LENGTH: 22
<212> TYPE: DNA
<213> ORGANISM: Homo sapiens

<400> SEQUENCE: 228
ctgggcaaca cagtgagatc ct                                              22

<210> SEQ ID NO 229
<211> LENGTH: 23
<212> TYPE: DNA
<213> ORGANISM: Homo sapiens

<400> SEQUENCE: 229
tcacaaattt ctttgctgtg tcc                                             23

<210> SEQ ID NO 230
<211> LENGTH: 23
<212> TYPE: DNA
<213> ORGANISM: Homo sapiens

<400> SEQUENCE: 230
catggaactc cagattagcc tgt                                             23

<210> SEQ ID NO 231
<211> LENGTH: 22
<212> TYPE: DNA
<213> ORGANISM: Homo sapiens

<400> SEQUENCE: 231
gattgttgca gatcgtggac at                                              22

<210> SEQ ID NO 232
<211> LENGTH: 22
<212> TYPE: DNA

<213> ORGANISM: Homo sapiens

<400> SEQUENCE: 232
cgcttaaatc ttcccattcc ag                                    22

<210> SEQ ID NO 233
<211> LENGTH: 22
<212> TYPE: DNA
<213> ORGANISM: Homo sapiens

<400> SEQUENCE: 233
ctccatggca ccatcattaa ca                                    22

<210> SEQ ID NO 234
<211> LENGTH: 22
<212> TYPE: DNA
<213> ORGANISM: Homo sapiens

<400> SEQUENCE: 234
ctcaggacac aagtgctctg ct                                    22

<210> SEQ ID NO 235
<211> LENGTH: 24
<212> TYPE: DNA
<213> ORGANISM: Homo sapiens

<400> SEQUENCE: 235
gcagttcatg gttcatcttc tttt                                  24

<210> SEQ ID NO 236
<211> LENGTH: 22
<212> TYPE: DNA
<213> ORGANISM: Homo sapiens

<400> SEQUENCE: 236
caaaatagcc caccctggat ta                                    22

<210> SEQ ID NO 237
<211> LENGTH: 21
<212> TYPE: DNA
<213> ORGANISM: Homo sapiens

<400> SEQUENCE: 237
ctttctgcat tgcccaagat g                                     21

<210> SEQ ID NO 238
<211> LENGTH: 22
<212> TYPE: DNA
<213> ORGANISM: Homo sapiens

<400> SEQUENCE: 238
caaggtctca gtgagtggtg ga                                    22

<210> SEQ ID NO 239
<211> LENGTH: 23
<212> TYPE: DNA
<213> ORGANISM: Homo sapiens

<400> SEQUENCE: 239
gagaagggtc tttctgactc tgc                                   23

<210> SEQ ID NO 240
<211> LENGTH: 22

<212> TYPE: DNA
<213> ORGANISM: Homo sapiens

<400> SEQUENCE: 240
caggtgtttc tcctgtgagg tg                                    22

<210> SEQ ID NO 241
<211> LENGTH: 22
<212> TYPE: DNA
<213> ORGANISM: Homo sapiens

<400> SEQUENCE: 241
cacattgcgg cctagaatgt ta                                    22

<210> SEQ ID NO 242
<211> LENGTH: 20
<212> TYPE: DNA
<213> ORGANISM: Homo sapiens

<400> SEQUENCE: 242
accccgtcac aaccttcagt                                       20

<210> SEQ ID NO 243
<211> LENGTH: 22
<212> TYPE: DNA
<213> ORGANISM: Homo sapiens

<400> SEQUENCE: 243
gccgtagccc caaagtgtac ta                                    22

<210> SEQ ID NO 244
<211> LENGTH: 22
<212> TYPE: DNA
<213> ORGANISM: Homo sapiens

<400> SEQUENCE: 244
tcagctcaaa cctgtgattt cc                                    22

<210> SEQ ID NO 245
<211> LENGTH: 24
<212> TYPE: DNA
<213> ORGANISM: Homo sapiens

<400> SEQUENCE: 245
ctcactctcc ataaatgcta cgaa                                  24

<210> SEQ ID NO 246
<211> LENGTH: 22
<212> TYPE: DNA
<213> ORGANISM: Homo sapiens

<400> SEQUENCE: 246
gacttaacgt gtcccctttt gc                                    22

<210> SEQ ID NO 247
<211> LENGTH: 22
<212> TYPE: DNA
<213> ORGANISM: Homo sapiens

<400> SEQUENCE: 247
gcctcttcgg ggtaatcaga ta                                    22

<210> SEQ ID NO 248

```
<211> LENGTH: 22
<212> TYPE: DNA
<213> ORGANISM: Homo sapiens

<400> SEQUENCE: 248
gaagtctgtg gtttagcgga ca                                              22

<210> SEQ ID NO 249
<211> LENGTH: 22
<212> TYPE: DNA
<213> ORGANISM: Homo sapiens

<400> SEQUENCE: 249
atcttttgcc tggaggaact tt                                              22

<210> SEQ ID NO 250
<211> LENGTH: 22
<212> TYPE: DNA
<213> ORGANISM: Homo sapiens

<400> SEQUENCE: 250
cagggtaaat tcatcccatt ga                                              22

<210> SEQ ID NO 251
<211> LENGTH: 22
<212> TYPE: DNA
<213> ORGANISM: Homo sapiens

<400> SEQUENCE: 251
cagcagccag cacaactact tt                                              22

<210> SEQ ID NO 252
<211> LENGTH: 23
<212> TYPE: DNA
<213> ORGANISM: Homo sapiens

<400> SEQUENCE: 252
ttggctagat gaaccattga tga                                             23

<210> SEQ ID NO 253
<211> LENGTH: 24
<212> TYPE: DNA
<213> ORGANISM: Homo sapiens

<400> SEQUENCE: 253
tgaatgaagc tcctgtgttt actc                                            24

<210> SEQ ID NO 254
<211> LENGTH: 22
<212> TYPE: DNA
<213> ORGANISM: Homo sapiens

<400> SEQUENCE: 254
atgttcatcg caggctaatg tg                                              22

<210> SEQ ID NO 255
<211> LENGTH: 24
<212> TYPE: DNA
<213> ORGANISM: Homo sapiens

<400> SEQUENCE: 255
aaaacaggga gaacttctaa gcaa                                            24
```

```
<210> SEQ ID NO 256
<211> LENGTH: 21
<212> TYPE: DNA
<213> ORGANISM: Homo sapiens

<400> SEQUENCE: 256
catggcagag tcattcccac t                                              21

<210> SEQ ID NO 257
<211> LENGTH: 22
<212> TYPE: DNA
<213> ORGANISM: Homo sapiens

<400> SEQUENCE: 257
caatgctaga acaacgcctg tc                                             22

<210> SEQ ID NO 258
<211> LENGTH: 22
<212> TYPE: DNA
<213> ORGANISM: Homo sapiens

<400> SEQUENCE: 258
tccctccact gaggacaaag tt                                             22

<210> SEQ ID NO 259
<211> LENGTH: 22
<212> TYPE: DNA
<213> ORGANISM: Homo sapiens

<400> SEQUENCE: 259
gggagagctt gagaaagttg ga                                             22

<210> SEQ ID NO 260
<211> LENGTH: 22
<212> TYPE: DNA
<213> ORGANISM: Homo sapiens

<400> SEQUENCE: 260
atttcctcgg atggatgtac ca                                             22

<210> SEQ ID NO 261
<211> LENGTH: 22
<212> TYPE: DNA
<213> ORGANISM: Homo sapiens

<400> SEQUENCE: 261
tcagagcctg tgtttctacc aa                                             22

<210> SEQ ID NO 262
<211> LENGTH: 22
<212> TYPE: DNA
<213> ORGANISM: Homo sapiens

<400> SEQUENCE: 262
tggtctcaca ggaccactga tt                                             22

<210> SEQ ID NO 263
<211> LENGTH: 24
<212> TYPE: DNA
<213> ORGANISM: Homo sapiens

<400> SEQUENCE: 263
aaataatcag tgtgattcgt ggag                                           24
```

```
<210> SEQ ID NO 264
<211> LENGTH: 22
<212> TYPE: DNA
<213> ORGANISM: Homo sapiens

<400> SEQUENCE: 264
gaggccagtg ctgtctctaa gg                                          22

<210> SEQ ID NO 265
<211> LENGTH: 21
<212> TYPE: DNA
<213> ORGANISM: Homo sapiens

<400> SEQUENCE: 265
acttcacagc cctgcgtaaa c                                           21

<210> SEQ ID NO 266
<211> LENGTH: 21
<212> TYPE: DNA
<213> ORGANISM: Homo sapiens

<400> SEQUENCE: 266
atgggacagg cactgatttg t                                           21

<210> SEQ ID NO 267
<211> LENGTH: 22
<212> TYPE: DNA
<213> ORGANISM: Homo sapiens

<400> SEQUENCE: 267
gcagcgggtt acatcttctt tc                                          22

<210> SEQ ID NO 268
<211> LENGTH: 22
<212> TYPE: DNA
<213> ORGANISM: Homo sapiens

<400> SEQUENCE: 268
cagctctggc tcacactacc ag                                          22

<210> SEQ ID NO 269
<211> LENGTH: 22
<212> TYPE: DNA
<213> ORGANISM: Homo sapiens

<400> SEQUENCE: 269
cctgaactcc gtcagactga aa                                          22

<210> SEQ ID NO 270
<211> LENGTH: 20
<212> TYPE: DNA
<213> ORGANISM: Homo sapiens

<400> SEQUENCE: 270
gcagctggac tcgatttcct                                             20

<210> SEQ ID NO 271
<211> LENGTH: 23
<212> TYPE: DNA
<213> ORGANISM: Homo sapiens

<400> SEQUENCE: 271
ccttacagca atcctgtgaa aca                                         23
```

-continued

<210> SEQ ID NO 272
<211> LENGTH: 22
<212> TYPE: DNA
<213> ORGANISM: Homo sapiens

<400> SEQUENCE: 272
tgcccaatga gtcaagaagt gt                                    22

<210> SEQ ID NO 273
<211> LENGTH: 22
<212> TYPE: DNA
<213> ORGANISM: Homo sapiens

<400> SEQUENCE: 273
atgtacagtg ctggcatggt ct                                    22

<210> SEQ ID NO 274
<211> LENGTH: 22
<212> TYPE: DNA
<213> ORGANISM: Homo sapiens

<400> SEQUENCE: 274
cactcacgga tgctgcttag tt                                    22

<210> SEQ ID NO 275
<211> LENGTH: 21
<212> TYPE: DNA
<213> ORGANISM: Homo sapiens

<400> SEQUENCE: 275
taaggcaccc acatcatgtc a                                     21

<210> SEQ ID NO 276
<211> LENGTH: 24
<212> TYPE: DNA
<213> ORGANISM: Homo sapiens

<400> SEQUENCE: 276
tggacctaaa aggcttacaa tcaa                                  24

<210> SEQ ID NO 277
<211> LENGTH: 24
<212> TYPE: DNA
<213> ORGANISM: Homo sapiens

<400> SEQUENCE: 277
gccttttagg tccactatgg aatg                                  24

<210> SEQ ID NO 278
<211> LENGTH: 22
<212> TYPE: DNA
<213> ORGANISM: Homo sapiens

<400> SEQUENCE: 278
ccaggcgatg ctactactgg tc                                    22

<210> SEQ ID NO 279
<211> LENGTH: 22
<212> TYPE: DNA
<213> ORGANISM: Homo sapiens

<400> SEQUENCE: 279

```
tcatagcaca cctccctcac tg                                              22

<210> SEQ ID NO 280
<211> LENGTH: 22
<212> TYPE: DNA
<213> ORGANISM: Homo sapiens

<400> SEQUENCE: 280
acacaacaaa gagcttgtgc ag                                              22

<210> SEQ ID NO 281
<211> LENGTH: 24
<212> TYPE: DNA
<213> ORGANISM: Homo sapiens

<400> SEQUENCE: 281
ccattacttt gagaaggaca ggaa                                            24

<210> SEQ ID NO 282
<211> LENGTH: 22
<212> TYPE: DNA
<213> ORGANISM: Homo sapiens

<400> SEQUENCE: 282
tattcttgct ggatgcgttt ct                                              22

<210> SEQ ID NO 283
<211> LENGTH: 21
<212> TYPE: DNA
<213> ORGANISM: Homo sapiens

<400> SEQUENCE: 283
aggagggcag aggactagct g                                               21

<210> SEQ ID NO 284
<211> LENGTH: 20
<212> TYPE: DNA
<213> ORGANISM: Homo sapiens

<400> SEQUENCE: 284
ggcaatgtga atgtgcactg                                                 20

<210> SEQ ID NO 285
<211> LENGTH: 20
<212> TYPE: DNA
<213> ORGANISM: Homo sapiens

<400> SEQUENCE: 285
cttgaacctg ggaggtggag                                                 20

<210> SEQ ID NO 286
<211> LENGTH: 22
<212> TYPE: DNA
<213> ORGANISM: Homo sapiens

<400> SEQUENCE: 286
atcagggtgg gaggagtaaa ga                                              22

<210> SEQ ID NO 287
<211> LENGTH: 22
<212> TYPE: DNA
<213> ORGANISM: Homo sapiens

<400> SEQUENCE: 287
```

```
cccacttacc tctcacctgt gc                                        22

<210> SEQ ID NO 288
<211> LENGTH: 22
<212> TYPE: DNA
<213> ORGANISM: Homo sapiens

<400> SEQUENCE: 288
gtgaacttcc ggtaggaaat gg                                        22

<210> SEQ ID NO 289
<211> LENGTH: 20
<212> TYPE: DNA
<213> ORGANISM: Homo sapiens

<400> SEQUENCE: 289
aggggacctc aagggagaag                                           20

<210> SEQ ID NO 290
<211> LENGTH: 22
<212> TYPE: DNA
<213> ORGANISM: Homo sapiens

<400> SEQUENCE: 290
agatcatgcc agtgaactcc ag                                        22

<210> SEQ ID NO 291
<211> LENGTH: 22
<212> TYPE: DNA
<213> ORGANISM: Homo sapiens

<400> SEQUENCE: 291
ggaccaggaa agtccttgct tt                                        22

<210> SEQ ID NO 292
<211> LENGTH: 22
<212> TYPE: DNA
<213> ORGANISM: Homo sapiens

<400> SEQUENCE: 292
ggtggggaac attaaactga gg                                        22

<210> SEQ ID NO 293
<211> LENGTH: 22
<212> TYPE: DNA
<213> ORGANISM: Homo sapiens

<400> SEQUENCE: 293
gcttcaggtt gttttgttgc ag                                        22

<210> SEQ ID NO 294
<211> LENGTH: 22
<212> TYPE: DNA
<213> ORGANISM: Homo sapiens

<400> SEQUENCE: 294
acccttgctt gagggaaata tg                                        22

<210> SEQ ID NO 295
<211> LENGTH: 22
<212> TYPE: DNA
<213> ORGANISM: Homo sapiens
```

```
<400> SEQUENCE: 295
cccagctcct agggtacagt ct                                              22

<210> SEQ ID NO 296
<211> LENGTH: 23
<212> TYPE: DNA
<213> ORGANISM: Homo sapiens

<400> SEQUENCE: 296
cagtcagctt caaaatccct ctt                                             23

<210> SEQ ID NO 297
<211> LENGTH: 24
<212> TYPE: DNA
<213> ORGANISM: Homo sapiens

<400> SEQUENCE: 297
tcacttccct gtgagtaaag aaaa                                            24

<210> SEQ ID NO 298
<211> LENGTH: 23
<212> TYPE: DNA
<213> ORGANISM: Homo sapiens

<400> SEQUENCE: 298
ggccatttaa ttcttgtcct tga                                             23

<210> SEQ ID NO 299
<211> LENGTH: 23
<212> TYPE: DNA
<213> ORGANISM: Homo sapiens

<400> SEQUENCE: 299
tggacttgtg caaactcaaa ctg                                             23

<210> SEQ ID NO 300
<211> LENGTH: 23
<212> TYPE: DNA
<213> ORGANISM: Homo sapiens

<400> SEQUENCE: 300
tcccaatata gggcagtcat gtt                                             23

<210> SEQ ID NO 301
<211> LENGTH: 23
<212> TYPE: DNA
<213> ORGANISM: Homo sapiens

<400> SEQUENCE: 301
tctcaatcag ttgagttgcc ttg                                             23

<210> SEQ ID NO 302
<211> LENGTH: 22
<212> TYPE: DNA
<213> ORGANISM: Homo sapiens

<400> SEQUENCE: 302
agctgtgcaa gtgtggaaac at                                              22

<210> SEQ ID NO 303
<211> LENGTH: 22
<212> TYPE: DNA
<213> ORGANISM: Homo sapiens
```

```
<400> SEQUENCE: 303
gctgtgaggg taaatgagac ca                                              22

<210> SEQ ID NO 304
<211> LENGTH: 22
<212> TYPE: DNA
<213> ORGANISM: Homo sapiens

<400> SEQUENCE: 304
gtctcctggt gagtgactgt gg                                              22

<210> SEQ ID NO 305
<211> LENGTH: 20
<212> TYPE: DNA
<213> ORGANISM: Homo sapiens

<400> SEQUENCE: 305
ccttccttcg tctccacagc                                                 20

<210> SEQ ID NO 306
<211> LENGTH: 21
<212> TYPE: DNA
<213> ORGANISM: Homo sapiens

<400> SEQUENCE: 306
gtccttgtgc caacagtcga g                                               21

<210> SEQ ID NO 307
<211> LENGTH: 22
<212> TYPE: DNA
<213> ORGANISM: Homo sapiens

<400> SEQUENCE: 307
gcttggcaag gagaagagaa ca                                              22

<210> SEQ ID NO 308
<211> LENGTH: 23
<212> TYPE: DNA
<213> ORGANISM: Homo sapiens

<400> SEQUENCE: 308
gcttgctttc ttgcttgaac aac                                             23

<210> SEQ ID NO 309
<211> LENGTH: 22
<212> TYPE: DNA
<213> ORGANISM: Homo sapiens

<400> SEQUENCE: 309
gctggtcacc ttgagcttct ct                                              22

<210> SEQ ID NO 310
<211> LENGTH: 21
<212> TYPE: DNA
<213> ORGANISM: Homo sapiens

<400> SEQUENCE: 310
ccatgctggg ctctttgatt a                                               21

<210> SEQ ID NO 311
<211> LENGTH: 22
<212> TYPE: DNA
```

```
<213> ORGANISM: Homo sapiens

<400> SEQUENCE: 311
caccactctg aagttggcct ct                                          22

<210> SEQ ID NO 312
<211> LENGTH: 21
<212> TYPE: DNA
<213> ORGANISM: Homo sapiens

<400> SEQUENCE: 312
atggctctgc acatttgttc c                                           21

<210> SEQ ID NO 313
<211> LENGTH: 22
<212> TYPE: DNA
<213> ORGANISM: Homo sapiens

<400> SEQUENCE: 313
cagagtggga aaaggcactt ca                                          22

<210> SEQ ID NO 314
<211> LENGTH: 22
<212> TYPE: DNA
<213> ORGANISM: Homo sapiens

<400> SEQUENCE: 314
ccagagtcct gtgcagacat tc                                          22

<210> SEQ ID NO 315
<211> LENGTH: 22
<212> TYPE: DNA
<213> ORGANISM: Homo sapiens

<400> SEQUENCE: 315
atggggatta actgggatgt tg                                          22

<210> SEQ ID NO 316
<211> LENGTH: 23
<212> TYPE: DNA
<213> ORGANISM: Homo sapiens

<400> SEQUENCE: 316
cgtagctcca gacatcacta gca                                         23

<210> SEQ ID NO 317
<211> LENGTH: 22
<212> TYPE: DNA
<213> ORGANISM: Homo sapiens

<400> SEQUENCE: 317
gcaacctggt ctgcaaagtc tc                                          22

<210> SEQ ID NO 318
<211> LENGTH: 20
<212> TYPE: DNA
<213> ORGANISM: Homo sapiens

<400> SEQUENCE: 318
acccagcagt ccagcatgag                                             20

<210> SEQ ID NO 319
<211> LENGTH: 22
```

<212> TYPE: DNA
<213> ORGANISM: Homo sapiens

<400> SEQUENCE: 319
gagtttcagt gagccaagat cg                                    22

<210> SEQ ID NO 320
<211> LENGTH: 22
<212> TYPE: DNA
<213> ORGANISM: Homo sapiens

<400> SEQUENCE: 320
ttacaggctt gagccactag gc                                    22

<210> SEQ ID NO 321
<211> LENGTH: 21
<212> TYPE: DNA
<213> ORGANISM: Homo sapiens

<400> SEQUENCE: 321
aagcttccag gagacgaggt c                                     21

<210> SEQ ID NO 322
<211> LENGTH: 21
<212> TYPE: DNA
<213> ORGANISM: Homo sapiens

<400> SEQUENCE: 322
gtccctgaaa tccctcaaac c                                     21

<210> SEQ ID NO 323
<211> LENGTH: 23
<212> TYPE: DNA
<213> ORGANISM: Homo sapiens

<400> SEQUENCE: 323
tgctccataa acgtgactat tgc                                   23

<210> SEQ ID NO 324
<211> LENGTH: 22
<212> TYPE: DNA
<213> ORGANISM: Homo sapiens

<400> SEQUENCE: 324
gtaagagggt gggctggaat ct                                    22

<210> SEQ ID NO 325
<211> LENGTH: 22
<212> TYPE: DNA
<213> ORGANISM: Homo sapiens

<400> SEQUENCE: 325
cttagaccat gtccgggaaa ac                                    22

<210> SEQ ID NO 326
<211> LENGTH: 22
<212> TYPE: DNA
<213> ORGANISM: Homo sapiens

<400> SEQUENCE: 326
cacatcactc tggtgggtga ac                                    22

<210> SEQ ID NO 327

```
<211> LENGTH: 22
<212> TYPE: DNA
<213> ORGANISM: Homo sapiens

<400> SEQUENCE: 327
aaatttcatc ccaaaaccaa cc                                              22

<210> SEQ ID NO 328
<211> LENGTH: 23
<212> TYPE: DNA
<213> ORGANISM: Homo sapiens

<400> SEQUENCE: 328
ccagtcccaa gttcttgatc att                                             23

<210> SEQ ID NO 329
<211> LENGTH: 21
<212> TYPE: DNA
<213> ORGANISM: Homo sapiens

<400> SEQUENCE: 329
acaagtcggc tagttgcatg g                                               21

<210> SEQ ID NO 330
<211> LENGTH: 22
<212> TYPE: DNA
<213> ORGANISM: Homo sapiens

<400> SEQUENCE: 330
tctcagatga aaccaccagc ac                                              22

<210> SEQ ID NO 331
<211> LENGTH: 23
<212> TYPE: DNA
<213> ORGANISM: Homo sapiens

<400> SEQUENCE: 331
ttcatctgag aagcaaggag tgg                                             23

<210> SEQ ID NO 332
<211> LENGTH: 22
<212> TYPE: DNA
<213> ORGANISM: Homo sapiens

<400> SEQUENCE: 332
ccagggagaa agcaggactc ta                                              22

<210> SEQ ID NO 333
<211> LENGTH: 22
<212> TYPE: DNA
<213> ORGANISM: Homo sapiens

<400> SEQUENCE: 333
ttctggcggt gttttgaaat ta                                              22

<210> SEQ ID NO 334
<211> LENGTH: 22
<212> TYPE: DNA
<213> ORGANISM: Homo sapiens

<400> SEQUENCE: 334
ctcaacattg acggcctttc tt                                              22
```

```
<210> SEQ ID NO 335
<211> LENGTH: 23
<212> TYPE: DNA
<213> ORGANISM: Homo sapiens

<400> SEQUENCE: 335
tcagctctta aacagggcat agc                                              23

<210> SEQ ID NO 336
<211> LENGTH: 22
<212> TYPE: DNA
<213> ORGANISM: Homo sapiens

<400> SEQUENCE: 336
gaaatgcagc agccactaaa ga                                               22

<210> SEQ ID NO 337
<211> LENGTH: 22
<212> TYPE: DNA
<213> ORGANISM: Homo sapiens

<400> SEQUENCE: 337
ctcaccttca aggacctggt gt                                               22

<210> SEQ ID NO 338
<211> LENGTH: 21
<212> TYPE: DNA
<213> ORGANISM: Homo sapiens

<400> SEQUENCE: 338
cagggagggg tagaaaccac a                                                21

<210> SEQ ID NO 339
<211> LENGTH: 21
<212> TYPE: DNA
<213> ORGANISM: Homo sapiens

<400> SEQUENCE: 339
ggagaggtgg agaggcttca g                                                21

<210> SEQ ID NO 340
<211> LENGTH: 22
<212> TYPE: DNA
<213> ORGANISM: Homo sapiens

<400> SEQUENCE: 340
gagactccca ggacagacac ct                                               22

<210> SEQ ID NO 341
<211> LENGTH: 20
<212> TYPE: DNA
<213> ORGANISM: Homo sapiens

<400> SEQUENCE: 341
cactcgttcc tcacccttcc                                                  20

<210> SEQ ID NO 342
<211> LENGTH: 22
<212> TYPE: DNA
<213> ORGANISM: Homo sapiens

<400> SEQUENCE: 342
aggactcaca cgtcactctg gt                                               22
```

```
<210> SEQ ID NO 343
<211> LENGTH: 23
<212> TYPE: DNA
<213> ORGANISM: Homo sapiens

<400> SEQUENCE: 343
ggacaatgtg atgaagattg ctg                                           23

<210> SEQ ID NO 344
<211> LENGTH: 22
<212> TYPE: DNA
<213> ORGANISM: Homo sapiens

<400> SEQUENCE: 344
atagcaggat cccaaaagac ca                                            22

<210> SEQ ID NO 345
<211> LENGTH: 22
<212> TYPE: DNA
<213> ORGANISM: Homo sapiens

<400> SEQUENCE: 345
ggcttgggga cctgtatttg ta                                            22

<210> SEQ ID NO 346
<211> LENGTH: 22
<212> TYPE: DNA
<213> ORGANISM: Homo sapiens

<400> SEQUENCE: 346
cagtggcctt tctgagcctt ac                                            22

<210> SEQ ID NO 347
<211> LENGTH: 23
<212> TYPE: DNA
<213> ORGANISM: Homo sapiens

<400> SEQUENCE: 347
gcactctagc tccctctttt agc                                           23

<210> SEQ ID NO 348
<211> LENGTH: 24
<212> TYPE: DNA
<213> ORGANISM: Homo sapiens

<400> SEQUENCE: 348
ttttacagta gagggcagac atgc                                          24

<210> SEQ ID NO 349
<211> LENGTH: 22
<212> TYPE: DNA
<213> ORGANISM: Homo sapiens

<400> SEQUENCE: 349
gccaccatag ctgcagaatt ag                                            22

<210> SEQ ID NO 350
<211> LENGTH: 22
<212> TYPE: DNA
<213> ORGANISM: Homo sapiens

<400> SEQUENCE: 350
cccaaggaca gatgtgatgc ta                                            22
```

<210> SEQ ID NO 351
<211> LENGTH: 22
<212> TYPE: DNA
<213> ORGANISM: Homo sapiens

<400> SEQUENCE: 351
gcctttgttc gagaggagtt gt                                          22

<210> SEQ ID NO 352
<211> LENGTH: 22
<212> TYPE: DNA
<213> ORGANISM: Homo sapiens

<400> SEQUENCE: 352
gttcacgctc tcaagcaggt ta                                          22

<210> SEQ ID NO 353
<211> LENGTH: 22
<212> TYPE: DNA
<213> ORGANISM: Homo sapiens

<400> SEQUENCE: 353
attccacaag ctctctccat ga                                          22

<210> SEQ ID NO 354
<211> LENGTH: 20
<212> TYPE: DNA
<213> ORGANISM: Homo sapiens

<400> SEQUENCE: 354
cttgccccaa gatgcctaag                                             20

<210> SEQ ID NO 355
<211> LENGTH: 23
<212> TYPE: DNA
<213> ORGANISM: Homo sapiens

<400> SEQUENCE: 355
tgcttggtat ttgctcatca tgt                                         23

<210> SEQ ID NO 356
<211> LENGTH: 22
<212> TYPE: DNA
<213> ORGANISM: Homo sapiens

<400> SEQUENCE: 356
cccttagcta gcccactgac aa                                          22

<210> SEQ ID NO 357
<211> LENGTH: 20
<212> TYPE: DNA
<213> ORGANISM: Homo sapiens

<400> SEQUENCE: 357
ctcctgggag tggtgtccaa                                             20

<210> SEQ ID NO 358
<211> LENGTH: 22
<212> TYPE: DNA
<213> ORGANISM: Homo sapiens

<400> SEQUENCE: 358
cctgggcaac agacagagta ag                                              22

<210> SEQ ID NO 359
<211> LENGTH: 21
<212> TYPE: DNA
<213> ORGANISM: Homo sapiens

<400> SEQUENCE: 359
cttcacttcc ccatgcgtac c                                               21

<210> SEQ ID NO 360
<211> LENGTH: 21
<212> TYPE: DNA
<213> ORGANISM: Homo sapiens

<400> SEQUENCE: 360
gggttcacaa tgcctacagg a                                               21

<210> SEQ ID NO 361
<211> LENGTH: 22
<212> TYPE: DNA
<213> ORGANISM: Homo sapiens

<400> SEQUENCE: 361
aaaatctgtg actttggctt gg                                              22

<210> SEQ ID NO 362
<211> LENGTH: 23
<212> TYPE: DNA
<213> ORGANISM: Homo sapiens

<400> SEQUENCE: 362
gggaggagac attctttgat ttg                                             23

<210> SEQ ID NO 363
<211> LENGTH: 22
<212> TYPE: DNA
<213> ORGANISM: Homo sapiens

<400> SEQUENCE: 363
gcagtcctga gaagaaaaca gc                                              22

<210> SEQ ID NO 364
<211> LENGTH: 22
<212> TYPE: DNA
<213> ORGANISM: Homo sapiens

<400> SEQUENCE: 364
cttcacatgc cccaaaatta ca                                              22

<210> SEQ ID NO 365
<211> LENGTH: 23
<212> TYPE: DNA
<213> ORGANISM: Homo sapiens

<400> SEQUENCE: 365
tgagccatgt atttcagagg tga                                             23

<210> SEQ ID NO 366
<211> LENGTH: 22
<212> TYPE: DNA
<213> ORGANISM: Homo sapiens

<400> SEQUENCE: 366

```
tacatttcag caggtgcgtg tt                                              22

<210> SEQ ID NO 367
<211> LENGTH: 24
<212> TYPE: DNA
<213> ORGANISM: Homo sapiens

<400> SEQUENCE: 367
ttgcctactc tgtagggata ttgc                                            24

<210> SEQ ID NO 368
<211> LENGTH: 21
<212> TYPE: DNA
<213> ORGANISM: Homo sapiens

<400> SEQUENCE: 368
atagggcatg tagcccagtg a                                               21

<210> SEQ ID NO 369
<211> LENGTH: 21
<212> TYPE: DNA
<213> ORGANISM: Homo sapiens

<400> SEQUENCE: 369
gctctgctgt tggtcctcac t                                               21

<210> SEQ ID NO 370
<211> LENGTH: 22
<212> TYPE: DNA
<213> ORGANISM: Homo sapiens

<400> SEQUENCE: 370
ttgcaaagca cacatcttct ga                                              22

<210> SEQ ID NO 371
<211> LENGTH: 22
<212> TYPE: DNA
<213> ORGANISM: Homo sapiens

<400> SEQUENCE: 371
tggcaatgtc aatgtcaagc at                                              22

<210> SEQ ID NO 372
<211> LENGTH: 22
<212> TYPE: DNA
<213> ORGANISM: Homo sapiens

<400> SEQUENCE: 372
gtatgttgcc ccactcaaca aa                                              22

<210> SEQ ID NO 373
<211> LENGTH: 22
<212> TYPE: DNA
<213> ORGANISM: Homo sapiens

<400> SEQUENCE: 373
tgcatttcct agctgagact cc                                              22

<210> SEQ ID NO 374
<211> LENGTH: 22
<212> TYPE: DNA
<213> ORGANISM: Homo sapiens
```

<400> SEQUENCE: 374
tgccatctcg cacgtagtaa at								22

<210> SEQ ID NO 375
<211> LENGTH: 22
<212> TYPE: DNA
<213> ORGANISM: Homo sapiens

<400> SEQUENCE: 375
ctctcctgtg ctgagcagct tt								22

<210> SEQ ID NO 376
<211> LENGTH: 22
<212> TYPE: DNA
<213> ORGANISM: Homo sapiens

<400> SEQUENCE: 376
tgtttccaat cactggcttt ca								22

<210> SEQ ID NO 377
<211> LENGTH: 20
<212> TYPE: DNA
<213> ORGANISM: Homo sapiens

<400> SEQUENCE: 377
gaaccatggg ctgtctctgg								20

<210> SEQ ID NO 378
<211> LENGTH: 22
<212> TYPE: DNA
<213> ORGANISM: Homo sapiens

<400> SEQUENCE: 378
atctgggata gcgaaggaga ca								22

<210> SEQ ID NO 379
<211> LENGTH: 20
<212> TYPE: DNA
<213> ORGANISM: Homo sapiens

<400> SEQUENCE: 379
attacaggcc acacgccatc								20

<210> SEQ ID NO 380
<211> LENGTH: 23
<212> TYPE: DNA
<213> ORGANISM: Homo sapiens

<400> SEQUENCE: 380
aaggcaagaa taagggagga aga							23

<210> SEQ ID NO 381
<211> LENGTH: 23
<212> TYPE: DNA
<213> ORGANISM: Homo sapiens

<400> SEQUENCE: 381
gctctcagga ctgcagaagt aca							23

<210> SEQ ID NO 382
<211> LENGTH: 22
<212> TYPE: DNA
<213> ORGANISM: Homo sapiens

<210> SEQ ID NO 382

<400> SEQUENCE: 382
gaggaaccaa tcccactcac ac                                    22

<210> SEQ ID NO 383
<211> LENGTH: 23
<212> TYPE: DNA
<213> ORGANISM: Homo sapiens

<400> SEQUENCE: 383
tcactctttg ccttctgtct ctg                                   23

<210> SEQ ID NO 384
<211> LENGTH: 22
<212> TYPE: DNA
<213> ORGANISM: Homo sapiens

<400> SEQUENCE: 384
gcactgtgct ttgctttctc ag                                    22

<210> SEQ ID NO 385
<211> LENGTH: 24
<212> TYPE: DNA
<213> ORGANISM: Homo sapiens

<400> SEQUENCE: 385
tgtctccttt atcgtaggtc tcca                                  24

<210> SEQ ID NO 386
<211> LENGTH: 22
<212> TYPE: DNA
<213> ORGANISM: Homo sapiens

<400> SEQUENCE: 386
caccacattt cctacagttc ca                                    22

<210> SEQ ID NO 387
<211> LENGTH: 22
<212> TYPE: DNA
<213> ORGANISM: Homo sapiens

<400> SEQUENCE: 387
cactgtgcac cagacagaca aa                                    22

<210> SEQ ID NO 388
<211> LENGTH: 24
<212> TYPE: DNA
<213> ORGANISM: Homo sapiens

<400> SEQUENCE: 388
tgtggttttc tgtatcagca gctt                                  24

<210> SEQ ID NO 389
<211> LENGTH: 22
<212> TYPE: DNA
<213> ORGANISM: Homo sapiens

<400> SEQUENCE: 389
cagggagtct gaaatcatca gg                                    22

<210> SEQ ID NO 390
<211> LENGTH: 23
<212> TYPE: DNA

```
<213> ORGANISM: Homo sapiens

<400> SEQUENCE: 390
tcaagtatct agccccaaat cca                                        23

<210> SEQ ID NO 391
<211> LENGTH: 24
<212> TYPE: DNA
<213> ORGANISM: Homo sapiens

<400> SEQUENCE: 391
ggcaatattg accattcatc attc                                       24

<210> SEQ ID NO 392
<211> LENGTH: 21
<212> TYPE: DNA
<213> ORGANISM: Homo sapiens

<400> SEQUENCE: 392
aggccaggag taagacgcaa c                                          21

<210> SEQ ID NO 393
<211> LENGTH: 22
<212> TYPE: DNA
<213> ORGANISM: Homo sapiens

<400> SEQUENCE: 393
aagaacgtac gtgtggtgtt gg                                         22

<210> SEQ ID NO 394
<211> LENGTH: 22
<212> TYPE: DNA
<213> ORGANISM: Homo sapiens

<400> SEQUENCE: 394
cgctatactt gctccatgca ct                                         22

<210> SEQ ID NO 395
<211> LENGTH: 21
<212> TYPE: DNA
<213> ORGANISM: Homo sapiens

<400> SEQUENCE: 395
aggaaacagc ctctggtcct c                                          21

<210> SEQ ID NO 396
<211> LENGTH: 22
<212> TYPE: DNA
<213> ORGANISM: Homo sapiens

<400> SEQUENCE: 396
gtcaatgctc agacagggag at                                         22

<210> SEQ ID NO 397
<211> LENGTH: 22
<212> TYPE: DNA
<213> ORGANISM: Homo sapiens

<400> SEQUENCE: 397
cccaggaagg caggtactgt ta                                         22

<210> SEQ ID NO 398
<211> LENGTH: 22
```

```
<212> TYPE: DNA
<213> ORGANISM: Homo sapiens

<400> SEQUENCE: 398 tttttacaacc accaagggtg tg                                              22

<210> SEQ ID NO 399
<211> LENGTH: 23
<212> TYPE: DNA
<213> ORGANISM: Homo sapiens

<400> SEQUENCE: 399
tcgtgtggtt acctccagat ttt                                              23

<210> SEQ ID NO 400
<211> LENGTH: 22
<212> TYPE: DNA
<213> ORGANISM: Homo sapiens

<400> SEQUENCE: 400
aaattagcca gggagtggag gt                                               22

<210> SEQ ID NO 401
<211> LENGTH: 20
<212> TYPE: DNA
<213> ORGANISM: Homo sapiens

<400> SEQUENCE: 401
catgccatgc tatggctcac                                                  20

<210> SEQ ID NO 402
<211> LENGTH: 22
<212> TYPE: DNA
<213> ORGANISM: Homo sapiens

<400> SEQUENCE: 402
aggctgagcg gagttctaat tg                                               22

<210> SEQ ID NO 403
<211> LENGTH: 22
<212> TYPE: DNA
<213> ORGANISM: Homo sapiens

<400> SEQUENCE: 403
atctcagcaa tccacaggag gt                                               22

<210> SEQ ID NO 404
<211> LENGTH: 22
<212> TYPE: DNA
<213> ORGANISM: Homo sapiens

<400> SEQUENCE: 404
atttgcctca cgaacacatc at                                               22

<210> SEQ ID NO 405
<211> LENGTH: 23
<212> TYPE: DNA
<213> ORGANISM: Homo sapiens

<400> SEQUENCE: 405
tggaaagttg tctatggcac ctc                                              23

<210> SEQ ID NO 406
```

```
<211> LENGTH: 22
<212> TYPE: DNA
<213> ORGANISM: Homo sapiens

<400> SEQUENCE: 406
atgggcagca aggacttact ct                                              22

<210> SEQ ID NO 407
<211> LENGTH: 22
<212> TYPE: DNA
<213> ORGANISM: Homo sapiens

<400> SEQUENCE: 407
caccccaata ttgtctgcct tc                                              22

<210> SEQ ID NO 408
<211> LENGTH: 22
<212> TYPE: DNA
<213> ORGANISM: Homo sapiens

<400> SEQUENCE: 408
ggctcgggaa catgtaatta gg                                              22

<210> SEQ ID NO 409
<211> LENGTH: 24
<212> TYPE: DNA
<213> ORGANISM: Homo sapiens

<400> SEQUENCE: 409
ccatcatgta tggcaaattc tctt                                            24

<210> SEQ ID NO 410
<211> LENGTH: 23
<212> TYPE: DNA
<213> ORGANISM: Homo sapiens

<400> SEQUENCE: 410
tggcgtctcc tagtaaagat gct                                             23

<210> SEQ ID NO 411
<211> LENGTH: 21
<212> TYPE: DNA
<213> ORGANISM: Homo sapiens

<400> SEQUENCE: 411
gccagattgc tggtttcatt g                                               21

<210> SEQ ID NO 412
<211> LENGTH: 22
<212> TYPE: DNA
<213> ORGANISM: Homo sapiens

<400> SEQUENCE: 412
ggctaaaaca caaagcacca tt                                              22

<210> SEQ ID NO 413
<211> LENGTH: 22
<212> TYPE: DNA
<213> ORGANISM: Homo sapiens

<400> SEQUENCE: 413
gggaagtcat ccacaaagac ct                                              22
```

```
<210> SEQ ID NO 414
<211> LENGTH: 20
<212> TYPE: DNA
<213> ORGANISM: Homo sapiens

<400> SEQUENCE: 414
ggtctgggtc acagctcctc                                          20

<210> SEQ ID NO 415
<211> LENGTH: 22
<212> TYPE: DNA
<213> ORGANISM: Homo sapiens

<400> SEQUENCE: 415
ttcttctgcc aagatgtggt gt                                       22

<210> SEQ ID NO 416
<211> LENGTH: 22
<212> TYPE: DNA
<213> ORGANISM: Homo sapiens

<400> SEQUENCE: 416
tgcagatgct gcaatcatgt ta                                       22

<210> SEQ ID NO 417
<211> LENGTH: 22
<212> TYPE: DNA
<213> ORGANISM: Homo sapiens

<400> SEQUENCE: 417
tggaccccga agataaata gg                                        22

<210> SEQ ID NO 418
<211> LENGTH: 22
<212> TYPE: DNA
<213> ORGANISM: Homo sapiens

<400> SEQUENCE: 418
ttctgcactc ctctggaaac tg                                       22

<210> SEQ ID NO 419
<211> LENGTH: 22
<212> TYPE: DNA
<213> ORGANISM: Homo sapiens

<400> SEQUENCE: 419
gggtgagagc caacactgat ct                                       22

<210> SEQ ID NO 420
<211> LENGTH: 22
<212> TYPE: DNA
<213> ORGANISM: Homo sapiens

<400> SEQUENCE: 420
ctgtgccctc tcatctcaca ct                                       22

<210> SEQ ID NO 421
<211> LENGTH: 22
<212> TYPE: DNA
<213> ORGANISM: Homo sapiens

<400> SEQUENCE: 421
agaacctagc ctccaagatt gc                                       22
```

<210> SEQ ID NO 422
<211> LENGTH: 22
<212> TYPE: DNA
<213> ORGANISM: Homo sapiens

<400> SEQUENCE: 422
acaccttcca agactccttc ca                                              22

<210> SEQ ID NO 423
<211> LENGTH: 20
<212> TYPE: DNA
<213> ORGANISM: Homo sapiens

<400> SEQUENCE: 423
gactcgaggg tgggagacag                                                 20

<210> SEQ ID NO 424
<211> LENGTH: 22
<212> TYPE: DNA
<213> ORGANISM: Homo sapiens

<400> SEQUENCE: 424
gctgtcacta ggtgtcctga gc                                              22

<210> SEQ ID NO 425
<211> LENGTH: 3878
<212> TYPE: DNA
<213> ORGANISM: Homo sapiens

<400> SEQUENCE: 425
cccggcgcag cgcggccgca gcagcctccg cccccgcac ggtgtgagcg cccgacgcgg        60
ccgaggcggc cggagtcccg agctagcccc ggcggccgcc gccgcccaga ccggacgaca      120
ggccacctcg tcggcgtccg cccgagtccc cgcctcgccg ccaacgccac aaccaccgcg      180
cacggccccc tgactccgtc cagtattgat cgggagagcc ggagcgagct cttcggggag      240
cagcgatgcg accctccggg acggccgggg cagcgctcct ggcgctgctg gctgcgctct      300
gcccggcgag tcgggctctg aggaaaaaga aagtttgcca aggcacgagt aacaagctca      360
cgcagttggg cacttttgaa gatcattttc tcagcctcca gaggatgttc ataactgtg       420 aggtggtcct tgggaatttg gaaattacct atgtgcagag gaattatgat cttccttct      480 taaagaccat ccaggaggtg ctggttatg tcctcattgc cctcaacaca gtggagcgaa      540
ttcctttgga aaacctgcag atcatcagag gaaatatgta ctacgaaaat tcctatgcct      600
tagcagtctt atctaactat gatgcaaata aaaccggact gaaggagctg cccatgagaa      660
atttacagga atcctgcat ggcgccgtgc ggttcagcaa caaccctgcc ctgtgcaacg       720
tggagagcat ccagtggcgg gacatagtca gcagtgactt tctcagcaac atgtcgatgg      780
acttccagaa cccactgggc agctgccaaa gtgtgatcc aagctgtccc aatgggagct      840
gctggggtgc aggagaggag aactgccaga aactgaccaa aatcatctgt gcccagcagt      900
gctccgggcg ctgccgtggc aagtccccca gtgactgctg ccacaaccag tgtgctgcag      960
gctgcacagg cccccgggag agcgactgcc tggtctgccg caattccga acgaagcca      1020 cgtgcaagga cacctgcccc ccactcatgc tctacaaccc caccacgtac cagatggatg      1080
tgaaccccga gggcaaatac agctttggtg ccacctgcgt gaagaagtgt ccccgtaatt      1140
atgtggtgac agatcacggc tcgtgcgtcc gagcctgtgg ggccgacagc tatgagatgg      1200
aggaagacgg cgtccgcaag tgtaagaagt gcgaagggcc ttgccgcaaa gtgtgtaacg      1260

```
gaataggtat tggtgaattt aaagactcac tctccataaa tgctacgaat attaaacact   1320
tcaaaaactg cacctccatc agtggcgatc tccacatcct gccggtggca tttaggggtg   1380
actccttcac acatactcct cctctggatc cacaggaact ggatattctg aaaaccgtaa   1440
aggaaatcac agggtttttg ctgattcagg cttggcctga aaacaggacg gacctccatg   1500
cctttgagaa cctagaaatc atacgcggca ggaccaagca acatggtcag ttttctcttg   1560
cagtcgtcag cctgaacata acatccttgg gattacgctc cctcaaggag ataagtgatg   1620
gagatgtgat aatttcagga aacaaaaatt tgtgctatgc aaatacaata aactggaaaa   1680
aactgtttgg gacctccggt cagaaaacca aaattataag caacagaggt gaaaacagct   1740
gcaaggccac aggccaggtc tgccatgcct tgtgctcccc cgagggctgc tggggcccgg   1800
agcccaggga ctgcgtctct tgccggaatg tcagccgagg cagggaatgc gtggacaagt   1860
gcaaccttct ggagggtgag ccaagggagt ttgtggagaa ctctgagtgc atacagtgcc   1920
acccagagtg cctgcctcag gccatgaaca tcacctgcac aggacgggga ccagacaact   1980
gtatccagtg tgcccactac attgacggcc cccactgcgt caagacctgc ccggcaggag   2040
tcatgggaga aaacaacacc ctggtctgga agtacgcaga cgccggccat gtgtgccacc   2100
tgtgccatcc aaactgcacc tacggatgca ctgggccagg tcttgaaggc tgtccaacga   2160
atgggcctaa gatcccgtcc atcgccactg ggatggtggg ggccctcctc ttgctgctgg   2220
tggtggccct ggggatcggc ctcttcatgc gaaggcgcca catcgttcgg aagcgcacgc   2280
tgcggaggct gctgcaggag agggagcttg tggagcctct tacacccagt ggagaagctc   2340
ccaaccaagc tctcttgagg atcttgaagg aaactgaatt caaaaagatc aaagtgctga   2400
gctccggtgc gttcggcacg gtgtataagg actctggat cccagaaggt gagaaagtta   2460
aaattcccgt cgctatcaag gaattaagag aagcaacatc tccgaaagcc aacaaggaaa   2520
tcctcgatga agcctacgtg atggccagcg tggacaaccc ccacgtgtgc cgcctgctgg   2580
gcatctgcct cacctccacc gtgcagctca tcacgcagct catgcccttc ggctgcctcc   2640
tggactatgt ccgggaacac aaagacaata ttggctccca gtacctgctc aactggtgtg   2700
tgcagatcgc aaagggcatg aactacttgg aggaccgtcg cttggtgcac cgcgacctgg   2760
cagccaggaa cgtactggtg aaaacaccgc agcatgtcaa gatcacagat tttgggctgg   2820
ccaaactgct gggtgcggaa gagaaagaat accatgcaga aggaggcaaa gtgcctatca   2880
agtggatggc attggaatca attttacaca gaatctatac ccaccagagt gatgtctgga   2940
gctacggggt gactgtttgg gagttgatga cctttggatc caagccatat gacggaatcc   3000
ctgccagcga gatctcctcc atcctggaga aggagaacg cctccctcag ccacccatat   3060
gtaccatcga tgtctacatg atcatggtca agtgctggat gatagacgca gatagtcgcc   3120
caaagttccg tgagttgatc atcgaattct ccaaaatggc ccgagacccc cagcgctacc   3180
ttgtcattca gggggatgaa agaatgcatt tgccaagtcc tacagactcc aacttctacc   3240
gtgccctgat ggatgaagaa gacatggacg acgtggtgga tgccgacgag tacctcatcc   3300
cacagcaggg cttcttcagc agcccctcca cgtcacggac tccctctg agctctctga   3360 gtgcaaccag caacaattcc accgtggctt gcattgatag aaatgggctg caaagctgtc   3420
ccatcaagga agacagcttc ttgcagcgat acagctcaga ccccacaggc gccttgactg   3480
aggacagcat agacgacacc ttcctcccag tgcctgaata cataaaccag tccgttccca   3540
aaaggcccgc tggctctgtg cagaatcctg tctatcacaa tcagcctctg aaccccgcgc   3600
```

| | |
|---|---|
| ccagcagaga cccacactac caggaccccc acagcactgc agtgggcaac cccgagtatc | 3660 |
| tcaacactgt ccagcccacc tgtgtcaaca gcacattcga cagccctgcc cactgggccc | 3720 |
| agaaaggcag ccaccaaatt agcctggaca accctgacta ccagcaggac ttctttccca | 3780 |
| aggaagccaa gccaaatggc atctttaagg gctccacagc tgaaaatgca gaatacctaa | 3840 |
| gggtcgcgcc acaaagcagt gaatttattg gagcatga | 3878 |

```
<210> SEQ ID NO 426
<211> LENGTH: 3878
<212> TYPE: DNA
<213> ORGANISM: Homo sapiens

<400> SEQUENCE: 426
```

| | |
|---|---|
| cccggcgcag cgcggccgca gcagcctccg cccccccgcac ggtgtgagcg ccgacgcgg | 60 |
| ccgaggcggc cggagtcccg agctagcccc ggcggccgcc gccgcccaga ccggacgaca | 120 |
| ggccacctcg tcggcgtccg cccgagtccc cgcctcgccg ccaacgccac aaccaccgcg | 180 |
| cacgcccccc tgactccgtc cagtattgat cgggagagcc ggagcgagct cttcggggag | 240 |
| cagcgatgcg accctccggg acggccgggg cagcgctcct ggcgctgctg gctgcgctct | 300 |
| gcccggcgag tcgggctctg gaggaaaaga agtttgccca aggcacgagt aacaagctca | 360 |
| cgcagttggg cacttttgaa gatcattttc tcagcctcca gaggatgttc aataactgtg | 420 |
| aggtggtcct tgggaatttg gaaattacct atgtgcagag gaattatgat cttttccttct | 480 |
| taaagaccat ccaggaggtg gctggttatg tcctcattgc cctcaacaca gtggagcgaa | 540 |
| ttccttttgga aaacctgcag atcatcagag gaaatatgta ctacgaaaat tcctatgcct | 600 |
| tagcagtctt atctaactat gatgcaaata aaaccggact gaaggagctg cccatgagaa | 660 |
| atttacagga atcctgcat ggcgccgtgc ggttcagcaa caaccctgcc ctgtgcaacg | 720 |
| tggagagcat ccagtggcgg gacatagtca gcagtgactt tctcagcaac atgtcgatgg | 780 |
| acttccagaa ccacctgggc agctgccaaa agtgtgatcc aagctgtccc aatgggagct | 840 |
| gctgggtgc aggagaggag aactgccaga aactgaccaa aatcatctgt gcccagcagt | 900 |
| gctcccggcg ctgccgtggc aagtccccca gtgactgctg ccacaaccag tgtgctgcag | 960 |
| gctgcacagg ccccgggag agcgactgcc tggtctgccg caaattccga gacgaagcca | 1020 |
| cgtgcaagga cacctgcccc ccactcatgc tctacaaccc caccacgtac cagatggatg | 1080 |
| tgaaccccga gggcaaatac agctttggtg ccacctgcgt gaagaagtgt ccccgtaatt | 1140 |
| atgtggtgac agatcacggc tcgtgcgtcc gagcctgtgg ggccgacagc tatgagatgg | 1200 |
| aggaagacgg cgtccgcaag tgtaagaagt gcgaagggcc ttgccgcaaa gtgtgtaacg | 1260 |
| gaataggtat tggtgaattt aaagactcac tctccataaa tgctacgaat attaaacact | 1320 |
| tcaaaaactg cacctccatc agtggcgatc tccacatcct gccggtggca tttagggtg | 1380 |
| actccttcac acatactcct cctctggatc cacaggaact ggatattctg aaaaccgtaa | 1440 |
| aggaaatcac agggttttg ctgattcagg cttggcctga aaacaggacg gacctccatg | 1500 |
| cctttgagaa cctagaaatc atacgcggca ggaccaagca acatggtcag ttttctcttg | 1560 |
| cagtcgtcag cctgaacata acatccttgg gattacgctc cctcaaggag ataagtgatg | 1620 |
| gagatgtgat aatttcagga aacaaaaatt tgtgctatgc aaatacaata aactggaaaa | 1680 |
| aactgttggg gacctccggt cagaaaacca aaattataag caacagaggt gaaaacagct | 1740 |
| gcaaggccac aggccaggtc tgccatgcct tgtgctcccc cgagggctgc tggggcccgg | 1800 |
| agcccaggga ctgcgtctct tgccggaatg tcagccgagg cagggaatgc gtggacaagt | 1860 |

```
gcaaccttct ggagggtgag ccaagggagt ttgtggagaa ctctgagtgc atacagtgcc    1920
acccagagtg cctgcctcag gccatgaaca tcacctgcac aggacgggga ccagacaact    1980
gtatccagtg tgcccactac attgacggcc ccactgcgt caagacctgc ccggcaggag     2040
tcatgggaga aaacaacacc ctggtctgga agtacgcaga cgccggccat gtgtgccacc    2100
tgtgccatcc aaactgcacc tacggatgca ctgggccagg tcttgaaggc tgtccaacga    2160
atgggcctaa gatcccgtcc atcgccactg ggatggtggg ggccctcctc ttgctgctgg    2220
tggtggccct ggggatcggc ctcttcatgc gaaggcgcca catcgttcgg aagcgcacgc    2280
tgcggaggct gctgcaggag agggagcttg tggagcctct tacacccagt ggagaagctc    2340
ccaaccaagc tctcttgagg atcttgaagg aaactgaatt caaaaagatc aaagtgctga    2400
gctccggtgc gttcggcacg gtgtataagg actctggat cccagaaggt gagaaagtta     2460
aaattcccgt cgctatcaag gaattaagag aagcaacatc tccgaaagcc aacaaggaaa    2520
tcctcgatga agcctacgtg atggccacgt ggacaaccc ccacgtgtgc cgcctgctgg     2580
gcatctgcct cacctccacc gtgcagctca tcacgcagct catgcccttc ggctgcctcc    2640
tggactatgt ccgggaacac aaagacaata ttggctccca gtacctgctc aactggtgtg    2700
tgcagatcgc aaagggcatg aactacttgg aggaccgtcg cttggtgcac cgcgacctgg    2760
cagccaggaa cgtactggtg aaaacaccgc agcatgtcaa gatcacagat tttgggctgg    2820
ccaaactgct gggtgcggaa gagaaagaat accatgcaga aggaggcaaa gtgcctatca    2880
agtggatggc attggaatca attttacaca gaatctatac ccaccagagt gatgtctgga    2940
gctacggggt gactgtttgg gagttgatga cctttggatc caagccatat gacggaatcc    3000
ctgccagcga gatcctctcc atcctggaga aggagaacg cctccctcag ccacccatat     3060
gtaccatcga tgtctacatg atcatggtca agtgctggat gatagacgca gatagtcgcc    3120
caaagttccg tgagttgatc atcgaattct ccaaaatggc ccgagacccc agcgctacc     3180 ttgtcattca ggggatgaa agaatgcatt tgccaagtcc tacagactcc aacttctacc     3240
gtgccctgat ggatgaagaa gacatggacg acgtggtgga tgccgacgag tacctcatcc    3300
cacagcaggg cttcttcagc agcccctcca cgtcacggac tccctcctg agctctctga     3360 gtgcaaccag caacaattcc accgtggctt gcattgatag aaatgggctg caaagctgtc    3420
ccatcaagga agacagcttc ttgcagcgat acagctcaga ccccacaggc gccttgactg    3480
aggacagcat agacgacacc ttcctcccag tgcctgaata cataaaccag tccgttccca    3540
aaaggcccgc tggctctgtg cagaatcctg tctatcacaa tcagcctctg aaccccgcgc    3600
ccagcagaga cccacactac caggacccc acagcactgc agtgggcaac cccgagtatc     3660
tcaacactgt ccagcccacc tgtgtcaaca gcacattcga cagccctgcc cactgggccc    3720
agaaaggcag ccaccaaatt agcctggaca accctgacta ccagcaggac ttctttccca    3780
aggaagccaa gccaaatggc atctttaagg gctccacagt gaaaatgca gaatacctaa     3840 gggtcgcgcc acaaagcagt gaatttattg gagcatga                            3878
```

<210> SEQ ID NO 427
<211> LENGTH: 3863
<212> TYPE: DNA
<213> ORGANISM: Homo sapiens

<400> SEQUENCE: 427

```
cccggcgcag cgcggccgca gcagcctccg cccccccgcac ggtgtgagcg cccgacgcgg     60
```

| | |
|---|---|
| ccgaggcggc cggagtcccg agctagcccc ggcggccgcc gccgcccaga ccggacgaca | 120 |
| ggccacctcg tcggcgtccg cccgagtccc cgcctcgccg ccaacgccac aaccaccgcg | 180 |
| cacggccccc tgactccgtc cagtattgat cgggagagcc ggagcgagct cttcggggag | 240 |
| cagcgatgcg accctccggg acggccgggg cagcgctcct ggcgctgctg gctgcgctct | 300 |
| gcccggcgag tcgggctctg gaggaaaaga aagtttgcca aggcacgagt aacaagctca | 360 |
| cgcagttggg cacttttgaa gatcattttc tcagcctcca gaggatgttc ataactgtg | 420 |
| aggtggtcct tgggaatttg gaaattacct atgtgcagag gaattatgat cttccttct | 480 |
| taaagaccat ccaggaggtg gctggttatg tcctcattgc cctcaacaca gtggagcgaa | 540 |
| ttcctttgga aaacctgcag atcatcagag gaaatatgta ctacgaaaat tcctatgcct | 600 |
| tagcagtctt atctaactat gatgcaaata aaaccggact gaaggagctg cccatgagaa | 660 |
| atttacagga atcctgcat ggcgccgtgc ggttcagcaa caaccctgcc ctgtgcaacg | 720 |
| tggagagcat ccagtggcgg gacatagtca gcagtgactt tctcagcaac atgtcgatgg | 780 |
| acttccagaa ccacctgggc agctgccaaa agtgtgatcc aagctgtccc aatgggagct | 840 |
| gctggggtgc aggagaggag aactgccaga aactgaccaa aatcatctgt gcccagcagt | 900 |
| gctcccggcg ctgccgtggc aagtccccca gtgactgctg ccacaaccag tgtgctgcag | 960 |
| gctgcacagg cccccgggag agcgactgcc tggtctgccg caaattccga gacgaagcca | 1020 |
| cgtgcaagga cacctgcccc ccactcatgc tctacaaccc caccacgtac cagatggatg | 1080 |
| tgaaccccga gggcaaatac agctttggtg ccacctgcgt gaagaagtgt ccccgtaatt | 1140 |
| atgtggtgac agatcacggc tcgtgcgtcc gagcctgtgg ggccgacagc tatgagatgg | 1200 |
| aggaagacgg cgtccgcaag tgtaagaagt gcgaagggcc ttgccgcaaa gtgtgtaacg | 1260 |
| gaataggtat tggtgaattt aaagactcac tctccataaa tgctacgaat attaaacact | 1320 |
| tcaaaaactg cacctccatc agtggcgatc tccacatcct gccggtggca tttagggtg | 1380 |
| actccttcac acatactcct cctctggatc cacaggaact ggatattctg aaaaccgtaa | 1440 |
| aggaaatcac agggtttttg ctgattcagg cttggcctga aaacaggacg gacctccatg | 1500 |
| cctttgagaa cctagaaatc atacgcggca ggaccaagca acatggtcag tttctcttg | 1560 |
| cagtcgtcag cctgaacata acatccttgg gattacgctc cctcaaggag ataagtgatg | 1620 |
| gagatgtgat aatttcagga aacaaaaatt tgtgctatgc aaatacaata aactggaaaa | 1680 |
| aactgttgg gacctccggt cagaaaacca aaattataag caacagaggt gaaaacagct | 1740 |
| gcaaggccac aggccaggtc tgccatgcct tgtgctcccc cgagggctgc tggggcccgg | 1800 |
| agcccaggga ctgcgtctct tgccggaatg tcagccgagg cagggaatgc gtggacaagt | 1860 |
| gcaaccttct ggagggtgag ccaagggagt tgtggagaa ctctgagtgc atacagtgcc | 1920 |
| acccagagtg cctgcctcag gccatgaaca tcacctgcac aggacgggga ccagacaact | 1980 |
| gtatccagtg tgcccactac attgacggcc cccactgcgt caagacctgc ccggcaggag | 2040 |
| tcatgggaga aaacaacacc ctggtctgga agtacgcaga cgccggccat gtgtgccacc | 2100 |
| tgtgccatcc aaactgcacc tacggatgca ctgggccagg tcttgaaggc tgtccaacga | 2160 |
| atgggcctaa gatcccgtcc atcgccactg ggatggtggg ggcctcctc ttgctgctgg | 2220 |
| tggtggccct ggggatcggc ctcttcatgc gaaggcgcca catcgttcgg aagcgcacgc | 2280 |
| tgcggaggct gctgcaggag agggagcttg tggagcctct tacacccagt ggagaagctc | 2340 |
| ccaaccaagc tctcttgagg atcttgaagg aaactgaatt caaaaagatc aaagtgctgg | 2400 |
| gctccggtgc gttcggcacg gtgtataagg gactctggat cccagaaggt gagaaagtta | 2460 |

| | | |
|---|---|---|
| aaattcccgt cgctatcaaa acatctccga aagccaacaa ggaaatcctc gatgaagcct | 2520 |
| acgtgatggc cagcgtggac aaccccacg tgtgccgcct gctgggcatc tgcctcacct | 2580 |
| ccaccgtgca gctcatcacg cagctcatgc ccttcggctg cctcctggac tatgtccggg | 2640 |
| aacacaaaga caatattggc tcccagtacc tgctcaactg gtgtgtgcag atcgcaaagg | 2700 |
| gcatgaacta cttggaggac cgtcgcttgg tgcaccgcga cctggcagcc aggaacgtac | 2760 |
| tggtgaaaac accgcagcat gtcaagatca cagattttgg gctggccaaa ctgctgggtg | 2820 |
| cggaagagaa agaataccat gcagaaggag gcaaagtgcc tatcaagtgg atggcattgg | 2880 |
| aatcaatttt acacagaatc tatacccacc agagtgatgt ctggagctac ggggtgactg | 2940 |
| tttgggagtt gatgaccttt ggatccaagc catatgacgg aatccctgcc agcgagatct | 3000 |
| cctccatcct ggagaaagga gaacgcctcc ctcagccacc catatgtacc atcgatgtct | 3060 |
| acatgatcat ggtcaagtgc tggatgatag acgcagatag tcgcccaaag ttccgtgagt | 3120 |
| tgatcatcga attctccaaa atggcccgag acccccagcg ctaccttgtc attcaggggg | 3180 |
| atgaaagaat gcatttgcca agtcctacag actccaactt ctaccgtgcc ctgatggatg | 3240 |
| aagaagacat ggacgacgtg gtggatgccg acgagtacct catcccacag cagggcttct | 3300 |
| tcagcagccc ctccacgtca cggactcccc tcctgagctc tctgagtgca accagcaaca | 3360 |
| attccaccgt ggcttgcatt gatagaaatg ggctgcaaag ctgtccatc aaggaagaca | 3420 |
| gcttcttgca gcgatacagc tcagacccca caggcgcctt gactgaggac agcatagacg | 3480 |
| acaccttcct cccagtgcct gaatacataa accagtccgt tcccaaaagg cccgctggct | 3540 |
| ctgtgcagaa tcctgtctat cacaatcagc ctctgaaccc cgcgcccagc agagacccac | 3600 |
| actaccagga ccccacagc actgcagtgg gcaaccccga gtatctcaac actgtccagc | 3660 |
| ccacctgtgt caacagcaca ttcgacagcc ctgcccactg ggcccagaaa ggcagccacc | 3720 |
| aaattagcct ggacaaccct gactaccagc aggacttctt tcccaaggaa gccaagccaa | 3780 |
| atggcatctt taagggctcc acagctgaaa atgcagaata cctaagggtc gcgccacaaa | 3840 |
| gcagtgaatt tattggagca tga | 3863 |

<210> SEQ ID NO 428
<211> LENGTH: 3863
<212> TYPE: DNA
<213> ORGANISM: Homo sapiens

<400> SEQUENCE: 428

| | | |
|---|---|---|
| cccggcgcag cgcggccgca gcagcctccg ccccccgcac ggtgtgagcg cccgacgcgg | 60 |
| ccgaggcggc cggagtcccg agctagcccc ggcggccgcc gccgcccaga ccggacgaca | 120 |
| ggccacctcg tcggcgtccg cccgagtccc cgcctcgccg ccaacgccac aaccaccgcg | 180 |
| cacggccccc tgactccgtc cagtattgat cgggagagcc ggagcgagct cttcggggag | 240 |
| cagcgatgcg accctccggg acggccgggg cagcgctcct ggcgctgctg ctgcgctct | 300 |
| gcccggcgag tcgggctctg aggaaaaga aagtttgcca aggcacgagt aacaagctca | 360 |
| cgcagttggg cacttttgaa gatcattttc tcagcctcca gaggatgttc aataactgtg | 420 |
| aggtggtcct tgggaatttg gaaattacct atgtgcagag gaattatgat ctttccttct | 480 |
| taaagaccat ccaggaggtg gctggttatg tcctcattgc cctcaacaca gtggagcgaa | 540 |
| ttcctttgga aaacctgcag atcatcgag gaaatatgta ctacgaaaat tcctatgcct | 600 |
| tagcagtctt atctaactat gatgcaaata aaaccggact gaaggagctg cccatgagaa | 660 |

```
atttacagga aatcctgcat ggcgccgtgc ggttcagcaa caaccctgcc ctgtgcaacg      720
tggagagcat ccagtggcgg gacatagtca gcagtgactt tctcagcaac atgtcgatgg      780
acttccagaa ccacctgggc agctgccaaa agtgtgatcc aagctgtccc aatgggagct      840
gctggggtgc aggagaggag aactgccaga aactgaccaa aatcatctgt gcccagcagt      900
gctccgggcg ctgccgtggc aagtccccca gtgactgctg ccacaaccag tgtgctgcag      960
gctgcacagg cccccgggag agcgactgcc tggtctgccg caaattccga gacgaagcca     1020
cgtgcaagga cacctgcccc ccactcatgc tctacaaccc caccacgtac cagatggatg     1080
tgaaccccga gggcaaatac agctttggtg ccacctgcgt gaagaagtgt ccccgtaatt     1140
atgtggtgac agatcacggc tcgtgcgtcc gagcctgtgg ggccgacagc tatgagatgg     1200
aggaagacgg cgtccgcaag tgtaagaagt gcgaagggcc ttgccgcaaa gtgtgtaacg     1260
gaataggtat tggtgaattt aaagactcac tctccataaa tgctacgaat attaaacact     1320
tcaaaaactg cacctccatc agtggcgatc tccacatcct gccggtggca tttaggggtg     1380
actccttcac acatactcct cctctggatc cacaggaact ggatattctg aaaaccgtaa     1440
aggaaatcac agggtttttg ctgattcagg cttggcctga aaacaggacg gacctccatg     1500
cctttgagaa cctagaaatc atacgcgcag ggaccaagca acatggtcag ttttctcttg     1560
cagtcgtcag cctgaacata acatccttgg gattacgctc cctcaaggag ataagtgatg     1620
gagatgtgat aatttcagga aacaaaaatt tgtgctatgc aaatacaata aactggaaaa     1680
aactgttttgg gacctccggt cagaaaacca aaattataag caacagaggt gaaaacagct     1740
gcaaggccac aggccaggtc tgccatgcct tgtgctcccc cgagggctgc tggggcccgg     1800
agcccaggga ctgcgtctct tgccggaatg tcagccgagg cagggaatgc gtggacaagt     1860
gcaaccttct ggagggtgag ccaagggagt ttgtggagaa ctctgagtgc atacagtgcc     1920
acccagagtg cctgcctcag gccatgaaca tcacctgcac aggacgggga ccagacaact     1980
gtatccagtg tgcccactac attgacggcc cccactgcgt caagacctgc ccggcaggag     2040
tcatgggaga aaacaacacc ctggtctgga agtacgcaga cgccggccat gtgtgccacc     2100
tgtgccatcc aaactgcacc tacgatgca ctgggccagg tcttgaaggc tgtccaacga     2160
atgggcctaa gatcccgtcc atcgccactg ggatggtggg ggcctcctc ttgctgctgg     2220
tggtggccct ggggatcggc ctcttcatgc gaaggcgcca catcgttcgg aagcgcacgc     2280
tgcggaggct gctgcaggag agggagcttg tggagcctct tacacccagt ggagaagctc     2340
ccaaccaagc tctcttgagg atcttgaagg aaactgaatt caaaaagatc aaagtgctgg     2400
gctccggtgc gttcggcacg gtgtataagg gactctggat cccagaaggt gagaaagtta     2460
aaattcccgt cgctatcaaa acatctccga aagccaacaa ggaaatcctc gatgaagcct     2520
acgtgatggc cagcgtggac aacccccacg tgtgccgcct gctgggcatc tgcctcacct     2580
ccaccgtgca gctcatcacg cagctcatgc ccttcggctg cctcctggac tatgtccggg     2640
aacacaaaga caatattggc tcccagtacc tgctcaactg gtgtgtgcag atcgcaaagg     2700
gcatgaacta cttggaggac cgtcgcttgg tgcaccgcga cctggcagcc aggaacgtac     2760
tggtgaaaac accgcagcat gtcaagatca cagattttgg gctggccaaa ctgctgggtg     2820
cggaagagaa agaataccat gcagaaggag gcaaagtgcc tatcaagtgg atggcattgg     2880
aatcaatttt acacagaatc tatacccacc agagtgatgt ctggagctac ggggtgactg     2940
tttgggagtt gatgaccttt ggatccaagc catatgacgg aatccctgcc agcgagatct     3000
cctccatcct ggagaaagga gaacgcctcc ctcagccacc catatgtacc atcgatgtct     3060
```

```
acatgatcat ggtcaagtgc tggatgatag acgcagatag tcgcccaaag ttccgtgagt    3120
tgatcatcga attctccaaa atggcccgag accccagcg ctaccttgtc attcaggggg    3180
atgaaagaat gcatttgcca agtcctacag actccaactt ctaccgtgcc ctgatggatg    3240
aagaagacat ggacgacgtg gtggatgccg acgagtacct catcccacag cagggcttct    3300
tcagcagccc ctccacgtca cggactcccc tcctgagctc tctgagtgca accagcaaca    3360
attccaccgt ggcttgcatt gatagaaatg ggctgcaaag ctgtcccatc aaggaagaca    3420
gcttcttgca gcgatacagc tcagacccca caggcgcctt gactgaggac agcatagacg    3480
acaccttcct cccagtgcct gaatacataa accagtccgt tcccaaaagg cccgctggct    3540
ctgtgcagaa tcctgtctat cacaatcagc ctctgaaccc cgcgcccagc agagacccac    3600
actaccagga cccccacagc actgcagtgg gcaaccccga gtatctcaac actgtccagc    3660
ccacctgtgt caacagcaca ttcgacagcc ctgcccactg ggcccagaaa ggcagccacc    3720
aaattagcct ggacaaccct gactaccagc aggacttctt tcccaaggaa gccaagccaa    3780
atggcatctt taagggctcc acagctgaaa atgcagaata cctaagggtc gcgccacaaa    3840
gcagtgaatt tattggagca tga                                           3863

<210> SEQ ID NO 429
<211> LENGTH: 3863
<212> TYPE: DNA
<213> ORGANISM: Homo sapiens

<400> SEQUENCE: 429
cccggcgcag cgcggccgca gcagcctccg ccccccgcac ggtgtgagcg cccgacgcgg      60
ccgaggcggc cggagtcccg agctagcccc ggcggccgcc gccgcccaga ccggacgaca     120
ggccacctcg tcggcgtccg cccgagtccc cgcctcgccg ccaacgccac aaccaccgcg     180
cacggccccc tgactccgtc cagtattgat cgggagagcc ggagcgagct cttcggggag     240
cagcgatgcg accctccggg acggccgggg cagcgctcct ggcgctgctg gctgcgctct     300
gcccggcgag tcgggctctg gaggaaaaga aagtttgcca aggcacgagt aacaagctca     360
cgcagttggg cacttttgaa gatcattttc tcagcctcca gaggatgttc aataactgtg     420
aggtggtcct tgggaatttg gaaattacct atgtgcagag gaattatgat cttccttct       480 taaagaccat ccaggaggtg gctggttatg tcctcattgc cctcaacaca gtggagcgaa     540
ttcctttgga aaacctgcag atcatcagag gaaatatgta ctacgaaaat tcctatgcct     600
tagcagtctt atctaactat gatgcaaata aaaccggact gaaggagctg cccatgagaa     660
atttacagga atcctgcat ggcgccgtgc ggttcagcaa caaccctgcc ctgtgcaacg      720
tggagagcat ccagtggcgg acatagtca gcagtgactt tctcagcaac atgtcgatgg       780
acttccagaa ccacctgggc agctgccaaa agtgtgatcc aagctgtccc aatgggagct     840
gctggggtgc aggagaggag aactgccaga aactgaccaa aatcatctgt gcccagcagt     900
gctccgggcg ctgccgtggc aagtccccca gtgactgctg ccacaaccag tgtgctgcag     960
gctgcacagg ccccccggag agcgactgcc tggtctgccg caaattccga gacgaagcca    1020
cgtgcaagga cacctgcccc ccactcatgc tctacaaccc caccacgtac cagatggatg    1080
tgaaccccga gggcaaatac agctttggtg ccacctgcgt gaagaagtgt ccccgtaatt    1140
atgtggtgac agatcacggc tcgtgcgtcc gagcctgtgg ggccgacagc tatgagatgg    1200
aggaagacgg cgtccgcaag tgtaagaagt gcgaagggcc ttgccgcaaa gtgtgtaacg    1260
```

```
gaataggtat tggtgaattt aaagactcac tctccataaa tgctacgaat attaaacact    1320
tcaaaaactg cacctccatc agtggcgatc tccacatcct gccggtggca tttaggggtg    1380
actccttcac acatactcct cctctggatc cacaggaact ggatattctg aaaaccgtaa    1440
aggaaatcac agggtttttg ctgattcagg cttggcctga aaacaggacg gacctccatg    1500
cctttgagaa cctagaaatc atacgcggca ggaccaagca acatggtcag ttttctcttg    1560
cagtcgtcag cctgaacata acatccttgg gattacgctc cctcaaggag ataagtgatg    1620
gagatgtgat aatttcagga aacaaaaatt tgtgctatgc aaatacaata aactggaaaa    1680
aactgtttgg gacctccggt cagaaaacca aaattataag caacagaggt gaaaacagct    1740
gcaaggccac aggccaggtc tgccatgcct tgtgctcccc cgagggctgc tggggcccgg    1800
agcccaggga ctgcgtctct tgccggaatg tcagccgagg cagggaatgc gtggacaagt    1860
gcaaccttct ggagggtgag ccaagggagt ttgtggagaa ctctgagtgc atacagtgcc    1920
acccagagtg cctgcctcag gccatgaaca tcacctgcac aggacgggga ccagacaact    1980
gtatccagtg tgcccactac attgacggcc cccactgcgt caagacctgc ccggcaggag    2040
tcatgggaga aaacaacacc ctggtctgga gtacgcaga cgccggccat gtgtgccacc    2100
tgtgccatcc aaactgcacc tacgatgca ctgggccagg tcttgaaggc tgtccaacga    2160
atgggcctaa gatcccgtcc atcgccactg ggatggtggg ggccctcctc ttgctgctgg    2220
tggtggccct ggggatcggc ctcttcatgc gaaggcgcca catcgttcgg aagcgcacgc    2280
tgcggaggct gctgcaggag agggagcttg tggagcctct tacacccagt ggagaagctc    2340
ccaaccaagc tctcttgagg atcttgaagg aaactgaatt caaaaagatc aaagtgctgg    2400
gctccggtgc gttcggcacg gtgtataagg actctggat cccagaaggt gagaaagtta    2460
aaattcccgt cgctatcaaa acatctccga agccaacaa ggaaatcctc gatgaagcct    2520
acgtgatggc cagcgtggac aaccccacg tgtgccgcct gctgggcatc tgcctcacct    2580
ccaccgtgca gctcatcacg cagctcatgc ccttcggctg cctcctggac tatgtccggg    2640
aacacaaaga caatattggc tcccagtacc tgctcaactg gtgtgtgcag atcgcaaagg    2700
gcatgaacta cttggaggac cgtcgcttgg tgcaccgcga cctggcagcc aggaacgtac    2760
tggtgaaaac accgcagcat gtcaagatca cagattttgg gctggccaaa ctgctgggtg    2820
cggaagagaa agaataccat gcagaaggag gcaaagtgcc tatcaagtgg atggcattgg    2880
aatcaatttt acacagaatc tatacccacc agagtgatgt ctggagctac ggggtgactg    2940
tttgggagtt gatgaccttt ggatccaagc catatgacgg aatccctgcc agcgagatct    3000
cctccatcct ggagaaagga gaacgcctcc ctcagccacc catatgtacc atcgatgtct    3060
acatgatcat ggtcaagtgc tggatgatag acgcagatag tcgcccaaag ttccgtgagt    3120
tgatcatcga attctccaaa atggcccgag acccccagcg ctaccttgtc attcaggggg    3180
atgaaagaat gcatttgcca agtcctacag actccaactt ctaccgtgcc ctgatggatg    3240
aagaagacat ggacgacgtg gtggatgccg acgagtacct catcccacag cagggcttct    3300
tcagcagccc ctccacgtca cggactcccc tcctgagctc tctgagtgca accagcaaca    3360
attccaccgt ggcttgcatt gatagaaatg ggctgcaaag ctgtcccatc aaggaagaca    3420
gcttcttgca gcgatacagc tcagacccca caggcgcctt gactgaggac agcatagacg    3480
acaccttcct cccagtgcct gaatacataa accagtccgt tcccaaaagg cccgctggct    3540
ctgtgcagaa tcctgtctat cacaatcagc ctctgaaccc cgcgcccagc agagacccac    3600
actaccagga cccccacagc actgcagtgg gcaaccccga gtatctcaac actgtccagc    3660
```

| | | | |
|---|---|---|---|
| ccacctgtgt | caacagcaca | ttcgacagcc ctgcccactg ggcccagaaa ggcagccacc | 3720 |
| aaattagcct | ggacaaccct | gactaccagc aggacttctt tcccaaggaa gccaagccaa | 3780 |
| atggcatctt | taagggctcc | acagctgaaa atgcagaata cctaagggtc gcgccacaaa | 3840 |
| gcagtgaatt | tattggagca | tga | 3863 |

<210> SEQ ID NO 430
<211> LENGTH: 3863
<212> TYPE: DNA
<213> ORGANISM: Homo sapiens

<400> SEQUENCE: 430

| | | | |
|---|---|---|---|
| cccggcgcag | cgcggccgca | gcagcctccg ccccccgcac ggtgtgagcg cccgacgcgg | 60 |
| ccgaggcggc | cggagtcccg | agctagcccc ggcggccgcc gccgcccaga ccggacgaca | 120 |
| ggccacctcg | tcggcgtccg | cccgagtccc cgcctcgccg ccaacgccac aaccaccgcg | 180 |
| cacggccccc | tgactccgtc | cagtattgat cgggagagcc ggagcgagct cttcggggag | 240 |
| cagcgatgcg | accctccggg | acggccgggg cagcgctcct ggcgctgctg gctgcgctct | 300 |
| gcccggcgag | tcgggctctg | gaggaaaaga agtttgccca aggcacgagt aacaagctca | 360 |
| cgcagttggg | cacttttgaa | gatcattttc tcagcctcca gaggatgttc aataactgtg | 420 |
| aggtggtcct | tgggaatttg | gaaattacct atgtgcagag gaattatgat cttccttct | 480 |
| taaagaccat | ccaggaggtg | gctggttatg tcctcattgc cctcaacaca gtggagcgaa | 540 |
| ttcctttgga | aaacctgcag | atcatcgaga gaaatatgta ctacgaaaat tcctatgcct | 600 |
| tagcagtctt | atctaactat | gatgcaaata aaaccggact gaaggagctg cccatgagaa | 660 |
| atttacagga | aatcctgcat | ggcgccgtgc ggttcagcaa caaccctgcc ctgtgcaacg | 720 |
| tggagagcat | ccagtggcgg | gacatagtca gcagtgactt tctcagcaac atgtcgatgg | 780 |
| acttccagaa | ccacctgggc | agctgccaaa agtgtgatcc aagctgtccc aatggggagct | 840 |
| gctgggggtgc | aggagaggag | aactgccaga aactgaccaa aatcatctgt gcccagcagt | 900 |
| gctccgggcg | ctgccgtggc | aagtccccca gtgactgctg ccacaaccag tgtgctgcag | 960 |
| gctgcacagg | cccccgggag | agcgactgcc tggtctgccg caaattccga gacgaagcca | 1020 |
| cgtgcaagga | cacctgcccc | ccactcatgc tctacaaccc caccacgtac cagatggatg | 1080 |
| tgaaccccga | gggcaaatac | agctttggtg ccacctgcgt gaagaagtgt ccccgtaatt | 1140 |
| atgtggtgac | agatcacggc | tcgtgcgtcc gagcctgtgg ggccgacagc tatgagatgg | 1200 |
| aggaagacgg | cgtccgcaag | tgtaagaagt gcgaagggcc ttgccgcaaa gtgtgtaacg | 1260 |
| gaataggtat | tggtgaattt | aaagactcac tctccataaa tgctacgaat attaaacact | 1320 |
| tcaaaaactg | cacctccatc | agtggcgatc tccacatcct gccggtggca tttaggggtg | 1380 |
| actccttcac | acatactcct | cctctggatc cacaggaact ggatattctg aaaaccgtaa | 1440 |
| aggaaatcac | agggtttttg | ctgattcagg cttggcctga aaacaggacg gacctccatg | 1500 |
| cctttgagaa | cctagaaatc | atacgcggca ggaccaagca acatggtcag ttttctcttg | 1560 |
| cagtcgtcag | cctgaacata | acatccttgg gattacgctc cctcaaggag ataagtgatg | 1620 |
| gagatgtgat | aatttcagga | aacaaaaatt tgtgctatgc aaatacaata aactggaaaa | 1680 |
| aactgtttgg | gacctccggt | cagaaaacca aaattataag caacagaggt gaaaacagct | 1740 |
| gcaaggccac | aggccaggtc | tgccatgcct tgtgctcccc cgagggctgc tggggcccgg | 1800 |
| agcccaggga | ctgcgtctct | tgccggaatg tcagccgagg cagggaatgc gtggacaagt | 1860 |

```
gcaaccttct ggagggtgag ccaagggagt ttgtggagaa ctctgagtgc atacagtgcc   1920
acccagagtg cctgcctcag gccatgaaca tcacctgcac aggacgggga ccagacaact   1980
gtatccagtg tgcccactac attgacggcc cccactgcgt caagacctgc ccggcaggag   2040
tcatgggaga aaacaacacc ctggtctgga agtacgcaga cgccggccat gtgtgccacc   2100
tgtgccatcc aaactgcacc tacggatgca ctgggccagg tcttgaaggc tgtccaacga   2160
atgggcctaa gatcccgtcc atcgccactg ggatggtggg ggccctcctc ttgctgctgg   2220
tggtggccct ggggatcggc ctcttcatgc gaaggcgcca catcgttcgg aagcgcacgc   2280
tgcggaggct gctgcaggag agggagcttg tggagcctct tacacccagt ggagaagctc   2340
ccaaccaagc tctcttgagg atcttgaagg aaactgaatt caaaaagatc aaagtgctgg   2400
gctccggtgc gttcggcacg tgtataagg actctggat cccagaaggt gagaaagtta   2460
aaattcccgt cgctatcaaa acatctccga aagccaacaa ggaaatcctc gatgaagcct   2520
acgtgatggc cagcgtggac aacccccacg tgtgccgcct gctgggcatc tgcctcacct   2580
ccaccgtgca gctcatcacg cagctcatgc ccttcggctg cctcctggac tatgtccggg   2640
aacacaaaga caatattggc tcccagtacc tgctcaactg gtgtgtgcag atcgcaaagg   2700
gcatgaacta cttggaggac gtcgcttgg tgcaccgcga cctggcagcc aggaacgtac   2760
tggtgaaaac accgcagcat gtcaagatca cagattttgg gctggccaaa ctgctgggtg   2820
cggaagagaa agaataccat gcagaaggag gcaaagtgcc tatcaagtgg atggcattgg   2880
aatcaatttt acacagaatc tatacccacc agagtgatgt ctggagctac ggggtgactg   2940
tttgggagtt gatgaccttt ggatccaagc catatgacgg aatccctgcc agcgagatct   3000
cctccatcct ggagaaagga gaacgcctcc ctcagccacc catatgtacc atcgatgtct   3060
acatgatcat ggtcaagtgc tggatgatag acgcagatag tcgcccaaag ttccgtgagt   3120
tgatcatcga attctccaaa atggcccgag accccagcg ctaccttgtc attcagggg   3180 atgaaagaat gcatttgcca agtcctacag actccaactt ctaccgtgcc ctgatggatg   3240
aagaagacat ggacgacgtg gtggatgccg acgagtacct catcccacag cagggcttct   3300
tcagcagccc ctccacgtca cggactcccc tcctgagctc tctgagtgca accagcaaca   3360
attccaccgt ggcttgcatt gatagaaatg ggctgcaaag ctgtcccatc aaggaagaca   3420
gcttcttgca gcgatacagc tcagaccccca caggcgcctt gactgaggac agcatagacg   3480
acaccttcct cccagtgcct gaatacataa accagtccgt tcccaaaagg cccgctggct   3540
ctgtgcagaa tcctgtctat cacaatcagc ctctgaaccc cgcgcccagc agagacccac   3600
actaccagga cccccacagc actgcagtgg gcaaccccga gtatctcaac actgtccagc   3660
ccacctgtgt caacagcaca ttcgacagcc ctgcccactg ggcccagaaa ggcagccacc   3720
aaattagcct ggacaaccct gactaccagc aggacttctt tcccaaggaa gccaagccaa   3780
atggcatctt taagggctcc acagctgaaa atgcagaata cctaagggtc gcgccacaaa   3840
gcagtgaatt tattggagca tga                                          3863

<210> SEQ ID NO 431
<211> LENGTH: 3863
<212> TYPE: DNA
<213> ORGANISM: Homo sapiens

<400> SEQUENCE: 431
cccggcgcag cgcggccgca gcagcctccg ccccccgcac ggtgtgagcg cccgacgcgg     60
ccgaggcggc cggagtcccg agctagcccc ggcggccgcc gccgcccaga ccggacgaca    120
```

```
ggccacctcg tcggcgtccg cccgagtccc cgcctcgccg ccaacgccac aaccaccgcg    180
cacggccccc tgactccgtc cagtattgat cgggagagcc ggagcgagct cttcggggag    240
cagcgatgcg accctccggg acggccgggg cagcgctcct ggcgctgctg gctgcgctct    300
gcccggcgag tcgggctctg gaggaaaaga agtttgccaa aggcacgagt aacaagctca    360
cgcagttggg cacttttgaa gatcattttc tcagcctcca gaggatgttc aataactgtg    420
aggtggtcct tgggaatttg gaaattacct atgtgcagag gaattatgat cttctcttct    480
taaagaccat ccaggaggtg gctggttatg tcctcattgc cctcaacaca gtggagcgaa    540
ttcctttgga aaacctgcag atcatcagag gaaatatgta ctacgaaaat tcctatgcct    600
tagcagtctt atctaactat gatgcaaata aaaccggact gaaggagctg cccatgagaa    660
atttacagga aatcctgcat ggcgccgtgc ggttcagcaa caaccctgcc ctgtgcaacg    720
tggagagcat ccagtggcgg gacatagtca gcagtgactt tctcagcaac atgtcgatgg    780
acttccagaa ccacctgggc agctgccaaa agtgtgatcc aagctgtccc aatgggagct    840
gctggggtgc aggagaggag aactgccaga aactgaccaa aatcatctgt gcccagcagt    900
gctccgggcg ctgccgtggc aagtccccca gtgactgctg ccacaaccag tgtgctgcag    960
gctgcacagg ccccgggag agcgactgcc tggtctgccg caaattccga gacgaagcca   1020
cgtgcaagga cacctgcccc ccactcatgc tctacaaccc caccacgtac cagatggatg   1080
tgaaccccga gggcaaatac agctttggtg ccacctgcgt gaagaagtgt ccccgtaatt   1140
atgtggtgac agatcacggc tcgtgcgtcc gagcctgtgg ggccgacagc tatgagatgg   1200
aggaagacgg cgtccgcaag tgtaagaagt gcgaagggcc ttgccgcaaa gtgtgtaacg   1260
gaataggtat tggtgaattt aaagactcac tctccataaa tgctacgaat attaaacact   1320
tcaaaaactg cacctccatc agtggcgatc tccacatcct gccggtggca tttagggtg   1380 actccttcac acatactcct cctctggatc cacaggaact ggatattctg aaaaccgtaa   1440
aggaaatcac agggtttttg ctgattcagg cttggcctga aaacaggacg gacctccatg   1500
cctttgagaa cctagaaatc atacgcggca ggaccaagca acatggtcag ttttctcttg   1560
cagtcgtcag cctgaacata acatccttgg gattacgctc cctcaaggag ataagtgatg   1620
gagatgtgat aatttcagga aacaaaaatt tgtgctatgc aaatacaata aactggaaaa   1680
aactgtttgg gacctccggt cagaaaacca aaattataag caacagaggt gaaaacagct   1740
gcaaggccac aggccaggtc tgccatgcct tgtgctcccc cgagggctgc tggggcccgg   1800
agcccaggga ctgcgtctct tgccggaatg tcagccgagg cagggaatgc gtggacaagt   1860
gcaaccttct ggagggtgag ccaagggagt ttgtggagaa ctctgagtgc atacagtgcc   1920
acccagagtg cctgcctcag gccatgaaca tcacctgcac aggacgggga ccagacaact   1980
gtatccagtg tgcccactac attgacggcc ccactgcgt caagacctgc ccggcaggag   2040
tcatgggaga aaacaacacc ctggtctgga agtacgcaga cgccggccat gtgtgccacc   2100
tgtgccatcc aaactgcacc tacggatgca ctgggccagg tcttgaaggc tgtccaacga   2160
atgggcctaa gatcccgtcc atcgccactg gatggtggg ggccctcctc ttgctgctgg   2220
tggtggccct ggggatcggc ctcttcatgc gaaggcgcca catcgttcgg aagcgcacgc   2280
tgcggaggct gctgcaggag agggagcttg tggagcctct tacacccagt ggagaagctc   2340
ccaaccaagc tctcttgagg atcttgaagg aaactgaatt caaaaagatc aaagtgctgg   2400
gctccggtgc gttcggcacg gtgtataagg gactctggat cccagaaggt gagaaagtta   2460
```

| | |
|---|---|
| aaattcccgt cgctatcaaa acatctccga aagccaacaa ggaaatcctc gatgaagcct | 2520 |
| acgtgatggc cagcgtggac aaccccacg tgtgccgcct gctgggcatc tgcctcacct | 2580 |
| ccaccgtgca gctcatcacg cagctcatgc ccttcggctg cctcctggac tatgtccggg | 2640 |
| aacacaaaga caatattggc tcccagtacc tgctcaactg gtgtgtgcag atcgcaaagg | 2700 |
| gcatgaacta cttggaggac cgtcgcttgg tgcaccgcga cctggcagcc aggaacgtac | 2760 |
| tggtgaaaac accgcagcat gtcaagatca cagattttgg gctggccaaa ctgctgggtg | 2820 |
| cggaagagaa agaataccat gcagaaggag gcaaagtgcc tatcaagtgg atggcattgg | 2880 |
| aatcaatttt acacagaatc tatcccacc agagtgatgt ctggagctac ggggtgactg | 2940 |
| tttgggagtt gatgaccttt ggatccaagc catatgacgg aatccctgcc agcgagatct | 3000 |
| cctccatcct ggagaaagga gaacgcctcc ctcagccacc catatgtacc atcgatgtct | 3060 |
| acatgatcat ggtcaagtgc tggatgatag acgcagatag tcgcccaaag ttccgtgagt | 3120 |
| tgatcatcga attctccaaa atggcccgag accccagcg ctaccttgtc attcagggg | 3180 |
| atgaaagaat gcatttgcca agtcctacag actccaactt ctaccgtgcc ctgatggatg | 3240 |
| aagaagacat ggacgacgtg gtggatgccg acgagtacct catcccacag cagggcttct | 3300 |
| tcagcagccc ctccacgtca cggactcccc tcctgagctc tctgagtgca ccagcaaca | 3360 |
| attccaccgt ggcttgcatt gatagaaatg ggctgcaaag ctgtcccatc aaggaagaca | 3420 |
| gcttcttgca gcgatacagc tcagacccca caggcgcctt gactgaggac agcatagacg | 3480 |
| acaccttcct cccagtgcct gaatacataa accagtccgt tcccaaaagg cccgctggct | 3540 |
| ctgtgcagaa tcctgtctat cacaatcagc ctctgaaccc cgcgcccagc agagacccac | 3600 |
| actaccagga cccccacagc actgcagtgg gcaaccccga gtatctcaac actgtccagc | 3660 |
| ccacctgtgt caacagcaca ttcgacagcc ctgcccactg ggcccagaaa ggcagccacc | 3720 |
| aaattagcct ggacaaccct gactaccagc aggacttctt tcccaaggaa gccaagccaa | 3780 |
| atggcatctt taagggctcc acagctgaaa atgcagaata cctaagggtc gcgccacaaa | 3840 |
| gcagtgaatt tattggagca tga | 3863 |

<210> SEQ ID NO 432
<211> LENGTH: 3863
<212> TYPE: DNA
<213> ORGANISM: Homo sapiens

<400> SEQUENCE: 432

| | |
|---|---|
| cccggcgcag cgcggccgca gcagcctccg ccccccgcac ggtgtgagcg cccgacgcgg | 60 |
| ccgaggcggc cggagtcccg agctagcccc ggcggccgcc gccgcccaga ccggacgaca | 120 |
| ggccacctcg tcggcgtccg cccgagtccc cgcctcgccg ccaacgccac aaccaccgcg | 180 |
| cacggccccc tgactccgtc cagtattgat cgggagagcc ggagcgagct cttcggggag | 240 |
| cagcgatgcg accctccggg acggccgggg cagcgctcct ggcgctgctg gctgcgctct | 300 |
| gcccggcgag tcgggctctg gaggaaaaga agtttgcca aggcacgagt aacaagctca | 360 |
| cgcagttggg cacttttgaa gatcattttc tcagcctcca gaggatgttc aataactgtg | 420 |
| aggtggtcct tgggaattg gaaattacct atgtgcagag gaattatgat ctttccttct | 480 |
| taaagaccat ccaggaggtg gctggttatg tcctcattgc cctcaacaca gtggagcgaa | 540 |
| ttcctttgga aaacctgcag atcatcagag gaaatatgta ctacgaaaat tcctatgcct | 600 |
| tagcagtctt atctaactat gatgcaaata aaaccggact gaaggagctg cccatgagaa | 660 |
| atttacagga atcctgcat ggcgccgtgc ggttcagcaa caaccctgcc ctgtgcaacg | 720 |

```
tggagagcat ccagtggcgg gacatagtca gcagtgactt tctcagcaac atgtcgatgg    780
acttccagaa ccacctgggc agctgccaaa agtgtgatcc aagctgtccc aatgggagct    840
gctggggtgc aggagaggag aactgccaga aactgaccaa aatcatctgt gcccagcagt    900
gctccgggcg ctgccgtggc aagtccccca gtgactgctg ccacaaccag tgtgctgcag    960
gctgcacagg cccccgggag agcgactgcc tggtctgccg caaattccga gacgaagcca   1020
cgtgcaagga cacctgcccc ccactcatgc tctacaaccc caccacgtac cagatggatg   1080
tgaaccccga gggcaaatac agctttggtg ccacctgcgt gaagaagtgt ccccgtaatt   1140
atgtggtgac agatcacggc tcgtgcgtcc gagcctgtgg ggccgacagc tatgagatgg   1200
aggaagacgg cgtccgcaag tgtaagaagt gcgaagggcc ttgccgcaaa gtgtgtaacg   1260
gaataggtat tggtgaattt aaagactcac tctccataaa tgctacgaat attaaacact   1320
tcaaaaactg cacctccatc agtggcgatc tccacatcct gccggtggca tttaggggtg   1380
actccttcac acatactcct cctctggatc cacaggaact ggatattctg aaaaccgtaa   1440
aggaaatcac agggttttg ctgattcagg cttggcctga aaacaggacg gacctccatg   1500
cctttgagaa cctagaaatc atacgcggca ggaccaagca acatggtcag ttttctcttg   1560
cagtcgtcag cctgaacata acatccttgg gattacgctc cctcaaggag ataagtgatg   1620
gagatgtgat aatttcagga aacaaaaatt tgtgctatgc aaatacaata aactggaaaa   1680
aactgtttgg gacctccggt cagaaaacca aaattataag caacagaggt gaaaacagct   1740
gcaaggccac aggccaggtc tgccatgcct tgtgctcccc cgagggctgc tggggcccgg   1800
agcccaggga ctgcgtctct tgccggaatg tcagccgagc agggaatgc gtggacaagt   1860 gcaaccttct ggagggtgag ccaagggagt tgtggagaa ctctgagtgc atacagtgcc   1920
acccagagtg cctgcctcag gccatgaaca tcacctgcac aggacgggga ccagacaact   1980
gtatccagtg tgcccactac attgacggcc cccactgcgt caagacctgc ccggcaggag   2040
tcatgggaga aacaacacc ctggtctgga agtacgcaga cgccggccat gtgtgccacc   2100
tgtgccatcc aaactgcacc tacgatgca ctgggccagg tcttgaaggc tgtccaacga   2160
atgggcctaa gatcccgtcc atcgccactg ggatggtggg ggccctcctc ttgctgctgg   2220
tggtggccct ggggatcggc ctcttcatgc gaaggcgcca catcgttcgg aagcgcacgc   2280
tgcggaggct gctgcaggag agggagcttg tggagcctct tacacccagt ggagaagctc   2340
ccaaccaagc tctcttgagg atcttgaagg aaactgaatt caaaaagatc aaagtgctgg   2400
gctccggtgc gttcggcacg gtgtataagg gactctggat cccagaaggt gagaaagtta   2460
aaattcccgt cgctatcaaa acatctccga aagccaacaa ggaaatcctc gatgaagcct   2520
acgtgatggc cagcgtggac aaccccacg tgtgccgcct gctgggcatc tgcctcacct   2580
ccaccgtgca gctcatcacg cagctcatgc ccttcggctg cctcctggac tatgtccggg   2640
aacacaaaga caatattggc tcccagtacc tgctcaactg gtgtgtgcag atcgcaaagg   2700
gcatgaacta cttggaggac gtcgcttgg tgcaccgcga cctggcagcc aggaacgtac   2760
tggtgaaaac accgcagcat gtcaagatca cagattttgg gctggccaaa ctgctgggtg   2820
cggaagagaa agaataccat gcagaaggag gcaaagtgcc tatcaagtgg atggcattgg   2880
aatcaatttt acacagaatc tatcccacc agagtgatgt ctggagctac ggggtgactg   2940
tttgggagtt gatgacctt ggatccaagc catatgacgg aatccctgcc agcgagatct   3000
cctccatcct ggagaaagga gaacgcctcc ctcagccacc catatgtacc atcgatgtct   3060
```

| | |
|---|---|
| acatgatcat ggtcaagtgc tggatgatag acgcagatag tcgcccaaag ttccgtgagt | 3120 |
| tgatcatcga attctccaaa atggcccgag accccagcg ctaccttgtc attcaggggg | 3180 |
| atgaaagaat gcatttgcca agtcctacag actccaactt ctaccgtgcc ctgatggatg | 3240 |
| aagaagacat ggacgacgtg gtggatgccg acgagtacct catcccacag cagggcttct | 3300 |
| tcagcagccc ctccacgtca cggactcccc tcctgagctc tctgagtgca accagcaaca | 3360 |
| attccaccgt ggcttgcatt gatagaaatg ggctgcaaag ctgtcccatc aaggaagaca | 3420 |
| gcttcttgca gcgatacagc tcagacccca caggcgcctt gactgaggac agcatagacg | 3480 |
| acaccttcct cccagtgcct gaatacataa accagtccgt tcccaaaagg cccgctggct | 3540 |
| ctgtgcagaa tcctgtctat cacaatcagc ctctgaaccc cgcgcccagc agagacccac | 3600 |
| actaccagga cccccacagc actgcagtgg gcaaccccga gtatctcaac actgtccagc | 3660 |
| ccacctgtgt caacagcaca ttcgacagcc ctgcccactg ggcccagaaa ggcagccacc | 3720 |
| aaattagcct ggacaaccct gactaccagc aggacttctt tcccaaggaa gccaagccaa | 3780 |
| atggcatctt taagggctcc acagctgaaa atgcagaata cctaagggtc gcgccacaaa | 3840 |
| gcagtgaatt tattggagca tga | 3863 |

<210> SEQ ID NO 433
<211> LENGTH: 3863
<212> TYPE: DNA
<213> ORGANISM: Homo sapiens

<400> SEQUENCE: 433

| | |
|---|---|
| cccggcgcag cgcggccgca gcagcctccg cccccccgcac ggtgtgagcg cccgacgcgg | 60 |
| ccgaggcggc cggagtcccg agctagcccc ggcggccgcc gccgcccaga ccggacgaca | 120 |
| ggccacctcg tcgcgtccg cccgagtccc cgcctcgccg ccaacgccac aaccaccgcg | 180 |
| cacggccccc tgactccgtc cagtattgat cgggagagcc ggagcgagct cttcggggag | 240 |
| cagcgatgcg accctccggg acggccgggg cagcgctcct ggcgctgctg gctgcgctct | 300 |
| gcccggcgag tcgggctctg gaggaaaaga aagtttgcca aggcacgagt aacaagctca | 360 |
| cgcagttggg cacttttgaa gatcattttc tcagcctcca gaggatgttc ataactgtg | 420 |
| aggtggtcct tgggaatttg gaaattacct atgtgcagag gaattatgat cttccttct | 480 |
| taaagaccat ccaggaggtg gctggttatg tcctcattgc cctcaacaca gtggagcgaa | 540 |
| ttcctttgga aaacctgcag atcatcagag gaaatatgta ctacgaaaat tcctatgcct | 600 |
| tagcagtctt atctaactat gatgcaaata aaaccggact gaaggagctg cccatgagaa | 660 |
| atttacagga atcctgcat ggcgccgtgc ggttcagcaa caaccctgcc ctgtgcaacg | 720 |
| tggagagcat ccagtggcgg gacatagtca gcagtgactt tctcagcaac atgtcgatgg | 780 |
| acttccagaa ccacctgggc agctgccaaa agtgtgatcc aagctgtccc aatgggagct | 840 |
| gctggggtgc aggagaggag aactgccaga actgaccaa atcatctgt gcccagcagt | 900 |
| gctccgggcg ctgccgtggc aagtccccca gtgactgctg ccacaaccag tgtgctgcag | 960 |
| gctgcacagg ccccgggag agcgactgcc tggtctgccg caaattccga gacgaagcca | 1020 |
| cgtgcaagga cacctgcccc ccactcatgc tctacaaccc caccacgtac cagatggatg | 1080 |
| tgaaccccga gggcaaatac agctttggtg ccacctgcgt gaagaagtgt ccccgtaatt | 1140 |
| atgtggtgac agatcacggc tcgtgcgtcc gagcctgtgg ggccgacagc tatgagatgg | 1200 |
| aggaagacgg cgtccgcaag tgtaagaagt gcgaagggcc ttgccgcaaa gtgtgtaacg | 1260 |
| gaataggtat tggtgaattt aaagactcac tctccataaa tgctacgaat attaaacact | 1320 |

```
tcaaaaactg cacctccatc agtggcgatc tccacatcct gccggtggca tttaggggtg    1380
actccttcac acatactcct cctctggatc cacaggaact ggatattctg aaaaccgtaa    1440
aggaaatcac agggtttttg ctgattcagg cttggcctga aaacaggacg gacctccatg    1500
cctttgagaa cctagaaatc atacgcggca ggaccaagca acatggtcag ttttctcttg    1560
cagtcgtcag cctgaacata acatccttgg gattacgctc cctcaaggag ataagtgatg    1620
gagatgtgat aatttcagga aacaaaaatt tgtgctatgc aaatacaata aactggaaaa    1680
aactgtttgg gacctccggt cagaaaacca aaattataag caacagaggt gaaaacagct    1740
gcaaggccac aggccaggtc tgccatgcct tgtgctcccc cgagggctgc tggggcccgg    1800
agcccaggga ctgcgtctct tgccggaatg tcagccgagg cagggaatgc gtggacaagt    1860
gcaaccttct ggagggtgag ccaagggagt tgtggagaa ctctgagtgc atacagtgcc    1920
acccagagtg cctgcctcag gccatgaaca tcacctgcac aggacgggga ccagacaact    1980
gtatccagtg tgcccactac attgacggcc cccactgcgt caagacctgc ccggcaggag    2040
tcatgggaga aaacaacacc ctggtctgga gtacgcaga cgccggccat gtgtgccacc    2100
tgtgccatcc aaactgcacc tacgatgca ctgggccagg tcttgaaggc tgtccaacga    2160
atgggcctaa gatcccgtcc atcgccactg ggatggtggg ggcctcctc ttgctgctgg    2220 tggtggccct ggggatcggc ctcttcatgc gaaggcgcca catcgttcgg aagcgcacgc    2280
tgcggaggct gctgcaggag agggagcttg tggagcctct tacacccagt ggagaagctc    2340
ccaaccaagc tctcttgagg atcttgaagg aaactgaatt caaaaagatc aaagtgctgg    2400
gctccggtgc gttcggcacg gtgtataagg gactctggat cccagaaggt gagaaagtta    2460
aaattcccgt cgctatcaaa acatctccga aagccaacaa ggaaatcctc gatgaagcct    2520
acgtgatggc cagcgtggac aacccccacg tgtgccgcct gctgggcatc tgcctcacct    2580
ccaccgtgca gctcatcacg cagctcatgc ccttcggctg cctcctggac tatgtccggg    2640
aacacaaaga caatattggc tcccagtacc tgctcaactg gtgtgtgcag atcgcaaagg    2700
gcatgaacta cttggaggac gtcgcttgg tgcaccgcga cctggcagcc aggaacgtac    2760
tggtgaaaac accgcagcat gtcaagatca cagattttgg gctggccaaa ctgctgggtg    2820
cggaagagaa agaataccat gcagaaggag gcaaagtgcc tatcaagtgg atggcattgg    2880
aatcaatttt acacagaatc tatcccacc agagtgatgt ctggagctac ggggtgactg    2940
tttgggagtt gatgaccttt ggatccaagc catatgacgg aatccctgcc agcgagatct    3000
cctccatcct ggagaaagga gaacgcctcc ctcagccacc catatgtacc atcgatgtct    3060
acatgatcat ggtcaagtgc tggatgatag acgcagatag tcgcccaaag ttccgtgagt    3120
tgatcatcga attctccaaa atggcccgag accccagcg ctaccttgtc attcagggga    3180
atgaaagaat gcatttgcca agtcctacag actccaactt ctaccgtgcc ctgatggatg    3240
aagaagacat ggacgacgtg gtggatgccg acgagtacct catcccacag cagggcttct    3300
tcagcagccc ctccacgtca cggactcccc tcctgagctc tctgagtgca accagcaaca    3360
attccaccgt ggcttgcatt gatagaaatg ggctgcaaag ctgtcccatc aaggaagaca    3420
gcttcttgca gcgatacagc tcagaccccca caggcgcctt gactgaggac agcatagacg    3480
acaccttcct cccagtgcct gaatacataa accagtccgt tcccaaaagg cccgctggct    3540
ctgtgcagaa tcctgtctat cacaatcagc ctctgaaccc cgcgcccagc agagacccac    3600
actaccagga cccccacagc actgcagtgg gcaaccccga gtatctcaac actgtccagc    3660
```

-continued

| | |
|---|---|
| ccacctgtgt caacagcaca ttcgacagcc ctgcccactg ggcccagaaa ggcagccacc | 3720 |
| aaattagcct ggacaaccct gactaccagc aggacttctt tcccaaggaa gccaagccaa | 3780 |
| atggcatctt taagggctcc acagctgaaa atgcagaata cctaagggtc gcgccacaaa | 3840 |
| gcagtgaatt tattggagca tga | 3863 |

<210> SEQ ID NO 434
<211> LENGTH: 3863
<212> TYPE: DNA
<213> ORGANISM: Homo sapiens

<400> SEQUENCE: 434

| | |
|---|---|
| cccggcgcag cgcggccgca gcagcctccg ccccccgcac ggtgtgagcg cccgacgcgg | 60 |
| ccgaggcggc cggagtcccg agctagcccc ggcggccgcc gccgcccaga ccggacgaca | 120 |
| ggccacctcg tcggcgtccg cccgagtccc cgcctcgccg ccaacgccac aaccaccgcg | 180 |
| cacggccccc tgactccgtc cagtattgat cgggagagcc ggagcgagct cttcggggag | 240 |
| cagcgatgcg accctccggg acggccgggg cagcgctcct ggcgctgctg gctgcgctct | 300 |
| gcccggcgag tcgggctctg gaggaaaaga agtttgccaa aggcacgagt aacaagctca | 360 |
| cgcagttggg cacttttgaa gatcattttc tcagcctcca gaggatgttc ataactgtg | 420 |
| aggtggtcct tgggaatttg gaaattacct atgtgcagag gaattatgat cttccttct | 480 |
| taaagaccat ccaggaggtg gctggttatg tcctcattgc cctcaacaca gtggagcgaa | 540 |
| ttcctttgga aaacctgcag atcatcagag gaaatatgta ctacgaaaat tcctatgcct | 600 |
| tagcagtctt atctaactat gatgcaaata aaaccggact gaaggagctg cccatgagaa | 660 |
| atttacagga atcctgcat ggcgccgtgc ggttcagcaa caaccctgcc ctgtgcaacg | 720 |
| tggagagcat ccagtggcgg gacatagtca gcagtgactt tctcagcaac atgtcgatgg | 780 |
| acttccagaa ccacctgggc agctgccaaa agtgtgatcc aagctgtccc aatgggagct | 840 |
| gctggggtgc aggagaggag aactgccaga aactgaccaa aatcatctgt gcccagcagt | 900 |
| gctccgggcg ctgccgtggc aagtcccca gtgactgctg ccacaaccag tgtgctgcag | 960 |
| gctgcacagg ccccgggag agcgactgcc tggtctgccg caaattccga gacgaagcca | 1020 |
| cgtgcaagga cacctgcccc ccactcatgc tctacaaccc caccacgtac cagatggatg | 1080 |
| tgaaccccga gggcaaatac agctttggtg ccacctgcgt gaagaagtgt ccccgtaatt | 1140 |
| atgtggtgac agatcacggc tcgtgcgtcc gagcctgtgg ggccgacagc tatgagatgg | 1200 |
| aggaagacgg cgtccgcaag tgtaagaagt gcgaagggcc ttgccgcaaa gtgtgtaacg | 1260 |
| gaataggtat tggtgaattt aaagactcac tctccataaa tgctacgaat attaaacact | 1320 |
| tcaaaaactg cacctccatc agtggcgatc tccacatcct gccggtggca tttaggggtg | 1380 |
| actccttcac acatactcct cctctggatc cacaggaact ggatattctg aaaaccgtaa | 1440 |
| aggaaatcac agggttttg ctgattcagg cttggcctga aaacaggacg gacctccatg | 1500 |
| cctttgagaa cctagaaatc atacgcggca ggaccaagca acatggtcag ttttctcttg | 1560 |
| cagtcgtcag cctgaacata acatccttgg gattacgctc cctcaaggag ataagtgatg | 1620 |
| gagatgtgat aatttcagga aacaaaaatt tgtgctatgc aaatacaata aactggaaaa | 1680 |
| aactgtttgg gacctccggt cagaaaacca aaattataag caacagaggt gaaaacagct | 1740 |
| gcaaggccac aggccaggtc tgccatgcct tgtgctcccc cgagggctgc tggggcccgg | 1800 |
| agcccaggga ctgcgtctct tgccggaatg tcagccgagg cagggaatgc gtggacaagt | 1860 |
| gcaaccttct ggagggtgag ccaagggagt ttgtggagaa ctctgagtgc atacagtgcc | 1920 |

```
acccagagtg cctgcctcag gccatgaaca tcacctgcac aggacgggga ccagacaact    1980
gtatccagtg tgcccactac attgacggcc cccactgcgt caagacctgc ccggcaggag    2040
tcatgggaga aaacaacacc ctggtctgga agtacgcaga cgccggccat gtgtgccacc    2100
tgtgccatcc aaactgcacc tacgatgca ctgggccagg tcttgaaggc tgtccaacga    2160
atgggcctaa gatcccgtcc atcgccactg ggatggtggg ggccctcctc ttgctgctgg    2220
tggtggccct ggggatcggc ctcttcatgc gaaggcgcca catcgttcgg aagcgcacgc    2280
tgcggaggct gctgcaggag agggagcttg tggagcctct tacacccagt ggagaagctc    2340
ccaaccaagc tctcttgagg atcttgaagg aaactgaatt caaaaagatc aaagtgctgg    2400
gctccggtgc gttcggcacg gtgtataagg actctggat cccagaaggt gagaaagtta    2460
aaattcccgt cgctatcaag acatctccga agccaacaa ggaaatcctc gatgaagcct    2520
acgtgatggc cagcgtggac aaccccacg tgtgccgcct gctgggcatc tgcctcacct    2580
ccaccgtgca gctcatcacg cagctcatgc ccttcggctg cctcctggac tatgtccggg    2640
aacacaaaga caatattggc tcccagtacc tgctcaactg gtgtgtgcag atcgcaaagg    2700
gcatgaacta cttggaggac cgtcgcttgg tgcaccgcga cctggcagcc aggaacgtac    2760
tggtgaaaac accgcagcat gtcaagatca cagattttgg gctggccaaa ctgctgggtg    2820
cggaagagaa agaataccat gcagaaggag gcaaagtgcc tatcaagtgg atggcattgg    2880
aatcaatttt acacagaatc tatacccacc agagtgatgt ctggagctac ggggtgactg    2940
tttgggagtt gatgaccttt ggatccaagc catatgacgg aatccctgcc agcgagatct    3000
cctccatcct ggagaaagga gaacgcctcc ctcagccacc catatgtacc atcgatgtct    3060
acatgatcat ggtcaagtgc tggatgatag acgcagatag tcgcccaaag ttccgtgagt    3120
tgatcatcga attctccaaa atggcccgag acccccagcg ctaccttgtc attcaggggg    3180
atgaaagaat gcatttgcca agtcctacag actccaactt ctaccgtgcc ctgatggatg    3240
aagaagacat ggacgacgtg gtggatgccg acgagtacct catcccacag cagggcttct    3300
tcagcagccc ctccacgtca cggactcccc tcctgagctc tctgagtgca accagcaaca    3360
attccaccgt ggcttgcatt gatagaaatg ggctgcaaag ctgtcccatc aaggaagaca    3420
gcttcttgca gcgatacagc tcagacccca caggcgcctt gactgaggac agcatagacg    3480
acaccttcct cccagtgcct gaatacataa accagtccgt tcccaaaagg cccgctggct    3540
ctgtgcagaa tcctgtctat cacaatcagc ctctgaaccc cgcgcccagc agagacccac    3600
actaccagga ccccccacagc actgcagtgg caaccccga gtatctcaac actgtccagc    3660
ccacctgtgt caacagcaca ttcgacagcc ctgcccactg ggcccagaaa ggcagccacc    3720
aaattagcct ggacaaccct gactaccagc aggacttctt tcccaaggaa gccaagccaa    3780
atggcatctt taagggctcc acagctgaaa atgcagaata cctaagggtc gcgccacaaa    3840
gcagtgaatt tattggagca tga                                            3863
```

<210> SEQ ID NO 435
<211> LENGTH: 3863
<212> TYPE: DNA
<213> ORGANISM: Homo sapiens

<400> SEQUENCE: 435

```
cccggcgcag cgcggccgca gcagcctccg cccccccgcac ggtgtgagcg cccgacgcgg      60
ccgaggcggc cggagtcccg agctagcccc ggcggccgcc gccgcccaga ccggacgaca     120
```

```
ggccacctcg tcggcgtccg cccgagtccc cgcctcgccg ccaacgccac aaccaccgcg    180
cacggccccc tgactccgtc cagtattgat cgggagagcc ggagcgagct cttcggggag    240
cagcgatgcg accctccggg acggccgggg cagcgctcct ggcgctgctg gctgcgctct    300
gcccggcgag tcgggctctg gaggaaaaga aagtttgcca aggcacgagt aacaagctca    360
cgcagttggg cacttttgaa gatcattttc tcagcctcca gaggatgttc aataactgtg    420
aggtggtcct tgggaatttg gaaattacct atgtgcagag gaattatgat cttcccttct    480
taaagaccat ccaggaggtg gctggttatg tcctcattgc cctcaacaca gtggagcgaa    540
ttcctttgga aaacctgcag atcatcagag gaaatatgta ctacgaaaat tcctatgcct    600
tagcagtctt atctaactat gatgcaaata aaaccggact gaaggagctg cccatgagaa    660
atttacagga atcctgcat ggcgccgtgc ggttcagcaa caaccctgcc ctgtgcaacg    720
tggagagcat ccagtggcgg gacatagtca gcagtgactt tctcagcaac atgtcgatgg    780
acttccagaa ccacctgggc agctgccaaa agtgtgatcc aagctgtccc aatgggagct    840
gctggggtgc aggagaggag aactgccaga aactgaccaa aatcatctgt gcccagcagt    900
gctcggggcg ctgccgtggc aagtcccca gtgactgctg ccacaaccag tgtgctgcag    960
gctgcacagg ccccgggag agcgactgcc tggtctgccg caaattccga gacgaagcca    1020
cgtgcaagga cacctgcccc ccactcatgc tctacaaccc caccacgtac cagatggatg    1080
tgaaccccga gggcaaatac agctttggtg ccacctgcgt gaagaagtgt ccccgtaatt    1140
atgtggtgac agatcacggc tcgtgcgtcc gagcctgtgg ggccgacagc tatgagatgg    1200
aggaagacgg cgtccgcaag tgtaagaagt gcgaagggcc ttgccgcaaa gtgtgtaacg    1260
gaataggtat tggtgaattt aaagactcac tctccataaa tgctacgaat attaaacact    1320
tcaaaaactg cacctccatc agtggcgatc tccacatcct gccggtggca tttaggggtg    1380
actccttcac acatactcct cctctggatc cacaggaact ggatattctg aaaaccgtaa    1440
aggaaatcac agggttttg ctgattcagg cttggcctga aaacaggacg gacctccatg    1500
cctttgagaa cctagaaatc atacgcggca ggaccaagca acatggtcag ttttctcttg    1560
cagtcgtcag cctgaacata acatccttgg gattacgctc cctcaaggag ataagtgatg    1620
gagatgtgat aatttcagga aacaaaaatt tgtgctatgc aaatacaata aactggaaaa    1680
aactgtttgg gacctccggt cagaaaacca aaattataag caacagaggt gaaaacagct    1740
gcaaggccac aggccaggtc tgccatgcct tgtgctcccc cgagggctgc tggggcccgg    1800
agcccaggga ctgcgtctct tgccggaatg tcagccgagg cagggaatgc gtggacaagt    1860
gcaaccttct ggagggtgag ccaagggagt ttgtggagaa ctctgagtgc atacagtgcc    1920
acccagagtg cctgcctcag gccatgaaca tcacctgcac aggacgggga ccagacaact    1980
gtatccagtg tgcccactac attgacggcc ccactgcgt caagacctgc ccggcaggag    2040
tcatgggaga aaacaacacc ctggtctgga agtacgcaga cgccggccat gtgtgccacc    2100
tgtgccatcc aaactgcacc tacgatgca ctgggccagg tcttgaaggc tgtccaacga    2160
atgggcctaa gatcccgtcc atcgccactg gatggtggg ggccctcctc ttgctgctgg    2220
tggtggccct ggggatcggc ctcttcatgc gaaggcgcca catcgttcgg aagcgcacgc    2280
tgcggaggct gctgcaggag agggagcttg tggagcctct acacccagt ggagaagctc    2340 ccaaccaagc tctcttgagg atcttgaagg aaactgaatt caaaaagatc aaagtgctgg    2400
gctccggtgc gttcggcacg gtgtataagg gactctggat cccagaaggt gagaaagtta    2460
aaattcccgt cgctatcaag acatctccga aagccaacaa ggaaatcctc gatgaagcct    2520
```

```
acgtgatggc cagcgtggac aaccccccacg tgtgccgcct gctgggcatc tgcctcacct    2580
ccaccgtgca gctcatcacg cagctcatgc ccttcggctg cctcctggac tatgtccggg    2640
aacacaaaga caatattggc tcccagtacc tgctcaactg gtgtgtgcag atcgcaaagg    2700
gcatgaacta cttggaggac cgtcgcttgg tgcaccgcga cctggcagcc aggaacgtac    2760
tggtgaaaac accgcagcat gtcaagatca cagattttgg gctggccaaa ctgctgggtg    2820
cggaagagaa agaataccat gcagaaggag gcaaagtgcc tatcaagtgg atggcattgg    2880
aatcaatttt acacagaatc tatacccacc agagtgatgt ctggagctac ggggtgactg    2940
tttgggagtt gatgaccttt ggatccaagc catatgacgg aatccctgcc agcgagatct    3000
cctccatcct ggagaaagga gaacgcctcc ctcagccacc catatgtacc atcgatgtct    3060
acatgatcat ggtcaagtgc tggatgatag acgcagatag tcgcccaaag ttccgtgagt    3120
tgatcatcga attctccaaa atggcccgag accccagcg ctaccttgtc attcagggg     3180 atgaaagaat gcatttgcca agtcctacag actccaactt ctaccgtgcc ctgatggatg    3240
aagaagacat ggacgacgtg gtggatgccg acgagtacct catcccacag cagggcttct    3300
tcagcagccc ctccacgtca cggactcccc tcctgagctc tctgagtgca ccagcaaca    3360 attccaccgt ggcttgcatt gatagaaatg ggctgcaaag ctgtcccatc aaggaagaca    3420
gcttcttgca gcgatacagc tcagacccca caggcgcctt gactgaggac agcatagacg    3480
acaccttcct cccagtgcct gaatacataa accagtccgt tcccaaaagg cccgctggct    3540
ctgtgcagaa tcctgtctat cacaatcagc ctctgaaccc cgcgcccagc agagacccac    3600
actaccagga ccccacagc actgcagtgg gcaaccccga gtatctcaac actgtccagc    3660
ccacctgtgt caacagcaca ttcgacagcc ctgcccactg ggcccagaaa ggcagccacc    3720
aaattagcct ggacaacccct gactaccagc aggacttctt tccaaggaa gccaagccaa    3780 atggcatctt taagggctcc acagctgaaa atgcagaata cctaagggtc gcgccacaaa    3840
gcagtgaatt tattggagca tga                                            3863
```

<210> SEQ ID NO 436
<211> LENGTH: 3863
<212> TYPE: DNA
<213> ORGANISM: Homo sapiens

<400> SEQUENCE: 436

```
cccggcgcag cgcggccgca gcagcctccg cccccgcac ggtgtgagcg cccgacgcgg       60
ccgaggcggc cggagtcccg agctagcccc ggcggccgcc gccgcccaga ccggacgaca     120
ggccacctcg tcggcgtccg cccgagtccc cgcctcgccg ccaacgccac aaccaccgcg     180
cacgcccccc tgactccgtc cagtattgat cgggagagcc ggagcgagct cttcggggag     240
cagcgatgcg accctccggg acggccgggg cagcgctcct ggcgctgctg gctgcgctct     300
gcccggcgag tcgggctctg gaggaaaaga agtttgccca aggcacgagt aacaagctca     360
cgcagttggg cacttttgaa gatcattttc tcagcctcca gaggatgttc aataactgtg     420
aggtggtcct tgggaatttg gaaattacct atgtgcagag gaattatgat ctttccttct     480
taaagaccat ccaggaggtg gctggttatg tcctcattgc cctcaacaca gtggagcgaa     540
ttcctttgga aaacctgcag atcatcagag gaaatatgta ctacgaaaat tcctatgcct     600
tagcagtctt atctaactat gatgcaaata aaaccggact gaaggagctg cccatgagaa     660
atttacagga atcctgcat ggcgccgtgc ggttcagcaa caaccctgcc ctgtgcaacg     720
```

```
tggagagcat ccagtggcgg gacatagtca gcagtgactt tctcagcaac atgtcgatgg    780
acttccagaa ccacctgggc agctgccaaa agtgtgatcc aagctgtccc aatgggagct    840
gctggggtgc aggagaggag aactgccaga aactgaccaa aatcatctgt gcccagcagt    900
gctccgggcg ctgccgtggc aagtccccca gtgactgctg ccacaaccag tgtgctgcag    960
gctgcacagg cccccgggag agcgactgcc tggtctgccg caaattccga gacgaagcca   1020
cgtgcaagga cacctgcccc ccactcatgc tctacaaccc caccacgtac cagatggatg   1080
tgaaccccga gggcaaatac agctttggtg ccacctgcgt gaagaagtgt ccccgtaatt   1140
atgtggtgac agatcacggc tcgtgcgtcc gagcctgtgg ggccgacagc tatgagatgg   1200
aggaagacgg cgtccgcaag tgtaagaagt gcgaagggcc ttgccgcaaa gtgtgtaacg   1260
gaataggtat tggtgaattt aaagactcac tctccataaa tgctacgaat attaaacact   1320
tcaaaaactg cacctccatc agtggcgatc tccacatcct gccggtggca tttaggggtg   1380
actccttcac acatactcct cctctggatc cacaggaact ggatattctg aaaaccgtaa   1440
aggaaatcac agggttttg ctgattcagg cttggcctga aaacaggacg gacctccatg   1500
cctttgagaa cctagaaatc atacgcggca ggaccaagca acatggtcag ttttctcttg   1560
cagtcgtcag cctgaacata acatccttgg gattacgctc cctcaaggag ataagtgatg   1620
gagatgtgat aatttcagga aacaaaaatt tgtgctatgc aaatacaata aactggaaaa   1680
aactgtttgg gacctccggt cagaaaacca aaattataag caacagaggt gaaaacagct   1740
gcaaggccac aggccaggtc tgccatgcct tgtgctcccc cgagggctgc tggggcccgg   1800
agcccaggga ctgcgtctct tgccggaatg tcagccgagg cagggaatgc gtggacaagt   1860
gcaaccttct ggagggtgag ccaagggagt ttgtggagaa ctctgagtgc atacagtgcc   1920
acccagagtg cctgcctcag gccatgaaca tcacctgcac aggacgggga ccagacaact   1980
gtatccagtg tgcccactac attgacggcc ccactgcgt caagacctgc ccggcaggag   2040
tcatgggaga aaacaacacc ctggtctgga agtacgcaga cgccggccat gtgtgccacc   2100
tgtgccatcc aaactgcacc tacggatgca ctgggccagg tcttgaaggc tgtccaacga   2160
atgggcctaa gatcccgtcc atcgccactg ggatggtggg ggccctcctc ttgctgctgg   2220
tggtggccct ggggatcggc ctcttcatgc gaaggcgcca catcgttcgg aagcgcacgc   2280
tgcggaggct gctgcaggag agggagcttg tggagcctct tacacccagt ggagaagctc   2340
ccaaccaagc tctcttgagg atcttgaagg aaactgaatt caaaaagatc aaagtgctgg   2400
gctccggtgc gttcggcacg gtgtataagg actctggat cccagaaggt gagaaagtta   2460
aaattcccgt cgctatcaag acatctccga agccaacaa ggaaatcctc gatgaagcct   2520
acgtgatggc cagcgtggac aaccccacg tgtgccgcct gctgggcatc tgcctcacct   2580
ccaccgtgca gctcatcacg cagctcatgc ccttcggctg cctcctggac tatgtccggg   2640
aacacaaaga caatattggc tcccagtacc tgctcaactg gtgtgtgcag atcgcaaagg   2700
gcatgaacta cttggaggac gtcgcttgg tgcaccgcga cctggcagcc aggaacgtac   2760
tggtgaaaac accgcagcat gtcaagatca cagattttgg gctggccaaa ctgctgggtg   2820
cggaagagaa agaataccat gcagaaggag gcaaagtgcc tatcaagtgg atggcattgg   2880
aatcaatttt acacagaatc tatcccacc agagtgatgt ctggagctac ggggtgactg   2940
tttgggagtt gatgacctt ggatccaagc catatgacgg aatccctgcc agcgagatct   3000
cctccatcct ggagaaagga gaacgcctcc ctcagccacc catatgtacc atcgatgtct   3060
acatgatcat ggtcaagtgc tggatgatag acgcagatag tcgcccaaag ttccgtgagt   3120
```

```
tgatcatcga attctccaaa atggcccgag accccccagcg ctaccttgtc attcaggggg      3180
atgaaagaat gcatttgcca agtcctacag actccaactt ctaccgtgcc ctgatggatg      3240
aagaagacat ggacgacgtg gtggatgccg acgagtacct catcccacag cagggcttct      3300
tcagcagccc ctccacgtca cggactcccc tcctgagctc tctgagtgca accagcaaca      3360
attccaccgt ggcttgcatt gatagaaatg ggctgcaaag ctgtcccatc aaggaagaca      3420
gcttcttgca gcgatacagc tcagacccca caggcgcctt gactgaggac agcatagacg      3480
acaccttcct cccagtgcct gaatacataa accagtccgt tcccaaaagg cccgctggct      3540
ctgtgcagaa tcctgtctat cacaatcagc ctctgaaccc cgcgcccagc agagacccac      3600
actaccagga cccccacagc actgcagtgg gcaaccccga gtatctcaac actgtccagc      3660
ccacctgtgt caacagcaca ttcgacagcc ctgcccactg ggcccagaaa ggcagccacc      3720
aaattagcct ggacaaccct gactaccagc aggacttctt tcccaaggaa gccaagccaa      3780
atggcatctt taagggctcc acagctgaaa atgcagaata cctaagggtc gcgccacaaa      3840
gcagtgaatt tattggagca tga                                             3863

<210> SEQ ID NO 437
<211> LENGTH: 3854
<212> TYPE: DNA
<213> ORGANISM: Homo sapiens

<400> SEQUENCE: 437
cccggcgcag cgcggccgca gcagcctccg ccccccgcac ggtgtgagcg cccgacgcgg       60
ccgaggcggc cggagtcccg agctagcccc ggcggccgcc gccgcccaga ccggacgaca      120
ggccacctcg tcggcgtccg cccgagtccc cgcctcgccg ccaacgccac aaccaccgcg      180
cacggccccc tgactccgtc cagtattgat cgggagagcc ggagcgagct cttcggggag      240
cagcgatgcg accctccggg acggccgggg cagcgctcct ggcgctgctg gctgcgctct      300
gcccggcgag tcgggctctg gaggaaaaga agtttgcca aggcacgagt aacaagctca      360
cgcagttggg cacttttgaa gatcattttc tcagcctcca gaggatgttc aataactgtg      420
aggtggtcct tgggaatttg gaaattacct atgtgcagag gaattatgat ctttccttct      480
taaagaccat ccaggaggtg gctggttatg tcctcattgc cctcaacaca gtggagcgaa      540
ttcctttgga aaacctgcag atcatcagag gaaatatgta ctacgaaaat tcctatgcct      600
tagcagtctt atctaactat gatgcaaata aaccggact gaaggagctg cccatgagaa      660
atttacagga atcctgcat ggcgccgtgc ggttcagcaa caccctgcc ctgtgcaacg      720
tggagagcat ccagtggcgg gacatagtca gcagtgactt tctcagcaac atgtcgatgg      780
acttccagaa ccacctgggc agctgccaaa agtgtgatcc aagctgtccc aatgggagct      840
gctggggtgc aggagaggag aactgccaga aactgaccaa aatcatctgt gcccagcagt      900
gctccgggcg ctgccgtggc aagtccccca gtgactgctg ccacaaccag tgtgctgcag      960
gctgcacagg ccccgggag agcgactgcc tggtctgccg caaattccga gacgaagcca     1020
cgtgcaagga cacctgcccc ccactcatgc tctacaaccc caccacgtac cagatggatg     1080
tgaaccccga gggcaaatac agctttggtg ccacctgcgt gaagaagtgt ccccgtaatt     1140
atgtggtgac agatcacggc tcgtgcgtcc gagcctgtgg ggccgacagc tatgagatgg     1200
aggaagacgt cgtccgcaag tgtaagaagt gcgaagggcc ttgccgcaaa gtgtgtaacg     1260
gaataggtat tggtgaattt aaagactcac tctccataaa tgctacgaat attaaacact     1320
```

```
tcaaaaactg cacctccatc agtggcgatc tccacatcct gccggtggca tttagggtg      1380 actccttcac acatactcct cctctggatc cacaggaact ggatattctg aaaaccgtaa     1440
aggaaatcac agggttttg ctgattcagg cttggcctga aaacaggacg gacctccatg      1500
cctttgagaa cctagaaatc atacgcggca ggaccaagca acatggtcag ttttctcttg     1560
cagtcgtcag cctgaacata acatccttgg gattacgctc cctcaaggag ataagtgatg     1620
gagatgtgat aatttcagga aacaaaaatt tgtgctatgc aaatacaata aactggaaaa     1680
aactgtttgg gacctccggt cagaaaacca aaattataag caacagaggt gaaaacagct     1740
gcaaggccac aggccaggtc tgccatgcct tgtgctcccc cgagggctgc tggggcccgg     1800
agcccaggga ctgcgtctct tgccggaatg tcagccgagg cagggaatgc gtggacaagt     1860
gcaaccttct ggagggtgag ccaagggagt ttgtggagaa ctctgagtgc atacagtgcc     1920
acccagagtg cctgcctcag gccatgaaca tcacctgcac aggacgggga ccagacaact     1980
gtatccagtg tgcccactac attgacggcc cccactgcgt caagacctgc ccggcaggag     2040
tcatgggaga aaacaacacc ctggtctgga gtacgcagag cgccggccat gtgtgccacc     2100
tgtgccatcc aaactgcacc tacggatgca ctgggccagg tcttgaaggc tgtccaacga     2160
atgggcctaa gatcccgtcc atcgccactg ggatggtggg ggccctcctc ttgctgctgg     2220
tggtggccct ggggatcggc ctcttcatgc gaaggcgcca catcgttcgg aagcgcacgc     2280
tgcggaggct gctgcaggag agggagcttg tggagcctct tacacccagt ggagaagctc     2340
ccaaccaagc tctcttgagg atcttgaagg aaactgaatt caaaaagatc aaagtgctgg     2400
gctccggtgc gttcggcacg gtgtataagg actctggat cccagaaggt gagaaagtta     2460
aaattcccgt cgctatcaag gaattaagag aagcaacact cgatgaagcc tacgtgatgg     2520
ccagcgtgga caacccccac gtgtgccgcc tgctgggcat ctgcctcacc tccaccgtgc     2580
agctcatcac gcagctcatg cccttcggct gcctcctgga ctatgtccgg gaacacaaag     2640
acaatattgg ctcccagtac ctgctcaact ggtgtgtgca gatcgcaaag ggcatgaact     2700
acttggagga ccgtcgcttg gtgcaccgcg acctggcagc caggaacgta ctggtgaaaa     2760
caccgcagca tgtcaagatc acagattttg gctggccaa actgctgggt gcggaagaga     2820
aagaatacca tgcagaagga ggcaaagtgc ctatcaagtg gatggcattg gaatcaattt     2880
tacacagaat ctatacccac cagagtgatg tctggagcta cggggtgact gtttgggagt     2940
tgatgacctt tggatccaag ccatatgacg gaatccctgc cagcgagatc tcctccatcc     3000
tggagaaagg agaacgcctc cctcagccac ccatatgtac catcgatgtc tacatgatca     3060
tggtcaagtg ctggatgata gacgcagata gtcgcccaaa gttccgtgag ttgatcatcg     3120
aattctccaa aatggcccga gaccccagc gctaccttgt cattcagggg gatgaaagaa     3180
tgcatttgcc aagtcctaca gactccaact tctaccgtgc cctgatggat gaagaagaca     3240
tggacgacgt ggtggatgcc gacgagtacc tcatcccaca gcagggcttc ttcagcagcc     3300
cctccacgtc acggactccc ctcctgagct ctctgagtgc aaccagcaac aattccaccg     3360
tggcttgcat tgatagaaat gggctgcaaa gctgtcccat caaggaagac agcttcttgc     3420
agcgatacag ctcagacccc acaggcgcct tgactgagga cagcatagac gacaccttcc     3480
tcccagtgcc tgaatacata aaccagtccg ttcccaaaag gcccgctggc tctgtgcaga     3540
atcctgtcta tcacaatcag cctctgaacc ccgcgcccag cagagaccca cactaccagg     3600
accccacaca cactgcagtg ggcaacccg agtatctcaa cactgtccag cccacctgtg     3660
tcaacagcac attcgacagc cctgcccact gggcccagaa aggcagccac caaattagcc     3720
```

-continued

| | |
|---|---|
| tggacaaccc tgactaccag caggacttct ttcccaagga agccaagcca aatggcatct | 3780 |
| ttaagggctc cacagctgaa aatgcagaat acctaagggt cgcgccacaa agcagtgaat | 3840 |
| ttattggagc atga | 3854 |

<210> SEQ ID NO 438
<211> LENGTH: 3878
<212> TYPE: DNA
<213> ORGANISM: Homo sapiens

<400> SEQUENCE: 438

| | |
|---|---|
| cccggcgcag cgcggccgca gcagcctccg ccccccgcac ggtgtgagcg cccgacgcgg | 60 |
| ccgaggcggc cggagtcccg agctagcccc ggcggccgcc gccgcccaga ccggacgaca | 120 |
| ggccacctcg tcggcgtccg cccgagtccc cgcctcgccg ccaacgccac aaccaccgcg | 180 |
| cacggccccc tgactccgtc cagtattgat cgggagagcc ggagcgagct cttcggggag | 240 |
| cagcgatgcg accctccggg acggccgggg cagcgctcct ggcgctgctg gctgcgctct | 300 |
| gcccggcgag tcgggctctg aggaaaaga aagtttgcca aggcacgagt aacaagctca | 360 |
| cgcagttggg cacttttgaa gatcattttc tcagcctcca gaggatgttc aataactgtg | 420 |
| aggtggtcct tgggaatttg gaaattacct atgtgcagag gaattatgat cttttccttct | 480 |
| taaagaccat ccaggaggtg gctggttatg tcctcattgc cctcaacaca gtggagcgaa | 540 |
| ttcctttgga aaacctgcag atcatcagag gaaatatgta ctacgaaaat tcctatgcct | 600 |
| tagcagtctt atctaactat gatgcaaata aaaccggact gaaggagctg cccatgagaa | 660 |
| atttacagga atcctgcat ggcgccgtgc ggttcagcaa caaccctgcc ctgtgcaacg | 720 |
| tggagagcat ccagtggcgg gacatagtca gcagtgactt tctcagcaac atgtcgatgg | 780 |
| acttccagaa ccacctgggc agctgccaaa agtgtgatcc aagctgtccc aatgggagct | 840 |
| gctgggggtgc aggagaggag aactgccaga aactgaccaa atcatctgt gcccagcagt | 900 |
| gctccgggcg ctgccgtggc aagtccccca gtgactgctg ccacaaccag tgtgctgcag | 960 |
| gctgcacagg ccccgggag agcgactgcc tggtctgccg caaattccga gacgaagcca | 1020 |
| cgtgcaagga cacctgcccc ccactcatgc tctacaaccc caccacgtac cagatggatg | 1080 |
| tgaaccccga gggcaaatac agctttggtg ccacctgcgt gaagaagtgt ccccgtaatt | 1140 |
| atgtggtgac agatcacggc tcgtgcgtcc gagcctgtgg ggccgacagc tatgagatgg | 1200 |
| aggaagacgg cgtccgcaag tgtaagaagt gcgaagggcc ttgccgcaaa gtgtgtaacg | 1260 |
| gaataggtat tggtgaattt aaagactcac tctccataaa tgctacgaat attaaacact | 1320 |
| tcaaaaactg cacctccatc agtggcgatc tccacatcct gccggtggca tttaggggtg | 1380 |
| actccttcac acatactcct cctctggatc cacaggaact ggatattctg aaaaccgtaa | 1440 |
| aggaaatcac agggttttg ctgattcagg cttggcctga aaacaggacg gacctccatg | 1500 |
| cctttgagaa cctagaaatc atacgcggca ggaccaagca acatggtcag ttttctcttg | 1560 |
| cagtcgtcag cctgaacata acatccttgg gattacgctc cctcaaggag ataagtgatg | 1620 |
| gagatgtgat aatttcagga aacaaaaatt tgtgctatgc aaatacaata aactggaaaa | 1680 |
| aactgtttgg gacctccggt cagaaaacca aaattataag caacagaggt gaaaacagct | 1740 |
| gcaaggccac aggccaggtc tgccatgcct tgtgctcccc cgagggctgc tggggccgg | 1800 |
| agcccaggga ctgcgtctct tgccggaatg tcagccgagg cagggaatgc gtggacaagt | 1860 |
| gcaaccttct ggagggtgag ccaagggagt ttgtggagaa ctctgagtgc atacagtgcc | 1920 |

| | |
|---|---|
| acccagagtg cctgcctcag gccatgaaca tcacctgcac aggacgggga ccagacaact | 1980 |
| gtatccagtg tgcccactac attgacggcc cccactgcgt caagacctgc ccggcaggag | 2040 |
| tcatgggaga aaacaacacc ctggtctgga agtacgcaga cgccggccat gtgtgccacc | 2100 |
| tgtgccatcc aaactgcacc tacgatgca ctgggccagg tcttgaaggc tgtccaacga | 2160 |
| atgggcctaa gatcccgtcc atcgccactg ggatggtggg ggccctcctc ttgctgctgg | 2220 |
| tggtggccct ggggatcggc ctcttcatgc gaaggcgcca catcgttcgg aagcgcacgc | 2280 |
| tgcggaggct gctgcaggag agggagcttg tggagcctct tacacccagt ggagaagctc | 2340 |
| ccaaccaagc tctcttgagg atcttgaagg aaactgaatt caaaaagatc aaagtgctgg | 2400 |
| gctccggtgc gttcggcacg gtgtataagg gactctggat cccagaaggt gagaaagtta | 2460 |
| aaattcccgt cgctatcaag gaattaagag aagcaacatc tccgaaagcc aacaaggaaa | 2520 |
| tcctcgatga agcctacgtg atggccagcg tggacaaccc ccacgtgtgc cgcctgctgg | 2580 |
| gcatctgcct cacctccacc gtgcagctca tcacgcagct catgcccttc ggctgcctcc | 2640 |
| tggactatgt ccgggaacac aaagacaata ttggctccca gtacctgctc aactggtgtg | 2700 |
| tgcagatcgc aaagggcatg aactacttgg aggaccgtcg cttggtgcac cgcgacctgg | 2760 |
| cagccaggaa cgtactggtg aaaacaccgc agcatgtcaa gatcacagat tttgggcggg | 2820 |
| ccaaactgct gggtgcggaa gagaaagaat accatgcaga aggaggcaaa gtgcctatca | 2880 |
| agtggatggc attggaatca attttacaca gaatctatac ccaccagagt gatgtctgga | 2940 |
| gctacggggt gactgtttgg gagttgatga cctttggatc caagccatat gacggaatcc | 3000 |
| ctgccagcga gatctcctcc atcctggaga aggagaacg cctccctcag ccacccatat | 3060 |
| gtaccatcga tgtctacatg atcatggtca agtgctggat gatagacgca gatagtcgcc | 3120 |
| caaagttccg tgagttgatc atcgaattct ccaaaatggc ccgagacccc cagcgctacc | 3180 |
| ttgtcattca gggggatgaa agaatgcatt tgccaagtcc tacagactcc aacttctacc | 3240 |
| gtgccctgat ggatgaagaa gacatggacg acgtggtgga tgccgacgag tacctcatcc | 3300 |
| cacagcaggg cttcttcagc agcccctcca cgtcacggac tcccctcctg agctctctga | 3360 |
| gtgcaaccag caacaattcc accgtggctt gcattgatag aaatgggctg caaagctgtc | 3420 |
| ccatcaagga agacagcttc ttgcagcgat acagctcaga ccccacaggc gccttgactg | 3480 |
| aggacagcat agacgacacc ttcctcccag tgcctgaata cataaaccag tccgttccca | 3540 |
| aaaggcccgc tggctctgtg cagaatcctg tctatcacaa tcagcctctg aaccccgcgc | 3600 |
| ccagcagaga cccacactac caggaccccc acagcactgc agtgggcaac cccgagtatc | 3660 |
| tcaacactgt ccagcccacc tgtgtcaaca gcacattcga cagccctgcc cactgggccc | 3720 |
| agaaaggcag ccaccaaatt agcctggaca accctgacta ccagcaggac ttcttcccca | 3780 |
| aggaagccaa gccaaatggc atctttaagg ctccacagc tgaaaatgca gaatacctaa | 3840 |
| gggtcgcgcc acaaagcagt gaatttattg gagcatga | 3878 |

<210> SEQ ID NO 439
<211> LENGTH: 3878
<212> TYPE: DNA
<213> ORGANISM: Homo sapiens

<400> SEQUENCE: 439

| | |
|---|---|
| cccggcgcag cgcggccgca gcagcctccg cccccgcac ggtgtgagcg cccgacgcgg | 60 |
| ccgaggcggc cggagtcccg agctagcccc ggcggccgcc gccgcccaga ccggacgaca | 120 |
| ggccacctcg tcggcgtccg cccgagtccc cgcctcgccg ccaacgccac aaccaccgcg | 180 |

-continued

```
cacggccccc tgactccgtc cagtattgat cgggagagcc ggagcgagct cttcggggag   240
cagcgatgcg accctccggg acggccgggg cagcgctcct ggcgctgctg gctgcgctct   300
gcccggcgag tcgggctctg gaggaaaaga agtttgcca aggcacgagt aacaagctca    360
cgcagttggg cacttttgaa gatcattttc tcagcctcca gaggatgttc aataactgtg   420
aggtggtcct tgggaatttg gaaattacct atgtgcagag gaattatgat ctttccttct   480
taaagaccat ccaggaggtg gctggttatg tcctcattgc cctcaacaca gtggagcgaa   540
ttcctttgga aaacctgcag atcatcagag gaaatatgta ctacgaaaat tcctatgcct   600
tagcagtctt atctaactat gatgcaaata aaaccggact gaaggagctg cccatgagaa   660
atttacagga atcctgcat ggcgccgtgc ggttcagcaa caaccctgcc ctgtgcaacg     720
tggagagcat ccagtggcgg gacatagtca gcagtgactt tctcagcaac atgtcgatgg   780
acttccagaa ccacctgggc agctgccaaa agtgtgatcc aagctgtccc aatgggagct   840
gctggggtgc aggagaggag aactgccaga aactgaccaa aatcatctgt gcccagcagt   900
gctccgggcg ctgccgtggc aagtccccca gtgactgctg ccacaaccag tgtgctgcag   960
gctgcacagg ccccgggag agcgactgcc tggtctgccg caaattccga gacgaagcca   1020
cgtgcaagga cacctgcccc ccactcatgc tctacaaccc caccacgtac cagatggatg   1080
tgaaccccga gggcaaatac agctttggtg ccacctgcgt gaagaagtgt ccccgtaatt   1140
atgtggtgac agatacggc tcgtgcgtcc gagcctgtgg ggccgacagc tatgagatgg    1200
aggaagacgg cgtccgcaag tgtaagaagt gcgaagggcc ttgccgcaaa gtgtgtaacg   1260
gaataggtat tggtgaattt aaagactcac tctccataaa tgctacgaat attaaacact   1320
tcaaaaactg cacctccatc agtggcgatc tccacatcct gccggtggca tttaggggtg   1380
actccttcac acatactcct cctctggatc cacaggaact ggatattctg aaaaccgtaa   1440
aggaaatcac agggttttg ctgattcagg cttggcctga aaacaggacg gacctccatg    1500
cctttgagaa cctagaaatc atacgcggca ggaccaagca acatggtcag ttttctcttg   1560
cagtcgtcag cctgaacata acatccttgg gattacgctc cctcaaggag ataagtgatg   1620
gagatgtgat aatttcagga aacaaaaatt tgtgctatgc aaatacaata aactggaaaa   1680
aactgtttgg gacctccggt cagaaaacca aaattataag caacagaggt gaaaacagct   1740
gcaaggccac aggccaggtc tgccatgcct tgtgctcccc cgagggctgc tggggccegg   1800 agcccaggga ctgcgtctct tgccggaatg tcagccgagg cagggaatgc gtggacaagt   1860
gcaaccttct ggagggtgag ccaagggagt ttgtggagaa ctctgagtgc atacagtgcc   1920
acccagagtg cctgcctcag gccatgaaca tcacctgcac aggacgggga ccagacaact   1980
gtatccagtg tgcccactac attgacggcc ccactgcgt caagacctgc ccggcaggag    2040
tcatgggaga aaacaacacc ctggtctgga agtacgcaga cgccggccat gtgtgccacc   2100
tgtgccatcc aaactgcacc tacgatgca ctggccagg tcttgaaggc tgtccaacga    2160
atgggcctaa gatcccgtcc atcgccactg ggatggtggg ggcctcctc ttgctgctgg    2220 tggtggccct ggggatcggc ctcttcatgc gaaggcgcca catcgttcgg aagcgcacgc   2280
tgcggaggct gctgcaggag agggagcttg tggagcctct acacccagt ggagaagctc    2340 ccaaccaagc tctcttgagg atcttgaagg aaactgaatt caaaaagatc aaagtgctgg   2400
gctccggtgc gttcggcacg gtgtataagg gactctggat cccagaaggt gagaagtta    2460 aaattcccgt cgctatcaag gaattaagag aagcaacatc tccgaaagcc aacaaggaaa   2520
```

```
tcctcgatga agcctacgtg atggccagcg tggacaaccc ccacgtgtgc cgcctgctgg    2580
gcatctgcct cacctccacc gtgcagctca tcacgcagct catgcccttc ggctgcctcc    2640
tggactatgt ccgggaacac aaagacaata ttggctccca gtacctgctc aactggtgtg    2700
tgcagatcgc aaagggcatg aactacttgg aggaccgtcg cttggtgcac cgcgacctgg    2760
cagccaggaa cgtactggtg aaaacaccgc agcatgtcaa gatcacagat tttgggcggg    2820
ccaaactgct gggtgcggaa gagaaagaat accatgcaga aggaggcaaa gtgcctatca    2880
agtggatggc attggaatca attttacaca gaatctatac ccaccagagt gatgtctgga    2940
gctacggggt gactgtttgg gagttgatga cctttggatc caagccatat gacgaatcc    3000 ctgccagcga gatctcctcc atcctggaga aaggagaacg cctccctcag ccacccatat    3060
gtaccatcga tgtctacatg atcatggtca agtgctggat gatagacgca gatagtcgcc    3120
caaagttccg tgagttgatc atcgaattct ccaaaatggc ccgagacccc cagcgctacc    3180
ttgtcattca gggggatgaa agaatgcatt tgccaagtcc tacagactcc aacttctacc    3240
gtgccctgat ggatgaagaa gacatggacg acgtggtgga tgccgacgag tacctcatcc    3300
cacagcaggg cttcttcagc agcccctcca cgtcacggac tcccctcctg agctctctga    3360
gtgcaaccag caacaattcc accgtggctt gcattgatag aaatgggctg caaagctgtc    3420
ccatcaagga agacagcttc ttgcagcgat acagctcaga ccccacaggc gccttgactg    3480
aggacagcat agacgacacc ttcctcccag tgcctgaata cataaaccag tccgttccca    3540
aaaggcccgc tggctctgtg cagaatcctg tctatcacaa tcagcctctg aaccccgcgc    3600
ccagcagaga cccacactac caggaccccc acagcactgc agtgggcaac cccgagtatc    3660
tcaacactgt ccagcccacc tgtgtcaaca gcacattcga cagccctgcc cactgggccc    3720
agaaaggcag ccaccaaatt agcctggaca accctgacta ccagcaggac ttctttccca    3780
aggaagccaa gccaaatggc atctttaagg ctccacagc tgaaaatgca gaatacctaa    3840
gggtcgcgcc acaaagcagt gaatttattg gagcatga                            3878
```

<210> SEQ ID NO 440
<211> LENGTH: 3878
<212> TYPE: DNA
<213> ORGANISM: Homo sapiens

<400> SEQUENCE: 440

```
cccggcgcag cgcggccgca gcagcctccg cccccccgcac ggtgtgagcg cccgacgcgg     60
ccgaggcggc cggagtcccg agctagcccc ggcggccgcc gccgcccaga ccggacgaca    120
ggccacctcg tcggcgtccg cccgagtccc cgcctcgccg ccaacgccac aaccaccgcg    180
cacgcccccc tgactccgtc cagtattgat cgggagagcc ggagcgagct cttcggggag    240
cagcgatgcg accctccggg acggccgggg cagcgctcct ggcgctgctg gctgcgctct    300
gcccggcgag tcgggctctg gaggaaaaga aagtttgcca aggcacgagt aacaagctca    360
cgcagttggg cacttttgaa gatcattttc tcagcctcca gaggatgttc ataactgtg    420 aggtggtcct tgggaatttg gaaattacct atgtgcagag gaattatgat cttcccttct    480
taaagaccat ccaggaggtg gctggttatg tcctcattgc cctcaacaca gtggagcgaa    540
ttcctttgga aaacctgcag atcatcagag gaaatatgta ctacgaaaat tcctatgcct    600
tagcagtctt atctaactat gatgcaaata aaaccggact gaaggagctg cccatgagaa    660
atttacagga aatcctgcat ggcgccgtgc ggttcagcaa caacccgcc ctgtgcaacg    720 tggagagcat ccagtggcgg gacatagtca gcagtgactt tctcagcaac atgtcgatgg    780
```

```
acttccagaa ccacctgggc agctgccaaa agtgtgatcc aagctgtccc aatgggagct      840
gctggggtgc aggagaggag aactgccaga aactgaccaa aatcatctgt gcccagcagt      900
gctccgggcg ctgccgtggc aagtccccca gtgactgctg ccacaaccag tgtgctgcag      960
gctgcacagg cccccgggag agcgactgcc tggtctgccg caaattccga gacgaagcca     1020
cgtgcaagga cacctgcccc ccactcatgc tctacaaccc caccacgtac cagatggatg     1080
tgaaccccga gggcaaatac agctttggtg ccacctgcgt gaagaagtgt ccccgtaatt     1140
atgtggtgac agatcacggc tcgtgcgtcc gagcctgtgg ggccgacagc tatgagatgg     1200
aggaagacgg cgtccgcaag tgtaagaagt gcgaagggcc ttgccgcaaa gtgtgtaacg     1260
gaataggtat tggtgaattt aaagactcac tctccataaa tgctacgaat attaaacact     1320
tcaaaaactg cacctccatc agtggcgatc tccacatcct gccggtggca tttaggggtg     1380
actccttcac acatactcct cctctggatc cacaggaact ggatattctg aaaaccgtaa     1440
aggaaatcac agggttttg ctgattcagg cttggcctga aaacaggacg gacctccatg     1500
cctttgagaa cctagaaatc atacgcggca ggaccaagca acatggtcag ttttctcttg     1560
cagtcgtcag cctgaacata acatccttgg gattacgctc cctcaaggag ataagtgatg     1620
gagatgtgat aatttcagga aacaaaaatt tgtgctatgc aaatacaata aactggaaaa     1680 aactgttttgg gacctccggt cagaaaacca aaattataag caacagaggt gaaaacagct     1740
gcaaggccac aggccaggtc tgccatgcct tgtgctcccc cgagggctgc tggggcccgg     1800
agcccaggga ctgcgtctct tgccggaatg tcagccgagg cagggaatgc gtggacaagt     1860
gcaaccttct ggagggtgag ccaagggagt ttgtggagaa ctctgagtgc atacagtgcc     1920
acccagagtg cctgcctcag gccatgaaca tcacctgcac aggacgggga ccagacaact     1980
gtatccagtg tgcccactac attgacggcc cccactgcgt caagacctgc ccggcaggag     2040
tcatgggaga aaacaacacc ctggtctgga gtacgcaga cgccggccat gtgtgccacc     2100
tgtgccatcc aaactgcacc tacgatgca ctgggccagg tcttgaaggc tgtccaacga     2160
atgggcctaa gatcccgtcc atcgccactg ggatggtggg ggccctcctc ttgctgctgg     2220
tggtggccct ggggatcggc ctcttcatgc gaaggcgcca catcgttcgg aagcgcacgc     2280
tgcggaggct gctgcaggag agggagcttg tggagcctct tacacccagt ggagaagctc     2340
ccaaccaagc tctcttgagg atcttgaagg aaactgaatt caaaaagatc aaagtgctgg     2400
gctccggtgc gttcggcacg gtgtataagg gactctggat cccagaaggt gagaaagtta     2460
aaattcccgt cgctatcaag gaattaagag aagcaacatc tccgaaagcc aacaaggaaa     2520
tcctcgatga agcctacgtg atggccagcg tggacaaccc ccacgtgtgc cgcctgctgg     2580
gcatctgcct cacctccacc gtgcagctca tcacgcagct catgcccttc ggctgcctcc     2640
tggactatgt ccgggaacac aaagacaata ttggctccca gtacctgctc aactggtgtg     2700
tgcagatcgc aaagggcatg aactacttgg aggaccgtcg cttggtgcac cgcgacctgg     2760
cagccaggaa cgtactggtg aaaacaccgc agcatgtcaa gatcacagat tttgggcggg     2820
ccaaactgct gggtgcggaa gagaaagaat accatgcaga aggaggcaaa gtgcctatca     2880
agtggatggc attggaatca attttacaca gaatctatac ccaccagagt gatgtctgga     2940
gctacggggt gactgtttgg gagttgatga cctttggatc caagccatat gacggaatcc     3000
ctgccagcga gatctcctcc atcctggaga aggagaacg cctccctcag ccacccatat     3060
gtaccatcga tgtctacatg atcatggtca agtgctggat gatagacgca gatagtcgcc     3120
```

| | |
|---|---|
| caaagttccg tgagttgatc atcgaattct ccaaaatggc ccgagacccc cagcgctacc | 3180 |
| ttgtcattca gggggatgaa agaatgcatt tgccaagtcc tacagactcc aacttctacc | 3240 |
| gtgccctgat ggatgaagaa gacatggacg acgtggtgga tgccgacgag tacctcatcc | 3300 |
| cacagcaggg cttcttcagc agcccctcca cgtcacggac tcccctcctg agctctctga | 3360 |
| gtgcaaccag caacaattcc accgtggctt gcattgatag aaatgggctg caaagctgtc | 3420 |
| ccatcaagga agacagcttc ttgcagcgat acagctcaga ccccacaggc gccttgactg | 3480 |
| aggacagcat agacgacacc ttcctcccag tgcctgaata cataaaccag tccgttccca | 3540 |
| aaaggcccgc tggctctgtg cagaatcctg tctatcacaa tcagcctctg aaccccgcgc | 3600 |
| ccagcagaga cccacactac caggaccccc acagcactgc agtgggcaac cccgagtatc | 3660 |
| tcaacactgt ccagcccacc tgtgtcaaca gcacattcga cagccctgcc cactgggccc | 3720 |
| agaaaggcag ccaccaaatt agcctggaca accctgacta ccagcaggac ttctttccca | 3780 |
| aggaagccaa gccaaatggc atctttaagg gctccacagc tgaaaatgca gaatacctaa | 3840 |
| gggtcgcgcc acaaagcagt gaatttattg gagcatga | 3878 |

<210> SEQ ID NO 441
<211> LENGTH: 3869
<212> TYPE: DNA
<213> ORGANISM: Homo sapiens

<400> SEQUENCE: 441

| | |
|---|---|
| cccggcgcag cgcggccgca gcagcctccg ccccccgcac ggtgtgagcg cccgacgcgg | 60 |
| ccgaggcggc cggagtcccg agctagcccc ggcggccgcc gccgcccaga ccggacgaca | 120 |
| ggccacctcg tcggcgtccg cccgagtccc cgcctcgccg ccaacgccac aaccaccgcg | 180 |
| cacgcccccc tgactccgtc cagtattgat cgggagagcc ggagcgagct cttcggggag | 240 |
| cagcgatgcg accctccggg acggccgggg cagcgctcct ggcgctgctg gctgcgctct | 300 |
| gcccggcgag tcgggctctg gaggaaaaga aagtttgcca aggcacgagt aacaagctca | 360 |
| cgcagttggg cactttttgaa gatcattttc tcagcctcca gaggatgttc aataactgtg | 420 |
| aggtggtcct tgggaatttg gaaattacct atgtgcagag gaattatgat cttttccttct | 480 |
| taaagaccat ccaggaggtg gctggttatg tcctcattgc cctcaacaca gtggagcgaa | 540 |
| ttcctttgga aaacctgcag atcatcagag gaaatatgta ctacgaaaat tcctatgcct | 600 |
| tagcagtctt atctaactat gatgcaaata aaaccggact gaaggagctg cccatgagaa | 660 |
| atttacagga atcctgcat ggcgccgtgc ggttcagcaa caccctgcc ctgtgcaacg | 720 |
| tggagagcat ccagtggcgg gacatagtca gcagtgactt tctcagcaac atgtcgatgg | 780 |
| acttccagaa ccacctgggc agctgccaaa agtgtgatcc aagctgtccc aatgggagct | 840 |
| gctggggtgc aggagaggag aactgccaga aactgaccaa aatcatctgt gcccagcagt | 900 |
| gctcccgggcg ctgccgtggc aagtccccca gtgactgctg ccacaaccag tgtgctgcag | 960 |
| gctgcacagg ccccggagag agcgactgcc tggtctgccg caaattccga gacgaagcca | 1020 |
| cgtgcaagga cacctgcccc ccactcatgc tctacaaccc caccacgtac cagatggatg | 1080 |
| tgaaccccga gggcaaatac agctttggtg ccacctgcgt gaagaagtgt ccccgtaatt | 1140 |
| atgtggtgac agatcacggc tcgtgcgtcc gagcctgtgg ggccgacagc tatgagatgg | 1200 |
| aggaagacgg cgtccgcaag tgtaagaagt gcgaagggcc ttgccgcaaa gtgtgtaacg | 1260 |
| gaataggtat tggtgaattt aaagactcac tctccataaa tgctacgaat attaaacact | 1320 |
| tcaaaaactg cacctccatc agtggcgatc tccacatcct gccggtggca tttaggggtg | 1380 |

```
actccttcac acatactcct cctctggatc cacaggaact ggatattctg aaaaccgtaa    1440
aggaaatcac agggtttttg ctgattcagg cttggcctga aaacaggacg gacctccatg    1500
cctttgagaa cctagaaatc atacgcggca ggaccaagca acatggtcag ttttctcttg    1560
cagtcgtcag cctgaacata acatccttgg gattacgctc cctcaaggag ataagtgatg    1620
gagatgtgat aatttcagga aacaaaaatt tgtgctatgc aaatacaata aactggaaaa    1680
aactgtttgg gacctccggt cagaaaacca aaattataag caacagaggt gaaaacagct    1740
gcaaggccac aggccaggtc tgccatgcct tgtgctcccc cgagggctgc tggggcccgg    1800
agcccaggga ctgcgtctct tgccggaatg tcagccgagg cagggaatgc gtggacaagt    1860
gcaaccttct ggagggtgag ccaagggagt tgtggagaa ctctgagtgc atacagtgcc    1920
acccagagtg cctgcctcag gccatgaaca tcacctgcac aggacgggga ccagacaact    1980
gtatccagtg tgcccactac attgacggcc cccactgcgt caagacctgc ccggcaggag    2040
tcatgggaga aaacaacacc ctggtctgga agtacgcaga cgccggccat gtgtgccacc    2100
tgtgccatcc aaactgcacc tacggatgca ctgggccagg tcttgaaggc tgtccaacga    2160
atgggcctaa gatcccgtcc atcgccactg ggatggtggg ggccctcctc ttgctgctgg    2220
tggtggccct ggggatcggc ctcttcatgc gaaggcgcca catcgttcgg aagcgcacgc    2280
tgcggaggct gctgcaggag agggagcttg tggagcctct tacacccagt ggagaagctc    2340
ccaaccaagc tctcttgagg atcttgaagg aaactgaatt caaaaagatc aaagtgctgg    2400
gctccggtgc gttcggcacg gtgtataagg gactctggat cccagaaggt gagaaagtta    2460
aaattcccgt cgctatcaag gaaccaacat ctccgaaagc caacaaggaa atcctcgatg    2520
aagcctacgt gatggccagc gtggacaacc cccacgtgtg ccgcctgctg ggcatctgcc    2580
tcacctccac cgtgcagctc atcacgcagc tcatgccctt cggctgcctc ctggactatg    2640
tccgggaaca caaagacaat attggctccc agtacctgct caactggtgt gtgcagatcg    2700
caaagggcat gaactacttg gaggaccgtc gcttggtgca ccgcgacctg gcagccagga    2760
acgtactggt gaaaacaccg cagcatgtca gatacacaga ttttgggctg gccaaactgc    2820
tgggtgcgga agagaaagaa taccatgcag aaggaggcaa agtgcctatc aagtggatgg    2880
cattggaatc aattttacac agaatcatcta cccaccagag tgatgtctgg agctacgggg    2940
tgactgtttg ggagttgatg acctttggat ccaagccata tgacggaatc cctgccagcg    3000
agatctcctc catcctggag aaaggagaac gcctccctca gccacccata tgtaccatcg    3060
atgtctacat gatcatggtc aagtgctgga tgatagacgc agatagtcgc ccaaagttcc    3120
gtgagttgat catcgaattc tccaaaatgg cccgagaccc ccagcgctac cttgtcattc    3180
agggggatga aagaatgcat ttgccaagtc ctacagactc caacttctac cgtgccctga    3240
tggatgaaga agacatggac gacgtggtgg atgccgacga gtacctcatc ccacagcagg    3300
gcttcttcag cagcccctcc acgtcacgga ctcccctcct gagctctctg agtgcaacca    3360
gcaacaattc caccgtggct tgcattgata gaaatgggct gcaaagctgt cccatcaagg    3420
aagacagctt cttgcagcga tacagctcag accccacagg cgccttgact gaggacagca    3480
tagacgacac cttcctccca gtgcctgaat acataaacca gtccgttccc aaaaggcccg    3540
ctggctctgt gcagaatcct gtctatcaca atcagcctct gaaccccgcg cccagcagag    3600
acccacacta ccaggacccc cacagcactg cagtgggcaa ccccgagtat ctcaacactg    3660
tccagcccac ctgtgtcaac agcacattcg acagccctgc ccactgggcc cagaaaggca    3720
```

```
gccaccaaat tagcctggac aaccctgact accagcagga cttctttccc aaggaagcca    3780
agccaaatgg catctttaag ggctccacag ctgaaaatgc agaataccta agggtcgcgc    3840
cacaaagcag tgaatttatt ggagcatga                                      3869

<210> SEQ ID NO 442
<211> LENGTH: 3869
<212> TYPE: DNA
<213> ORGANISM: Homo sapiens

<400> SEQUENCE: 442
cccggcgcag cgcggccgca gcagcctccg ccccccgcac ggtgtgagcg cccgacgcgg      60
ccgaggcggc cggagtcccg agctagcccc ggcggccgcc gccgcccaga ccggacgaca     120
ggccacctcg tcggcgtccg cccgagtccc cgcctcgccg ccaacgccac aaccaccgcg     180
cacggccccc tgactccgtc cagtattgat cgggagagcc ggagcgagct cttcggggag     240
cagcgatgcg accctccggg acggccgggg cagcgctcct ggcgctgctg gctgcgctct     300
gcccggcgag tcgggctctg gaggaaaaga agtttgccca aggcacgagt aacaagctca     360
cgcagttggg cacttttgaa gatcattttc tcagcctcca gaggatgttc aataactgtg     420
aggtggtcct tgggaatttg gaaattacct atgtgcagag gaattatgat ctttccttct     480
taaagaccat ccaggaggtg gctggttatg tcctcattgc cctcaacaca gtggagcgaa     540
ttcctttgga aaacctgcag atcatcagag gaaatatgta ctacgaaaat cctatgcct      600 tagcagtctt atctaactat gatgcaaata aaaccggact gaaggagctg cccatgagaa     660
atttacagga atcctgcat ggcgccgtgc ggttcagcaa caaccctgcc ctgtgcaacg      720
tggagagcat ccagtggcgg gacatagtca gcagtgactt tctcagcaac atgtcgatgg     780
acttccagaa ccacctgggc agctgccaaa agtgtgatcc aagctgtccc aatgggagct     840
gctggggtgc aggagaggag aactgccaga actgaccaa atcatctgt gcccagcagt       900 gctccgggcg ctgccgtggc aagtccccca gtgactgctg ccacaaccag tgtgctgcag     960
gctgcacagg ccccgggag agcgactgcc tggtctgccg caaattccga gacgaagcca    1020
cgtgcaagga cacctgcccc ccactcatgc tctacaaccc caccacgtac cagatggatg    1080
tgaaccccga gggcaaatac agctttggtg ccacctgcgt gaagaagtgt ccccgtaatt    1140
atgtggtgac agatcacggc tcgtgcgtcc gagcctgtgg ggccgacagc tatgagatgg    1200
aggaagacgg cgtccgcaag tgtaagaagt gcgaagggcc ttgccgcaaa gtgtgtaacg    1260
gaataggtat tggtgaattt aaagactcac tctccataaa tgctacgaat attaaacact    1320
tcaaaaactg cacctccatc agtggcgatc tccacatcct gccggtggca tttagggggtg    1380 actccttcac acatactcct cctctggatc cacaggaact ggatattctg aaaaccgtaa    1440
aggaaatcac agggttttg ctgattcagg cttggcctga aaacaggacg gacctccatg     1500
cctttgagaa cctagaaatc atacgcggca ggaccaagca acatggtcag ttttctcttg    1560
cagtcgtcag cctgaacata acatccttgg gattacgctc cctcaaggag ataagtgatg    1620
gagatgtgat aatttcagga aacaaaaatt tgtgctatgc aaatacaata aactggaaaa    1680
aactgtttgg gacctccggt cagaaaacca aaattataag caacagaggt gaaaacagct    1740
gcaaggccac aggccaggtc tgccatgcct tgtgctcccc cgagggctgc tggggcccgg    1800
agcccaggga ctgcgtctct tgccggaatg tcagccgagg cagggaatgc gtggacaagt    1860
gcaaccttct ggagggtgag ccaagggagt ttgtggagaa ctctgagtgc atacagtgcc    1920
acccagagtg cctgcctcag gccatgaaca tcacctgcac aggacgggga ccagacaact    1980
```

```
gtatccagtg tgcccactac attgacggcc cccactgcgt caagacctgc ccggcaggag    2040
tcatgggaga aaacaacacc ctggtctgga agtacgcaga cgccggccat gtgtgccacc    2100
tgtgccatcc aaactgcacc tacggatgca ctgggccagg tcttgaaggc tgtccaacga    2160
atgggcctaa gatcccgtcc atcgccactg ggatggtggg ggccctcctc ttgctgctgg    2220
tggtggccct ggggatcggc ctcttcatgc gaaggcgcca catcgttcgg aagcgcacgc    2280
tgcggaggct gctgcaggag agggagcttg tggagcctct tacacccagt ggagaagctc    2340
ccaaccaagc tctcttgagg atcttgaagg aaactgaatt caaaaagatc aaagtgctgg    2400
gctccggtgc gttcggcacg gtgtataagg gactctggat cccagaaggt gagaaagtta    2460
aaattcccgt cgctatcaag gaaccaacat ctccgaaagc caacaaggaa atcctcgatg    2520
aagcctacgt gatggccagc gtggacaacc cccacgtgtg ccgcctgctg ggcatctgcc    2580
tcacctccac cgtgcagctc atcacgcagc tcatgcccct cggctgcctc ctggactatg    2640
tccgggaaca caaagacaat attggctccc agtacctgct caactggtgt gtgcagatcg    2700
caaagggcat gaactacttg gaggaccgtc gcttggtgca ccgcgacctg cagccagga     2760 acgtactggt gaaaacaccg cagcatgtca agatcacaga ttttgggctg gccaaactgc    2820
tgggtgcgga agagaaagaa taccatgcag aaggaggcaa agtgcctatc aagtggatgg    2880
cattggaatc aattttacac agaatctata cccaccagag tgatgtctgg agctacgggg    2940
tgactgtttg ggagttgatg acctttggat ccaagccata tgacggaatc cctgccagcg    3000
agatctcctc catcctggag aaaggagaac gcctccctca gccacccata tgtaccatcg    3060
atgtctacat gatcatggtc aagtgctgga tgatagacgc agatagtcgc ccaaagttcc    3120
gtgagttgat catcgaattc tccaaaatgg cccgagaccc ccagcgctac cttgtcattc    3180 aggggatga agaatgcat tgccaagtc ctacagactc caacttctac cgtgccctga      3240
tggatgaaga agacatggac gacgtggtgg atgccgacga gtacctcatc ccacagcagg    3300
gcttcttcag cagcccctcc acgtcacgga ctcccctcct gagctctctg agtgcaacca    3360
gcaacaattc caccgtggct tgcattgata gaaatgggct gcaaagctgt cccatcaagg    3420
aagacagctt cttgcagcga tacagctcag accccacagg cgccttgact gaggacagca    3480
tagacgacac cttcctccca gtgcctgaat acataaacca gtccgttccc aaaaggcccg    3540
ctggctctgt gcagaatcct gtctatcaca atcagcctct gaaccccgcg ccagcagag    3600 acccacacta ccaggacccc cacagcactg cagtgggcaa ccccgagtat ctcaacactg    3660
tccagcccac ctgtgtcaac agcacattcg acagccctgc ccactgggcc cagaaaggca    3720
gccaccaaat tagcctggac aaccctgact accagcagga cttctttccc aaggaagcca    3780
agccaaatgg catctttaag ggctccacag ctgaaaatgc agaataccta agggtcgcgc    3840
cacaaagcag tgaatttatt ggagcatga                                      3869
```

<210> SEQ ID NO 443
<211> LENGTH: 3860
<212> TYPE: DNA
<213> ORGANISM: Homo sapiens

<400> SEQUENCE: 443

```
cccggcgcag cgcggccgca gcagcctccg ccccccgcac ggtgtgagcg cccgacgcgg      60
ccgaggcggc cggagtcccg agctagcccc ggcggccgcc gccgcccaga ccggacgaca     120
ggccacctcg tcggcgtccg cccgagtccc cgcctcgccg ccaacgccac aaccaccgcg     180
```

```
cacggccccc tgactccgtc cagtattgat cgggagagcc ggagcgagct cttcggggag    240
cagcgatgcg accctccggg acggccgggg cagcgctcct ggcgctgctg gctgcgctct    300
gcccggcgag tcgggctctg gaggaaaaga aagtttgcca aggcacgagt aacaagctca    360
cgcagttggg cacttttgaa gatcattttc tcagcctcca gaggatgttc ataactgtg     420 aggtggtcct tgggaatttg gaaattacct atgtgcagag gaattatgat ctttccttct    480
taaagaccat ccaggaggtg gctggttatg tcctcattgc cctcaacaca gtggagcgaa    540
ttcctttgga aaacctgcag atcatcagag gaaatatgta ctacgaaaat tcctatgcct    600
tagcagtctt atctaactat gatgcaaata aaaccggact gaaggagctg cccatgagaa    660
atttacagga atcctgcat ggcgccgtgc ggttcagcaa caaccctgcc ctgtgcaacg      720
tggagagcat ccagtggcgg gacatagtca gcagtgactt tctcagcaac atgtcgatgg    780
acttccagaa ccacctgggc agctgccaaa agtgtgatcc aagctgtccc aatgggagct    840
gctggggtgc aggagaggag aactgccaga actgaccaa aatcatctgt gcccagcagt      900
gctccgggcg ctgccgtggc aagtccccca gtgactgctg ccacaaccag tgtgctgcag    960
gctgcacagg cccccgggag agcgactgcc tggtctgccg caaattccga gacgaagcca    1020
cgtgcaagga caccttgcccc ccactcatgc tctacaaccc caccacgtac cagatggatg   1080
tgaaccccga gggcaaatac agctttggtg ccacctgcgt gaagaagtgt ccccgtaatt    1140
atgtggtgac agatcacggc tcgtgcgtcc gagcctgtgg ggccgacagc tatgagatgg    1200
aggaagacgg cgtccgcaag tgtaagaagt gcgaagggcc ttgccgcaaa gtgtgtaacg    1260
gaataggtat tggtgaattt aaagactcac tctccataaa tgctacgaat attaaacact    1320
tcaaaaactg cacctccatc agtggcgatc tccacatcct gccggtggca tttaggggtg    1380
actccttcac acatactcct cctctggatc cacaggaact ggatattctg aaaaccgtaa    1440
aggaaatcac agggtttttg ctgattcagg cttggcctga aaacaggacg gacctccatg    1500
cctttgagaa cctagaaatc atacgcggca ggaccaagca acatggtcag ttttctcttg    1560
cagtcgtcag cctgaacata acatccttgg gattacgctc cctcaaggag ataagtgatg    1620
gagatgtgat aatttcagga aacaaaaatt tgtgctatgc aaatacaata aactggaaaa    1680
aactgtttgg gacctccggt cagaaaacca aaattataag caacagaggt gaaaacagct    1740
gcaaggccac aggccaggtc tgccatgcct tgtgctcccc cgagggctgc tggggcccgg    1800
agcccaggga ctgcgtctct tgccggaatg tcagccgagg cagggaatgc gtggacaagt    1860
gcaaccttct ggagggtgag ccaagggagt tgtggagaa ctctgagtgc atacagtgcc     1920
acccagagtg cctgcctcag gccatgaaca tcacctgcac aggacgggga ccagacaact    1980
gtatccagtg tgcccactac attgacggcc cccactgcgt caagacctgc ccggcaggag    2040
tcatgggaga aaacaacacc ctggtctgga agtacgcaga cgccggccat gtgtgccacc    2100
tgtgccatcc aaactgcacc tacgatgca ctgggccagg tcttgaaggc tgtccaacga     2160
atgggcctaa gatcccgtcc atcgccactg ggatggtggg ggccctcctc ttgctgctgg    2220
tggtggccct ggggatcggc ctcttcatgc gaaggcgcca catcgttcgg aagcgcacgc    2280
tgcggaggct gctgcaggag agggagcttg tggagcctct tacacccagt ggagaagctc    2340
ccaaccaagc tctcttgagg atcttgaagg aaactgaatt caaaaagatc aaagtgctgg    2400
gctccggtgc gttcggcacg gtgtataagg gactctggat cccagaaggt gagaaagtta    2460
aaattcccgt cgctatcaag gaatcgaaag ccaacaagga aatcctcgat gaagcctacg    2520
tgatggccag cgtggacaac ccccacgtgt gccgcctgct gggcatctgc ctcacctcca    2580
```

```
ccgtgcagct catcacgcag ctcatgccct tcggctgcct cctggactat gtccgggaac      2640
acaaagacaa tattggctcc cagtacctgc tcaactggtg tgtgcagatc gcaaagggca      2700
tgaactactt ggaggaccgt cgcttggtgc accgcgacct ggcagccagg aacgtactgg      2760
tgaaaacacc gcagcatgtc aagatcacag attttgggct ggccaaactg ctgggtgcgg      2820
aagagaaaga ataccatgca gaaggaggca aagtgcctat caagtggatg gcattggaat      2880
caattttaca cagaatctat acccaccaga gtgatgtctg gagctacggg gtgactgttt      2940
gggagttgat gacctttgga tccaagccat atgacggaat ccctgccagc gagatctcct      3000
ccatcctgga gaaggagaaa cgcctccctc agccacccat atgtaccatc gatgtctaca      3060
tgatcatggt caagtgctgg atgatagacg cagatagtcg cccaaagttc cgtgagttga      3120
tcatcgaatt ctccaaaatg gcccgagacc ccagcgcta ccttgtcatt caggggatg       3180 aaagaatgca tttgccaagt cctacagact ccaacttcta ccgtgccctg atggatgaag      3240
aagacatgga cgacgtggtg gatgccgacg agtacctcat cccacagcag ggcttcttca      3300
gcagcccctc cacgtcacgg actcccctcc tgagctctct gagtgcaacc agcaacaatt      3360
ccaccgtggc ttgcattgat agaaatgggc tgcaaagctg tcccatcaag gaagacagct      3420
tcttgcagcg atacagctca gaccccacag gcgccttgac tgaggacagc atagacgaca      3480
ccttcctccc agtgcctgaa tacataaacc agtccgttcc caaaaggccc gctggctctg      3540
tgcagaatcc tgtctatcac aatcagcctc tgaacccgc gcccagcaga gacccacact      3600
accaggaccc ccacagcact gcagtgggca acccgagta tctcaacact gtccagccca      3660
cctgtgtcaa cagcacattc gacagccctg cccactgggc ccagaaaggc agccaccaaa      3720
ttagcctgga caaccctgac taccagcagg acttctttcc caaggaagcc aagccaaatg      3780
gcatctttaa gggctccaca gctgaaaatg cagaatacct aagggtcgcg ccacaaagca      3840
gtgaatttat tggagcatga                                                 3860
```

<210> SEQ ID NO 444
<211> LENGTH: 3860
<212> TYPE: DNA
<213> ORGANISM: Homo sapiens

<400> SEQUENCE: 444

```
cccggcgcag cgcggccgca gcagcctccg cccccccgcac ggtgtgagcg cccgacgcgg       60
ccgaggcggc cggagtcccg agctagcccc ggcggccgcc gccgcccaga ccggacgaca      120
ggccacctcg tcgcgtccg cccgagtccc cgcctcgccg ccaacgccac aaccaccgcg       180
cacggccccc tgactccgtc cagtattgat cgggagagcc ggagcgagct cttcggggag      240
cagcgatgcg accctccggg acggccgggg cagcgctcct ggcgctgctg gctgcgctct      300
gcccggcgag tcgggctctg gaggaaaaga aagtttgcca aggcacgagt aacaagctca      360
cgcagttggg cacttttgaa gatcattttc tcagcctcca gaggatgttc aataactgtg      420
aggtggtcct tgggaatttg gaaattacct atgtgcagag gaattatgat ctttccttct      480
taaagaccat ccaggaggtg gctggttatg tcctcattgc cctcaacaca gtggagcgaa      540
ttcctttgga aaacctgcag atcatcagag gaaatatgta ctacgaaaat tcctatgcct      600
tagcagtctt atctaactat gatgcaaata aaaccggact gaaggagctg cccatgagaa      660
atttacagga atcctgcat ggcgccgtgc ggttcagcaa caaccctgcc ctgtgcaacg       720
tggagagcat ccagtggcgg gacatagtca gcagtgactt tctcagcaac atgtcgatgg      780
```

```
acttccagaa ccacctgggc agctgccaaa agtgtgatcc aagctgtccc aatgggagct      840
gctggggtgc aggagaggag aactgccaga aactgaccaa aatcatctgt gcccagcagt      900
gctccgggcg ctgccgtggc aagtccccca gtgactgctg ccacaaccag tgtgctgcag      960
gctgcacagg ccccccggga gcgactgcc tggtctgccg caattccga gacgaagcca       1020
cgtgcaagga cacctgcccc ccactcatgc tctacaaccc caccacgtac cagatggatg     1080
tgaaccccga gggcaaatac agctttggtg ccacctgcgt gaagaagtgt ccccgtaatt     1140
atgtggtgac agatcacggc tcgtgcgtcc gagcctgtgg ggccgacagc tatgagatgg     1200
aggaagacgg cgtccgcaag tgtaagaagt gcgaagggcc ttgccgcaaa gtgtgtaacg     1260
gaataggtat tggtgaattt aaagactcac tctccataaa tgctacgaat attaaacact     1320
tcaaaaactg cacctccatc agtggcgatc tccacatcct gccggtggca tttaggggtg     1380
actccttcac acatactcct cctctggatc cacaggaact ggatattctg aaaaccgtaa     1440
aggaaatcac agggttttg ctgattcagg cttggcctga aaacaggacg gacctccatg      1500
cctttgagaa cctagaaatc atacgcggca ggaccaagca acatggtcag ttttctcttg     1560
cagtcgtcag cctgaacata acatccttgg gattacgctc cctcaaggag ataagtgatg     1620
gagatgtgat aatttcagga aacaaaaatt tgtgctatgc aaatacaata aactggaaaa     1680
aactgtttgg gacctccggt cagaaaacca aaattataag caacagaggt gaaacagct      1740
gcaaggccac aggccaggtc tgccatgcct tgtgctcccc cgagggctgc tggggcccgg     1800
agcccaggga ctgcgtctct tgccggaatg tcagccgagg cagggaatgc gtggacaagt     1860
gcaaccttct ggagggtgag ccaagggagt ttgtggagaa ctctgagtgc atacagtgcc     1920
acccagagtg cctgcctcag gccatgaaca tcacctgcac aggacgggga ccagacaact     1980
gtatccagtg tgcccactac attgacggcc cccactgcgt caagacctgc ccggcaggag     2040
tcatgggaga aaacaacacc ctggtctgga gtacgcaga cgccggccat gtgtgccacc      2100
tgtgccatcc aaactgcacc tacgatgca ctgggccagg tcttgaaggc tgtccaacga      2160
atgggcctaa gatcccgtcc atcgccactg ggatggtggg ggcctcctc ttgctgctgg      2220
tggtggccct ggggatcggc ctcttcatgc gaaggcgcca catcgttcgg aagcgcacgc     2280
tgcggaggct gctgcaggag agggagcttg tggagcctct tacacccagt ggagaagctc     2340
ccaaccaagc tctcttgagg atcttgaagg aaactgaatt caaaaagatc aaagtgctgg     2400
gctccggtgc gttcggcacg gtgtataagg gactctggat cccagaaggt gagaaagtta     2460
aaattcccgt cgctatcaag gttccgaaag ccaacaagga aatcctcgat gaagcctacg     2520
tgatggccag cgtggacaac ccccacgtgt gccgcctgct gggcatctgc ctcacctcca     2580
ccgtgcagct catcacgcag ctcatgccct tcggctgcct cctggactat gtccgggaac     2640
acaaagacaa tattggctcc cagtacctgc tcaactggtg tgtgcagatc gcaaagggca     2700
tgaactactt ggaggaccgt cgcttggtgc accgcgacct ggcagccagg aacgtactgg     2760
tgaaaacacc gcagcatgtc aagatcacag attttgggct ggccaaactg ctgggtgcgg     2820
aagagaaaga ataccatgca gaaggaggca agtgcctat caagtggatg gcattggaat      2880
caattttaca cagaatctat acccaccaga gtgatgtctg gagctacggg gtgactgttt     2940
gggagttgat gacctttgga tccaagccat atgacggaat ccctgccagc gagatctcct     3000
ccatcctgga gaaggagaa cgcctccctc agccacccat atgtaccatc gatgtctaca      3060
tgatcatggt caagtgctgg atgatagacg cagatagtcg cccaaagttc cgtgagttga     3120
tcatcgaatt ctccaaaatg gcccgagacc cccagcgcta ccttgtcatt caggggatg      3180
```

| | |
|---|---|
| aaagaatgca tttgccaagt cctacagact ccaacttcta ccgtgccctg atggatgaag | 3240 |
| aagacatgga cgacgtggtg gatgccgacg agtacctcat cccacagcag ggcttcttca | 3300 |
| gcagcccctc cacgtcacgg actccctcc tgagctctct gagtgcaacc agcaacaatt | 3360 |
| ccaccgtggc ttgcattgat agaaatgggc tgcaaagctg tcccatcaag gaagacagct | 3420 |
| tcttgcagcg atacagctca gaccccacag gcgccttgac tgaggacagc atagacgaca | 3480 |
| ccttcctccc agtgcctgaa tacataaacc agtccgttcc caaaaggccc gctggctctg | 3540 |
| tgcagaatcc tgtctatcac aatcagcctc tgaaccccgc gcccagcaga gacccacact | 3600 |
| accaggaccc ccacagcact gcagtgggca accccgagta tctcaacact gtccagccca | 3660 |
| cctgtgtcaa cagcacattc gacagccctg cccactgggc ccagaaaggc agccaccaaa | 3720 |
| ttagcctgga caaccctgac taccagcagg acttctttcc caaggaagcc aagccaaatg | 3780 |
| gcatctttaa gggctccaca gctgaaaatg cagaatacct aagggtcgcg ccacaaagca | 3840 |
| gtgaatttat tggagcatga | 3860 |

<210> SEQ ID NO 445
<211> LENGTH: 3878
<212> TYPE: DNA
<213> ORGANISM: Homo sapiens

<400> SEQUENCE: 445

| | |
|---|---|
| cccggcgcag cgcggccgca gcagcctccg ccccccgcac ggtgtgagcg cccgacgcgg | 60 |
| ccgaggcggc cggagtcccg agctagcccc ggcggccgcc gccgcccaga ccggacgaca | 120 |
| ggccacctcg tcggcgtccg cccgagtccc cgcctcgccg ccaacgccac aaccaccgcg | 180 |
| cacgccccc tgactccgtc cagtattgat cgggagagcc ggagcgagct cttcggggag | 240 |
| cagcgatgcg accctccggg acggccgggg cagcgctcct ggcgctgctg gctgcgctct | 300 |
| gcccggcgag tcgggctctg gaggaaaaga aagtttgcca aggcacgagt aacaagctca | 360 |
| cgcagttggg cacttttgaa gatcattttc tcagcctcca gaggatgttc aataactgtg | 420 |
| aggtggtcct tgggaatttg gaaattacct atgtgcagag gaattatgat ctttccttct | 480 |
| taaagaccat ccaggaggtg gctggttatg tcctcattgc cctcaacaca gtggagcgaa | 540 |
| ttcctttgga aaacctgcag atcatcagag gaaatatgta ctacgaaaat tcctatgcct | 600 |
| tagcagtctt atctaactat gatgcaaata aaaccggact gaaggagctg cccatgagaa | 660 |
| atttacagga atcctgcat ggcgccgtgc ggttcagcaa caaccctgcc ctgtgcaacg | 720 |
| tggagagcat ccagtggcgg gacatagtca gcagtgactt tctcagcaac atgtcgatgg | 780 |
| acttccagaa ccacctgggc agctgccaaa agtgtgatcc aagctgtccc aatgggagct | 840 |
| gctggggtgc aggagaggag aactgccaga aactgaccaa aatcatctgt gcccagcagt | 900 |
| gctccgggcg ctgccgtggc aagtccccca gtgactgctg ccacaaccag tgtgctgcag | 960 |
| gctgcacagg cccccgggag agcgactgcc tggtctgccg caaattccga gacgaagcca | 1020 |
| cgtgcaagga cacctgcccc ccactcatgc tctacaaccc caccacgtac cagatggatg | 1080 |
| tgaaccccga gggcaaatac agctttggtg ccacctgcgt gaagaagtgt ccccgtaatt | 1140 |
| atgtggtgac agatcacggc tcgtgcgtcc gagcctgtgg ggccgacagc tatgagatgg | 1200 |
| aggaagacgg cgtccgcaag tgtaagaagt gcgaagggcc ttgccgcaaa gtgtgtaacg | 1260 |
| gaataggtat tggtgaattt aaagactcac tctccataaa tgctacgaat attaaacact | 1320 |
| tcaaaaactg cacctccatc agtggcgatc tccacatcct gccggtggca tttagggggtg | 1380 |

```
actccttcac acatactcct cctctggatc cacaggaact ggatattctg aaaaccgtaa    1440
aggaaatcac agggttttg ctgattcagg cttggcctga aaacaggacg gacctccatg    1500
cctttgagaa cctagaaatc atacgcggca ggaccaagca acatggtcag ttttctcttg    1560
cagtcgtcag cctgaacata acatccttgg gattacgctc cctcaaggag ataagtgatg   1620
gagatgtgat aatttcagga aacaaaaatt tgtgctatgc aaatacaata aactggaaaa    1680
aactgtttgg gacctccggt cagaaaacca aaattataag caacagaggt gaaaacagct    1740
gcaaggccac aggccaggtc tgccatgcct tgtgctcccc cgagggctgc tggggcccgg   1800
agcccaggga ctgcgtctct tgccggaatg tcagccgagg cagggaatgc gtggacaagt    1860
gcaaccttct ggagggtgag ccaagggagt ttgtggagaa ctctgagtgc atacagtgcc    1920
acccagagtg cctgcctcag gccatgaaca tcacctgcac aggacgggga ccagacaact    1980
gtatccagtg tgcccactac attgacggcc cccactgcgt caagacctgc ccggcaggag    2040
tcatgggaga aaacaacacc ctggtctgga agtacgcaga cgccggccat gtgtgccacc    2100
tgtgccatcc aaactgcacc tacgatgca ctgggccagg tcttgaaggc tgtccaacga    2160
atgggcctaa gatcccgtcc atcgccactg ggatggtggg ggccctcctc ttgctgctgg    2220
tggtggccct ggggatcggc ctcttcatgc gaaggcgcca catcgttcgg aagcgcacgc    2280
tgcggaggct gctgcaggag agggagcttg tggagcctct tacacccagt ggagaagctc    2340
ccaaccaagc tctcttgagg atcttgaagg aaactgaatt caaaaagatc aaagtgctgg    2400
gctccggtgc gttcggcacg gtgtataagg gactctggat cccagaaggt gagaaagtta    2460
aaattcccgt cgctatcaag gaattaagag aagcaacatc tccgaaagcc aacaaggaaa    2520
tcctcgatga agcctacgtg atggccagcg tggacaaccc ccacgtgtgc cgcctgctgg    2580
gcatctgcct cacctccacc gtgcagctca tcacgcagct catgcccttc ggctgcctcc    2640
tggactatgt ccgggaacac aaagacaata ttggctccca gtacctgctc aactggtgtg    2700
tgcagatcgc aaagggcatg aactacttgg aggaccgtcg cttggtgcac cgcgacctgg    2760
cagccaggaa cgtactggtg aaaacaccgc agcatgtcaa gatcacagat tttgggcggg    2820
ccaaactgct gggtgcggaa gagaaagaat accatgcaga aggaggcaaa gtgcctatca    2880
agtggatggc attggaatca attttacaca gaatctatac ccaccagagt gatgtctgga    2940
gctacggggt gactgtttgg gagttgatga cctttggatc caagccatat gacggaatcc    3000
ctgccagcga gatctcctcc atcctggaga aggagaacg cctccctcag ccacccatat    3060
gtaccatcga tgtctacatg atcatggtca agtgctggat gatagacgca gatagtcgcc    3120
caaagttccg tgagttgatc atcgaattct ccaaaatggc ccgagacccc cagcgctacc    3180
ttgtcattca gggggatgaa agaatgcatt tgccaagtcc tacagactcc aacttctacc    3240
gtgccctgat ggatgaagaa gacatggacg acgtggtgga tgccgacgag tacctcatcc    3300
cacagcaggg cttcttcagc agcccctcca cgtcacggac tccctcctg agctctctga    3360 gtgcaaccag caacaattcc accgtggctt gcattgatag aaatgggctg caaagctgtc    3420
ccatcaagga agacagcttc ttgcagcgat acagctcaga ccccacaggc gccttgactg    3480
aggacagcat agacgacacc ttcctcccag tgcctgaata cataaaccag tccgttccca    3540
aaaggcccgc tggctctgtg cagaatcctg tctatcacaa tcagcctctg aacccgcgc    3600 ccagcagaga cccacactac caggacccc acagcactgc agtgggcaac ccgagtatc    3660 tcaacactgt ccagcccacc tgtgtcaaca gcacattcga cagccctgcc cactgggccc    3720
agaaaggcag ccaccaaatt agcctggaca accctgacta ccagcaggac ttctttccca    3780
```
aggaagccaa gccaaatggc atctttaagg gctccacagc tgaaaatgca gaatacctaa    3840
gggtcgcgcc acaaagcagt gaatttattg gagcatga    3878

<210> SEQ ID NO 446
<211> LENGTH: 3878
<212> TYPE: DNA
<213> ORGANISM: Homo sapiens

<400> SEQUENCE: 446
cccggcgcag cgcggccgca gcagcctccg cccccgcac ggtgtgagcg cccgacgcgg      60
ccgaggcggc cggagtcccg agctagcccc ggcggccgcc gccgcccaga ccggacgaca     120
ggccacctcg tcggcgtccg cccgagtccc cgcctcgccg ccaacgccac aaccaccgcg     180
cacggccccc tgactccgtc cagtattgat cgggagagcc ggagcgagct cttcggggag     240
cagcgatgcg accctccggg acggccgggg cagcgctcct ggcgctgctg gctgcgctct     300
gcccggcgag tcgggctctg gaggaaaaga aagtttgcca aggcacgagt aacaagctca     360
cgcagttggg cacttttgaa gatcattttc tcagcctcca gaggatgttc ataactgtg      420 aggtggtcct tgggaatttg gaaattacct atgtgcagag gaattatgat cttccttct     480 taaagaccat ccaggaggtg gctggttatg tcctcattgc cctcaacaca gtggagcgaa     540
ttcctttgga aaacctgcag atcatcagag gaaatatgta ctacgaaaat tcctatgcct     600
tagcagtctt atctaactat gatgcaaata aaaccggact gaaggagctg cccatgagaa     660
atttacagga atcctgcat ggcgccgtgc ggttcagcaa caaccctgcc ctgtgcaacg     720
tggagagcat ccagtggcgg gacatagtca gcagtgactt tctcagcaac atgtcgatgg     780
acttccagaa ccacctgggc agctgccaaa agtgtgatcc aagctgtccc aatgggagct     840 gctgggggtgc aggagaggag aactgccaga aactgaccaa aatcatctgt gcccagcagt     900
gctccgggcg ctgccgtggc aagtccccca gtgactgctg ccacaaccag tgtgctgcag     960
gctgcacagg cccccgggag agcgactgcc tggtctgccg caaattccga gacgaagcca    1020
cgtgcaagga cacctgcccc ccactcatgc tctacaaccc caccacgtac cagatggatg    1080
tgaaccccga gggcaaatac agctttggtg ccacctgcgt gaagaagtgt ccccgtaatt    1140
atgtggtgac agatcacggc tcgtgcgtcc gagcctgtgg ggccgacagc tatgagatgg    1200
aggaagacgg cgtccgcaag tgtaagaagt gcgaagggcc ttgccgcaaa gtgtgtaacg    1260
gaataggtat tggtgaattt aaagactcac tctccataaa tgctacgaat attaaacact    1320
tcaaaaactg cacctccatc agtggcgatc tccacatcct gccggtggca tttaggggtg    1380
actccttcac acatactcct cctctggatc cacaggaact ggatattctg aaaaccgtaa    1440
aggaaatcac agggttttg ctgattcagg cttggcctga aaacaggacg gacctccatg    1500
cctttgagaa cctagaaatc atacgcggca ggaccaagca acatggtcag ttttctcttg    1560
cagtcgtcag cctgaacata acatccttgg gattacgctc cctcaaggag ataagtgatg    1620
gagatgtgat aatttcagga aacaaaaatt tgtgctatgc aaatacaata aactggaaaa    1680 aactgttttgg gacctccggt cagaaaacca aaattataag caacagaggt gaaaacagct    1740
gcaaggccac aggccaggtc tgccatgcct tgtgctcccc cgagggctgc tggggcccgg    1800
agcccaggga ctgcgtctct tgccggaatg tcagccgagg cagggaatgc gtggacaagt    1860
gcaaccttct ggagggtgag ccaagggagt tgtggagaa ctctgagtgc atacagtgcc    1920
acccagagtg cctgcctcag gccatgaaca tcacctgcac aggacgggga ccagacaact    1980

```
gtatccagtg tgcccactac attgacggcc cccactgcgt caagacctgc ccggcaggag    2040
tcatgggaga aaacaacacc ctggtctgga agtacgcaga cgccggccat gtgtgccacc    2100
tgtgccatcc aaactgcacc tacggatgca ctgggccagg tcttgaaggc tgtccaacga    2160
atgggcctaa gatcccgtcc atcgccactg ggatggtggg ggccctcctc ttgctgctgg    2220
tggtggccct ggggatcggc ctcttcatgc gaaggcgcca catcgttcgg aagcgcacgc    2280
tgcggaggct gctgcaggag agggagcttg tggagcctct tacacccagt ggagaagctc    2340
ccaaccaagc tctcttgagg atcttgaagg aaactgaatt caaaaagatc aaagtgctgg    2400
gctccggtgc gttcggcacg gtgtataagg actctggat cccagaaggt gagaaagtta    2460
aaattcccgt cgctatcaag gaattaagag aagcaacatc tccgaaagcc aacaaggaaa    2520
tcctcgatga agcctacgtg atggccagcg tggacaaccc ccacgtgtgc cgcctgctgg    2580
gcatctgcct cacctccacc gtgcagctca tcacgcagct catgcccttc ggctgcctcc    2640
tggactatgt ccgggaacac aaagacaata ttggctccca gtacctgctc aactggtgtg    2700
tgcagatcgc aaagggcatg aactacttgg aggaccgtcg cttggtgcac cgcgacctgg    2760
cagccaggaa cgtactggtg aaaacaccgc agcatgtcaa gatcacagat tttgggcggg    2820
ccaaactgct gggtgcggaa gagaaagaat accatgcaga aggaggcaaa gtgcctatca    2880
agtggatggc attggaatca attttacaca gaatctatac ccaccagagt gatgtctgga    2940
gctacggggt gactgtttgg gagttgatga ccttttggatc caagccatat gacggaatcc    3000
ctgccagcga gatctcctcc atcctggaga aggagaacg cctccctcag ccacccatat    3060
gtaccatcga tgtctacatg atcatggtca agtgctggat gatagacgca gatagtcgcc    3120
caaagttccg tgagttgatc atcgaattct ccaaaatggc ccgagacccc cagcgctacc    3180
ttgtcattca gggggatgaa agaatgcatt tgccaagtcc tacagactcc aacttctacc    3240
gtgccctgat ggatgaagaa gacatggacg acgtggtgga tgccgacgag tacctcatcc    3300
cacagcaggg cttcttcagc agcccctcca cgtcacggac tcccctcctg agctctctga    3360
gtgcaaccag caacaattcc accgtggctt gcattgatag aaatgggctg caaagctgtc    3420
ccatcaagga agacagcttc ttgcagcgat acagctcaga ccccacaggc gccttgactg    3480
aggacagcat agacgacacc ttcctcccag tgcctgaata cataaaccag tccgttccca    3540
aaaggcccgc tggctctgtg cagaatcctg tctatcacaa tcagcctctg aaccccgcgc    3600
ccagcagaga cccacactac caggacccc acagcactgc agtgggcaac cccgagtatc    3660
tcaacactgt ccagcccacc tgtgtcaaca gcacattcga cagccctgcc cactgggccc    3720
agaaaggcag ccaccaaatt agcctggaca accctgacta ccagcaggac ttctttccca    3780
aggaagccaa gccaaatggc atctttaagg gctccacagc tgaaaatgca gaatacctaa    3840
gggtcgcgcc acaaagcagt gaatttattg gagcatga                           3878
```

<210> SEQ ID NO 447
<211> LENGTH: 36
<212> TYPE: DNA
<213> ORGANISM: Homo sapiens

<400> SEQUENCE: 447
tgtaaaacga cggccagtcg cccagaccgg acgaca                                36

<210> SEQ ID NO 448
<211> LENGTH: 39
<212> TYPE: DNA
<213> ORGANISM: Homo sapiens

```
<400> SEQUENCE: 448
caggaaacag ctatgaccag ggcaatgagg acataacca                            39

<210> SEQ ID NO 449
<211> LENGTH: 38
<212> TYPE: DNA
<213> ORGANISM: Homo sapiens

<400> SEQUENCE: 449
tgtaaaacga cggccagtgg tggtccttgg gaatttgg                             38

<210> SEQ ID NO 450
<211> LENGTH: 40
<212> TYPE: DNA
<213> ORGANISM: Homo sapiens

<400> SEQUENCE: 450
caggaaacag ctatgacccc atcgacatgt tgctgagaaa                           40

<210> SEQ ID NO 451
<211> LENGTH: 38
<212> TYPE: DNA
<213> ORGANISM: Homo sapiens

<400> SEQUENCE: 451
tgtaaaacga cggccagtga aggagctgcc catgagaa                             38

<210> SEQ ID NO 452
<211> LENGTH: 38
<212> TYPE: DNA
<213> ORGANISM: Homo sapiens

<400> SEQUENCE: 452
caggaaacag ctatgacccg tggcttcgtc tcggaatt                             38

<210> SEQ ID NO 453
<211> LENGTH: 40
<212> TYPE: DNA
<213> ORGANISM: Homo sapiens

<400> SEQUENCE: 453
tgtaaaacga cggccagtga aactgaccaa aatcatctgt                           40

<210> SEQ ID NO 454
<211> LENGTH: 40
<212> TYPE: DNA
<213> ORGANISM: Homo sapiens

<400> SEQUENCE: 454
caggaaacag ctatgaccta cctattccgt tacacacttt                           40

<210> SEQ ID NO 455
<211> LENGTH: 40
<212> TYPE: DNA
<213> ORGANISM: Homo sapiens

<400> SEQUENCE: 455
tgtaaaacga cggccagtcc gtaattatgt ggtgacagat                           40

<210> SEQ ID NO 456
<211> LENGTH: 40
<212> TYPE: DNA
```

```
<213> ORGANISM: Homo sapiens

<400> SEQUENCE: 456
caggaaacag ctatgaccgc gtatgatttc taggttctca                                40

<210> SEQ ID NO 457
<211> LENGTH: 41
<212> TYPE: DNA
<213> ORGANISM: Homo sapiens

<400> SEQUENCE: 457
tgtaaaacga cggccagtct gaaaaccgta aaggaaatca c                              41

<210> SEQ ID NO 458
<211> LENGTH: 37
<212> TYPE: DNA
<213> ORGANISM: Homo sapiens

<400> SEQUENCE: 458
caggaaacag ctatgacccc tgcctcggct gacattc                                   37

<210> SEQ ID NO 459
<211> LENGTH: 40
<212> TYPE: DNA
<213> ORGANISM: Homo sapiens

<400> SEQUENCE: 459
tgtaaaacga cggccagtta agcaacagag gtgaaaacag                                40

<210> SEQ ID NO 460
<211> LENGTH: 40
<212> TYPE: DNA
<213> ORGANISM: Homo sapiens

<400> SEQUENCE: 460
caggaaacag ctatgaccgg tgttgttttc tcccatgact                                40

<210> SEQ ID NO 461
<211> LENGTH: 38
<212> TYPE: DNA
<213> ORGANISM: Homo sapiens

<400> SEQUENCE: 461
tgtaaaacga cggccagtgg accagacaac tgtatcca                                  38

<210> SEQ ID NO 462
<211> LENGTH: 40
<212> TYPE: DNA
<213> ORGANISM: Homo sapiens

<400> SEQUENCE: 462
caggaaacag ctatgacctt ccttcaagat cctcaagaga                                40

<210> SEQ ID NO 463
<211> LENGTH: 38
<212> TYPE: DNA
<213> ORGANISM: Homo sapiens

<400> SEQUENCE: 463
tgtaaaacga cggccagtga tcggcctctt catgcgaa                                  38

<210> SEQ ID NO 464
<211> LENGTH: 38
```

<212> TYPE: DNA
<213> ORGANISM: Homo sapiens

<400> SEQUENCE: 464
caggaaacag ctatgaccac ggtggaggtg aggcagat                              38

<210> SEQ ID NO 465
<211> LENGTH: 39
<212> TYPE: DNA
<213> ORGANISM: Homo sapiens

<400> SEQUENCE: 465
tgtaaaacga cggccagtcg aaagccaaca aggaaatcc                             39

<210> SEQ ID NO 466
<211> LENGTH: 40
<212> TYPE: DNA
<213> ORGANISM: Homo sapiens

<400> SEQUENCE: 466
caggaaacag ctatgaccat tccaatgcca tccacttgat                            40

<210> SEQ ID NO 467
<211> LENGTH: 39
<212> TYPE: DNA
<213> ORGANISM: Homo sapiens

<400> SEQUENCE: 467
tgtaaaacga cggccagtaa caccgcagca tgtcaagat                             39

<210> SEQ ID NO 468
<211> LENGTH: 39
<212> TYPE: DNA
<213> ORGANISM: Homo sapiens

<400> SEQUENCE: 468
caggaaacag ctatgaccct cgggccattt tggagaatt                             39

<210> SEQ ID NO 469
<211> LENGTH: 39
<212> TYPE: DNA
<213> ORGANISM: Homo sapiens

<400> SEQUENCE: 469
tgtaaaacga cggccagttc agccacccat atgtaccat                             39

<210> SEQ ID NO 470
<211> LENGTH: 39
<212> TYPE: DNA
<213> ORGANISM: Homo sapiens

<400> SEQUENCE: 470
caggaaacag ctatgaccgc tttgcagccc atttctatc                             39

<210> SEQ ID NO 471
<211> LENGTH: 38
<212> TYPE: DNA
<213> ORGANISM: Homo sapiens

<400> SEQUENCE: 471
tgtaaaacga cggccagtac agcagggctt cttcagca                              38

<210> SEQ ID NO 472

```
<211> LENGTH: 38
<212> TYPE: DNA
<213> ORGANISM: Homo sapiens

<400> SEQUENCE: 472
caggaaacag ctatgacctg acacaggtgg gctggaca                              38

<210> SEQ ID NO 473
<211> LENGTH: 40
<212> TYPE: DNA
<213> ORGANISM: Homo sapiens

<400> SEQUENCE: 473
tgtaaaacga cggccagtga atcctgtcta tcacaatcag                            40

<210> SEQ ID NO 474
<211> LENGTH: 40
<212> TYPE: DNA
<213> ORGANISM: Homo sapiens

<400> SEQUENCE: 474
caggaaacag ctatgaccgg tatcgaaaga gtctggattt                            40

<210> SEQ ID NO 475
<211> LENGTH: 38
<212> TYPE: DNA
<213> ORGANISM: Homo sapiens

<400> SEQUENCE: 475
tgtaaaacga cggccagtgc tccacagctg aaaatgca                              38

<210> SEQ ID NO 476
<211> LENGTH: 39
<212> TYPE: DNA
<213> ORGANISM: Homo sapiens

<400> SEQUENCE: 476
caggaaacag ctatgaccac gttgcaaaac cagtctgtg                             39

<210> SEQ ID NO 477
<211> LENGTH: 25
<212> TYPE: PRT
<213> ORGANISM: Homo sapiens

<400> SEQUENCE: 477

Lys Thr Pro Gln His Val Lys Ile Thr Asp Phe Gly Arg Ala Lys Leu
1               5                   10                  15

Leu Gly Ala Glu Glu Lys Glu Tyr His
            20                  25

<210> SEQ ID NO 478
<211> LENGTH: 25
<212> TYPE: PRT
<213> ORGANISM: Homo sapiens

<400> SEQUENCE: 478

Lys Thr Pro Gln His Val Lys Ile Thr Asp Phe Gly Leu Ala Lys Leu
1               5                   10                  15

Leu Gly Ala Glu Glu Lys Glu Tyr His
            20                  25

<210> SEQ ID NO 479
<211> LENGTH: 25
```

```
<212> TYPE: PRT
<213> ORGANISM: Homo sapiens

<400> SEQUENCE: 479

His Glu Asp Leu Thr Val Lys Ile Gly Asp Phe Gly Leu Ala Thr Val
1               5                   10                  15

Lys Ser Arg Trp Ser Gly Ser His Gln
            20                  25

<210> SEQ ID NO 480
<211> LENGTH: 25
<212> TYPE: PRT
<213> ORGANISM: Homo sapiens

<400> SEQUENCE: 480

Glu Thr Glu Phe Lys Lys Ile Lys Val Leu Ser Ser Gly Ala Phe Gly
1               5                   10                  15

Thr Val Tyr Lys Gly Leu Trp Ile Pro
            20                  25

<210> SEQ ID NO 481
<211> LENGTH: 25
<212> TYPE: PRT
<213> ORGANISM: Homo sapiens

<400> SEQUENCE: 481

Glu Thr Glu Phe Lys Lys Ile Lys Val Leu Gly Ser Gly Ala Phe Gly
1               5                   10                  15

Thr Val Tyr Lys Gly Leu Trp Ile Pro
            20                  25

<210> SEQ ID NO 482
<211> LENGTH: 25
<212> TYPE: PRT
<213> ORGANISM: Homo sapiens

<400> SEQUENCE: 482

Asp Gly Gln Ile Thr Val Gly Gln Arg Ile Gly Ser Gly Ser Phe Gly
1               5                   10                  15

Thr Val Tyr Lys Gly Lys Trp His Gly
            20                  25

<210> SEQ ID NO 483
<211> LENGTH: 19
<212> TYPE: PRT
<213> ORGANISM: Homo sapiens

<400> SEQUENCE: 483

Val Ala Ile Lys Thr Ser Pro Lys Ala Asn Lys Glu Ile Leu Asp Glu
1               5                   10                  15

Ala Tyr Val

<210> SEQ ID NO 484
<211> LENGTH: 16
<212> TYPE: PRT
<213> ORGANISM: Homo sapiens

<400> SEQUENCE: 484

Val Ala Ile Lys Glu Leu Arg Glu Ala Thr Leu Asp Glu Ala Tyr Val
1               5                   10                  15

<210> SEQ ID NO 485
```

```
<211> LENGTH: 21
<212> TYPE: PRT
<213> ORGANISM: Homo sapiens

<400> SEQUENCE: 485

Val Ala Ile Lys Glu Pro Thr Ser Pro Lys Ala Asn Lys Glu Ile Leu
1               5                   10                  15

Asp Glu Ala Tyr Val
            20

<210> SEQ ID NO 486
<211> LENGTH: 18
<212> TYPE: PRT
<213> ORGANISM: Homo sapiens

<400> SEQUENCE: 486

Val Ala Ile Lys Glu Ser Lys Ala Asn Lys Glu Ile Leu Asp Glu Ala
1               5                   10                  15

Tyr Val

<210> SEQ ID NO 487
<211> LENGTH: 18
<212> TYPE: PRT
<213> ORGANISM: Homo sapiens

<400> SEQUENCE: 487

Val Ala Ile Lys Val Pro Lys Ala Asn Lys Glu Ile Leu Asp Glu Ala
1               5                   10                  15

Tyr Val

<210> SEQ ID NO 488
<211> LENGTH: 24
<212> TYPE: PRT
<213> ORGANISM: Homo sapiens

<400> SEQUENCE: 488

Val Ala Ile Lys Glu Leu Arg Glu Ala Thr Ser Pro Lys Ala Asn Lys
1               5                   10                  15

Glu Ile Leu Asp Glu Ala Tyr Val
            20

<210> SEQ ID NO 489
<211> LENGTH: 25
<212> TYPE: PRT
<213> ORGANISM: Homo sapiens

<400> SEQUENCE: 489

Val Ala Val Lys Met Leu Asn Val Thr Ala Pro Thr Pro Gln Gln Leu
1               5                   10                  15

Gln Ala Phe Lys Asn Glu Val Gly Val
            20                  25

<210> SEQ ID NO 490
<211> LENGTH: 6
<212> TYPE: PRT
<213> ORGANISM: Artificial Sequence
<220> FEATURE:
<223> OTHER INFORMATION: Description of Artificial Sequence:
      illustrative mutation motif
<220> FEATURE:
<221> NAME/KEY: MOD_RES
<222> LOCATION: (2)
<223> OTHER INFORMATION: variable residue
<220> FEATURE:
```

```
<221> NAME/KEY: MOD_RES
<222> LOCATION: (4)..(5)
<223> OTHER INFORMATION: variable residue

<400> SEQUENCE: 490

Gly Xaa Gly Xaa Xaa Gly
1               5

<210> SEQ ID NO 491
<211> LENGTH: 252
<212> TYPE: PRT
<213> ORGANISM: Homo sapiens

<400> SEQUENCE: 491

Ile Thr Met Lys His Lys Leu Gly Gly Gly Gln Tyr Gly Glu Val Tyr
1               5                   10                  15

Glu Gly Val Trp Lys Lys Tyr Ser Leu Thr Val Ala Val Lys Thr Leu
            20                  25                  30

Lys Glu Asp Thr Met Glu Val Glu Glu Phe Leu Lys Glu Ala Ala Val
        35                  40                  45

Met Lys Glu Ile Lys His Pro Asn Leu Val Gln Leu Leu Gly Val Cys
50                  55                  60

Thr Arg Glu Pro Pro Phe Tyr Ile Ile Thr Glu Phe Met Thr Tyr Gly
65                  70                  75                  80

Asn Leu Leu Asp Tyr Leu Arg Glu Cys Asn Arg Gln Glu Val Asn Ala
                85                  90                  95

Val Val Leu Leu Tyr Met Ala Thr Gln Ile Ser Ser Ala Met Glu Tyr
            100                 105                 110

Leu Glu Lys Lys Asn Phe Ile His Arg Asp Leu Ala Ala Arg Asn Cys
        115                 120                 125

Leu Val Gly Glu Asn His Leu Val Lys Val Ala Asp Phe Gly Leu Ser
130                 135                 140

Arg Leu Met Thr Gly Asp Thr Tyr Thr Ala His Ala Gly Ala Lys Phe
145                 150                 155                 160

Pro Ile Lys Trp Thr Ala Pro Glu Ser Leu Ala Tyr Asn Lys Phe Ser
                165                 170                 175

Ile Lys Ser Asp Val Trp Ala Phe Gly Val Leu Leu Trp Glu Ile Ala
            180                 185                 190

Thr Tyr Gly Met Ser Pro Tyr Pro Gly Ile Asp Leu Ser Gln Val Tyr
        195                 200                 205

Glu Leu Leu Glu Lys Asp Tyr Arg Met Glu Arg Pro Glu Gly Cys Pro
210                 215                 220

Glu Lys Val Tyr Glu Leu Met Arg Ala Cys Trp Gln Trp Asn Pro Ser
225                 230                 235                 240

Asp Arg Pro Ser Phe Ala Glu Ile His Gln Ala Phe
                245                 250

<210> SEQ ID NO 492
<211> LENGTH: 268
<212> TYPE: PRT
<213> ORGANISM: Homo sapiens

<400> SEQUENCE: 492

Phe Lys Lys Ile Lys Val Leu Gly Ser Gly Ala Phe Gly Thr Val Tyr
1               5                   10                  15

Lys Gly Leu Trp Ile Pro Glu Gly Glu Lys Val Lys Ile Pro Val Ala
            20                  25                  30
```

```
Ile Lys Glu Leu Arg Glu Ala Thr Ser Pro Lys Ala Asn Lys Glu Ile
            35                  40                  45
Leu Asp Glu Ala Tyr Val Met Ala Ser Val Asp Asn Pro His Val Cys
 50                  55                  60
Arg Leu Leu Gly Ile Cys Leu Thr Ser Thr Val Gln Leu Ile Thr Gln
 65                  70                  75                  80
Leu Met Pro Phe Gly Cys Leu Leu Asp Tyr Val Arg Glu His Lys Asp
                 85                  90                  95
Asn Ile Gly Ser Gln Tyr Leu Leu Asn Trp Cys Val Gln Ile Ala Lys
            100                 105                 110
Gly Met Asn Tyr Leu Glu Asp Arg Arg Leu Val His Arg Asp Leu Ala
            115                 120                 125
Ala Arg Asn Val Leu Val Lys Thr Pro Gln His Val Lys Ile Thr Asp
130                 135                 140
Phe Gly Leu Ala Lys Leu Leu Gly Ala Glu Glu Lys Glu Tyr His Ala
145                 150                 155                 160
Glu Gly Gly Lys Val Pro Ile Lys Trp Met Ala Leu Glu Ser Ile Leu
                165                 170                 175
His Arg Ile Tyr Thr His Gln Ser Asp Val Trp Ser Tyr Gly Val Thr
            180                 185                 190
Val Trp Glu Leu Met Thr Phe Gly Ser Lys Pro Tyr Asp Gly Ile Pro
            195                 200                 205
Ala Ser Glu Ile Ser Ser Ile Leu Glu Lys Gly Glu Arg Leu Pro Gln
210                 215                 220
Pro Pro Ile Cys Thr Ile Asp Val Tyr Met Ile Met Val Lys Cys Trp
225                 230                 235                 240
Met Ile Asp Ala Asp Ser Arg Pro Lys Phe Arg Glu Leu Ile Ile Glu
                245                 250                 255
Phe Ser Lys Met Ala Arg Asp Pro Gln Arg Tyr Leu
            260                 265

<210> SEQ ID NO 493
<211> LENGTH: 54
<212> TYPE: DNA
<213> ORGANISM: Homo sapiens

<400> SEQUENCE: 493
aaaattcccg tcgctatcaa ggaattaaga gaagcaacat ctccgaaagc caac          54

<210> SEQ ID NO 494
<211> LENGTH: 24
<212> TYPE: DNA
<213> ORGANISM: Homo sapiens

<400> SEQUENCE: 494
tttgggctgg ccaaactgct gggt                                            24

<210> SEQ ID NO 495
<211> LENGTH: 39
<212> TYPE: DNA
<213> ORGANISM: Homo sapiens

<400> SEQUENCE: 495
aaaattcccg tcgctatcaa aacatctccg aaagccaac                            39

<210> SEQ ID NO 496
<211> LENGTH: 24
<212> TYPE: DNA
```

<213> ORGANISM: Homo sapiens

<400> SEQUENCE: 496
tttgggctgg ccaaactgct gggt                                          24

<210> SEQ ID NO 497
<211> LENGTH: 42
<212> TYPE: DNA
<213> ORGANISM: Homo sapiens

<400> SEQUENCE: 497
aaaattcccg tcgctatcaa ggaatcatct ccgaaagcca ac                      42

<210> SEQ ID NO 498
<211> LENGTH: 24
<212> TYPE: DNA
<213> ORGANISM: Homo sapiens

<400> SEQUENCE: 498
tttgggctgg ccaaactgct gggt                                          24

<210> SEQ ID NO 499
<211> LENGTH: 36
<212> TYPE: DNA
<213> ORGANISM: Homo sapiens

<400> SEQUENCE: 499
aaaattcccg tcgctatcaa ggaatcgaaa gccaac                             36

<210> SEQ ID NO 500
<211> LENGTH: 24
<212> TYPE: DNA
<213> ORGANISM: Homo sapiens

<400> SEQUENCE: 500
tttgggctgg ccaaactgct gggt                                          24

<210> SEQ ID NO 501
<211> LENGTH: 54
<212> TYPE: DNA
<213> ORGANISM: Homo sapiens

<400> SEQUENCE: 501
aaaattcccg tcgctatcaa ggaattaaga gaagcaacat ctccgaaagc caac         54

<210> SEQ ID NO 502
<211> LENGTH: 24
<212> TYPE: DNA
<213> ORGANISM: Homo sapiens

<400> SEQUENCE: 502
tttgggcggg ccaaactgct gggt                                          24

<210> SEQ ID NO 503
<211> LENGTH: 54
<212> TYPE: DNA
<213> ORGANISM: Homo sapiens

<400> SEQUENCE: 503
aaaattcccg tcgctatcaa ggaattaaga gaagcaacat ctccgaaagc caac         54

<210> SEQ ID NO 504
<211> LENGTH: 24

```
<212> TYPE: DNA
<213> ORGANISM: Homo sapiens

<400> SEQUENCE: 504
tttgggctgg ccaaacagct gggt                                    24

<210> SEQ ID NO 505
<211> LENGTH: 25
<212> TYPE: DNA
<213> ORGANISM: Homo sapiens

<400> SEQUENCE: 505
gcaatatcag ccttaggtgc ggctc                                   25

<210> SEQ ID NO 506
<211> LENGTH: 26
<212> TYPE: DNA
<213> ORGANISM: Homo sapiens

<400> SEQUENCE: 506
catagaaagt gaacatttag gatgtg                                  26

<210> SEQ ID NO 507
<211> LENGTH: 24
<212> TYPE: DNA
<213> ORGANISM: Homo sapiens

<400> SEQUENCE: 507
ctaacgttcg ccagccataa gtcc                                    24

<210> SEQ ID NO 508
<211> LENGTH: 26
<212> TYPE: DNA
<213> ORGANISM: Homo sapiens

<400> SEQUENCE: 508
gctgcgagct cacccagaat gtctgg                                  26

<210> SEQ ID NO 509
<211> LENGTH: 18
<212> TYPE: PRT
<213> ORGANISM: Homo sapiens

<400> SEQUENCE: 509

Lys Ile Pro Val Ala Ile Lys Glu Leu Arg Glu Ala Thr Ser Pro Lys
1               5                   10                  15

Ala Asn

<210> SEQ ID NO 510
<211> LENGTH: 8
<212> TYPE: PRT
<213> ORGANISM: Homo sapiens

<400> SEQUENCE: 510

Phe Gly Leu Ala Lys Leu Leu Gly
1               5

<210> SEQ ID NO 511
<211> LENGTH: 3878
<212> TYPE: DNA
<213> ORGANISM: Homo sapiens
<220> FEATURE:
<221> NAME/KEY: CDS
<222> LOCATION: (246)..(3875)
```

<400> SEQUENCE: 511

```
cccggcgcag cgcggccgca gcagcctccg ccccccgcac ggtgtgagcg cccgacgcgg      60
ccgaggcggc cggagtcccg agctagcccc ggcggccgcc gccgcccaga ccggacgaca     120
ggccacctcg tcggcgtccg cccgagtccc cgcctcgccg ccaacgccac aaccaccgcg     180
cacggccccc tgactccgtc cagtattgat cgggagagcc ggagcgagct cttcggggag     240 cagcg atg cga ccc tcc ggg acg gcc ggg gca gcg ctc ctg gcg ctg ctg    290
      Met Arg Pro Ser Gly Thr Ala Gly Ala Ala Leu Leu Ala Leu Leu
        1               5                  10                  15 gct gcg ctc tgc ccg gcg agt cgg gct ctg gag gaa aag aaa gtt tgc     338
Ala Ala Leu Cys Pro Ala Ser Arg Ala Leu Glu Glu Lys Lys Val Cys
                 20                  25                  30 caa ggc acg agt aac aag ctc acg cag ttg ggc act ttt gaa gat cat     386
Gln Gly Thr Ser Asn Lys Leu Thr Gln Leu Gly Thr Phe Glu Asp His
             35                  40                  45 ttt ctc agc ctc cag agg atg ttc aat aac tgt gag gtg gtc ctt ggg     434
Phe Leu Ser Leu Gln Arg Met Phe Asn Asn Cys Glu Val Val Leu Gly
         50                  55                  60 aat ttg gaa att acc tat gtg cag agg aat tat gat ctt tcc ttc tta     482
Asn Leu Glu Ile Thr Tyr Val Gln Arg Asn Tyr Asp Leu Ser Phe Leu
     65                  70                  75 aag acc atc cag gag gtg gct ggt tat gtc ctc att gcc ctc aac aca     530
Lys Thr Ile Gln Glu Val Ala Gly Tyr Val Leu Ile Ala Leu Asn Thr
 80                  85                  90                  95 gtg gag cga att cct ttg gaa aac ctg cag atc atc aga gga aat atg     578
Val Glu Arg Ile Pro Leu Glu Asn Leu Gln Ile Ile Arg Gly Asn Met
                100                 105                 110 tac tac gaa aat tcc tat gcc tta gca gtc tta tct aac tat gat gca     626
Tyr Tyr Glu Asn Ser Tyr Ala Leu Ala Val Leu Ser Asn Tyr Asp Ala
            115                 120                 125 aat aaa acc gga ctg aag gag ctg ccc atg aga aat tta cag gaa atc     674
Asn Lys Thr Gly Leu Lys Glu Leu Pro Met Arg Asn Leu Gln Glu Ile
        130                 135                 140 ctg cat ggc gcc gtg cgg ttc agc aac aac cct gcc ctg tgc aac gtg     722
Leu His Gly Ala Val Arg Phe Ser Asn Asn Pro Ala Leu Cys Asn Val
    145                 150                 155 gag agc atc cag tgg cgg gac ata gtc agc agt gac ttt ctc agc aac     770
Glu Ser Ile Gln Trp Arg Asp Ile Val Ser Ser Asp Phe Leu Ser Asn
160                 165                 170                 175 atg tcg atg gac ttc cag aac cac ctg ggc agc tgc caa aag tgt gat     818
Met Ser Met Asp Phe Gln Asn His Leu Gly Ser Cys Gln Lys Cys Asp
                180                 185                 190 cca agc tgt ccc aat ggg agc tgc tgg ggt gca gga gag gag aac tgc     866
Pro Ser Cys Pro Asn Gly Ser Cys Trp Gly Ala Gly Glu Glu Asn Cys
            195                 200                 205 cag aaa ctg acc aaa atc atc tgt gcc cag cag tgc tcc ggg cgc tgc     914
Gln Lys Leu Thr Lys Ile Ile Cys Ala Gln Gln Cys Ser Gly Arg Cys
        210                 215                 220 cgt ggc aag tcc ccc agt gac tgc tgc cac aac cag tgt gct gca ggc     962
Arg Gly Lys Ser Pro Ser Asp Cys Cys His Asn Gln Cys Ala Ala Gly
    225                 230                 235 tgc aca ggc ccc cgg gag agc gac tgc ctg gtc tgc cgc aaa ttc cga    1010
Cys Thr Gly Pro Arg Glu Ser Asp Cys Leu Val Cys Arg Lys Phe Arg
240                 245                 250                 255 gac gaa gcc acg tgc aag gac acc tgc ccc cca ctc atg ctc tac aac    1058
Asp Glu Ala Thr Cys Lys Asp Thr Cys Pro Pro Leu Met Leu Tyr Asn
                260                 265                 270
```

-continued

| | | |
|---|---|---|
| ccc acc acg tac cag atg gat gtg aac ccc gag ggc aaa tac agc ttt<br>Pro Thr Thr Tyr Gln Met Asp Val Asn Pro Glu Gly Lys Tyr Ser Phe<br>275                            280                       285 | 1106 |
| ggt gcc acc tgc gtg aag aag tgt ccc cgt aat tat gtg gtg aca gat<br>Gly Ala Thr Cys Val Lys Lys Cys Pro Arg Asn Tyr Val Val Thr Asp<br>     290                       295                     300 | 1154 |
| cac ggc tcg tgc gtc cga gcc tgt ggg gcc gac agc tat gag atg gag<br>His Gly Ser Cys Val Arg Ala Cys Gly Ala Asp Ser Tyr Glu Met Glu<br>305                       310                    315 | 1202 |
| gaa gac ggc gtc cgc aag tgt aag aag tgc gaa ggg cct tgc cgc aaa<br>Glu Asp Gly Val Arg Lys Cys Lys Lys Cys Glu Gly Pro Cys Arg Lys<br>320                       325                 330             335 | 1250 |
| gtg tgt aac gga ata ggt att ggt gaa ttt aaa gac tca ctc tcc ata<br>Val Cys Asn Gly Ile Gly Ile Gly Glu Phe Lys Asp Ser Leu Ser Ile<br>                   340                   345             350 | 1298 |
| aat gct acg aat att aaa cac ttc aaa aac tgc acc tcc atc agt ggc<br>Asn Ala Thr Asn Ile Lys His Phe Lys Asn Cys Thr Ser Ile Ser Gly<br>           355                     360                  365 | 1346 |
| gat ctc cac atc ctg ccg gtg gca ttt agg ggt gac tcc ttc aca cat<br>Asp Leu His Ile Leu Pro Val Ala Phe Arg Gly Asp Ser Phe Thr His<br>370                       375                    380 | 1394 |
| act cct cct ctg gat cca cag gaa ctg gat att ctg aaa acc gta aag<br>Thr Pro Pro Leu Asp Pro Gln Glu Leu Asp Ile Leu Lys Thr Val Lys<br>385                       390                    395 | 1442 |
| gaa atc aca ggg ttt ttg ctg att cag gct tgg cct gaa aac agg acg<br>Glu Ile Thr Gly Phe Leu Leu Ile Gln Ala Trp Pro Glu Asn Arg Thr<br>400                       405                    410             415 | 1490 |
| gac ctc cat gcc ttt gag aac cta gaa atc ata cgc ggc agg acc aag<br>Asp Leu His Ala Phe Glu Asn Leu Glu Ile Ile Arg Gly Arg Thr Lys<br>                   420                   425                  430 | 1538 |
| caa cat ggt cag ttt tct ctt gca gtc gtc agc ctg aac ata aca tcc<br>Gln His Gly Gln Phe Ser Leu Ala Val Val Ser Leu Asn Ile Thr Ser<br>           435                     440                  445 | 1586 |
| ttg gga tta cgc tcc ctc aag gag ata agt gat gga gat gtg ata att<br>Leu Gly Leu Arg Ser Leu Lys Glu Ile Ser Asp Gly Asp Val Ile Ile<br>450                       455                    460 | 1634 |
| tca gga aac aaa aat ttg tgc tat gca aat aca ata aac tgg aaa aaa<br>Ser Gly Asn Lys Asn Leu Cys Tyr Ala Asn Thr Ile Asn Trp Lys Lys<br>465                       470                    475 | 1682 |
| ctg ttt ggg acc tcc ggt cag aaa acc aaa att ata agc aac aga ggt<br>Leu Phe Gly Thr Ser Gly Gln Lys Thr Lys Ile Ile Ser Asn Arg Gly<br>480                       485                    490             495 | 1730 |
| gaa aac agc tgc aag gcc aca ggc cag gtc tgc cat gcc ttg tgc tcc<br>Glu Asn Ser Cys Lys Ala Thr Gly Gln Val Cys His Ala Leu Cys Ser<br>                   500                   505                  510 | 1778 |
| ccc gag ggc tgc tgg ggc ccg gag ccc agg gac tgc gtc tct tgc cgg<br>Pro Glu Gly Cys Trp Gly Pro Glu Pro Arg Asp Cys Val Ser Cys Arg<br>           515                     520                  525 | 1826 |
| aat gtc agc cga ggc agg gaa tgc gtg gac aag tgc aac ctt ctg gag<br>Asn Val Ser Arg Gly Arg Glu Cys Val Asp Lys Cys Asn Leu Leu Glu<br>530                       535                    540 | 1874 |
| ggt gag cca agg gag ttt gtg gag aac tct gag tgc ata cag tgc cac<br>Gly Glu Pro Arg Glu Phe Val Glu Asn Ser Glu Cys Ile Gln Cys His<br>545                       550                    555 | 1922 |
| cca gag tgc ctg cct cag gcc atg aac atc acc tgc aca gga cgg gga<br>Pro Glu Cys Leu Pro Gln Ala Met Asn Ile Thr Cys Thr Gly Arg Gly<br>560                       565                    570             575 | 1970 |
| cca gac aac tgt atc cag tgt gcc cac tac att gac ggc ccc cac tgc<br>Pro Asp Asn Cys Ile Gln Cys Ala His Tyr Ile Asp Gly Pro His Cys<br>                   580                   585                  590 | 2018 |

| | | |
|---|---|---|
| gtc aag acc tgc ccg gca gga gtc atg gga gaa aac aac acc ctg gtc<br>Val Lys Thr Cys Pro Ala Gly Val Met Gly Glu Asn Asn Thr Leu Val<br>           595                      600                   605 | 2066 |
| tgg aag tac gca gac gcc ggc cat gtg tgc cac ctg tgc cat cca aac<br>Trp Lys Tyr Ala Asp Ala Gly His Val Cys His Leu Cys His Pro Asn<br>           610                      615                   620 | 2114 |
| tgc acc tac gga tgc act ggg cca ggt ctt gaa ggc tgt cca acg aat<br>Cys Thr Tyr Gly Cys Thr Gly Pro Gly Leu Glu Gly Cys Pro Thr Asn<br>    625                      630                   635 | 2162 |
| ggg cct aag atc ccg tcc atc gcc act ggg atg gtg ggg gcc ctc ctc<br>Gly Pro Lys Ile Pro Ser Ile Ala Thr Gly Met Val Gly Ala Leu Leu<br>640                    645                   650               655 | 2210 |
| ttg ctg ctg gtg gtg gcc ctg ggg atc ggc ctc ttc atg cga agg cgc<br>Leu Leu Leu Val Val Ala Leu Gly Ile Gly Leu Phe Met Arg Arg Arg<br>                  660                   665               670 | 2258 |
| cac atc gtt cgg aag cgc acg ctg cgg agg ctg ctg cag gag agg gag<br>His Ile Val Arg Lys Arg Thr Leu Arg Arg Leu Leu Gln Glu Arg Glu<br>           675                      680                   685 | 2306 |
| ctt gtg gag cct ctt aca ccc agt gga gaa gct ccc aac caa gct ctc<br>Leu Val Glu Pro Leu Thr Pro Ser Gly Glu Ala Pro Asn Gln Ala Leu<br>          690                     695                    700 | 2354 |
| ttg agg atc ttg aag gaa act gaa ttc aaa aag atc aaa gtg ctg ggc<br>Leu Arg Ile Leu Lys Glu Thr Glu Phe Lys Lys Ile Lys Val Leu Gly<br>705                    710                   715 | 2402 |
| tcc ggt gcg ttc ggc acg gtg tat aag gga ctc tgg atc cca gaa ggt<br>Ser Gly Ala Phe Gly Thr Val Tyr Lys Gly Leu Trp Ile Pro Glu Gly<br>720                    725                   730               735 | 2450 |
| gag aaa gtt aaa att ccc gtc gct atc aag gaa tta aga gaa gca aca<br>Glu Lys Val Lys Ile Pro Val Ala Ile Lys Glu Leu Arg Glu Ala Thr<br>                740                   745               750 | 2498 |
| tct ccg aaa gcc aac aag gaa atc ctc gat gaa gcc tac gtg atg gcc<br>Ser Pro Lys Ala Asn Lys Glu Ile Leu Asp Glu Ala Tyr Val Met Ala<br>                  755                   760               765 | 2546 |
| agc gtg gac aac ccc cac gtg tgc cgc ctg ctg ggc atc tgc ctc acc<br>Ser Val Asp Asn Pro His Val Cys Arg Leu Leu Gly Ile Cys Leu Thr<br>770                    775                   780 | 2594 |
| tcc acc gtg cag ctc atc acg cag ctc atg ccc ttc ggc tgc ctc ctg<br>Ser Thr Val Gln Leu Ile Thr Gln Leu Met Pro Phe Gly Cys Leu Leu<br>     785                    790                   795 | 2642 |
| gac tat gtc cgg gaa cac aaa gac aat att ggc tcc cag tac ctg ctc<br>Asp Tyr Val Arg Glu His Lys Asp Asn Ile Gly Ser Gln Tyr Leu Leu<br>800                    805                   810               815 | 2690 |
| aac tgg tgt gtg cag atc gca aag ggc atg aac tac ttg gag gac cgt<br>Asn Trp Cys Val Gln Ile Ala Lys Gly Met Asn Tyr Leu Glu Asp Arg<br>                820                   825               830 | 2738 |
| cgc ttg gtg cac cgc gac ctg gca gcc agg aac gta ctg gtg aaa aca<br>Arg Leu Val His Arg Asp Leu Ala Ala Arg Asn Val Leu Val Lys Thr<br>                  835                   840               845 | 2786 |
| ccg cag cat gtc aag atc aca gat ttt ggg ctg gcc aaa ctg ctg ggt<br>Pro Gln His Val Lys Ile Thr Asp Phe Gly Leu Ala Lys Leu Leu Gly<br>                850                   855               860 | 2834 |
| gcg gaa gag aaa gaa tac cat gca gaa gga ggc aaa gtg cct atc aag<br>Ala Glu Glu Lys Glu Tyr His Ala Glu Gly Gly Lys Val Pro Ile Lys<br>865                    870                   875 | 2882 |
| tgg atg gca ttg gaa tca att tta cac aga atc tat acc cac cag agt<br>Trp Met Ala Leu Glu Ser Ile Leu His Arg Ile Tyr Thr His Gln Ser<br>880                    885                   890               895 | 2930 |
| gat gtc tgg agc tac ggg gtg act gtt tgg gag ttg atg acc ttt gga<br>Asp Val Trp Ser Tyr Gly Val Thr Val Trp Glu Leu Met Thr Phe Gly | 2978 |

```
                    900             905             910
tcc aag cca tat gac gga atc cct gcc agc gag atc tcc tcc atc ctg    3026
Ser Lys Pro Tyr Asp Gly Ile Pro Ala Ser Glu Ile Ser Ser Ile Leu
        915             920             925 gag aaa gga gaa cgc ctc cct cag cca ccc ata tgt acc atc gat gtc    3074
Glu Lys Gly Glu Arg Leu Pro Gln Pro Pro Ile Cys Thr Ile Asp Val
        930             935             940 tac atg atc atg gtc aag tgc tgg atg ata gac gca gat agt cgc cca    3122
Tyr Met Ile Met Val Lys Cys Trp Met Ile Asp Ala Asp Ser Arg Pro
        945             950             955 aag ttc cgt gag ttg atc atc gaa ttc tcc aaa atg gcc cga gac ccc    3170
Lys Phe Arg Glu Leu Ile Ile Glu Phe Ser Lys Met Ala Arg Asp Pro
960             965             970             975 cag cgc tac ctt gtc att cag ggg gat gaa aga atg cat ttg cca agt    3218
Gln Arg Tyr Leu Val Ile Gln Gly Asp Glu Arg Met His Leu Pro Ser
                980             985             990 cct aca gac tcc aac ttc tac cgt gcc ctg atg gat gaa gaa gac atg    3266
Pro Thr Asp Ser Asn Phe Tyr Arg Ala Leu Met Asp Glu Glu Asp Met
            995             1000            1005 gac gac gtg gtg gat gcc gac gag tac ctc atc cca cag cag ggc ttc    3314
Asp Asp Val Val Asp Ala Asp Glu Tyr Leu Ile Pro Gln Gln Gly Phe
        1010            1015            1020 ttc agc agc ccc tcc acg tca cgg act ccc ctc ctg agc tct ctg agt    3362
Phe Ser Ser Pro Ser Thr Ser Arg Thr Pro Leu Leu Ser Ser Leu Ser
    1025            1030            1035 gca acc agc aac aat tcc acc gtg gct tgc att gat aga aat ggg ctg    3410
Ala Thr Ser Asn Asn Ser Thr Val Ala Cys Ile Asp Arg Asn Gly Leu
1040            1045            1050            1055 caa agc tgt ccc atc aag gaa gac agc ttc ttg cag cga tac agc tca    3458
Gln Ser Cys Pro Ile Lys Glu Asp Ser Phe Leu Gln Arg Tyr Ser Ser
            1060            1065            1070 gac ccc aca ggc gcc ttg act gag gac agc ata gac gac acc ttc ctc    3506
Asp Pro Thr Gly Ala Leu Thr Glu Asp Ser Ile Asp Asp Thr Phe Leu
        1075            1080            1085 cca gtg cct gaa tac ata aac cag tcc gtt ccc aaa agg ccc gct ggc    3554
Pro Val Pro Glu Tyr Ile Asn Gln Ser Val Pro Lys Arg Pro Ala Gly
        1090            1095            1100 tct gtg cag aat cct gtc tat cac aat cag cct ctg aac ccc gcg ccc    3602
Ser Val Gln Asn Pro Val Tyr His Asn Gln Pro Leu Asn Pro Ala Pro
1105            1110            1115 agc aga gac cca cac tac cag gac ccc cac agc act gca gtg ggc aac    3650
Ser Arg Asp Pro His Tyr Gln Asp Pro His Ser Thr Ala Val Gly Asn
1120            1125            1130            1135 ccc gag tat ctc aac act gtc cag ccc acc tgt gtc aac agc aca ttc    3698
Pro Glu Tyr Leu Asn Thr Val Gln Pro Thr Cys Val Asn Ser Thr Phe
        1140            1145            1150 gac agc cct gcc cac tgg gcc cag aaa ggc agc cac caa att agc ctg    3746
Asp Ser Pro Ala His Trp Ala Gln Lys Gly Ser His Gln Ile Ser Leu
        1155            1160            1165 gac aac cct gac tac cag cag gac ttc ttt ccc aag gaa gcc aag cca    3794
Asp Asn Pro Asp Tyr Gln Gln Asp Phe Phe Pro Lys Glu Ala Lys Pro
        1170            1175            1180 aat ggc atc ttt aag ggc tcc aca gct gaa aat gca gaa tac cta agg    3842
Asn Gly Ile Phe Lys Gly Ser Thr Ala Glu Asn Ala Glu Tyr Leu Arg
    1185            1190            1195 gtc gcg cca caa agc agt gaa ttt att gga gca tga                    3878
Val Ala Pro Gln Ser Ser Glu Phe Ile Gly Ala
1200            1205            1210
```

```
<210> SEQ ID NO 512
<211> LENGTH: 1210
<212> TYPE: PRT
<213> ORGANISM: Homo sapiens

<400> SEQUENCE: 512

Met Arg Pro Ser Gly Thr Ala Gly Ala Ala Leu Leu Ala Leu Leu Ala
1               5                   10                  15

Ala Leu Cys Pro Ala Ser Arg Ala Leu Glu Glu Lys Lys Val Cys Gln
            20                  25                  30

Gly Thr Ser Asn Lys Leu Thr Gln Leu Gly Thr Phe Glu Asp His Phe
        35                  40                  45

Leu Ser Leu Gln Arg Met Phe Asn Asn Cys Glu Val Val Leu Gly Asn
    50                  55                  60

Leu Glu Ile Thr Tyr Val Gln Arg Asn Tyr Asp Leu Ser Phe Leu Lys
65                  70                  75                  80

Thr Ile Gln Glu Val Ala Gly Tyr Val Leu Ile Ala Leu Asn Thr Val
                85                  90                  95

Glu Arg Ile Pro Leu Glu Asn Leu Gln Ile Ile Arg Gly Asn Met Tyr
            100                 105                 110

Tyr Glu Asn Ser Tyr Ala Leu Ala Val Leu Ser Asn Tyr Asp Ala Asn
        115                 120                 125

Lys Thr Gly Leu Lys Glu Leu Pro Met Arg Asn Leu Gln Glu Ile Leu
    130                 135                 140

His Gly Ala Val Arg Phe Ser Asn Asn Pro Ala Leu Cys Asn Val Glu
145                 150                 155                 160

Ser Ile Gln Trp Arg Asp Ile Val Ser Ser Asp Phe Leu Ser Asn Met
                165                 170                 175

Ser Met Asp Phe Gln Asn His Leu Gly Ser Cys Gln Lys Cys Asp Pro
            180                 185                 190

Ser Cys Pro Asn Gly Ser Cys Trp Gly Ala Gly Glu Glu Asn Cys Gln
        195                 200                 205

Lys Leu Thr Lys Ile Ile Cys Ala Gln Gln Cys Ser Gly Arg Cys Arg
    210                 215                 220

Gly Lys Ser Pro Ser Asp Cys Cys His Asn Gln Cys Ala Ala Gly Cys
225                 230                 235                 240

Thr Gly Pro Arg Glu Ser Asp Cys Leu Val Cys Arg Lys Phe Arg Asp
                245                 250                 255

Glu Ala Thr Cys Lys Asp Thr Cys Pro Pro Leu Met Leu Tyr Asn Pro
            260                 265                 270

Thr Thr Tyr Gln Met Asp Val Asn Pro Glu Gly Lys Tyr Ser Phe Gly
        275                 280                 285

Ala Thr Cys Val Lys Lys Cys Pro Arg Asn Tyr Val Val Thr Asp His
    290                 295                 300

Gly Ser Cys Val Arg Ala Cys Gly Ala Asp Ser Tyr Glu Met Glu Glu
305                 310                 315                 320

Asp Gly Val Arg Lys Cys Lys Lys Cys Glu Gly Pro Cys Arg Lys Val
                325                 330                 335

Cys Asn Gly Ile Gly Ile Gly Glu Phe Lys Asp Ser Leu Ser Ile Asn
            340                 345                 350

Ala Thr Asn Ile Lys His Phe Lys Asn Cys Thr Ser Ile Ser Gly Asp
        355                 360                 365

Leu His Ile Leu Pro Val Ala Phe Arg Gly Asp Ser Phe Thr His Thr
    370                 375                 380
```

```
Pro Pro Leu Asp Pro Gln Glu Leu Asp Ile Leu Lys Thr Val Lys Glu
385                 390                 395                 400

Ile Thr Gly Phe Leu Leu Ile Gln Ala Trp Pro Glu Asn Arg Thr Asp
            405                 410                 415

Leu His Ala Phe Glu Asn Leu Glu Ile Ile Arg Gly Arg Thr Lys Gln
            420                 425                 430

His Gly Gln Phe Ser Leu Ala Val Val Ser Leu Asn Ile Thr Ser Leu
        435                 440                 445

Gly Leu Arg Ser Leu Lys Glu Ile Ser Asp Gly Asp Val Ile Ile Ser
    450                 455                 460

Gly Asn Lys Asn Leu Cys Tyr Ala Asn Thr Ile Asn Trp Lys Lys Leu
465                 470                 475                 480

Phe Gly Thr Ser Gly Gln Lys Thr Lys Ile Ile Ser Asn Arg Gly Glu
            485                 490                 495

Asn Ser Cys Lys Ala Thr Gly Gln Val Cys His Ala Leu Cys Ser Pro
            500                 505                 510

Glu Gly Cys Trp Gly Pro Glu Pro Arg Asp Cys Val Ser Cys Arg Asn
            515                 520                 525

Val Ser Arg Gly Arg Glu Cys Val Asp Lys Cys Asn Leu Leu Glu Gly
    530                 535                 540

Glu Pro Arg Glu Phe Val Glu Asn Ser Glu Cys Ile Gln Cys His Pro
545                 550                 555                 560

Glu Cys Leu Pro Gln Ala Met Asn Ile Thr Cys Thr Gly Arg Gly Pro
                565                 570                 575

Asp Asn Cys Ile Gln Cys Ala His Tyr Ile Asp Gly Pro His Cys Val
            580                 585                 590

Lys Thr Cys Pro Ala Gly Val Met Gly Glu Asn Asn Thr Leu Val Trp
            595                 600                 605

Lys Tyr Ala Asp Ala Gly His Val Cys His Leu Cys His Pro Asn Cys
            610                 615                 620

Thr Tyr Gly Cys Thr Gly Pro Gly Leu Glu Gly Cys Pro Thr Asn Gly
625                 630                 635                 640

Pro Lys Ile Pro Ser Ile Ala Thr Gly Met Val Gly Ala Leu Leu Leu
                645                 650                 655

Leu Leu Val Val Ala Leu Gly Ile Gly Leu Phe Met Arg Arg Arg His
            660                 665                 670

Ile Val Arg Lys Arg Thr Leu Arg Arg Leu Leu Gln Glu Arg Glu Leu
            675                 680                 685

Val Glu Pro Leu Thr Pro Ser Gly Glu Ala Pro Asn Gln Ala Leu Leu
    690                 695                 700

Arg Ile Leu Lys Glu Thr Glu Phe Lys Lys Ile Lys Val Leu Gly Ser
705                 710                 715                 720

Gly Ala Phe Gly Thr Val Tyr Lys Gly Leu Trp Ile Pro Glu Gly Glu
            725                 730                 735

Lys Val Lys Ile Pro Val Ala Ile Lys Glu Leu Arg Glu Ala Thr Ser
            740                 745                 750

Pro Lys Ala Asn Lys Glu Ile Leu Asp Glu Ala Tyr Val Met Ala Ser
        755                 760                 765

Val Asp Asn Pro His Val Cys Arg Leu Leu Gly Ile Cys Leu Thr Ser
    770                 775                 780

Thr Val Gln Leu Ile Thr Gln Leu Met Pro Phe Gly Cys Leu Leu Asp
785                 790                 795                 800

Tyr Val Arg Glu His Lys Asp Asn Ile Gly Ser Gln Tyr Leu Leu Asn
```

-continued

```
                805                 810                 815
Trp Cys Val Gln Ile Ala Lys Gly Met Asn Tyr Leu Glu Asp Arg Arg
        820                 825                 830
Leu Val His Arg Asp Leu Ala Ala Arg Asn Val Leu Val Lys Thr Pro
            835                 840                 845
Gln His Val Lys Ile Thr Asp Phe Gly Leu Ala Lys Leu Leu Gly Ala
    850                 855                 860
Glu Glu Lys Glu Tyr His Ala Glu Gly Gly Lys Val Pro Ile Lys Trp
865                 870                 875                 880
Met Ala Leu Glu Ser Ile Leu His Arg Ile Tyr Thr His Gln Ser Asp
                885                 890                 895
Val Trp Ser Tyr Gly Val Thr Val Trp Glu Leu Met Thr Phe Gly Ser
            900                 905                 910
Lys Pro Tyr Asp Gly Ile Pro Ala Ser Glu Ile Ser Ser Ile Leu Glu
        915                 920                 925
Lys Gly Glu Arg Leu Pro Gln Pro Pro Ile Cys Thr Ile Asp Val Tyr
    930                 935                 940
Met Ile Met Val Lys Cys Trp Met Ile Asp Ala Asp Ser Arg Pro Lys
945                 950                 955                 960
Phe Arg Glu Leu Ile Ile Glu Phe Ser Lys Met Ala Arg Asp Pro Gln
                965                 970                 975
Arg Tyr Leu Val Ile Gln Gly Asp Glu Arg Met His Leu Pro Ser Pro
            980                 985                 990
Thr Asp Ser Asn Phe Tyr Arg Ala Leu Met Asp Glu Glu Asp Met Asp
        995                 1000                1005
Asp Val Val Asp Ala Asp Glu Tyr Leu Ile Pro Gln Gln Gly Phe Phe
    1010                1015                1020
Ser Ser Pro Ser Thr Ser Arg Thr Pro Leu Leu Ser Ser Leu Ser Ala
1025                1030                1035                1040
Thr Ser Asn Asn Ser Thr Val Ala Cys Ile Asp Arg Asn Gly Leu Gln
                1045                1050                1055
Ser Cys Pro Ile Lys Glu Asp Ser Phe Leu Gln Arg Tyr Ser Ser Asp
            1060                1065                1070
Pro Thr Gly Ala Leu Thr Glu Asp Ser Ile Asp Asp Thr Phe Leu Pro
        1075                1080                1085
Val Pro Glu Tyr Ile Asn Gln Ser Val Pro Lys Arg Pro Ala Gly Ser
    1090                1095                1100
Val Gln Asn Pro Val Tyr His Asn Gln Pro Leu Asn Pro Ala Pro Ser
1105                1110                1115                1120
Arg Asp Pro His Tyr Gln Asp Pro His Ser Thr Ala Val Gly Asn Pro
                1125                1130                1135
Glu Tyr Leu Asn Thr Val Gln Pro Thr Cys Val Asn Ser Thr Phe Asp
            1140                1145                1150
Ser Pro Ala His Trp Ala Gln Lys Gly Ser His Gln Ile Ser Leu Asp
        1155                1160                1165
Asn Pro Asp Tyr Gln Gln Asp Phe Phe Pro Lys Glu Ala Lys Pro Asn
    1170                1175                1180
Gly Ile Phe Lys Gly Ser Thr Ala Glu Asn Ala Glu Tyr Leu Arg Val
1185                1190                1195                1200
Ala Pro Gln Ser Ser Glu Phe Ile Gly Ala
                1205                1210
```

<210> SEQ ID NO 513

```
<211> LENGTH: 25
<212> TYPE: DNA
<213> ORGANISM: Homo sapiens

<400> SEQUENCE: 513
cagatttggc tcgacctgga catag                                        25

<210> SEQ ID NO 514
<211> LENGTH: 22
<212> TYPE: DNA
<213> ORGANISM: Homo sapiens

<400> SEQUENCE: 514
cagctgatct caaggaaaca gg                                           22

<210> SEQ ID NO 515
<211> LENGTH: 24
<212> TYPE: DNA
<213> ORGANISM: Homo sapiens

<400> SEQUENCE: 515
gtattatcag tcactaaagc tcac                                         24

<210> SEQ ID NO 516
<211> LENGTH: 22
<212> TYPE: DNA
<213> ORGANISM: Homo sapiens

<400> SEQUENCE: 516
cacacttcaa gtggaattct gc                                           22

<210> SEQ ID NO 517
<211> LENGTH: 19
<212> TYPE: DNA
<213> ORGANISM: Homo sapiens

<400> SEQUENCE: 517
tgcattaggg ttcaactgg                                               19

<210> SEQ ID NO 518
<211> LENGTH: 26
<212> TYPE: DNA
<213> ORGANISM: Homo sapiens

<400> SEQUENCE: 518
ccttctccga ggtggaattg agtgac                                       26

<210> SEQ ID NO 519
<211> LENGTH: 26
<212> TYPE: DNA
<213> ORGANISM: Homo sapiens

<400> SEQUENCE: 519
gctaattgcg ggactcttgt tcgcac                                       26

<210> SEQ ID NO 520
<211> LENGTH: 22
<212> TYPE: DNA
<213> ORGANISM: Homo sapiens

<400> SEQUENCE: 520
tacatgcttt tctagtggtc ag                                           22
```

```
<210> SEQ ID NO 521
<211> LENGTH: 25
<212> TYPE: DNA
<213> ORGANISM: Homo sapiens

<400> SEQUENCE: 521
ggtctcaagt gattctacaa accag                                   25

<210> SEQ ID NO 522
<211> LENGTH: 24
<212> TYPE: DNA
<213> ORGANISM: Homo sapiens

<400> SEQUENCE: 522
ccttcaccta ctggttcaca tctg                                    24

<210> SEQ ID NO 523
<211> LENGTH: 26
<212> TYPE: DNA
<213> ORGANISM: Homo sapiens

<400> SEQUENCE: 523
catggtttga cttagtttga atgtgg                                  26

<210> SEQ ID NO 524
<211> LENGTH: 27
<212> TYPE: DNA
<213> ORGANISM: Homo sapiens

<400> SEQUENCE: 524
ggatactaaa gatactttgt caccagg                                 27

<210> SEQ ID NO 525
<211> LENGTH: 26
<212> TYPE: DNA
<213> ORGANISM: Homo sapiens

<400> SEQUENCE: 525
gaacactagg ctgcaaagac agtaac                                  26

<210> SEQ ID NO 526
<211> LENGTH: 24
<212> TYPE: DNA
<213> ORGANISM: Homo sapiens

<400> SEQUENCE: 526
ccaagcaagg caaacacatc cacc                                    24

<210> SEQ ID NO 527
<211> LENGTH: 23
<212> TYPE: DNA
<213> ORGANISM: Homo sapiens

<400> SEQUENCE: 527
ggaggatgga gcctttccat cac                                     23

<210> SEQ ID NO 528
<211> LENGTH: 24
<212> TYPE: DNA
<213> ORGANISM: Homo sapiens

<400> SEQUENCE: 528
gaagaggaag atgtgttcct ttgg                                    24
```

```
<210> SEQ ID NO 529
<211> LENGTH: 24
<212> TYPE: DNA
<213> ORGANISM: Homo sapiens

<400> SEQUENCE: 529
gaatgaagga tgatgtggca gtgg                                          24

<210> SEQ ID NO 530
<211> LENGTH: 21
<212> TYPE: DNA
<213> ORGANISM: Homo sapiens

<400> SEQUENCE: 530
caaaacatca gccattaacg g                                             21

<210> SEQ ID NO 531
<211> LENGTH: 26
<212> TYPE: DNA
<213> ORGANISM: Homo sapiens

<400> SEQUENCE: 531
ccacttactg ttcatataat acagag                                        26

<210> SEQ ID NO 532
<211> LENGTH: 25
<212> TYPE: DNA
<213> ORGANISM: Homo sapiens

<400> SEQUENCE: 532
catgtgagat agcatttggg aatgc                                         25

<210> SEQ ID NO 533
<211> LENGTH: 26
<212> TYPE: DNA
<213> ORGANISM: Homo sapiens

<400> SEQUENCE: 533
catgacctac catcattgga aagcag                                        26

<210> SEQ ID NO 534
<211> LENGTH: 21
<212> TYPE: DNA
<213> ORGANISM: Homo sapiens

<400> SEQUENCE: 534
gtaatttcac agttaggaat c                                             21

<210> SEQ ID NO 535
<211> LENGTH: 25
<212> TYPE: DNA
<213> ORGANISM: Homo sapiens

<400> SEQUENCE: 535
gtcacccaag gtcatggagc acagg                                         25

<210> SEQ ID NO 536
<211> LENGTH: 23
<212> TYPE: DNA
<213> ORGANISM: Homo sapiens

<400> SEQUENCE: 536
cagaatgcct gtaaagctat aac                                           23
```

<210> SEQ ID NO 537
<211> LENGTH: 24
<212> TYPE: DNA
<213> ORGANISM: Homo sapiens

<400> SEQUENCE: 537
gtcctggagt cccaactcct tgac          24

<210> SEQ ID NO 538
<211> LENGTH: 25
<212> TYPE: DNA
<213> ORGANISM: Homo sapiens

<400> SEQUENCE: 538
ggaagtggct ctgatggccg tcctg         25

<210> SEQ ID NO 539
<211> LENGTH: 27
<212> TYPE: DNA
<213> ORGANISM: Homo sapiens

<400> SEQUENCE: 539
ccactcacac acactaaata ttttaag       27

<210> SEQ ID NO 540
<211> LENGTH: 27
<212> TYPE: DNA
<213> ORGANISM: Homo sapiens

<400> SEQUENCE: 540
gaccaaaaca ccttaagtaa ctgactc       27

<210> SEQ ID NO 541
<211> LENGTH: 24
<212> TYPE: DNA
<213> ORGANISM: Homo sapiens

<400> SEQUENCE: 541
ccaatccaac atccagacac atag          24

<210> SEQ ID NO 542
<211> LENGTH: 24
<212> TYPE: DNA
<213> ORGANISM: Homo sapiens

<400> SEQUENCE: 542
ccagagccat agaaacttga tcag          24

<210> SEQ ID NO 543
<211> LENGTH: 29
<212> TYPE: DNA
<213> ORGANISM: Homo sapiens

<400> SEQUENCE: 543
gtatggacta tggcacttca attgcatgg     29

<210> SEQ ID NO 544
<211> LENGTH: 28
<212> TYPE: DNA
<213> ORGANISM: Homo sapiens

<400> SEQUENCE: 544
ccagagaaca tgcaaccag cacaggac                                28

<210> SEQ ID NO 545
<211> LENGTH: 25
<212> TYPE: DNA
<213> ORGANISM: Homo sapiens

<400> SEQUENCE: 545
caaatgagct ggcaagtgcc gtgtc                                  25

<210> SEQ ID NO 546
<211> LENGTH: 25
<212> TYPE: DNA
<213> ORGANISM: Homo sapiens

<400> SEQUENCE: 546
gagtttccca aacactcagt gaaac                                  25

<210> SEQ ID NO 547
<211> LENGTH: 25
<212> TYPE: DNA
<213> ORGANISM: Homo sapiens

<400> SEQUENCE: 547
gcaatatcag ccttaggtgc ggctc                                  25

<210> SEQ ID NO 548
<211> LENGTH: 26
<212> TYPE: DNA
<213> ORGANISM: Homo sapiens

<400> SEQUENCE: 548
catagaaagt gaacatttag gatgtg                                 26

<210> SEQ ID NO 549
<211> LENGTH: 24
<212> TYPE: DNA
<213> ORGANISM: Homo sapiens

<400> SEQUENCE: 549
ccatgagtac gtattttgaa actc                                   24

<210> SEQ ID NO 550
<211> LENGTH: 24
<212> TYPE: DNA
<213> ORGANISM: Homo sapiens

<400> SEQUENCE: 550
catatcccca tggcaaactc ttgc                                   24

<210> SEQ ID NO 551
<211> LENGTH: 24
<212> TYPE: DNA
<213> ORGANISM: Homo sapiens

<400> SEQUENCE: 551
ctaacgttcg ccagccataa gtcc                                   24

<210> SEQ ID NO 552
<211> LENGTH: 26
<212> TYPE: DNA
<213> ORGANISM: Homo sapiens

<400> SEQUENCE: 552

| | |
|---|---|
| gctgcgagct cacccagaat gtctgg | 26 |

<210> SEQ ID NO 553
<211> LENGTH: 25
<212> TYPE: DNA
<213> ORGANISM: Homo sapiens

<400> SEQUENCE: 553

| | |
|---|---|
| gacgggtcct ggggtgatct ggctc | 25 |

<210> SEQ ID NO 554
<211> LENGTH: 3866
<212> TYPE: DNA
<213> ORGANISM: Homo sapiens

<400> SEQUENCE: 554

| | |
|---|---|
| cccggcgcag cgcggccgca gcagcctccg cccccccgcac ggtgtgagcg cccgacgcgg | 60 |
| ccgaggcggc cggagtcccg agctagcccc ggcggccgcc gccgcccaga ccggacgaca | 120 |
| ggccacctcg tcggcgtccg cccgagtccc cgcctcgccg ccaacgccac aaccaccgcg | 180 |
| cacggccccc tgactccgtc cagtattgat cgggagagcc ggagcgagct cttcggggag | 240 |
| cagcgatgcg accctccggg acggccgggg cagcgctcct ggcgctgctg gctgcgctct | 300 |
| gcccggcgag tcgggctctg gaggaaaaga aagtttgcca aggcacgagt aacaagctca | 360 |
| cgcagttggg cactttgaa gatcattttc tcagcctcca gaggatgttc aataactgtg | 420 |
| aggtggtcct tgggaatttg gaaattacct atgtgcagag gaattatgat ctttccttct | 480 |
| taaagaccat ccaggaggtg gctggttatg tcctcattgc cctcaacaca gtggagcgaa | 540 |
| ttcctttgga aaacctgcag atcatcagag gaaatatgta ctacgaaaat tcctatgcct | 600 |
| tagcagtctt atctaactat gatgcaaata aaaccggact gaaggagctg cccatgagaa | 660 |
| atttacagga atcctgcat ggcgccgtgc ggttcagcaa caaccctgcc ctgtgcaacg | 720 |
| tggagagcat ccagtggcgg gacatagtca gcagtgactt tctcagcaac atgtcgatgg | 780 |
| acttccagaa ccacctgggc agctgccaaa agtgtgatcc aagctgtccc aatgggagct | 840 |
| gctggggtgc aggagaggag aactgccaga aactgaccaa aatcatctgt gcccagcagt | 900 |
| gctccgggcg ctgccgtggc aagtccccca gtgactgctg ccacaaccag tgtgctgcag | 960 |
| gctgcacagg cccccgggag agcgactgcc tggtctgccg caaattccga gacgaagcca | 1020 |
| cgtgcaagga cacctgcccc ccactcatgc tctacaaccc caccacgtac cagatggatg | 1080 |
| tgaaccccga gggcaaatac agctttggtg ccacctgcgt gaagaagtgt ccccgtaatt | 1140 |
| atgtggtgac agatcacggc tcgtgcgtcc gagcctgtgg ggccgacagc tatgagatgg | 1200 |
| aggaagacgg cgtccgcaag tgtaagaagt gcgaagggcc ttgccgcaaa gtgtgtaacg | 1260 |
| gaataggtat tggtgaattt aaagactcac tctccataaa tgctacgaat attaaacact | 1320 |
| tcaaaaactg cacctccatc agtggcgatc tccacatcct gccggtggca tttaggggtg | 1380 |
| actccttcac acatactcct cctctggatc cacaggaact ggatattctg aaaaccgtaa | 1440 |
| aggaaatcac agggtttttg ctgattcagg cttggcctga aaacaggacg gacctccatg | 1500 |
| cctttgagaa cctagaaatc atacgcggca ggaccaagca acatggtcag ttttctcttg | 1560 |
| cagtcgtcag cctgaacata acatccttgg gattacgctc cctcaaggag ataagtgatg | 1620 |
| gagatgtgat aatttcagga aacaaaaatt tgtgctatgc aaatacaata aactggaaaa | 1680 |
| aactgtttgg gacctccggt cagaaaacca aaattataag caacagaggt gaaaacagct | 1740 |

| | |
|---|---|
| gcaaggccac aggccaggtc tgccatgcct tgtgctcccc cgagggctgc tggggcccgg | 1800 |
| agcccaggga ctgcgtctct tgccggaatg tcagccgagg cagggaatgc gtggacaagt | 1860 |
| gcaaccttct ggagggtgag ccaagggagt ttgtggagaa ctctgagtgc atacagtgcc | 1920 |
| acccagagtg cctgcctcag gccatgaaca tcacctgcac aggacgggga ccagacaact | 1980 |
| gtatccagtg tgcccactac attgacggcc cccactgcgt caagacctgc ccggcaggag | 2040 |
| tcatgggaga aaacaacacc ctggtctgga agtacgcaga cgccggccat gtgtgccacc | 2100 |
| tgtgccatcc aaactgcacc tacgatgca ctgggccagg tcttgaaggc tgtccaacga | 2160 |
| atgggcctaa gatcccgtcc atcgccactg ggatggtggg ggccctcctc ttgctgctgg | 2220 |
| tggtggccct ggggatcggc ctcttcatgc gaaggcgcca catcgttcgg aagcgcacgc | 2280 |
| tgcggaggct gctgcaggag agggagcttg tggagcctct tacacccagt ggagaagctc | 2340 |
| ccaaccaagc tctcttgagg atcttgaagg aaactgaatt caaaaagatc aaagtgctgg | 2400 |
| gctccggtgc gttcggcacg gtgtataagg actctggat cccagaaggt gagaaagtta | 2460 |
| aaattcccgt cgctatcaag gaaccatctc cgaaagccaa caaggaaatc ctcgatgaag | 2520 |
| cctacgtgat ggccagcgtg gacaacccc acgtgtgccg cctgctgggc atctgcctca | 2580 |
| cctccaccgt gcagctcatc acgcagctca tgcccttcgg ctgcctcctg gactatgtcc | 2640 |
| gggaacacaa agacaatatt ggctcccagt acctgctcaa ctggtgtgtg cagatcgcaa | 2700 |
| agggcatgaa ctacttggag gaccgtcgct tggtgcaccg cgacctggca gccaggaacg | 2760 |
| tactggtgaa acaccgcag catgtcaaga tcacagattt tgggctggcc aaactgctgg | 2820 |
| gtgcggaaga gaaagaatac catgcagaag gaggcaaagt gcctatcaag tggatggcat | 2880 |
| tggaatcaat tttacacaga atctataccc accagagtga tgtctggagc tacggggtga | 2940 |
| ctgtttggga gttgatgacc tttgatcca agccatga cggaatccct gccagcgaga | 3000 |
| tctcctccat cctggagaaa ggagaacgcc tccctcagcc acccatatgt accatcgatg | 3060 |
| tctacatgat catggtcaag tgctggatga tagacgcaga tagtcgccca aagttccgtg | 3120 |
| agttgatcat cgaattctcc aaaatggccc gagaccccca gcgctacctt gtcattcagg | 3180 |
| gggatgaaag aatgcatttg ccaagtccta cagactccaa cttctaccgt gccctgatgg | 3240 |
| atgaagaaga catggacgac gtggtggatg ccgacgagta cctcatccca cagcagggct | 3300 |
| tcttcagcag cccctccacg tcaggactcc cctcctgag ctctctgagt gcaaccagca | 3360 |
| acaattccac cgtggcttgc attgatagaa atgggctgca aagctgtccc atcaaggaag | 3420 |
| acagcttctt gcagcgatac agctcagacc ccacaggcgc cttgactgag gacagcatag | 3480 |
| acgacacctt cctcccagtg cctgaataca taaaccagtc cgttcccaaa aggcccgctg | 3540 |
| gctctgtgca gaatcctgtc tatcacaatc agcctctgaa ccccgcgccc agcagagacc | 3600 |
| cacactacca ggaccccac agcactgcag tgggcaaccc cgagtatctc aacactgtcc | 3660 |
| agcccacctg tgtcaacagc acattcgaca gccctgccca ctgggcccag aaaggcagcc | 3720 |
| accaaattag cctggacaac cctgactacc agcaggactt ctttcccaag gaagccaagc | 3780 |
| caaatggcat ctttaagggc tccacagctg aaaatgcaga ataccatagg gtcgcgccac | 3840 |
| aaagcagtga atttattgga gcatga | 3866 |

<210> SEQ ID NO 555
<211> LENGTH: 24
<212> TYPE: DNA
<213> ORGANISM: Homo sapiens

<400> SEQUENCE: 555
caggactaca gaaatgtagg tttc 24

<210> SEQ ID NO 556
<211> LENGTH: 26
<212> TYPE: DNA
<213> ORGANISM: Homo sapiens

<400> SEQUENCE: 556
gtgcctgcct taagtaatgt gatgac 26

<210> SEQ ID NO 557
<211> LENGTH: 25
<212> TYPE: DNA
<213> ORGANISM: Homo sapiens

<400> SEQUENCE: 557
gactggaagt gtcgcatcac caatg 25

<210> SEQ ID NO 558
<211> LENGTH: 25
<212> TYPE: DNA
<213> ORGANISM: Homo sapiens

<400> SEQUENCE: 558
ggtttaataa tgcgatctgg gacac 25

<210> SEQ ID NO 559
<211> LENGTH: 25
<212> TYPE: DNA
<213> ORGANISM: Homo sapiens

<400> SEQUENCE: 559
gcagctataa tttagagaac caagg 25

<210> SEQ ID NO 560
<211> LENGTH: 21
<212> TYPE: DNA
<213> ORGANISM: Homo sapiens

<400> SEQUENCE: 560
aaaattgact tcatttccat g 21

<210> SEQ ID NO 561
<211> LENGTH: 22
<212> TYPE: DNA
<213> ORGANISM: Homo sapiens

<400> SEQUENCE: 561
cctagttgct ctaaaactaa cg 22

<210> SEQ ID NO 562
<211> LENGTH: 24
<212> TYPE: DNA
<213> ORGANISM: Homo sapiens

<400> SEQUENCE: 562
ctgtgaggcg tgacagccgt gcag 24

<210> SEQ ID NO 563
<211> LENGTH: 25
<212> TYPE: DNA
<213> ORGANISM: Homo sapiens

<400> SEQUENCE: 563
caacctacta atcagaacca gcatc                                        25

<210> SEQ ID NO 564
<211> LENGTH: 24
<212> TYPE: DNA
<213> ORGANISM: Homo sapiens

<400> SEQUENCE: 564
ccttcactgt gtctgcaaat ctgc                                         24

<210> SEQ ID NO 565
<211> LENGTH: 24
<212> TYPE: DNA
<213> ORGANISM: Homo sapiens

<400> SEQUENCE: 565
cctgtcataa gtctccttgt tgag                                         24

<210> SEQ ID NO 566
<211> LENGTH: 25
<212> TYPE: DNA
<213> ORGANISM: Homo sapiens

<400> SEQUENCE: 566
cagtctgtgg gtctaagagc taatg                                        25

<210> SEQ ID NO 567
<211> LENGTH: 24
<212> TYPE: DNA
<213> ORGANISM: Homo sapiens

<400> SEQUENCE: 567
caggaatggg tgagtctctg tgtg                                         24

<210> SEQ ID NO 568
<211> LENGTH: 23
<212> TYPE: DNA
<213> ORGANISM: Homo sapiens

<400> SEQUENCE: 568
gtggaattct gcccaggcct ttc                                          23

<210> SEQ ID NO 569
<211> LENGTH: 25
<212> TYPE: DNA
<213> ORGANISM: Homo sapiens

<400> SEQUENCE: 569
gattctacaa accagccagc caaac                                        25

<210> SEQ ID NO 570
<211> LENGTH: 24
<212> TYPE: DNA
<213> ORGANISM: Homo sapiens

<400> SEQUENCE: 570
cctactggtt cacatctgac cctg                                         24

<210> SEQ ID NO 571
<211> LENGTH: 24
<212> TYPE: DNA
<213> ORGANISM: Homo sapiens

<400> SEQUENCE: 571
gtttgaatgt ggtttcgttg gaag                                    24

<210> SEQ ID NO 572
<211> LENGTH: 27
<212> TYPE: DNA
<213> ORGANISM: Homo sapiens

<400> SEQUENCE: 572
ctttgtcacc aggcagaggg caatatc                                 27

<210> SEQ ID NO 573
<211> LENGTH: 23
<212> TYPE: DNA
<213> ORGANISM: Homo sapiens

<400> SEQUENCE: 573
gacagtaact tgggctttct gac                                     23

<210> SEQ ID NO 574
<211> LENGTH: 23
<212> TYPE: DNA
<213> ORGANISM: Homo sapiens

<400> SEQUENCE: 574
catccaccca aagactctcc aag                                     23

<210> SEQ ID NO 575
<211> LENGTH: 25
<212> TYPE: DNA
<213> ORGANISM: Homo sapiens

<400> SEQUENCE: 575
ctgttcatat aatacagagt ccctg                                   25

<210> SEQ ID NO 576
<211> LENGTH: 22
<212> TYPE: DNA
<213> ORGANISM: Homo sapiens

<400> SEQUENCE: 576
gagagatgca ggagctctgt gc                                      22

<210> SEQ ID NO 577
<211> LENGTH: 25
<212> TYPE: DNA
<213> ORGANISM: Homo sapiens

<400> SEQUENCE: 577
gcagtttgta gtcaatcaaa ggtgg                                   25

<210> SEQ ID NO 578
<211> LENGTH: 22
<212> TYPE: DNA
<213> ORGANISM: Homo sapiens

<400> SEQUENCE: 578
gtaatttaaa tgggaatagc cc                                      22

<210> SEQ ID NO 579
<211> LENGTH: 24
<212> TYPE: DNA

```
<213> ORGANISM: Homo sapiens

<400> SEQUENCE: 579
caactccttg accattacct caag                                    24

<210> SEQ ID NO 580
<211> LENGTH: 23
<212> TYPE: DNA
<213> ORGANISM: Homo sapiens

<400> SEQUENCE: 580
gatggccgtc ctgcccacac agg                                     23

<210> SEQ ID NO 581
<211> LENGTH: 21
<212> TYPE: DNA
<213> ORGANISM: Homo sapiens

<400> SEQUENCE: 581
gagtagttta gcatatattg c                                       21

<210> SEQ ID NO 582
<211> LENGTH: 23
<212> TYPE: DNA
<213> ORGANISM: Homo sapiens

<400> SEQUENCE: 582
gacagtcaga aatgcaggaa agc                                     23

<210> SEQ ID NO 583
<211> LENGTH: 26
<212> TYPE: DNA
<213> ORGANISM: Homo sapiens

<400> SEQUENCE: 583
caagtgccgt gtcctggcac ccaagc                                  26

<210> SEQ ID NO 584
<211> LENGTH: 24
<212> TYPE: DNA
<213> ORGANISM: Homo sapiens

<400> SEQUENCE: 584
ccaaacactc agtgaaacaa agag                                    24

<210> SEQ ID NO 585
<211> LENGTH: 21
<212> TYPE: DNA
<213> ORGANISM: Homo sapiens

<400> SEQUENCE: 585
ccttaggtgc ggctccacag c                                       21

<210> SEQ ID NO 586
<211> LENGTH: 22
<212> TYPE: DNA
<213> ORGANISM: Homo sapiens

<400> SEQUENCE: 586
catttaggat gtggagatga gc                                      22

<210> SEQ ID NO 587
<211> LENGTH: 23
```

```
<212> TYPE: DNA
<213> ORGANISM: Homo sapiens

<400> SEQUENCE: 587
gaaactcaag atcgcattca tgc                                          23

<210> SEQ ID NO 588
<211> LENGTH: 23
<212> TYPE: DNA
<213> ORGANISM: Homo sapiens

<400> SEQUENCE: 588
gcaaactctt gctatcccag gag                                          23

<210> SEQ ID NO 589
<211> LENGTH: 22
<212> TYPE: DNA
<213> ORGANISM: Homo sapiens

<400> SEQUENCE: 589
cagccataag tcctcgacgt gg                                           22

<210> SEQ ID NO 590
<211> LENGTH: 24
<212> TYPE: DNA
<213> ORGANISM: Homo sapiens

<400> SEQUENCE: 590
catcctcccc tgcatgtgtt aaac                                         24

<210> SEQ ID NO 591
<211> LENGTH: 24
<212> TYPE: DNA
<213> ORGANISM: Homo sapiens

<400> SEQUENCE: 591
gtaggtttct aaacatcaag aaac                                         24

<210> SEQ ID NO 592
<211> LENGTH: 24
<212> TYPE: DNA
<213> ORGANISM: Homo sapiens

<400> SEQUENCE: 592
gtgatgacat ttctccaggg atgc                                         24

<210> SEQ ID NO 593
<211> LENGTH: 23
<212> TYPE: DNA
<213> ORGANISM: Homo sapiens

<400> SEQUENCE: 593
catcaccaat gccttcttta agc                                          23

<210> SEQ ID NO 594
<211> LENGTH: 24
<212> TYPE: DNA
<213> ORGANISM: Homo sapiens

<400> SEQUENCE: 594
gctggagggt ttaataatgc gatc                                         24

<210> SEQ ID NO 595
```

-continued

```
<211> LENGTH: 24
<212> TYPE: DNA
<213> ORGANISM: Homo sapiens

<400> SEQUENCE: 595
gcaaacacac aggcacctgc tggc                                              24

<210> SEQ ID NO 596
<211> LENGTH: 21
<212> TYPE: DNA
<213> ORGANISM: Homo sapiens

<400> SEQUENCE: 596
catgtgagtt tcactagatg g                                                 21

<210> SEQ ID NO 597
<211> LENGTH: 24
<212> TYPE: DNA
<213> ORGANISM: Homo sapiens

<400> SEQUENCE: 597
gaccggacga caggccacct cgtc                                              24

<210> SEQ ID NO 598
<211> LENGTH: 25
<212> TYPE: DNA
<213> ORGANISM: Homo sapiens

<400> SEQUENCE: 598
gaagaacgaa acgtcccgtt cctcc                                             25

<210> SEQ ID NO 599
<211> LENGTH: 23
<212> TYPE: DNA
<213> ORGANISM: Homo sapiens

<400> SEQUENCE: 599
gttgagcact cgtgtgcatt agg                                               23

<210> SEQ ID NO 600
<211> LENGTH: 22
<212> TYPE: DNA
<213> ORGANISM: Homo sapiens

<400> SEQUENCE: 600
ctcagtgcac gtgtactggg ta                                                22

<210> SEQ ID NO 601
<211> LENGTH: 35
<212> TYPE: DNA
<213> ORGANISM: Homo sapiens

<400> SEQUENCE: 601
gttcactggg ctaattgcgg gactcttgtt cgcac                                  35

<210> SEQ ID NO 602
<211> LENGTH: 28
<212> TYPE: DNA
<213> ORGANISM: Homo sapiens

<400> SEQUENCE: 602
ggtaaataca tgcttttcta gtggtcag                                          28
```

```
<210> SEQ ID NO 603
<211> LENGTH: 23
<212> TYPE: DNA
<213> ORGANISM: Homo sapiens

<400> SEQUENCE: 603
ggaggatgga gcctttccat cac                                               23

<210> SEQ ID NO 604
<211> LENGTH: 24
<212> TYPE: DNA
<213> ORGANISM: Homo sapiens

<400> SEQUENCE: 604
gaagaggaag atgtgttcct ttgg                                              24

<210> SEQ ID NO 605
<211> LENGTH: 24
<212> TYPE: DNA
<213> ORGANISM: Homo sapiens

<400> SEQUENCE: 605
gaatgaagga tgatgtggca gtgg                                              24

<210> SEQ ID NO 606
<211> LENGTH: 25
<212> TYPE: DNA
<213> ORGANISM: Homo sapiens

<400> SEQUENCE: 606
gtatgtgtga aggagtcact gaaac                                             25

<210> SEQ ID NO 607
<211> LENGTH: 22
<212> TYPE: DNA
<213> ORGANISM: Homo sapiens

<400> SEQUENCE: 607
ggtgagtcac aggttcagtt gc                                                22

<210> SEQ ID NO 608
<211> LENGTH: 21
<212> TYPE: DNA
<213> ORGANISM: Homo sapiens

<400> SEQUENCE: 608
caaaacatca gccattaacg g                                                 21

<210> SEQ ID NO 609
<211> LENGTH: 22
<212> TYPE: DNA
<213> ORGANISM: Homo sapiens

<400> SEQUENCE: 609
gtagccagca tgtctgtgtc ac                                                22

<210> SEQ ID NO 610
<211> LENGTH: 23
<212> TYPE: DNA
<213> ORGANISM: Homo sapiens

<400> SEQUENCE: 610
cagaatgcct gtaaagctat aac                                               23
```

```
<210> SEQ ID NO 611
<211> LENGTH: 23
<212> TYPE: DNA
<213> ORGANISM: Homo sapiens

<400> SEQUENCE: 611
catttggctt tccccactca cac                                              23

<210> SEQ ID NO 612
<211> LENGTH: 27
<212> TYPE: DNA
<213> ORGANISM: Homo sapiens

<400> SEQUENCE: 612
gaccaaaaca ccttaagtaa ctgactc                                          27

<210> SEQ ID NO 613
<211> LENGTH: 25
<212> TYPE: DNA
<213> ORGANISM: Homo sapiens

<400> SEQUENCE: 613
gaagctacat agtgtctcac tttcc                                            25

<210> SEQ ID NO 614
<211> LENGTH: 25
<212> TYPE: DNA
<213> ORGANISM: Homo sapiens

<400> SEQUENCE: 614
cacaactgct aatggcccgt tctcg                                            25

<210> SEQ ID NO 615
<211> LENGTH: 23
<212> TYPE: DNA
<213> ORGANISM: Homo sapiens

<400> SEQUENCE: 615
gctcctgctc cctgtcataa gtc                                              23

<210> SEQ ID NO 616
<211> LENGTH: 25
<212> TYPE: DNA
<213> ORGANISM: Homo sapiens

<400> SEQUENCE: 616
gaagtcctgc tggtagtcag ggttg                                            25

<210> SEQ ID NO 617
<211> LENGTH: 24
<212> TYPE: DNA
<213> ORGANISM: Homo sapiens

<400> SEQUENCE: 617
ctgcagtggg caaccccgag tatc                                             24

<210> SEQ ID NO 618
<211> LENGTH: 20
<212> TYPE: DNA
<213> ORGANISM: Homo sapiens

<400> SEQUENCE: 618
tgtgggtcta agagctaatg                                                  20
```

```
<210> SEQ ID NO 619
<211> LENGTH: 22
<212> TYPE: DNA
<213> ORGANISM: Homo sapiens

<400> SEQUENCE: 619
gacaggccac ctcgtcggcg tc                                              22

<210> SEQ ID NO 620
<211> LENGTH: 22
<212> TYPE: DNA
<213> ORGANISM: Homo sapiens

<400> SEQUENCE: 620
cagctgatct caaggaaaca gg                                              22

<210> SEQ ID NO 621
<211> LENGTH: 25
<212> TYPE: DNA
<213> ORGANISM: Homo sapiens

<400> SEQUENCE: 621
ctcgtgtgca ttagggttca actgg                                           25

<210> SEQ ID NO 622
<211> LENGTH: 26
<212> TYPE: DNA
<213> ORGANISM: Homo sapiens

<400> SEQUENCE: 622
ccttctccga ggtggaattg agtgac                                          26

<210> SEQ ID NO 623
<211> LENGTH: 26
<212> TYPE: DNA
<213> ORGANISM: Homo sapiens

<400> SEQUENCE: 623
gctaattgcg ggactcttgt tcgcac                                          26

<210> SEQ ID NO 624
<211> LENGTH: 22
<212> TYPE: DNA
<213> ORGANISM: Homo sapiens

<400> SEQUENCE: 624
tacatgcttt tctagtggtc ag                                              22

<210> SEQ ID NO 625
<211> LENGTH: 23
<212> TYPE: DNA
<213> ORGANISM: Homo sapiens

<400> SEQUENCE: 625
cctttccatc acccctcaag agg                                             23

<210> SEQ ID NO 626
<211> LENGTH: 25
<212> TYPE: DNA
<213> ORGANISM: Homo sapiens

<400> SEQUENCE: 626
```
gatgtgttcc tttggaggtg gcatg                    25

<210> SEQ ID NO 627
<211> LENGTH: 24
<212> TYPE: DNA
<213> ORGANISM: Homo sapiens

<400> SEQUENCE: 627
gatgtggcag tggcggttcc ggtg                     24

<210> SEQ ID NO 628
<211> LENGTH: 24
<212> TYPE: DNA
<213> ORGANISM: Homo sapiens

<400> SEQUENCE: 628
ggagtcactg aaacaaacaa cagg                     24

<210> SEQ ID NO 629
<211> LENGTH: 21
<212> TYPE: DNA
<213> ORGANISM: Homo sapiens

<400> SEQUENCE: 629
ggttcagttg cttgtataaa g                        21

<210> SEQ ID NO 630
<211> LENGTH: 24
<212> TYPE: DNA
<213> ORGANISM: Homo sapiens

<400> SEQUENCE: 630
ccattaacgg taaaatttca gaag                     24

<210> SEQ ID NO 631
<211> LENGTH: 20
<212> TYPE: DNA
<213> ORGANISM: Homo sapiens

<400> SEQUENCE: 631
ccaaggtcat ggagcacagg                          20

<210> SEQ ID NO 632
<211> LENGTH: 25
<212> TYPE: DNA
<213> ORGANISM: Homo sapiens

<400> SEQUENCE: 632
ctgtaaagct ataacaacaa cctgg                    25

<210> SEQ ID NO 633
<211> LENGTH: 27
<212> TYPE: DNA
<213> ORGANISM: Homo sapiens

<400> SEQUENCE: 633
ccactcacac acactaaata ttttaag                  27

<210> SEQ ID NO 634
<211> LENGTH: 24
<212> TYPE: DNA
<213> ORGANISM: Homo sapiens

<400> SEQUENCE: 634

```
gtaactgact caaatacaaa ccac                                            24

<210> SEQ ID NO 635
<211> LENGTH: 25
<212> TYPE: DNA
<213> ORGANISM: Homo sapiens

<400> SEQUENCE: 635
gaagctacat agtgtctcac tttcc                                           25

<210> SEQ ID NO 636
<211> LENGTH: 20
<212> TYPE: DNA
<213> ORGANISM: Homo sapiens

<400> SEQUENCE: 636
ctgctaatgg cccgttctcg                                                 20

<210> SEQ ID NO 637
<211> LENGTH: 24
<212> TYPE: DNA
<213> ORGANISM: Homo sapiens

<400> SEQUENCE: 637
cctgtcataa gtctccttgt tgag                                            24

<210> SEQ ID NO 638
<211> LENGTH: 20
<212> TYPE: DNA
<213> ORGANISM: Homo sapiens

<400> SEQUENCE: 638
ggtagtcagg gttgtccagg                                                 20

<210> SEQ ID NO 639
<211> LENGTH: 23
<212> TYPE: DNA
<213> ORGANISM: Homo sapiens

<400> SEQUENCE: 639
cgagtatctc aacactgtcc agc                                             23

<210> SEQ ID NO 640
<211> LENGTH: 25
<212> TYPE: DNA
<213> ORGANISM: Homo sapiens

<400> SEQUENCE: 640
ctaagagcta atgcgggcat ggctg                                           25

<210> SEQ ID NO 641
<211> LENGTH: 372
<212> TYPE: DNA
<213> ORGANISM: Homo sapiens

<400> SEQUENCE: 641
gcaatatcag ccttaggtgc ggctccacag ccccagtgtc cctcaccttc ggggtgcatc     60
gctggtaaca tccacccaga tcactgggca gcatgtggca ccatctcaca attgccagtt    120
aacgtcttcc ttctctctct gtcataggga ctctggatcc cagaaggtga gaaagttaaa    180
attcccgtcg ctatcaagga attaagagaa gcaacatctc cgaaagccaa caaggaaatc    240
```

```
ctcgatgtga gtttctgctt tgctgtgtgg gggtccatgg ctctgaacct caggcccacc      300 tttctcatg tctggcagct gctctgctct agaccctgct catctccaca tcctaaatgt       360
tcactttcta tg                                                          372
```

<210> SEQ ID NO 642
<211> LENGTH: 415
<212> TYPE: DNA
<213> ORGANISM: Homo sapiens

<400> SEQUENCE: 642

```
ctaacgttcg ccagccataa gtcctcgacg tggagaggct cagagcctgg catgaacatg       60
accctgaatt cggatgcaga gcttcttccc atgatgatct gtccctcaca gcagggtctt      120
ctctgtttca gggcatgaac tacttggagg accgtcgctt ggtgcaccgc gacctggcag      180
ccaggaacgt actggtgaaa acaccgcagc atgtcaagat cacagatttt gggctggcca      240
aactgctggg tgcggaagag aaagaatacc atgcagaagg aggcaaagta aggaggtggc      300
tttaggtcag ccagcatttt cctgacacca gggaccaggc tgccttccca ctagctgtat      360
tgtttaacac atgcagggga ggatgctctc cagacattct gggtgagctc gcagc           415
```

<210> SEQ ID NO 643
<211> LENGTH: 35
<212> TYPE: DNA
<213> ORGANISM: Homo sapiens

<400> SEQUENCE: 643

```
tatcaaggaa ttaagagaag caacatctcc gaaag                                  35
```

<210> SEQ ID NO 644
<211> LENGTH: 24
<212> TYPE: DNA
<213> ORGANISM: Homo sapiens

<400> SEQUENCE: 644

```
cgaaagccaa caaggaaatc ctcg                                              24
```

<210> SEQ ID NO 645
<211> LENGTH: 18
<212> TYPE: DNA
<213> ORGANISM: Homo sapiens

<400> SEQUENCE: 645

```
tgtaaaacga cggccagt                                                     18
```

<210> SEQ ID NO 646
<211> LENGTH: 22
<212> TYPE: DNA
<213> ORGANISM: Homo sapiens

<400> SEQUENCE: 646

```
tggtctcaca ggaccactga tt                                                22
```

<210> SEQ ID NO 647
<211> LENGTH: 22
<212> TYPE: DNA
<213> ORGANISM: Homo sapiens

<400> SEQUENCE: 647

```
gaggccagtg ctgtctctaa gg                                                22
```

```
<210> SEQ ID NO 648
<211> LENGTH: 21
<212> TYPE: DNA
<213> ORGANISM: Homo sapiens

<400> SEQUENCE: 648
atgggacagg cactgatttg t                                          21

<210> SEQ ID NO 649
<211> LENGTH: 22
<212> TYPE: DNA
<213> ORGANISM: Homo sapiens

<400> SEQUENCE: 649
cagctctggc tcacactacc ag                                         22

<210> SEQ ID NO 650
<211> LENGTH: 20
<212> TYPE: DNA
<213> ORGANISM: Homo sapiens

<400> SEQUENCE: 650
gcagctggac tcgatttcct                                            20

<210> SEQ ID NO 651
<211> LENGTH: 22
<212> TYPE: DNA
<213> ORGANISM: Homo sapiens

<400> SEQUENCE: 651
tgcccaatga gtcaagaagt gt                                         22

<210> SEQ ID NO 652
<211> LENGTH: 22
<212> TYPE: DNA
<213> ORGANISM: Homo sapiens

<400> SEQUENCE: 652
cactcacgga tgctgcttag tt                                         22

<210> SEQ ID NO 653
<211> LENGTH: 22
<212> TYPE: DNA
<213> ORGANISM: Homo sapiens

<400> SEQUENCE: 653
tcagagcctg tgtttctacc aa                                         22

<210> SEQ ID NO 654
<211> LENGTH: 24
<212> TYPE: DNA
<213> ORGANISM: Homo sapiens

<400> SEQUENCE: 654
aaataatcag tgtgattcgt ggag                                       24

<210> SEQ ID NO 655
<211> LENGTH: 21
<212> TYPE: DNA
<213> ORGANISM: Homo sapiens

<400> SEQUENCE: 655
acttcacagc cctgcgtaaa c                                          21
```

```
<210> SEQ ID NO 656
<211> LENGTH: 22
<212> TYPE: DNA
<213> ORGANISM: Homo sapiens

<400> SEQUENCE: 656
gcagcgggtt acatcttctt tc                                              22

<210> SEQ ID NO 657
<211> LENGTH: 22
<212> TYPE: DNA
<213> ORGANISM: Homo sapiens

<400> SEQUENCE: 657
cctgaactcc gtcagactga aa                                              22

<210> SEQ ID NO 658
<211> LENGTH: 23
<212> TYPE: DNA
<213> ORGANISM: Homo sapiens

<400> SEQUENCE: 658
ccttacagca atcctgtgaa aca                                             23

<210> SEQ ID NO 659
<211> LENGTH: 22
<212> TYPE: DNA
<213> ORGANISM: Homo sapiens

<400> SEQUENCE: 659
atgtacagtg ctggcatggt ct                                              22

<210> SEQ ID NO 660
<211> LENGTH: 20
<212> TYPE: DNA
<213> ORGANISM: Homo sapiens

<400> SEQUENCE: 660
tccaaatgag ctggcaagtg                                                 20

<210> SEQ ID NO 661
<211> LENGTH: 20
<212> TYPE: DNA
<213> ORGANISM: Homo sapiens

<400> SEQUENCE: 661
gtgcatcgct ggtaacatcc                                                 20

<210> SEQ ID NO 662
<211> LENGTH: 20
<212> TYPE: DNA
<213> ORGANISM: Homo sapiens

<400> SEQUENCE: 662
atcgcattca tgcgtcttca                                                 20

<210> SEQ ID NO 663
<211> LENGTH: 19
<212> TYPE: DNA
<213> ORGANISM: Homo sapiens

<400> SEQUENCE: 663
gctcagagcc tggcatgaa                                                  19
```

<210> SEQ ID NO 664
<211> LENGTH: 20
<212> TYPE: DNA
<213> ORGANISM: Homo sapiens

<400> SEQUENCE: 664
tggctcgtct gtgtgtgtca                                            20

<210> SEQ ID NO 665
<211> LENGTH: 20
<212> TYPE: DNA
<213> ORGANISM: Homo sapiens

<400> SEQUENCE: 665
tgaagcaaat tgcccaagac                                            20

<210> SEQ ID NO 666
<211> LENGTH: 20
<212> TYPE: DNA
<213> ORGANISM: Homo sapiens

<400> SEQUENCE: 666
aagtgtcgca tcaccaatgc                                            20

<210> SEQ ID NO 667
<211> LENGTH: 23
<212> TYPE: DNA
<213> ORGANISM: Homo sapiens

<400> SEQUENCE: 667
tcccaaacac tcagtgaaac aaa                                        23

<210> SEQ ID NO 668
<211> LENGTH: 20
<212> TYPE: DNA
<213> ORGANISM: Homo sapiens

<400> SEQUENCE: 668
tgtggagatg agcagggtct                                            20

<210> SEQ ID NO 669
<211> LENGTH: 20
<212> TYPE: DNA
<213> ORGANISM: Homo sapiens

<400> SEQUENCE: 669
atccccatgg caaactcttg                                            20

<210> SEQ ID NO 670
<211> LENGTH: 19
<212> TYPE: DNA
<213> ORGANISM: Homo sapiens

<400> SEQUENCE: 670
catcctcccc tgcatgtgt                                             19

<210> SEQ ID NO 671
<211> LENGTH: 25
<212> TYPE: DNA
<213> ORGANISM: Homo sapiens

<400> SEQUENCE: 671
cgaaagaaaa tacttgcatg tcaga                                          25

<210> SEQ ID NO 672
<211> LENGTH: 20
<212> TYPE: DNA
<213> ORGANISM: Homo sapiens

<400> SEQUENCE: 672
tgacatttct ccagggatgc                                                20

<210> SEQ ID NO 673
<211> LENGTH: 19
<212> TYPE: DNA
<213> ORGANISM: Homo sapiens

<400> SEQUENCE: 673
atgcgatctg ggacacagg                                                 19

<210> SEQ ID NO 674
<211> LENGTH: 16
<212> TYPE: DNA
<213> ORGANISM: Homo sapiens

<400> SEQUENCE: 674
aacagctatg accatg                                                    16

<210> SEQ ID NO 675
<211> LENGTH: 26
<212> TYPE: DNA
<213> ORGANISM: Homo sapiens

<400> SEQUENCE: 675
caagtgccgt gtcctggcac ccaagc                                         26

<210> SEQ ID NO 676
<211> LENGTH: 24
<212> TYPE: DNA
<213> ORGANISM: Homo sapiens

<400> SEQUENCE: 676
ccaaacactc agtgaaacaa agag                                           24

<210> SEQ ID NO 677
<211> LENGTH: 25
<212> TYPE: DNA
<213> ORGANISM: Homo sapiens

<400> SEQUENCE: 677
gcacccaagc ccatgccgtg gctgc                                          25

<210> SEQ ID NO 678
<211> LENGTH: 26
<212> TYPE: DNA
<213> ORGANISM: Homo sapiens

<400> SEQUENCE: 678
gaaacaaaga gtaaagtaga tgatgg                                         26

<210> SEQ ID NO 679
<211> LENGTH: 24
<212> TYPE: DNA
<213> ORGANISM: Homo sapiens

<400> SEQUENCE: 679

```
caccttcaca atatccctc catg                                              24
```

<210> SEQ ID NO 680
<211> LENGTH: 22
<212> TYPE: DNA
<213> ORGANISM: Homo sapiens

<400> SEQUENCE: 680

```
gacagccgtg cagggaaaaa cc                                               22
```

<210> SEQ ID NO 681
<211> LENGTH: 24
<212> TYPE: DNA
<213> ORGANISM: Homo sapiens

<400> SEQUENCE: 681

```
gaaccagcat ctcaaggaga tctc                                             24
```

<210> SEQ ID NO 682
<211> LENGTH: 24
<212> TYPE: DNA
<213> ORGANISM: Homo sapiens

<400> SEQUENCE: 682

```
gagcacctgg cttggacact ggag                                             24
```

<210> SEQ ID NO 683
<211> LENGTH: 26
<212> TYPE: DNA
<213> ORGANISM: Homo sapiens

<400> SEQUENCE: 683

```
gagcagccct gaactccgtc agactg                                           26
```

<210> SEQ ID NO 684
<211> LENGTH: 26
<212> TYPE: DNA
<213> ORGANISM: Homo sapiens

<400> SEQUENCE: 684

```
ctcagtacaa tagatagaca gcaatg                                           26
```

<210> SEQ ID NO 685
<211> LENGTH: 25
<212> TYPE: DNA
<213> ORGANISM: Homo sapiens

<400> SEQUENCE: 685

```
gacgggtcct ggggtgatct ggctc                                            25
```

<210> SEQ ID NO 686
<211> LENGTH: 26
<212> TYPE: DNA
<213> ORGANISM: Homo sapiens

<400> SEQUENCE: 686

```
ctcagtacaa tagatagaca gcaatg                                           26
```

<210> SEQ ID NO 687
<211> LENGTH: 26
<212> TYPE: DNA
<213> ORGANISM: Homo sapiens

```
<400> SEQUENCE: 687
cgtggagagg ctcagagcct ggcatg                                          26

<210> SEQ ID NO 688
<211> LENGTH: 21
<212> TYPE: DNA
<213> ORGANISM: Homo sapiens

<400> SEQUENCE: 688 cacagattt gggcgggcca a                                                21

<210> SEQ ID NO 689
<211> LENGTH: 21
<212> TYPE: DNA
<213> ORGANISM: Homo sapiens

<400> SEQUENCE: 689
gctatcaaaa catctccgaa a                                               21

<210> SEQ ID NO 690
<211> LENGTH: 35
<212> TYPE: DNA
<213> ORGANISM: Homo sapiens

<400> SEQUENCE: 690
tatcaaggaa ttaagagaag caacatctcc gaaag                                35

<210> SEQ ID NO 691
<211> LENGTH: 29
<212> TYPE: DNA
<213> ORGANISM: Homo sapiens

<400> SEQUENCE: 691
agttaaaatt cccgtcgcta tcaaggaat                                       29

<210> SEQ ID NO 692
<211> LENGTH: 35
<212> TYPE: DNA
<213> ORGANISM: Homo sapiens

<400> SEQUENCE: 692
tatcaaggaa ttaagagaag caacatctcc gaaag                                35

<210> SEQ ID NO 693
<211> LENGTH: 29
<212> TYPE: DNA
<213> ORGANISM: Homo sapiens

<400> SEQUENCE: 693
aacatctccg aaagccaaca aggaaatcc                                       29

<210> SEQ ID NO 694
<211> LENGTH: 35
<212> TYPE: DNA
<213> ORGANISM: Homo sapiens

<400> SEQUENCE: 694
tatcaaggaa ttaagagaag caacatctcc gaaag                                35

<210> SEQ ID NO 695
<211> LENGTH: 21
<212> TYPE: DNA
<213> ORGANISM: Homo sapiens
```

```
<400> SEQUENCE: 695
taaaattccc gtcgctatca a                                          21

<210> SEQ ID NO 696
<211> LENGTH: 35
<212> TYPE: DNA
<213> ORGANISM: Homo sapiens

<400> SEQUENCE: 696
tatcaaggaa ttaagagaag caacatctcc gaaag                           35

<210> SEQ ID NO 697
<211> LENGTH: 25
<212> TYPE: DNA
<213> ORGANISM: Homo sapiens

<400> SEQUENCE: 697
ccatctccga aagccaacaa ggaaa                                      25

<210> SEQ ID NO 698
<211> LENGTH: 35
<212> TYPE: DNA
<213> ORGANISM: Homo sapiens

<400> SEQUENCE: 698
tatcaaggaa ttaagagaag caacatctcc gaaag                           35

<210> SEQ ID NO 699
<211> LENGTH: 23
<212> TYPE: DNA
<213> ORGANISM: Homo sapiens

<400> SEQUENCE: 699
aattcccgtc gctatcaagg aac                                        23

<210> SEQ ID NO 700
<211> LENGTH: 15
<212> TYPE: DNA
<213> ORGANISM: Homo sapiens

<400> SEQUENCE: 700
gggctggcca aactg                                                 15

<210> SEQ ID NO 701
<211> LENGTH: 15
<212> TYPE: DNA
<213> ORGANISM: Homo sapiens

<400> SEQUENCE: 701
gggcgggcca aactg                                                 15

<210> SEQ ID NO 702
<211> LENGTH: 15
<212> TYPE: DNA
<213> ORGANISM: Homo sapiens

<400> SEQUENCE: 702
gggctggcca aactg                                                 15

<210> SEQ ID NO 703
<211> LENGTH: 15
<212> TYPE: DNA
```

```
<213> ORGANISM: Homo sapiens

<400> SEQUENCE: 703
gggctggcca aacag                                                      15

<210> SEQ ID NO 704
<211> LENGTH: 27
<212> TYPE: DNA
<213> ORGANISM: Homo sapiens

<400> SEQUENCE: 704
gatcaaagtg ctgggctccg gtgcgtt                                         27

<210> SEQ ID NO 705
<211> LENGTH: 27
<212> TYPE: DNA
<213> ORGANISM: Homo sapiens
<220> FEATURE:
<221> NAME/KEY: modified_base
<222> LOCATION: (14)
<223> OTHER INFORMATION: a, t, c, g, other or unknown

<400> SEQUENCE: 705
gatcaaagtg ctgngctccg gtgcgtt                                         27

<210> SEQ ID NO 706
<211> LENGTH: 31
<212> TYPE: DNA
<213> ORGANISM: Homo sapiens

<400> SEQUENCE: 706
tcacagattt tgggctggcc aaactgctgg g                                    31

<210> SEQ ID NO 707
<211> LENGTH: 31
<212> TYPE: DNA
<213> ORGANISM: Homo sapiens
<220> FEATURE:
<221> NAME/KEY: modified_base
<222> LOCATION: (16)
<223> OTHER INFORMATION: a, t, c, g, other or unknown

<400> SEQUENCE: 707
tcacagattt tgggcnggcc aaactgctgg g                                    31

<210> SEQ ID NO 708
<211> LENGTH: 21
<212> TYPE: DNA
<213> ORGANISM: Homo sapiens

<400> SEQUENCE: 708
tatcaaggaa ttaagagaag c                                               21

<210> SEQ ID NO 709
<211> LENGTH: 21
<212> TYPE: DNA
<213> ORGANISM: Homo sapiens
<220> FEATURE:
<221> NAME/KEY: modified_base
<222> LOCATION: (17)
<223> OTHER INFORMATION: a, t, c, g, other or unknown

<400> SEQUENCE: 709
tatcaaggaa ttaaganaag c                                               21
```

```
<210> SEQ ID NO 710
<211> LENGTH: 22
<212> TYPE: DNA
<213> ORGANISM: Homo sapiens

<400> SEQUENCE: 710
tatcaaggaa ttaagagaag ca                                              22

<210> SEQ ID NO 711
<211> LENGTH: 27
<212> TYPE: DNA
<213> ORGANISM: Homo sapiens

<400> SEQUENCE: 711
cgtcgctatc aaggaattaa gagaagc                                         27

<210> SEQ ID NO 712
<211> LENGTH: 20
<212> TYPE: DNA
<213> ORGANISM: Homo sapiens

<400> SEQUENCE: 712
cgctatcaag gaacaacatc                                                 20

<210> SEQ ID NO 713
<211> LENGTH: 19
<212> TYPE: DNA
<213> ORGANISM: Homo sapiens

<400> SEQUENCE: 713
sgatcaygga ascaacatc                                                  19

<210> SEQ ID NO 714
<211> LENGTH: 28
<212> TYPE: DNA
<213> ORGANISM: Homo sapiens

<400> SEQUENCE: 714
aggaattaag agaagcaaca tctccgaa                                        28

<210> SEQ ID NO 715
<211> LENGTH: 28
<212> TYPE: DNA
<213> ORGANISM: Homo sapiens

<400> SEQUENCE: 715
aggaattaaa agaaaccaca tctctcat                                        28

<210> SEQ ID NO 716
<211> LENGTH: 28
<212> TYPE: DNA
<213> ORGANISM: Homo sapiens

<400> SEQUENCE: 716
aggaaccaag agaagccacg tattcgaa                                        28

<210> SEQ ID NO 717
<211> LENGTH: 37
<212> TYPE: DNA
<213> ORGANISM: Homo sapiens

<400> SEQUENCE: 717
tatcaaggaa ttaagagaag caacatctcc gaaagcc                              37
```

<210> SEQ ID NO 718
<211> LENGTH: 19
<212> TYPE: DNA
<213> ORGANISM: Homo sapiens

<400> SEQUENCE: 718
tatcaaggtt ccgaaagcc                                                    19

<210> SEQ ID NO 719
<211> LENGTH: 19
<212> TYPE: DNA
<213> ORGANISM: Homo sapiens

<400> SEQUENCE: 719
tatcaaggtt ccgaaagcc                                                    19

<210> SEQ ID NO 720
<211> LENGTH: 3867
<212> TYPE: DNA
<213> ORGANISM: Homo sapiens

<400> SEQUENCE: 720

| | |
|---|---|
| cccggcgcag cgcggccgca gcagcctccg cccccccgcac ggtgtgagcg cccgacgcgg | 60 |
| ccgaggcggc cggagtcccg agctagcccc ggcggccgcc gccgcccaga ccggacgaca | 120 |
| ggccacctcg tcggcgtccg cccgagtccc cgcctcgccg ccaacgccac aaccaccgcg | 180 |
| cacggccccc tgactccgtc cagtattgat cgggagagcc ggagcgagct cttcggggag | 240 |
| cagcgatgcg accctccggg acggccgggg cagcgctcct ggcgctgctg gctgcgctct | 300 |
| gcccggcgag tcgggctctg gaggaaaaga aagtttgcca aggcacgagt aacaagctca | 360 |
| cgcagttggg cactttgaa gatcattttc tcagcctcca gaggatgttc aataactgtg | 420 |
| aggtggtcct tgggaattg gaaattacct atgtgcagag gaattatgat cttccttct | 480 |
| taaagaccat ccaggaggtg gctggttatg tcctcattgc cctcaacaca gtggagcgaa | 540 |
| ttcctttgga aaacctgcag atcatcagag gaaatatgta ctacgaaaat tcctatgcct | 600 |
| tagcagtctt atctaactat gatgcaaata aaaccggact gaaggagctg cccatgagaa | 660 |
| atttacagga atcctgcat ggcgccgtgc ggttcagcaa caaccctgcc ctgtgcaacg | 720 |
| tggagagcat ccagtggcgg gacatagtca gcagtgactt tctcagcaac atgtcgatgg | 780 |
| acttccagaa ccacctgggc agctgccaaa agtgtgatcc aagctgtccc aatgggagct | 840 |
| gctgggggtgc aggagaggag aactgccaga aactgaccaa aatcatctgt gcccagcagt | 900 |
| gctcggggcg ctgccgtggc aagtcccca gtgactgctg ccacaaccag tgtgctgcag | 960 |
| gctgcacagg cccccgggag agcgactgcc tggtctgccg caattccga gacgaagcca | 1020 |
| cgtgcaagga cacctgcccc ccactcatgc tctacaaccc caccacgtac cagatggatg | 1080 |
| tgaaccccga gggcaaatac agctttggtg ccacctgcgt gaagaagtgt ccccgtaatt | 1140 |
| atgtggtgac agatcacggc tcgtgcgtcc gagcctgtgg ggccgacagc tatgagatgg | 1200 |
| aggaagacgg cgtccgcaag tgtaagaagt gcgaagggcc ttgccgcaaa gtgtgtaacg | 1260 |
| gaataggtat tggtgaattt aaagactcac tctccataaa tgctacgaat attaaacact | 1320 |
| tcaaaaactg cacctccatc agtggcgatc tccacatcct gccggtggca tttagggtg | 1380 |
| actccttcac acatactcct cctctggatc cacaggaact ggatattctg aaaaccgtaa | 1440 |
| aggaaatcac agggttttg ctgattcagg cttggcctga aaacaggacg gacctccatg | 1500 |
| cctttgagaa cctagaaatc atacgcggca ggaccaagca acatggtcag ttttctcttg | 1560 |

-continued

```
cagtcgtcag cctgaacata acatccttgg gattacgctc cctcaaggag ataagtgatg    1620
gagatgtgat aatttcagga aacaaaaatt tgtgctatgc aaatacaata aactggaaaa    1680
aactgtttgg gacctccggt cagaaaacca aaattataag caacagaggt gaaaacagct    1740
gcaaggccac aggccaggtc tgccatgcct tgtgctcccc cgagggctgc tggggcccgg    1800
agcccaggga ctgcgtctct tgccggaatg tcagccgagg cagggaatgc gtggacaagt    1860
gcaaccttct ggagggtgag ccaagggagt ttgtggagaa ctctgagtgc atacagtgcc    1920
acccagagtg cctgcctcag gccatgaaca tcacctgcac aggacgggga ccagacaact    1980
gtatccagtg tgcccactac attgacggcc cccactgcgt caagacctgc ccggcaggag    2040
tcatgggaga aaacaacacc ctggtctgga agtacgcaga cgccggccat gtgtgccacc    2100
tgtgccatcc aaactgcacc tacgatgca ctgggccagg tcttgaaggc tgtccaacga    2160
atgggcctaa gatcccgtcc atcgccactg ggatggtggg ggcctcctc ttgctgctgg    2220 tggtggccct ggggatcggc ctcttcatgc gaaggcgcca catcgttcgg aagcgcacgc    2280
tgcggaggct gctgcaggag agggagcttg tggagcctct tacacccagt ggagaagctc    2340
ccaaccaagc tctcttgagg atcttgaagg aaactgaatt caaaaagatc aaagtgctgg    2400
gctccggtgc gttcggcacg gtgtataagg actctggat cccagaaggt gagaaagtta    2460
aaattcccgt cgctatcaag gaatacatct ccgaaagcca acaaggaaat cctcgatgaa    2520
gcctacgtga tggccagcgt ggacaacccc cacgtgtgcc gcctgctggg catctgcctc    2580
acctccaccg tgcagctcat cacgcagctc atgcccttcg gctgcctcct ggactatgtc    2640
cgggaacaca agacaatat tggctcccag tacctgctca actggtgtgt gcagatcgca    2700
aagggcatga actacttgga ggaccgtcgc ttggtgcacc gcgacctggc agccaggaac    2760
gtactggtga aaacaccgca gcatgtcaag atcacagatt ttgggctggc caaactgctg    2820
ggtgcggaag agaaagaata ccatgcagaa ggaggcaaag tgcctatcaa gtggatggca    2880
ttggaatcaa ttttacacag aatctatacc caccagagtg atgtctggag ctacggggtg    2940
actgtttggg agttgatgac ctttggatcc aagccatatg acggaatccc tgccagcgag    3000
atctcctcca tcctggagaa aggagaacgc ctccctcagc cacccatatg taccatcgat    3060
gtctacatga tcatggtcaa gtgctggatg atagacgcag atagtcgccc aaagttccgt    3120
gagttgatca tcgaattctc caaaatggcc cgagaccccc agcgctacct tgtcattcag    3180
ggggatgaaa gaatgcattt gccaagtcct acagactcca acttctaccg tgccctgatg    3240
gatgaagaag acatggacga cgtggtggat gccgacgagt acctcatccc acagcagggc    3300
ttcttcagca gcccctccac gtcacggact cccctcctga gctctctgag tgcaaccagc    3360
aacaattcca ccgtggcttg cattgataga aatgggctgc aaagctgtcc catcaaggaa    3420
gacagcttct tgcagcgata cagctcagac cccacaggcg ccttgactga ggacagcata    3480
gacgacacct tcctcccagt gcctgaatac ataaaccagt ccgttcccaa aaggcccgct    3540
ggctctgtgc agaatcctgt ctatcacaat cagcctctga ccccgcgcc cagcagagac    3600 ccacactacc aggaccccca cagcactgca gtgggcaacc ccgagtatct caacactgtc    3660
cagcccacct gtgtcaacag cacattcgac agccctgccc actgggccca gaaaggcagc    3720
caccaaatta gcctggacaa ccctgactac cagcaggact tctttcccaa ggaagccaag    3780
ccaaatggca tctttaaggg ctccacagct gaaaatgcag ataccctaag ggtcgcgcca    3840
caaagcagtg aatttattgg agcatga                                        3867
```

<210> SEQ ID NO 721
<211> LENGTH: 3863
<212> TYPE: DNA
<213> ORGANISM: Homo sapiens

<400> SEQUENCE: 721

| | | | | | | |
|---|---|---|---|---|---|---|
| cccggcgcag | cgcggccgca | gcagcctccg | ccccccgcac | ggtgtgagcg | cccgacgcgg | 60 |
| ccgaggcggc | cggagtcccg | agctagcccc | ggcggccgcc | gccgcccaga | ccggacgaca | 120 |
| ggccacctcg | tcggcgtccg | cccgagtccc | cgcctcgccg | ccaacgccac | aaccaccgcg | 180 |
| cacggccccc | tgactccgtc | cagtattgat | cgggagagcc | ggagcgagct | cttcggggag | 240 |
| cagcgatgcg | accctccggg | acggccgggg | cagcgctcct | ggcgctgctg | gctgcgctct | 300 |
| gcccggcgag | tcgggctctg | gaggaaaaga | aagtttgcca | aggcacgagt | aacaagctca | 360 |
| cgcagttggg | cacttttgaa | gatcattttc | tcagcctcca | gaggatgttc | aataactgtg | 420 |
| aggtggtcct | tgggaatttg | gaaattacct | atgtgcagag | gaattatgat | cttccttct | 480 |
| taaagaccat | ccaggaggtg | gctggttatg | tcctcattgc | cctcaacaca | gtggagcgaa | 540 |
| ttcctttgga | aaacctgcag | atcatcagag | gaaatatgta | ctacgaaaat | tcctatgcct | 600 |
| tagcagtctt | atctaactat | gatgcaaata | aaaccggact | gaaggagctg | cccatgagaa | 660 |
| atttacagga | atcctgcat | ggcgccgtgc | ggttcagcaa | caccctgcc | ctgtgcaacg | 720 |
| tggagagcat | ccagtggcgg | gacatagtca | gcagtgactt | tctcagcaac | atgtcgatgg | 780 |
| acttccagaa | ccacctgggc | agctgccaaa | agtgtgatcc | aagctgtccc | aatgggagct | 840 |
| gctggggtgc | aggagaggag | aactgccaga | aactgaccaa | aatcatctgt | gcccagcagt | 900 |
| gctcccggcg | ctgccgtggc | aagtcccca | gtgactgctg | ccacaaccag | tgtgctgcag | 960 |
| gctgcacagg | ccccccgggag | agcgactgcc | tggtctgccg | caaattccga | gacgaagcca | 1020 |
| cgtgcaagga | cacctgcccc | ccactcatgc | tctacaaccc | caccacgtac | cagatggatg | 1080 |
| tgaaccccga | gggcaaatac | agctttggtg | ccacctgcgt | gaagaagtgt | ccccgtaatt | 1140 |
| atgtggtgac | agatcacggc | tcgtgcgtcc | gagcctgtgg | ggccgacagc | tatgagatgg | 1200 |
| aggaagacgc | cgtccgcaag | tgtaagaagt | gcgaagggcc | ttgccgcaaa | gtgtgtaacg | 1260 |
| gaataggtat | tggtgaattt | aaagactcac | tctccataaa | tgctacgaat | attaaacact | 1320 |
| tcaaaaactg | cacctccatc | agtggcgatc | tccacatcct | gccggtggca | tttaggggtg | 1380 |
| actccttcac | acatactcct | cctctggatc | cacaggaact | ggatattctg | aaaaccgtaa | 1440 |
| aggaaatcac | agggttttg | ctgattcagg | cttggcctga | aaacaggacg | gacctccatg | 1500 |
| cctttgagaa | cctagaaatc | atacgcggca | ggaccaagca | acatggtcag | ttttctcttg | 1560 |
| cagtcgtcag | cctgaacata | acatccttgg | gattacgctc | cctcaaggag | ataagtgatg | 1620 |
| gagatgtgat | aatttcagga | aacaaaaatt | tgtgctatgc | aaatacaata | aactggaaaa | 1680 |
| aactgttggg | gacctccggt | cagaaaacca | aaattataag | caacagaggt | gaaaacagct | 1740 |
| gcaaggccac | aggccaggtc | tgccatgcct | tgtgctcccc | cgagggctgc | tggggcccgg | 1800 |
| agcccaggga | ctgcgtctct | tgccggaatg | tcagccgagg | cagggaatgc | gtggacaagt | 1860 |
| gcaaccttct | ggagggtgag | ccaagggagt | tgtggagaa | ctctgagtgc | atacagtgcc | 1920 |
| acccagagtg | cctgcctcag | gccatgaaca | tcacctgcac | aggacgggga | ccagacaact | 1980 |
| gtatccagtg | tgcccactac | attgacggcc | ccactgcgt | caagacctgc | ccggcaggag | 2040 |
| tcatgggaga | aaacaacacc | ctggtctgga | agtacgcaga | cgccggccat | gtgtgccacc | 2100 |
| tgtgccatcc | aaactgcacc | tacggatgca | ctgggccagg | tcttgaaggc | tgtccaacga | 2160 |

```
atgggcctaa gatcccgtcc atcgccactg ggatggtggg ggccctcctc ttgctgctgg    2220
tggtggccct ggggatcggc ctcttcatgc gaaggcgcca catcgttcgg aagcgcacgc    2280
tgcggaggct gctgcaggag agggagcttg tggagcctct tacacccagt ggagaagctc    2340
ccaaccaagc tctcttgagg atcttgaagg aaactgaatt caaaaagatc aaagtgctgg    2400
gctccggtgc gttcggcacg gtgtataagg gactctggat cccagaaggt gagaaagtta    2460
aaattcccgt cgctatcaag gaattaagag aagcaacatc tgaaatcctc gatgaagcct    2520
acgtgatggc cagcgtggac aaccccacg tgtgccgcct gctgggcatc tgcctcacct    2580
ccaccgtgca gctcatcacg cagctcatgc ccttcggctg cctcctggac tatgtccggg    2640
aacacaaaga caatattggc tcccagtacc tgctcaactg gtgtgtgcag atcgcaaagg    2700
gcatgaacta cttggaggac cgtcgcttgg tgcaccgcga cctggcagcc aggaacgtac    2760
tggtgaaaac accgcagcat gtcaagatca cagattttgg gctggccaaa ctgctgggtg    2820
cggaagagaa agaataccat gcagaaggag gcaaagtgcc tatcaagtgg atggcattgg    2880
aatcaatttt acacagaatc tatcccacc agagtgatgt ctggagctac ggggtgactg    2940
tttgggagtt gatgaccttt ggatccaagc catatgacgg aatccctgcc agcgagatct    3000
cctccatcct ggagaaagga gaacgcctcc ctcagccacc catatgtacc atcgatgtct    3060
acatgatcat ggtcaagtgc tggatgatag acgcagatag tcgcccaaag ttccgtgagt    3120
tgatcatcga attctccaaa atggcccgag accccagcg ctaccttgtc attcagggg    3180 atgaaagaat gcatttgcca agtcctacag actccaactt ctaccgtgcc ctgatggatg    3240
aagaagacat ggacgacgtg gtggatgccg acgagtacct catcccacag cagggcttct    3300
tcagcagccc ctccacgtca cggactcccc tcctgagctc tctgagtgca ccagcaaca    3360 attccaccgt ggcttgcatt gatagaaatg ggctgcaaag ctgtcccatc aaggaagaca    3420
gcttcttgca gcgatacagc tcagacccca caggcgcctt gactgaggac agcatagacg    3480
acaccttcct cccagtgcct gaatacataa accagtccgt tcccaaaagg cccgctggct    3540
ctgtgcagaa tcctgtctat cacaatcagc ctctgaaccc cgcgcccagc agagacccac    3600
actaccagga ccccccacagc actgcagtgg gcaaccccga gtatctcaac actgtccagc    3660
ccacctgtgt caacagcaca ttcgacagcc ctgcccactg ggcccagaaa ggcagccacc    3720
aaattagcct ggacaaccct gactaccagc aggacttctt tcccaaggaa gccaagccaa    3780
atggcatctt taagggctcc acagctgaaa atgcagaata cctaagggtc gcgccacaaa    3840
gcagtgaatt tattggagca tga                                             3863
```

<210> SEQ ID NO 722
<211> LENGTH: 3886
<212> TYPE: DNA
<213> ORGANISM: Homo sapiens

<400> SEQUENCE: 722

```
cccggcgcag cgcggccgca gcagcctccg ccccccgcac ggtgtgagcg cccgacgcgg      60
ccgaggcggc cggagtcccg agctagcccc ggcggccgcc gccgcccaga ccggacgaca     120
ggccacctcg tcgcgtccg cccgagtccc cgcctcgccg ccaacgccac aaccaccgcg     180
cacggccccc tgactccgtc cagtattgat cgggagagcc ggagcgagct cttcggggag     240
cagcgatgcg accctccggg acggccgggg cagcgctcct ggcgctgctg gctgcgctct     300
gcccggcgag tcgggctctg gaggaaaaga agtttgccca aggcacgagt aacaagctca     360
```

-continued

```
cgcagttggg cacttttgaa gatcattttc tcagcctcca gaggatgttc aataactgtg    420
aggtggtcct tgggaatttg gaaattacct atgtgcagag gaattatgat ctttccttct    480
taaagaccat ccaggaggtg gctggttatg tcctcattgc cctcaacaca gtggagcgaa    540
ttcctttgga aaacctgcag atcatcagag gaaatatgta ctacgaaaat tcctatgcct    600
tagcagtctt atctaactat gatgcaaata aaaccggact gaaggagctg cccatgagaa    660
atttacagga atcctgcat ggcgccgtgc ggttcagcaa caaccctgcc ctgtgcaacg    720
tggagagcat ccagtggcgg gacatagtca gcagtgactt tctcagcaac atgtcgatgg    780
acttccagaa ccacctgggc agctgccaaa agtgtgatcc aagctgtccc aatgggagct    840
gctggggtgc aggagaggag aactgccaga aactgaccaa aatcatctgt gcccagcagt    900
gctccgggcg ctgccgtggc aagtccccca gtgactgctg ccacaaccag tgtgctgcag    960
gctgcacagg cccccgggag agcgactgcc tggtctgccg caaattccga gacgaagcca   1020
cgtgcaagga cacctgcccc ccactcatgc tctacaaccc caccacgtac cagatggatg   1080
tgaaccccga gggcaaatac agctttggtg ccacctgcgt gaagaagtgt ccccgtaatt   1140
atgtggtgac agatcacggc tcgtgcgtcc gagcctgtgg ggccgacagc tatgagatgg   1200
aggaagacgg cgtccgcaag tgtaagaagt gcgaagggcc ttgccgcaaa gtgtgtaacg   1260
gaataggtat tggtgaattt aaagactcac tctccataaa tgctacgaat attaaacact   1320
tcaaaaactg cacctccatc agtggcgatc tccacatcct gccggtggca tttaggggtg   1380
actccttcac acatactcct cctctggatc cacaggaact ggatattctg aaaaccgtaa   1440
aggaaatcac agggtttttg ctgattcagg cttggcctga aaacaggacg gacctccatg   1500
cctttgagaa cctagaaatc atacgcggca ggaccaagca acatggtcag ttttctcttg   1560
cagtcgtcag cctgaacata acatccttgg gattacgctc cctcaaggag ataagtgatg   1620
gagatgtgat aatttcagga aacaaaaatt tgtgctatgc aaatacaata aactggaaaa   1680 aactgttttgg gacctccggt cagaaaacca aaattataag caacagaggt gaaaacagct   1740
gcaaggccac aggccaggtc tgccatgcct tgtgctcccc cgagggctgc tggggcccgg   1800
agcccaggga ctgcgtctct tgccggaatg tcagccgagg cagggaatgc gtggacaagt   1860
gcaaccttct ggagggtgag ccaagggagt ttgtggagaa ctctgagtgc atacagtgcc   1920
acccagagtg cctgcctcag gccatgaaca tcacctgcac aggacgggga ccagacaact   1980
gtatccagtg tgcccactac attgacggcc ccactgcgt caagacctgc ccggcaggag   2040
tcatgggaga aaacaacacc ctggtctgga agtacgcaga cgccggccat gtgtgccacc   2100
tgtgccatcc aaactgcacc tacggatgca ctgggccagg tcttgaaggc tgtccaacga   2160
atgggcctaa gatcccgtcc atcgccactg ggatggtggg ggcctcctc ttgctgctgg   2220 tggtggccct ggggatcggc ctcttcatgc gaaggcgcca catcgttcgg aagcgcacgc   2280 tgcgaggct gctgcaggag agggagcttg tggagcctct tacacccagt ggagaagctc   2340
ccaaccaagc tctcttgagg atcttgaagg aaactgaatt caaaaagatc aaagtgctgg   2400
gctccggtgc gttcggcacg gtgtataagg gactctggat cccagaaggt gagaaagtta   2460
aaattcccgt cgctatcaag gaattaagag aagcaacatc tccgaaagcc aacaaggaaa   2520
tcctcgatga agcctacgtg atggccagcg tggacaaccc ggcaacccc acgtgtgccg   2580 cctgctgggc atctgcctca cctccaccgt gcagctcatc acgcagctca tgcccttcgg   2640
ctgcctcctg gactatgtcc gggaacacaa agacaatatt ggctcccagt acctgctcaa   2700
ctggtgtgtg cagatcgcaa agggcatgaa ctacttggag gaccgtcgct tggtgcaccg   2760
```

| | | | | |
|---|---|---|---|---|
| cgacctggca | gccaggaacg | tactggtgaa | aacaccgcag | catgtcaaga tcacagattt | 2820 |
| tgggctggcc | aaactgctgg | gtgcggaaga | gaaagaatac | catgcagaag gaggcaaagt | 2880 |
| gcctatcaag | tggatggcat | tggaatcaat | tttacacaga | atctataccc accagagtga | 2940 |
| tgtctggagc | tacggggtga | ctgtttggga | gttgatgacc | tttggatcca agccatatga | 3000 |
| cggaatccct | gccagcgaga | tctcctccat | cctggagaaa | ggagaacgcc tccctcagcc | 3060 |
| acccatatgt | accatcgatg | tctacatgat | catggtcaag | tgctggatga tagacgcaga | 3120 |
| tagtcgccca | aagttccgtg | agttgatcat | cgaattctcc | aaaatggccc gagaccccca | 3180 |
| gcgctacctt | gtcattcagg | gggatgaaag | aatgcatttg | ccaagtccta cagactccaa | 3240 |
| cttctaccgt | gccctgatgg | atgaagaaga | catggacgac | gtggtggatg ccgacgagta | 3300 |
| cctcatccca | cagcagggct | tcttcagcag | cccctccacg | tcacggactc ccctcctgag | 3360 |
| ctctctgagt | gcaaccagca | acaattccac | cgtggcttgc | attgatagaa atgggctgca | 3420 |
| aagctgtccc | atcaaggaag | acagcttctt | gcagcgatac | agctcagacc ccacaggcgc | 3480 |
| cttgactgag | gacagcatag | acgacacctt | cctcccagtg | cctgaataca taaaccagtc | 3540 |
| cgttcccaaa | aggcccgctg | gctctgtgca | gaatcctgtc | tatcacaatc agcctctgaa | 3600 |
| ccccgcgccc | agcagagacc | cacactacca | ggaccccac | agcactgcag tgggcaaccc | 3660 |
| cgagtatctc | aacactgtcc | agcccacctg | tgtcaacagc | acattcgaca gccctgccca | 3720 |
| ctgggcccag | aaaggcagcc | accaaattag | cctggacaac | cctgactacc agcaggactt | 3780 |
| cttttcccaag | gaagccaagc | caaatggcat | ctttaagggc | tccacagctg aaaatgcaga | 3840 |
| atacctaagg | gtcgcgccac | aaagcagtga | atttattgga | gcatga | 3886 |

<210> SEQ ID NO 723
<211> LENGTH: 3887
<212> TYPE: DNA
<213> ORGANISM: Homo sapiens

<400> SEQUENCE: 723

| | | | | |
|---|---|---|---|---|
| cccggcgcag | cgcggccgca | gcagcctccg | cccccgcac | ggtgtgagcg cccgacgcgg | 60 |
| ccgaggcggc | cggagtcccg | agctagcccc | ggcggccgcc | gccgcccaga ccggacgaca | 120 |
| ggccacctcg | tcggcgtccg | cccgagtccc | cgcctcgccg | ccaacgccac aaccaccgcg | 180 |
| cacggccccc | tgactccgtc | cagtattgat | cgggagagcc | ggagcgagct cttcggggag | 240 |
| cagcgatgcg | accctccggg | acggccgggg | cagcgctcct | ggcgctgctg gctgcgctct | 300 |
| gcccggcgag | tcgggctctg | gaggaaaaga | agtttgccca | aggcacgagt aacaagctca | 360 |
| cgcagttggg | cacttttgaa | gatcattttc | tcagcctcca | gaggatgttc aataactgtg | 420 |
| aggtggtcct | tgggaatttg | gaaattacct | atgtgcagag | gaattatgat ctttccttct | 480 |
| taaagaccat | ccaggaggtg | gctggttatg | tcctcattgc | cctcaacaca gtggagcgaa | 540 |
| ttcctttgga | aaacctgcag | atcatcagag | gaaatatgta | ctacgaaaat tcctatgcct | 600 |
| tagcagtctt | atctaactat | gatgcaaata | aaaccggact | gaaggagctg cccatgagaa | 660 |
| atttacagga | atcctgcat | ggcgccgtgc | ggttcagcaa | caaccctgcc ctgtgcaacg | 720 |
| tggagagcat | ccagtggcgg | gacatagtca | gcagtgactt | tctcagcaac atgtcgatgg | 780 |
| acttccagaa | ccacctgggc | agctgccaaa | agtgtgatcc | aagctgtccc aatgggagct | 840 |
| gctggggtgc | aggagaggag | aactgccaga | aactgaccaa | aatcatctgt gcccagcagt | 900 |
| gctcccggcg | ctgccgtggc | aagtccccca | gtgactgctg | ccacaaccag tgtgctgcag | 960 |

```
gctgcacagg ccccccgggag agcgactgcc tggtctgccg caaattccga gacgaagcca   1020
cgtgcaagga cacctgcccc ccactcatgc tctacaaccc caccacgtac cagatggatg   1080
tgaaccccga gggcaaatac agctttggtg ccacctgcgt gaagaagtgt ccccgtaatt   1140
atgtggtgac agatcacggc tcgtgcgtcc gagcctgtgg ggccgacagc tatgagatgg   1200
aggaagacgg cgtccgcaag tgtaagaagt gcgaagggcc ttgccgcaaa gtgtgtaacg   1260
gaataggtat tggtgaattt aaagactcac tctccataaa tgctacgaat attaaacact   1320
tcaaaaactg cacctccatc agtggcgatc tccacatcct gccggtggca tttagggggtg   1380
actccttcac acatactcct cctctggatc cacaggaact ggatattctg aaaaccgtaa   1440
aggaaatcac agggttttttg ctgattcagg cttggcctga aaacaggacg gacctccatg   1500
cctttgagaa cctagaaatc atacgcggca ggaccaagca acatggtcag ttttctcttg   1560
cagtcgtcag cctgaacata acatccttgg gattacgctc cctcaaggag ataagtgatg   1620
gagatgtgat aatttcagga aacaaaaatt tgtgctatgc aaatacaata aactggaaaa   1680
aactgtttgg gacctccggt cagaaaacca aaattataag caacagaggt gaaaacagct   1740
gcaaggccac aggccaggtc tgccatgcct tgtgctcccc cgagggctgc tggggcccgg   1800
agcccaggga ctgcgtctct tgccggaatg tcagccgagg cagggaatgc gtggacaagt   1860
gcaaccttct ggagggtgag ccaagggagt ttgtggagaa ctctgagtgc atacagtgcc   1920
acccagagtg cctgcctcag gccatgaaca tcacctgcac aggacgggga ccagacaact   1980
gtatccagtg tgcccactac attgacggcc cccactgcgt caagacctgc ccggcaggag   2040
tcatgggaga aaacaacacc ctggtctgga gtacgcaga cgccggccat gtgtgccacc   2100
tgtgccatcc aaactgcacc tacggatgca ctgggccagg tcttgaaggc tgtccaacga   2160
atgggcctaa gatcccgtcc atcgccactg ggatggtggg ggccctcctc ttgctgctgg   2220
tggtggccct ggggatcggc ctcttcatgc gaaggcgcca catcgttcgg aagcgcacgc   2280
tgcggaggct gctgcaggag agggagcttg tggagcctct tacacccagt ggagaagctc   2340
ccaaccaagc tctcttgagg atcttgaagg aaactgaatt caaaaagatc aaagtgctgg   2400
gctccggtgc gttcggcacg gtgtataagg actctggat cccagaaggt gagaaagtta   2460
aaattcccgt cgctatcaag gaattaagag aagcaacatc tccgaaagcc aacaaggaaa   2520
tcctcgatga agcctacgtg atggccagcg tggacagcgt ggacaacccc cacgtgtgcc   2580
gcctgctggg catctgcctc acctccaccg tgcagctcat cacgcagctc atgcccttcg   2640
gctgcctcct ggactatgtc cgggaacaca aagacaatat tggctcccag tacctgctca   2700
actggtgtgt gcagatcgca aagggcatga actacttgga ggaccgtcgc ttggtgcacc   2760
gcgacctggc agccaggaac gtactggtga aaacaccgca gcatgtcaag atcacagatt   2820
ttgggctggc caaactgctg ggtgcggaag agaaagaata ccatgcagaa ggaggcaaag   2880
tgcctatcaa gtggatggca ttggaatcaa ttttacacag aatctatacc caccagagtg   2940
atgtctggag ctacggggtg actgtttggg agttgatgac ctttggatcc aagccatatg   3000
acggaatccc tgccagcgag atctcctcca tcctggagaa aggagaacgc ctccctcagc   3060
cacccatatg taccatcgat gtctacatga tcatggtcaa gtgctggatg atagacgcag   3120
atagtcgccc aaagttccgt gagttgatca tcgaattctc caaaatggcc cgagaccccc   3180
agcgctacct tgtcattcag ggggatgaaa gaatgcattt gccaagtcct acagactcca   3240
acttctaccg tgccctgatg gatgaagaag acatggacga cgtggtggat gccgacgagt   3300
acctcatccc acagcagggc ttcttcagca gccccctcca gtcacggact cccctcctga   3360
```

```
gctctctgag tgcaaccagc aacaattcca ccgtggcttg cattgataga aatgggctgc    3420
aaagctgtcc catcaaggaa gacagcttct tgcagcgata cagctcagac cccacaggcg    3480
ccttgactga ggacagcata gacgacacct tcctcccagt gcctgaatac ataaaccagt    3540
ccgttcccaa aaggcccgct ggctctgtgc agaatcctgt ctatcacaat cagcctctga    3600
accccgcgcc cagcagagac ccacactacc aggaccccca cagcactgca gtgggcaacc    3660
ccgagtatct caacactgtc cagcccacct gtgtcaacag cacattcgac agccctgccc    3720
actgggccca gaaaggcagc accaaattag cctggacaa ccctgactac cagcaggact     3780
tctttcccaa ggaagccaag ccaaatggca tctttaaggg ctccacagct gaaaatgcag    3840
aatacctaag ggtcgcgcca caaagcagtg aatttattgg agcatga                  3887
```

<210> SEQ ID NO 724
<211> LENGTH: 3881
<212> TYPE: DNA
<213> ORGANISM: Homo sapiens

<400> SEQUENCE: 724

```
cccggcgcag cgcggccgca gcagcctccg ccccccgcac ggtgtgagcg cccgacgcgg      60
ccgaggcggc cggagtcccg agctagcccc ggcggccgcc gccgcccaga ccggacgaca     120
ggccacctcg tcggcgtccg cccgagtccc cgcctcgccg ccaacgccac aaccaccgcg     180
cacggccccc tgactccgtc cagtattgat cgggagagcc ggagcgagct cttcggggag     240
cagcgatgcg accctccggg acggccgggg cagcgctcct ggcgctgctg gctgcgctct     300
gcccggcgag tcgggctctg gaggaaaaga agtttgcca aggcacgagt aacaagctca      360
cgcagttggg cacttttgaa gatcattttc tcagcctcca gaggatgttc aataactgtg     420
aggtggtcct tgggaatttg gaaattacct atgtgcagag gaattatgat cttttccttct    480 taaagaccat ccaggaggtg gctggttatg tcctcattgc cctcaacaca gtggagcgaa    540
ttcctttgga aaacctgcag atcatcagag gaaatatgta ctacgaaaat tcctatgcct    600
tagcagtctt atctaactat gatgcaaata aaaccggact gaaggagctg cccatgagaa    660
atttacagga aatcctgcat ggcgccgtgc ggttcagcaa caaccctgcc ctgtgcaacg    720
tggagagcat ccagtggcgg gacatagtca gcagtgactt tctcagcaac atgtcgatgg    780
acttccagaa ccacctgggc agctgccaaa agtgtgatcc aagctgtccc aatgggagct    840
gctggggtgc aggagaggag aactgccaga aactgaccaa aatcatctgt gcccagcagt    900
gctccgggcg ctgccgtggc aagtccccca gtgactgctg ccacaaccag tgtgctgcag    960
gctgcacagg ccccgggag agcgactgcc tggtctgccg caaattccga gacgaagcca   1020
cgtgcaagga cacctgcccc ccactcatgc tctacaaccc caccacgtac cagatggatg   1080
tgaaccccga gggcaaatac agctttggtg ccacctgcgt gaagaagtgt ccccgtaatt   1140
atgtggtgac agatcacggc tcgtgcgtcc gagcctgtgg ggccgacagc tatgagatgg   1200
aggaagacgg cgtccgcaag tgtaagaagt gcgaagggcc ttgccgcaaa gtgtgtaacg   1260
gaataggtat tggtgaattt aaaagactca ctctccataa tgctacgaat attaaacact   1320
tcaaaaactg cacctccatc agtggcgatc tccacatcct gccggtggca tttaggggtg   1380
actccttcac acatactcct cctctggatc cacaggaact ggatattctg aaaaccgtaa   1440
aggaaatcac aggtttttg ctgattcagg cttggcctga aaacaggacg gacctccatg   1500
cctttgagaa cctagaaatc atacgcggca ggaccaagca acatggtcag ttttctcttg   1560
```

-continued

```
cagtcgtcag cctgaacata acatccttgg gattacgctc cctcaaggag ataagtgatg    1620
gagatgtgat aatttcagga aacaaaaatt tgtgctatgc aaatacaata aactggaaaa    1680
aactgtttgg gacctccggt cagaaaacca aaattataag caacagaggt gaaaacagct    1740
gcaaggccac aggccaggtc tgccatgcct tgtgctcccc cgagggctgc tggggcccgg    1800
agcccaggga ctgcgtctct tgccggaatg tcagccgagg cagggaatgc gtggacaagt    1860
gcaaccttct ggagggtgag ccaagggagt tgtggagaa ctctgagtgc atacagtgcc     1920
acccagagtg cctgcctcag gccatgaaca tcacctgcac aggacgggga ccagacaact    1980
gtatccagtg tgcccactac attgacggcc ccactgcgt caagacctgc ccggcaggag     2040
tcatgggaga aaacaacacc ctggtctgga agtacgcaga cgccggccat gtgtgccacc    2100
tgtgccatcc aaactgcacc tacgatgca ctgggccagg tcttgaaggc tgtccaacga     2160
atgggcctaa gatcccgtcc atcgccactg ggatggtggg ggcctcctc ttgctgctgg     2220
tggtggccct ggggatcggc ctcttcatgc gaaggcgcca catcgttcgg aagcgcacgc    2280
tgcggaggct gctgcaggag agggagcttg tggagcctct acacccagt ggagaagctc     2340
ccaaccaagc tctcttgagg atcttgaagg aaactgaatt caaaaagatc aaagtgctgg    2400
gctccggtgc gttcggcacg tgtataagg actctggat cccagaaggt gagaaagtta     2460
aaattcccgt cgctatcaag gaattaagag aagcaacatc tccgaaagcc aacaaggaaa    2520
tcctcgatga agcctacgtg atggccacg tggacaaccc cggtcacgtg tgccgcctgc     2580
tgggcatctg cctcacctcc accgtgcagc tcatcacgca gctcatgccc ttcggctgcc    2640
tcctggacta tgtccgggaa cacaaagaca atattggctc ccagtacctg ctcaactggt    2700
gtgtgcagat cgcaaagggc atgaactact ggaggaccg tcgcttggtg caccgcgacc    2760
tggcagccag gaacgtactg gtgaaaacac cgcagcatgt caagatcaca gattttgggc    2820
tggccaaact gctgggtgcg gaagagaaag aataccatgc agaaggaggc aaagtgccta    2880
tcaagtggat ggcattggaa tcaattttac acagaatcta tacccaccag agtgatgtct    2940
ggagctacgg ggtgactgtt tgggagttga tgacctttgg atccaagcca tatgacggaa    3000
tccctgccag cgagatctcc tccatcctgg agaaaggaga acgcctccct cagccaccca    3060
tatgtaccat cgatgtctac atgatcatgg tcaagtgctg gatgatagac gcagatagtc    3120
gcccaaagtt ccgtgagttg atcatcgaat tctccaaaat ggcccgagac ccccagcgct    3180
accttgtcat tcaggggat gaaagaatgc atttgccaag tcctacagac tccaacttct     3240
accgtgccct gatggatgaa gaagacatgg acgacgtggt ggatgccgac gagtacctca    3300
tcccacagca gggcttcttc agcagcccct ccacgtcacg gactcccctc ctgagctctc    3360
tgagtgcaac cagcaacaat tccaccgtgg cttgcattga tagaaatggg ctgcaaagct    3420
gtcccatcaa ggaagacagc ttcttgcagc gatacagctc agacccccac ggcgccttga    3480
ctgaggacag catagacgac accttcctcc cagtgcctga atacataaac cagtccgttc    3540
ccaaaaggcc cgctggctct gtgcagaatc ctgtctatca caatcagcct ctgaaccccg    3600
cgcccagcag agacccacac taccaggacc ccacagcac tgcagtgggc aaccccgagt    3660
atctcaacac tgtccagccc acctgtgtca acagcacatt cgacagccct gcccactggg    3720
cccagaaagg cagccaccaa attagcctgg acaaccctga ctaccagcag gacttctttc    3780
ccaaggaagc caagccaaat ggcatctttt agggctccac agctgaaaat gcagaatacc    3840
taagggtcgc gccacaaagc agtgaattta ttggagcatg a                        3881
```

<210> SEQ ID NO 725
<211> LENGTH: 3878
<212> TYPE: DNA
<213> ORGANISM: Homo sapiens

<400> SEQUENCE: 725

```
cccggcgcag cgcggccgca gcagcctccg ccccccgcac ggtgtgagcg cccgacgcgg      60
ccgaggcggc cggagtcccg agctagcccc ggcggccgcc gccgcccaga ccggacgaca     120
ggccacctcg tcggcgtccg cccgagtccc cgcctcgccg ccaacgccac aaccaccgcg     180
cacggccccc tgactccgtc cagtattgat cgggagagcc ggagcgagct cttcggggag     240
cagcgatgcg accctccggg acggccgggg cagcgctcct ggcgctgctg gctgcgctct     300
gcccggcgag tcgggctctg gaggaaaaga agtttgccca aggcacgagt aacaagctca     360
cgcagttggg cacttttgaa gatcattttc tcagcctcca gaggatgttc aataactgtg     420
aggtggtcct tgggaatttg gaaattacct atgtgcagag gaattatgat cttttccttct     480
taaagaccat ccaggaggtg gctggttatg tcctcattgc cctcaacaca gtggagcgaa     540
ttcctttgga aaacctgcag atcatcagag gaaatatgta ctacgaaaat tcctatgcct     600
tagcagtctt atctaactat gatgcaaata aaaccggact gaaggagctg cccatgagaa     660
atttacagga atcctgcat ggcgccgtgc ggttcagcaa caaccctgcc ctgtgcaacg     720
tggagagcat ccagtggcgg gacatagtca gcagtgactt tctcagcaac atgtcgatgg     780
acttccagaa ccacctgggc agctgccaaa agtgtgatcc aagctgtccc aatgggagct     840
gctggggtgc aggagaggag aactgccaga aactgaccaa aatcatctgt gcccagcagt     900
gctccgggcg ctgccgtggc aagtccccca gtgactgctg ccacaaccag tgtgctgcag     960
gctgcacagg cccccgggag agcgactgcc tggtctgccg caaattccga gacgaagcca    1020
cgtgcaagga cacctgcccc ccactcatgc tctacaaccc caccacgtac cagatggatg    1080
tgaaccccga gggcaaatac agctttggtg ccacctgcgt gaagaagtgt ccccgtaatt    1140
atgtggtgac agatcacggc tcgtgcgtcc gagcctgtgg ggccgacagc tatgagatgg    1200
aggaagacgg cgtccgcaag tgtaagaagt gcgaagggcc ttgccgcaaa gtgtgtaacg    1260
gaataggtat tggtgaattt aaagactcac tctccataaa tgctacgaat attaaacact    1320
tcaaaaactg cacctccatc agtggcgatc tccacatcct gccggtggca tttaggggtg    1380
actccttcac acatactcct cctctggatc cacaggaact ggatattctg aaaaccgtaa    1440
aggaaatcac agggttttg ctgattcagg cttggcctga aaacaggacg gacctccatg    1500
cctttgagaa cctagaaatc atacgcggca ggaccaagca acatggtcag tttttctcttg    1560
cagtcgtcag cctgaacata acatccttgg gattacgctc cctcaaggag ataagtgatg    1620
gagatgtgat aatttcagga aacaaaaatt tgtgctatgc aaatacaata aactggaaaa    1680
aactgtttgg gacctccggt cagaaaacca aaattataag caacagaggt gaaaacagct    1740
gcaaggccac aggccaggtc tgccatgcct tgtgctcccc cgagggctgc tggggcccgg    1800
agcccaggga ctgcgtctct tgccggaatg tcagccgagg cagggaatgc gtggacaagt    1860
gcaaccttct ggagggtgag ccaagggagt tgtggagaa ctctgagtgc atacagtgcc    1920
acccagagtg cctgcctcag gccatgaaca tcacctgcac aggacgggga ccagacaact    1980
gtatccagtg tgcccactac attgacggcc ccactgcgt caagacctgc ccggcaggag    2040
tcatgggaga aaacaacacc ctggtctgga agtacgcaga cgccggccat gtgtgccacc    2100
tgtgccatcc aaactgcacc tacggatgca ctgggccagg tcttgaaggc tgtccaacga    2160
```

| | |
|---|---|
| atgggcctaa gatcccgtcc atcgccactg ggatggtggg ggccctcctc ttgctgctgg | 2220 |
| tggtggccct ggggatcggc ctcttcatgc gaaggcgcca catcgttcgg aagcgcacgc | 2280 |
| tgcggaggct gctgcaggag agggagcttg tggagcctct tacacccagt ggagaagctc | 2340 |
| ccaaccaagc tctcttgagg atcttgaagg aaactgaatt caaaaagatc aaagtgctgg | 2400 |
| gctccggtgc gttcggcacg gtgtataagg gactctggat cccagaaggt gagaaagtta | 2460 |
| aaattcccgt cgctatcaag gaattaagag aagcaacatc tccgaaagcc aacaaggaaa | 2520 |
| tcctcgatga agcctacgtg atggccagcg tggacaaccc ccacgtgtgc cgcctgctaa | 2580 |
| gcatctgcct cacctccacc gtgcagctca tcacgcagct catgcccttc ggctgcctcc | 2640 |
| tggactatgt ccgggaacac aaagacaata ttggctccca gtacctgctc aactggtgtg | 2700 |
| tgcagatcgc aaagggcatg aactacttgg aggaccgtcg cttggtgcac cgcgacctgg | 2760 |
| cagccaggaa cgtactggtg aaaacaccgc agcatgtcaa gatcacagat tttgggctgg | 2820 |
| ccaaactgct gggtgcggaa gagaaagaat accatgcaga aggaggcaaa gtgcctatca | 2880 |
| agtggatggc attggaatca attttacaca gaatctatac ccaccagagt gatgtctgga | 2940 |
| gctacggggt gactgtttgg gagttgatga ccttttggatc caagccatat gacggaatcc | 3000 |
| ctgccagcga gatctcctcc atcctggaga aggagaacg cctccctcag ccacccatat | 3060 |
| gtaccatcga tgtctacatg atcatggtca agtgctggat gatagacgca gatagtcgcc | 3120 |
| caaagttccg tgagttgatc atcgaattct ccaaaatggc ccgagacccc cagcgctacc | 3180 |
| ttgtcattca gggggatgaa agaatgcatt tgccaagtcc tacagactcc aacttctacc | 3240 |
| gtgccctgat ggatgaagaa gacatggacg acgtggtgga tgccgacgag tacctcatcc | 3300 |
| cacagcaggg cttcttcagc agcccctcca cgtcacggac tcccctcctg agctctctga | 3360 |
| gtgcaaccag caacaattcc accgtggctt gcattgatag aaatgggctg caaagctgtc | 3420 |
| ccatcaagga agacagcttc ttgcagcgat acagctcaga ccccacaggc gccttgactg | 3480 |
| aggacagcat agacgacacc ttcctcccag tgcctgaata cataaaccag tccgttccca | 3540 |
| aaaggcccgc tggctctgtg cagaatcctg tctatcacaa tcagcctctg aaccccgcgc | 3600 |
| ccagcagaga cccacactac caggaccccc acagcactgc agtgggcaac cccgagtatc | 3660 |
| tcaacactgt ccagcccacc tgtgtcaaca gcacattcga cagccctgcc cactgggccc | 3720 |
| agaaaggcag ccaccaaatt agcctggaca accctgacta ccagcaggac ttctttccca | 3780 |
| aggaagccaa gccaaatggc atctttaagg ctccacagc tgaaaatgca gaatacctaa | 3840 |
| gggtcgcgcc acaaagcagt gaatttattg gagcatga | 3878 |

<210> SEQ ID NO 726
<211> LENGTH: 3878
<212> TYPE: DNA
<213> ORGANISM: Homo sapiens

<400> SEQUENCE: 726

| | |
|---|---|
| cccggcgcag cgcggccgca gcagcctccg ccccccgcac ggtgtgagcg cccgacgcgg | 60 |
| ccgaggcggc cggagtcccg agctagcccc ggcggccgcc gccgcccaga ccggacgaca | 120 |
| ggccacctcg tcgcgtccg cccgagtccc cgcctcgccg ccaacgccac aaccaccgcg | 180 |
| cacggccccc tgactccgtc cagtattgat cgggagagcc ggagcgagct cttcggggag | 240 |
| cagcgatgcg accctccggg acggccgggg cagcgctcct ggcgctgctg gctgcgctct | 300 |
| gcccggcgag tcgggctctg gaggaaaaga agtttgccaa aggcacgagt aacaagctca | 360 |
| cgcagttggg cactttttgaa gatcatttc tcagcctcca gaggatgttc aataactgtg | 420 |

```
aggtggtcct tgggaatttg gaaattacct atgtgcagag gaattatgat ctttccttct    480
taaagaccat ccaggaggtg gctggttatg tcctcattgc cctcaacaca gtggagcgaa    540
ttcctttgga aaacctgcag atcatcagag gaaatatgta ctacgaaaat tcctatgcct    600
tagcagtctt atctaactat gatgcaaata aaaccggact gaaggagctg cccatgagaa    660
atttacagga atcctgcat ggcgccgtgc ggttcagcaa caaccctgcc ctgtgcaacg    720
tggagagcat ccagtggcgg acatagtca gcagtgactt tctcagcaac atgtcgatgg    780
acttccagaa ccacctgggc agctgccaaa agtgtgatcc aagctgtccc aatgggagct    840
gctggggtgc aggagaggag aactgccaga aactgaccaa atcatctgt gcccagcagt    900
gctccgggcg ctgccgtggc aagtccccca gtgactgctg ccacaaccag tgtgctgcag    960
gctgcacagg ccccggggag agcgactgcc tggtctgccg caaattccga gacgaagcca   1020
cgtgcaagga cacctgcccc ccactcatgc tctacaaccc caccacgtac cagatggatg   1080
tgaaccccga gggcaaatac agctttggtg ccacctgcgt gaagaagtgt ccccgtaatt   1140
atgtggtgac agatcacggc tcgtgcgtcc gagcctgtgg ggccgacagc tatgagatgg   1200
aggaagacgg cgtccgcaag tgtaagaagt gcgaagggcc ttgccgcaaa gtgtgtaacg   1260
gaataggtat tggtgaattt aaagactcac tctccataaa tgctacgaat attaaacact   1320
tcaaaaactg cacctccatc agtggcgatc tccacatcct gccggtggca tttaggggtg   1380
actccttcac acatactcct cctctggatc cacaggaact ggatattctg aaaaccgtaa   1440
aggaaatcac agggttttg ctgattcagg cttggcctga aaacaggacg gacctccatg   1500
cctttgagaa cctagaaatc atacgcggca ggaccaagca acatggtcag ttttctcttg   1560
cagtcgtcag cctgaacata acatccttgg gattacgctc cctcaaggag ataagtgatg   1620
gagatgtgat aatttcagga aacaaaaatt tgtgctatgc aaatacaata aactggaaaa   1680
aactgttggg gacctccggt cagaaaacca aaattataag caacagaggt gaaaacagct   1740
gcaaggccac aggccaggtc tgccatgcct tgtgctcccc cgagggctgc tggggcccgg   1800
agcccaggga ctgcgtctct tgccggaatg tcagccgagg cagggaatgc gtggacaagt   1860
gcaaccttct ggagggtgag ccaagggagt ttgtggagaa ctctgagtgc atacagtgcc   1920
acccagagtg cctgcctcag gccatgaaca tcacctgcac aggacgggga ccagacaact   1980
gtatccagtg tgcccactac attgacggcc cccactgcgt caagacctgc ccggcaggag   2040
tcatgggaga aaacaacacc ctggtctgga agtacgcaga cgccggccat gtgtgccacc   2100
tgtgccatcc aaactgcacc tacgatgca ctgggccagg tcttgaaggc tgtccaacga   2160
atgggcctaa gatcccgtcc atcgccactg ggatggtggg ggccctcctc ttgctgctgg   2220
tggtggccct ggggatcggc ctcttcatgc gaaggcgcca catcgttcgg aagcgcacgc   2280
tgcggaggct gctgcaggag agggagcttg tggagcctct tacacccagt ggagaagctc   2340
ccaaccaagc tctcttgagg atcttgaagg aaactgaatt caaaaagatc aaagtgctgg   2400
gctccggtgc gttcggcacg gtgtataagg gactctggat cccagaaggt gagaaagtta   2460
aaattcccgt cgctatcaag gaattaagag aagcaacatc tccgaaagcc aacaaggaaa   2520
tcctcgatga agcctacgtg atggccagcg tggacaaccc ccacgtgtgc cgcctgctgg   2580
gcatctgcct cacctccacc gtgcagctca tcacgcagct catgcccttc ggctgcctcc   2640
tggactatgt ccgggaacac aaagacaata ttggctccca gtacctgctc aactggtgtg   2700
tgcagatcgc aaagggcatg aactacttgg aggaccgtcg cttggtgcac cgcgacctgg   2760
```

```
cagccaggaa cgtactggtg aaaacaccgc agcatgtcaa gatcacagat tttgtgctgg    2820
ccaaactgct gggtgcggaa gagaaagaat accatgcaga aggaggcaaa gtgcctatca    2880
agtggatggc attggaatca attttacaca gaatctatac ccaccagagt gatgtctgga    2940 gctacgggt gactgtttgg gagttgatga cctttggatc caagccatat gacggaatcc     3000
ctgccagcga gatctcctcc atcctggaga aggagaacg cctccctcag ccacccatat     3060
gtaccatcga tgtctacatg atcatggtca agtgctggat gatagacgca gatagtcgcc    3120
caaagttccg tgagttgatc atcgaattct ccaaaatggc ccgagacccc cagcgctacc    3180
ttgtcattca gggggatgaa agaatgcatt tgccaagtcc tacagactcc aacttctacc    3240
gtgccctgat ggatgaagaa gacatggacg acgtggtgga tgccgacgag tacctcatcc    3300
cacagcaggg cttcttcagc agcccctcca cgtcacggac tcccctcctg agctctctga    3360
gtgcaaccag caacaattcc accgtggctt gcattgatag aaatgggctg caaagctgtc    3420
ccatcaagga agacagcttc ttgcagcgat acagctcaga ccccacaggc gccttgactg    3480
aggacagcat agacgacacc ttcctcccag tgcctgaata cataaaccag tccgttccca    3540
aaaggcccgc tggctctgtg cagaatcctg tctatcacaa tcagcctctg aaccccgcgc    3600
ccagcagaga cccacactac caggacccc acagcactgc agtgggcaac cccgagtatc    3660
tcaacactgt ccagcccacc tgtgtcaaca gcacattcga cagccctgcc cactgggccc    3720
agaaaggcag ccaccaaatt agcctggaca accctgacta ccagcaggac ttctttccca    3780
aggaagccaa gccaaatggc atctttaagg gctccacagc tgaaaatgca gaatacctaa    3840
gggtcgcgcc acaaagcagt gaatttattg gagcatga                           3878

<210> SEQ ID NO 727
<211> LENGTH: 3878
<212> TYPE: DNA
<213> ORGANISM: Homo sapiens

<400> SEQUENCE: 727
cccggcgcag cgcggccgca gcagcctccg ccccccgcac ggtgtgagcg cccgacgcgg      60
ccgaggcggc cggagtcccg agctagcccc ggcggccgcc gccgcccaga ccggacgaca     120
ggccacctcg tcggcgtccg cccgagtccc cgcctcgccg ccaacgccac aaccaccgcg     180 cacgccccc tgactccgtc cagtattgat cgggagagcc ggagcgagct cttcggggag      240
cagcgatgcg accctccggg acggccgggg cagcgctcct ggcgctgctg gctgcgctct     300
gcccggcgag tcgggctctg gaggaaaaga aagtttgcca aggcacgagt aacaagctca    360
cgcagttggg cacttttgaa gatcattttc tcagcctcca gaggatgttc aataactgtg    420
aggtggtcct tgggaatttg gaaattacct atgtgcagag gaattatgat cttccttct     480 taaagaccat ccaggaggtg gctggttatg tcctcattgc cctcaacaca gtggagcgaa    540
ttcctttgga aaacctgcag atcatcagag gaaatatgta ctacgaaaat tcctatgcct    600
tagcagtctt atctaactat gatgcaaata aaaccggact gaaggagctg cccatgagaa    660
atttacagga atcctgcat ggcgccgtgc ggttcagcaa caaccctgcc ctgtgcaacg     720
tggagagcat ccagtggcgg gacatagtca gcagtgactt tctcagcaac atgtcgatgg    780
acttccagaa ccacctgggc agctgccaaa agtgtgatcc aagctgtccc aatgggagct    840
gctggggtgc aggagaggag aactgccaga aactgaccaa aatcatctgt gcccagcagt    900 gctccggcc tctgccgtgg caagtccccca gtgactgctg ccacaaccag tgtgctgcag    960
gctgcacagg ccccgggag agcgactgcc tggtctgccg caaattccga gacgaagcca   1020
```

```
cgtgcaagga cacctgcccc ccactcatgc tctacaaccc caccacgtac cagatggatg   1080
tgaaccccga gggcaaatac agctttggtg ccacctgcgt gaagaagtgt ccccgtaatt   1140
atgtggtgac agatcacggc tcgtgcgtcc gagcctgtgg ggccgacagc tatgagatgg   1200
aggaagacgg cgtccgcaag tgtaagaagt gcgaagggcc ttgccgcaaa gtgtgtaacg   1260
gaataggtat tggtgaattt aaagactcac tctccataaa tgctacgaat attaaacact   1320
tcaaaaactg cacctccatc agtggcgatc tccacatcct gccggtggca tttaggggtg   1380
actccttcac acatactcct cctctggatc cacaggaact ggatattctg aaaaccgtaa   1440
aggaaatcac agggtttttg ctgattcagg cttggcctga aaacaggacg gacctccatg   1500
cctttgagaa cctagaaatc atacgcggca ggaccaagca acatggtcag ttttctcttg   1560
cagtcgtcag cctgaacata acatccttgg gattacgctc cctcaaggag ataagtgatg   1620
gagatgtgat aatttcagga aacaaaaatt tgtgctatgc aaatacaata aactggaaaa   1680
aactgtttgg gacctccggt cagaaaacca aaattataag caacagaggt gaaaacagct   1740
gcaaggccac aggccaggtc tgccatgcct tgtgctcccc cgagggctgc tggggcccgg   1800
agcccaggga ctgcgtctct tgccggaatg tcagccgagg cagggaatgc gtggacaagt   1860
gcaaccttct ggagggtgag ccaagggagt ttgtggagaa ctctgagtgc atacagtgcc   1920
acccagagtg cctgcctcag gccatgaaca tcacctgcac aggacgggga ccagacaact   1980
gtatccagtg tgcccactac attgacggcc cccactgcgt caagacctgc ccggcaggag   2040
tcatgggaga aaacaacacc ctggtctgga agtacgcaga cgccggccat gtgtgccacc   2100
tgtgccatcc aaactgcacc tacgatgcac tgggccaggt cttgaaggc tgtccaacga   2160 atgggcctaa gatcccgtcc atcgccactg gatggtggg ggccctcctc ttgctgctgg   2220
tggtggccct ggggatcggc ctcttcatgc gaaggcgcca catcgttcgg aagcgcacgc   2280
tgcggaggct gctgcaggag agggagcttg tggagcctct tacacccagt ggagaagctc   2340
ccaaccaagc tctcttgagg atcttgaagg aaactgaatt caaaaagatc aaagtgctgg   2400
gctccggtgc gttcggcacg gtgtataagg actctggat cccagaaggt gagaaagtta   2460
aaattcccgt cgctatcaag gaattaagag aagcaacatc tccgaaagcc aacaaggaaa   2520
tcctcgatga agcctacgtg atggccagcg tggacaaccc ccacgtgtgc cgcctgctgg   2580
gcatctgcct cacctccacc gtgcagctca tcacgcagct catgcccttc ggctgcctcc   2640
tggactatgt ccgggaacac aaagacaata ttggctccca gtacctgctc aactggtgtg   2700
tgcagatcgc aaagggcatg aactacttgg aggaccgtcg cttggtgcac cgcgacctgg   2760
cagccaggaa cgtactggtg aaaacaccgc agcatgtcaa gatcacagat tttgggctgg   2820
ccaaacagct gggtgcggaa gagaaagaat accatgcaga aggaggcaaa gtgcctatca   2880
agtggatggc attggaatca attttacaca gaatctatac ccaccagagt gatgtctgga   2940
gctacggggt gactgtttgg gagttgatga cctttggatc caagccatat gacggaatcc   3000
ctgccagcga gatctcctcc atcctggaga aggagaacg cctccctcag ccacccatat   3060
gtaccatcga tgtctacatg atcatggtca agtgctggat gatagacgca gatagtcgcc   3120
caaagttccg tgagttgatc atcgaattct ccaaaatggc ccgagacccc cagcgctacc   3180
ttgtcattca gggggatgaa agaatgcatt tgccaagtcc tacagactcc aacttctacc   3240
gtgccctgat ggatgaagaa gacatggacg acgtggtgga tgccgacgag tacctcatcc   3300
cacagcaggg cttcttcagc agcccctcca cgtcacggac tcccctcctg agctctctga   3360
```

| | |
|---|---|
| gtgcaaccag caacaattcc accgtggctt gcattgatag aaatgggctg caaagctgtc | 3420 |
| ccatcaagga agacagcttc ttgcagcgat acagctcaga ccccacaggc gccttgactg | 3480 |
| aggacagcat agacgacacc ttcctcccag tgcctgaata cataaaccag tccgttccca | 3540 |
| aaaggcccgc tggctctgtg cagaatcctg tctatcacaa tcagcctctg aaccccgcgc | 3600 |
| ccagcagaga cccacactac caggaccccc acagcactgc agtgggcaac cccgagtatc | 3660 |
| tcaacactgt ccagcccacc tgtgtcaaca gcacattcga cagccctgcc cactgggccc | 3720 |
| agaaaggcag ccaccaaatt agcctggaca accctgacta ccagcaggac ttctttccca | 3780 |
| aggaagccaa gccaaatggc atctttaagg gctccacagc tgaaaatgca gaatacctaa | 3840 |
| gggtcgcgcc acaaagcagt gaatttattg gagcatga | 3878 |

<210> SEQ ID NO 728
<211> LENGTH: 3878
<212> TYPE: DNA
<213> ORGANISM: Homo sapiens

<400> SEQUENCE: 728

| | |
|---|---|
| cccggcgcag cgcggccgca gcagcctccg ccccccgcac ggtgtgagcg cccgacgcgg | 60 |
| ccgaggcggc cggagtcccg agctagcccc ggcggccgcc gccgcccaga ccggacgaca | 120 |
| ggccacctcg tcggcgtccg cccgagtccc cgcctcgccg ccaacgccac aaccaccgcg | 180 |
| cacggccccc tgactccgtc cagtattgat cgggagagcc ggagcgagct cttcggggag | 240 |
| cagcgatgcg accctccggg acggccgggg cagcgctcct ggcgctgctg gctgcgctct | 300 |
| gcccggcgag tcgggctctg aggaaaaga agtttgccca aggcacgagt aacaagctca | 360 |
| cgcagttggg cacttttgaa gatcattttc tcagcctcca gaggatgttc aataactgtg | 420 |
| aggtggtcct tgggaatttg gaaattacct atgtgcagag gaattatgat ctttccttct | 480 |
| taaagaccat ccaggaggtg gctggttatg tcctcattgc cctcaacaca gtggagcgaa | 540 |
| ttcctttgga aaacctgcag atcatcagag gaaatatgta ctacgaaaat tcctatgcct | 600 |
| tagcagtctt atctaactat gatgcaaata aaaccggact gaaggagctg cccatgagaa | 660 |
| atttacagga atcctgcat ggcgccgtgc ggttcagcaa caaccctgcc ctgtgcaacg | 720 |
| tggagagcat ccagtggcgg gacatagtca gcagtgactt tctcagcaac atgtcgatgg | 780 |
| acttccagaa ccacctgggc agctgccaaa agtgtgatcc aagctgtccc aatgggagct | 840 |
| gctggggtgc aggagaggag aactgccaga aactgaccaa aatcatctgt gcccagcagt | 900 |
| gctcggggcg ctgccgtggc aagtccccca gtgactgctg ccacaaccag tgtgctgcag | 960 |
| gctgcacagg ccccgggag agcgactgcc tggtctgccg caaattccga gacgaagcca | 1020 |
| cgtgcaagga cacctgcccc ccactcatgc tctacaaccc caccacgtac cagatggatg | 1080 |
| tgaaccccga gggcaaatac agctttggtg ccacctgcgt gaagaagtgt ccccgtaatt | 1140 |
| atgtggtgac agatcacggc tcgtgcgtcc gagcctgtgg ggccgacagc tatgagatgg | 1200 |
| aggaagacgg cgtccgcaag tgtaagaagt gcgaagggcc ttgccgcaaa gtgtgtaacg | 1260 |
| gaataggtat tggtgaattt aaagactcac tctccataaa tgctacgaat attaaacact | 1320 |
| tcaaaaactg cacctccatc agtggcgatc tccacatcct gccggtggca tttaggggtg | 1380 |
| actccttcac acatactcct cctctggatc cacaggaact ggatattctg aaaaccgtaa | 1440 |
| aggaaatcac aggtttttg ctgattcagg cttggcctga aaacaggacg gacctccatg | 1500 |
| cctttgagaa cctagaaatc atacgcggca ggaccaagca acatggtcag ttttctcttg | 1560 |
| cagtcgtcag cctgaacata acatccttgg gattacgctc cctcaaggag ataagtgatg | 1620 |

```
gagatgtgat aatttcagga acaaaaatt tgtgctatgc aaatacaata aactggaaaa    1680
aactgtttgg gacctccggt cagaaaacca aaattataag caacagaggt gaaaacagct    1740
gcaaggccac aggccaggtc tgccatgcct tgtgctcccc cgagggctgc tggggcccgg    1800
agcccaggga ctgcgtctct tgccggaatg tcagccgagg cagggaatgc gtggacaagt    1860
gcaaccttct ggagggtgag ccaagggagt tgtggagaa ctctgagtgc atacagtgcc    1920
acccagagtg cctgcctcag gccatgaaca tcacctgcac aggacgggga ccagacaact    1980
gtatccagtg tgcccactac attgacggcc ccactgcgt caagacctgc ccggcaggag    2040
tcatgggaga aaacaacacc ctggtctgga agtacgcaga cgccggccat gtgtgccacc    2100
tgtgccatcc aaactgcacc tacggatgca ctgggccagg tcttgaaggc tgtccaacga    2160
atgggcctaa gatcccgtcc atcgccactg ggatggtggg ggccctcctc ttgctgctgg    2220
tggtggccct ggggatcggc ctcttcatgc gaaggcgcca catcgttcgg aagcgcacgc    2280
tgcggaggct gctgcaggag agggagcttg tggagcctct tacacccagt ggagaagctc    2340
ccaaccaagc tctcttgagg atcttgaagg aaactgaatt caaaaagatc aaagtgctgg    2400
gctccggtgc gttcggcacg gtgtataagg actctggat cccagaaggt gagaaagtta    2460
aaattcccgt cgctatcaag gaattaagag aagcaacatc tccgaaagcc aacaaggaaa    2520
tcctcgatga agcctacgtg atggccagcg tggacaaccc ccacgtgtgc cgcctgctgg    2580
gcatctgcct cacctccacc gtgcagctca tcacgcagct catgcccttc ggctgcctcc    2640
tggactatgt ccgggaacac aaagacaata ttggctccca gtacctgctc aactggtgtg    2700
tgcagatcgc aaagggcatg aactacttgg aggaccgtcg cttggtgcac cgcgacctgg    2760
cagccaggaa cgtactggtg aaaacaccgc agcatgtcaa gatcacagat tttgggctgg    2820
ccaaactgct gggtgcggaa gagaaagaat accatgcaga aggaggcaaa gtgcctatca    2880
agtggatggc atcggaatca attttacaca gaatctatac ccaccagagt gatgtctgga    2940
gctacggggt gactgtttgg gagttgatga cctttggatc caagccatat gacggaatcc    3000
ctgccagcga gatctcctcc atcctggaga aggagaacg cctccctcag ccacccatat    3060
gtaccatcga tgtctacatg atcatggtca agtgctggat gatagacgca gatagtcgcc    3120
caaagttccg tgagttgatc atcgaattct ccaaaatggc ccgagacccc cagcgctacc    3180
ttgtcattca gggggatgaa agaatgcatt gccaagtcc tacagactcc aacttctacc    3240
gtgccctgat ggatgaagaa gacatggacg acgtggtgga tgccgacgag tacctcatcc    3300
cacagcaggg cttcttcagc agcccctcca cgtcacggac tcccctcctg agctctctga    3360
gtgcaaccag caacaattcc accgtggctt gcattgatag aaatgggctg caaagctgtc    3420
ccatcaagga agacagcttc ttgcagcgat acagctcaga ccccacaggc gccttgactg    3480
aggacagcat agacgacacc ttcctcccag tgcctgaata cataaaccag tccgttccca    3540
aaaggcccgc tggctctgtg cagaatcctg tctatcacaa tcagcctctg aaccccgcgc    3600
ccagcagaga cccacactac caggacccc acagcactgc agtgggcaac cccgagtatc    3660
tcaacactgt ccagcccacc tgtgtcaaca gcacattcga cagccctgcc cactgggccc    3720
agaaaggcag ccaccaaatt agcctggaca accctgacta ccagcaggac ttctttccca    3780
aggaagccaa gccaaatggc atctttaagg ctccacagc tgaaaatgca gaatacctaa    3840
gggtcgcgcc acaaagcagt gaatttattg gagcatga                            3878
```

<210> SEQ ID NO 729

<211> LENGTH: 3878
<212> TYPE: DNA
<213> ORGANISM: Homo sapiens

<400> SEQUENCE: 729

| | | | | | |
|---|---|---|---|---|---|
| cccggcgcag | cgcggccgca | gcagcctccg | cccccgcac | ggtgtgagcg | cccgacgcgg | 60 |
| ccgaggcggc | cggagtcccg | agctagcccc | ggcggccgcc | gccgcccaga | ccggacgaca | 120 |
| ggccacctcg | tcggcgtccg | cccgagtccc | cgcctcgccg | ccaacgccac | aaccaccgcg | 180 |
| cacggccccc | tgactccgtc | cagtattgat | cgggagagcc | ggagcgagct | cttcggggag | 240 |
| cagcgatgcg | accctccggg | acggccgggg | cagcgctcct | ggcgctgctg | gctgcgctct | 300 |
| gcccggcgag | tcgggctctg | gaggaaaaga | aagtttgcca | aggcacgagt | aacaagctca | 360 |
| cgcagttggg | cacttttgaa | gatcattttc | tcagcctcca | gaggatgttc | aataactgtg | 420 |
| aggtggtcct | tgggaatttg | gaaattacct | atgtgcagag | gaattatgat | ctttccttct | 480 |
| taaagaccat | ccaggaggtg | gctggttatg | tcctcattgc | cctcaacaca | gtggagcgaa | 540 |
| ttcctttgga | aaacctgcag | atcatcagag | gaaatatgta | ctacgaaaat | tcctatgcct | 600 |
| tagcagtctt | atctaactat | gatgcaaata | aaaccggact | gaaggagctg | cccatgagaa | 660 |
| atttacagga | atcctgcat | ggcgccgtgc | ggttcagcaa | caaccctgcc | ctgtgcaacg | 720 |
| tggagagcat | ccagtggcgg | gacatagtca | gcagtgactt | tctcagcaac | atgtcgatgg | 780 |
| acttccagaa | ccacctgggc | agctgccaaa | agtgtgatcc | aagctgtccc | aatgggagct | 840 |
| gctggggtgc | aggagaggag | aactgccaga | aactgaccaa | aatcatctgt | gcccagcagt | 900 |
| gctccgggcg | ctgccgtggc | aagtcccca | gtgactgctg | ccacaaccag | tgtgctgcag | 960 |
| gctgcacagg | ccccgggag | agcgactgcc | tggtctgccg | caaattccga | gacgaagcca | 1020 |
| cgtgcaagga | cacctgcccc | ccactcatgc | tctacaaccc | caccacgtac | cagatggatg | 1080 |
| tgaaccccga | gggcaaatac | agctttggtg | ccacctgcgt | gaagaagtgt | ccccgtaatt | 1140 |
| atgtggtgac | agatcacggc | tcgtgcgtcc | gagcctgtgg | ggccgacagc | tatgagatgg | 1200 |
| aggaagacgg | cgtccgcaag | tgtaagaagt | gcgaagggcc | ttgccgcaaa | gtgtgtaacg | 1260 |
| gaataggtat | tggtgaattt | aaagactcac | tctccataaa | tgctacgaat | attaaacact | 1320 |
| tcaaaaactg | cacctccatc | agtggcgatc | tccacatcct | gccggtggca | tttaggggtg | 1380 |
| actccttcac | acatactcct | cctctggatc | cacaggaact | ggatattctg | aaaaccgtaa | 1440 |
| aggaaatcac | agggtttttg | ctgattcagg | cttggcctga | aaacaggacg | gacctccatg | 1500 |
| cctttgagaa | cctagaaatc | atacgcggca | ggaccaagca | acatggtcag | ttttctcttg | 1560 |
| cagtcgtcag | cctgaacata | acatccttgg | gattacgctc | cctcaaggag | ataagtgatg | 1620 |
| gagatgtgat | aatttcagga | aacaaaaatt | tgtgctatgc | aaatacaata | aactggaaaa | 1680 |
| aactgtttgg | gacctccggt | cagaaaacca | aaattataag | caacagaggt | gaaaacagct | 1740 |
| gcaaggccac | aggccaggtc | tgccatgcct | tgtgctcccc | cgagggctgc | tggggcccgg | 1800 |
| agcccaggga | ctgcgtctct | tgccggaatg | tcagccgagg | cagggaatgc | gtggacaagt | 1860 |
| gcaaccttct | ggagggtgag | ccaagggagt | ttgtggagaa | ctctgagtgc | atacagtgcc | 1920 |
| acccagagtg | cctgcctcag | gccatgaaca | tcacctgcac | aggacgggga | ccagacaact | 1980 |
| gtatccagtg | tgcccactac | attgacggcc | cccactgcgt | caagacctgc | ccggcaggag | 2040 |
| tcatgggaga | aaacaacacc | ctggtctgga | agtacgcaga | cgccggccat | gtgtgccacc | 2100 |
| tgtgccatcc | aaactgcacc | tacgatgca | ctgggccagg | tcttgaaggc | tgtccaacga | 2160 |
| atgggcctaa | gatcccgtcc | atcgccactg | ggatggtggg | ggccctcctc | ttgctgctgg | 2220 |

```
tggtggccct gggatcggc ctcttcatgc gaaggcgcca catcgttcgg aagcgcacgc    2280
tgcggaggct gctgcaggag agggagcttg tggagcctct tacacccagt ggagaagctc    2340
ccaaccaagc tctcttgagg atcttgaagg aaactgaatt caaaaagatc aaagtgctgg    2400
gctccggtgc gttcggcacg gtgtataagg actctggat cccagaaggt gagaaagtta    2460
aaattcccgt cgctatcaag gaattaagag aagcaacatc tccgaaagcc aacaaggaaa    2520
tcctcgatga agcctacgtg atggccagcg tggacaaccc ccacgtgtgc cgcctgctgg    2580
gcatctgcct cacctccacc gtgcagctca tcacgcagct catgcccttc ggctgcctcc    2640
tggactatgt ccgggaacac aaagacaata ttggctccca gtacctgctc aactggtgtg    2700
tgcagatcgc aaagggcatg aactacttgg aggaccgtcg cttggtgcac cgcgacctgg    2760
cagccaggaa cgtactggtg aaaacaccgc agcatgtcaa gatcacagat tttgggctgg    2820
ccaaactgct gggtgcggaa gagaaagaat accatgcaga aggaggcaaa gtgcctatca    2880
agtggatggc attggaatca attttacaca gaatctatac ccaccagagt tatgtctgga    2940
gctacggggt gactgtttgg gagttgatga cctttggatc caagccatat gacggaatcc    3000
ctgccagcga gatctcctcc atcctggaga aggagaacg cctccctcag ccacccatat    3060
gtaccatcga tgtctacatg atcatggtca agtgctggat gatagacgca gatagtcgcc    3120
caaagttccg tgagttgatc atcgaattct ccaaaatggc ccgagacccc cagcgctacc    3180
ttgtcattca gggggatgaa agaatgcatt tgccaagtcc tacagactcc aacttctacc    3240
gtgccctgat ggatgaagaa gacatggacg acgtggtgga tgccgacgag tacctcatcc    3300
cacagcaggg cttcttcagc agcccctcca cgtcacggac tcccctcctg agctctctga    3360
gtgcaaccag caacaattcc accgtggctt gcattgatag aaatgggctg caaagctgtc    3420
ccatcaagga agacagcttc ttgcagcgat acagctcaga ccccacaggc gccttgactg    3480
aggacagcat agacgacacc ttcctcccag tgcctgaata cataaaccag tccgttccca    3540
aaaggcccgc tggctctgtg cagaatcctg tctatcacaa tcagcctctg aaccccgcgc    3600
ccagcagaga cccacactac caggaccccc acagcactgc agtgggcaac cccgagtatc    3660
tcaacactgt ccagcccacc tgtgtcaaca gcacattcga cagccctgcc cactgggccc    3720
agaaaggcag ccaccaaatt agcctggaca accctgacta ccagcaggac ttctttccca    3780
aggaagccaa gccaaatggc atctttaagg gctccacagc tgaaaatgca gaatacctaa    3840
gggtcgcgcc acaaagcagt gaatttattg gagcatga    3878
```

<210> SEQ ID NO 730
<211> LENGTH: 3863
<212> TYPE: DNA
<213> ORGANISM: Homo sapiens

<400> SEQUENCE: 730

```
cccggcgcag cgcggccgca gcagcctccg cccccgcac ggtgtgagcg cccgacgcgg      60
ccgaggcggc cggagtcccg agctagcccc ggcggccgcc gccgcccaga ccggacgaca     120
ggccacctcg tcggcgtccg cccgagtccc cgcctcgccg ccaacgccac aaccaccgcg     180
cacggccccc tgactccgtc cagtattgat cgggagagcc ggagcgagct cttcggggag     240
cagcgatgcg accctccggg acggccgggg cagcgctcct ggcgctgctg gctgcgctct     300
gcccggcgag tcgggctctg gaggaaaaga agtttgccca aggcacgagt aacaagctca     360
cgcagttggg cacttttgaa gatcattttc tcagcctcca gaggatgttc aataactgtg     420
```

-continued

```
aggtggtcct tgggaatttg gaaattacct atgtgcagag gaattatgat ctttccttct    480
taaagaccat ccaggaggtg gctggttatg tcctcattgc cctcaacaca gtggagcgaa    540
ttcctttgga aaacctgcag atcatcagag gaaatatgta ctacgaaaat tcctatgcct    600
tagcagtctt atctaactat gatgcaaata aaaccggact gaaggagctg cccatgagaa    660
atttacagga atcctgcat ggcgccgtgc ggttcagcaa caaccctgcc ctgtgcaacg      720
tggagagcat ccagtggcgg gacatagtca gcagtgactt tctcagcaac atgtcgatgg    780
acttccagaa ccacctgggc agctgccaaa agtgtgatcc aagctgtccc aatgggagct    840
gctggggtgc aggagaggag aactgccaga aactgaccaa aatcatctgt gcccagcagt    900
gctccgggcg ctgccgtggc aagtccccca gtgactgctg ccacaaccag tgtgctgcag    960
gctgcacagg ccccgggag agcgactgcc tggtctgccg caaattccga gacgaagcca    1020
cgtgcaagga cacctgcccc ccactcatgc tctacaaccc caccacgtac cagatggatg    1080
tgaaccccga gggcaaatac agctttggtg ccacctgcgt gaagaagtgt ccccgtaatt    1140
atgtggtgac agatcacggc tcgtgcgtcc gagcctgtgg ggccgacagc tatgagatgg    1200
aggaagacgg cgtccgcaag tgtaagaagt gcgaagggcc ttgccgcaaa gtgtgtaacg    1260
gaataggtat tggtgaattt aaagactcac tctccataaa tgctacgaat attaaacact    1320
tcaaaaactg cacctccatc agtggcgatc tccacatcct gccggtggca tttaggggtg    1380
actccttcac acatactcct cctctggatc cacaggaact ggatattctg aaaaccgtaa    1440
aggaaatcac agggttttg ctgattcagg cttggcctga aaacaggacg gacctccatg     1500
cctttgagaa cctagaaatc atacgcgcca ggaccaagca acatggtcag ttttctcttg    1560
cagtcgtcag cctgaacata acatccttgg gattacgctc cctcaaggag ataagtgatg    1620
gagatgtgat aatttcagga aacaaaaatt tgtgctatgc aaatacaata aactggaaaa    1680
aactgtttgg gacctccggt cagaaaacca aaattataag caacagaggt gaaaacagct    1740
gcaaggccac aggccaggtc tgccatgcct tgtgctcccc cgagggctgc tggggcccgg    1800
agcccaggga ctgcgtctct tgccggaatg tcagccgagg cagggaatgc gtggacaagt    1860
gcaaccttct ggagggtgag ccaagggagt ttgtggagaa ctctgagtgc atacagtgcc    1920
acccagagtg cctgcctcag gccatgaaca tcacctgcac aggacgggga ccagacaact    1980
gtatccagtg tgcccactac attgacggcc cccactgcgt caagacctgc ccggcaggag    2040
tcatgggaga aaacaacacc ctggtctgga agtacgcaga cgccggccat gtgtgccacc    2100
tgtgccatcc aaactgcacc tacgatgca ctgggccagg tcttgaaggc tgtccaacga     2160
atgggcctaa gatcccgtcc atcgccactg ggatggtggg ggcctcctc ttgctgctgg     2220
tggtggccct ggggatcggc ctcttcatgc gaaggcgcca catcgttcgg aagcgcacgc    2280
tgcggaggct gctgcaggag agggagcttg tggagcctct tacacccagt ggagaagctc    2340
ccaaccaagc tctcttgagg atcttgaagg aaactgaatt caaaaagatc aaagtgctgg    2400
gctccggtgc gttcggcacg gtgtataagg gactctggat cccagaaggt gagaaagtta    2460
aaattcccgt cgctatcaaa acatctccga aagccaacaa ggaaatcctc gatgaagcct    2520
acgtgatggc cagcgtggac aaccccacgt gtgccgcct gctgggcatc tgcctcacct    2580
ccaccgtgca gctcatcacg cagctcatgc ccttcggctg cctcctggac tatgtccggg    2640
aacacaaaga caatattggc tcccagtacc tgctcaactg gtgtgtgcag atcgcaaagg    2700
gcatgaacta cttggaggac gtcgcttgg tgcaccgcga cctggcagcc aggaacgtac     2760
tggtgaaaac accgcagcat gtcaagatca cagattttgg gctggccaaa ctgctgggtg    2820
```

```
cggaagagaa agaataccat gcagaaggag gcaaagtgcc tatcaagtgg atggcattgg    2880
aatcaatttt acacagaatc tatacccacc agagtgatgt ctggagctac ggggtgactg    2940
tttgggagtt gatgaccttt ggatccaagc catatgacgg aatccctgcc agcgagatct    3000
cctccatcct ggagaaagga gaacgcctcc ctcagccacc catatgtacc atcgatgtct    3060
acatgatcat ggtcaagtgc tggatgatag acgcagatag tcgcccaaag ttccgtgagt    3120
tgatcatcga attctccaaa atggcccgag acccccagcg ctaccttgtc attcagggga    3180
atgaaagaat gcatttgcca agtcctacag actccaactt ctaccgtgcc ctgatggatg    3240
aagaagacat ggacgacgtg gtggatgccg acgagtacct catcccacag cagggcttct    3300
tcagcagccc ctccacgtca cggactcccc tcctgagctc tctgagtgca ccagcaaca    3360 attccaccgt ggcttgcatt gatagaaatg ggctgcaaag ctgtcccatc aaggaagaca    3420
gcttcttgca gcgatacagc tcagacccca caggcgcctt gactgaggac agcatagacg    3480
acaccttcct cccagtgcct gaatacataa accagtccgt tcccaaaagg cccgctggct    3540
ctgtgcagaa tcctgtctat cacaatcagc ctctgaaccc cgcgcccagc agagacccac    3600
actaccagga ccccacagc actgcagtgg gcaaccccga gtatctcaac actgtccagc    3660
ccacctgtgt caacagcaca ttcgacagcc ctgcccactg ggcccagaaa ggcagccacc    3720
aaattagcct ggacaaccct gactaccagc aggacttctt tcccaaggaa gccaagccaa    3780
atggcatctt taagggctcc acagctgaaa atgcagaata cctaagggtc gcgccacaaa    3840
gcagtgaatt tattggagca tga                                            3863

<210> SEQ ID NO 731
<211> LENGTH: 3866
<212> TYPE: DNA
<213> ORGANISM: Homo sapiens

<400> SEQUENCE: 731
cccggcgcag cgcggccgca gcagcctccg ccccccgcac ggtgtgagcg cccgacgcgg      60
ccgaggcggc cggagtcccg agctagcccc ggcggccgcc gccgcccaga ccggacgaca     120
ggccacctcg tcggcgtccg cccgagtccc cgcctcgccg ccaacgccac aaccaccgcg     180
cacggccccc tgactccgtc cagtattgat cgggagagcc ggagcgagct cttcggggag     240
cagcgatgcg accctccggg acggccgggg cagcgctcct ggcgctgctg gctgcgctct     300
gcccggcgag tcgggctctg aggaaaaaga agtttgccaa aggcacgagt aacaagctca     360
cgcagttggg cacttttgaa gatcattttc tcagcctcca gaggatgttc aataactgtg     420
aggtggtcct tgggaatttg gaaattacct atgtgcagag gaattatgat ctttccttct     480
taaagaccat ccaggaggtg gctggttatg tcctcattgc cctcaacaca gtggagcgaa     540
ttcctttgga aaacctgcag atcatcagag gaaatatgta ctacgaaaat tcctatgcct     600
tagcagtctt atctaactat gatgcaaata aaaccggact gaaggagctg cccatgagaa     660
atttacagga atcctgcat ggcgccgtgc ggttcagcaa caaccctgcc ctgtgcaacg     720
tggagagcat ccagtggcgg gacatagtca gcagtgactt tctcagcaac atgtcgatgg     780
acttccagaa ccacctgggc agctgccaaa agtgtgatcc aagctgtccc aatgggagct     840
gctggggtgc aggagaggag aactgccaga aactgaccaa aatcatctgt gcccagcagt     900
gctccgggcg ctgccgtggc aagtccccca gtgactgctg ccacaaccag tgtgctgcag     960
gctgcacagg ccccgggag agcgactgcc tggtctgccg caaattccga gacgaagcca    1020
```

```
cgtgcaagga cacctgcccc ccactcatgc tctacaaccc caccacgtac cagatggatg    1080
tgaaccccga gggcaaatac agctttggtg ccacctgcgt gaagaagtgt ccccgtaatt    1140
atgtggtgac agatcacggc tcgtgcgtcc gagcctgtgg ggccgacagc tatgagatgg    1200
aggaagacgg cgtccgcaag tgtaagaagt gcgaagggcc ttgccgcaaa gtgtgtaacg    1260
gaataggtat tggtgaattt aaagactcac tctccataaa tgctacgaat attaaacact    1320
tcaaaaactg cacctccatc agtggcgatc tccacatcct gccggtggca tttaggggtg    1380
actccttcac acatactcct cctctggatc cacaggaact ggatattctg aaaaccgtaa    1440
aggaaatcac agggttttg ctgattcagg cttggcctga aaacaggacg gacctccatg    1500
cctttgagaa cctagaaatc atacgcggca ggaccaagca acatggtcag tttttctcttg    1560 cagtcgtcag cctgaacata acatccttgg gattacgctc cctcaaggag ataagtgatg    1620
gagatgtgat aatttcagga aacaaaaatt tgtgctatgc aaatacaata aactggaaaa    1680
aactgtttgg gacctccggt cagaaaacca aaattataag caacagaggt gaaaacagct    1740
gcaaggccac aggccaggtc tgccatgcct tgtgctcccc cgagggctgc tggggcccgg    1800
agcccaggga ctgcgtctct tgccggaatg tcagccgagg cagggaatgc gtggacaagt    1860
gcaaccttct ggagggtgag ccaagggagt ttgtggagaa ctctgagtgc atacagtgcc    1920
acccagagtg cctgcctcag gccatgaaca tcacctgcac aggacgggga ccagacaact    1980
gtatccagtg tgcccactac attgacggcc cccactgcgt caagacctgc ccggcaggag    2040
tcatgggaga aaacaacacc ctggtctgga gtacgcaga cgccggccat gtgtgccacc    2100
tgtgccatcc aaactgcacc tacgatgca ctgggccagg tcttgaaggc tgtccaacga    2160
atgggcctaa gatcccgtcc atcgccactg ggatggtggg ggccctcctc ttgctgctgg    2220
tggtggccct ggggatcggc ctcttcatgc gaaggcgcca catcgttcgg aagcgcacgc    2280
tgcggaggct gctgcaggag agggagcttg tggagcctct tacacccagt ggagaagctc    2340
ccaaccaagc tctcttgagg atcttgaagg aaactgaatt caaaaagatc aaagtgctgg    2400
gctccggtgc gttcggcacg gtgtataagg actctggat cccagaaggt gagaaagtta    2460
aaattcccgt cgctatcaag gaatcatctc cgaaagccaa caaggaaatc ctcgatgaag    2520
cctacgtgat ggccagcgtg gacaaccccc acgtgtgccg cctgctgggc atctgcctca    2580
cctccaccgt gcagctcatc acgcagctca tgccctttcgg ctgcctcctg gactatgtcc    2640
gggaacacaa agacaatatt ggctcccagt acctgctcaa ctggtgtgtg cagatcgcaa    2700
agggcatgaa ctacttggag gaccgtcgct tggtgcaccg cgacctggca gccaggaacg    2760
tactggtgaa aacaccgcag catgtcaaga tcacagattt tgggctggcc aaactgctgg    2820
gtgcggaaga gaaagaatac catgcagaag gaggcaaagt gcctatcaag tggatggcat    2880
tggaatcaat tttacacaga atctataccc accagagtga tgtctggagc tacggggtga    2940
ctgtttggga gttgatgacc tttggatcca agccatatga cggaatccct gccagcgaga    3000
tctcctccat cctggagaaa ggagaacgcc tccctcagcc acccatatgt accatcgatg    3060
tctacatgat catggtcaag tgctggatga tagacgcaga tagtcgccca agttccgtg    3120 agttgatcat cgaattctcc aaaatggccc gagaccccca gcgctacctt gtcattcagg    3180
gggatgaaag aatgcatttg ccaagtccta cagactccaa cttctaccgt gccctgatgg    3240
atgaagaaga catggacgac gtggtggatg ccgacgagta cctcatccca cagcagggct    3300
tcttcagcag cccctccacg tcacggactc ccctcctgag ctctctgagt gcaaccagca    3360
acaattccac cgtggcttgc attgatagaa atgggctgca aagctgtccc atcaaggaag    3420
```

```
acagcttctt gcagcgatac agctcagacc ccacaggcgc cttgactgag gacagcatag    3480
acgacacctt cctcccagtg cctgaataca taaaccagtc cgttcccaaa aggcccgctg    3540
gctctgtgca gaatcctgtc tatcacaatc agcctctgaa ccccgcgccc agcagagacc    3600
cacactacca ggaccccac agcactgcag tgggcaaccc cgagtatctc aacactgtcc    3660
agcccacctg tgtcaacagc acattcgaca gccctgccca ctgggccag aaaggcagcc    3720 accaaattag cctggacaac cctgactacc agcaggactt ctttcccaag gaagccaagc    3780
caaatggcat ctttaagggc tccacagctg aaaatgcaga atacctaagg gtcgcgccac    3840
aaagcagtga atttattgga gcatga                                         3866
```

<210> SEQ ID NO 732
<211> LENGTH: 3860
<212> TYPE: DNA
<213> ORGANISM: Homo sapiens

<400> SEQUENCE: 732

```
cccggcgcag cgcggccgca gcagcctccg cccccgcac ggtgtgagcg cccgacgcgg      60
ccgaggcggc cggagtcccg agctagcccc ggcggccgcc gccgcccaga ccggacgaca    120
ggccacctcg tcggcgtccg cccgagtccc cgcctcgccg ccaacgccac aaccaccgcg    180
cacgcccccc tgactccgtc cagtattgat cgggagagcc ggagcgagct cttcggggag    240
cagcgatgcg accctccggg acggccgggg cagcgctcct ggcgctgctg gctgcgctct    300
gcccggcgag tcgggctctg gaggaaaaga aagtttgcca aggcacgagt aacaagctca    360
cgcagttggg cacttttgaa gatcattttc tcagcctcca gaggatgttc aataactgtg    420
aggtggtcct tgggaatttg gaaattacct atgtgcagag gaattatgat ctttccttct    480
taaagaccat ccaggaggtg gctggttatg tcctcattgc cctcaacaca gtggagcgaa    540
ttcctttgga aaacctgcag atcatcagag gaaatatgta ctacgaaaat tcctatgcct    600
tagcagtctt atctaactat gatgcaaata aaaccggact gaaggagctg cccatgagaa    660
atttacagga atcctgcat ggcgccgtgc ggttcagcaa caaccctgcc ctgtgcaacg    720
tggagagcat ccagtggcgg gacatagtca gcagtgactt tctcagcaac atgtcgatgg    780
acttccagaa ccacctgggc agctgccaaa agtgtgatcc aagctgtccc aatgggagct    840 gctgggggtgc aggagaggag aactgccaga aactgaccaa aatcatctgt gcccagcagt    900
gctcccggcg ctgccgtggc aagtccccca gtgactgctg ccacaaccag tgtgctgcag    960
gctgcacagg ccccgggag agcgactgcc tggtctgccg caaattccga gacgaagcca   1020
cgtgcaagga cacctgcccc ccactcatgc tctacaaccc caccacgtac cagatggatg   1080
tgaaccccga gggcaaatac agctttggtg ccacctgcgt gaagaagtgt cccgtaatt   1140 atgtggtgac agatcacggc tcgtgcgtcc gagcctgtgg ggccgacagc tatgagatgg   1200
aggaagacgg cgtccgcaag tgtaagaagt gcgaagggcc ttgccgcaaa gtgtgtaacg   1260
gaataggtat tggtgaattt aaagactcac tctccataaa tgctacgaat attaaacact   1320
tcaaaaactg cacctccatc agtggcgatc tccacatcct gccggtggca tttaggggtg   1380
actccttcac acatactcct cctctggatc cacaggaact ggatattctg aaaaccgtaa   1440
aggaaatcac agggtttttg ctgattcagg cttggcctga aaacaggacg gacctccatg   1500
cctttgagaa cctagaaatc atacgcggca ggaccaagca acatggtcag ttttctcttg   1560
cagtcgtcag cctgaacata acatccttgg gattacgctc cctcaaggag ataagtgatg   1620
```

-continued

```
gagatgtgat aatttcagga acaaaaatt tgtgctatgc aaatacaata aactggaaaa    1680
aactgtttgg gacctccggt cagaaaacca aaattataag caacagaggt gaaaacagct    1740
gcaaggccac aggccaggtc tgccatgcct tgtgctcccc cgagggctgc tggggcccgg    1800
agcccaggga ctgcgtctct tgccggaatg tcagccgagg cagggaatgc gtggacaagt    1860
gcaaccttct ggagggtgag ccaagggagt ttgtggagaa ctctgagtgc atacagtgcc    1920
acccagagtg cctgcctcag gccatgaaca tcacctgcac aggacgggga ccagacaact    1980
gtatccagtg tgcccactac attgacggcc cccactgcgt caagacctgc ccggcaggag    2040
tcatgggaga aaacaacacc ctggtctgga agtacgcaga cgccggccat gtgtgccacc    2100
tgtgccatcc aaactgcacc tacgatgca ctgggccagg tcttgaaggc tgtccaacga    2160
atgggcctaa gatcccgtcc atcgccactg gatggtggg ggcctcctc ttgctgctgg    2220 tggtggccct ggggatcggc ctcttcatgc gaaggcgcca catcgttcgg aagcgcacgc    2280 tgcgaggct gctgcaggag agggagcttg tggagcctct tacacccagt ggagaagctc    2340
ccaaccaagc tctcttgagg atcttgaagg aaactgaatt caaaaagatc aaagtgctgg    2400
gctccggtgc gttcggcacg tgtataagg gactctggat cccagaaggt gagaaagtta    2460
aaattcccgt cgctatcaag gaatcgaaag ccaacaagga aatcctcgat gaagcctacg    2520
tgatggccag cgtggacaac ccccacgtgt gccgcctgct gggcatctgc ctcacctcca    2580
ccgtgcagct catcacgcag ctcatgccct tcggctgcct cctggactat gtccgggaac    2640
acaaagacaa tattggctcc cagtacctgc tcaactggtg tgtgcagatc gcaaagggca    2700
tgaactactt ggaggaccgt cgcttggtgc accgcgacct ggcagccagg aacgtactgg    2760
tgaaaacacc gcagcatgtc aagatcacag attttgggct ggccaaactg ctgggtgcgg    2820
aagagaaaga ataccatgca gaaggaggca aagtgcctat caagtggatg gcattggaat    2880
caattttaca cagaatctat acccaccaga gtgatgtctg gagctacggg gtgactgttt    2940
gggagttgat gacctttgga tccaagccat atgacggaat ccctgccagc gagatctcct    3000
ccatcctgga gaaaggagaa cgcctccctc agccacccat atgtaccatc gatgtctaca    3060
tgatcatggt caagtgctgg atgatagacg cagatagtcg cccaaagttc cgtgagttga    3120
tcatcgaatt ctccaaaatg gcccgagacc cccagcgcta ccttgtcatt caggggatg    3180 aaagaatgca tttgccaagt cctacagact ccaacttcta ccgtgccctg atggatgaag    3240
aagacatgga cgacgtggtg gatgccgacg agtacctcat cccacagcag ggcttcttca    3300
gcagcccctc cacgtcacgg actccctcc tgagctctct gagtgcaacc agcaacaatt    3360
ccaccgtggc ttgcattgat agaaatgggc tgcaaagctg tccatcaag gaagacagct    3420 tcttgcagcg atacagctca gaccccacag gcgccttgac tgaggacagc atagacgaca    3480
ccttcctccc agtgcctgaa tacataaacc agtccgttcc caaaggccc gctggctctg    3540 tgcagaatcc tgtctatcac aatcagcctc tgaaccccgc gcccagcaga gacccacact    3600
accaggaccc ccacagcact gcagtgggca acccccgagta tctcaacact gtccagccca    3660
cctgtgtcaa cagcacattc gacagccctg cccactgggc ccagaaaggc agccaccaaa    3720
ttagcctgga caaccctgac taccagcagg acttctttcc caaggaagcc aagccaaatg    3780
gcatctttaa gggctccaca gctgaaaatg cagaatacct aagggtcgcg ccacaaagca    3840
gtgaatttat tggagcatga                                              3860
```

<210> SEQ ID NO 733
<211> LENGTH: 3860

<212> TYPE: DNA
<213> ORGANISM: Homo sapiens

<400> SEQUENCE: 733

```
cccggcgcag cgcggccgca gcagcctccg ccccccgcac ggtgtgagcg cccgacgcgg      60
ccgaggcggc cggagtcccg agctagcccc ggcggccgcc gccgcccaga ccggacgaca     120
ggccacctcg tcggcgtccg cccgagtccc cgcctcgccg ccaacgccac aaccaccgcg     180
cacggccccc tgactccgtc cagtattgat cgggagagcc ggagcgagct cttcggggag     240
cagcgatgcg accctccggg acggccgggg cagcgctcct ggcgctgctg gctgcgctct     300
gcccggcgag tcgggctctg gaggaaaaga aagtttgcca aggcacgagt aacaagctca     360
cgcagttggg cacttttgaa gatcattttc tcagcctcca gaggatgttc aataactgtg     420
aggtggtcct tgggaatttg gaaattacct atgtgcagag gaattatgat ctttccttct     480
taaagaccat ccaggaggtg gctggttatg tcctcattgc cctcaacaca gtggagcgaa     540
ttcctttgga aaacctgcag atcatcagag gaaatatgta ctacgaaaat tcctatgcct     600
tagcagtctt atctaactat gatgcaaata aaaccggact gaaggagctg cccatgagaa     660
atttacagga aatcctgcat ggcgccgtgc ggttcagcaa caaccctgcc ctgtgcaacg     720
tggagagcat ccagtggcgg gacatagtca gcagtgactt tctcagcaac atgtcgatgg     780
acttccagaa ccacctgggc agctgccaaa agtgtgatcc aagctgtccc aatgggagct     840
gctggggtgc aggagaggag aactgccaga aactgaccaa aatcatctgt gcccagcagt     900
gctcccggcg ctgccgtggc aagtccccca gtgactgctg ccacaaccag tgtgctgcag     960
gctgcacagg ccccgggag agcgactgcc tggtctgccg caaattccga gacgaagcca    1020
cgtgcaagga cacctgcccc ccactcatgc tctacaaccc caccacgtac cagatggatg    1080
tgaaccccga gggcaaatac agctttggtg ccacctgcgt gaagaagtgt ccccgtaatt    1140
atgtggtgac agatcacggc tcgtgcgtcc gagcctgtgg ggccgacagc tatgagatgg    1200
aggaagacgg cgtccgcaag tgtaagaagt gcgaagggcc ttgccgcaaa gtgtgtaacg    1260
gaataggtat tggtgaattt aaagactcac tctccataaa tgctacgaat attaaacact    1320
tcaaaaactg cacctccatc agtggcgatc tccacatcct gccggtggca tttagggggtg    1380
actccttcac acatactcct cctctggatc cacaggaact ggatattctg aaaaccgtaa    1440
aggaaatcac agggttttg ctgattcagg cttggcctga aaacaggacg gacctccatg    1500
cctttgagaa cctagaaatc atacgcggca ggaccaagca acatggtcag ttttctcttg    1560
cagtcgtcag cctgaacata acatccttgg gattacgctc cctcaaggag ataagtgatg    1620
gagatgtgat aatttcagga aacaaaaatt tgtgctatgc aaatacaata aactggaaaa    1680
aactgttttgg gacctccggt cagaaaacca aaattataag caacagaggt gaaaacagct    1740
gcaaggccac aggccaggtc tgccatgcct tgtgctcccc cgagggctgc tggggccccgg    1800
agcccaggga ctgcgtctct tgccggaatg tcagccgagg cagggaatgc gtggacaagt    1860
gcaaccttct ggagggtgag ccaagggagt tgtggagaa ctctgagtgc atacagtgcc    1920
acccagagtg cctgcctcag gccatgaaca tcacctgcac aggacgggga ccagacaact    1980
gtatccagtg tgcccactac attgacggcc ccactgcgt caagacctgc ccggcaggag    2040
tcatgggaga aaacaacacc ctggtctgga gtacgcaga cgccggccat gtgtgccacc    2100
tgtgccatcc aaactgcacc tacgatgca ctgggcagg tcttgaaggc tgtccaacga    2160
atgggcctaa gatcccgtcc atcgccactg ggatggtggg ggccctcctc ttgctgctgg    2220
```

-continued

```
tggtggccct ggggatcggc ctcttcatgc gaaggcgcca catcgttcgg aagcgcacgc     2280
tgcggaggct gctgcaggag agggagcttg tggagcctct tacacccagt ggagaagctc     2340
ccaaccaagc tctcttgagg atcttgaagg aaactgaatt caaaaagatc aaagtgctgg     2400
gctccggtgc gttcggcacg gtgtataagg actctggat cccagaaggt gagaaagtta     2460
aaattcccgt cgctatcaag gaatcgaaag ccaacaagga aatcctcgat gaagcctacg     2520
tgatggccag cgtggacaac ccccacgtgt gccgcctgct gggcatctgc ctcacctcca     2580
ccgtgcagct catcacgcag ctcatgccct tcggctgcct cctggactat gtccgggaac     2640
acaaagacaa tattggctcc cagtacctgc tcaactggtg tgtgcagatc gcaagggca      2700 tgaactactt ggaggaccgt cgcttggtgc accgcgacct ggcagccagg aacgtactgg     2760
tgaaaacacc gcagcatgtc aagatcacag attttgggct ggccaaactg ctgggtgcgg     2820
aagagaaaga ataccatgca gaaggaggca aagtgcctat caagtggatg gcattggaat     2880
caattttaca cagaatctat acccaccaga gtgatgtctg gagctacggg gtgactgttt     2940
gggagttgat gacctttgga tccaagccat atgacgaat ccctgccagc gagatctcct      3000
ccatcctgga gaaggagaa cgcctccctc agccacccat atgtaccatc gatgtctaca     3060
tgatcatggt caagtgctgg atgatagacg cagatagtcg cccaaagttc cgtgagttga     3120
tcatcgaatt ctccaaaatg gcccgagacc cccagcgcta ccttgtcatt caggggatg      3180 aaagaatgca tttgccaagt cctacagact ccaacttcta ccgtgccctg atggatgaag     3240
aagacatgga cgacgtggtg gatgccgacg agtacctcat cccacagcag ggcttcttca     3300
gcagcccctc cacgtcacgg actcccctcc tgagctctct gagtgcaacc agcaacaatt     3360
ccaccgtggc ttgcattgat agaaatgggc tgcaaagctg tcccatcaag gaagacagct     3420
tcttgcagcg atacagctca gaccccacag gcgccttgac tgaggacagc atagacgaca     3480
ccttcctccc agtgcctgaa tacataaacc agtccgttcc caaaaggccc gctggctctg     3540
tgcagaatcc tgtctatcac aatcagcctc tgaaccccgc gcccagcaga gacccacact     3600
accaggaccc ccacagcact gcagtgggca accccgagta tctcaacact gtccagccca     3660
cctgtgtcaa cagcacattc gacagccctg cccactgggc ccagaaaggc agccaccaaa     3720
ttagcctgga caaccctgac taccagcagg acttcttcc caaggaagcc aagccaaatg     3780
gcatctttaa gggctccaca gctgaaaatg cagaatacct aagggtcgcg ccacaaagca     3840
gtgaatttat tggagcatga                                                 3860
```

<210> SEQ ID NO 734
<211> LENGTH: 3878
<212> TYPE: DNA
<213> ORGANISM: Homo sapiens

<400> SEQUENCE: 734

```
cccggcgcag cgcggccgca gcagcctccg cccccgcac ggtgtgagcg cccgacgcgg       60
ccgaggcggc cggagtcccg agctagcccc ggcggccgcc gccgcccaga ccggacgaca      120
ggccacctcg tcggcgtccg cccgagtccc cgcctcgccg ccaacgccac aaccaccgcg      180
cacgcccccc tgactccgtc cagtattgat cgggagagcc ggagcgagct cttcggggag      240
cagcgatgcg accctccggg acggccgggg cagcgctcct ggcgctgctg gctgcgctct      300
gcccggcgag tcgggctctg gaggaaaaga agtttgccca aggcacgagt aacaagctca      360
cgcagttggg cactttgaa gatcatttc tcagcctcca gaggatgttc aataactgtg       420
aggtggtcct tgggaatttg gaaattacct atgtgcagag gaattatgat ctttccttct     480
```

| | |
|---|---|
| taaagaccat ccaggaggtg gctggttatg tcctcattgc cctcaacaca gtggagcgaa | 540 |
| ttcctttgga aaacctgcag atcatcagag gaaatatgta ctacgaaaat tcctatgcct | 600 |
| tagcagtctt atctaactat gatgcaaata aaaccggact gaaggagctg cccatgagaa | 660 |
| atttacagga atcctgcat ggcgccgtgc ggttcagcaa caaccctgcc ctgtgcaacg | 720 |
| tggagagcat ccagtggcgg gacatagtca gcagtgactt tctcagcaac atgtcgatgg | 780 |
| acttccagaa ccacctgggc agctgccaaa agtgtgatcc aagctgtccc aatgggagct | 840 |
| gctggggtgc aggagaggag aactgccaga aactgaccaa aatcatctgt gcccagcagt | 900 |
| gctccgggcg ctgccgtggc aagtcccca gtgactgctg ccacaaccag tgtgctgcag | 960 |
| gctgcacagg cccccgggag agcgactgcc tggtctgccg caaattccga gacgaagcca | 1020 |
| cgtgcaagga cacctgcccc ccactcatgc tctacaaccc caccacgtac cagatggatg | 1080 |
| tgaaccccga gggcaaatac agctttggtg ccacctgcgt gaagaagtgt ccccgtaatt | 1140 |
| atgtggtgac agatcacggc tcgtgcgtcc gagcctgtgg ggccgacagc tatgagatgg | 1200 |
| aggaagacgg cgtccgcaag tgtaagaagt gcgaagggcc ttgccgcaaa gtgtgtaacg | 1260 |
| gaataggtat tggtgaattt aaagactcac tctccataaa tgctacgaat attaaacact | 1320 |
| tcaaaaactg cacctccatc agtggcgatc tccacatcct gccggtggca tttagggggtg | 1380 |
| actccttcac acatactcct cctctggatc cacaggaact ggatattctg aaaaccgtaa | 1440 |
| aggaaatcac agggtttttg ctgattcagg cttggcctga aaacaggacg gacctccatg | 1500 |
| cctttgagaa cctagaaatc atacgcggca ggaccaagca acatggtcag ttttctcttg | 1560 |
| cagtcgtcag cctgaacata acatccttgg gattacgctc cctcaaggag ataagtgatg | 1620 |
| gagatgtgat aatttcagga aacaaaaatt tgtgctatgc aaatacaata aactggaaaa | 1680 |
| aactgtttgg gacctccggt cagaaaacca aaattataag caacagaggt gaaaacagct | 1740 |
| gcaaggccac aggccaggtc tgccatgcct tgtgctcccc cgagggctgc tggggcccgg | 1800 |
| agcccaggga ctgcgtctct tgccggaatg tcagccgagg cagggaatgc gtggacaagt | 1860 |
| gcaaccttct ggagggtgag ccaagggagt ttgtggagaa ctctgagtgc atacagtgcc | 1920 |
| acccagagtg cctgcctcag gccatgaaca tcacctgcac aggacgggga ccagacaact | 1980 |
| gtatccagtg tgcccactac attgacggcc cccactgcgt caagacctgc ccggcaggag | 2040 |
| tcatgggaga aaacaacacc ctggtctgga agtacgcaga cgccggccat gtgtgccacc | 2100 |
| tgtgccatcc aaactgcacc tacggatgca ctgggccagg tcttgaaggc tgtccaacga | 2160 |
| atgggcctaa gatcccgtcc atcgccactg ggatggtggg ggcctcctc ttgctgctgg | 2220 |
| tggtggccct ggggatcggc ctcttcatgc gaaggcgcca catcgttcgg aagcgcacgc | 2280 |
| tgcgaggct gctgcaggag agggagcttg tggagcctct tacacccagt ggagaagctc | 2340 |
| ccaaccaagc tctcttgagg atcttgaagg aaactgaatt caaaaagatc aaagtgctgg | 2400 |
| gctccggtgc gttcggcacg gtgtataagg gactctggat cccagaaggt gagaaagtta | 2460 |
| aaattcccgt cgctatcaag gaattaagag aagcaacatc tccgaaagcc aacaaggaaa | 2520 |
| tcctcgatga agcctacgtg atggccagcg tggacaaccc ccacgtgtgc cgcctgctgg | 2580 |
| gcatctgcct cacctccacc gtgcagctca tcacgcagct catgcccttc ggctgcctcc | 2640 |
| tggactatgt ccgggaacac aaagacaata ttggctccca gtacctgctc aactggtgtg | 2700 |
| tgcagatcgc aaagggcatg aactacttgg aggaccgtcg cttggtgcac cgcgacctgg | 2760 |
| cagccaggaa cgtactggtg aaaacaccgc agcatgtcaa gatcacagat tttgggcggg | 2820 |

```
ccaaactgct gggtgcggaa gagaaagaat accatgcaga aggaggcaaa gtgcctatca    2880
agtggatggc attggaatca attttacaca gaatctatac ccaccagagt gatgtctgga    2940 gctacgggt  gactgtttgg gagttgatga cctttggatc caagccatat gacggaatcc    3000
ctgccagcga gatctcctcc atcctggaga aaggagaacg cctccctcag ccacccatat    3060
gtaccatcga tgtctacatg atcatggtca agtgctggat gatagacgca gatagtcgcc    3120
caaagttccg tgagttgatc atcgaattct ccaaaatggc ccgagacccc cagcgctacc    3180
ttgtcattca gggggatgaa agaatgcatt tgccaagtcc tacagactcc aacttctacc    3240
gtgccctgat ggatgaagaa gacatggacg acgtggtgga tgccgacgag tacctcatcc    3300
cacagcaggg cttcttcagc agcccctcca cgtcacggac tcccctcctg agctctctga    3360
gtgcaaccag caacaattcc accgtggctt gcattgatag aaatgggctg caaagctgtc    3420
ccatcaagga agacagcttc ttgcagcgat acagctcaga ccccacaggc gccttgactg    3480
aggacagcat agacgacacc ttcctcccag tgcctgaata cataaaccag tccgttccca    3540
aaaggcccgc tggctctgtg cagaatcctg tctatcacaa tcagcctctg aaccccgcgc    3600
ccagcagaga cccacactac caggaccccc acagcactgc agtgggcaac cccgagtatc    3660
tcaacactgt ccagccccacc tgtgtcaaca gcacattcga cagccctgcc cactgggccc   3720
agaaaggcag ccaccaaatt agcctggaca accctgacta ccagcaggac ttctttccca    3780
aggaagccaa gccaaatggc atctttaagg gctccacagc tgaaaatgca gaatacctaa    3840
gggtcgcgcc acaaagcagt gaatttattg gagcatga                           3878
```

<210> SEQ ID NO 735  
<211> LENGTH: 3878  
<212> TYPE: DNA  
<213> ORGANISM: Homo sapiens

<400> SEQUENCE: 735

```
cccggcgcag cgcggccgca gcagcctccg cccccgcac  ggtgtgagcg cccgacgcgg      60
ccgaggcggc cggagtcccg agctagcccc ggcggccgcc gccgcccaga ccggacgaca     120
ggccacctcg tcggcgtccg cccgagtccc cgcctcgccg ccaacgccac aaccaccgcg     180
cacggccccc tgactccgtc cagtattgat cgggagagcc ggagcgagct cttcggggag     240
cagcgatgcg accctccggg acggccgggg cagcgctcct ggcgctgctg gctgcgctct     300
gcccggcgag tcgggctctg gaggaaaaga aagtttgcca aggcacgagt aacaagctca     360
cgcagttggg cacttttgaa gatcattttc tcagcctcca gaggatgttc ataactgtg      420 aggtggtcct tgggaatttg gaaattacct atgtgcagag gaattatgat ctttccttct     480
taaagaccat ccaggaggtg gctggttatg tcctcattgc cctcaacaca gtgagcgaa      540 ttcctttgga aaacctgcag atcatcagag gaaatatgta ctacgaaaat tcctatgcct     600
tagcagtctt atctaactat gatgcaaata aaaccggact gaaggagctg cccatgagaa     660
atttacagga aatcctgcat ggcgccgtgc ggttcagcaa caacccctgcc ctgtgcaacg    720 tggagagcat ccagtggcgg gacatagtca gcagtgactt tctcagcaac atgtcgatgg    780
acttccagaa cccacctggg cagctgccaaa agtgtgatcc aagctgtccc aatgggagct    840 gctgggggtgc aggagaggag aactgccaga aactgaccaa aatcatctgt gcccagcagt    900
gctccgggcg ctgccgtggc aagtccccca gtgactgctg ccacaaccag tgtgctgcag    960
gctgcacagg cccccgggag agcgactgcc tggtctgccg caattccga  gacgaagcca    1020 cgtgcaagga cacctgcccc ccactcatgc tctacaaccc caccacgtac cagatggatg   1080
```

-continued

```
tgaacccga gggcaaatac agctttggtg ccacctgcgt gaagaagtgt ccccgtaatt      1140
atgtggtgac agatcacggc tcgtgcgtcc gagcctgtgg ggccgacagc tatgagatgg      1200
aggaagacgg cgtccgcaag tgtaagaagt gcgaagggcc ttgccgcaaa gtgtgtaacg      1260
gaataggtat tggtgaattt aaagactcac tctccataaa tgctacgaat attaaacact      1320
tcaaaaactg cacctccatc agtggcgatc tccacatcct gccggtggca tttaggggtg      1380
actccttcac acatactcct cctctggatc cacaggaact ggatattctg aaaccgtaa      1440 aggaaatcac agggtttttg ctgattcagg cttggcctga aaacaggacg gacctccatg      1500
cctttgagaa cctagaaatc atacgcggca ggaccaagca acatggtcag ttttctcttg      1560
cagtcgtcag cctgaacata acatccttgg gattacgctc cctcaaggag ataagtgatg      1620
gagatgtgat aatttcagga aacaaaaatt tgtgctatgc aaatacaata aactggaaaa      1680
aactgtttgg gacctccggt cagaaaacca aaattataag caacagaggt gaaaacagct      1740
gcaaggccac aggccaggtc tgccatgcct tgtgctcccc cgagggctgc tggggcccgg      1800
agcccaggga ctgcgtctct tgccggaatg tcagccgagg cagggaatgc gtggacaagt      1860
gcaaccttct ggagggtgag ccaagggagt tgtggagaa ctctgagtgc atacagtgcc      1920
acccagagtg cctgcctcag gccatgaaca tcacctgcac aggacgggga ccagacaact      1980
gtatccagtg tgcccactac attgacggcc cccactgcgt caagacctgc ccggcaggag      2040
tcatgggaga aaacaacacc ctggtctgga agtacgcaga cgccggccat gtgtgccacc      2100
tgtgccatcc aaactgcacc tacggatgca ctgggccagg tcttgaaggc tgtccaacga      2160
atgggcctaa gatcccgtcc atcgccactg ggatggtggg ggccctcctc ttgctgctgg      2220
tggtggccct ggggatcggc ctcttcatgc gaaggcgcca catcgttcgg aagcgcacgc      2280
tgcggaggct gctgcaggag agggagcttg tggagcctct acacccagt ggagaagctc      2340 ccaaccaagc tctcttgagg atcttgaagg aaactgaatt caaaaagatc aaagtgctgg      2400
gctccggtgc gttcggcacg gtgtataagg gactctggat cccagaaggt gagaaagtta      2460
aaattcccgt cgctatcaag gaattaagag aagcaacatc tccgaaagcc aacaaggaaa      2520
tcctcgatga agcctacgtg atggccagcg tggacaaccc ccacgtgtgc cgcctgctgg      2580
gcatctgcct cacctccacc gtgcagctca tcacgcagct catgcccttc ggctgcctcc      2640
tggactatgt ccgggaacac aaagacaata ttggctccca gtacctgctc aactggtgtg      2700
tgcagatcgc aaagggcatg aactacttgg aggaccgtcg cttggtgcac cgcgacctgg      2760
cagccaggaa cgtactggtg aaaacaccgc agcatgtcaa gatcacagat tttgggcggg      2820
ccaaactgct gggtgcggaa gagaaagaat accatgcaga aggaggcaaa gtgcctatca      2880
agtggatggc attggaatca attttacaca gaatctatac ccaccagagt gatgtctgga      2940
gctacggggt gactgtttgg gagttgatga cctttggatc caagccatat gacggaatcc      3000
ctgccagcga gatctcctcc atcctggaga aggagaacg cctccctcag ccacccatat      3060
gtaccatcga tgtctacatg atcatggtca agtgctggat gatagacgca gatagtcgcc      3120
caaagttccg tgagttgatc atcgaattct ccaaaatggc ccgagacccc cagcgctacc      3180
ttgtcattca gggggatgaa agaatgcatt tgccaagtcc tacagactcc aacttctacc      3240
gtgccctgat ggatgaagaa gacatggacg acgtggtgga tgccgacgag tacctcatcc      3300
cacagcaggg cttcttcagc agcccctcca cgtcacggac tcccctcctg agctctctga      3360
gtgcaaccag caacaattcc accgtggctt gcattgatag aaatgggctg caaagctgtc      3420
```

```
ccatcaagga agacagcttc ttgcagcgat acagctcaga ccccacaggc gccttgactg    3480
aggacagcat agacgacacc ttcctcccag tgcctgaata cataaaccag tccgttccca    3540
aaaggcccgc tggctctgtg cagaatcctg tctatcacaa tcagcctctg aaccccgcgc    3600
ccagcagaga cccacactac caggacccccc acagcactgc agtgggcaac ccgagtatc    3660 tcaacactgt ccagcccacc tgtgtcaaca gcacattcga cagccctgcc cactgggccc    3720
agaaaggcag ccaccaaatt agcctggaca accctgacta ccagcaggac ttctttccca    3780
aggaagccaa gccaaatggc atctttaagg ctccacagc tgaaaatgca gaatacctaa    3840
gggtcgcgcc acaaagcagt gaatttattg gagcatga                           3878
```

<210> SEQ ID NO 736
<211> LENGTH: 3878
<212> TYPE: DNA
<213> ORGANISM: Homo sapiens

<400> SEQUENCE: 736

```
cccggcgcag cgcggccgca gcagcctccg ccccccgcac ggtgtgagcg cccgacgcgg      60
ccgaggcggc cggagtcccg agctagcccc ggcggccgcc gccgcccaga ccggacgaca     120
ggccacctcg tcggcgtccg cccgagtccc cgcctcgccg ccaacgccac aaccaccgcg     180
cacggccccc tgactccgtc cagtattgat cgggagagcc ggagcgagct cttcggggag     240
cagcgatgcg accctccggg acggccgggg cagcgctcct ggcgctgctg gctgcgctct     300
gcccggcgag tcgggctctg gaggaaaaga aagtttgcca aggcacgagt aacaagctca     360
cgcagttggg cacttttgaa gatcattttc tcagcctcca gaggatgttc aataactgtg     420
aggtggtcct tgggaatttg gaaattacct atgtgcagag gaattatgat ctttccttct     480
taaagaccat ccaggaggtg gctggttatg tcctcattgc cctcaacaca gtggagcgaa     540
ttcctttgga aaacctgcag atcatcagag gaaatatgta ctacgaaaat tcctatgcct     600
tagcagtctt atctaactat gatgcaaata aaaccggact gaaggagctg cccatgagaa     660
atttacagga atcctgcat ggcgccgtgc ggttcagcaa caaccctgcc ctgtgcaacg     720
tggagagcat ccagtggcgg gacatagtca gcagtgactt tctcagcaac atgtcgatgg     780
acttccagaa ccacctgggc agctgccaaa agtgtgatcc aagctgtccc aatgggagct     840
gctggggtgc aggagaggag aactgccaga aactgaccaa aatcatctgt gcccagcagt     900
gctcggggcg ctgccgtggc aagtccccca gtgactgctg ccacaaccag tgtgctgcag     960
gctgcacagg ccccgggag agcgactgcc tggtctgccg caaattccga gacgaagcca    1020
cgtgcaagga cacctgcccc ccactcatgc tctacaaccc caccacgtac cagatggatg    1080
tgaaccccga gggcaaatac agctttggtg ccacctgcgt gaagaagtgt ccccgtaatt    1140
atgtggtgac agatcacggc tcgtgcgtcc gagcctgtgg ggccgacagc tatgagatgg    1200
aggaagacgg cgtccgcaag tgtaagaagt gcgaagggcc ttgccgcaaa gtgtgtaacg    1260
gaataggtat tggtgaattt aaagactcac tctccataaa tgctacgaat attaaacact    1320
tcaaaaactg cacctccatc agtggcgatc tccacatcct gccggtggca tttaggggtg    1380
actccttcac acatactcct cctctggatc cacaggaact ggatattctg aaaaccgtaa    1440
aggaaatcac agggtttttg ctgattcagg cttggcctga aaacaggacg gacctccatg    1500
cctttgagaa cctagaaatc atacgcggca ggaccaagca acatggtcag ttttctcttg    1560
cagtcgtcag cctgaacata acatccttgg gattacgctc cctcaaggag ataagtgatg    1620
gagatgtgat aatttcagga aacaaaaatt tgtgctatgc aaatacaata aactggaaaa    1680
```

```
aactgtttgg gacctccggt cagaaaacca aaattataag caacagaggt gaaaacagct    1740
gcaaggccac aggccaggtc tgccatgcct tgtgctcccc cgagggctgc tggggcccgg    1800
agcccaggga ctgcgtctct tgccggaatg tcagccgagg cagggaatgc gtggacaagt    1860
gcaaccttct ggagggtgag ccaagggagt ttgtggagaa ctctgagtgc atacagtgcc    1920
acccagagtg cctgcctcag gccatgaaca tcacctgcac aggacgggga ccagacaact    1980
gtatccagtg tgcccactac attgacggcc cccactgcgt caagacctgc ccggcaggag    2040
tcatgggaga aaacaacacc ctggtctgga agtacgcaga cgccggccat gtgtgccacc    2100
tgtgccatcc aaactgcacc tacgatgca ctgggccagg tcttgaaggc tgtccaacga    2160
atgggcctaa gatcccgtcc atcgccactg ggatggtggg ggccctcctc ttgctgctgg    2220
tggtggccct ggggatcggc ctcttcatgc gaaggcgcca catcgttcgg aagcgcacgc    2280
tgcggaggct gctgcaggag agggagcttg tggagcctct tacacccagt ggagaagctc    2340
ccaaccaagc tctcttgagg atcttgaagg aaactgaatt caaaaagatc aaagtgctgg    2400
gctccggtgc gttcggcacg gtgtataagg actctggat cccagaaggt gagaaagtta    2460
aaattcccgt cgctatcaag gaattaagag aagcaacatc tccgaaagcc aacaaggaaa    2520
tcctcgatga agcctacgtg atggccagcg tggacaaccc ccacgtgtgc cgcctgctgg    2580
gcatctgcct cacctccacc gtgcagctca tcacgcagct catgcccttc ggctgcctcc    2640
tggactatgt ccgggaacac aaagacaata ttggctccca gtacctgctc aactggtgtg    2700
tgcagatcgc aaagggcatg aactacttgg aggaccgtcg cttggtgcac cgcgacctgg    2760
cagccaggaa cgtactggtg aaaacaccgc agcatgtcaa gatcacagat tttgggctgg    2820
ccaaacagct gggtgcggaa gagaaagaat accatgcaga aggaggcaaa gtgcctatca    2880
agtggatggc attggaatca attttacaca gaatctatac ccaccagagt gatgtctgga    2940 gctacgggt gactgtttgg gagttgatga cctttggatc caagccatat gacggaatcc    3000
ctgccagcga gatctcctcc atcctggaga aaggagaacg cctccctcag ccacccatat    3060
gtaccatcga tgtctacatg atcatggtca agtgctggat gatagacgca gatagtcgcc    3120
caaagttccg tgagttgatc atcgaattct ccaaaatggc ccgagacccc cagcgctacc    3180
ttgtcattca gggggatgaa agaatgcatt tgccaagtcc tacagactcc aacttctacc    3240
gtgccctgat ggatgaagaa gacatggacg acgtggtgga tgccgacgag tacctcatcc    3300
cacagcaggg cttcttcagc agcccctcca cgtcacggac tcccctcctg agctctctga    3360
gtgcaaccag caacaattcc accgtggctt gcattgatag aaatgggctg caaagctgtc    3420
ccatcaagga agacagcttc ttgcagcgat acagctcaga ccccacaggc gccttgactg    3480
aggacagcat agacgacacc ttcctcccag tgcctgaata cataaaccag tccgttccca    3540
aaaggcccgc tggctctgtg cagaatcctg tctatcacaa tcagcctctg aaccccgcgc    3600
ccagcagaga cccacactac caggaccccc acagcactgc agtgggcaac ccgagtatc    3660 tcaacactgt ccagcccacc tgtgtcaaca gcacattcga cagccctgcc cactgggccc    3720
agaaaggcag ccaccaaatt agcctggaca accctgacta ccagcaggac ttctttccca    3780
aggaagccaa gccaaatggc atctttaagg ctccacagc tgaaaatgca gaatacctaa    3840
gggtcgcgcc acaaagcagt gaatttattg gagcatga                           3878
```

<210> SEQ ID NO 737
<211> LENGTH: 3878
<212> TYPE: DNA

<213> ORGANISM: Homo sapiens

<400> SEQUENCE: 737

```
cccggcgcag cgcggccgca gcagcctccg cccccccgcac ggtgtgagcg cccgacgcgg      60
ccgaggcggc cggagtcccg agctagcccc ggcggccgcc gccgcccaga ccggacgaca     120
ggccacctcg tcggcgtccg cccgagtccc cgcctcgccg ccaacgccac aaccaccgcg     180
cacggccccc tgactccgtc cagtattgat cgggagagcc ggagcgagct cttcggggag     240
cagcgatgcg accctccggg acggccgggg cagcgctcct ggcgctgctg gctgcgctct     300
gcccggcgag tcgggctctg gaggaaaaga aagtttgcca aggcacgagt aacaagctca     360
cgcagttggg cacttttgaa gatcattttc tcagcctcca gaggatgttc aataactgtg     420
aggtggtcct tgggaatttg gaaattacct atgtgcagag gaattatgat ctttccttct     480
taaagaccat ccaggaggtg gctggttatg tcctcattgc cctcaacaca gtggagcgaa     540
ttcctttgga aaacctgcag atcatcagag gaaatatgta ctacgaaaat tcctatgcct     600
tagcagtctt atctaactat gatgcaaata aaaccggact gaaggagctg cccatgagaa     660
atttacagga atcctgcat ggcgccgtgc ggttcagcaa caaccctgcc ctgtgcaacg     720
tggagagcat ccagtggcgg gacatagtca gcagtgactt tctcagcaac atgtcgatgg     780
acttccagaa ccacctgggc agctgccaaa agtgtgatcc aagctgtccc aatgggagct     840
gctggggtgc aggagaggag aactgccaga aactgaccaa aatcatctgt gcccagcagt     900
gctccgggcg ctgccgtggc aagtccccca gtgactgctg ccacaaccag tgtgctgcag     960
gctgcacagg cccccgggag agcgactgcc tggtctgccg caaattccga gacgaagcca    1020
cgtgcaagga cacctgcccc ccactcatgc tctacaaccc caccacgtac cagatggatg    1080
tgaaccccga gggcaaatac agctttggtg ccacctgcgt gaagaagtgt cccgtaatt    1140
atgtggtgac agatcacggc tcgtgcgtcc gagcctgtgg ggccgacagc tatgagatgg    1200
aggaagacgc cgtccgcaag tgtaagaagt gcgaagggcc ttgccgcaaa gtgtgtaacg    1260
gaataggtat tggtgaattt aaagactcac tctccataaa tgctacgaat attaaacact    1320
tcaaaaactg cacctccatc agtggcgatc tccacatcct gccggtggca tttaggggtg    1380
actccttcac acatactcct cctctggatc cacaggaact ggatattctg aaaaccgtaa    1440
aggaaatcac agggttttttg ctgattcagg cttggcctga aaacaggacg gacctccatg    1500
cctttgagaa cctagaaatc atacgcggca ggaccaagca acatggtcag ttttctcttg    1560
cagtcgtcag cctgaacata acatccttgg gattacgctc cctcaaggag ataagtgatg    1620
gagatgtgat aatttcagga aacaaaaatt tgtgctatgc aaatacaata aactggaaaa    1680
aactgtttgg gacctccggt cagaaaacca aaattataag caacagaggt gaaaacagct    1740
gcaaggccac aggccaggtc tgccatgcct tgtgctcccc cgagggctgc tggggcccgg    1800
agcccaggga ctgcgtctct tgccggaatg tcagccgagg cagggaatgc gtggacaagt    1860
gcaaccttct ggagggtgag ccaagggagt ttgtggagaa ctctgagtgc atacagtgcc    1920
acccagagtg cctgcctcag gccatgaaca tcacctgcac aggacgggga ccagacaact    1980
gtatccagtg tgcccactac attgacggcc cccactgcgt caagacctgc ccggcaggag    2040
tcatgggaga aaacaacacc ctggtctgga agtacgcaga cgccggccat gtgtgccacc    2100
tgtgccatcc aaactgcacc tacggatgca ctgggccagg tcttgaaggc tgtccaacga    2160
atgggcctaa gatcccgtcc atcgccactg ggatggtggg ggccctcctc ttgctgctgg    2220
tggtggccct ggggatcggc ctcttcatgc gaaggcgcca catcgttcgg aagcgcacgc    2280
```

```
tgcggaggct gctgcaggag agggagcttg tggagcctct tacacccagt ggagaagctc     2340
ccaaccaagc tctcttgagg atcttgaagg aaactgaatt caaaaagatc aaagtgctgt     2400
gctccggtgc gttcggcacg gtgtataagg gactctggat cccagaaggt gagaaagtta     2460
aaattcccgt cgctatcaag gaattaagag aagcaacatc tccgaaagcc aacaaggaaa     2520
tcctcgatga agcctacgtg atggccagcg tggacaaccc ccacgtgtgc cgcctgctgg     2580
gcatctgcct cacctccacc gtgcagctca tcacgcagct catgcccttc ggctgcctcc     2640
tggactatgt ccgggaacac aaagacaata ttggctccca gtacctgctc aactggtgtg     2700
tgcagatcgc aaagggcatg aactacttgg aggaccgtcg cttggtgcac cgcgacctgg     2760
cagccaggaa cgtactggtg aaaacaccgc agcatgtcaa gatcacagat tttgggctgg     2820
ccaaactgct gggtgcggaa gagaaagaat accatgcaga aggaggcaaa gtgcctatca     2880
agtggatggc attggaatca attttacaca gaatctatac ccaccagagt gatgtctgga     2940
gctacggggt gactgtttgg gagttgatga ccttttggatc caagccatat gacgaatcc      3000 ctgccagcga gatctcctcc atcctggaga aaggagaacg cctccctcag ccacccatat     3060
gtaccatcga tgtctacatg atcatggtca agtgctggat gatagacgca gatagtcgcc     3120
caaagttccg tgagttgatc atcgaattct ccaaaatggc ccgagacccc cagcgctacc     3180
ttgtcattca gggggatgaa agaatgcatt tgccaagtcc tacagactcc aacttctacc     3240
gtgccctgat ggatgaagaa gacatggacg acgtggtgga tgccgacgag tacctcatcc     3300
cacagcaggg cttcttcagc agcccctcca cgtcacggac tccctcctg agctctctga      3360 gtgcaaccag caacaattcc accgtggctt gcattgatag aaatgggctg caaagctgtc     3420
ccatcaagga agacagcttc ttgcagcgat acagctcaga ccccacaggc gccttgactg     3480
aggacagcat agacgacacc ttcctcccag tgcctgaata cataaaccag tccgttccca     3540
aaaggcccgc tggctctgtg cagaatcctg tctatcacaa tcagcctctg aaccccgcgc     3600
ccagcagaga cccacactac caggaccccc acagcactgc agtgggcaac cccgagtatc     3660
tcaacactgt ccagcccacc tgtgtcaaca gcacattcga cagccctgcc cactgggccc     3720
agaaaggcag ccaccaaatt agcctggaca accctgacta ccagcaggac ttcttcccca     3780
aggaagccaa gccaaatggc atcttttaagg gctccacagc tgaaaatgca gaatacctaa     3840
gggtcgcgcc acaaagcagt gaatttattg gagcatga                             3878
```

<210> SEQ ID NO 738
<211> LENGTH: 3860
<212> TYPE: DNA
<213> ORGANISM: Homo sapiens

<400> SEQUENCE: 738

```
cccggcgcag cgcggccgca gcagcctccg cccccccgcac ggtgtgagcg cccgacgcgg        60
ccgaggcggc cggagtcccg agctagcccc ggcggccgcc gccgcccaga ccggacgaca       120
ggccacctcg tcggcgtccg cccgagtccc cgcctcgccg ccaacgccac aaccaccgcg       180
cacggccccc tgactccgtc cagtattgat cgggagagcc ggagcgagct cttcggggag       240
cagcgatgcg accctccggg acggccgggg cagcgctcct ggcgctgctg gctgcgctct       300
gcccggcgag tcgggctctg gaggaaaaga agtttgccca aggcacgagt aacaagctca       360
cgcagttggg cactttttgaa gatcattttc tcagcctcca gaggatgttc aataactgtg       420
aggtggtcct tgggaatttg gaaattacct atgtgcagag gaattatgat cttttccttct      480
```

-continued

```
taaagaccat ccaggaggtg gctggttatg tcctcattgc cctcaacaca gtggagcgaa      540
ttcctttgga aaacctgcag atcatcagag gaaatatgta ctacgaaaat tcctatgcct      600
tagcagtctt atctaactat gatgcaaata aaaccggact gaaggagctg cccatgagaa      660
atttacagga atcctgcat ggcgccgtgc ggttcagcaa caaccctgcc ctgtgcaacg       720
tggagagcat ccagtggcgg gacatagtca gcagtgactt tctcagcaac atgtcgatgg      780
acttccagaa ccacctgggc agctgccaaa agtgtgatcc aagctgtccc aatgggagct      840
gctggggtgc aggagaggag aactgccaga aactgaccaa aatcatctgt gcccagcagt      900
gctccgggcg ctgccgtggc aagtccccca gtgactgctg ccacaaccag tgtgctgcag      960
gctgcacagg cccccgggag agcgactgcc tggtctgccg caaattccga gacgaagcca     1020
cgtgcaagga cacctgcccc ccactcatgc tctacaaccc caccacgtac cagatggatg     1080
tgaaccccga gggcaaatac agctttggtg ccacctgcgt gaagaagtgt ccccgtaatt     1140
atgtggtgac agatcacggc tcgtgcgtcc gagcctgtgg ggccgacagc tatgagatgg     1200
aggaagacgg cgtccgcaag tgtaagaagt gcgaagggcc ttgccgcaaa gtgtgtaacg     1260
gaataggtat tggtgaattt aaagactcac tctccataaa tgctacgaat attaaacact     1320
tcaaaaactg cacctccatc agtggcgatc tccacatcct gccggtggca tttaggggtg     1380
actccttcac acatactcct cctctggatc cacaggaact ggatattctg aaaaccgtaa     1440
aggaaatcac agggtttttg ctgattcagg cttggcctga aaacaggacg gacctccatg     1500
cctttgagaa cctagaaatc atacgcggca ggaccaagca acatggtcag ttttctcttg     1560
cagtcgtcag cctgaacata acatccttgg gattacgctc cctcaaggag ataagtgatg     1620
gagatgtgat aatttcagga aacaaaaatt tgtgctatgc aaatacaata aactggaaaa     1680
aactgttggg gacctccggt cagaaaacca aaattataag caacagaggt gaaaacagct     1740
gcaaggccac aggccaggtc tgccatgcct tgtgctcccc cgagggctgc tggggcccgg     1800
agcccaggga ctgcgtctct tgccggaatg tcagccgagg cagggaatgc gtggacaagt     1860
gcaaccttct ggagggtgag ccaagggagt ttgtggagaa ctctgagtgc atacagtgcc     1920
acccagagtg cctgcctcag gccatgaaca tcacctgcac aggacgggga ccagacaact     1980
gtatccagtg tgcccactac attgacggcc cccactgcgt caagacctgc ccggcaggag     2040
tcatgggaga aaacaacacc ctggtctgga agtacgcaga cgccggccat gtgtgccacc     2100
tgtgccatcc aaactgcacc tacggatgca ctgggccagg tcttgaaggc tgtccaacga     2160
atgggcctaa gatcccgtcc atcgccactg ggatggtggg ggccctcctc ttgctgctgg     2220
tggtggccct ggggatcggc ctcttcatgc gaaggcgcca catcgttcgg aagcgcacgc     2280 tgcgaggct gctgcaggag agggagcttg tggagcctct tacacccagt ggagaagctc     2340
ccaaccaagc tctcttgagg atcttgaagg aaactgaatt caaaaagatc aaagtgctgg     2400
gctccggtgc gttcggcacg gtgtataagg gactctggat cccagaaggt gagaaagtta     2460
aaattcccgt cgctatcaag gaatcgaaag ccaacaagga aatcctcgat gaagcctacg     2520
tgatggccag cgtggacaac ccccacgtgt gccgcctgct gggcatctgc ctcacctcca     2580
ccgtgcagct catcacgcag ctcatgccct cggctgcct cctggactat gtccgggaac     2640
acaaagacaa tattggctcc cagtacctgc tcaactggtg tgtgcagatc gcaagggca     2700 tgaactactt ggaggaccgt cgcttggtgc accgcgacct ggcagccagg aacgtactgg     2760
tgaaaacacc gcagcatgtc aagatacag attttgggct ggccaaactg ctgggtgcgg     2820
aagagaaaga ataccatgca gaaggaggca aagtgcctat caagtggatg gcattggaat     2880
```

```
caattttaca cagaatctat acccaccaga gtgatgtctg gagctacggg gtgactgttt    2940
gggagttgat gacctttgga tccaagccat atgacggaat ccctgccagc gagatctcct    3000
ccatcctgga gaaaggagaa cgcctccctc agccacccat atgtaccatc gatgtctaca    3060
tgatcatggt caagtgctgg atgatagacg cagatagtcg cccaaagttc cgtgagttga    3120
tcatcgaatt ctccaaaatg gcccgagacc cccagcgcta ccttgtcatt caggggatg     3180 aaagaatgca tttgccaagt cctacagact ccaacttcta ccgtgccctg atggatgaag    3240
aagacatgga cgacgtggtg gatgccgacg agtacctcat cccacagcag ggcttcttca    3300 gcagccctc cacgtcacgg actcccctcc tgagctctct gagtgcaacc agcaacaatt     3360
ccaccgtggc ttgcattgat agaaatgggc tgcaaagctg tcccatcaag gaagacagct    3420
tcttgcagcg atacagctca gaccccacag gcgccttgac tgaggacagc atagacgaca    3480
ccttcctccc agtgcctgaa tacataaacc agtccgttcc caaaaggccc gctggctctg    3540
tgcagaatcc tgtctatcac aatcagcctc tgaaccccgc gcccagcaga gacccacact    3600
accaggaccc ccacagcact gcagtgggca accccgagta tctcaacact gtccagccca    3660
cctgtgtcaa cagcacattc gacagccctg cccactgggc ccagaaaggc agccaccaaa    3720
ttagcctgga caaccctgac taccagcagg acttcttttcc caaggaagcc aagccaaatg    3780
gcatctttaa gggctccaca gctgaaaatg cagaatacct aagggtcgcg ccacaaagca    3840
gtgaatttat tggagcatga                                                3860
```

<210> SEQ ID NO 739
<211> LENGTH: 3863
<212> TYPE: DNA
<213> ORGANISM: Homo sapiens

<400> SEQUENCE: 739

```
cccggcgcag cgcggccgca gcagcctccg ccccccgcac ggtgtgagcg ccgacgcgg      60 ccgaggcggc cggagtcccg agctagcccc ggcggccgcc gccgcccaga ccggacgaca     120
ggccacctcg tcggcgtccg cccgagtccc cgcctcgccg ccaacgccac aaccaccgcg     180
cacggccccc tgactccgtc cagtattgat cgggagagcc ggagcgagct cttcggggag    240
cagcgatgcg accctccggg acggccgggg cagcgctcct ggcgctgctg gctgcgctct    300
gcccggcgag tcgggctctg gaggaaaaga aagtttgcca aggcacgagt aacaagctca    360
cgcagttggg cacttttgaa gatcattttc tcagcctcca gaggatgttc aataactgtg    420
aggtggtcct tgggaatttg gaaattacct atgtgcagag gaattatgat ctttccttct    480
taaagaccat ccaggaggtg gctggttatg tcctcattgc cctcaacaca gtggagcgaa    540
ttcctttgga aaacctgcag atcatcagag gaaatatgta ctacgaaaat tcctatgcct    600
tagcagtctt atctaactat gatgcaaata aaaccggact gaaggagctg cccatgagaa    660
atttacagga aatcctgcat ggcgccgtgc ggttcagcaa caaccctgcc ctgtgcaacg    720
tggagagcat ccagtggcgg gacatagtca gcagtgactt tctcagcaac atgtcgatgg    780
acttccagaa ccacctgggc agctgccaaa agtgtgatcc aagctgtccc aatgggagct    840 gctgggggtgc aggagaggag aactgccaga aactgaccaa aatcatctgt gcccagcagt    900
gctccgggcg ctgccgtggc aagtcccca gtgactgctg ccacaaccag tgtgctgcag    960
gctgcacagg ccccgggag agcgactgcc tggtctgccg caaattccga gacgaagcca    1020
cgtgcaagga cacctgcccc ccactcatgc tctacaaccc caccacgtac cagatggatg    1080
```

-continued

```
tgaaccccga gggcaaatac agctttggtg ccacctgcgt gaagaagtgt ccccgtaatt    1140
atgtggtgac agatcacggc tcgtgcgtcc gagcctgtgg ggccgacagc tatgagatgg    1200
aggaagacgg cgtccgcaag tgtaagaagt gcgaagggcc ttgccgcaaa gtgtgtaacg    1260
gaataggtat tggtgaattt aaagactcac tctccataaa tgctacgaat attaaacact    1320
tcaaaaactg cacctccatc agtggcgatc tccacatcct gccggtggca tttaggggtg    1380
actccttcac acatactcct cctctggatc cacaggaact ggatattctg aaaaccgtaa    1440
aggaaatcac agggtttttg ctgattcagg cttggcctga aaacaggacg gacctccatg    1500
cctttgagaa cctagaaatc atacgcggca ggaccaagca acatggtcag ttttctcttg    1560
cagtcgtcag cctgaacata acatccttgg gattacgctc cctcaaggag ataagtgatg    1620
gagatgtgat aatttcagga aacaaaaatt tgtgctatgc aaatacaata aactggaaaa    1680
aactgtttgg gacctccggt cagaaaacca aaattataag caacagaggt gaaaacagct    1740
gcaaggccac aggccaggtc tgccatgcct tgtgctcccc cgagggctgc tggggcccgg    1800
agcccaggga ctgcgtctct tgccggaatg tcagccgagg cagggaatgc gtggacaagt    1860
gcaaccttct ggagggtgag ccaagggagt ttgtggagaa ctctgagtgc atacagtgcc    1920
acccagagtg cctgcctcag gccatgaaca tcacctgcac aggacgggga ccagacaact    1980
gtatccagtg tgcccactac attgacggcc ccactgcgt caagacctgc ccggcaggag    2040
tcatgggaga aaacaacacc ctggtctgga gtacgcaga cgccggccat gtgtgccacc    2100
tgtgccatcc aaactgcacc tacggatgca ctgggccagg tcttgaaggc tgtccaacga    2160
atgggcctaa gatcccgtcc atcgccactg ggatggtggg ggccctcctc ttgctgctgg    2220
tggtggccct ggggatcggc ctcttcatgc gaaggcgcca catcgttcgg aagcgcacgc    2280
tgcggaggct gctgcaggag agggagcttg tggagcctct tacacccagt ggagaagctc    2340
ccaaccaagc tctcttgagg atcttgaagg aaactgaatt caaaaagatc aaagtgctgg    2400
gctccggtgc gttcggcacg gtgtataagg actctggat cccagaaggt gagaaagtta    2460
aaattcccgt cgctatcaaa acatctccga aagccaacaa ggaaatcctc gatgaagcct    2520
acgtgatggc agcgtggac aaccccacg tgtgccgcct gctgggcatc tgcctcacct    2580
ccaccgtgca gctcatcacg cagctcatgc ccttcggctg cctcctggac tatgtccggg    2640
aacacaaaga caatattggc tcccagtacc tgctcaactg gtgtgtgcag atcgcaaagg    2700
gcatgaacta cttggaggac gtcgcttgg tgcaccgcga cctggcagcc aggaacgtac    2760
tggtgaaaac accgcagcat gtcaagatca cagattttgg gctggccaaa ctgctgggtg    2820
cggaagagaa agaataccat gcagaaggag gcaaagtgcc tatcaagtgg atggcattgg    2880
aatcaatttt acacagaatc tatacccacc agagtgatgt ctggagctac ggggtgactg    2940
tttgggagtt gatgaccttt ggatccaagc catatgacgg aatccctgcc agcgagatct    3000
cctccatcct ggagaaagga gaacgcctcc ctcagccacc catatgtacc atcgatgtct    3060
acatgatcat ggtcaagtgc tggatgatag acgcagatag tcgcccaaag ttccgtgagt    3120
tgatcatcga attctccaaa atggcccgag accccagcg ctaccttgtc attcagggg    3180
atgaaagaat gcatttgcca agtcctacag actccaactt ctaccgtgcc ctgatggatg    3240
aagaagacat ggacgacgtg gtggatgccg acgagtacct catcccacag cagggcttct    3300
tcagcagccc ctccacgtca cggactcccc tcctgagctc tctgagtgca accagcaaca    3360
attccaccgt ggcttgcatt gatagaaatg ggctgcaaag ctgtcccatc aaggaagaca    3420
gcttcttgca gcgatacagc tcagaccccca caggcgcctt gactgaggac agcatagacg    3480
```

```
acaccttcct cccagtgcct gaatacataa accagtccgt tcccaaaagg cccgctggct    3540
ctgtgcagaa tcctgtctat cacaatcagc ctctgaaccc cgcgcccagc agagacccac    3600
actaccagga cccccacagc actgcagtgg gcaaccccga gtatctcaac actgtccagc    3660
ccacctgtgt caacagcaca ttcgacagcc ctgcccactg ggcccagaaa ggcagccacc    3720
aaattagcct ggacaaccct gactaccagc aggacttctt tcccaaggaa gccaagccaa    3780
atggcatctt taagggctcc acagctgaaa atgcagaata cctaagggtc gcgccacaaa    3840
gcagtgaatt tattggagca tga                                          3863
```

<210> SEQ ID NO 740
<211> LENGTH: 3878
<212> TYPE: DNA
<213> ORGANISM: Homo sapiens

<400> SEQUENCE: 740

```
cccggcgcag cgcggccgca gcagcctccg ccccccgcac ggtgtgagcg cccgacgcgg      60
ccgaggcggc cggagtcccg agctagcccc ggcggccgcc gccgcccaga ccggacgaca     120
ggccacctcg tcggcgtccg cccgagtccc cgcctcgccg ccaacgccac aaccaccgcg     180
cacggccccc tgactccgtc cagtattgat cgggagagcc ggagcgagct cttcggggag     240
cagcgatgcg accctccggg acggccgggg cagcgctcct ggcgctgctg gctgcgctct     300
gcccggcgag tcgggctctg gaggaaaaga aagtttgcca aggcacgagt aacaagctca     360
cgcagttggg cacttttgaa gatcattttc tcagcctcca gaggatgttc aataactgtg     420
aggtggtcct tgggaatttg gaaattacct atgtgcagag gaattatgat cttcttct      480 taaagaccat ccaggaggtg gctggttatg tcctcattgc cctcaacaca gtggagcgaa     540
ttcctttgga aaacctgcag atcatcagag gaaatatgta ctacgaaaat tcctatgcct     600
tagcagtctt atctaactat gatgcaaata aaaccggact gaaggagctg cccatgagaa     660
atttacagga atcctgcat ggcgccgtgc ggttcagcaa caaccctgcc ctgtgcaacg     720
tggagagcat ccagtggcgg gacatagtca gcagtgactt tctcagcaac atgtcgatgg     780
acttccagaa ccacctgggc agctgccaaa agtgtgatcc aagctgtccc aatgggagct     840
gctggggtgc aggagaggag aactgccaga aactgaccaa aatcatctgt gcccagcagt     900 gctcccgggcg ctgccgtggc aagtccccca gtgactgctg ccacaaccag tgtgctgcag     960
gctgcacagg ccccgggag agcgactgcc tggtctgccg caaattccga gacgaagcca    1020
cgtgcaagga cacctgcccc ccactcatgc tctacaaccc caccacgtac cagatggatg    1080
tgaaccccga gggcaaatac agctttggtg ccacctgcgt gaagaagtgt ccccgtaatt    1140
atgtggtgac agatcacggc tcgtgcgtcc gagcctgtgg ggccgacagc tatgagatgg    1200
aggaagacgg cgtccgcaag tgtaagaagt gcgaagggcc ttgccgcaaa gtgtgtaacg    1260
gaataggtat tggtgaattt aaagactcac tctccataaa tgctacgaat attaaacact    1320
tcaaaaactg cacctccatc agtggcgatc tccacatcct gccggtggca tttagggtg    1380 actccttcac acatactcct cctctggatc cacaggaact ggatattctg aaaaccgtaa    1440
aggaaatcac agggttttg ctgattcagg cttggcctga aaacaggacg gacctccatg    1500
cctttgagaa cctagaaatc atacgcggca ggaccaagca acatggtcag ttttctcttg    1560
cagtcgtcag cctgaacata acatccttgg gattacgctc cctcaaggag ataagtgatg    1620
gagatgtgat aatttcagga aacaaaaatt tgtgctatgc aaatacaata aactggaaaa    1680
```

```
aactgtttgg gacctccggt cagaaaacca aaattataag caacagaggt gaaaacagct    1740
gcaaggccac aggccaggtc tgccatgcct tgtgctcccc cgagggctgc tggggcccgg    1800
agcccaggga ctgcgtctct tgccggaatg tcagccgagg cagggaatgc gtggacaagt    1860
gcaaccttct ggagggtgag ccaagggagt tgtggagaa ctctgagtgc atacagtgcc     1920
acccagagtg cctgcctcag gccatgaaca tcacctgcac aggacgggga ccagacaact    1980
gtatccagtg tgcccactac attgacggcc cccactgcgt caagacctgc ccggcaggag    2040
tcatgggaga aacaacacc ctggtctgga agtacgcaga cgccggccat gtgtgccacc     2100
tgtgccatcc aaactgcacc tacggatgca ctgggccagg tcttgaaggc tgtccaacga    2160
atgggcctaa gatcccgtcc atcgccactg ggatggtggg ggccctcctc ttgctgctgg    2220
tggtggccct ggggatcggc ctcttcatgc gaaggcgcca catcgttcgg aagcgcacgc    2280
tgcggaggct gctgcaggag agggagcttg tggagcctct tacacccagt ggagaagctc    2340
ccaaccaagc tctcttgagg atcttgaagg taactgaatt caaaaagatc aaagtgctga    2400
gctccggtgc gttcggcacg gtgtataagg actctggat cccagaaggt gagaaagtta     2460
aaattcccgt cgctatcaag gaattaagag aagcaacatc tccgaaagcc aacaaggaaa    2520
tcctcgatga agcctacgtg atggccacg tggacaaccc ccacgtgtgc cgcctgctgg     2580
gcatctgcct cacctccacc gtgcagctca tcacgcagct catgcccttc ggctgcctcc    2640
tggactatgt ccgggaacac aaagacaata ttggctccca gtacctgctc aactggtgtg    2700
tgcagatcgc aaagggcatg aactacttgg aggaccgtcg cttggtgcac gcgacctgg     2760 cagccaggaa cgtactggtg aaaacaccgc agcatgtcaa gatcacagat tttgggctgg    2820
ccaaactgct gggtgcggaa gagaaagaat accatgcaga aggaggcaaa gtgcctatca    2880
agtggatggc attggaatca attttacaca gaatctatac ccaccagagt gatgtctgga    2940
gctacggggt gactgtttgg gagttgatga cctttggatc caagccatat gacggaatcc    3000
ctgccagcga gatctcctcc atcctggaga aaggagaacg cctccctcag ccacccatat    3060
gtaccatcga tgtctacatg atcatggtca agtgctggat gatagacgca gatagtcgcc    3120
caaagttccg tgagttgatc atcgaattct ccaaaatggc ccgagacccc cagcgctacc    3180
ttgtcattca gggggatgaa agaatgcatt tgccaagtcc tacagactcc aacttctacc    3240
gtgccctgat ggatgaagaa gacatggacg acgtggtgga tgccgacgag tacctcatcc    3300
cacagcaggg cttcttcagc agcccctcca cgtcacggac tccccctcctg agctctctga   3360 gtgcaaccag caacaattcc accgtggctt gcattgatag aaatgggctg caaagctgtc    3420
ccatcaagga agacagcttc ttgcagcgat acagctcaga ccccacaggc gccttgactg    3480
aggacagcat agacgacacc ttcctcccag tgcctgaata cataaaccag tccgttccca    3540
aaaggcccgc tggctctgtg cagaatcctg tctatcacaa tcagcctctg aacccgcgc    3600 ccagcagaga cccacactac caggacccc acagcactgc agtgggcaac cccgagtatc     3660
tcaacactgt ccagcccacc tgtgtcaaca gcacattcga cagccctgcc cactgggccc    3720
agaaaggcag ccaccaaatt agcctggaca accctgacta ccagcaggac ttctttccca    3780
aggaagccaa gccaaatggc atctttaagg gctccacagc tgaaaatgca gaatacctaa    3840
gggtcgcgcc acaaagcagt gaatttattg gagcatga                            3878
```

<210> SEQ ID NO 741
<211> LENGTH: 3878
<212> TYPE: DNA
<213> ORGANISM: Homo sapiens

<400> SEQUENCE: 741

```
cccggcgcag cgcggccgca gcagcctccg ccccccgcac ggtgtgagcg cccgacgcgg      60
ccgaggcggc cggagtcccg agctagcccc ggcggccgcc gccgcccaga ccggacgaca     120
ggccacctcg tcggcgtccg cccgagtccc cgcctcgccg ccaacgccac aaccaccgcg     180
cacggccccc tgactccgtc cagtattgat cgggagagcc ggagcgagct cttcggggag     240
cagcgatgcg accctccggg acggccgggg cagcgctcct ggcgctgctg gctgcgctct     300
gcccggcgag tcgggctctg gaggaaaaga aagtttgcca aggcacgagt aacaagctca     360
cgcagttggg cacttttgaa gatcattttc tcagcctcca gaggatgttc ataactgtg     420
aggtggtcct tgggaatttg gaaattacct atgtgcagag gaattatgat ctttccttct     480
taaagaccat ccaggaggtg gctggttatg tcctcattgc cctcaacaca gtggagcgaa     540
ttcctttgga aaacctgcag atcatcagag gaaatatgta ctacgaaaat tcctatgcct     600
tagcagtctt atctaactat gatgcaaata aaaccggact gaaggagctg cccatgagaa     660
atttacagga atcctgcat ggcgccgtgc ggttcagcaa caaccctgcc ctgtgcaacg     720
tggagagcat ccagtggcgg gacatagtca gcagtgactt tctcagcaac atgtcgatgg     780
acttccagaa ccacctgggc agctgccaaa agtgtgatcc aagctgtccc aatgggagct     840
gctgggggtgc aggagaggag aactgccaga aactgaccaa aatcatctgt gcccagcagt     900
gctccgggcg ctgccgtggc aagtcccca gtgactgctg ccacaaccag tgtgctgcag     960
gctgcacagg ccccgggag agcgactgcc tggtctgccg caaattccga gacgaagcca    1020
cgtgcaagga cacctgcccc ccactcatgc tctacaaccc caccacgtac cagatggatg    1080
tgaaccccga gggcaaatac agctttggtg ccacctgcgt gaagaagtgt ccccgtaatt    1140
atgtggtgac agatcacggc tcgtgcgtcc gagcctgtgg ggccgacagc tatgagatgg    1200
aggaagacgg cgtccgcaag tgtaagaagt gcgaagggcc ttgccgcaaa gtgtgtaacg    1260
gaataggtat tggtgaattt aaagactcac tctccataaa tgctacgaat attaaacact    1320
tcaaaaactg cacctccatc agtggcgatc tccacatcct gccggtggca tttaggggtg    1380
actccttcac acatactcct cctctggatc cacaggaact ggatattctg aaaaccgtaa    1440
aggaaatcac aggggttttt ctgattcagg cttggcctga aaacaggacg gacctccatg    1500
cctttgagaa cctagaaatc atacgcggca ggaccaagca acatggtcag ttttctcttg    1560
cagtcgtcag cctgaacata acatccttgg gattacgctc cctcaaggag ataagtgatg    1620
gagatgtgat aatttcagga aacaaaaatt tgtgctatgc aaatacaata aactggaaaa    1680
aactgtttgg gacctccggt cagaaaacca aaattataag caacagaggt gaaaacagct    1740
gcaaggccac aggccaggtc tgccatgcct tgtgctcccc cgagggctgc tggggcccgg    1800
agcccaggga ctgcgtctct tgccggaatg tcagccgagg cagggaatgc gtggacaagt    1860
gcaaccttct ggagggtgag ccaagggagt tgtggagaa ctctgagtgc atacagtgcc    1920
acccagagtg cctgcctcag gccatgaaca tcacctgcac aggacgggga ccagacaact    1980
gtatccagtg tgcccactac attgacggcc cccactgcgt caagacctgc ccggcaggag    2040
tcatgggaga aaacaacacc ctggtctgga agtacgcaga cgccggccat gtgtgccacc    2100
tgtgccatcc aaactgcacc tacggatgca ctgggccagg tcttgaaggc tgtccaacga    2160
atgggcctaa gatcccgtcc atcgccactg ggatggtggg ggcctcctc ttgctgctgg    2220
tggtggccct ggggatcggc ctcttcatgc gaaggcgcca catcgttcgg aagcgcacgc    2280
```

| | |
|---|---:|
| tgcggaggct gctgcaggag agggagcttg tggagcctct tacacccagt ggagaagctc | 2340 |
| ccaaccaagc tctcttgagg atcttgaagg aaactgaatt caaaaagatc aaagtgctgg | 2400 |
| cctccggtgc gttcggcacg gtgtataagg gactctggat cccagaaggt gagaaagtta | 2460 |
| aaattcccgt cgctatcaag gaattaagag aagcaacatc tccgaaagcc aacaaggaaa | 2520 |
| tcctcgatga agcctacgtg atggccagcg tggacaaccc ccacgtgtgc cacctgctgg | 2580 |
| gcatctgcct cacctccacc gtgcagctca tcacgcagct catgcccttc ggctgcctcc | 2640 |
| tggactatgt ccgggaacac aaagacaata ttggctccca gtacctgctc aactggtgtg | 2700 |
| tgcagatcgc aaagggcatg aactacttgg aggaccgtcg cttggtgcac cgcgacctgg | 2760 |
| cagccaggaa cgtactggtg aaaacaccgc agcatgtcaa gatcacagat tttgggctgg | 2820 |
| ccaaactgct gggtgcggaa gagaaagaat accatgcaga aggaggcaaa gtgcctatca | 2880 |
| agtggatggc attggaatca attttacaca gaatctatac ccaccagagt gatgtctgga | 2940 |
| gctacggggt gactgtttgg gagttgatga ccttttggatc caagccatat gacggaatcc | 3000 |
| ctgccagcga gatctcctcc atcctggaga aaggagaacg cctccctcag ccacccatat | 3060 |
| gtaccatcga tgtctacatg atcatggtca agtgctggat gatagacgca gatagtcgcc | 3120 |
| caaagttccg tgagttgatc atcgaattct ccaaaatggc ccgagacccc cagcgctacc | 3180 |
| ttgtcattca gggggatgaa agaatgcatt tgccaagtcc tacagactcc aacttctacc | 3240 |
| gtgccctgat ggatgaagaa gacatggacg acgtggtgga tgccgacgag tacctcatcc | 3300 |
| cacagcaggg cttcttcagc agccctccca cgtcacggac tcccctcctg agctctctga | 3360 |
| gtgcaaccag caacaattcc accgtggctt gcattgatag aaatgggctg caaagctgtc | 3420 |
| ccatcaagga agacagcttc ttgcagcgat acagctcaga ccccacaggc gccttgactg | 3480 |
| aggacagcat agacgacacc ttcctcccag tgcctgaata cataaaccag tccgttccca | 3540 |
| aaaggcccgc tggctctgtg cagaatcctg tctatcacaa tcagcctctg aaccccgcgc | 3600 |
| ccagcagaga cccacactac caggaccccc acagcactgc agtgggcaac cccgagtatc | 3660 |
| tcaacactgt ccagcccacc tgtgtcaaca gcacattcga cagccctgcc cactgggccc | 3720 |
| agaaaggcag ccaccaaatt agcctggaca accctgacta ccagcaggac ttctttccca | 3780 |
| aggaagccaa gccaaatggc atctttaagg gctccacagc tgaaaatgca gaatacctaa | 3840 |
| gggtcgcgcc acaaagcagt gaatttattg gagcatga | 3878 |

<210> SEQ ID NO 742
<211> LENGTH: 3863
<212> TYPE: DNA
<213> ORGANISM: Homo sapiens

<400> SEQUENCE: 742

| | |
|---|---:|
| cccggcgcag cgcggccgca gcagcctccg ccccccgcac ggtgtgagcg cccgacgcgg | 60 |
| ccgaggcggc cggagtcccg agctagcccc ggcggccgcc gccgcccaga ccggacgaca | 120 |
| ggccacctcg tcggcgtccg cccgagtccc cgcctcgccg ccaacgccac aaccaccgcg | 180 |
| cacggccccc tgactccgtc cagtattgat cgggagagcc ggagcgagct cttcggggag | 240 |
| cagcgatgcg accctccggg acggccgggg cagcgctcct ggcgctgctg gctgcgctct | 300 |
| gcccggcgag tcgggctctg gaggaaaaga aagtttgcca aggcacgagt aacaagctca | 360 |
| cgcagttggg cactttttga agatcatttt tcagcctcca gaggatgttc ataactgtg | 420 |
| aggtggtcct tgggaatttg gaaattacct atgtgcagag gaattatgat ctttccttct | 480 |
| taaagaccat ccaggaggtg gctggttatg tcctcattgc cctcaacaca gtggagcgaa | 540 |

```
ttcctttgga aaacctgcag atcatcagag gaaatatgta ctacgaaaat tcctatgcct      600
tagcagtctt atctaactat gatgcaaata aaaccggact gaaggagctg cccatgagaa      660
atttacagga aatcctgcat ggcgccgtgc ggttcagcaa caaccctgcc ctgtgcaacg      720
tggagagcat ccagtggcgg acatagtca gcagtgactt tctcagcaac atgtcgatgg      780
acttccagaa ccacctgggc agctgccaaa agtgtgatcc aagctgtccc aatgggagct      840
gctggggtgc aggagaggag aactgccaga aactgaccaa aatcatctgt gcccagcagt      900
gctccgggcg ctgccgtggc aagtccccca gtgactgctg ccacaaccag tgtgctgcag      960
gctgcacagg ccccgggag agcgactgcc tggtctgccg caaattccga gacgaagcca     1020
cgtgcaagga cacctgcccc ccactcatgc tctacaaccc caccacgtac cagatggatg     1080
tgaaccccga gggcaaatac agctttggtg ccacctgcgt gaagaagtgt ccccgtaatt     1140
atgtggtgac agatcacggc tcgtgcgtcc gagcctgtgg ggccgacagc tatgagatgg     1200
aggaagacgc cgtccgcaag tgtaagaagt gcgaagggcc ttgccgcaaa gtgtgtaacg     1260
gaataggtat tggtgaattt aaagactcac tctccataaa tgctacgaat attaaacact     1320
tcaaaaactg cacctccatc agtggcgatc tccacatcct gccggtggca tttaggggtg     1380
actccttcac acatactcct cctctggatc cacaggaact ggatattctg aaaaccgtaa     1440
aggaaatcac agggttttg ctgattcagg cttggcctga aaacaggacg gacctccatg     1500
cctttgagaa cctagaaatc atacgcggca ggaccaagca acatggtcag ttttctcttg     1560
cagtcgtcag cctgaacata acatccttgg gattacgctc cctcaaggag ataagtgatg     1620
gagatgtgat aattttcagga aacaaaaatt tgtgctatgc aaatacaata aactggaaaa     1680 aactgttttgg gacctccggt cagaaaacca aaattataag caacagaggt gaaaacagct     1740
gcaaggccac aggccaggtc tgccatgcct tgtgctcccc cgagggctgc tggggcccgg     1800
agcccaggga ctgcgtctct tgccggaatg tcagccgagg cagggaatgc gtggacaagt     1860
gcaaccttct ggagggtgag ccaagggagt ttgtggagaa ctctgagtgc atacagtgcc     1920
acccagagtg cctgcctcag gccatgaaca tcacctgcac aggacgggga ccagacaact     1980
gtatccagtg tgcccactac attgacggcc cccactgcgt caagacctgc ccggcaggag     2040
tcatgggaga aaacaacacc ctggtctgga agtacgcaga cgccggccat gtgtgccacc     2100
tgtgccatcc aaactgcacc tacgatgca ctgggccagg tcttgaaggc tgtccaacga     2160
atgggcctaa gatcccgtcc atcgccactg gatggtggg ggcctcctc ttgctgctgg     2220 tggtggccct ggggatcggc ctcttcatgc gaaggcgcca catcgttcgg aagcgcacgc     2280
tgcggaggct gctgcaggag agggagcttg tggagcctct tacacccagt ggagaagctc     2340
ccaaccaagc tctcttgagg atcttgaagg aaactgaatt caaaaagatc aaagtgctgg     2400
gctccggtgc gttcggcacg gtgtataagg actctggat cccagaaggt gagaaagtta     2460
aaattcccgt cgctatcaaa acatctccga aagccaacaa ggaaatcctc gatgaagcct     2520
acgtgatggc cagcgtggac aaccccacg tgtgccgcct gctgggcatc tgcctcacct     2580
ccaccgtgca gctcatcacg cagctcatgc ccttcggctg cctcctggac tatgtccggg     2640
aacacaaaga caatattggc tcccagtacc tgctcaactg tgtgtgcag atcgcaaagg     2700 gcatgaacta cttggaggac gtcgcttgg tgcaccgcga cctggcagcc aggaacgtac     2760
tggtgaaaac accgcagcat gtcaagatca cagattttgg gctggccaaa ctgctgggtg     2820
cggaagagaa agaataccat gcagaaggag gcaaagtgcc tatcaagtgg atggcattgg     2880
```

-continued

| | |
|---|---|
| aatcaattttt acacagaatc tatacccacc agagtgatgt ctggagctac ggggtgactg | 2940 |
| tttgggagtt gatgaccttt ggatccaagc catatgacgg aatccctgcc agcgagatct | 3000 |
| cctccatcct ggagaaagga gaacgcctcc ctcagccacc catatgtacc atcgatgtct | 3060 |
| acatgatcat ggtcaagtgc tggatgatag acgcagatag tcgcccaaag ttccgtgagt | 3120 |
| tgatcatcga attctccaaa atggcccgag accccagcg ctaccttgtc attcaggggg | 3180 |
| atgaaagaat gcatttgcca agtcctacag actccaactt ctaccgtgcc ctgatggatg | 3240 |
| aagaagacat ggacgacgtg gtggatgccg acgagtacct catcccacag cagggcttct | 3300 |
| tcagcagccc ctccacgtca cggactcccc tcctgagctc tctgagtgca accagcaaca | 3360 |
| attccaccgt ggcttgcatt gatagaaatg ggctgcaaag ctgtcccatc aaggaagaca | 3420 |
| gcttcttgca gcgatacagc tcagacccca caggcgcctt gactgaggac agcatagacg | 3480 |
| acaccttcct cccagtgcct gaatacataa accagtccgt tcccaaaagg cccgctggct | 3540 |
| ctgtgcagaa tcctgtctat cacaatcagc ctctgaaccc cgcgcccagc agagacccac | 3600 |
| actaccagga ccccacagc actgcagtgg gcaacccga gtatctcaac actgtccagc | 3660 |
| ccacctgtgt caacagcaca ttcgacagcc ctgcccactg ggcccagaaa ggcagccacc | 3720 |
| aaattagcct ggacaaccct gactaccagc aggacttctt tcccaaggaa gccaagccaa | 3780 |
| atggcatctt taagggctcc acagctgaaa atgcagaata cctaagggtc gcgccacaaa | 3840 |
| gcagtgaatt tattgggagca tga | 3863 |

<210> SEQ ID NO 743
<211> LENGTH: 3863
<212> TYPE: DNA
<213> ORGANISM: Homo sapiens

<400> SEQUENCE: 743

| | |
|---|---|
| cccggcgcag cgcggccgca gcagcctccg ccccccgcac ggtgtgagcg cccgacgcgg | 60 |
| ccgaggcggc cggagtcccg agctagcccc ggcggccgcc gccgcccaga ccggacgaca | 120 |
| ggccacctcg tcggcgtccg cccgagtccc cgcctcgccg ccaacgccac aaccaccgcg | 180 |
| cacgccccc tgactccgtc cagtattgat cgggagagcc ggagcgagct cttcggggag | 240 |
| cagcgatgcg accctccggg acggccgggg cagcgctcct ggcgctgctg gctgcgctct | 300 |
| gcccggcgag tcgggctctg gaggaaaaga aagtttgcca aggcacgagt aacaagctca | 360 |
| cgcagttggg cacttttgaa gatcattttc tcagcctcca gaggatgttc aataactgtg | 420 |
| aggtggtcct tgggaatttg gaaattacct atgtgcagag gaattatgat ctttccttct | 480 |
| taaagaccat ccaggaggtg gctggttatg tcctcattgc cctcaacaca gtggagcgaa | 540 |
| ttccttgga aaacctgcag atcatcagag gaaatatgta ctacgaaaat tcctatgcct | 600 |
| tagcagtctt atctaactat gatgcaaata aaaccggact gaaggagctg cccatgagaa | 660 |
| atttacagga atcctgcat ggcgccgtgc ggttcagcaa caaccctgcc ctgtgcaacg | 720 |
| tggagagcat ccagtggcgg gacatagtca gcagtgactt tctcagcaac atgtcgatgg | 780 |
| acttccagaa ccacctgggc agctgccaaa agtgtgatcc aagctgtccc aatgggagct | 840 |
| gctgggggtgc aggagaggag aactgccaga aactgaccaa aatcatctgt gcccagcagt | 900 |
| gctcggggcg ctgccgtggc aagtccccca gtgactgctg ccacaaccag tgtgctgcag | 960 |
| gctgcacagg ccccggggag agcgactgcc tggtctgccg caaattccga gacgaagcca | 1020 |
| cgtgcaagga cacctgcccc ccactcatgc tctacaaccc caccacgtac cagatggatg | 1080 |
| tgaaccccga gggcaaatac agctttggtg ccacctgcgt gaagaagtgt ccccgtaatt | 1140 |

```
atgtggtgac agatcacggc tcgtgcgtcc gagcctgtgg ggccgacagc tatgagatgg    1200
aggaagacgg cgtccgcaag tgtaagaagt gcgaagggcc ttgccgcaaa gtgtgtaacg    1260
gaataggtat tggtgaattt aaagactcac tctccataaa tgctacgaat attaaacact    1320
tcaaaaactg cacctccatc agtggcgatc tccacatcct gccggtggca tttaggggtg    1380
actccttcac acatactcct cctctggatc cacaggaact ggatattctg aaaaccgtaa    1440
aggaaatcac agggtttttg ctgattcagg cttggcctga aaacaggacg gacctccatg    1500
cctttgagaa cctagaaatc atacgcggca ggaccaagca acatggtcag ttttctcttg    1560
cagtcgtcag cctgaacata acatccttgg gattacgctc cctcaaggag ataagtgatg    1620
gagatgtgat aatttcagga aacaaaaatt tgtgctatgc aaatacaata aactggaaaa    1680
aactgtttgg gacctccggt cagaaaacca aaattataag caacagaggt gaaaacagct    1740
gcaaggccac aggccaggtc tgccatgcct tgtgctcccc cgagggctgc tggggcccgg    1800
agcccaggga ctgcgtctct tgccggaatg tcagccgagg cagggaatgc gtggacaagt    1860
gcaaccttct ggagggtgag ccaagggagt ttgtggagaa ctctgagtgc atacagtgcc    1920
acccagagtg cctgcctcag gccatgaaca tcacctgcac aggacgggga ccagacaact    1980
gtatccagtg tgcccactac attgacggcc cccactgcgt caagacctgc ccggcaggag    2040
tcatgggaga aaacaacacc ctggtctgga agtacgcaga cgccggccat gtgtgccacc    2100
tgtgccatcc aaactgcacc tacgatgca ctgggccagg tcttgaaggc tgtccaacga    2160
atgggcctaa gatcccgtcc atcgccactg ggatggtggg ggccctcctc ttgctgctgg    2220
tggtggccct ggggatcggc ctcttcatgc gaaggcgcca catcgttcgg aagcgcacgc    2280
tgcggaggct gctgcaggag agggagcttg tggagcctct tacacccagt ggagaagctc    2340
ccaaccaagc tctcttgagg atcttgaagg aaactgaatt caaaaagatc aaagtgctgg    2400
gctccggtgc gttcggcacg gtgtataagg gactctggat cccagaaggt gagaaagtta    2460
aaattcccgt cgctatcaaa acatctccga agccaacaa ggaaatcctc gatgaagcct    2520
acgtgatggc cagcgtggac aaccccacg tgtgccgcct gctgggcatc tgcctcacct    2580
ccaccgtgca gctcatcacg cagctcatgc ccttcggctg cctcctggac tatgtccggg    2640
aacacaaaga caatattggc tcccagtacc tgctcaactg gtgtgtgcag atcgcaaagg    2700
gcatgaacta cttggaggac gtcgcttgg tgcaccgcga cctggcagcc aggaacgtac    2760
tggtgaaaac accgcagcat gtcaagatca cagattttgg gctggccaaa ctgctgggtg    2820
cggaagagaa agaataccat gcagaaggag gcaaagtgcc tatcaagtgg atggcattgg    2880
aatcaatttt acacagaatc tatacccacc agagtgatgt ctggagctac ggggtgactg    2940
tttgggagtt gatgacctt ggatccaagc catatgacgg aatccctgcc agcgagatct    3000
cctccatcct ggagaaagga gaacgcctcc ctcagccacc catatgtacc atcgatgtct    3060
acatgatcat ggtcaagtgc tggatgatag acgcagatag tcgcccaaag ttccgtgagt    3120
tgatcatcga attctccaaa atggcccgag accccagcg ctaccttgtc attcaggggg    3180
atgaaagaat gcatttgcca agtcctacag actccaactt ctaccgtgcc ctgatggatg    3240
aagaagacat ggacgacgtg gtggatgccg acgagtacct catcccacag cagggcttct    3300
tcagcagccc ctccacgtca cggactcccc tcctgagctc tctgagtgca accagcaaca    3360
attccaccgt ggcttgcatt gatagaaatg ggctgcaaag ctgtcccatc aaggaagaca    3420
gcttcttgca gcgatacagc tcagacccca caggcgcctt gactgaggac agcatagacg    3480
```

| | |
|---|---|
| acaccttcct cccagtgcct gaatacataa accagtccgt tcccaaaagg cccgctggct | 3540 |
| ctgtgcagaa tcctgtctat cacaatcagc ctctgaaccc cgcgcccagc agagacccac | 3600 |
| actaccagga cccccacagc actgcagtgg gcaaccccga gtatctcaac actgtccagc | 3660 |
| ccacctgtgt caacagcaca ttcgacagcc ctgcccactg ggcccagaaa ggcagccacc | 3720 |
| aaattagcct ggacaaccct gactaccagc aggacttctt tcccaaggaa gccaagccaa | 3780 |
| atggcatctt taagggctcc acagctgaaa atgcagaata cctaagggtc gcgccacaaa | 3840 |
| gcagtgaatt tattggagca tga | 3863 |

<210> SEQ ID NO 744
<211> LENGTH: 3863
<212> TYPE: DNA
<213> ORGANISM: Homo sapiens

<400> SEQUENCE: 744

| | |
|---|---|
| cccggcgcag cgcggccgca gcagcctccg ccccccgcac ggtgtgagcg cccgacgcgg | 60 |
| ccgaggcggc cggagtcccg agctagcccc ggcggccgcc gccgcccaga ccggacgaca | 120 |
| ggccacctcg tcggcgtccg cccgagtccc cgcctcgccg ccaacgccac aaccaccgcg | 180 |
| cacggccccc tgactccgtc cagtattgat cgggagagcc ggagcgagct cttcggggag | 240 |
| cagcgatgcg accctccggg acggccgggg cagcgctcct ggcgctgctg gctgcgctct | 300 |
| gcccggcgag tcgggctctg gaggaaaaga agtttgccca aggcacgagt aacaagctca | 360 |
| cgcagttggg cacttttgaa gatcattttc tcagcctcca gaggatgttc aataactgtg | 420 |
| aggtggtcct tgggaatttg gaaattacct atgtgcagag gaattatgat ctttccttct | 480 |
| taaagaccat ccaggaggtg gctggttatg tcctcattgc cctcaacaca gtggagcgaa | 540 |
| ttcctttgga aaacctgcag atcatcagag gaaatatgta ctacgaaaat tcctatgcct | 600 |
| tagcagtctt atctaactat gatgcaaata aaaccggact gaaggagctg cccatgagaa | 660 |
| atttacagga atcctgcat ggcgccgtgc ggttcagcaa caaccctgcc ctgtgcaacg | 720 |
| tggagagcat ccagtggcgg gacatagtca gcagtgactt tctcagcaac atgtcgatgg | 780 |
| acttccagaa ccacctgggc agctgccaaa agtgtgatcc aagctgtccc aatgggagct | 840 |
| gctggggtgc aggagaggag aactgccaga aactgaccaa aatcatctgt gcccagcagt | 900 |
| gctccgggcg ctgccgtggc aagtccccca gtgactgctg ccacaaccag tgtgctgcag | 960 |
| gctgcacagg ccccgggag agcgactgcc tggtctgccg caaattccga gacgaagcca | 1020 |
| cgtgcaagga cacctgcccc ccactcatgc tctacaaccc caccacgtac cagatggatg | 1080 |
| tgaaccccga gggcaaatac agctttggtg ccacctgcgt gaagaagtgt ccccgtaatt | 1140 |
| atgtggtgac agatcacggc tcgtgcgtcc gagcctgtgg ggccgacagc tatgagatgg | 1200 |
| aggaagacgg cgtccgcaag tgtaagaagt gcgaagggcc ttgccgcaaa gtgtgtaacg | 1260 |
| gaataggtat tggtgaattt aaagactcac tctccataaa tgctacgaat attaaacact | 1320 |
| tcaaaaactg cacctccatc agtggcgatc tccacatcct gccggtggca tttagggtg | 1380 |
| actccttcac acatactcct cctctggatc cacaggaact ggatattctg aaaaccgtaa | 1440 |
| aggaaatcac agggttttg ctgattcagg cttggcctga aaacaggacg gacctccatg | 1500 |
| cctttgagaa cctagaaatc atacgcggca ggaccaagca acatggtcag ttttctcttg | 1560 |
| cagtcgtcag cctgaacata acatccttgg gattacgctc cctcaaggag ataagtgatg | 1620 |
| gagatgtgat aatttcagga aacaaaaatt tgtgctatgc aaatacaata aactggaaaa | 1680 |
| aactgtttgg gacctccggt cagaaaacca aaattataag caacagaggt gaaaacagct | 1740 |

```
gcaaggccac aggccaggtc tgccatgcct tgtgctcccc cgagggctgc tggggcccgg    1800
agcccaggga ctgcgtctct tgccggaatg tcagccgagg cagggaatgc gtggacaagt    1860
gcaaccttct ggagggtgag ccaagggagt ttgtggagaa ctctgagtgc atacagtgcc    1920
acccagagtg cctgcctcag gccatgaaca tcacctgcac aggacgggga ccagacaact    1980
gtatccagtg tgcccactac attgacggcc ccactgcgt caagacctgc ccggcaggag     2040
tcatgggaga aaacaacacc ctggtctgga agtacgcaga cgccggccat gtgtgccacc    2100
tgtgccatcc aaactgcacc tacggatgca ctgggccagg tcttgaaggc tgtccaacga    2160
atgggcctaa gatcccgtcc atcgccactg ggatggtggg ggccctcctc ttgctgctgg    2220
tggtggccct ggggatcggc ctcttcatgc gaaggcgcca catcgttcgg aagcgcacgc    2280 tgcgaggct gctgcaggag agggagcttg tggagcctct tacacccagt ggagaagctc     2340
ccaaccaagc tctcttgagg atcttgaagg aaactgaatt caaaaagatc aaagtgctgg    2400
gctccggtgc gttcggcacg gtgtataagg actctggat cccagaaggt gagaaagtta     2460
aaattcccgt cgctatcaaa acatctccga agccaacaa ggaaatcctc gatgaagcct     2520
acgtgatggc cagcgtggac aacccccacg tgtgccgcct gctgggcatc tgcctcacct    2580
ccaccgtgca gctcatcacg cagctcatgc ccttcggctg cctcctggac tatgtccggg    2640
aacacaaaga caatattggc tcccagtacc tgctcaactg gtgtgtgcag atcgcaaagg    2700
gcatgaacta cttggaggac cgtcgcttgg tgcaccgcga cctggcagcc aggaacgtac    2760
tggtgaaaac accgcagcat gtcaagatca cagattttgg gctggccaaa ctgctgggtg    2820
cggaagagaa agaataccat gcagaaggag gcaaagtgcc tatcaagtgg atggcattgg    2880
aatcaatttt acacagaatc tatacccacc agagtgatgt ctggagctac ggggtgactg    2940
tttgggagtt gatgaccttt ggatccaagc catatgacgg aatccctgcc agcgagatct    3000
cctccatcct ggagaaagga gaacgcctcc ctcagccacc catatgtacc atcgatgtct    3060
acatgatcat ggtcaagtgc tggatgatag acgcagatag tcgcccaaag ttccgtgagt    3120
tgatcatcga attctccaaa atgggcccgag acccccagcg ctaccttgtc attcaggggg    3180
atgaaagaat gcatttgcca agtcctacag actccaactt ctaccgtgcc ctgatggatg    3240
aagaagacat ggacgacgtg gtggatgccg acgagtacct catcccacag cagggcttct    3300
tcagcagccc ctccacgtca cggactcccc tcctgagctc tctgagtgca accagcaaca    3360
attccaccgt ggcttgcatt gatagaaatg ggctgcaaag ctgtcccatc aaggaagaca    3420
gcttcttgca gcgatacagc tcagacccca caggcgcctt gactgaggac agcatagacg    3480
acaccttcct cccagtgcct gaatacataa accagtccgt tcccaaaagg cccgctggct    3540
ctgtgcagaa tcctgtctat cacaatcagc ctctgaaccc cgcgcccagc agagaccac    3600 actaccagga cccccacagc actgcagtgg gcaaccccga gtatctcaac actgtccagc    3660
ccacctgtgt caacagcaca ttcgacagcc ctgcccactg ggcccagaaa ggcagccacc    3720
aaattagcct ggacaaccct gactaccagc aggacttctt tcccaaggaa gccaagccaa    3780
atggcatctt taagggctcc acagctgaaa atgcagaata cctaagggtc gcgccacaaa    3840
gcagtgaatt tattggagca tga                                           3863

<210> SEQ ID NO 745
<211> LENGTH: 3863
<212> TYPE: DNA
<213> ORGANISM: Homo sapiens
```

<400> SEQUENCE: 745

```
cccggcgcag cgcggccgca gcagcctccg cccccgcac ggtgtgagcg cccgacgcgg      60
ccgaggcggc cggagtcccg agctagcccc ggcggccgcc gccgcccaga ccggacgaca     120
ggccacctcg tcggcgtccg cccgagtccc cgcctcgccg ccaacgccac aaccaccgcg     180
cacggccccc tgactccgtc cagtattgat cgggagagcc ggagcgagct cttcggggag     240
cagcgatgcg accctccggg acggccgggg cagcgctcct ggcgctgctg gctgcgctct     300
gcccggcgag tcgggctctg gaggaaaaga aagtttgcca aggcacgagt aacaagctca     360
cgcagttggg cacttttgaa gatcattttc tcagcctcca gaggatgttc aataactgtg     420
aggtggtcct tgggaatttg gaaattacct atgtgcagag gaattatgat cttccttct      480
taaagaccat ccaggaggtg gctggttatg tcctcattgc cctcaacaca gtggagcgaa     540
ttcctttgga aaacctgcag atcatcagag gaaatatgta ctacgaaaat tcctatgcct     600
tagcagtctt atctaactat gatgcaaata aaaccggact gaaggagctg cccatgagaa     660
atttacagga atcctgcat ggcgccgtgc ggttcagcaa caaccctgcc ctgtgcaacg      720
tggagagcat ccagtggcgg gacatagtca gcagtgactt tctcagcaac atgtcgatgg    780
acttccagaa ccacctgggc agctgccaaa agtgtgatcc aagctgtccc aatgggagct    840
gctgggggtgc aggagaggag aactgccaga aactgaccaa aatcatctgt gcccagcagt    900
gctccgggcg ctgccgtggc aagtccccca gtgactgctg ccacaaccag tgtgctgcag    960
gctgcacagg ccccgggag agcgactgcc tggtctgccg caaattccga gacgaagcca    1020
cgtgcaagga cacctgcccc ccactcatgc tctacaaccc caccacgtac cagatggatg    1080
tgaaccccga gggcaaatac agctttggtg ccacctgcgt gaagaagtgt ccccgtaatt    1140
atgtggtgac agatcacggc tcgtgcgtcc gagcctgtgg ggccgacagc tatgagatgg    1200
aggaagacgg cgtccgcaag tgtaagaagt gcgaagggcc ttgccgcaaa gtgtgtaacg    1260
gaataggtat tggtgaattt aaagactcac tctccataaa tgctacgaat attaaacact    1320
tcaaaaactg cacctccatc agtggcgatc tccacatcct gccggtggca tttaggggtg    1380
actccttcac acatactcct cctctggatc cacaggaact ggatattctg aaaaccgtaa    1440
aggaaatcac agggttttg ctgattcagg cttggcctga aaacaggacg gacctccatg    1500
cctttgagaa cctagaaatc atacgcggca ggaccaagca acatggtcag ttttctcttg    1560
cagtcgtcag cctgaacata acatccttgg gattacgctc cctcaaggag ataagtgatg    1620
gagatgtgat aatttcagga aacaaaaatt tgtgctatgc aaatacaata aactggaaaa    1680
aactgtttgg gacctccggt cagaaaacca aaattataag caacagaggt gaaaacagct    1740
gcaaggccac aggccaggtc tgccatgcct tgtgctcccc cgagggctgc tggggccgg     1800
agcccaggga ctgcgtctct tgccggaatg tcagccgagg cagggaatgc gtggacaagt    1860
gcaaccttct ggagggtgag ccaagggagt tgtggagaa ctctgagtgc atacagtgcc    1920
acccagagtg cctgcctcag gccatgaaca tcacctgcac aggacgggga ccagacaact    1980
gtatccagtg tgcccactac attgacggcc cccactgcgt caagacctgc ccggcaggag    2040
tcatgggaga aaacaacacc ctggtctgga agtacgcaga cgccggccat gtgtgccacc    2100
tgtgccatcc aaactgcacc tacggatgca ctgggccagg tcttgaaggc tgtccaacga    2160
atgggcctaa gatcccgtcc atcgccactg gatggtggg ggccctcctc ttgctgctgg     2220
tggtggccct gggatcggc ctcttcatgc gaaggcgcca catcgttcgg aagcgcacgc     2280
tgcggaggct gctgcaggag agggagcttg tggagcctct tacacccagt ggagaagctc    2340
```

| | |
|---|---|
| ccaaccaagc tctcttgagg atcttgaagg aaactgaatt caaaaagatc aaagtgctgg | 2400 |
| gctccggtgc gttcggcacg gtgtataagg actctggat cccagaaggt gagaaagtta | 2460 |
| aaattcccgt cgctatcaaa acatctccga aagccaacaa ggaaatcctc gatgaagcct | 2520 |
| acgtgatggc cagcgtggac aaccccacg tgtgccgcct gctgggcatc tgcctcacct | 2580 |
| ccaccgtgca gctcatcacg cagctcatgc ccttcggctg cctcctggac tatgtccggg | 2640 |
| aacacaaaga caatattggc tcccagtacc tgctcaactg tgtgtgcag atcgcaaagg | 2700 |
| gcatgaacta cttggaggac cgtcgcttgg tgcaccgcga cctggcagcc aggaacgtac | 2760 |
| tggtgaaaac accgcagcat gtcaagatca cagattttgg gctggccaaa ctgctgggtg | 2820 |
| cggaagagaa agaataccat gcagaaggag gcaaagtgcc tatcaagtgg atggcattgg | 2880 |
| aatcaatttt acacagaatc tatacccacc agagtgatgt ctggagctac ggggtgactg | 2940 |
| tttgggagtt gatgaccttt ggatccaagc catatgacgg aatccctgcc agcgagatct | 3000 |
| cctccatcct ggagaaagga gaacgcctcc ctcagccacc catatgtacc atcgatgtct | 3060 |
| acatgatcat ggtcaagtgc tggatgatag acgcagatag tcgcccaaag ttccgtgagt | 3120 |
| tgatcatcga attctccaaa atggcccgag acccccagcg ctaccttgtc attcaggggg | 3180 |
| atgaaagaat gcatttgcca agtcctacag actccaactt ctaccgtgcc ctgatggatg | 3240 |
| aagaagacat ggacgacgtg gtggatgccg acgagtacct catcccacag cagggcttct | 3300 |
| tcagcagccc ctccacgtca cggactcccc tcctgagctc tctgagtgca accagcaaca | 3360 |
| attccaccgt ggcttgcatt gatagaaatg ggctgcaaag ctgtcccatc aaggaagaca | 3420 |
| gcttcttgca gcgatacagc tcagacccca caggcgcctt gactgaggac agcatagacg | 3480 |
| acaccttcct cccagtgcct gaatacataa accagtccgt tcccaaaagg cccgctggct | 3540 |
| ctgtgcagaa tcctgtctat cacaatcagc ctctgaaccc cgcgcccagc agagacccac | 3600 |
| actaccagga cccccacagc actgcagtgg gcaaccccga gtatctcaac actgtccagc | 3660 |
| ccacctgtgt caacagcaca ttcgacagcc ctgcccactg ggcccagaaa ggcagccacc | 3720 |
| aaattagcct ggacaaccct gactaccagc aggacttctt tcccaaggaa gccaagccaa | 3780 |
| atggcatctt taagggctcc acagctgaaa atgcagaata cctaagggtc gcgccacaaa | 3840 |
| gcagtgaatt tattggagca tga | 3863 |

<210> SEQ ID NO 746
<211> LENGTH: 3863
<212> TYPE: DNA
<213> ORGANISM: Homo sapiens

<400> SEQUENCE: 746

| | |
|---|---|
| cccggcgcag cgcggccgca gcagcctccg ccccccgcac ggtgtgagcg cccgacgcgg | 60 |
| ccgaggcggc cggagtcccg agctagcccc ggcggccgcc gccgcccaga ccggacgaca | 120 |
| ggccacctcg tcggcgtccg cccgagtccc cgcctcgccg ccaacgccac aaccaccgcg | 180 |
| cacggccccc tgactccgtc cagtattgat cgggagagcc ggagcgagct cttcggggag | 240 |
| cagcgatgcg accctccggg acggccgggg cagcgctcct ggcgctgctg gctgcgctct | 300 |
| gcccggcgag tcgggctctg gaggaaaaga agtttgccaa aggcacgagt aacaagctca | 360 |
| cgcagttggg cacttttgaa gatcattttc tcagcctcca gaggatgttc aataactgtg | 420 |
| aggtggtcct tggaaatttg gaaattacct atgtgcagag gaattatgat cttccttct | 480 |
| taaagaccat ccaggaggtg gctggttatg tcctcattgc cctcaacaca gtggagcgaa | 540 |

```
ttcctttgga aaacctgcag atcatcagag gaaatatgta ctacgaaaat tcctatgcct    600
tagcagtctt atctaactat gatgcaaata aaaccggact gaaggagctg cccatgagaa    660
atttacagga atcctgcat ggcgccgtgc ggttcagcaa caaccctgcc ctgtgcaacg     720
tggagagcat ccagtggcgg gacatagtca gcagtgactt tctcagcaac atgtcgatgg    780
acttccagaa ccacctgggc agctgccaaa agtgtgatcc aagctgtccc aatgggagct    840
gctggggtgc aggagaggag aactgccaga aactgaccaa aatcatctgt gcccagcagt    900
gctccgggcg ctgccgtggc aagtccccca gtgactgctg ccacaaccag tgtgctgcag    960
gctgcacagg cccccgggag agcgactgcc tggtctgccg caaattccga dacgaagcca   1020
cgtgcaagga cacctgcccc ccactcatgc tctacaaccc caccacgtac cagatggatg   1080
tgaaccccga gggcaaatac agctttggtg ccacctgcgt gaagaagtgt ccccgtaatt   1140
atgtggtgac agatcacggc tcgtgcgtcc gagcctgtgg ggccgacagc tatgagatgg   1200
aggaagacgg cgtccgcaag tgtaagaagt gcgaagggcc ttgccgcaaa gtgtgtaacg   1260
gaataggtat tggtgaattt aaagactcac tctccataaa tgctacgaat attaaacact   1320
tcaaaaactg cacctccatc agtggcgatc tccacatcct gccggtggca tttaggggtg   1380
actccttcac acatactcct cctctggatc cacaggaact ggatattctg aaaaccgtaa   1440
aggaaatcac agggtttttg ctgattcagg cttggcctga aaacaggacg gacctccatg   1500
cctttgagaa cctagaaatc atacgcggca ggaccaagca acatggtcag ttttctcttg   1560
cagtcgtcag cctgaacata acatccttgg gattacgctc cctcaaggag ataagtgatg   1620
gagatgtgat aatttcagga aacaaaaatt tgtgctatgc aaatacaata aactggaaaa   1680
aactgttggg gacctccggt cagaaaacca aaattataag caacagaggt gaaaacagct   1740
gcaaggccac aggccaggtc tgccatgcct tgtgctcccc cgagggctgc tggggcccgg   1800
agcccaggga ctgcgtctct tgccggaatg tcagccgagg cagggaatgc gtggacaagt   1860
gcaaccttct ggagggtgag ccaagggagt tgtggagaa ctctgagtgc atacagtgcc    1920
acccagagtg cctgcctcag gccatgaaca tcacctgcac aggacgggga ccagacaact   1980
gtatccagtg tgcccactac attgacggcc cccactgcgt caagacctgc ccggcaggag   2040
tcatgggaga aaacaacacc ctggtctgga agtacgcaga cgccggccat gtgtgccacc   2100
tgtgccatcc aaactgcacc tacgatgca ctgggccagg tcttgaaggc tgtccaacga    2160
atgggcctaa gatcccgtcc atcgccactg ggatggtggg ggcctcctc ttgctgctgg    2220
tggtggccct ggggatcggc ctcttcatgc gaaggcgcca catcgttcgg aagcgcacgc   2280
tgcggaggct gctgcaggag agggagcttg tggagcctct acacccagt ggagaagctc    2340
ccaaccaagc tctcttgagg atcttgaagg aaactgaatt caaaaagatc aaagtgctgg   2400
gctccggtgc gttcggcacg gtgtataagg gactctggat cccagaaggt gagaaagtta   2460
aaattcccgt cgctatcaag acatctccga aagccaacaa ggaaatcctc gatgaagcct   2520
acgtgatggc cagcgtggac aaccccccacg tgtgccgcct gctgggcatc tgcctcacct   2580
ccaccgtgca gctcatcacg cagctcatgc ccttcggctg cctcctggac tatgtccggg   2640
aacacaaaga caatattggc tcccagtacc tgctcaactg gtgtgtgcag atcgcaaagg   2700
gcatgaacta cttggaggac gtcgcttgg tgcaccgcga cctggcagcc aggaacgtac    2760
tggtgaaaac accgcagcat gtcaagatca cagattttgg gctggccaaa ctgctgggtg   2820
cggaagagaa agaataccat gcagaaggag gcaaagtgcc tatcaagtgg atggcattgg   2880
aatcaatttt acacagaatc tatacccacc agagtgatgt ctggagctac ggggtgactg   2940
```

```
tttgggagtt gatgaccttt ggatccaagc catatgacgg aatccctgcc agcgagatct    3000
cctccatcct ggagaaagga gaacgcctcc ctcagccacc catatgtacc atcgatgtct    3060
acatgatcat ggtcaagtgc tggatgatag acgcagatag tcgcccaaag ttccgtgagt    3120
tgatcatcga attctccaaa atggcccgag acccccagcg ctaccttgtc attcaggggg    3180
atgaaagaat gcatttgcca agtcctacag actccaactt ctaccgtgcc ctgatggatg    3240
aagaagacat ggacgacgtg gtggatgccg acgagtacct catcccacag cagggcttct    3300
tcagcagccc ctccacgtca cggactcccc tcctgagctc tctgagtgca accagcaaca    3360
attccaccgt ggcttgcatt gatagaaatg ggctgcaaag ctgtcccatc aaggaagaca    3420
gcttcttgca gcgatacagc tcagacccca caggcgcctt gactgaggac agcatagacg    3480
acaccttcct cccagtgcct gaatacataa accagtccgt tcccaaaagg cccgctggct    3540
ctgtgcagaa tcctgtctat cacaatcagc ctctgaaccc cgcgcccagc agagacccac    3600
actaccagga cccccacagc actgcagtgg gcaaccccga gtatctcaac actgtccagc    3660
ccacctgtgt caacagcaca ttcgacagcc ctgcccactg ggcccagaaa ggcagccacc    3720
aaattagcct ggacaaccct gactaccagc aggacttctt tcccaaggaa gccaagccaa    3780
atggcatctt taagggctcc acagctgaaa atgcagaata cctaagggtc gcgccacaaa    3840
gcagtgaatt tattggagca tga                                            3863
```

<210> SEQ ID NO 747
<211> LENGTH: 3863
<212> TYPE: DNA
<213> ORGANISM: Homo sapiens

<400> SEQUENCE: 747

```
cccggcgcag cgcggccgca gcagcctccg ccccccgcac ggtgtgagcg cccgacgcgg      60
ccgaggcggc cggagtcccg agctagcccc ggcggccgcc gccgcccaga ccggacgaca     120
ggccacctcg tcggcgtccg cccgagtccc cgcctcgccg ccaacgccac aaccaccgcg     180
cacggccccc tgactccgtc cagtattgat cgggagagcc ggagcgagct cttcggggag     240
cagcgatgcg accctccggg acggccgggg cagcgctcct ggcgctgctg gctgcgctct     300
gcccggcgag tcgggctctg gaggaaaaga aagtttgcca aggcacgagt aacaagctca     360
cgcagttggg cacttttgaa gatcattttc tcagcctcca gaggatgttc aataactgtg     420
aggtggtcct tggaaatttg gaaattacct atgtgcagag gaattatgat ctttccttct     480
taaagaccat ccaggaggtg gctggttatg tcctcattgc cctcaacaca gtggagcgaa     540
ttcctttgga aaacctgcag atcatcagag gaaatatgta ctacgaaaat tcctatgcct     600
tagcagtctt atctaactat gatgcaaata aaaccggact gaaggagctg cccatgagaa     660
atttacagga atcctgcat ggcgccgtgc ggttcagcaa caaccctgcc ctgtgcaacg     720
tggagagcat ccagtggcgg gacatagtca gcagtgactt tctcagcaac atgtcgatgg     780
acttccagaa ccacctgggc agctgccaaa agtgtgatcc aagctgtccc aatgggagct     840
gctggggtgc aggagaggag aactgccaga aactgaccaa aatcatctgt gcccagcagt     900 gctcgggcg ctgccgtggc aagtccccca gtgactgctg ccacaaccag tgtgctgcag     960
gctgcacagg ccccgggag agcgactgcc tggtctgccg caaattccga gacgaagcca    1020
cgtgcaagga cacctgcccc ccactcatgc tctacaaccc caccacgtac cagatggatg    1080
tgaaccccga gggcaaatac agctttggtg ccacctgcgt gaagaagtgt ccccgtaatt    1140
```

-continued

```
atgtggtgac agatcacggc tcgtgcgtcc gagcctgtgg ggccgacagc tatgagatgg    1200
aggaagacgg cgtccgcaag tgtaagaagt gcgaagggcc ttgccgcaaa gtgtgtaacg    1260
gaataggtat tggtgaattt aaagactcac tctccataaa tgctacgaat attaaacact    1320
tcaaaaactg cacctccatc agtggcgatc tccacatcct gccggtggca tttaggggtg    1380
actccttcac acatactcct cctctggatc cacaggaact ggatattctg aaaaccgtaa    1440
aggaaatcac agggttttg ctgattcagg cttggcctga aaacaggacg gacctccatg    1500
cctttgagaa cctagaaatc atacgcggca ggaccaagca acatggtcag ttttctcttg    1560
cagtcgtcag cctgaacata acatccttgg gattacgctc cctcaaggag ataagtgatg    1620
gagatgtgat aatttcagga aacaaaaatt tgtgctatgc aaatacaata aactggaaaa    1680
aactgtttgg gacctccggt cagaaaacca aaattataag caacagaggt gaaacagct    1740 gcaaggccac aggccaggtc tgccatgcct tgtgctcccc cgagggctgc tggggcccgg    1800
agcccaggga ctgcgtctct tgccggaatg tcagccgagg cagggaatgc gtggacaagt    1860
gcaaccttct ggagggtgag ccaagggagt ttgtggagaa ctctgagtgc atacagtgcc    1920
acccagagtg cctgcctcag gccatgaaca tcacctgcac aggacgggga ccagacaact    1980
gtatccagtg tgcccactac attgacggcc cccactgcgt caagacctgc ccggcaggag    2040
tcatgggaga aaacaacacc tggtctgga agtacgcaga cgccggccat gtgtgccacc    2100
tgtgccatcc aaactgcacc tacgatgca ctggccagg tcttgaaggc tgtccaacga    2160
atgggcctaa gatcccgtcc atcgccactg ggatggtggg ggccctcctc ttgctgctgg    2220
tggtggccct ggggatcggc ctcttcatgc gaaggcgcca catcgttcgg aagcgcacgc    2280
tgcggaggct gctgcaggag agggagcttg tggagcctct tacacccagt ggagaagctc    2340
ccaaccaagc tctcttgagg atcttgaagg aaactgaatt caaaaagatc aaagtgctgg    2400
gctccggtgc gttcggcacg gtgtataagg actctggat cccagaaggt gagaaagtta    2460
aaattcccgt cgctatcaag acatctccga agccaacaa ggaaatcctc gatgaagcct    2520
acgtgatggc cagcgtggac aaccccacg tgtgccgcct gctgggcatc tgcctcacct    2580
ccaccgtgca gctcatcacg cagctcatgc ccttcggctg cctcctggac tatgtccggg    2640
aacacaaaga caatattggc tcccagtacc tgctcaactg gtgtgtgcag atcgcaaagg    2700
gcatgaacta cttggaggac cgtcgcttgg tgcaccgcga cctggcagcc aggaacgtac    2760
tggtgaaaac accgcagcat gtcaagatca cagattttgg gctggccaaa ctgctgggtg    2820
cggaagagaa agaataccat gcagaaggag gcaaagtgcc tatcaagtgg atggcattgg    2880
aatcaatttt acacagaatc tatacccacc agagtgatgt ctggagctac ggggtgactg    2940
tttgggagtt gatgaccttt ggatccaagc catatgacgg aatccctgcc agcgagatct    3000
cctccatcct ggagaaagga gaacgcctcc ctcagccacc catatgtacc atcgatgtct    3060
acatgatcat ggtcaagtgc tggatgatag acgcagatag tcgcccaaag ttccgtgagt    3120
tgatcatcga attctccaaa atggcccgag accccagcg ctaccttgtc attcaggggg    3180
atgaaagaat gcatttgcca agtcctacag actccaactt ctaccgtgcc ctgatggatg    3240
aagaagacat ggacgacgtg gtggatgccg acgagtacct catcccacag cagggcttct    3300
tcagcagccc ctccacgtca cggactcccc tcctgagctc tctgagtgca accagcaaca    3360
attccaccgt ggcttgcatt gatagaaatg ggctgcaaag ctgtcccatc aaggaagaca    3420
gcttcttgca gcgatacagc tcagacccca caggcgcctt gactgaggac agcatagacg    3480
acaccttcct cccagtgcct gaatacataa accagtccgt tcccaaaagg cccgctggct    3540
```

```
ctgtgcagaa tcctgtctat cacaatcagc ctctgaaccc cgcgcccagc agagacccac    3600
actaccagga cccccacagc actgcagtgg gcaaccccga gtatctcaac actgtccagc    3660
ccacctgtgt caacagcaca ttcgacagcc ctgcccactg ggcccagaaa ggcagccacc    3720
aaattagcct ggacaaccct gactaccagc aggacttctt tcccaaggaa gccaagccaa    3780
atggcatctt taagggctcc acagctgaaa atgcagaata cctaagggtc gcgccacaaa    3840
gcagtgaatt tattggagca tga                                            3863
```

<210> SEQ ID NO 748
<211> LENGTH: 3863
<212> TYPE: DNA
<213> ORGANISM: Homo sapiens

<400> SEQUENCE: 748

```
cccggcgcag cgcggccgca gcagcctccg ccccccgcac ggtgtgagcg cccgacgcgg      60
ccgaggcggc cggagtcccg agctagcccc ggcggccgcc gccgcccaga ccggacgaca     120
ggccacctcg tcggcgtccg cccgagtccc cgcctcgccg ccaacgccac aaccaccgcg     180
cacggccccc tgactccgtc cagtattgat cgggagagcc ggagcgagct cttcggggag     240
cagcgatgcg accctccggg acggccgggg cagcgctcct ggcgctgctg gctgcgctct     300
gcccggcgag tcgggctctg gaggaaaaga agtttgccca aggcacgagt aacaagctca     360
cgcagttggg cacttttgaa gatcattttc tcagcctcca gaggatgttc aataactgtg     420
aggtggtcct tgggaatttg gaaattacct atgtgcagag gaattatgat cttttccttct     480 taaagaccat ccaggaggtg gctggttatg tcctcattgc cctcaacaca gtggagcgaa     540
ttcctttgga aaacctgcag atcatcagag gaaatatgta ctacgaaaat tcctatgcct     600
tagcagtctt atctaactat gatgcaaata aaaccggact gaaggagctg cccatgagaa     660
atttacagga atcctgcat ggcgccgtgc ggttcagcaa caaccctgcc ctgtgcaacg     720
tggagagcat ccagtggcgg gacatagtca gcagtgactt tctcagcaac atgtcgatgg     780
acttccagaa ccacctgggc agctgccaaa agtgtgatcc aagctgtccc aatgggagct     840
gctggggtgc aggagaggag aactgccaga aactgaccaa aatcatctgt gcccagcagt     900 gctcccgggcg ctgccgtggc aagtccccca gtgactgctg ccacaaccag tgtgctgcag     960
gctgcacagg ccccccggag agcgactgcc tggtctgccg caaattccga gacgaagcca    1020
cgtgcaagga cacctgcccc ccactcatgc tctacaaccc caccacgtac cagatggatg    1080
tgaaccccga gggcaaatac agctttggtg ccacctgcgt gaagaagtgt ccccgtaatt    1140
atgtggtgac agatcacggc tcgtgcgtcc gagcctgtgg ggccgacagc tatgagatgg    1200
aggaagacgc cgtccgcaag tgtaagaagt gcgaagggcc ttgccgcaaa gtgtgtaacg    1260
gaataggtat tggtgaattt aaagactcac tctccataaa tgctacgaat attaaacact    1320
tcaaaaactg cacctccatc agtggcgatc tccacatcct gccggtggca tttaggggtg    1380
actccttcac acatactcct cctctggatc cacaggaact ggatattctg aaaaccgtaa    1440
aggaaatcac agggtttttg ctgattcagg cttggcctga aaacaggacg gacctccatg    1500
cctttgagaa cctagaaatc atacgcggca ggaccaagca acatggtcag ttttctcttg    1560
cagtcgtcag cctgaacata acatccttgg gattacgctc cctcaaggag ataagtgatg    1620
gagatgtgat aatttcagga aacaaaaatt tgtgctatgc aaatacaata aactggaaaa    1680
aactgtttgg gacctccggt cagaaaacca aaattataag caacagaggt gaaaacagct    1740
```

```
gcaaggccac aggccaggtc tgccatgcct tgtgctcccc cgagggctgc tggggcccgg    1800
agcccaggga ctgcgtctct tgccggaatg tcagccgagg cagggaatgc gtggacaagt    1860
gcaaccttct ggagggtgag ccaagggagt ttgtggagaa ctctgagtgc atacagtgcc    1920
acccagagtg cctgcctcag gccatgaaca tcacctgcac aggacgggga ccagacaact    1980
gtatccagtg tgcccactac attgacggcc cccactgcgt caagacctgc ccggcaggag    2040
tcatgggaga aaacaacacc ctggtctgga agtacgcaga cgccggccat gtgtgccacc    2100
tgtgccatcc aaactgcacc tacgatgca ctgggccagg tcttgaaggc tgtccaacga    2160
atgggcctaa gatcccgtcc atcgccactg ggatggtggg ggccctcctc ttgctgctgg    2220
tggtggccct ggggatcggc ctcttcatgc gaaggcgcca catcgttcgg aagcgcacgc    2280
tgcggaggct gctgcaggag agggagcttg tggagcctct tacacccagt ggagaagctc    2340
ccaaccaagc tctcttgagg atcttgaagg aaactgaatt caaaaagatc aaagtgctgg    2400
gctccggtgc gttcggcacg gtgtataagg gactctggat cccagaaggt gagaaagtta    2460
aaattcccgt cgctatcaag acatctccga aagccaacaa ggaaatcctc gatgaagcct    2520
acgtgatggc cagcgtggac aacccccacg tgtgccgcct gctgggcatc tgcctcacct    2580
ccaccgtgca gctcatcacg cagctcatgc ccttcggctg cctcctggac tatgtccggg    2640
aacacaaaga caatattggc tcccagtacc tgctcaactg gtgtgtgcag atcgcaaagg    2700
gcatgaacta cttggaggac gtcgcttgg tgcaccgcga cctggcagcc aggaacgtac    2760
tggtgaaaac accgcagcat gtcaagatca cagattttgg gctggccaaa ctgctgggtg    2820
cggaagagaa agaataccat gcagaaggag gcaaagtgcc tatcaagtgg atggcattgg    2880
aatcaatttt acacagaatc tatacccacc agagtgatgt ctggagctac ggggtgactg    2940
tttgggagtt gatgaccttt ggatccaagc catatgacgg aatccctgcc agcgagatct    3000
cctccatcct ggagaaagga gaacgcctcc ctcagccacc catatgtacc atcgatgtct    3060
acatgatcat ggtcaagtgc tggatgatag acgcagatag tcgcccaaag ttccgtgagt    3120
tgatcatcga attctccaaa atggcccgag accccagcg ctaccttgtc attcagggg    3180 atgaaagaat gcatttgcca agtcctacag actccaactt ctaccgtgcc ctgatggatg    3240
aagaagacat ggacgacgtg gtggatgccg acgagtacct catcccacag cagggcttct    3300
tcagcagccc ctccacgtca cggactcccc tcctgagctc tctgagtgca accagcaaca    3360
attccaccgt ggcttgcatt gatagaaatg ggctgcaaag ctgtcccatc aaggaagaca    3420
gcttcttgca gcgatacagc tcagaccccca caggcgcctt gactgaggac agcatagacg    3480
acaccttcct cccagtgcct gaatacataa accagtccgt tcccaaaagg cccgctggct    3540
ctgtgcagaa tcctgtctat cacaatcagc ctctgaaccc cgcgcccagc agagacccac    3600
actaccagga cccccacagc actgcagtgg caaccccga gtatctcaac actgtccagc    3660
ccacctgtgt caacagcaca ttcgacagcc ctgcccactg ggcccagaaa ggcagccacc    3720
aaattagcct ggacaaccct gactaccagc aggacttctt tcccaaggaa gccaagccaa    3780
atggcatctt taagggctcc acagctgaaa atgcagaata cctaagggtc gcgccacaaa    3840
gcagtgaatt tattggagca tga                                            3863
```

<210> SEQ ID NO 749
<211> LENGTH: 3860
<212> TYPE: DNA
<213> ORGANISM: Homo sapiens

<400> SEQUENCE: 749

-continued

```
cccggcgcag cgcggccgca gcagcctccg ccccccgcac ggtgtgagcg cccgacgcgg    60
ccgaggcggc cggagtcccg agctagcccc ggcggccgcc gccgcccaga ccggacgaca   120
ggccacctcg tcggcgtccg cccgagtccc cgcctcgccg ccaacgccac aaccaccgcg   180
cacggccccc tgactccgtc cagtattgat cgggagagcc ggagcgagct cttcggggag   240
cagcgatgcg accctccggg acggccgggg cagcgctcct ggcgctgctg gctgcgctct   300
gcccggcgag tcgggctctg gaggaaaaga aagtttgcca aggcacgagt aacaagctca   360
cgcagttggg cacttttgaa gatcattttc tcagcctcca gaggatgttc aataactgtg   420
aggtggtcct tgggaatttg gaaattacct atgtgcagag gaattatgat ctttccttct   480
taaagaccat ccaggaggtg gctggttatg tcctcattgc cctcaacaca gtggagcgaa   540
ttcctttgga aaacctgcag atcatcagag gaaatatgta ctacgaaaat tcctatgcct   600
tagcagtctt atctaactat gatgcaaata aaaccggact gaaggagctg cccatgagaa   660
atttacagga aatcctgcat ggcgccgtgc ggttcagcaa caaccctgcc ctgtgcaacg   720
tggagagcat ccagtggcgg gacatagtca gcagtgactt tctcagcaac atgtcgatgg   780
acttccagaa ccacctgggc agctgccaaa agtgtgatcc aagctgtccc aatgggagct   840
gctggggtgc aggagaggag aactgccaga aactgaccaa aatcatctgt gcccagcagt   900
gctccgggcg ctgccgtggc aagtccccca gtgactgctg ccacaaccag tgtgctgcag   960
gctgcacagg ccccgggag agcgactgcc tggtctgccg caaattccga gacgaagcca  1020
cgtgcaagga cacctgcccc ccactcatgc tctacaaccc caccacgtac cagatggatg  1080
tgaaccccga gggcaaatac agctttggtg ccacctgcgt gaagaagtgt ccccgtaatt  1140
atgtggtgac agatcacggc tcgtgcgtcc gagcctgtgg ggccgacagc tatgagatgg  1200
aggaagacgg cgtccgcaag tgtaagaagt gcgaagggcc ttgccgcaaa gtgtgtaacg  1260
gaataggtat tggtgaattt aaagactcac tctccataaa tgctacgaat attaaacact  1320
tcaaaaactg cacctccatc agtggcgatc tccacatcct gccggtggca tttagggggtg  1380 actccttcac acatactcct cctctggatc cacaggaact ggatattctg aaaaccgtaa  1440
aggaaatcac agggtttttg ctgattcagg cttggcctga aaacaggacg gacctccatg  1500
cctttgagaa cctagaaatc atacgcggca ggaccaagca acatggtcag ttttctcttg  1560
cagtcgtcag cctgaacata acatccttgg gattacgctc cctcaaggag ataagtgatg  1620
gagatgtgat aatttcagga aacaaaaatt tgtgctatgc aaatacaata aactggaaaa  1680
aactgtttgg gacctccggt cagaaaacca aaattataag caacagaggt gaaaacagct  1740
gcaaggccac aggccaggtc tgccatgcct tgtgctcccc cgagggctgc tggggcccgg  1800
agcccaggga ctgcgtctct tgccggaatg tcagccgagg cagggaatgc gtggacaagt  1860
gcaaccttct ggagggtgag ccaagggagt tgtggagaa ctctgagtgc atacagtgcc  1920
acccagagtg cctgcctcag gccatgaaca tcacctgcac aggacgggga ccagacaact  1980
gtatccagtg tgcccactac attgacggcc cccactgcgt caagacctgc ccggcaggag  2040
tcatgggaga aaacaacacc ctggtctgga agtacgcaga cgccggccat gtgtgccacc  2100
tgtgccatcc aaactgcacc tacgatgca ctgggccagg tcttgaaggc tgtccaacga  2160
atgggcctaa gatcccgtcc atcgccactg ggatggtggg ggccctcctc ttgctgctgg  2220
tggtggccct ggggatcggc ctcttcatgc gaaggcgcca catcgttcgg aagcgcacgc  2280
tgcggaggct gctgcaggag agggagcttg tggagcctct tacacccagt ggagaagctc  2340
```

```
ccaaccaagc tctcttgagg atcttgaagg aaactgaatt caaaaagatc aaagtgctgg    2400
gctccggtgc gttcggcacg gtgtataagg gactctggat cccagaaggt gagaaagtta    2460
aaattcccgt cgctatcaag gttccgaaag ccaacaagga aatcctcgat gaagcctacg    2520
tgatggccag cgtggacaac ccccacgtgt gccgcctgct gggcatctgc ctcacctcca    2580
ccgtgcagct catcacgcag ctcatgccct tcggctgcct cctggactat gtccgggaac    2640
acaaagacaa tattggctcc cagtacctgc tcaactggtg tgtgcagatc gcaagggca    2700
tgaactactt ggaggaccgt cgcttggtgc accgcgacct ggcagccagg aacgtactgg    2760
tgaaaacacc gcagcatgtc aagatcacag attttgggct ggccaaactg ctgggtgcgg    2820
aagagaaaga ataccatgca gaaggaggca aagtgcctat caagtggatg gcattggaat    2880
caattttaca cagaatctat acccaccaga gtgatgtctg gagctacggg gtgactgttt    2940
gggagttgat gacctttgga tccaagccat atgacggaat ccctgccagc gagatctcct    3000
ccatcctgga gaaggagaa cgcctccctc agccacccat atgtaccatc gatgtctaca    3060
tgatcatggt caagtgctgg atgatagacg cagatagtcg cccaaagttc cgtgagttga    3120
tcatcgaatt ctccaaaatg gcccgagacc cccagcgcta ccttgtcatt caggggatg    3180
aaagaatgca tttgccaagt cctacagact ccaacttcta ccgtgccctg atggatgaag    3240
aagacatgga cgacgtggtg gatgccgacg agtacctcat cccacagcag ggcttcttca    3300
gcagcccctc cacgtcacgg actcccctcc tgagctctct gagtgcaacc agcaacaatt    3360
ccaccgtggc ttgcattgat agaaatgggc tgcaaagctg tcccatcaag gaagacagct    3420
tcttgcagcg atacagctca gaccccacag gcgccttgac tgaggacagc atagacgaca    3480
ccttcctccc agtgcctgaa tacataaacc agtccgttcc caaaaggccc gctggctctg    3540
tgcagaatcc tgtctatcac aatcagcctc tgaaccccgc gcccagcaga gacccacact    3600
accaggaccc ccacagcact gcagtgggca ccccgagta tctcaacact gtccagccca    3660
cctgtgtcaa cagcacattc gacagccctg cccactgggc ccagaaaggc agccaccaaa    3720
ttagcctgga caaccctgac taccagcagg acttcttttcc caaggaagcc aagccaaatg    3780
gcatctttaa gggctccaca gctgaaaatg cagaatacct aagggtcgcg ccacaaagca    3840
gtgaatttat tggagcatga                                              3860
```

<210> SEQ ID NO 750
<211> LENGTH: 3869
<212> TYPE: DNA
<213> ORGANISM: Homo sapiens

<400> SEQUENCE: 750

```
cccggcgcag cgcggccgca gcagcctccg cccccccgcac ggtgtgagcg cccgacgcgg    60
ccgaggcggc cggagtcccg agctagcccc ggcggccgcc gccgcccaga ccggacgaca   120
ggccacctcg tcggcgtccg cccgagtccc cgcctcgccg ccaacgccac aaccaccgcg   180
cacggccccc tgactccgtc cagtattgat cgggagagcc ggagcgagct cttcggggag   240
cagcgatgcg accctccggg acggccgggg cagcgctcct ggcgctgctg ctgcgctct   300
gcccggcgag tcgggctctg gaggaaaaga aagtttgcca aggcacgagt aacaagctca   360
cgcagttggg cactttgaa gatcatttc tcagcctcca gaggatgttc aataactgtg   420
aggtggtcct tgggaatttg gaaattacct atgtgcagag gaattatgat ctttccttct   480
taaagaccat ccaggaggtg gctggttatg tcctcattgc cctcaacaca gtggagcgaa   540
ttcctttgga aaacctgcag atcatcagag gaaatatgta ctacgaaaat tcctatgcct   600
```

```
tagcagtctt atctaactat gatgcaaata aaaccggact gaaggagctg cccatgagaa    660
atttacagga aatcctgcat ggcgccgtgc ggttcagcaa caaccctgcc ctgtgcaacg    720
tggagagcat ccagtggcgg gacatagtca gcagtgactt tctcagcaac atgtcgatgg    780
acttccagaa ccacctgggc agctgccaaa agtgtgatcc aagctgtccc aatgggagct    840
gctggggtgc aggagaggag aactgccaga aactgaccaa aatcatctgt gcccagcagt    900
gctccgggcg ctgccgtggc aagtccccca gtgactgctg ccacaaccag tgtgctgcag    960
gctgcacagg cccccgggag agcgactgcc tggtctgccg caaattccga gacgaagcca   1020
cgtgcaagga cacctgcccc ccactcatgc tctacaaccc caccacgtac agatggatg    1080 tgaaccccga gggcaaatac agctttggtg ccacctgcgt gaagaagtgt ccccgtaatt   1140
atgtggtgac agatcacggc tcgtgcgtcc gagcctgtgg ggccgacagc tatgagatgg   1200
aggaagacgg cgtccgcaag tgtaagaagt gcgaagggcc ttgccgcaaa gtgtgtaacg   1260
gaataggtat tggtgaattt aaagactcac tctccataaa tgctacgaat attaaacact   1320
tcaaaaactg cacctccatc agtggcgatc tccacatcct gccggtggca tttaggggtg   1380
actccttcac acatactcct cctctggatc cacaggaact ggatattctg aaaaccgtaa   1440
aggaaatcac agggtttttg ctgattcagg cttggcctga aaacaggacg gacctccatg   1500
cctttgagaa cctagaaatc atacgcggca ggaccaagca acatggtcag ttttctcttg   1560
cagtcgtcag cctgaacata acatccttgg gattacgctc cctcaaggag ataagtgatg   1620
gagatgtgat aatttcagga aacaaaaatt tgtgctatgc aaatacaata aactggaaaa   1680
aactgtttgg gacctccggt cagaaaacca aaattataag caacagaggt gaaaacagct   1740
gcaaggccac aggccaggtc tgccatgcct tgtgctcccc cgagggctgc tggggcccgg   1800
agcccaggga ctgcgtctct tgccggaatg tcagccgagg cagggaatgc gtggacaagt   1860
gcaaccttct ggagggtgag ccaagggagt ttgtggagaa ctctgagtgc atacagtgcc   1920
acccagagtg cctgcctcag gccatgaaca tcacctgcac aggacgggga ccagacaact   1980
gtatccagtg tgcccactac attgacggcc ccactgcgt caagacctgc ccggcaggag   2040
tcatgggaga aaacaacacc ctggtctgga gtacgcaga cgccggccat gtgtgccacc   2100
tgtgccatcc aaactgcacc tacgatgca ctgggccagg tcttgaaggc tgtccaacga   2160
atgggcctaa gatcccgtcc atcgccactg ggatggtggg ggcccctcctc ttgctgctgg   2220 tggtggccct ggggatcggc ctcttcatgc gaaggcgcca catcgttcgg aagcgcacgc   2280
tgcggaggct gctgcaggag agggagcttg tggagcctct tacacccagt ggagaagctc   2340
ccaaccaagc tctcttgagg atcttgaagg aaactgaatt caaaaagatc aaagtgctgg   2400
gctccggtgc gttcggcacg gtgtataagg gactctggat cccagaaggt gagaaagtta   2460
aaattcccgt cgctatcaag gaaccaacat ctccgaaagc caacaaggaa atcctcgatg   2520
aagcctacgt gatggccagc gtggacaacc cccacgtgtg ccgcctgctg ggcatctgcc   2580
tcacctccac cgtgcagctc atcacgcagc tcatgccctt cggctgcctc ctggactatg   2640
tccgggaaca caaagacaat attggctccc agtacctgct caactggtgt gtgcagatcg   2700
caaagggcat gaactacttg gaggaccgtc gcttggtgca ccgcgacctg gcagccagga   2760
acgtactggt gaaaacaccg cagcatgtca agatcacaga ttttgggctg gccaaactgc   2820
tgggtgcgga agagaaagaa taccatgcag aaggaggcaa agtgcctatc aagtggatgg   2880
cattggaatc aattttacac agaatctata cccaccagag tgatgtctgg agctacgggg   2940
```

```
tgactgtttg ggagttgatg acctttggat ccaagccata tgacggaatc cctgccagcg   3000
agatctcctc catcctggag aaaggagaac gcctccctca gccacccata tgtaccatcg   3060
atgtctacat gatcatggtc aagtgctgga tgatagacgc agatagtcgc ccaaagttcc   3120
gtgagttgat catcgaattc tccaaaatgg cccgagaccc ccagcgctac cttgtcattc   3180
aggggggatga aagaatgcat ttgccaagtc ctacagactc caacttctac cgtgccctga   3240
tggatgaaga agacatggac gacgtggtgg atgccgacga gtacctcatc ccacagcagg   3300
gcttcttcag cagcccctcc acgtcacgga ctccctcct gagctctctg agtgcaacca   3360
gcaacaattc caccgtggct tgcattgata gaaatgggct gcaaagctgt cccatcaagg   3420
aagacagctt cttgcagcga tacagctcag accccacagg cgccttgact gaggacagca   3480
tagacgacac cttcctccca gtgcctgaat acataaacca gtccgttccc aaaaggcccg   3540
ctggctctgt gcagaatcct gtctatcaca atcagcctct gaaccccgcg cccagcagag   3600
acccacacta ccaggacccc cacagcactg cagtgggcaa ccccgagtat ctcaacactg   3660
tccagcccac ctgtgtcaac agcacattcg acagccctgc ccactgggcc cagaaaggca   3720
gccaccaaat tagcctggac aaccctgact accagcagga cttctttccc aaggaagcca   3780
agccaaatgg catctttaag ggctccacag ctgaaaatgc agaataccta agggtcgcgc   3840
cacaaagcag tgaatttatt ggagcatga                                     3869

<210> SEQ ID NO 751
<211> LENGTH: 3866
<212> TYPE: DNA
<213> ORGANISM: Homo sapiens

<400> SEQUENCE: 751
cccggcgcag cgcggccgca gcagcctccg ccccccgcac ggtgtgagcg cccgacgcgg     60
ccgaggcggc cggagtcccg agctagcccc ggcggccgcc gccgcccaga ccggacgaca    120
ggccacctcg tcggcgtccg cccgagtccc cgcctcgccg ccaacgccac aaccaccgcg    180
cacggccccc tgactccgtc cagtattgat cgggagagcc ggagcgagct cttcggggag    240
cagcgatgcg accctccggg acggccgggg cagcgctcct ggcgctgctg gctgcgctct    300
gcccggcgag tcgggctctg gaggaaaaga aagtttgcca aggcacgagt aacaagctca    360
cgcagttggg cacttttgaa gatcattttc tcagcctcca gaggatgttc aataactgtg    420
aggtggtcct tgggaatttg gaaattacct atgtgcagag gaattatgat cttcccttct    480
taaagaccat ccaggaggtg gctggttatg tcctcattgc cctcaacaca gtggagcgaa    540
ttcctttgga aaacctgcag atcatcagag gaaatatgta ctacgaaaat tcctatgcct    600
tagcagtctt atctaactat gatgcaaata aaaccggact gaaggagctg cccatgagaa    660
atttacagga atcctgcat ggcgccgtgc ggttcagcaa caaccctgcc ctgtgcaacg    720
tggagagcat ccagtggcgg gacatagtca gcagtgactt tctcagcaac atgtcgatgg    780
acttccagaa ccacctgggc agctgccaaa agtgtgatcc aagctgtccc aatgggagct    840
gctggggtgc aggagaggag aactgccaga aactgaccaa aatcatctgt gcccagcagt    900
gctccgggcg ctgccgtggc aagtccccca gtgactgctg ccacaaccag tgtgctgcag    960
gctgcacagg ccccgggag agcgactgcc tggtctgccg caaattccga gacgaagcca   1020
cgtgcaagga cacctgcccc ccactcatgc tctacaaccc caccacgtac cagatggatg   1080
tgaacccga gggcaaatac agctttggtg ccacctgcgt gaagaagtgt cccgtcaatt   1140
atgtggtgac agatcacggc tcgtgcgtcc gagcctgtgg ggccgacagc tatgagatgg   1200
```

```
aggaagacgg cgtccgcaag tgtaagaagt gcgaagggcc ttgccgcaaa gtgtgtaacg    1260
gaataggtat tggtgaattt aaagactcac tctccataaa tgctacgaat attaaacact    1320
tcaaaaactg cacctccatc agtggcgatc tccacatcct gccggtggca tttaggggtg    1380
actccttcac acatactcct cctctggatc cacaggaact ggatattctg aaaaccgtaa    1440
aggaaatcac agggtttttg ctgattcagg cttggcctga aaacaggacg gacctccatg    1500
cctttgagaa cctagaaatc atacgcggca ggaccaagca acatggtcag ttttctcttg    1560
cagtcgtcag cctgaacata acatccttgg gattacgctc cctcaaggag ataagtgatg    1620
gagatgtgat aatttcagga aacaaaaatt tgtgctatgc aaatacaata aactggaaaa    1680
aactgtttgg gacctccggt cagaaaacca aaattataag caacagaggt gaaaacagct    1740
gcaaggccac aggccaggtc tgccatgcct tgtgctcccc cgagggctgc tggggcccgg    1800
agcccaggga ctgcgtctct tgccggaatg tcagccgagg cagggaatgc gtggacaagt    1860
gcaaccttct ggagggtgag ccaagggagt tgtggagaa ctctgagtgc atacagtgcc    1920
acccagagtg cctgcctcag gccatgaaca tcacctgcac aggacgggga ccagacaact    1980
gtatccagtg tgcccactac attgacggcc cccactgcgt caagacctgc ccggcaggag    2040
tcatgggaga aaacaacacc ctggtctgga gtacgcaga cgccggccat gtgtgccacc    2100
tgtgccatcc aaactgcacc tacgatgca ctgggccagg tcttgaaggc tgtccaacga    2160
atgggcctaa gatcccgtcc atcgccactg ggatggtggg ggcctcctc ttgctgctgg    2220 tggtggccct ggggatcggc ctcttcatgc gaaggcgcca catcgttcgg aagcgcacgc    2280
tgcggaggct gctgcaggag agggagcttg tggagcctct tacacccagt ggagaagctc    2340
ccaaccaagc tctcttgagg atcttgaagg aaactgaatt caaaaagatc aaagtgctgg    2400
gctccggtgc gttcggcacg gtgtataagg gactctggat cccagaaggt gagaaagtta    2460
aaattcccgt cgctatcaag gaaccatctc cgaaagccaa caggaaatc ctcgatgaag    2520 cctacgtgat ggccagcgtg gacaaccccc acgtgtgccg cctgctgggc atctgcctca    2580
cctccaccgt gcagctcatc acgcagctca tgcccttcgg ctgcctcctg gactatgtcc    2640
gggaacacaa agacaatatt ggctcccagt acctgctcaa ctggtgtgtg cagatcgcaa    2700
agggcatgaa ctacttggag gaccgtcgct tggtgcaccg cgacctggca gccaggaacg    2760
tactggtgaa aacaccgcag catgtcaaga tcacagattt tgggctggcc aaactgctgg    2820
gtgcggaaga gaaagaatac catgcagaag gaggcaaagt gcctatcaag tggatggcat    2880
tggaatcaat tttacacaga atctatacc accagagtga tgtctggagc tacggggtga    2940
ctgtttggga gttgatgacc tttggatcca agccatatga cggaatccct gccagcgaga    3000
tctcctccat cctggagaaa ggagaacgcc tccctcagcc acccatatgt accatcgatg    3060
tctacatgat catggtcaag tgctggatga tagacgcaga tagtcgccca agttccgtg    3120 agttgatcat cgaattctcc aaaatggccc gagaccccca cgctaccctt gtcattcagg    3180
gggatgaaag aatgcatttg ccaagtccta cagactccaa cttctaccgt gccctgatgg    3240
atgaagaaga catggacgac gtggtggatg ccgacgagta cctcatccca cagcagggct    3300
tcttcagcag ccccctccacg tcacggactc ccctcctgag ctctctgagt gcaaccagca    3360
acaattccac cgtggcttgc attgatagaa atgggctgca agctgtccc atcaaggaag    3420 acagcttctt gcagcgatac agctcagacc ccacaggcgc cttgactgag gacagcatag    3480
acgacacctt cctcccagtg cctgaataca taaaccagtc cgttcccaaa aggcccgctg    3540
```

| | |
|---|---|
| gctctgtgca gaatcctgtc tatcacaatc agcctctgaa ccccgcgccc agcagagacc | 3600 |
| cacactacca ggaccccac agcactgcag tgggcaaccc cgagtatctc aacactgtcc | 3660 |
| agcccacctg tgtcaacagc acattcgaca gccctgccca ctgggccag aaaggcagcc | 3720 |
| accaaattag cctggacaac cctgactacc agcaggactt ctttcccaag gaagccaagc | 3780 |
| caaatggcat cttttaagggc tccacagctg aaaatgcaga taccctaagg gtcgcgccac | 3840 |
| aaagcagtga atttattgga gcatga | 3866 |

<210> SEQ ID NO 752
<211> LENGTH: 3854
<212> TYPE: DNA
<213> ORGANISM: Homo sapiens

<400> SEQUENCE: 752

| | |
|---|---|
| cccggcgcag cgcggccgca gcagcctccg ccccccgcac ggtgtgagcg cccgacgcgg | 60 |
| ccgaggcggc cggagtcccg agctagcccc ggcggccgcc gccgcccaga ccggacgaca | 120 |
| ggccacctcg tcggcgtccg cccgagtccc cgcctcgccg ccaacgccac aaccaccgcg | 180 |
| cacggcccc tgactccgtc cagtattgat cgggagagcc ggagcgagct cttcggggag | 240 |
| cagcgatgcg accctccggg acggccgggg cagcgctcct ggcgctgctg gctgcgctct | 300 |
| gcccggcgag tcgggctctg gaggaaaaga agtttgccaa aggcacgagt aacaagctca | 360 |
| cgcagttggg cactttgaa gatcattttc tcagcctcca gaggatgttc aataactgtg | 420 |
| aggtggtcct tgggaatttg gaaattacct atgtgcagag gaattatgat ctttccttct | 480 |
| taaagaccat ccaggaggtg gctggttatg tcctcattgc cctcaacaca gtggagcgaa | 540 |
| ttcctttgga aaacctgcag atcatcagag gaaatatgta ctacgaaaat tcctatgcct | 600 |
| tagcagtctt atctaactat gatgcaaata aaaccggact gaaggagctg cccatgagaa | 660 |
| atttacagga atcctgcat ggcgccgtgc ggttcagcaa caaccctgcc ctgtgcaacg | 720 |
| tggagagcat ccagtggcgg gacatagtca gcagtgactt tctcagcaac atgtcgatgg | 780 |
| acttccagaa ccacctgggc agctgccaaa agtgtgatcc aagctgtccc aatgggagct | 840 |
| gctggggtgc aggagaggag aactgccaga aactgaccaa aatcatctgt gcccagcagt | 900 |
| gctccgggcg ctgccgtggc aagtcccca gtgactgctg ccacaaccag tgtgctgcag | 960 |
| gctgcacagg cccccgggag agcgactgcc tggtctgccg caaattccga gacgaagcca | 1020 |
| cgtgcaagga cacctgcccc ccactcatgc tctacaaccc caccacgtac cagatggatg | 1080 |
| tgaaccccga gggcaaatac agctttggtg ccacctgcgt gaagaagtgt ccccgtaatt | 1140 |
| atgtggtgac agatcacggc tcgtgcgtcc gagcctgtgg ggccgacagc tatgagatgg | 1200 |
| aggaagacgg cgtccgcaag tgtaagaagt gcgaagggcc ttgccgcaaa gtgtgtaacg | 1260 |
| gaataggtat tggtgaattt aaagactcac tctccataaa tgctacgaat attaaacact | 1320 |
| tcaaaaactg cacctccatc agtggcgatc tccacatcct gccggtggca tttagggtg | 1380 |
| actccttcac acatactcct cctctggatc cacaggaact ggatattctg aaaaccgtaa | 1440 |
| aggaaatcac aggttttttg ctgattcagg cttggcctga aaacaggacg gacctccatg | 1500 |
| cctttgagaa cctagaaatc atacgcggca ggaccaagca acatggtcag ttttctcttg | 1560 |
| cagtcgtcag cctgaacata acatccttgg gattacgctc cctcaaggag ataagtgatg | 1620 |
| gagatgtgat aatttcagga aacaaaaatt tgtgctatgc aaatacaata aactggaaaa | 1680 |
| aactgttgg gacctccggt cagaaaacca aaattataag caacagaggt gaaaacagct | 1740 |
| gcaaggccac aggccaggtc tgccatgcct tgtgctcccc cgagggctgc tggggccgg | 1800 |

```
agcccaggga ctgcgtctct tgccggaatg tcagccgagg cagggaatgc gtggacaagt     1860
gcaaccttct ggagggtgag ccaagggagt ttgtggagaa ctctgagtgc atacagtgcc     1920
acccagagtg cctgcctcag gccatgaaca tcacctgcac aggacgggga ccagacaact     1980
gtatccagtg tgcccactac attgacggcc cccactgcgt caagacctgc ccggcaggag     2040
tcatgggaga aaacaacacc ctggtctgga agtacgcaga cgccggccat gtgtgccacc     2100
tgtgccatcc aaactgcacc tacgatgca ctgggccagg tcttgaaggc tgtccaacga     2160
atgggcctaa gatcccgtcc atcgccactg ggatggtggg ggccctcctc ttgctgctgg     2220
tggtggccct ggggatcggc ctcttcatgc gaaggcgcca catcgttcgg aagcgcacgc     2280
tgcggaggct gctgcaggag agggagcttg tggagcctct tacacccagt ggagaagctc     2340
ccaaccaagc tctcttgagg atcttgaagg aaactgaatt caaaaagatc aaagtgctgg     2400
gctccggtgc gttcggcacg gtgtataagg actctggat cccagaaggt gagaaagtta     2460
aaattcccgt cgctatcaag gaattaagag aagcaaccct cgatgaagcc tacgtgatgg     2520
ccagcgtgga caaccccac gtgtgccgcc tgctgggcat ctgcctcacc tccaccgtgc     2580
agctcatcac gcagctcatg cccttcggct gcctcctgga ctatgtccgg gaacacaaag     2640
acaatattgg ctcccagtac ctgctcaact ggtgtgtgca gatcgcaaag ggcatgaact     2700
acttggagga ccgtcgcttg gtgcaccgcg acctggcagc caggaacgta ctggtgaaaa     2760
caccgcagca tgtcaagatc acagattttg ggctggccaa actgctgggt gcggaagaga     2820
aagaatacca tgcagaagga ggcaaagtgc ctatcaagtg gatggcattg gaatcaattt     2880
tacacagaat ctatacccac cagagtgatg tctggagcta cggggtgact gtttgggagt     2940
tgatgacctt tggatccaag ccatatgacg gaatccctgc cagcgagatc tcctccatcc     3000
tggagaaagg agaacgcctc cctcagccac ccatatgtac catcgatgtc tacatgatca     3060
tggtcaagtg ctggatgata gacgcagata gtcgcccaaa gttccgtgag ttgatcatcg     3120
aattctccaa aatggcccga acccccagc gctaccttgt cattcagggg gatgaaagaa     3180
tgcatttgcc aagtcctaca gactccaact tctaccgtgc cctgatggat gaagaagaca     3240
tggacgacgt ggtggatgcc gacgagtacc tcatcccaca gcagggcttc ttcagcagcc     3300
cctccacgtc acggactccc ctcctgagct ctctgagtgc aaccagcaac aattccaccg     3360
tggcttgcat tgatagaaat gggctgcaaa gctgtcccat caaggaagac agcttcttgc     3420
agcgatacag ctcagacccc acaggcgcct tgactgagga cagcatagac gacaccttcc     3480
tcccagtgcc tgaatacata aaccagtccg ttcccaaaag gcccgctggc tctgtgcaga     3540
atcctgtcta tcacaatcag cctctgaacc ccgcgcccag cagagaccca cactaccagg     3600 accccacag cactgcagtg gcaaccccg agtatctcaa cactgtccag cccacctgtg     3660
tcaacagcac attcgacagc cctgcccact gggcccagaa aggcagccac caaattagcc     3720
tggacaaccc tgactaccag caggacttct ttcccaagga agccaagcca aatggcatct     3780
ttaagggctc cacagctgaa aatgcagaat acctaagggt cgcgccacaa agcagtgaat     3840
ttattggagc atga                                                      3854

<210> SEQ ID NO 753
<211> LENGTH: 3854
<212> TYPE: DNA
<213> ORGANISM: Homo sapiens

<400> SEQUENCE: 753
```

```
cccggcgcag cgcggccgca gcagcctccg ccccccgcac ggtgtgagcg cccgacgcgg    60
ccgaggcggc cggagtcccg agctagcccc ggcggccgcc gccgcccaga ccggacgaca   120
ggccacctcg tcggcgtccg cccgagtccc cgcctcgccg ccaacgccac aaccaccgcg   180
cacgccccc tgactccgtc cagtattgat cgggagagcc ggagcgagct cttcggggag    240
cagcgatgcg accctccggg acggccgggg cagcgctcct ggcgctgctg gctgcgctct   300
gcccggcgag tcgggctctg gaggaaaaga aagtttgcca aggcacgagt aacaagctca   360
cgcagttggg cacttttgaa gatcattttc tcagcctcca gaggatgttc aataactgtg   420
aggtggtcct tgggaatttg gaaattacct atgtgcagag gaattatgat ctttccttct   480
taaagaccat ccaggaggtg gctggttatg tcctcattgc cctcaacaca gtggagcgaa   540
ttcctttgga aaacctgcag atcatcagag gaaatatgta ctacgaaaat tcctatgcct   600
tagcagtctt atctaactat gatgcaaata aaaccggact gaaggagctg cccatgagaa   660
atttacagga aatcctgcat ggcgccgtgc ggttcagcaa caaccctgcc ctgtgcaacg   720
tggagagcat ccagtggcgg gacatagtca gcagtgactt tctcagcaac atgtcgatgg   780
acttccagaa ccacctgggc agctgccaaa agtgtgatcc aagctgtccc aatgggagct   840
gctgggggtgc aggagaggag aactgccaga aactgaccaa aatcatctgt gcccagcagt   900
gctccgggcg ctgccgtggc aagtccccca gtgactgctg ccacaaccag tgtgctgcag   960
gctgcacagg cccccgggag agcgactgcc tggtctgccg caaattccga gacgaagcca  1020
cgtgcaagga cacctgcccc ccactcatgc tctacaaccc caccacgtac cagatggatg  1080
tgaaccccga gggcaaatac agctttggtg ccacctgcgt gaagaagtgt ccccgtaatt  1140
atgtggtgac agatcacggc tcgtgcgtcc gagcctgtgg ggccgacagc tatgagatgg  1200
aggaagacgg cgtccgcaag tgtaagaagt gcgaagggcc ttgccgcaaa gtgtgtaacg  1260
gaataggtat tggtgaattt aaagactcac tctccataaa tgctacgaat attaaacact  1320
tcaaaaactg cacctccatc agtggcgatc tccacatcct gccggtggca tttaggggtg  1380
actccttcac acatactcct cctctggatc cacaggaact ggatattctg aaaaccgtaa  1440
aggaaatcac agggttttg ctgattcagg cttggcctga aaacaggacg gacctccatg   1500
cctttgagaa cctagaaatc atacgcggca ggaccaagca acatggtcag ttttctcttg  1560
cagtcgtcag cctgaacata acatccttgg gattacgctc cctcaaggag ataagtgatg  1620
gagatgtgat aatttcagga aacaaaaatt tgtgctatgc aaatacaata aactggaaaa  1680
aactgtttgg gacctccggt cagaaaacca aaattataag caacagaggt gaaaacagct  1740
gcaaggccac aggccaggtc tgccatgcct tgtgctcccc cgagggctgc tggggcccgg  1800
agcccaggga ctgcgtctct tgccggaatg tcagccgagg cagggaatgc gtggacaagt  1860
gcaaccttct ggagggtgag ccaagggagt tgtggagaa ctctgagtgc atacagtgcc   1920
acccagagtg cctgcctcag gccatgaaca tcacctgcac aggacgggga ccagacaact  1980
gtatccagtg tgcccactac attgacggcc ccactgcgt caagacctgc ccggcaggag   2040
tcatgggaga aaacaacacc ctggtctgga agtacgcaga cgccggccat gtgtgccacc  2100
tgtgccatcc aaactgcacc tacgatgca ctgggccagg tcttgaaggc tgtccaacga   2160
atgggcctaa gatcccgtcc atcgccactg ggatggtggg ggccctcctc ttgctgctgg  2220
tggtggccct ggggatcggc ctcttcatgc gaaggcgcca catcgttcgg aagcgcacgc  2280
tgcggaggct gctgcaggag agggagcttg tggagcctct tacacccagt ggagaagctc  2340
ccaaccaagc tctcttgagg atcttgaagg aaactgaatt caaaaagatc aaagtgctgg  2400
```

```
gctccggtgc gttcggcacg gtgtataagg gactctggat cccagaaggt gagaaagtta    2460
aaattcccgt cgctatcaag gaattaagag aagcaacact cgatgaagcc tacgtgatgg    2520
ccagcgtgga caaccccac gtgtgccgcc tgctgggcat ctgcctcacc tccaccgtgc     2580
agctcatcac gcagctcatg cccttcggct gcctcctgga ctatgtccgg gaacacaaag    2640
acaatattgg ctcccagtac ctgctcaact ggtgtgtgca gatcgcaaag ggcatgaact    2700
acttggagga ccgtcgcttg gtgcaccgcg acctggcagc caggaacgta ctggtgaaaa    2760
caccgcagca tgtcaagatc acagattttg ggctggccaa actgctgggt gcggaagaga    2820
aagaatacca tgcagaagga ggcaaagtgc ctatcaagtg gatggcattg gaatcaattt    2880
tacacagaat ctatcccac cagagtgatg tctggagcta cggggtgact gtttgggagt     2940
tgatgacctt tggatccaag ccatatgacg gaatccctgc cagcgagatc tcctccatcc    3000
tggagaaagg agaacgcctc cctcagccac ccatatgtac catcgatgtc tacatgatca    3060
tggtcaagtg ctggatgata gacgcagata gtcgcccaaa gttccgtgag ttgatcatcg    3120
aattctccaa aatggcccga cccccagc gctaccttgt cattcagggg gatgaaagaa       3180
tgcatttgcc aagtcctaca gactccaact tctaccgtgc cctgatggat gaagaagaca    3240
tggacgacgt ggtggatgcc gacgagtacc tcatcccaca gcagggcttc ttcagcagcc    3300
cctccacgtc acggactccc ctcctgagct ctctgagtgc aaccagcaac aattccaccg    3360
tggcttgcat tgatagaaat gggctgcaaa gctgtcccat caaggaagac agcttcttgc    3420
agcgatacag ctcagacccc acaggcgcct tgactgagga cagcatagac gacaccttcc    3480
tcccagtgcc tgaatacata aaccagtccg ttcccaaaag gcccgctggc tctgtgcaga    3540
atcctgtcta tcacaatcag cctctgaacc ccgcgcccag cagagaccca cactaccagg    3600 accccacag cactgcagtg ggcaaccccg agtatctcaa cactgtccag cccacctgtg     3660
tcaacagcac attcgacagc cctgcccact gggcccagaa aggcagccac caaattagcc    3720
tggacaaccc tgactaccag caggacttct ttcccaagga agccaagcca aatggcatct    3780
ttaagggctc cacagctgaa aatgcagaat acctaagggt cgcgccacaa agcagtgaat    3840
ttattggagc atga                                                      3854

<210> SEQ ID NO 754
<211> LENGTH: 3887
<212> TYPE: DNA
<213> ORGANISM: Homo sapiens

<400> SEQUENCE: 754
cccggcgcag cgcggccgca gcagcctccg cccccgcac ggtgtgagcg cccgacgcgg       60
ccgaggcggc cggagtcccg agctagcccc ggcggccgcc gccgcccaga ccggacgaca     120
ggccacctcg tcggcgtccg cccgagtccc cgcctcgccg ccaacgccac aaccaccgcg     180
cacggccccc tgactccgtc cagtattgat cgggagagcc ggagcgagct cttcggggag     240
cagcgatgcg accctccggg acggccgggg cagcgctcct ggcgctgctg gctgcgctct     300
gcccggcgag tcgggctctg gaggaaaaga agtttgccca aggcacgagt aacaagctca     360
cgcagttggg cacttttgaa gatcattttc tcagcctcca gaggatgttc aataactgtg     420
aggtggtcct tgggaatttg gaaattacct atgtgcagag gaattatgat ctttccttct    480
taaagaccat ccaggaggtg gctggttatg tcctcattgc cctcaacaca gtggagcgaa    540
ttccttggga aaacctgcag atcatcagag gaaatatgta ctacgaaaat tcctatgcct    600
```

```
tagcagtctt atctaactat gatgcaaata aaaccggact gaaggagctg cccatgagaa    660
atttacagga aatcctgcat ggcgccgtgc ggttcagcaa caaccctgcc ctgtgcaacg    720
tggagagcat ccagtggcgg gacatagtca gcagtgactt tctcagcaac atgtcgatgg    780
acttccagaa ccacctgggc agctgccaaa agtgtgatcc aagctgtccc aatgggagct    840
gctggggtgc aggagaggag aactgccaga aactgaccaa aatcatctgt gcccagcagt    900
gctccgggcg ctgccgtggc aagtccccca gtgactgctg ccacaaccag tgtgctgcag    960
gctgcacagg cccccgggag agcgactgcc tggtctgccg caaattccga gacgaagcca   1020
cgtgcaagga cacctgcccc ccactcatgc tctacaaccc caccacgtac cagatggatg   1080
tgaaccccga gggcaaatac agctttggtg ccacctgcgt gaagaagtgt ccccgtaatt   1140
atgtggtgac agatcacggc tcgtgcgtcc gagcctgtgg ggccgacagc tatgagatgg   1200
aggaagacgg cgtccgcaag tgtaagaagt gcgaagggcc ttgccgcaaa gtgtgtaacg   1260
gaataggtat tggtgaattt aaagactcac tctccataaa tgctacgaat attaaacact   1320
tcaaaaactg cacctccatc agtggcgatc tccacatcct gccggtggca tttaggggtg   1380
actccttcac acatactcct cctctggatc cacaggaact ggatattctg aaaaccgtaa   1440
aggaaatcac agggtttttg ctgattcagg cttggcctga aaacaggacg gacctccatg   1500
cctttgagaa cctagaaatc atacgcggca ggaccaagca acatggtcag ttttctcttg   1560
cagtcgtcag cctgaacata acatccttgg gattacgctc cctcaaggag ataagtgatg   1620
gagatgtgat aatttcagga aacaaaaatt tgtgctatgc aaatacaata aactggaaaa   1680
aactgtttgg gacctccggt cagaaaacca aaattataag caacagaggt gaaaacagct   1740
gcaaggccac aggccaggtc tgccatgcct tgtgctcccc cgagggctgc tggggcccgg   1800
agcccaggga ctgcgtctct tgccggaatg tcagccgagg cagggaatgc gtggacaagt   1860
gcaaccttct ggagggtgag ccaagggagt ttgtggagaa ctctgagtgc atacagtgcc   1920
acccagagtg cctgcctcag gccatgaaca tcacctgcac aggacgggga ccagacaact   1980
gtatccagtg tgcccactac attgacggcc ccactgcgt caagacctgc ccggcaggag   2040
tcatgggaga aaacaacacc ctggtctgga agtacgcaga cgccggccat gtgtgccacc   2100
tgtgccatcc aaactgcacc tacggatgca ctgggccagg tcttgaaggc tgtccaacga   2160
atgggcctaa gatcccgtcc atcgccactg ggatggtggg ggccctcctc ttgctgctgg   2220
tggtggccct ggggatcggc ctcttcatgc gaaggcgcca catcgttcgg aagcgcacgc   2280 tgcgaggct gctgcaggag agggagcttg tggagcctct tacacccagt ggagaagctc   2340
ccaaccaagc tctcttgagg atcttgaagg aaactgaatt caaaaagatc aaagtgctgg   2400
gctccggtgc gttcggcacg gtgtataagg actctggat cccagaaggt gagaaagtta   2460
aaattcccgt cgctatcaag gaattaagag aagcaacatc tccgaaagcc aacaaggaaa   2520
tcctcgatga agcctacgtg atggccagct ggacagcgt ggacaacccc cacgtgtgcc   2580
gcctgctggg catctgcctc acctccaccg tgcagctcat cacgcagctc atgcccttcg   2640
gctgcctcct ggactatgtc cgggaacaca aagacaatat tggctcccag tacctgctca   2700
actggtgtgt gcagatcgca aagggcatga actacttgga ggaccgtcgc ttggtgcacc   2760
gcgacctggc agccaggaac gtactggtga aaacccgca gcatgtcaag atcacagatt   2820
ttgggctggc caaactgctg ggtgcggaag agaaagaata ccatgcagaa ggaggcaaag   2880
tgcctatcaa gtggatggca ttggaatcaa ttttacacag aatctatacc accagagtg   2940 atgtctggag ctacggggtg actgtttggg agttgatgac ctttggatcc aagccatatg   3000
```

```
acggaatccc tgccagcgag atctcctcca tcctggagaa aggagaacgc ctccctcagc    3060
cacccatatg taccatcgat gtctacatga tcatggtcaa gtgctggatg atagacgcag    3120
atagtcgccc aaagttccgt gagttgatca tcgaattctc caaaatggcc cgagaccccc    3180
agcgctacct tgtcattcag ggggatgaaa gaatgcattt gccaagtcct acagactcca    3240
acttctaccg tgccctgatg gatgaagaag acatggacga cgtggtggat gccgacgagt    3300
acctcatccc acagcagggc ttcttcagca gcccctccac gtcacggact cccctcctga    3360
gctctctgag tgcaaccagc aacaattcca ccgtggcttg cattgataga aatgggctgc    3420
aaagctgtcc catcaaggaa gacagcttct tgcagcgata cagctcagac cccacaggcg    3480
ccttgactga ggacagcata gacgacacct tcctcccagt gcctgaatac ataaaccagt    3540
ccgttcccaa aaggcccgct ggctctgtgc agaatcctgt ctatcacaat cagcctctga    3600
accccgcgcc cagcagagac ccacactacc aggaccccca cagcactgca gtgggcaacc    3660
ccgagtatct caacactgtc cagcccacct gtgtcaacag cacattcgac agccctgccc    3720
actgggccca gaaaggcagc caccaaatta gcctggacaa ccctgactac cagcaggact    3780
tctttcccaa ggaagccaag ccaaatggca tctttaaggg ctccacagct gaaaatgcag    3840
aatacctaag ggtcgcgcca caaagcagtg aatttattgg agcatga                  3887
```

<210> SEQ ID NO 755  
<211> LENGTH: 3884  
<212> TYPE: DNA  
<213> ORGANISM: Homo sapiens

<400> SEQUENCE: 755

```
cccggcgcag cgcggccgca gcagcctccg cccccccgcac ggtgtgagcg cccgacgcgg      60
ccgaggcggc cggagtcccg agctagcccc ggcggccgcc gccgcccaga ccggacgaca     120
ggccacctcg tcggcgtccg cccgagtccc cgcctcgccg ccaacgccac aaccaccgcg     180
cacggccccc tgactccgtc cagtattgat cgggagagcc ggagcgagct cttcggggag     240
cagcgatgcg accctccggg acggccgggg cagcgctcct ggcgctgctg gctgcgctct     300
gcccggcgag tcgggctctg gaggaaaaga aagtttgcca aggcacgagt aacaagctca     360
cgcagttggg cactttttgaa gatcattttc tcagcctcca gaggatgttc aataactgtg     420
aggtggtcct tgggaatttg gaaattacct atgtgcagag gaattatgat ctttccttct     480
taaagaccat ccaggaggtg gctggttatg tcctcattgc cctcaacaca gtggagcgaa     540
ttcctttgga aaacctgcag atcatcagag gaaatatgta ctacgaaaat tcctatgcct     600
tagcagtctt atctaactat gatgcaaata aaaccggact gaaggagctg cccatgagaa     660
atttacagga atcctgcat ggcgccgtgc ggttcagcaa caaccctgcc ctgtgcaacg     720
tggagagcat ccagtggcgg gacatagtca gcagtgactt tctcagcaac atgtcgatgg     780
acttccagaa ccacctgggc agctgccaaa agtgtgatcc aagctgtccc aatgggagct     840
gctggggtgc aggagaggag aactgccaga aactgaccaa aatcatctgt gcccagcagt     900
gctccgggcg ctgccgtggc aagtccccca gtgactgctg ccacaaccag tgtgctgcag     960
gctgcacagg ccccgggag agcgactgcc tggtctgccg caaattccga gacgaagcca    1020
cgtgcaagga cacctgcccc ccactcatgc tctacaaccc caccacgtac cagatggatg    1080
tgaaccccga gggcaaatac agctttggtg ccacctgcgt gaagaagtgt ccccgtaatt    1140
atgtggtgac agatcacggc tcgtgcgtcc gagcctgtgg ggccgacagc tatgagatgg    1200
```

```
aggaagacgg cgtccgcaag tgtaagaagt gcgaagggcc ttgccgcaaa gtgtgtaacg    1260
gaataggtat tggtgaattt aaagactcac tctccataaa tgctacgaat attaaacact    1320
tcaaaaactg cacctccatc agtggcgatc tccacatcct gccggtggca tttaggggtg    1380
actccttcac acatactcct cctctggatc cacaggaact ggatattctg aaaaccgtaa    1440
aggaaatcac agggtttttg ctgattcagg cttggcctga aacaggacg gacctccatg    1500 cctttgagaa cctagaaatc atacgcggca ggaccaagca acatggtcag ttttctcttg    1560
cagtcgtcag cctgaacata acatccttgg gattacgctc cctcaaggag ataagtgatg    1620
gagatgtgat aatttcagga aacaaaaatt tgtgctatgc aaatacaata aactggaaaa    1680
aactgtttgg gacctccggt cagaaaacca aaattataag caacagaggt gaaaacagct    1740
gcaaggccac aggccaggtc tgccatgcct tgtgctcccc cgagggctgc tgggccccgg    1800
agcccaggga ctgcgtctct tgccggaatg tcagccgagg cagggaatgc gtggacaagt    1860
gcaaccttct ggagggtgag ccaagggagt ttgtggagaa ctctgagtgc atacagtgcc    1920
acccagagtg cctgcctcag gccatgaaca tcacctgcac aggacgggga ccagacaact    1980
gtatccagtg tgcccactac attgacggcc cccactgcgt caagacctgc ccggcaggag    2040
tcatgggaga aaacaacacc ctggtctgga gtacgcaga cgccggccat gtgtgccacc    2100
tgtgccatcc aaactgcacc tacggatgca ctgggccagg tcttgaaggc tgtccaacga    2160
atgggcctaa gatcccgtcc atcgccactg ggatggtggg ggcctcctc ttgctgctgg    2220 tggtggccct ggggatcggc ctcttcatgc gaaggcgcca catcgttcgg aagcgcacgc    2280
tgcggaggct gctgcaggag agggagcttg tggagcctct tacacccagt ggagaagctc    2340
ccaaccaagc tctcttgagg atcttgaagg aaactgaatt caaaaagatc aaagtgctgg    2400
gctccggtgc gttcggcacg gtgtataagg gactctggat cccagaaggt gagaaagtta    2460
aaattcccgt cgctatcaag gaattaagag aagcaacatc tccgaaagcc aacaaggaaa    2520
tcctcgatga agcctacgtg atggccacg tggacaaccc ccaccccac gtgtgccgcc    2580 tgctgggcat ctgcctcacc tccaccgtgc agctcatcac gcagctcatg cccttcggct    2640
gcctcctgga ctatgtccgg gaacacaaag acaatattgg ctcccagtac ctgctcaact    2700
ggtgtgtgca gatcgcaaag ggcatgaact acttggagga ccgtcgcttg gtgcaccgcg    2760
acctggcagc caggaacgta ctggtgaaaa caccgcagca tgtcaagatc acagattttg    2820
ggctggccaa actgctgggt gcggaagaga agaatacca tgcagaagga ggcaaagtgc    2880
ctatcaagtg gatggcattg gaatcaattt tacacagaat ctatacccac cagagtgatg    2940
tctggagcta cgggggtgact gtttgggagt tgatgacctt tggatccaag ccatatgacg    3000
gaatccctgc cagcgagatc tcctccatcc tggagaaagg agaacgcctc cctcagccac    3060
ccatatgtac catcgatgtc tacatgatca tggtcaagtg ctggatgata gacgcagata    3120
gtcgcccaaa gttccgtgag ttgatcatcg aattctccaa aatggcccga gaccccagc    3180 gctaccttgt cattcagggg gatgaaagaa tgcatttgcc aagtcctaca gactccaact    3240
tctaccgtgc cctgatggat gaagaagaca tggacgacgt ggtggatgcc gacgagtacc    3300
tcatcccaca gcaggcttc ttcagcagcc cctccacgtc acggactccc ctcctgagct    3360
ctctgagtgc aaccagcaac aattccaccg tggcttgcat tgatagaaat gggctgcaaa    3420
gctgtcccat caaggaagac agcttcttgc agcgatacag ctcagacccc acaggcgcct    3480
tgactgagga cagcatagac gacaccttcc tcccagtgcc tgaatacata aaccagtccg    3540
ttcccaaaag gcccgctggc tctgtgcaga atcctgtcta tcacaatcag cctctgaacc    3600
```

| | | |
|---|---|---|
| ccgcgcccag cagagaccca cactaccagg accccacag cactgcagtg ggcaaccccg | 3660 | |
| agtatctcaa cactgtccag cccacctgtg tcaacagcac attcgacagc cctgcccact | 3720 | |
| gggcccagaa aggcagccac caaattagcc tggacaaccc tgactaccag caggacttct | 3780 | |
| ttcccaagga agccaagcca aatggcatct ttaagggctc cacagctgaa aatgcagaat | 3840 | |
| acctaagggt cgcgccacaa agcagtgaat ttattggagc atga | 3884 | |

<210> SEQ ID NO 756
<211> LENGTH: 3878
<212> TYPE: DNA
<213> ORGANISM: Homo sapiens

<400> SEQUENCE: 756

| | | |
|---|---|---|
| cccggcgcag cgcggccgca gcagcctccg cccccgcac ggtgtgagcg cccgacgcgg | 60 | |
| ccgaggcggc cggagtcccg agctagcccc ggcggccgcc gccgcccaga ccggacgaca | 120 | |
| ggccacctcg tcggcgtccg cccgagtccc cgcctcgccg ccaacgccac aaccaccgcg | 180 | |
| cacggccccc tgactccgtc cagtattgat cgggagagcc ggagcgagct cttcggggag | 240 | |
| cagcgatgcg accctccggg acggccgggg cagcgctcct ggcgctgctg gctgcgctct | 300 | |
| gcccggcgag tcgggctctg gaggaaaaga aagtttgcca aggcacgagt aacaagctca | 360 | |
| cgcagttggg cactttgaa gatcattttc tcagcctcca gaggatgttc aataactgtg | 420 | |
| aggtggtcct tgggaatttg gaaattacct atgtgcagag gaattatgat ctttccttct | 480 | |
| taaagaccat ccaggaggtg gctggttatg tcctcattgc cctcaacaca gtggagcgaa | 540 | |
| ttcctttgga aaacctgcag atcatcagag gaaatatgta ctacgaaaat tcctatgcct | 600 | |
| tagcagtctt atctaactat gatgcaaata aaaccggact gaaggagctg cccatgagaa | 660 | |
| atttacagga atcctgcat ggcgccgtgc ggttcagcaa caaccctgcc ctgtgcaacg | 720 | |
| tggagagcat ccagtggcgg gacatagtca gcagtgactt tctcagcaac atgtcgatgg | 780 | |
| acttccagaa ccacctgggc agctgccaaa agtgtgatcc aagctgtccc aatgggagct | 840 | |
| gctggggtgc aggagaggag aactgccaga aactgaccaa atcatctgt gcccagcagt | 900 | |
| gctccgggcg ctgccgtggc aagtccccca gtgactgctg ccacaaccag tgtgctgcag | 960 | |
| gctgcacagg ccccgggag agcgactgcc tggtctgccg caaattccga gacgaagcca | 1020 | |
| cgtgcaagga cacctgcccc ccactcatgc tctacaaccc caccacgtac cagatggatg | 1080 | |
| tgaaccccga gggcaaatac agctttggtg ccacctgcgt gaagaagtgt ccccgtaatt | 1140 | |
| atgtggtgac agatcacggc tcgtgcgtcc gagcctgtgg ggccgacagc tatgagatgg | 1200 | |
| aggaagacgg cgtccgcaag tgtaagaagt gcgaagggcc ttgccgcaaa gtgtgtaacg | 1260 | |
| gaataggtat tggtgaattt aaagactcac tctccataaa tgctacgaat attaaacact | 1320 | |
| tcaaaaactg cacctccatc agtggcgatc tccacatcct gccggtggca tttaggggtg | 1380 | |
| actccttcac acatactcct cctctggatc cacaggaact ggatattctg aaaaccgtaa | 1440 | |
| aggaaatcac agggttttg ctgattcagg cttggcctga aaacaggacg gacctccatg | 1500 | |
| cctttgagaa cctagaaatc atacgcggca ggaccaagca acatggtcag tttctcttg | 1560 | |
| cagtcgtcag cctgaacata acatccttgg gattacgctc cctcaaggag ataagtgatg | 1620 | |
| gagatgtgat aatttcagga aacaaaaatt tgtgctatgc aaatacaata aactggaaaa | 1680 | |
| aactgttgg gacctccggt cagaaaacca aaattataag caacagaggt gaaaacagct | 1740 | |
| gcaaggccac aggccaggtc tgccatgcct tgtgctcccc cgagggctgc tggggcccgg | 1800 | |

```
agcccaggga ctgcgtctct tgccggaatg tcagccgagg cagggaatgc gtggacaagt    1860
gcaaccttct ggagggtgag ccaagggagt ttgtggagaa ctctgagtgc atacagtgcc    1920
acccagagtg cctgcctcag gccatgaaca tcacctgcac aggacgggga ccagacaact    1980
gtatccagtg tgcccactac attgacggcc cccactgcgt caagacctgc ccggcaggag    2040
tcatgggaga aaacaacacc ctggtctgga agtacgcaga cgccggccat gtgtgccacc    2100
tgtgccatcc aaactgcacc tacgatgca ctgggccagg tcttgaaggc tgtccaacga     2160
atgggcctaa gatcccgtcc atcgccactg ggatggtggg ggccctcctc ttgctgctgg    2220
tggtggccct ggggatcggc ctcttcatgc gaaggcgcca catcgttcgg aagcgcacgc    2280
tgcggaggct gctgcaggag agggagcttg tggagcctct tacacccagt ggagaagctc    2340
ccaaccaagc tctcttgagg atcttgaagg aaactgaatt caaaaagatc aaagtgctgg    2400
gctccggtgc gttcggcacg gtgtataagg actctggat cccagaaggt gagaaagtta     2460
aaattcccgt cgctatcaag gaattaagag aagcaacatc tccgaaagcc aacaaggaaa    2520
tcctcgatga agcctacgtg atggccacg tggacaaccc ccacgtgtgc cgcctgctgg     2580
gcatctgcct cacctccacc gtgcagctca tcacgcagct catgcccttc ggctgcctcc    2640
tggactatgt ccgggaacac aaagacaata ttggctccca gtacctgctc aactggtgtg    2700
tgcagatcgc aaagggcatg aactacttgg aggaccgtcg cttggtgcac cgcgacctgg    2760
cagccaggaa cgtactggtg aaaacactgc agcatgtcaa gatcacagat tttgggctgg    2820
ccaaactgct gggtgcggaa gagaaagaat accatgcaga aggaggcaaa gtgcctatca    2880
agtggatggc attggaatca attttacaca gaatctatac ccaccagagt gatgtctgga    2940
gctacggggt gactgtttgg gagttgatga cctttggatc caagccatat gacggaatcc    3000
ctgccagcga gatctcctcc atcctggaga aggagaacg cctccctcag ccacccatat     3060
gtaccatcga tgtctacatg atcatggtca agtgctggat gatagacgca gatagtcgcc    3120
caaagttccg tgagttgatc atcgaattct ccaaaatggc ccgagacccc cagcgctacc    3180
ttgtcattca ggggatgaa agaatgcatt tgccaagtcc tacagactcc aacttctacc     3240
gtgccctgat ggatgaagaa acatggacg acgtggtgga tgccgacgag tacctcatcc     3300
cacagcaggg cttcttcagc agcccctcca cgtcacggac tcccctcctg agctctctga    3360
gtgcaaccag caacaattcc accgtggctt gcattgatag aaatgggctg caaagctgtc    3420
ccatcaagga agacagcttc ttgcagcgat acagctcaga cccacaggc gccttgactg      3480
aggacagcat agacgacacc ttcctcccag tgcctgaata cataaaccag tccgttccca    3540
aaaggcccgc tggctctgtg cagaatcctg tctatcacaa tcagcctctg aaccccgcgc    3600
ccagcagaga cccacactac caggacccc acagcactgc agtgggcaac cccgagtatc      3660
tcaacactgt ccagcccacc tgtgtcaaca gcacattcga cagccctgcc cactgggccc    3720
agaaaggcag ccaccaaatt agcctggaca accctgacta ccagcaggac ttctttccca    3780
aggaagccaa gccaaatggc atctttaagg ctccacagc tgaaaatgca gaatacctaa     3840
gggtcgcgcc acaaagcagt gaatttattg gagcatga                            3878
```

<210> SEQ ID NO 757
<211> LENGTH: 3878
<212> TYPE: DNA
<213> ORGANISM: Homo sapiens

<400> SEQUENCE: 757

```
cccggcgcag cgcggccgca gcagcctccg cccccccgcac ggtgtgagcg cccgacgcgg       60
```

```
ccgaggcggc cggagtcccg agctagcccc ggcggccgcc gccgcccaga ccggacgaca      120
ggccacctcg tcggcgtccg cccgagtccc cgcctcgccg ccaacgccac aaccaccgcg      180
cacggccccc tgactccgtc cagtattgat cgggagagcc ggagcgagct cttcggggag      240
cagcgatgcg acccteeggg acggccgggg cagegetect ggegetgetg getgegetet      300 gcccggcgag tcgggctctg gaggaaaaga aagtttgcca aggcacgagt aacaagctca      360
cgcagttggg cacttttgaa gatcattttc tcagcctcca gaggatgttc aataactgtg      420
aggtggtcct tgggaatttg gaaattacct atgtgcagag gaattatgat cttccttct       480 taaagaccat ccaggaggtg gctggttatg tcctcattgc cctcaacaca gtggagcgaa      540
ttcctttgga aaacctgcag atcatcagag gaaatatgta ctacgaaaat tcctatgcct      600
tagcagtctt atctaactat gatgcaaata aaaccggact gaaggagctg cccatgagaa      660
atttacagga atcctgcat ggcgccgtgc ggttcagcaa caaccctgcc ctgtgcaacg       720
tggagagcat ccagtggcgg gacatagtca gcagtgactt tctcagcaac atgtcgatgg      780
acttccagaa ccacctgggc agctgccaaa agtgtgatcc aagctgtccc aatgggagct      840
gctggggtgc aggagaggag aactgccaga aactgaccaa aatcatctgt gcccagcagt      900
gctccgggcg ctgccgtggc aagtccccca gtgactgctg ccacaaccag tgtgctgcag      960
gctgcacagg cccccgggag agcgactgcc tggtctgccg caaattccga gacgaagcca     1020
cgtgcaagga cacctgcccc ccactcatgc tctacaaccc caccacgtac cagatggatg     1080
tgaaccccga gggcaaatac agctttggtg ccacctgcgt gaagaagtgt ccccgtaatt     1140
atgtggtgac agatcacggc tcgtgcgtcc gagcctgtgg ggccgacagc tatgagatgg     1200
aggaagacgg cgtccgcaag tgtaagaagt gcgaagggcc ttgccgcaaa gtgtgtaacg     1260
gaataggtat tggtgaattt aaagactcac tctccataaa tgctacgaat attaaacact     1320
tcaaaaactg cacctccatc agtggcgatc tccacatcct gccggtggca tttaggggtg     1380
actccttcac acatactcct cctctggatc cacaggaact ggatattctg aaaaccgtaa     1440
aggaaatcac agggtttttg ctgattcagg cttggcctga aaacaggacg gacctccatg     1500
cctttgagaa cctagaaatc atacgcggca ggaccaagca acatggtcag ttttctcttg     1560
cagtcgtcag cctgaacata acatccttgg gattacgctc cctcaaggag ataagtgatg     1620
gagatgtgat aatttcagga aacaaaaatt tgtgctatgc aaatacaata aactggaaaa     1680
aactgtttgg gacctccggt cagaaaacca aaattataag caacagaggt gaaaacagct     1740
gcaaggccac aggccaggtc tgccatgcct tgtgctcccc cgagggctgc tggggcccgg     1800
agcccaggga ctgcgtctct tgccggaatg tcagccgagg cagggaatgc gtggacaagt     1860
gcaaccttct ggagggtgag ccaagggagt ttgtggagaa ctctgagtgc atacagtgcc     1920
acccagagtg cctgcctcag gccatgaaca tcacctgcac aggacgggga ccagacaact     1980
gtatccagtg tgcccactac attgacggcc ccactgcgt caagacctgc ccggcaggag      2040
tcatgggaga aaacaacacc ctggtctgga agtacgcaga cgccggccat gtgtgccacc     2100
tgtgccatcc aaactgcacc tacgatgca ctgggccagg tcttgaaggc tgtccaacga      2160
atgggcctaa gatcccgtcc atcgccactg ggatggtggg ggcctcctc ttgctgctgg      2220 tggtggccct ggggatcggc ctcttcatgc gaaggcgcca catcgttcgg aagcgcacgc     2280
tgcggaggct gctgcaggag agggagcttg tggagcctct tacacccagt ggagaagctc     2340
ccaaccaagc tctcttgagg atcttgaagg aaactgaatt caaaaagatc aaagtgctgg     2400
```

```
gctccggtgc gttcggcacg gtgtataagg gactctggat cccagaaggt gagaaagtta    2460
aaattcccgt cgctatcaag gaattaagag aagcaacatc tccgaaagcc aacaaggaaa    2520
tcctcgatga agcctacgtg atggccagcg tggacaaccc ccacgtgtgc cgcctgctgg    2580
gcatctgcct cacctccacc gtgcagctca tcacgcagct catgcccttc ggctgcctcc    2640
tggactatgt ccgggaacac aaagacaata ttggctccca gtacctgctc aactggtgtg    2700
tgcagatcgc aaagggcatg aactacttgg aggaccgtcg cttggtgcac cgcgacctgg    2760
cagccaggaa cgtactggtg aaaacaccgc agcatgtcaa gatcacagat tttgggcggg    2820
ccaaactgct gggtgcggaa gagaaagaat accatgcaga aggaggcaaa gtgcctatca    2880
agtggatggc attggaatca attttacaca gaatctatac ccaccagagt gatgtctgga    2940 gctacgggt gactgtttgg gagttgatga cctttggatc caagccatat gacgaatcc     3000 ctgccagcga gatctcctcc atcctggaga aaggagaacg cctccctcag ccacccatat    3060
gtaccatcga tgtctacatg atcatggtca agtgctggat gatagacgca gatagtcgcc    3120
caaagttccg tgagttgatc atcgaattct ccaaaatggc ccgagacccc cagcgctacc    3180
ttgtcattca gggggatgaa agaatgcatt tgccaagtcc tacagactcc aacttctacc    3240
gtgccctgat ggatgaagaa gacatggacg acgtggtgga tgccgacgag tacctcatcc    3300
cacagcaggg cttcttcagc agcccctcca cgtcacggac tccccctcctg agctctctga    3360 gtgcaaccag caacaattcc accgtggctt gcattgatag aaatgggctg caaagctgtc    3420
ccatcaagga agacagcttc ttgcagcgat acagctcaga ccccacaggc gccttgactg    3480
aggacagcat agacgacacc ttcctcccag tgcctgaata cataaaccag tccgttccca    3540
aaaggcccgc tggctctgtg cagaatcctg tctatcacaa tcagcctctg aaccccgcgc    3600
ccagcagaga cccacactac caggaccccc acagcactgc agtgggcaac cccgagtatc    3660
tcaacactgt ccagcccacc tgtgtcaaca gcacattcga cagccctgcc cactgggccc    3720
agaaaggcag ccaccaaatt agcctggaca accctgacta ccagcaggac ttctttccca    3780
aggaagccaa gccaaatggc atctttaagg ctccacagc tgaaaatgca gaatacctaa     3840
gggtcgcgcc acaaagcagt gaatttattg gagcatga                            3878
```

<210> SEQ ID NO 758
<211> LENGTH: 3878
<212> TYPE: DNA
<213> ORGANISM: Homo sapiens

<400> SEQUENCE: 758

```
cccggcgcag cgcggccgca gcagcctccg ccccccgcac ggtgtgagcg cccgacgcgg      60
ccgaggcggc cggagtcccg agctagcccc ggcggccgcc gccgcccaga ccggacgaca     120
ggccacctcg tcggcgtccg cccgagtccc cgcctcgccg ccaacgccac aaccaccgcg     180 cacgccccc tgactccgtc cagtattgat cgggagagcc ggagcgagct cttcggggag     240
cagcgatgcg accctccggg acggccgggg cagcgctcct ggcgctgctg gctgcgctct     300
gcccggcgag tcgggctctg gaggaaaaga agtttgccaa aggcacgagt aacaagctca     360
cgcagttggg cacttttgaa gatcattttc tcagcctcca gaggatgttc aataactgtg     420
aggtggtcct tgggaatttg gaaattacct atgtgcagag gaattatgat ctttccttct     480
taaagaccat ccaggaggtg gctggttatg tcctcattgc cctcaacaca gtggagcgaa     540
ttcctttgga aaacctgcag atcatcagag gaaatatgta ctacgaaaat tcctatgcct     600
tagcagtctt atctaactat gatgcaaata aaaccggact gaaggagctg cccatgagaa     660
```

-continued

```
atttacagga aatcctgcat ggcgccgtgc ggttcagcaa caaccctgcc ctgtgcaacg      720
tggagagcat ccagtggcgg gacatagtca gcagtgactt tctcagcaac atgtcgatgg      780
acttccagaa ccacctgggc agctgccaaa agtgtgatcc aagctgtccc aatgggagct      840
gctggggtgc aggagaggag aactgccaga aactgaccaa atcatctgt gcccagcagt       900 gctccgggcg ctgccgtggc aagtccccca gtgactgctg ccacaaccag tgtgctgcag      960
gctgcacagg cccccgggag agcgactgcc tggtctgccg caaattccga gacgaagcca     1020
cgtgcaagga cacctgcccc ccactcatgc tctacaaccc caccacgtac cagatggatg     1080
tgaaccccga gggcaaatac agctttggtg ccacctgcgt gaagaagtgt ccccgtaatt     1140
atgtggtgac agatcacggc tcgtgcgtcc gagcctgtgg ggccgacagc tatgagatgg     1200
aggaagacgg cgtccgcaag tgtaagaagt gcgaagggcc ttgccgcaaa gtgtgtaacg     1260
gaataggtat tggtgaattt aaagactcac tctccataaa tgctacgaat attaaacact     1320
tcaaaaactg cacctccatc agtggcgatc tccacatcct gccggtggca tttaggggtg     1380
actccttcac acatactcct cctctggatc cacaggaact ggatattctg aaaaccgtaa     1440
aggaaatcac agggttttg ctgattcagg cttggcctga aaacaggacg gacctccatg      1500
cctttgagaa cctagaaatc atacgcggca ggaccaagca acatggtcag ttttctcttg     1560
cagtcgtcag cctgaacata acatccttgg gattacgctc cctcaaggag ataagtgatg     1620
gagatgtgat aatttcagga aacaaaaatt tgtgctatgc aaatacaata aactggaaaa     1680
aactgtttgg gacctccggt cagaaaacca aaattataag caacagaggt gaaaacagct     1740
gcaaggccac aggccaggtc tgccatgcct tgtgctcccc cgagggctgc tggggcccgg     1800
agcccaggga ctgcgtctct tgccggaatg tcagccgagg cagggaatgc gtggacaagt     1860
gcaaccttct ggagggtgag ccaagggagt ttgtggagaa ctctgagtgc atacagtgcc     1920
acccagagtg cctgcctcag gccatgaaca tcacctgcac aggacgggga ccagacaact     1980
gtatccagtg tgcccactac attgacggcc cccactgcgt caagacctgc ccggcaggag     2040
tcatgggaga aaacaacacc ctggtctgga agtacgcaga cgccggccat gtgtgccacc     2100
tgtgccatcc aaactgcacc tacgatgca ctgggccagg tcttgaaggc tgtccaacga      2160
atgggcctaa gatcccgtcc atcgccactg ggatggtggg ggccctcctc ttgctgctgg     2220
tggtggccct ggggatcggc ctcttcatgc gaaggcgcca catcgttcgg aagcgcacgc     2280
tgcggaggct gctgcaggag agggagcttg tggagcctct tacacccagt ggagaagctc     2340
ccaaccaagc tctcttgagg atcttgaagg aaactgaatt caaaaagatc aaagtgctgg     2400
gctccggtgc gttcggcacg gtgtataagg gactctggat cccagaaggt gagaaagtta     2460
aaattcccgt cgctatcaag gaattaagag aagcaacatc tccgaaagcc aacaaggaaa     2520
tcctcgatga agcctacgtg atggccagcg tggacaaccc ccacgtgtgc cgcctgctgg     2580
gcatctgcct cacctccacc gtgcagctca tcacgcagct catgcccttc ggctgcctcc     2640
tggactatgt ccgggaacac aaagacaata ttggctccca gtacctgctc aactggtgtg     2700
tgcagatcgc aaagggcatg aactacttgg aggaccgtcg cttggtgcac cgcgacctgg     2760
cagccaggaa cgtactggtg aaaacaccgc agcatgtcaa gatcacagat tttgggcggg     2820
ccaaactgct gggtgcggaa gagaaagaat accatgcaga aggaggcaaa gtgcctatca     2880
agtggatggc attggaatca attttacaca gaatctatac ccaccagagt gatgtctgga     2940
gctacggggt gactgtttgg gagttgatga cctttggatc caagccatat gacggaatcc     3000
```

|                                                                  |      |
|------------------------------------------------------------------|------|
| ctgccagcga gatctcctcc atcctggaga aaggagaacg cctccctcag ccacccatat | 3060 |
| gtaccatcga tgtctacatg atcatggtca agtgctggat gatagacgca gatagtcgcc | 3120 |
| caaagttccg tgagttgatc atcgaattct ccaaaatggc ccgagacccc cagcgctacc | 3180 |
| ttgtcattca gggggatgaa agaatgcatt tgccaagtcc tacagactcc aacttctacc | 3240 |
| gtgccctgat ggatgaagaa gacatggacg acgtggtgga tgccgacgag tacctcatcc | 3300 |
| cacagcaggg cttcttcagc agcccctcca cgtcacggac tcccctcctg agctctctga | 3360 |
| gtgcaaccag caacaattcc accgtggctt gcattgatag aaatgggctg caaagctgtc | 3420 |
| ccatcaagga agacagcttc ttgcagcgat acagctcaga ccccacaggc gccttgactg | 3480 |
| aggacagcat agacgacacc ttcctcccag tgcctgaata cataaaccag tccgttccca | 3540 |
| aaaggcccgc tggctctgtg cagaatcctg tctatcacaa tcagcctctg aaccccgcgc | 3600 |
| ccagcagaga cccacactac caggacccccc acagcactgc agtgggcaac cccgagtatc | 3660 |
| tcaacactgt ccagcccacc tgtgtcaaca gcacattcga cagccctgcc cactgggccc | 3720 |
| agaaaggcag ccaccaaatt agcctggaca accctgacta ccagcaggac ttctttccca | 3780 |
| aggaagccaa gccaaatggc atctttaagg gctccacagc tgaaaatgca gaatacctaa | 3840 |
| gggtcgcgcc acaaagcagt gaatttattg gagcatga | 3878 |

<210> SEQ ID NO 759
<211> LENGTH: 3878
<212> TYPE: DNA
<213> ORGANISM: Homo sapiens

<400> SEQUENCE: 759

|                                                                  |      |
|------------------------------------------------------------------|------|
| cccggcgcag cgcggccgca gcagcctccg cccccccgcac ggtgtgagcg cccgacgcgg | 60   |
| ccgaggcggc cggagtcccg agctagcccc ggcggccgcc gccgcccaga ccggacgaca | 120  |
| ggccacctcg tcggcgtccg cccgagtccc cgcctcgccg ccaacgccac aaccaccgcg | 180  |
| cacgcccccc tgactccgtc cagtattgat cgggagagcc ggagcgagct cttcggggag | 240  |
| cagcgatgcg accctccggg acggccgggg cagcgctcct ggcgctgctg gctgcgctct | 300  |
| gcccggcgag tcgggctctg gaggaaaaga aagtttgcca aggcacgagt aacaagctca | 360  |
| cgcagttggg cacttttgaa gatcattttc tcagcctcca gaggatgttc aataactgtg | 420  |
| aggtggtcct tgggaatttg gaaattacct atgtgcagag gaattatgat ctttccttct | 480  |
| taaagaccat ccaggaggtg gctggttatg tcctcattgc cctcaacaca gtggagcgaa | 540  |
| ttccttttgga aaacctgcag atcatcgag gaaatatgta ctacgaaaat tcctatgcct | 600  |
| tagcagtctt atctaactat gatgcaaata aaaccggact gaaggagctg cccatgagaa | 660  |
| atttacagga atcctgcat ggcgccgtgc ggttcagcaa caaccctgcc ctgtgcaacg | 720  |
| tggagagcat ccagtggcgg gacatagtca gcagtgactt tctcagcaac atgtcgatgg | 780  |
| acttccagaa ccacctgggc agctgccaaa agtgtgatcc aagctgtccc aatgggagct | 840  |
| gctggggtgc aggagaggag aactgccaga aactgaccaa aatcatctgt gcccagcagt | 900  |
| gctccgggcg ctgccgtggc aagtccccca gtgactgctg ccacaaccag tgtgctgcag | 960  |
| gctgcacagg ccccgggag agcgactgcc tggtctgccg caaattccga gacgaagcca | 1020 |
| cgtgcaagga cacctgcccc ccactcatgc tctacaaccc caccacgtac cagatggatg | 1080 |
| tgaacccga gggcaaatac agcttggtg ccacctgcgt gaagaagtgt cccgtaatt | 1140 |
| atgtggtgac agatcacggc tcgtgcgtcc gagcctgtgg ggccgacagc tatgagatgg | 1200 |
| aggaagacgg cgtccgcaag tgtaagaagt gcgaagggcc ttgccgcaaa gtgtgtaacg | 1260 |

```
gaataggtat tggtgaattt aaagactcac tctccataaa tgctacgaat attaaacact   1320
tcaaaaactg cacctccatc agtggcgatc tccacatcct gccggtggca tttagggggtg  1380 actccttcac acatactcct cctctggatc cacaggaact ggatattctg aaaaccgtaa   1440
aggaaatcac agggttttg ctgattcagg cttggcctga aaacaggacg gacctccatg    1500
cctttgagaa cctagaaatc atacgcggca ggaccaagca acatggtcag ttttctcttg   1560
cagtcgtcag cctgaacata acatccttgg gattacgctc cctcaaggag ataagtgatg   1620
gagatgtgat aatttcagga aacaaaaatt tgtgctatgc aaatacaata aactggaaaa   1680
aactgtttgg gacctccggt cagaaaacca aaattataag caacagaggt gaaaacagct   1740
gcaaggccac aggccaggtc tgccatgcct tgtgctcccc cgagggctgc tggggcccgg   1800
agcccaggga ctgcgtctct tgccggaatg tcagccgagg cagggaatgc gtggacaagt   1860
gcaaccttct ggagggtgag ccaagggagt ttgtggagaa ctctgagtgc atacagtgcc   1920
acccagagtg cctgcctcag gccatgaaca tcacctgcac aggacgggga ccagacaact   1980
gtatccagtg tgcccactac attgacggcc cccactgcgt caagacctgc ccggcaggag   2040
tcatgggaga aaacaacacc ctggtctgga agtacgcaga cgccggccat gtgtgccacc   2100
tgtgccatcc aaactgcacc tacggatgca ctgggccagg tcttgaaggc tgtccaacga   2160
atgggcctaa gatcccgtcc atcgccactg ggatggtggg ggccctcctc ttgctgctgg   2220
tggtggccct ggggatcggc ctcttcatgc gaaggcgcca catcgttcgg aagcgcacgc   2280
tgcggaggct gctgcaggag agggagcttg tggagcctct tacacccagt ggagaagctc   2340
ccaaccaagc tctcttgagg atcttgaagg aaactgaatt caaaaagatc aaagtgctgg   2400
gctccggtgc gttcggcacg gtgtataagg gactctggat cccagaaggt gagaaagtta   2460
aaattcccgt cgctatcaag gaattaagag aagcaacatc tccgaaagcc aacaaggaaa   2520
tcctcgatga agcctacgtg atggccagcg tggacaaccc ccacgtgtgc cgcctgctgg   2580
gcatctgcct cacctccacc gtgcagctca tcacgcagct catgcccttc ggctgcctcc   2640
tggactatgt ccgggaacac aaaagacaat ttggctccca gtacctgctc aactggtgtg   2700
tgcagatcgc aaagggcatg aactacttgg aggaccgtcg cttggtgcac cgcgacctgg   2760
cagccaggaa cgtactggtg aaaacaccgc agcatgtcaa gatcacagat tttgggcggg   2820
ccaaactgct gggtgcggaa gagaaagaat accatgcaga aggaggcaaa gtgcctatca   2880
agtggatggc attggaatca attttacaca gaatctatac ccaccagagt gatgtctgga   2940
gctacggggt gactgtttgg gagttgatga cctttggatc caagccatat gacggaatcc   3000
ctgccagcga gatctcctcc atcctggaga aggagaacg cctccctcag ccacccatat   3060
gtaccatcga tgtctacatg atcatggtca agtgctggat gatagacgca gatagtcgcc   3120
caaagttccg tgagttgatc atcgaattct ccaaaatggc ccgagacccc cagcgctacc   3180
ttgtcattca gggggatgaa agaatgcatt tgccaagtcc tacagactcc aacttctacc   3240
gtgccctgat ggatgaagaa gacatggacg acgtggtgga tgccgacgag tacctcatcc   3300
cacagcaggg cttcttcagc agcccctcca cgtcacggac tcccctcctg agctctctga   3360
gtgcaaccag caacaattcc accgtggctt gcattgatag aaatgggctg caaagctgtc   3420
ccatcaagga agacagcttc ttgcagcgat acagctcaga ccccacaggc gccttgactg   3480
aggacagcat agacgacacc ttcctcccag tgcctgaata cataaaccag tccgttccca   3540
aaaggcccgc tggctctgtg cagaatcctg tctatcacaa tcagcctctg aacccgcgc   3600
```

| | |
|---|---:|
| ccagcagaga cccacactac caggacccca acagcactgc agtgggcaac ccgagtatc | 3660 |
| tcaacactgt ccagcccacc tgtgtcaaca gcacattcga cagccctgcc cactgggccc | 3720 |
| agaaaggcag ccaccaaatt agcctggaca accctgacta ccagcaggac ttctttccca | 3780 |
| aggaagccaa gccaaatggc atctttaagg gctccacagc tgaaaatgca gaatacctaa | 3840 |
| gggtcgcgcc acaaagcagt gaatttattg gagcatga | 3878 |

<210> SEQ ID NO 760
<211> LENGTH: 3878
<212> TYPE: DNA
<213> ORGANISM: Homo sapiens

<400> SEQUENCE: 760

| | |
|---|---:|
| cccggcgcag cgcggccgca gcagcctccg cccccgcac ggtgtgagcg ccgacgcgg | 60 |
| ccgaggcggc cggagtcccg agctagcccc ggcggccgcc gccgcccaga ccggacgaca | 120 |
| ggccacctcg tcggcgtccg cccgagtccc cgcctcgccg caacgccac aaccaccgcg | 180 |
| cacggccccc tgactccgtc cagtattgat cgggagagcc ggagcgagct cttcggggag | 240 |
| cagcgatgcg accctccggg acggccgggg cagcgctcct ggcgctgctg gctgcgctct | 300 |
| gcccggcgag tcgggctctg gaggaaaaga agtttgccca aggcacgagt aacaagctca | 360 |
| cgcagttggg cacttttgaa gatcattttc tcagcctcca gaggatgttc aataactgtg | 420 |
| aggtggtcct tgggaatttg gaaattacct atgtgcagag gaattatgat cttccttct | 480 |
| taaagaccat ccaggaggtg gctggttatg tcctcattgc cctcaacaca gtggagcgaa | 540 |
| ttcctttgga aaacctgcag atcatcagag gaaatatgta ctacgaaaat tcctatgcct | 600 |
| tagcagtctt atctaactat gatgcaaata aaaccggact gaaggagctg cccatgagaa | 660 |
| atttacagga atcctgcat ggcgccgtgc ggttcagcaa caaccctgcc ctgtgcaacg | 720 |
| tggagagcat ccagtggcgg gacatagtca gcagtgactt tctcagcaac atgtcgatgg | 780 |
| acttccagaa ccacctgggc agctgccaaa agtgtgatcc aagctgtccc aatgggagct | 840 |
| gctggggtgc aggagaggag aactgccaga aactgaccaa aatcatctgt gcccagcagt | 900 |
| gctccgggcg ctgccgtggc aagtccccca gtgactgctg ccacaaccag tgtgctgcag | 960 |
| gctgcacagg ccccgggag agcgactgcc tggtctgccg caaattccga gacgaagcca | 1020 |
| cgtgcaagga cacctgcccc ccactcatgc tctacaaccc caccacgtac cagatggatg | 1080 |
| tgaaccccga gggcaaatac agctttggtg ccacctgcgt gaagaagtgt ccccgtaatt | 1140 |
| atgtggtgac agatcacggc tcgtgcgtcc gagcctgtgg ggccgacagc tatgagatgg | 1200 |
| aggaagacgg cgtccgcaag tgtaagaagt gcgaagggcc ttgccgcaaa gtgtgtaacg | 1260 |
| gaataggtat tggtgaattt aaagactcac tctccataaa tgctacgaat attaaacact | 1320 |
| tcaaaaactg cacctccatc agtggcgatc tccacatcct gccggtggca tttagggggtg | 1380 |
| actccttcac acatactcct cctctggatc cacaggaact ggatattctg aaaaccgtaa | 1440 |
| aggaaatcac agggttttg ctgattcagg cttggcctga aaacaggacg gacctccatg | 1500 |
| cctttgagaa cctagaaatc atacgcggca ggaccaagca acatggtcag ttttctcttg | 1560 |
| cagtcgtcag cctgaacata acatccttgg gattacgctc cctcaaggag ataagtgatg | 1620 |
| gagatgtgat aatttcagga aacaaaaatt tgtgctatgc aaatacaata aactggaaaa | 1680 |
| aactgttgg gacctccggt cagaaaacca aaattataag caacagaggt gaaaacagct | 1740 |
| gcaaggccac aggccaggtc tgccatgcct tgtgctcccc cgagggctgc tggggcccgg | 1800 |
| agcccaggga ctgcgtctct tgccggaatg tcagccgagg cagggaatgc gtggacaagt | 1860 |

```
gcaaccttct ggagggtgag ccaagggagt ttgtggagaa ctctgagtgc atacagtgcc   1920
acccagagtg cctgcctcag gccatgaaca tcacctgcac aggacgggga ccagacaact   1980
gtatccagtg tgcccactac attgacggcc cccactgcgt caagacctgc ccggcaggag   2040
tcatgggaga aaacaacacc ctggtctgga agtacgcaga cgccggccat gtgtgccacc   2100
tgtgccatcc aaactgcacc tacggatgca ctgggccagg tcttgaaggc tgtccaacga   2160
atgggcctaa gatcccgtcc atcgccactg ggatggtggg ggccctcctc ttgctgctgg   2220
tggtggccct ggggatcggc ctcttcatgc gaaggcgcca catcgttcgg aagcgcacgc   2280
tgcggaggct gctgcaggag agggagcttg tggagcctct tacacccagt ggagaagctc   2340
ccaaccaagc tctcttgagg atcttgaagg aaactgaatt caaaaagatc aaagtgctgg   2400
gctccggtgc gttcggcacg tgtataagg actctggat cccagaaggt gagaaagtta   2460
aaattcccgt cgctatcaag gaattaagag aagcaacatc tccgaaagcc aacaaggaaa   2520
tcctcgatga agcctacgtg atggccagcg tggacaaccc ccacgtgtgc cgcctgctgg   2580
gcatctgcct cacctccacc gtgcagctca tcacgcagct catgcccttc ggctgcctcc   2640
tggactatgt ccgggaacac aaagacaata ttggctccca gtacctgctc aactggtgtg   2700
tgcagatcgc aaagggcatg aactacttgg aggaccgtcg cttggtgcac cgcgacctgg   2760
cagccaggaa cgtactggtg aaaacaccgc agcatgtcaa gatcacagat tttgggcggg   2820
ccaaactgct gggtgcggaa gagaaagaat accatgcaga aggaggcaaa gtgcctatca   2880
agtggatggc attggaatca attttacaca gaatctatac ccaccagagt gatgtctgga   2940
gctacggggt gactgtttgg gagttgatga cctttggatc caagccatat gacggaatcc   3000
ctgccagcga gatcctctcc atcctggaga aggagaacg cctccctcag ccacccatat   3060
gtaccatcga tgtctacatg atcatggtca agtgctggat gatagacgca gatagtcgcc   3120
caaagttccg tgagttgatc atcgaattct ccaaaatggc ccgagacccc cagcgctacc   3180
ttgtcattca gggggatgaa agaatgcatt tgccaagtcc tacagactcc aacttctacc   3240
gtgccctgat ggatgaagaa gacatggacg acgtggtgga tgccgacgag tacctcatcc   3300
cacagcaggg cttcttcagc agcccctcca cgtcacggac tcccctcctg agctctctga   3360
gtgcaaccag caacaattcc accgtggctt gcattgatag aaatgggctg caaagctgtc   3420
ccatcaagga agacagcttc ttgcagcgat acagctcaga ccccacaggc gccttgactg   3480
aggacagcat agacgacacc ttcctcccag tgcctgaata cataaaccag tccgttccca   3540
aaaggcccgc tggctctgtg cagaatcctg tctatcacaa tcagcctctg aaccccgcgc   3600
ccagcagaga cccacactac caggaccccc acagcactgc agtgggcaac cccgagtatc   3660
tcaacactgt ccagcccacc tgtgtcaaca gcacattcga cagccctgcc cactgggccc   3720
agaaaggcag ccaccaaatt agcctggaca accctgacta ccagcaggac ttctttccca   3780
aggaagccaa gccaaatggc atctttaagg gctccacagt gaaaatgca gaatacctaa   3840 gggtcgcgcc acaaagcagt gaatttattg gagcatga                           3878
```

<210> SEQ ID NO 761
<211> LENGTH: 3878
<212> TYPE: DNA
<213> ORGANISM: Homo sapiens

<400> SEQUENCE: 761

```
cccggcgcag cgcggccgca gcagcctccg ccccccgcac ggtgtgagcg cccgacgcgg   60
```

-continued

```
ccgaggcggc cggagtcccg agctagcccc ggcggccgcc gccgcccaga ccggacgaca    120
ggccacctcg tcggcgtccg cccgagtccc cgcctcgccg ccaacgccac aaccaccgcg    180
cacggccccc tgactccgtc cagtattgat cgggagagcc ggagcgagct cttcggggag    240
cagcgatgcg accctccggg acggccgggg cagcgctcct ggcgctgctg gctgcgctct    300
gcccggcgag tcgggctctg gaggaaaaga aagtttgcca aggcacgagt aacaagctca    360
cgcagttggg cacttttgaa gatcattttc tcagcctcca gaggatgttc ataactgtg    420
aggtggtcct tgggaatttg gaaattacct atgtgcagag gaattatgat ctttccttct    480
taaagaccat ccaggaggtg gctggttatg tcctcattgc cctcaacaca gtggagcgaa    540
ttcctttgga aaacctgcag atcatcagag gaaatatgta ctacgaaaat tcctatgcct    600
tagcagtctt atctaactat gatgcaaata aaaccggact gaaggagctg cccatgagaa    660
atttacagga atcctgcat ggcgccgtgc ggttcagcaa caaccctgcc ctgtgcaacg    720
tggagagcat ccagtggcgg gacatagtca gcagtgactt tctcagcaac atgtcgatgg    780
acttccagaa ccacctgggc agctgccaaa agtgtgatcc aagctgtccc aatgggagct    840
gctggggtgc aggagaggag aactgccaga aactgaccaa aatcatctgt gcccagcagt    900
gctccgggcg ctgccgtggc aagtccccca gtgactgctg ccacaaccag tgtgctgcag    960
gctgcacagg cccccgggag agcgactgcc tggtctgccg caaattccga gacgaagcca    1020
cgtgcaagga cacctgcccc ccactcatgc tctacaaccc caccacgtac cagatggatg    1080
tgaaccccga gggcaaatac agctttggtg ccacctgcgt gaagaagtgt ccccgtaatt    1140
atgtggtgac agatcacggc tcgtgcgtcc gagcctgtgg ggccgacagc tatgagatgg    1200
aggaagacgg cgtccgcaag tgtaagaagt gcgaagggcc ttgccgcaaa gtgtgtaacg    1260
gaataggtat tggtgaattt aaagactcac tctccataaa tgctacgaat attaaacact    1320
tcaaaaactg cacctccatc agtggcgatc tccacatcct gccggtggca tttaggggtg    1380
actccttcac acatactcct cctctggatc cacaggaact ggatattctg aaaaccgtaa    1440
aggaaatcac agggtttttg ctgattcagg cttggcctga aaacaggacg gacctccatg    1500
cctttgagaa cctagaaatc atacgcggca ggaccaagca acatggtcag ttttctcttg    1560
cagtcgtcag cctgaacata acatccttgg gattacgctc cctcaaggag ataagtgatg    1620
gagatgtgat aatttcagga aacaaaaatt tgtgctatgc aaatacaata aactggaaaa    1680
aactgtttgg gacctccggt cagaaaacca aaattataag caacagaggt gaaaacagct    1740
gcaaggccac aggccaggtc tgccatgcct tgtgctcccc cgagggctgc tggggcccgg    1800
agcccaggga ctgcgtctct tgccggaatg tcagccgagg cagggaatgc gtggacaagt    1860
gcaaccttct ggagggtgag ccaagggagt tgtggagaa ctctgagtgc atacagtgcc    1920
acccagagtg cctgcctcag gccatgaaca tcacctgcac aggacgggga ccagacaact    1980
gtatccagtg tgcccactac attgacggcc ccactgcgt caagacctgc ccggcaggag    2040
tcatgggaga aaacaacacc ctggtctgga agtacgcaga cgccggccat gtgtgccacc    2100
tgtgccatcc aaactgcacc tacggatgca ctgggccagg tcttgaaggc tgtccaacga    2160
atgggcctaa gatcccgtcc atcgccactg ggatggtggg ggcctcctc ttgctgctgg    2220
tggtggccct ggggatcggc ctcttcatgc gaaggcgcca catcgttcgg aagcgcacgc    2280
tgcggaggct gctgcaggag agggagcttg tggagcctct tacacccagt ggagaagctc    2340
ccaaccaagc tctcttgagg atcttgaagg aaactgaatt caaaaagatc aaagtgctgg    2400
gctccggtgc gttcggcacg gtgtataagg gactctggat cccagaaggt gagaaagtta    2460
```

```
aaattcccgt cgctatcaag gaattaagag aagcaacatc tccgaaagcc aacaaggaaa    2520
tcctcgatga agcctacgtg atggccagcg tggacaaccc ccacgtgtgc cgcctgctgg    2580
gcatctgcct cacctccacc gtgcagctca tcacgcagct catgcccttc ggctgcctcc    2640
tggactatgt ccgggaacac aaagacaata ttggctccca gtacctgctc aactggtgtg    2700
tgcagatcgc aaagggcatg aactacttgg aggaccgtcg cttggtgcac cgcgacctgg    2760
cagccaggaa cgtactggtg aaaacaccgc agcatgtcaa gatcacagat tttgggcggg    2820
ccaaactgct gggtgcggaa gagaaagaat accatgcaga aggaggcaaa gtgcctatca    2880
agtggatggc attggaatca attttacaca gaatctatac ccaccagagt gatgtctgga    2940
gctacggggt gactgtttgg gagttgatga cctttggatc caagccatat gacggaatcc    3000
ctgccagcga gatctcctcc atcctggaga aggagaacg cctccctcag ccacccatat    3060
gtaccatcga tgtctacatg atcatggtca agtgctggat gatagacgca gatagtcgcc    3120
caaagttccg tgagttgatc atcgaattct ccaaaatggc ccgagacccc cagcgctacc    3180
ttgtcattca gggggatgaa agaatgcatt tgccaagtcc tacagactcc aacttctacc    3240
gtgccctgat ggatgaagaa gacatggacg acgtggtgga tgccgacgag tacctcatcc    3300
cacagcaggg cttcttcagc agcccctcca cgtcacggac tcccctcctg agctctctga    3360
gtgcaaccag caacaattcc accgtggctt gcattgatag aaatgggctg caaagctgtc    3420
ccatcaagga agacagcttc ttgcagcgat acagctcaga ccccacaggc gccttgactg    3480
aggacagcat agacgacacc ttcctcccag tgcctgaata cataaaccag tccgttccca    3540
aaaggcccgc tggctctgtg cagaatcctg tctatcacaa tcagcctctg aaccccgcgc    3600
ccagcagaga cccacactac caggaccccc acagcactgc agtgggcaac ccgagtatc    3660
tcaacactgt ccagcccacc tgtgtcaaca gcacattcga cagccctgcc cactgggccc    3720
agaaaggcag ccaccaaatt agcctggaca accctgacta ccagcaggac ttctttccca    3780
aggaagccaa gccaaatggc atctttaagg gctccacagc tgaaaatgca gaatacctaa    3840
gggtcgcgcc acaaagcagt gaatttattg gagcatga                            3878
```

<210> SEQ ID NO 762
<211> LENGTH: 3878
<212> TYPE: DNA
<213> ORGANISM: Homo sapiens

<400> SEQUENCE: 762

```
cccggcgcag cgcggccgca gcagcctccg ccccccgcac ggtgtgagcg cccgacgcgg      60
ccgaggcggc cggagtcccg agctagcccc ggcggccgcc gcgcccagga ccggacgaca     120
ggccacctcg tcggcgtccg cccgagtccc cgcctcgccg ccaacgccac aaccaccgcg     180
cacggccccc tgactccgtc cagtattgat cgggagagcc ggagcgagct cttcggggag     240
cagcgatgcg accctccggg acggccgggg cagcgctcct ggcgctgctg ctgcgctct     300
gcccggcgag tcgggctctg gaggaaaaga aagtttgcca aggcacgagt aacaagctca     360
cgcagttggg cacttttgaa gatcattttc tcagcctcca gaggatgttc ataactgtg     420
aggtggtcct tgggaatttg gaaattacct atgtgcagag gaattatgat ctttccttct     480
taaagaccat ccaggaggtg gctggttatg tcctcattgc cctcaacaca gtggagcgaa     540
ttcctttgga aaacctgcag atcatcagag gaaatatgta ctacgaaaat tcctatgcct     600
tagcagtctt atctaactat gatgcaaata aaaccggact gaaggagctg cccatgagaa     660
```

```
atttacagga aatcctgcat ggcgccgtgc ggttcagcaa caaccctgcc ctgtgcaacg    720
tggagagcat ccagtggcgg gacatagtca gcagtgactt tctcagcaac atgtcgatgg    780
acttccagaa ccacctgggc agctgccaaa agtgtgatcc aagctgtccc aatgggagct    840
gctggggtgc aggagaggag aactgccaga aactgaccaa aatcatctgt gcccagcagt    900
gctccgggcg ctgccgtggc aagtccccca gtgactgctg ccacaaccag tgtgctgcag    960
gctgcacagg cccccgggag agcgactgcc tggtctgccg caaattccga gacgaagcca    1020
cgtgcaagga cacctgcccc ccactcatgc tctacaaccc caccacgtac cagatggatg    1080
tgaaccccga gggcaaatac agctttggtg ccacctgcgt gaagaagtgt ccccgtaatt    1140
atgtggtgac agatcacggc tcgtgcgtcc gagcctgtgg ggccgacagc tatgagatgg    1200
aggaagacgg cgtccgcaag tgtaagaagt gcgaagggcc ttgccgcaaa gtgtgtaacg    1260
gaataggtat tggtgaattt aaagactcac tctccataaa tgctacgaat attaaacact    1320
tcaaaaactg cacctccatc agtggcgatc tccacatcct gccggtggca tttaggggtg    1380
actccttcac acatactcct cctctggatc cacaggaact ggatattctg aaaaccgtaa    1440
aggaaatcac agggtttttg ctgattcagg cttggcctga aaacaggacg gacctccatg    1500
cctttgagaa cctagaaatc atacgcgcca ggaccaagca acatggtcag ttttctcttg    1560
cagtcgtcag cctgaacata acatccttgg gattacgctc cctcaaggag ataagtgatg    1620
gagatgtgat aatttcagga aacaaaaatt tgtgctatgc aaatacaata aactggaaaa    1680
aactgtttgg gacctccggt cagaaaacca aaattataag caacagaggt gaaaacagct    1740
gcaaggccac aggccaggtc tgccatgcct tgtgctcccc cgagggctgc tggggcccgg    1800
agcccaggga ctgcgtctct tgccggaatg tcagccgagg cagggaatgc gtggacaagt    1860
gcaaccttct ggagggtgag ccaagggagt tgtggagaa ctctgagtgc atacagtgcc    1920
acccagagtg cctgcctcag gccatgaaca tcacctgcac aggacgggga ccagacaact    1980
gtatccagtg tgcccactac attgacggcc ccactgcgt caagacctgc ccggcaggag    2040
tcatgggaga aaacaacacc ctggtctgga gtacgcaga cgccggccat gtgtgccacc    2100
tgtgccatcc aaactgcacc tacgatgca ctgggccagg tcttgaaggc tgtccaacga    2160
atgggcctaa gatcccgtcc atcgccactg ggatggtggg ggccctcctc ttgctgctgg    2220
tggtggccct ggggatcggc ctcttcatgc gaaggcgcca catcgttcgg aagcgcacgc    2280
tgcggaggct gctgcaggag agggagcttg tggagcctct tacacccagt ggagaagctc    2340
ccaaccaagc tctcttgagg atcttgaagg aaactgaatt caaaaagatc aaagtgctgg    2400
gctccggtgc gttcggcacg gtgtataagg gactctggat cccagaaggt gagaaagtta    2460
aaattcccgt cgctatcaag gaattaagag aagcaacatc tccgaaagcc aacaaggaaa    2520
tcctcgatga agcctacgtg atggccagcg tggacaaccc ccacgtgtgc cgcctgctgg    2580
gcatctgcct cacctccacc gtgcagctca tcacgcagct catgcccttc ggctgcctcc    2640
tggactatgt ccgggaacac aaagacaata ttggctccca gtacctgctc aactggtgtg    2700
tgcagatcgc aaagggcatg aactacttgg aggaccgtcg cttggtgcac cgcgacctgg    2760
cagccaggaa cgtactggtg aaaacaccgc agcatgtcaa gatcacagat tttgggctgg    2820
ccaaacagct gggtgcggaa gagaaagaat accatgcaga aggaggcaaa gtgcctatca    2880
agtggatggc attggaatca attttacaca gaatctatac ccaccagagt gatgtctgga    2940
gctacggggt gactgtttgg gagttgatga cctttggatc caagccatat gacggaatcc    3000
ctgccagcga gatctcctcc atcctggaga aaggagaacg cctccctcag ccacccatat    3060
```

```
gtaccatcga tgtctacatg atcatggtca agtgctggat gatagacgca gatagtcgcc  3120
caaagttccg tgagttgatc atcgaattct ccaaaatggc ccgagacccc cagcgctacc  3180
ttgtcattca gggggatgaa agaatgcatt tgccaagtcc tacagactcc aacttctacc  3240
gtgccctgat ggatgaagaa gacatggacg acgtggtgga tgccgacgag tacctcatcc  3300
cacagcaggg cttcttcagc agcccctcca cgtcacggac tcccctcctg agctctctga  3360
gtgcaaccag caacaattcc accgtggctt gcattgatag aaatgggctg caaagctgtc  3420
ccatcaagga agacagcttc ttgcagcgat acagctcaga ccccacaggc gccttgactg  3480
aggacagcat agacgacacc ttcctcccag tgcctgaata cataaaccag tccgttccca  3540
aaaggcccgc tggctctgtg cagaatcctg tctatcacaa tcagcctctg aaccccgcgc  3600
ccagcagaga cccacactac caggaccccc acagcactgc agtgggcaac ccgagtatc   3660 tcaacactgt ccagcccacc tgtgtcaaca gcacattcga cagccctgcc cactgggccc  3720
agaaaggcag ccaccaaatt agcctggaca accctgacta ccagcaggac ttctttccca  3780
aggaagccaa gccaaatggc atctttaagg gctccacagc tgaaaatgca gaatacctaa  3840
gggtcgcgcc acaaagcagt gaatttattg gagcatga                         3878
```

METHOD TO DETERMINE RESPONSIVENESS OF CANCER TO EPIDERMAL GROWTH FACTOR RECEPTOR TARGETING TREATMENTS

CROSS REFERENCE TO RELATED APPLICATIONS

This application is a continuation of U.S. application Ser. No. 14/638,779, filed Mar. 4, 2015, which is a continuation of U.S. application Ser. No. 13/896,772, filed May 17, 2013, now U.S. Pat. No. 9,035,036, issued May 19, 2015, which is a continuation of U.S. application Ser. No. 11/894,160, filed Aug. 20, 2007, now U.S. Pat. No. 8,465,916, issued Jun. 18, 2013, which is a continuation of U.S. application Ser. No. 11/294,621, filed Dec. 5, 2005, now U.S. Pat. No. 7,294,468, issued Nov. 13, 2007, which is a continuation of International Application No. PCT/US2005/010645, filed Mar. 31, 2005, which is hereby incorporated by reference in its entirety, which claims benefit under 35 U.S.C. § 119(e) of U.S. Provisional Application Ser. No. 60/558,218 filed Mar. 31, 2004, U.S. Provisional Application Ser. No. 60/561,095 filed Apr. 9, 2004, U.S. Provisional Application Ser. No. 60/565,753 filed Apr. 27, 2004, U.S. Provisional Application No. 60/565,985 filed Apr. 27, 2004, U.S. Provisional Application Ser. No. 60/574,035 filed May 25, 2004, U.S. Provisional Application Ser. No. 60/577,916 filed Jun. 7, 2004 and U.S. Provisional Application Ser. No. 60/592,287 filed Jul. 29, 2004, the contents of which are herein incorporated by reference in their entirety.

GOVERNMENT SUPPORT

This invention was made with government support under Grant Nos. RO1 CA 092824, P50 CA 090578, PO1 95281, and 1K12CA87723-01 awarded by The National Institutes for Health. The government has certain rights in the invention.

SEQUENCE LISTING

The instant application contains a Sequence Listing which has been submitted in ASCII format via EFS-Web and is hereby incorporated by reference in its entirety. Said ASCII copy, created on Apr. 30, 2008, is named Sequence_Listing_Text.txt and is 456,205 bytes in size.

BACKGROUND

Epithelial cell cancers, for example, prostate cancer, breast cancer, colon cancer, lung cancer, pancreatic cancer, ovarian cancer, cancer of the spleen, testicular cancer, cancer of the thymus, etc., are diseases characterized by abnormal, accelerated growth of epithelial cells. This accelerated growth initially causes a tumor to form. Eventually, metastasis to different organ sites can also occur. Although progress has been made in the diagnosis and treatment of various cancers, these diseases still result in significant mortality.

Lung cancer remains the leading cause of cancer death in industrialized countries. Cancers that begin in the lungs are divided into two major types, non-small cell lung cancer and small cell lung cancer, depending on how the cells appear under a microscope. Non-small cell lung cancer (squamous cell carcinoma, adenocarcinoma, and large cell carcinoma) generally spreads to other organs more slowly than does small cell lung cancer. About 75 percent of lung cancer cases are categorized as non-small cell lung cancer (e.g., adenocarcinomas), and the other 25 percent are small cell lung cancer. Non-small cell lung cancer (NSCLC) is the leading cause of cancer deaths in the United States, Japan and Western Europe. For patients with advanced disease, chemotherapy provides a modest benefit in survival, but at the cost of significant toxicity, underscoring the need for therapeutic agents that are specifically targeted to the critical genetic lesions that direct tumor growth (Schiller J H et al., N Engl J Med, 346: 92-98, 2002).

Epidermal growth factor receptor (EGFR) is a 170 kilodalton (kDa) membrane-bound protein expressed on the surface of epithelial cells. EGFR is a member of the growth factor receptor family of protein tyrosine kinases, a class of cell cycle regulatory molecules. (W. J. Gullick et al., 1986, Cancer Res., 46:285-292). EGFR is activated when its ligand (either EGF or TGF-α) binds to the extracellular domain, resulting in autophosphorylation of the receptor's intracellular tyrosine kinase domain (S. Cohen et al., 1980, J. Biol. Chem., 255:4834-4842; A. B. Schreiber et al., 1983, J. Biol. Chem., 258:846-853).

EGFR is the protein product of a growth promoting oncogene, erbB or ErbB1, that is but one member of a family, i.e., the ERBB family of protooncogenes, believed to play pivotal roles in the development and progression of many human cancers. In particular, increased expression of EGFR has been observed in breast, bladder, lung, head, neck and stomach cancer as well as glioblastomas. The ERBB family of oncogenes encodes four, structurally-related transmembrane receptors, namely, EGFR, HER-2/neu (erbB2), HER-3 (erbB3) and HER-4 (erbB4). Clinically, ERBB oncogene amplification and/or receptor overexpression in tumors have been reported to correlate with disease recurrence and poor patient prognosis, as well as with responsiveness in therapy. (L. Harris et al., 1999, Int. J. Biol. Markers, 14:8-15; and J. Mendelsohn and J. Baselga, 2000, Oncogene, 19:6550-6565).

EGFR is composed of three principal domains, namely, the extracellular domain (ECD), which is glycosylated and contains the ligand-binding pocket with two cysteine-rich regions; a short transmembrane domain, and an intracellular domain that has intrinsic tyrosine kinase activity. The transmembrane region joins the ligand-binding domain to the intracellular domain. Amino acid and DNA sequence analysis, as well as studies of nonglycosylated forms of EGFR, indicate that the protein backbone of EGFR has a mass of 132 kDa, with 1186 amino acid residues (A. L. Ullrich et al., 1984, Nature, 307:418-425; J. Downward et al., 1984, Nature, 307:521-527; C. R. Carlin et al., 1986, Mol. Cell. Biol., 6:257-264; and F. L. V. Mayes and M. D. Waterfield, 1984, The EMBO J., 3:531-537).

The binding of EGF or TGF-α to EGFR activates a signal transduction pathway and results in cell proliferation. The dimerization, conformational changes and internalization of EGFR molecules function to transmit intracellular signals leading to cell growth regulation (G. Carpenter and S. Cohen, 1979, Ann. Rev. Biochem., 48:193-216). Genetic alterations that affect the regulation of growth factor receptor function, or lead to overexpression of receptor and/or ligand, result in cell proliferation. In addition, EGFR has been determined to play a role in cell differentiation, enhancement of cell motility, protein secretion, neovascularization, invasion, metastasis and resistance of cancer cells to chemotherapeutic agents and radiation. (M.-J. Oh et al., 2000, Clin. Cancer Res., 6:4760-4763).

A variety of inhibitors of EGFR have been identified, including a number already undergoing clinical trials for treatment of various cancers. For a recent summary, see de Bono, J. S. and Rowinsky, E. K. (2002), "The ErbB Receptor Family: A Therapeutic Target For Cancer", *Trends in Molecular Medicine*, 8, S19-26.

A promising set of targets for therapeutic intervention in the treatment of cancer includes the members of the HER-kinase axis. They are frequently upregulated in solid epithelial tumors of, by way of example, the prostate, lung and breast, and are also upregulated in glioblastoma tumors. Epidermal growth factor receptor (EGFR) is a member of the HER-kinase axis, and has been the target of choice for the development of several different cancer therapies. EGFR tyrosine kinase inhibitors (EGFR-TKIs) are among these therapies, since the reversible phosphorylation of tyrosine residues is required for activation of the EGFR pathway. In other words, EGFR-TKIs block a cell surface receptor responsible for triggering and/or maintaining the cell signaling pathway that induces tumor cell growth and division. Specifically, it is believed that these inhibitors interfere with the EGFR kinase domain, referred to as HER-1. Among the more promising EGFR-TKIs are three series of compounds: quinazolines, pyridopyrimidines and pyrrolopyrimidines.

Two of the more advanced compounds in clinical development include Gefitinib (compound ZD1839 developed by AstraZeneca UK Ltd.; available under the tradename IRESSA; hereinafter "IRESSA") and Erlotinib (compound OSI-774 developed by Genentech, Inc. and OSI Pharmaceuticals, Inc.; available under the tradename TARCEVA; hereinafter "TARCEVA"); both have generated encouraging clinical results. Conventional cancer treatment with both IRESSA and TARCEVA involves the daily, oral administration of no more than 500 mg of the respective compounds. In May, 2003, IRESSA became the first of these products to reach the United States market, when it was approved for the treatment of advanced non-small cell lung cancer patients.

IRESSA is an orally active quinazoline that functions by directly inhibiting tyrosine kinase phosphorylation on the EGFR molecule. It competes for the adenosine triphosphate (ATP) binding site, leading to suppression of the HER-kinase axis. The exact mechanism of the IRESSA response is not completely understood, however, studies suggest that the presence of EGFR is a necessary prerequisite for its action.

A significant limitation in using these compounds is that recipients thereof may develop a resistance to their therapeutic effects after they initially respond to therapy, or they may not respond to EGFR-TKIs to any measurable degree at all. In fact, only 10-15 percent of advanced non-small cell lung cancer patients respond to EGFR kinase inhibitors. Thus, a better understanding of the molecular mechanisms underlying sensitivity to IRESSA and TARCEVA would be extremely beneficial in targeting therapy to those individuals whom are most likely to benefit from such therapy.

There is a significant need in the art for a satisfactory treatment of cancer, and specifically epithelial cell cancers such as lung, ovarian, breast, brain, colon and prostate cancers, which incorporates the benefits of TKI therapy and overcoming the non-responsiveness exhibited by patients. Such a treatment could have a dramatic impact on the health of individuals, and especially older individuals, among whom cancer is especially common.

SUMMARY

Tyrosine kinase inhibitor (TKI) therapy such as gefitinib (IRESSA®) is not effective in the vast majority of individuals that are affected with the cancers noted above. The present inventors have surprisingly discovered that the presence of somatic mutations in the kinase domain of EGFR substantially increases sensitivity of the EGFR to TKI such as IRESSA, TARCEVA. For example less than 30% of patients having such cancer are susceptible to treatment by current TKIs, whereas greater than 50%, more preferably 60, 70, 80, 90% of patients having a mutation in the EGFR kinase domain are susceptible. In addition, these mutations confer increased kinase activity of the EGFR. Thus, patients having these mutations will likely be responsive to current tyrosine kinase inhibitor (TKI) therapy, for example, gefitinib.

Accordingly, the present invention provides a novel method to determine the likelihood of effectiveness of an epidermal growth factor receptor (EGFR) targeting treatment in a human patient affected with cancer. The method comprises detecting the presence or absence of at least one nucleic acid variance in the kinase domain of the erbB1 gene of said patient relative to the wildtype erbB1 gene. The presence of at least one variance indicates that the EGFR targeting treatment is likely to be effective. Preferably, the nucleic acid variance increases the kinase activity of the EGFR. The patient can then be treated with an EGFR targeting treatment. In one embodiment of the present invention, the EGFR targeting treatment is a tyrosine kinase inhibitor. In a preferred embodiment, the tyrosine kinase inhibitor is an anilinoquinazoline. The anilinoquinazoline may be a synthetic anilinoquinazoline. Preferably, the synthetic anilinoquinazoline is either gefitinib or erlotinib. In another embodiment, the EGFR targeting treatment is an irreversible EGFR inhibitor, including 4-dimethylamino-but-2-enoic acid [4-(3-chloro-4-fluoro-phenylamino)-3-cyano-7-ethoxy-quinolin-6-yl]-amide ("EKB-569", sometimes also referred to as "EKI-569", see for example WO/2005/018677 and Torrance et al., Nature Medicine, vol. 6, No. 9, September 2000, p. 1024) and/or HKI-272 or HKI-357 (Wyeth; see Greenberger et al., Proc. 11$^{th}$ NCI EORTC-AACR Symposium on New Drugs in Cancer Therapy, Clinical Cancer Res. Vol. 6 Supplement, November 2000, ISSN 1078-0432; in Rabindran et al., Cancer Res. 64: 3958-3965 (2004); Holbro and Hynes, Ann. Rev. Pharm. Tox. 44:195-217 (2004); Tsou et al, j. Med. Chem. 2005, 48, 1107-1131; and Tejpar et al., J. Clin. Oncol. ASCO Annual Meeting Proc. Vol. 22, No. 14S: 3579 (2004)).

In one embodiment of the present invention, the EGFR is obtained from a biological sample from a patient with or at risk for developing cancer. The variance in the kinase domain of EGFR (or the erbB1 gene) effects the conformational structure of the ATP-binding pocket. Preferably, the variance in the kinase domain of EGFR is an in frame deletion or a substitution in exon 18, 19, 20 or 21.

In one embodiment, the in frame deletion is in exon 19 of EGFR (erbB1). The in frame deletion in exon 19 preferably comprises at deletion of at least amino acids leucine, arginine, glutamic acid and alanine, at codons 747, 748, 749, and 750. In one embodiment, the in-frame deletion comprises nucleotides 2235 to 2249 and deletes amino acids 746 to 750 (the sequence glutamic acid, leucine, arginine, glutamic acid, and alanine), see Table 2, Table S2, FIG. 2B, FIG. 4A, FIG. 5, SEQ ID NO: 511, FIG. 6C, and FIG. 8C. In another embodiment, the in-frame deletion comprises nucleotides 2236 to 2250 and deletes amino acids 746 to 750, see Table S2, FIG. 5, SEQ ID NO: 511, and FIG. 6C. Alternatively, the in-frame deletion comprises nucleotides 2240 to 2251, see Table 2, FIG. 2C, FIG. 4A, FIG. 5, SEQ ID NO: 511, or nucleotides 2240 to 2257, see Table 2, Table S3A, FIG. 2A, FIG. 4A, FIG. 5, SEQ ID NO: 511, FIG. 6C, and FIG. 8E. Alternatively, the in-frame deletion comprises nucleotides 2239 to 2247 together with a substitution of cytosine for guanine at nucleotide 2248, see Table S3A and FIG. 8D, or a deletion of nucleotides 2238 to 2255 together with a substitution of thymine for adenine at nucleotide 2237, see Table S3A and FIG. 8F, or a deletion of nucleotides 2254 to 2277, see Table S2 (SEQ ID NO: 437). Alternatively, the in-frame deletion comprises nucleotides 2239-2250delTTAAGAGAAGCA (SEQ ID NO: 554); 2251A>C, or 2240-2250delTAAGAGAAGCA (SEQ ID NO: 720), or 2257-2271delCCGAAAGCCAACAAG (SEQ ID NO: 721), as shown in Table S3B.

In another embodiment, the substitution is in exon 21 of EGFR. The substitution in exon 21 comprises at least one amino acid. In one embodiment, the substitution in exon 21 comprises a substitution of a guanine for a thymine at nucleotide 2573, see FIG. 4A and FIG. 5, SEQ ID NO: 511. This substitution results in an amino acid substitution, where the wildtype Leucine is replaced with an Arginine at amino acid 858, see FIG. 5, Table 2, Table S2, Table S3A, FIG. 2D, FIG. 6A, FIG. 8B, and SEQ ID NO: 512. Alternatively, the substitution in exon 21 comprises a substitution of an adenine for a thymine at nucleotide 2582, see FIG. 4A and FIG. 5, SEQ ID NO: 511. This substitution results in an amino acid substitution, where the wildtype Leucine is replaced with a Glutamine at amino acid 861, see FIG. 5 (SEQ ID NOS 740-762, respectively, in order of appearance), Table 2 (SEQ ID NOS 730-739, respectively, in order of appearance), FIG. 2E, Table S3B (SEQ ID NOS 554 & 720-729, respectively, in order of appearance), and SEQ ID NO: 512.

The substitution may also be in exon 18 of EGFR. In one embodiment, the substitution is in exon 18 is a thymine for a guanine at nucleotide 2155, see FIG. 4A and FIG. 5, SEQ ID NO: 511. This substitution results in an amino acid substitution, where the wildtype Glycine is substituted with a Cysteine at codon 719, see FIG. 5, SEQ ID NO: 512. In another embodiment, the substitution in exon 18 is an adenine for a guanine at nucleotide 2155 resulting in an amino acid substitution, where the wildtype Glycine is substituted for a Serine at codon 719, see Table S2, FIG. 6B, FIG. 8A, FIG. 5, SEQ ID NO: 511 and 512.

In another embodiment, the substitution is an insertion of guanine, guanine and thymine (GGT) after nucleotide 2316 and before nucleotide 2317 of SEQ ID NO: 511 (2316_2317 ins GGT). This can also be described as an insertion of valine (V) at amino acid 772 (P772_H733 insV). Other mutations are shown in Table S3B and include, for example, and insertion of CAACCCGG after nucleotide 2309 and before nucleotide 2310 of SEQ ID NO 511 and an insertion of GCGTGGACA after nucleotide 2311 and before nucleotide 2312 of SEQ ID NO 511. The substitution may also be in exon 20 and in one embodiment is a substitution of AA for GG at nucleotides 2334 and 2335, see Table S3B.

In summary, in preferred embodiments, the nucleic acid variance of the erbB1 gene is a substitution of a thymine for a guanine or an adenine for a guanine at nucleotide 2155 of SEQ ID NO 511, a deletion of nucleotides 2235 to 2249, 2240 to 2251, 2240 to 2257, 2236 to 2250, 2254 to 2277, or 2236 to 2244 of SEQ ID NO 511, an insertion of nucleotides guanine, guanine, and thymine (GGT) after nucleotide 2316 and before nucleotide 2317 of SEQ ID NO 511, and a substitution of a guanine for a thymine at nucleotide 2573 or an adenine for a thymine at nucleotide 2582 of SEQ ID NO 511.

The detection of the presence or absence of at least one nucleic acid variance can be determined by amplifying a segment of nucleic acid encoding the receptor. The segment to be amplified is 1000 nucleotides in length, preferably, 500 nucleotides in length, and most preferably 100 nucleotides in length or less. The segment to be amplified can include a plurality of variances.

In another embodiment, the detection of the presence or absence of at least one variance provides for contacting EGFR nucleic acid containing a variance site with at least one nucleic acid probe. The probe preferentially hybridizes with a nucleic acid sequence including a variance site and containing complementary nucleotide bases at the variance site under selective hybridization conditions. Hybridization can be detected with a detectable label.

In yet another embodiment, the detection of the presence or absence of at least one variance comprises sequencing at least one nucleic acid sequence and comparing the obtained sequence with the known erbB1 nucleic acid sequence. Alternatively, the presence or absence of at least one variance comprises mass spectrometric determination of at least one nucleic acid sequence.

In a preferred embodiment, the detection of the presence or absence of at least one nucleic acid variance comprises performing a polymerase chain reaction (PCR). The erbB1 nucleic acid sequence containing the hypothetical variance is amplified and the nucleotide sequence of the amplified nucleic acid is determined. Determining the nucleotide sequence of the amplified nucleic acid comprises sequencing at least one nucleic acid segment. Alternatively, amplification products can analyzed by using any method capable of separating the amplification products according to their size, including automated and manual gel electrophoresis and the like.

Alternatively, the detection of the presence or absence of at least one variance comprises determining the haplotype of a plurality of variances in a gene.

In another embodiment, the presence or absence of an EGFR variance can be detected by analyzing the erbB1 gene product (protein). In this embodiment, a probe that specifically binds to a variant EGFR is utilized. In a preferred embodiment, the probe is an antibody that preferentially binds to a variant EGFR. The presence of a variant EGFR predicts the likelihood of effectiveness of an EGFR targeting treatment. Alternatively, the probe may be an antibody fragment, chimeric antibody, humanized antibody or an aptamer.

The present invention further provides a probe which specifically binds under selective binding conditions to a nucleic acid sequence comprising at least one nucleic acid variance in the EGFR gene (erbB1). In one embodiment, the variance is a mutation in the kinase domain of erbB1 that confers a structural change in the ATP-binding pocket.

The probe of the present invention may comprise a nucleic acid sequence of about 500 nucleotide bases, preferably about 100 nucleotides bases, and most preferably about 50 or about 25 nucleotide bases or fewer in length. The probe may be composed of DNA, RNA, or peptide nucleic acid (PNA). Furthermore, the probe may contain a detectable label, such as, for example, a fluorescent or enzymatic label.

The present invention additionally provides a novel method to determine the likelihood of effectiveness of an epidermal growth factor receptor (EGFR) targeting treatment in a patient affected with cancer. The method comprises determining the kinase activity of the EGFR in a biological sample from a patient. An increase in kinase activity following stimulation with an EGFR ligand, compared to a normal control, indicates that the EGFR targeting treatment is likely to be effective.

The present invention further provides a novel method for treating a patient affected with or at risk for developing cancer. The method involves determining whether the kinase domain of the EGFR of a patient contains at least one nucleic acid variance. Preferably, the EGFR is located at the site of the tumor or cancer and the nucleic acid variance is somatic. The presence of such a variance indicates that an EGFR targeted treatment will be effective. If the variance is present, the tyrosine kinase inhibitor is administered to the patient.

As above, the tyrosine kinase inhibitor administered to an identified patient may be an anilinoquinazoline or an irreversible tyrosine kinase inhibitor, such as for example, EKB-569, HKI-272 and/or HKI-357 (Wyeth). Preferably, the anilinoquinazoline is a synthetic anilinoquinazoline and most preferably the synthetic anilinoquinazoline is gefitinib and erlotinib.

The cancer to be treated by the methods of the present invention include, for example, but are not limited to, gastrointestinal cancer, prostate cancer, ovarian cancer, breast cancer, head and neck cancer, lung cancer, non-small cell lung cancer, cancer of the nervous system, kidney cancer, retina cancer, skin cancer, liver cancer, pancreatic cancer, genital-urinary cancer and bladder cancer. In a preferred embodiment, the cancer is non-small cell lung cancer.

A kit for implementing the PCR methods of the present invention is also encompassed. The kit includes at least one degenerate primer pair designed to anneal to nucleic acid regions bordering the genes that encode for the ATP-binding pocket of the EGFR kinase domain. Additionally, the kit contains the products and reagents required to carry out PCR amplification, and instructions.

In a preferred embodiment, the primer pairs contained within the kit are selected from the group consisting of SEQ ID NO: 505, SEQ ID NO: 506, SEQ ID NO: 507, and SEQ ID NO: 508. Also preferred are the primers listed in Table 6 and 7 in the examples.

In yet another embodiment, the present invention discloses a method for selecting a compound that inhibits the catalytic kinase activity of a variant epidermal growth factor receptor (EGFR). As a first step, a variant EGFR is contacted with a potential compound. The resultant kinase activity of the variant EGFR is then detected and a compound is selected that inhibits the kinase activity of the variant EGFR. In one embodiment, the variant EGFR is contained within a cell. The method can also be used to select a compound that inhibits the kinase activity of a variant EGFR having a secondary mutation in the kinase domain that confers resistance to a TKI, e.g., gefitinib or erlotinib.

In one embodiment, the variant EGFR is labeled. In another embodiment, the EGFR is bound to a solid support. In a preferred embodiment, the solid support is a protein chip.

In yet another embodiment of the present invention, a pharmaceutical composition that inhibits the catalytic kinase activity of a variant epidermal growth factor receptor (EGFR) is disclosed. The compound that inhibits the catalytic kinase activity of a variant EGFR is selected from the group consisting of an antibody, antibody fragment, small molecule, peptide, protein, antisense nucleic acid, ribozyme, PNA, siRNA, oligonucleotide aptamer, and peptide aptamer.

A method for treating a patient having an EGFR mediated disease is also disclosed. In accordance with the method, the patient is administered the pharmaceutical composition that inhibits the catalytic kinase activity of a variant epidermal growth factor receptor (EGFR).

In one embodiment, the EGFR mediated disease is cancer. In a preferred embodiment, the cancer is of epithelial origin. For example, the cancer is gastrointestinal cancer, prostate cancer, ovarian cancer, breast cancer, head and neck cancer, lung cancer, non-small cell lung cancer, cancer of the nervous system, kidney cancer, retina cancer, skin cancer, liver cancer, pancreatic cancer, genital-urinary cancer and bladder cancer. In a preferred embodiment, the cancer is non-small cell lung cancer.

In another embodiment, a method for predicting the acquisition of secondary mutations (or selecting for mutations) in the kinase domain of the erbB1 gene is disclosed. A cell expressing a variant form of the erbB1 gene is contacted with an effective, yet sub-lethal dose of a tyrosine kinase inhibitor. Cells that are resistant to a growth arrest effect of the tyrosine kinase inhibitor are selected and the erbB1 nucleic acid is analyzed for the presence of additional mutations in the erbB1 kinase domain. In one embodiment, the cell is in vitro. In another embodiment, the cell is obtained from a transgenic animal. In one embodiment, the transgenic animal is a mouse. In this mouse model, cells to be studied are obtained from a tumor biopsy. Cells containing a secondary mutation in the erbB1 kinase domain selected by the present invention can be used in the above methods to select a compound that inhibits the kinase activity of the variant EGFR having a secondary mutation in the kinase domain.

In an alternative embodiment for predicting the acquisition of secondary mutations in the kinase domain of the erbB1 gene, cells expressing a variant form of the erbB1 gene are first contacted with an effective amount of a mutagenizing agent. The mutagenizing is, for example, ethyl methanesulfonate (EMS), N-ethyl-N-nitrosourea (ENU), N-methyl-N-nitrosourea (MNU), phocarbaxine hydrochloride (Prc), methyl methanesulfonate (MeMS), chlorambucil (Chl), melphalan, porcarbazine hydrochloride, cyclophosphamide (Cp), diethyl sulfate ($Et_2SO_4$), acrylamide monomer (AA), triethylene melamin (TEM), nitrogen mustard, vincristine, dimethylnitrosamine, N-methyl-N'-nitro-Nitrosoguanidine (MNNG), 7,12 dimethylbenz(a)anthracene (DMBA), ethylene oxide, hexamethylphosphoramide, bisulfan, or ethyl methanesulforate (EtMs). The cell is then contacted with an effective, yet sub-lethal dose of a tyrosine kinase inhibitor. Cells that are resistant to a growth arrest effect of the tyrosine kinase inhibitor are selected and the erbB1 nucleic acid is analyzed for the presence of additional mutations in the erbB1 kinase domain.

BRIEF DESCRIPTION OF THE FIGURES

FIGS. 2A-2F show EGFR mutations in Gefitinib-responsive tumors.

FIGS. 2A-2C show nucleotide sequence of the EGFR gene in tumor specimens with heterozygous in-frame deletions within the kinase domain (double peaks) (SEQ ID NOS 643, 644 and 690-699, respectively, in order of appearance). Tracings in both sense and antisense directions are shown to demonstrate the two breakpoints of the deletion; wild-type nucleotide sequence is shown in capital letters, and the mutant sequence is in lowercase letters. The 5' breakpoint of the delL747-T751insS mutation is preceded by a T to C substitution that does not alter the encoded amino acid.

Figure 2A:
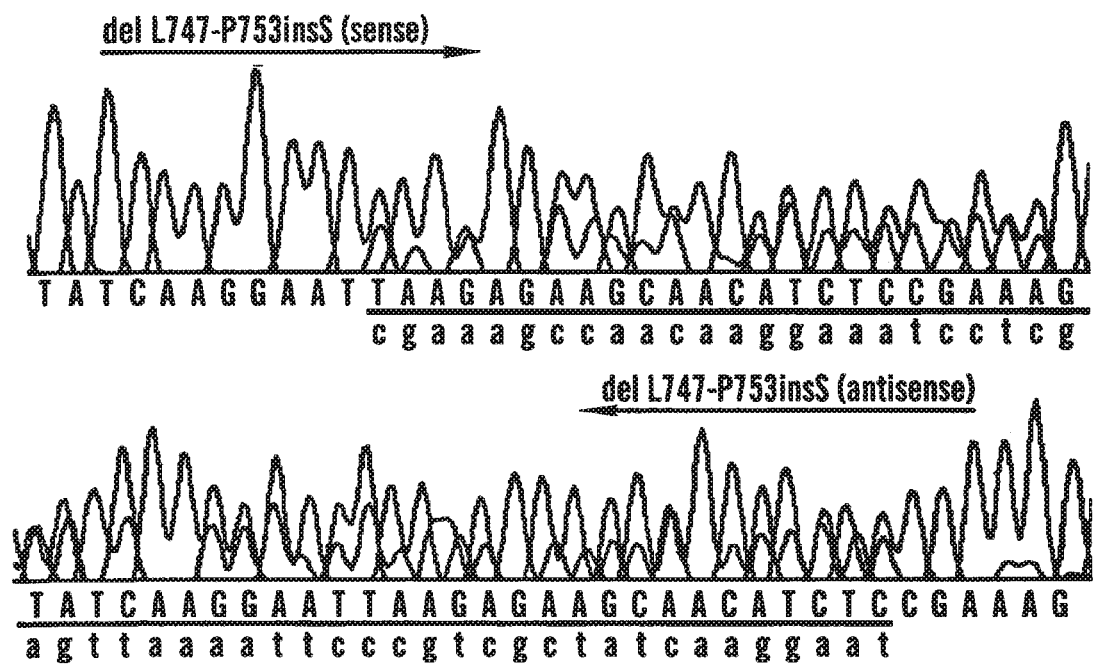
Figure 2B:
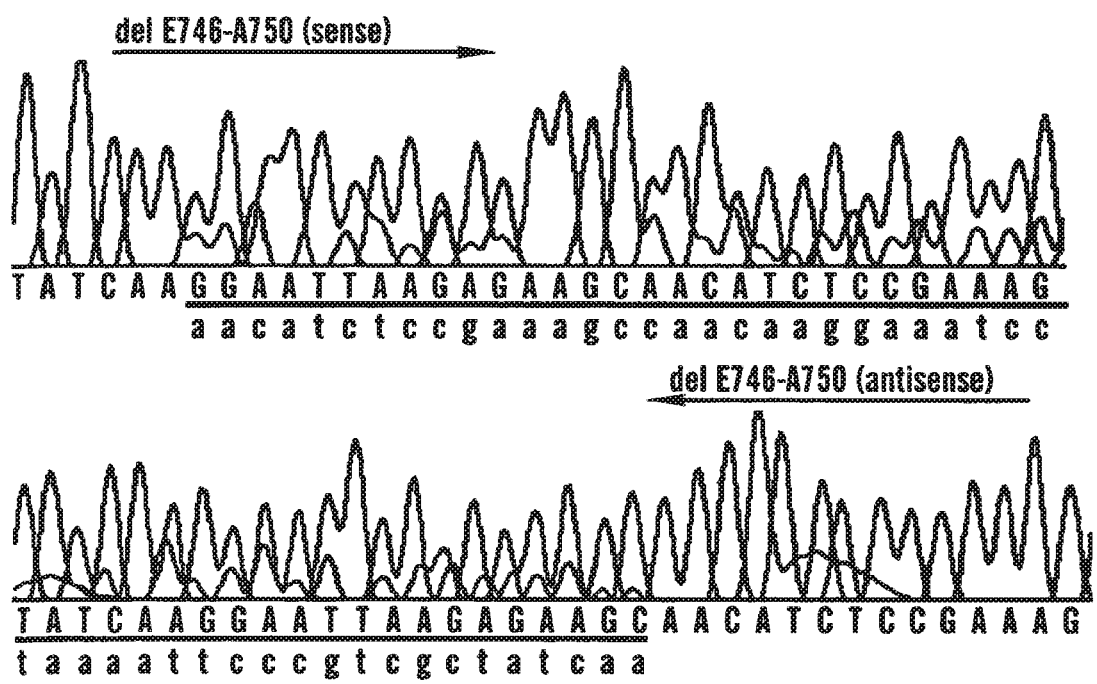
Figure 2C:
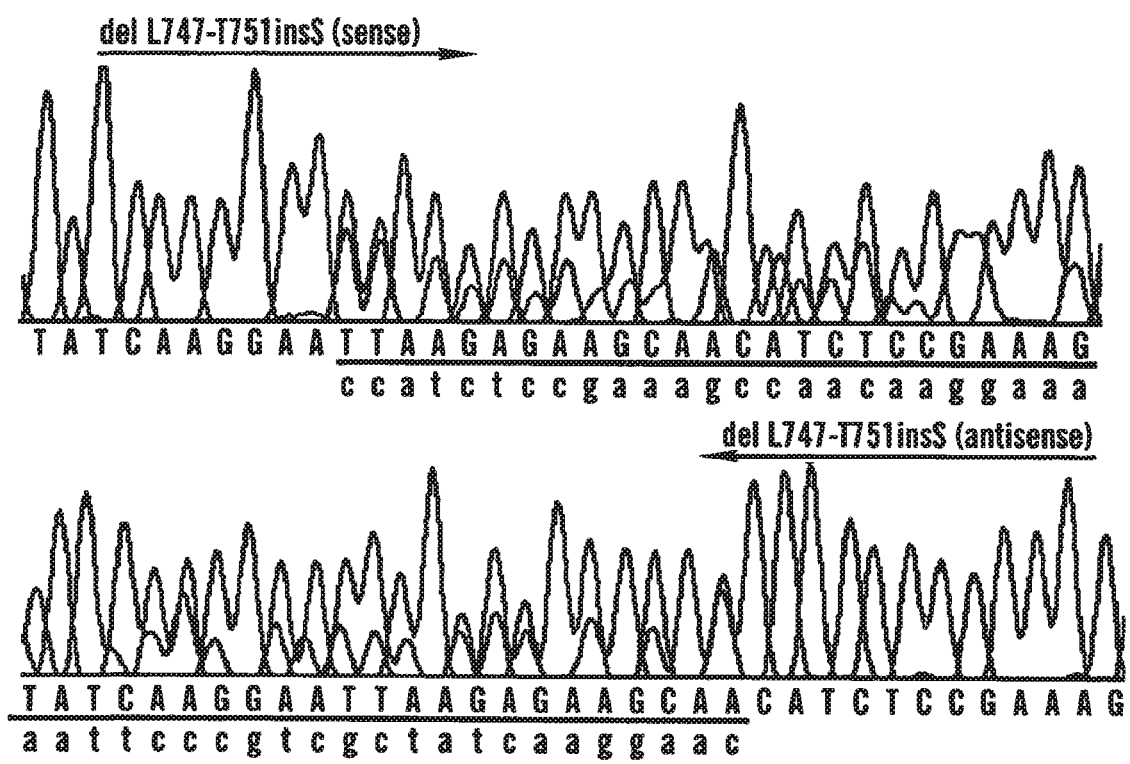

FIG. 2D and FIG. 2E show heterozygous missense mutations (arrows) resulting in amino acid substitutions within the tyrosine kinase domain (SEQ ID NOS 701 & 703). The double peaks represent two nucleotides at the site of heterozygous mutations. For comparison, the corresponding wild-type sequence is also shown (SEQ ID NOS 700 & 702).

Figure 2F:
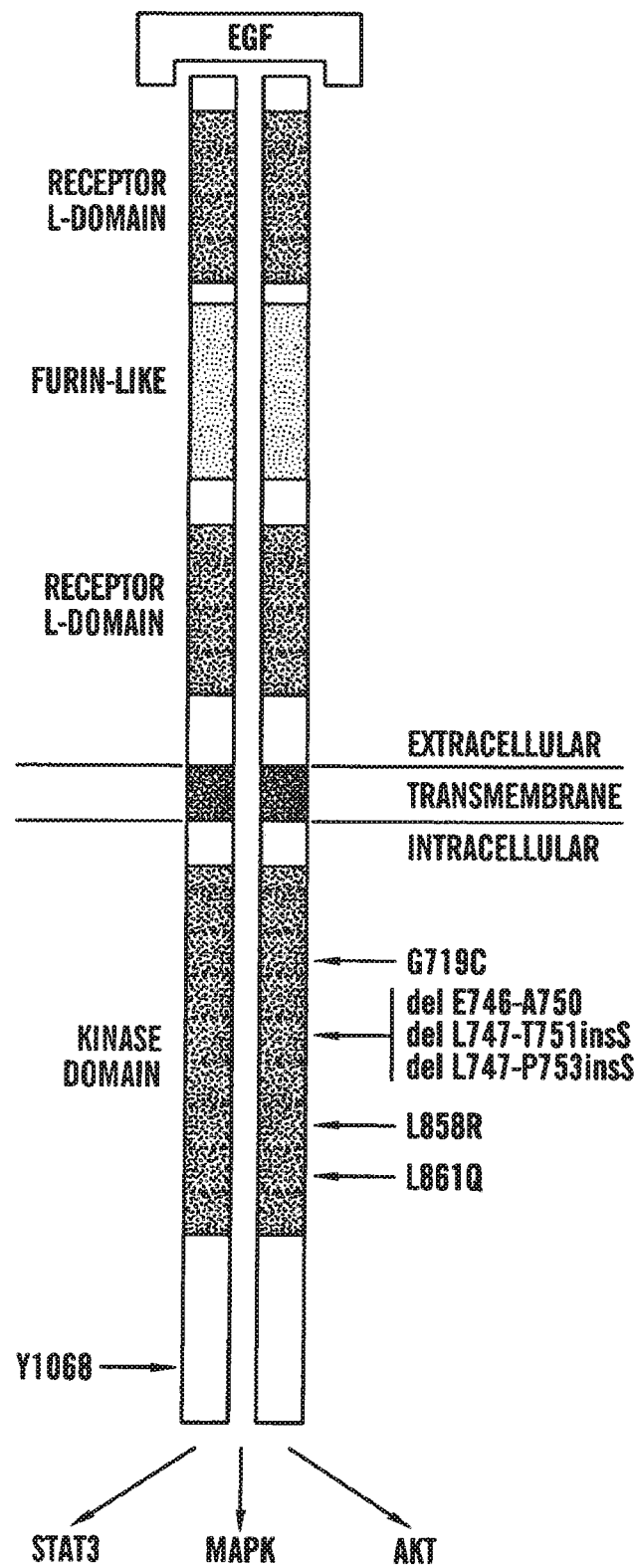

FIG. 2F is a schematic representation of dimerized EGFR molecules bound by the EGF ligand. The extracellular domain (containing two receptor ligand [L]-domains and a furin-like domain), transmembrane region, and the cytoplasmic domain (containing the catalytic kinase domain) are highlighted. The position of tyrosine$^{1068}$ (Y-1068), a site of autophosphorylation used as a marker of receptor activation, is indicated, along with downstream effectors activated by EGFR autophosphorylation (STAT3, MAP Kinase (MAPK), and AKT). The location of tumor-associated mutations, all within the tyrosine kinase domain, is shown.

FIGS. 3A-3D demonstrate enhanced EGF-dependent activation of mutant EGFR and increased sensitivity of mutant EGFR to Gefitinib.

Figure 3B:
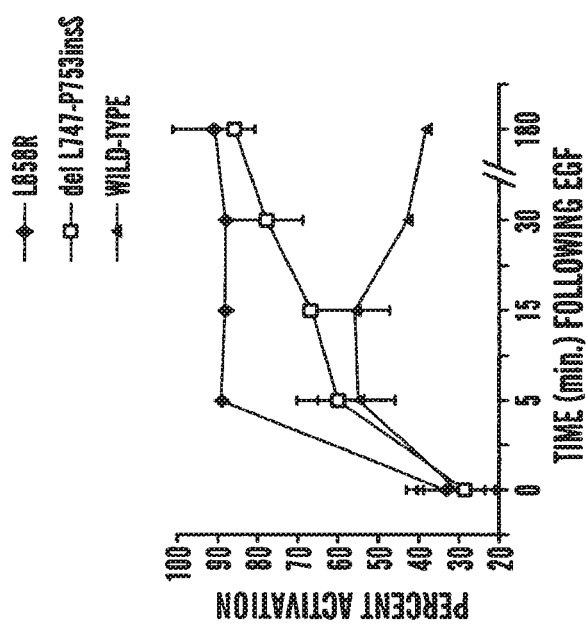
Figure 3A:
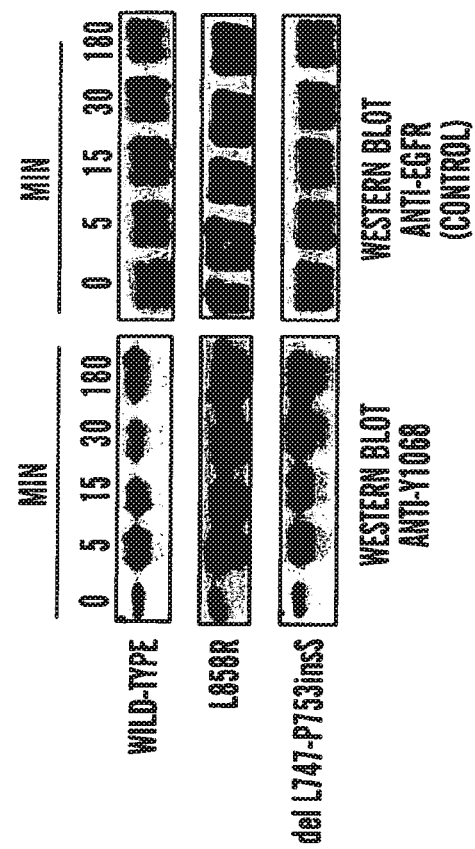

FIG. 3A shows a time course of ligand-induced activation of the delL747-P753insS and L858R mutants, compared with wild type EGFR, following addition of EGF to serum starved cells. EGFR autophosphorylation is used as a marker of receptor activation, using Western blotting with an antibody that specifically recognizes the phosphorylated tyrosine 1068 residue of EGFR (left panel), compared with the total levels of EGFR expressed in Cos-7 cells (control; right panel). Autophosphorylation of EGFR is measured at intervals following addition of EGF (10 ng/ml).

FIG. 3B is a graphical representation of EGF-induction of wild-type and mutant receptor phosphorylation (see panel A). Autoradiographs from three independent experiments were quantified using the NIH image software; intensity of EGFR phosphorylation is normalized to total protein expression, and shown as percent activation of the receptor, with standard deviation.

Figure 3D:
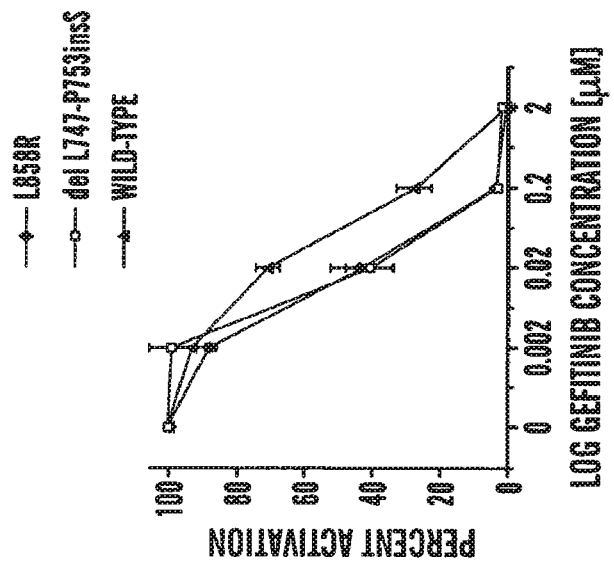
Figure 3C:
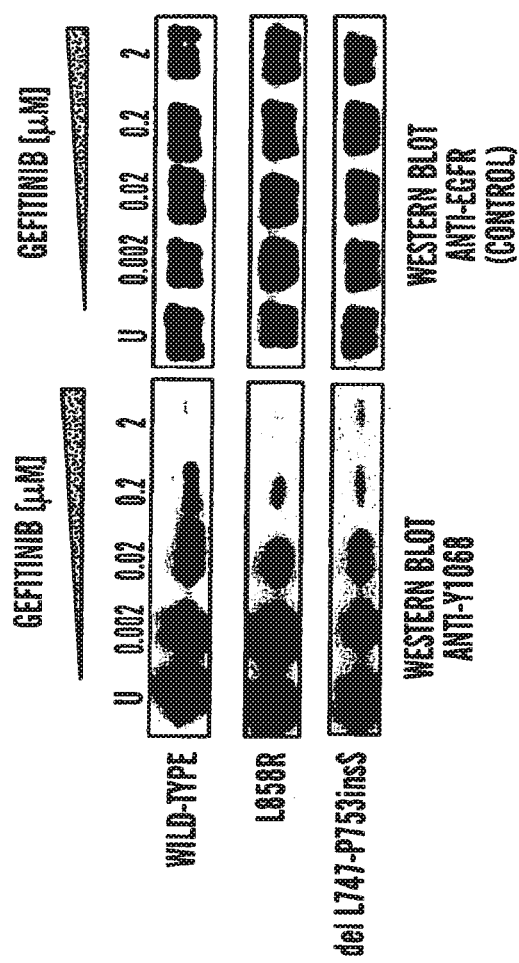

FIG. 3C shows a dose-dependent inhibition of EGFR activation by Gefitinib. Autophosphorylation of EGFR tyrosine$^{1068}$ is demonstrated by Western blotting analysis of Cos-7 cells expressing wild-type or mutant receptors, and stimulated with 100 ng/ml of EGF for 30 min. Cells were untreated (U) or pretreated for 3 hrs with increasing concentrations of Gefitinib as shown (left panel). Total amounts of EGFR protein expressed are shown as control (right panel).

FIG. 3D shows the quantification of results from two experiments described for panel 3C (NIH image software). Concentrations of phosphorylated EGFR were normalized to protein expression levels and expressed as percent activation of the receptor.

Figure 4A:
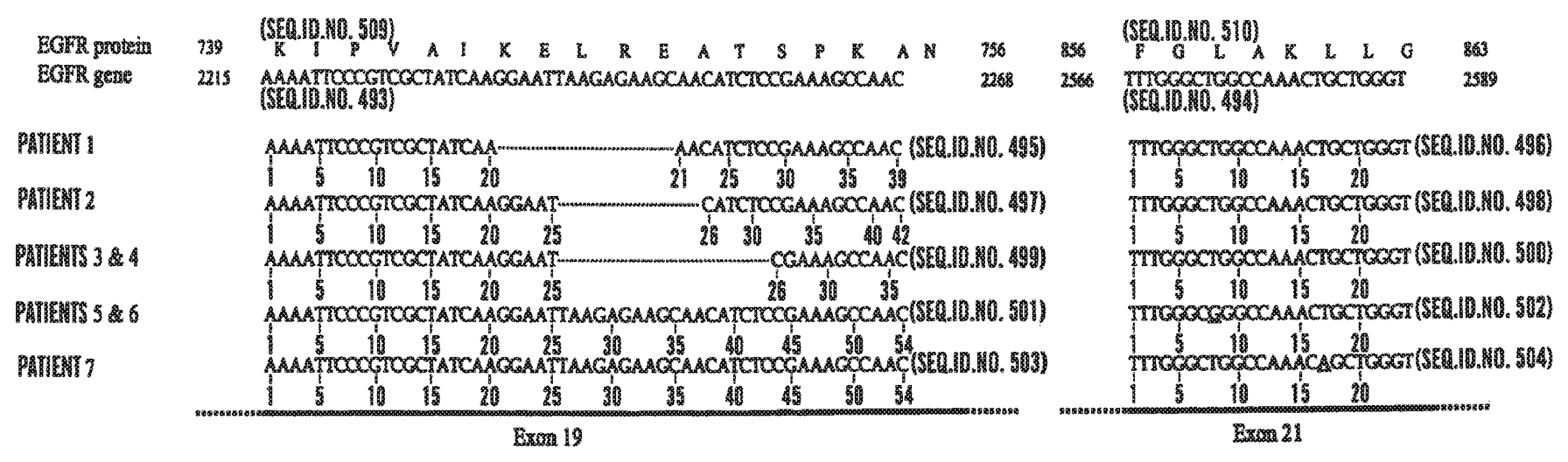
Figure 4C:
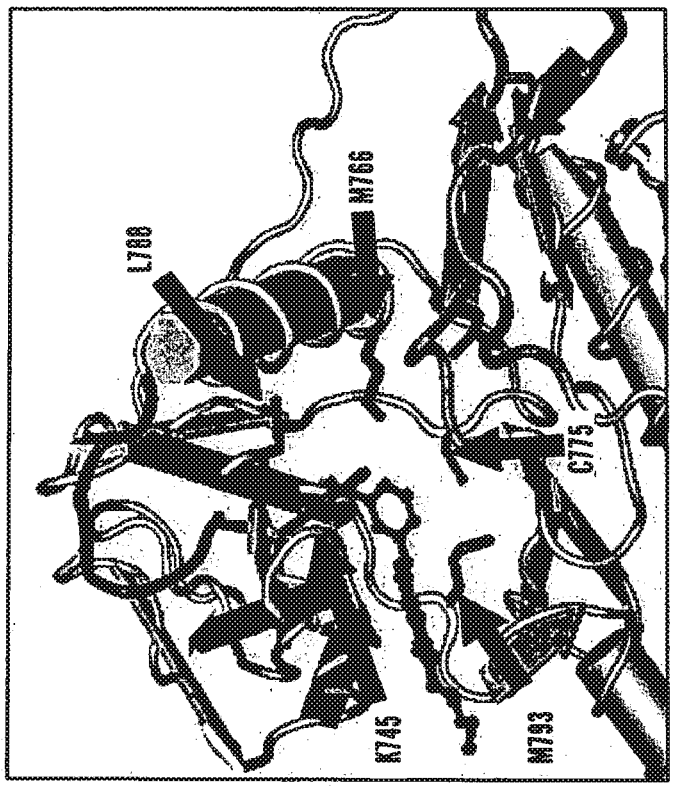
Figure 4B:
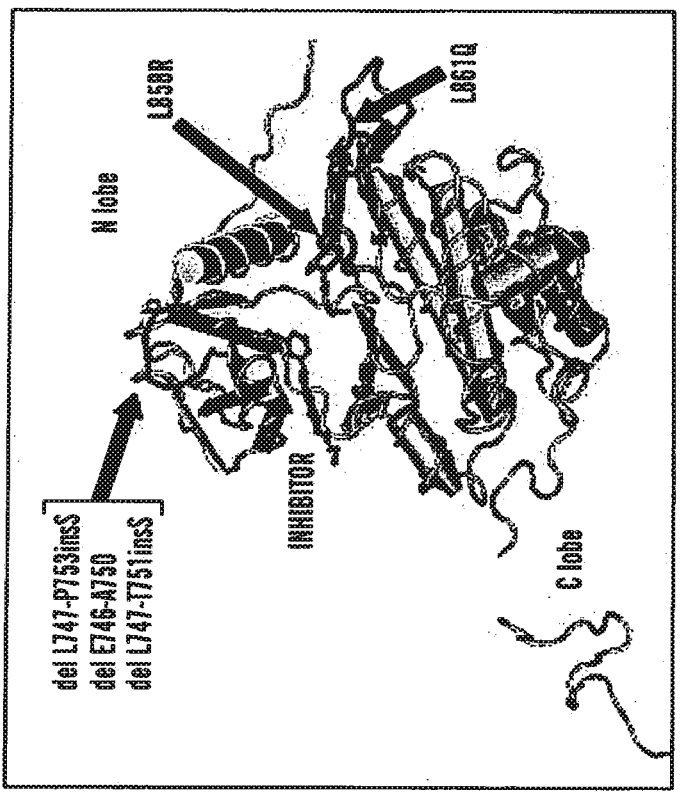

FIGS. 4A-4C demonstrate clustering of mutations at critical sites within the ATP-binding pocket of EGFR.

FIG. 4A shows the position of overlapping in-frame deletions in exon 19 and missense mutations in exon 21 of the EGFR gene, in multiple cases of NSCLC (SEQ ID NOS 495-504 (DNA)). Partial nucleotide sequence is shown for each exon, with deletions marked by dashed lines and missense mutations highlighted and underlined; the wild-type EGFR nucleotide and amino acid sequences are shown (SEQ ID NOS 493 & 494 (DNA) & 509-510 (amino acid)).

FIG. 4B shows the tridimensional structure of the EGFR ATP cleft flanked by the amino (N) and carboxy (C) lobes of the kinase domain (coordinates derived from PDB 1M14, and displayed using Cn3D software). The inhibitor, representing Gefitinib, is pictured occupying the ATP cleft. The locations of the two missense mutations are shown, within the activating loop of the kinase; the three in-frame deletions are all present within another loop, which flanks the ATP cleft.

FIG. 4C is a close-up of the EGFR kinase domain, showing the critical amino acid residues implicated in binding to either ATP or to the inhibitor. Specifically, 4-anilinoquinazoline compounds such as gefitinib inhibit catalysis by occupying the ATP-binding site, where they form hydrogen bonds with methionine$^{793}$ (M793) and cysteine$^{775}$ (C775) residues, whereas their anilino ring is close to methionine$^{766}$ (M766), lysine$^{745}$ (K745), and leucine$^{788}$ (L788) residues. In-frame deletions within the loop that is targeted by mutations are predicted to alter the position of these amino acids relative to the inhibitor. Mutated residues are shown within the activation loop of the tyrosine kinase.

FIG. 5 shows the nucleotide and amino acid sequence of the erbB1 gene. The amino acids are depicted as single letters, known to those of skill in the art. Nucleotide variances in the kinase domain are highlighted by patient number, see Table 2. SEQ ID NO: 511 includes nucleotides 1 through 3633. SEQ ID NO: 512 includes amino acids 1 through 1210.

FIGS. 6A-6C: Sequence alignment of selected regions within the EGFR and B-Raf kinase domains. Depiction of EGFR mutations in human NSCLC. EGFR (gb:X00588) mutations in NSCLC tumors are highlighted in gray. B-Raf (gb:M95712) mutations in multiple tumor types (5) are highlighted in black. Asterisks denote residues conserved between EGFR and B-Raf. FIG. 6A depicts L858R mutations in the activation loop (SEQ ID NOS 477-479). FIG. 6B depicts the G719S mutant in the P-loop (SEQ ID NOS 480-482). FIG. 6C depicts deletion mutants in EGFR exon 19 (SEQ ID NOS 483-489).

Figure 7:
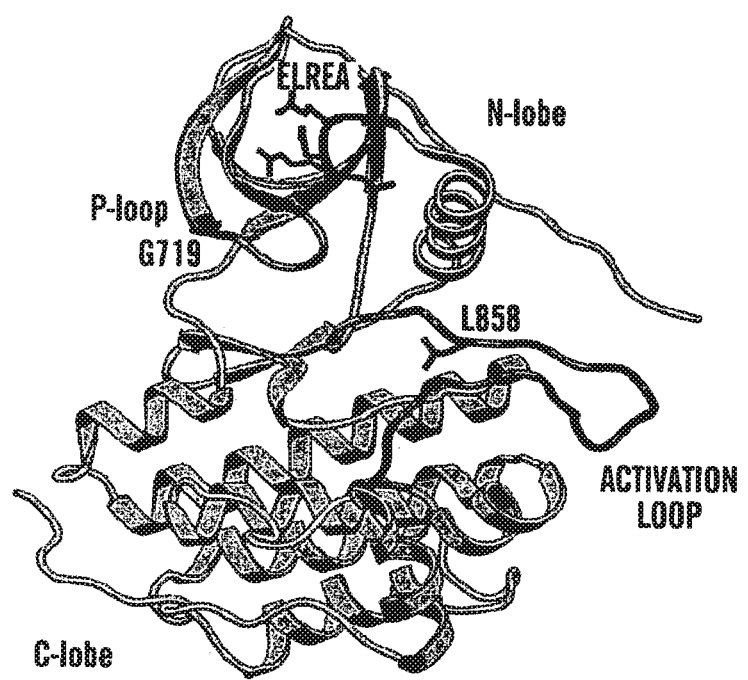

FIG. 7: Positions of missense mutations G719S and L858R and the Del-1 deletion in the three-dimensional structure of the EGFR kinase domain. The activation loop is shown in yellow, the P-loop is in blue and the C-lobe and N-lobe are as indicated. The residues targeted by mutation or deletion are highlighted in red. The Del-1 mutation targets the residues ELREA in codons 746 to 750. The mutations are located in highly conserved regions within kinases and are found in the p-loop and activation loop, which surround the region where ATP and also gefitinib and erlotinib are predicted to bind.

Figure 8A:
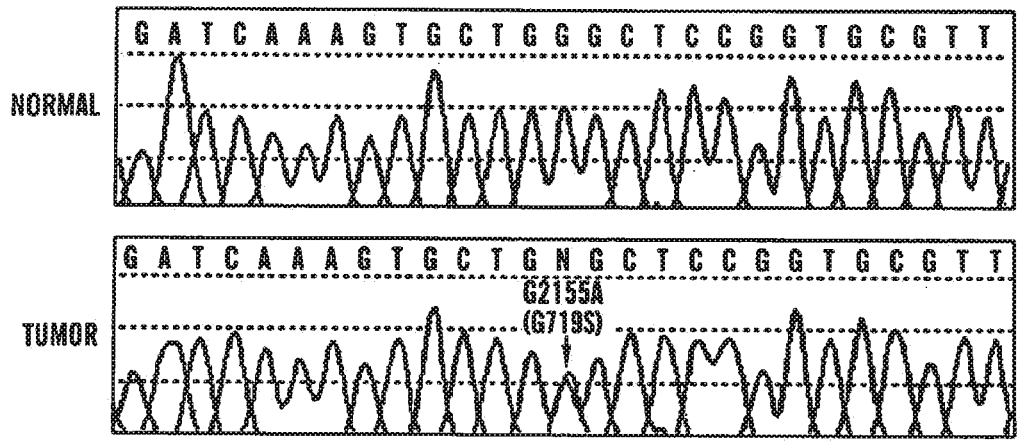
Figure 8B:
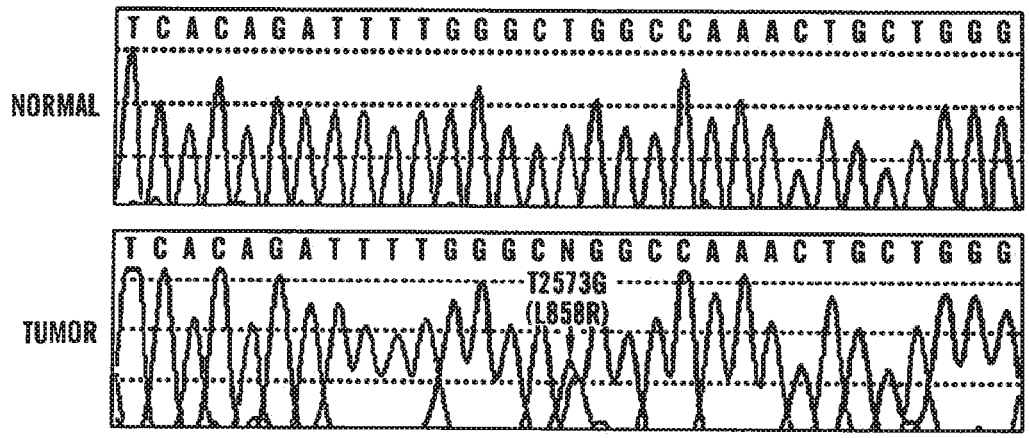
Figure 8C:
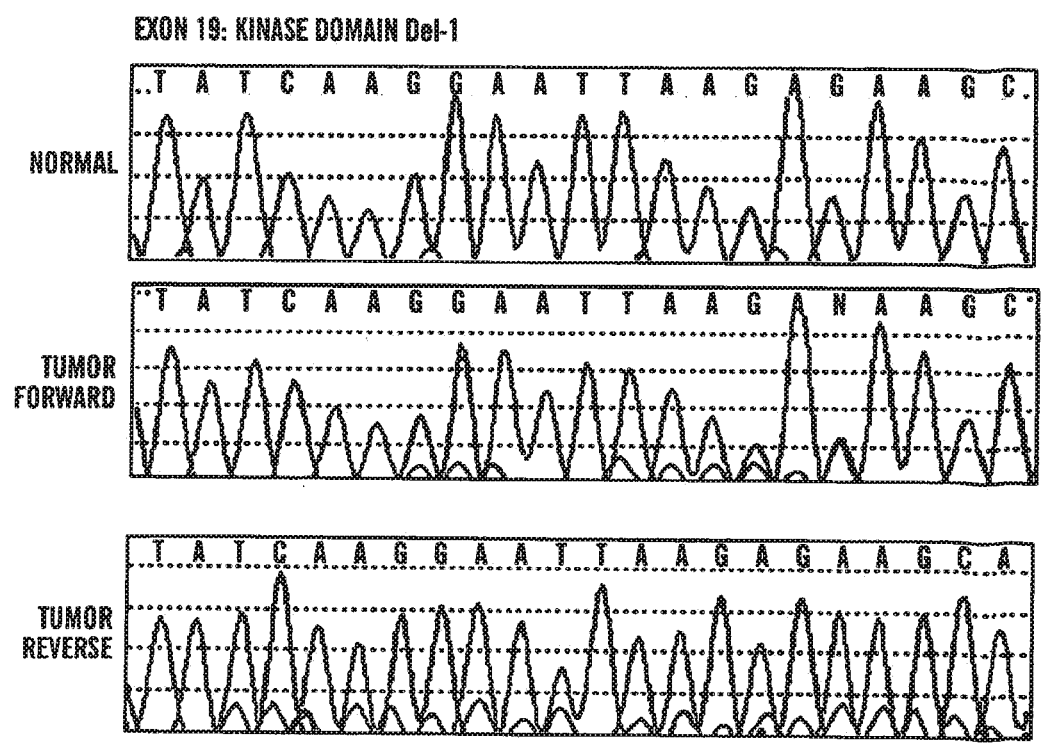
Figure 8D:
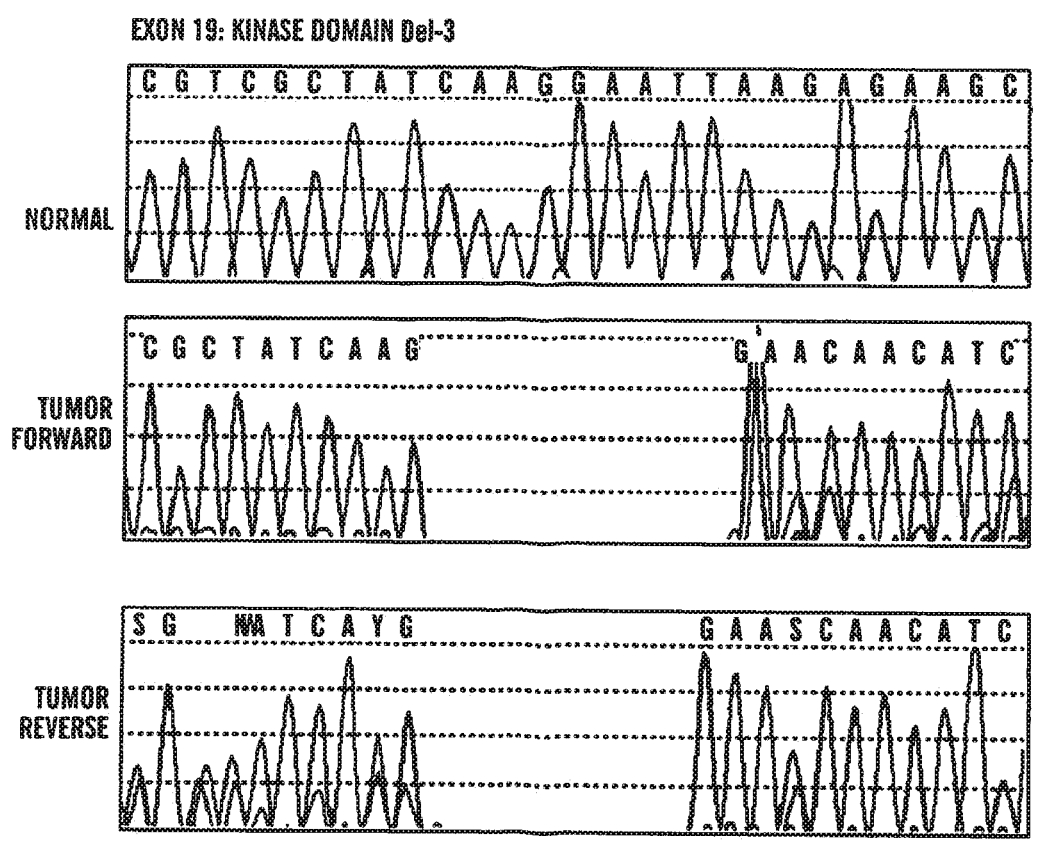
Figure 8E:
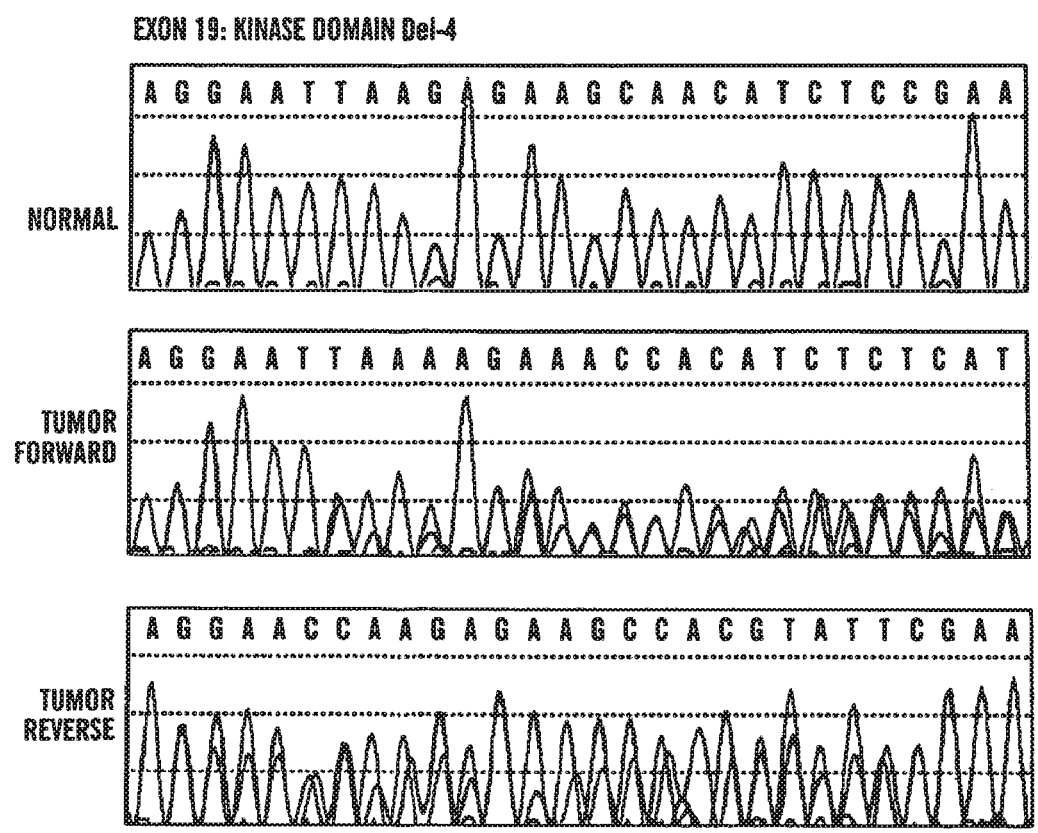
Figure 8F:
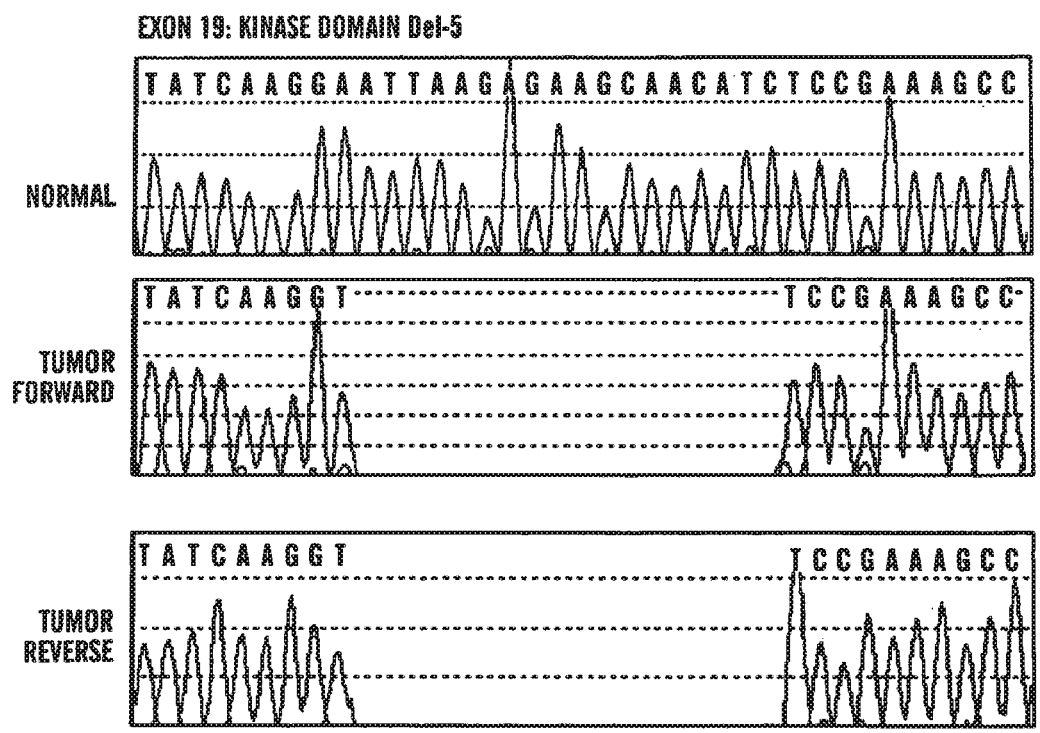

FIGS. 8A-8F. Representative chromatograms of EGFR DNA from normal tissue and from tumor tissues. The locations of the identified mutations are as follows. FIG. 8A depicts the Exon 18 Kinase domain P loop (SEQ ID NOS 704-705). FIG. 8B depicts the Exon 21 Kinase domain A-loop (SEQ ID NOS 706-707). FIG. 8C depicts the Exon 19 Kinase domain Del-1 (SEQ ID NOS 708-710). FIG. 8D depicts the Exon 19 Kinase domain Del-3 (SEQ ID NOS 711-713). FIG. 8E depicts the Exon 19 Kinase domain Del-4 (SEQ ID NOS 714-716). FIG. 8F depicts the Exon 19 Kinase domain Del-5 (SEQ ID NOS 717-719).

FIG. 9: Sequence alignment of the EGFR and BCR-ABL polypeptides and the location of residues conferring a drug resistant phenotype. The EGFR polypeptide (SEQ ID NO:492) encoded by the nucleotide sequence disclosed in GenBank accno. NM_005228 and the BCR-ABL polypeptide (SEQ ID NO:491) encoded by the nucleotide sequence disclosed in GenBank accno. M14752 are aligned and conserved residues are shaded. BCR-ABL mutations conferring resistance to the tyrosine kinase inhibitor imatinib (STI571, Glivec/Gleevec) are denoted by asterisks.

Figure 10:
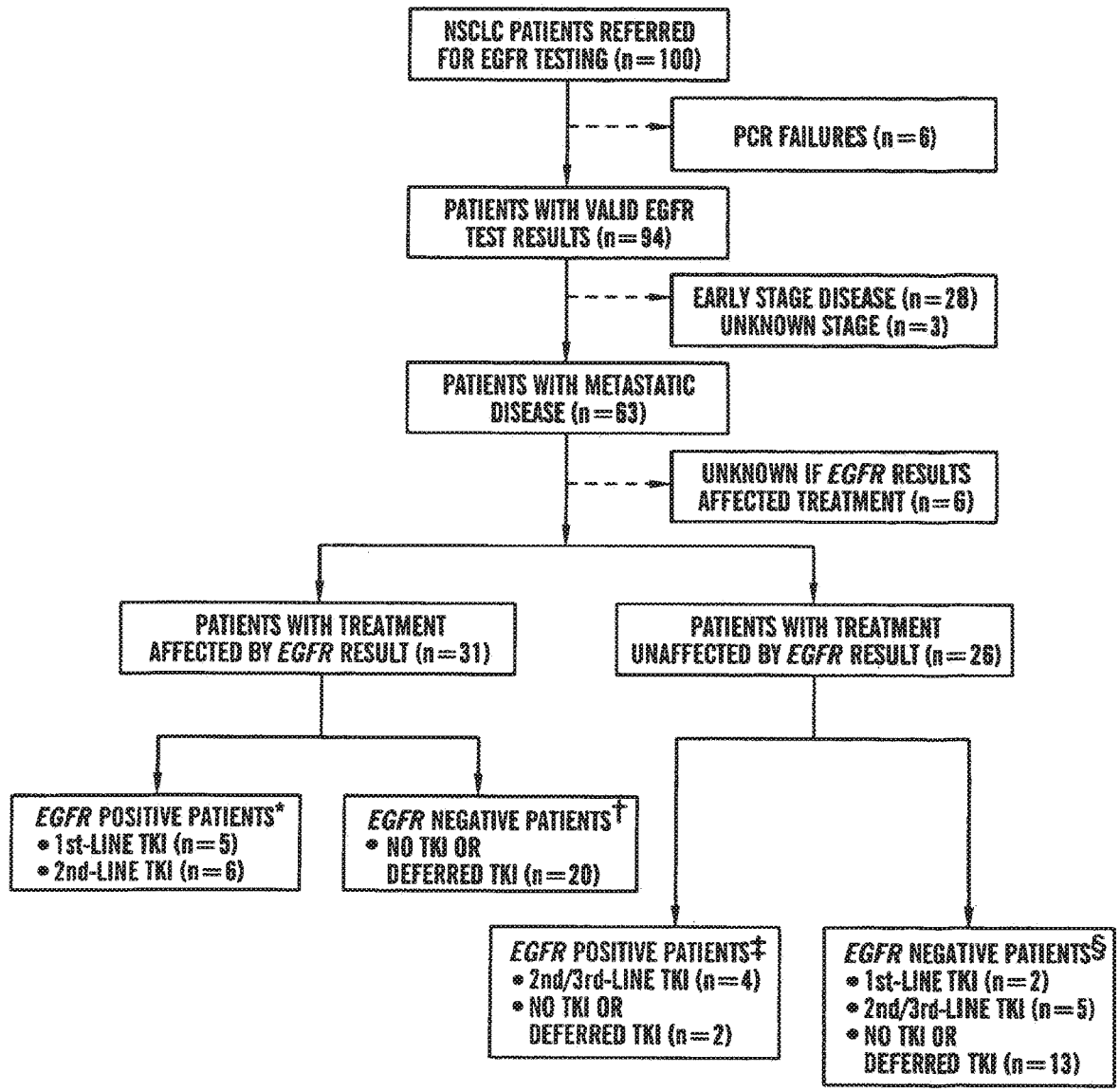

FIG. 10 shows the decision making process for patient with metastatic NSCLC undergoing EGFR testing.

Figure 11:
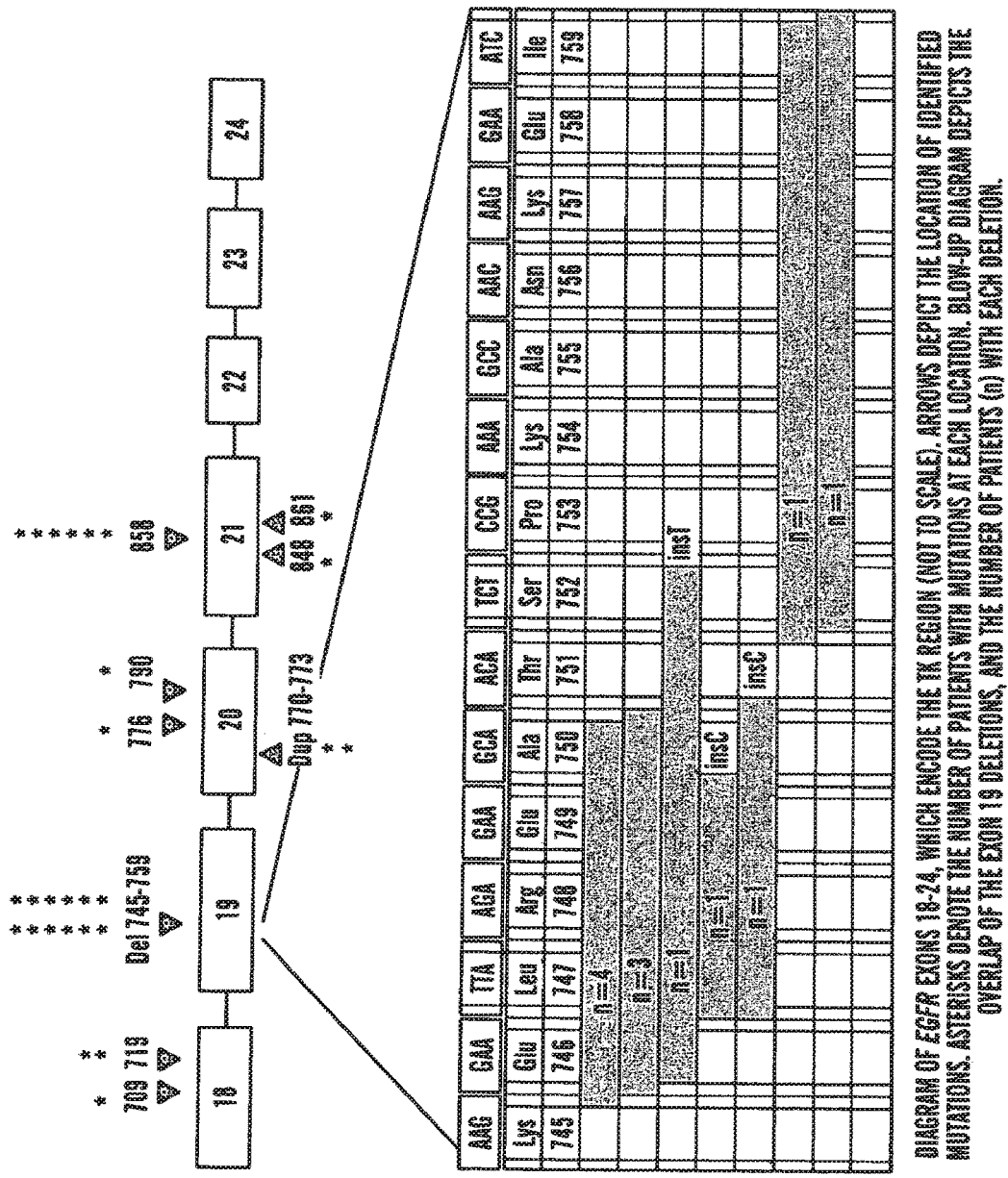

FIG. 11 shows a diagram of EGFR exons 18-24 (not to scale). Arrows depict the location of identified mutations. Asterisks denote the number of patients with mutations at each location. The blow-up diagram depicts the overlap of the exon 19 deletions, and the number of patients (n) with each deletion (nucleotides 2233-2277 of SEQ ID NO: 511 and residues 745-759 of SEQ ID NO: 512). Note that these are the results are not meant to be inclusive of all the EGFR mutations to date.

DETAILED DESCRIPTION

The present invention provides a novel method to determine the likelihood of effectiveness of an epidermal growth factor receptor (EGFR) targeting treatment in a patient affected with cancer. The method comprises detecting the presence or absence of at least one nucleic acid variance in the kinase domain of the erbB1 gene of said patient. The presence of at least one variance indicates that the EGFR targeting treatment is likely to be effective. Preferably, the nucleic acid variance increases the kinase activity of the EGFR. The patient can then be treated with an EGFR targeting treatment. In one embodiment of the present invention, the EGFR targeting treatment is a tyrosine kinase inhibitor. In a preferred embodiment, the tyrosine kinase inhibitor is an anilinoquinazoline. The anilinoquinazoline may be a synthetic anilinoquinazoline. Preferably, the synthetic anilinoquinazoline is either gefitinib or erlotinib.

Definitions

The terms "ErbB1", "epidermal growth factor receptor" and "EGFR" are used interchangeably herein and refer to native sequence EGFR as disclosed, for example, in Carpenter et al. Ann. Rev. Biochem. 56:881-914 (1987), including variants thereof (e.g. a deletion mutant EGFR as in Humphrey et al. PNAS (USA) 87:4207-4211 (1990)). erbB1 refers to the gene encoding the EGFR protein product.

The term "kinase activity increasing nucleic acid variance" as used herein refers to a variance (i.e. mutation) in the nucleotide sequence of a gene that results in an increased kinase activity. The increased kinase activity is a direct result of the variance in the nucleic acid and is associated with the protein for which the gene encodes.

The term "drug" or "compound" as used herein refers to a chemical entity or biological product, or combination of chemical entities or biological products, administered to a person to treat or prevent or control a disease or condition. The chemical entity or biological product is preferably, but not necessarily a low molecular weight compound, but may also be a larger compound, for example, an oligomer of nucleic acids, amino acids, or carbohydrates including without limitation proteins, oligonucleotides, ribozymes, DNAzymes, glycoproteins, siRNAs, lipoproteins, aptamers, and modifications and combinations thereof.

The term "genotype" in the context of this invention refers to the particular allelic form of a gene, which can be defined by the particular nucleotide(s) present in a nucleic acid sequence at a particular site(s).

The terms "variant form of a gene", "form of a gene", or "allele" refer to one specific form of a gene in a population, the specific form differing from other forms of the same gene in the sequence of at least one, and frequently more than one, variant sites within the sequence of the gene. The sequences at these variant sites that differ between different alleles of the gene are termed "gene sequence variances" or "variances" or "variants". Other terms known in the art to be equivalent include mutation and polymorphism, although mutation is often used to refer to an allele associated with a deleterious phenotype. In preferred aspects of this invention, the variances are selected from the group consisting of the variances listed in the variance tables herein.

In the context of this invention, the term "probe" refers to a molecule which can detectably distinguish between target molecules differing in structure. Detection can be accomplished in a variety of different ways depending on the type of probe used and the type of target molecule. Thus, for example, detection may be based on discrimination of activity levels of the target molecule, but preferably is based on detection of specific binding. Examples of such specific binding include antibody binding and nucleic acid probe hybridization. Thus, for example, probes can include enzyme substrates, antibodies and antibody fragments, and preferably nucleic acid hybridization probes.

As used herein, the terms "effective" and "effectiveness" includes both pharmacological effectiveness and physiological safety. Pharmacological effectiveness refers to the ability of the treatment to result in a desired biological effect in the patient. Physiological safety refers to the level of toxicity, or other adverse physiological effects at the cellular, organ and/or organism level (often referred to as side-effects) resulting from administration of the treatment. "Less effective" means that the treatment results in a therapeutically significant lower level of pharmacological effectiveness and/or a therapeutically greater level of adverse physiological effects.

The term "primer", as used herein, refers to an oligonucleotide which is capable of acting as a point of initiation of polynucleotide synthesis along a complementary strand when placed under conditions in which synthesis of a primer extension product which is complementary to a polynucleotide is catalyzed. Such conditions include the presence of four different nucleotide triphosphates or nucleoside analogs and one or more agents for polymerization such as DNA polymerase and/or reverse transcriptase, in an appropriate buffer ("buffer" includes substituents which are cofactors, or which affect pH, ionic strength, etc.), and at a suitable temperature. A primer must be sufficiently long to prime the synthesis of extension products in the presence of an agent for polymerase. A typical primer contains at least about 5 nucleotides in length of a sequence substantially complementary to the target sequence, but somewhat longer primers are preferred. Usually primers contain about 15-26 nucleotides, but longer primers may also be employed.

A primer will always contain a sequence substantially complementary to the target sequence, that is the specific sequence to be amplified, to which it can anneal. A primer may, optionally, also comprise a promoter sequence. The term "promoter sequence" defines a single strand of a nucleic acid sequence that is specifically recognized by an RNA polymerase that binds to a recognized sequence and initiates the process of transcription by which an RNA transcript is produced. In principle, any promoter sequence may be employed for which there is a known and available polymerase that is capable of recognizing the initiation sequence. Known and useful promoters are those that are recognized by certain bacteriophage polymerases, such as bacteriophage T3, T7 or SP6.

A "microarray" is a linear or two-dimensional array of preferably discrete regions, each having a defined area, formed on the surface of a solid support. The density of the discrete regions on a microarray is determined by the total numbers of target polynucleotides to be detected on the surface of a single solid phase support, preferably at least about $50/cm^2$, more preferably at least about $100/cm^2$, even more preferably at least about $500/cm^2$, and still more preferably at least about $1,000/cm^2$. As used herein, a DNA microarray is an array of oligonucleotide primers placed on a chip or other surfaces used to amplify or clone target polynucleotides. Since the position of each particular group of primers in the array is known, the identities of the target polynucleotides can be determined based on their binding to a particular position in the microarray.

The term "label" refers to a composition capable of producing a detectable signal indicative of the presence of the target polynucleotide in an assay sample. Suitable labels include radioisotopes, nucleotide chromophores, enzymes, substrates, fluorescent molecules, chemiluminescent moieties, magnetic particles, bioluminescent moieties, and the like. As such, a label is any composition detectable by spectroscopic, photochemical, biochemical, immunochemical, electrical, optical or chemical means.

The term "support" refers to conventional supports such as beads, particles, dipsticks, fibers, filters, membranes and silane or silicate supports such as glass slides.

The term "amplify" is used in the broad sense to mean creating an amplification product which may include, for example, additional target molecules, or target-like molecules or molecules complementary to the target molecule, which molecules are created by virtue of the presence of the target molecule in the sample. In the situation where the target is a nucleic acid, an amplification product can be made enzymatically with DNA or RNA polymerases or reverse transcriptases.

As used herein, a "biological sample" refers to a sample of tissue or fluid isolated from an individual, including but not limited to, for example, blood, plasma, serum, tumor biopsy, urine, stool, sputum, spinal fluid, pleural fluid, nipple aspirates, lymph fluid, the external sections of the skin, respiratory, intestinal, and genitourinary tracts, tears, saliva, milk, cells (including but not limited to blood cells), tumors, organs, and also samples of in vitro cell culture constituent. In a preferred embodiment, the sample is from a resection, bronchoscopic biopsy, or core needle biopsy of a primary or metastatic tumor, or a cellblock from pleural fluid. In addition, fine needle aspirate samples are used. Samples may be either paraffin-embedded or frozen tissue.

The term "antibody" is meant to be an immunoglobulin protein that is capable of binding an antigen. Antibody as used herein is meant to include antibody fragments, e.g. F(ab')2, Fab', Fab, capable of binding the antigen or antigenic fragment of interest. Preferably, the binding of the antibody to the antigen inhibits the activity of a variant form of EGFR.

The term "humanized antibody" is used herein to describe complete antibody molecules, i.e. composed of two complete light chains and two complete heavy chains, as well as antibodies consisting only of antibody fragments, e.g. Fab, Fab', F (ab') 2, and Fv, wherein the CDRs are derived from a non-human source and the remaining portion of the Ig molecule or fragment thereof is derived from a human antibody, preferably produced from a nucleic acid sequence encoding a human antibody.

The terms "human antibody" and "humanized antibody" are used herein to describe an antibody of which all portions of the antibody molecule are derived from a nucleic acid sequence encoding a human antibody. Such human antibodies are most desirable for use in antibody therapies, as such antibodies would elicit little or no immune response in the human patient.

The term "chimeric antibody" is used herein to describe an antibody molecule as well as antibody fragments, as described above in the definition of the term "humanized antibody." The term "chimeric antibody" encompasses humanized antibodies. Chimeric antibodies have at least one portion of a heavy or light chain amino acid sequence derived from a first mammalian species and another portion of the heavy or light chain amino acid sequence derived from a second, different mammalian species.

Preferably, the variable region is derived from a non-human mammalian species and the constant region is derived from a human species. Specifically, the chimeric antibody is preferably produced from a 9 nucleotide sequence from a non-human mammal encoding a variable region and a nucleotide sequence from a human encoding a constant region of an antibody.

Table 2 is a partial list of DNA sequence variances in the kinase domain of erbB1 relevant to the methods described in the present invention. These variances were identified by the inventors in studies of biological samples from patients with NSCLC who responded to gefitinib and patients with no exposure to gefitinb.

Nucleic acid molecules can be isolated from a particular biological sample using any of a number of procedures, which are well-known in the art, the particular isolation procedure chosen being appropriate for the particular biological sample. For example, freeze-thaw and alkaline lysis procedures can be useful for obtaining nucleic acid molecules from solid materials; heat and alkaline lysis procedures can be useful for obtaining nucleic acid molecules from urine; and proteinase K extraction can be used to obtain nucleic acid from blood (Rolff, A et al. PCR: Clinical Diagnostics and Research, Springer (1994).

Detection Methods

Determining the presence or absence of a particular variance or plurality of variances in the kinase domain of the erbB1 gene in a patient with or at risk for developing cancer can be performed in a variety of ways. Such tests are commonly performed using DNA or RNA collected from biological samples, e.g., tissue biopsies, urine, stool, sputum, blood, cells, tissue scrapings, breast aspirates or other cellular materials, and can be performed by a variety of methods including, but not limited to, PCR, hybridization with allele-specific probes, enzymatic mutation detection, chemical cleavage of mismatches, mass spectrometry or DNA sequencing, including minisequencing. In particular embodiments, hybridization with allele specific probes can be conducted in two formats: (1) allele specific oligonucleotides bound to a solid phase (glass, silicon, nylon membranes) and the labeled sample in solution, as in many DNA chip applications, or (2) bound sample (often cloned DNA or PCR amplified DNA) and labeled oligonucleotides in solution (either allele specific or short so as to allow sequencing by hybridization). Diagnostic tests may involve a panel of variances, often on a solid support, which enables the simultaneous determination of more than one variance.

In another aspect, determining the presence of at least one kinase activity increasing nucleic acid variance in the erbB1 gene may entail a haplotyping test. Methods of determining haplotypes are known to those of skill in the art, as for example, in WO 00/04194.

Preferably, the determination of the presence or absence of a kinase activity increasing nucleic acid variance involves determining the sequence of the variance site or sites by methods such as polymerase chain reaction (PCR). Alternatively, the determination of the presence or absence of a kinase activity increasing nucleic acid variance may encompass chain terminating DNA sequencing or minisequencing, oligonucleotide hybridization or mass spectrometry.

The methods of the present invention may be used to predict the likelihood of effectiveness (or lack of effectiveness) of an EGFR targeting treatment in a patient affected with or at risk for developing cancer. Preferably, cancers include cancer of epithelial origin, including, but are not limited to, gastrointestinal cancer, prostate cancer, ovarian cancer, breast cancer, head and neck cancer, lung cancer, non-small cell lung cancer, cancer of the nervous system, kidney cancer, retina cancer, skin cancer, liver cancer, pancreatic cancer, genital-urinary cancer and bladder cancer. In a preferred embodiment, the cancer is non-small cell lung cancer.

The present invention generally concerns the identification of variances in the kinase domain of the erbB1 gene which are indicative of the effectiveness of an EGFR targeting treatment in a patient with or at risk for developing cancer. Additionally, the identification of specific variances in the kinase domain of EGFR, in effect, can be used as a diagnostic or prognostic test. For example, the presence of at least one variance in the kinase domain of erbB1 indicates that a patient will likely benefit from treatment with an EGFR targeting compound, such as, for example, a tyrosine kinase inhibitor.

Methods for diagnostic tests are well known in the art and disclosed in patent application WO 00/04194, incorporated herein by reference. In an exemplary method, the diagnostic test comprises amplifying a segment of DNA or RNA (generally after converting the RNA to cDNA) spanning one or more known variances in the kinase domain of the erbB1 gene sequence. This amplified segment is then sequenced and/or subjected to polyacrylamide gel electrophoresis in order to identify nucleic acid variances in the amplified segment.

PCR

In one embodiment, the invention provides a method of screening for variants in the kinase domain of the erbB1 gene in a test biological sample by PCR or, alternatively, in a ligation chain reaction (LCR) (see, e.g., Landegran, et al., 1988. Science 241: 1077-1080; and Nakazawa, et al., 1994. Proc. Natl. Acad. Sci. USA 91: 360-364), the latter of which can be particularly useful for detecting point mutations in the EGFR-gene (see, Abravaya, et al., 1995. Nucl. Acids Res. 23: 675-682). The method comprises the steps of designing degenerate primers for amplifying the target sequence, the primers corresponding to one or more conserved regions of the gene, amplifying reaction with the primers using, as a template, a DNA or cDNA obtained from a test biological sample and analyzing the PCR products. Comparison of the PCR products of the test biological sample to a control sample indicates variances in the test biological sample. The change can be either and absence or presence of a nucleic acid variance in the test biological sample.

Alternative amplification methods include: self sustained sequence replication (see, Guatelli, et al., 1990. Proc. Natl. Acad. Sci. USA 87: 1874-1878), transcriptional amplification system (see, Kwoh, et al., 1989. Proc. Natl. Acad. Sci. USA 86: 1173-1177); Qb Replicase (see, Lizardi, et al, 1988. BioTechnology 6: 1197), or any other nucleic acid amplification method, followed by the detection of the amplified molecules using techniques well known to those of skill in the art. These detection schemes are especially useful for the detection of nucleic acid molecules if such molecules are present in very low numbers.

Primers useful according to the present invention are designed using amino acid sequences of the protein or nucleic acid sequences of the kinase domain of the erbB1 gene as a guide, e.g. SEQ ID NO: 493, SEQ ID NO: 494, SEQ ID NO: 509, and SEQ ID NO: 510. The primers are designed in the homologous regions of the gene wherein at least two regions of homology are separated by a divergent region of variable sequence, the sequence being variable either in length or nucleic acid sequence.

For example, the identical or highly, homologous, preferably at least 80%-85% more preferably at least 90-99% homologous amino acid sequence of at least about 6, preferably at least 8-10 consecutive amino acids. Most preferably, the amino acid sequence is 100% identical. Forward and reverse primers are designed based upon the maintenance of codon degeneracy and the representation of the various amino acids at a given position among the known gene family members. Degree of homology as referred to herein is based upon analysis of an amino acid sequence using a standard sequence comparison software, such as protein-BLAST using the default settings.

Table 3 below represents the usage of degenerate codes and their standard symbols:

|   | T | C | A | G |
|---|---|---|---|---|
| T | TTT Phe (F) | TCT Ser (S) | TAT Tyr (Y) | TGT Cys (C) |
|   | TTC Phe (F) | TCC Ser (S) | TAC | TGC |
|   | TTA Leu (L) | TCA Ser (S) | TAA Ter | TGA Ter |
|   | TTG Leu (L) | TCG Ser (S) | TAG Ter | TGG Trp (W) |
| C | CTT Leu (L) | CCT Pro (P) | CAT His (H) | CGT Arg (R) |
|   | CTC Leu (L) | CCC Pro (P) | CAC His (H) | CGC Arg (R) |
|   | CTA Leu (L) | CCA Pro (P) | CAA Gln (Q) | CGA Arg (R) |
|   | CTG Leu (L) | CCG Pro (P) | CAG Gln (Q) | CGG Arg (R) |
| A | ATT Ile (I) | ACT Thr (T) | AAT Asn (N) | AGT Ser (S) |
|   | ATC Ile (I) | ACC Thr (T) | AAC Asn (N) | AGC Ser (S) |
|   | ATA Ile (I) | ACA Thr (T) | AAA Lys (K) | AGA Arg (R) |
|   | ATG Met (M) | ACG Thr (T) | AAG Lys (K) | AGG Arg (R) |
| G | GTT Val (V) | GCT Ala (A) | GAT Asp (D) | GGT Gly (G) |
|   | GTC Val (V) | GCC Ala (A) | GAC Asp (D) | GGC Gly (G) |
|   | GTA Val (V) | GCA Ala (A) | GAA Glu (E) | GGA Gly (G) |
|   | GTG Val (V) | GCG Ala (A) | GAG Glu (E) | GGG Gly (G) |

Preferably any 6-fold degenerate codons such as L, R and S are avoided since in practice they will introduce higher than 6-fold degeneracy. In the case of L, TTR and CTN are compromised YTN (8-fold degeneracy), in the case of R, CGN and AGR compromises at MGN (8-fold degeneracy), and finally S, TCN and AGY which can be compromised to WSN (16-fold degeneracy). In all three cases on 6 of these will match the target sequence. To avoid this loss of specificity, it is preferable to avoid these regions, or to make two populations, each with the alternative degenerate codon, e.g. for S include TCN in one pool, and AGY in the other.

Primers may be designed using a number of available computer programs, including, but not limited to Oligo Analyzer3.0; Oligo
Calculator; NetPrimer; Methprimer; Primer3; WebPrimer; PrimerFinder; Primer9; Oligo2002; Pride or GenomePride; Oligos; and Codehop.

Primers may be labeled using labels known to one skilled in the art. Such labels include, but are not limited to radioactive, fluorescent, dye, and enzymatic labels.

Analysis of amplification products can be performed using any method capable of separating the amplification products according to their size, including automated and manual gel electrophoresis, mass spectrometry, and the like.

Alternatively, the amplification products can be separated using sequence differences, using SSCP, DGGE, TGGE, chemical cleavage or restriction fragment polymorphisms as well as hybridization to, for example, a nucleic acid arrays.

The methods of nucleic acid isolation, amplification and analysis are routine for one skilled in the art and examples of protocols can be found, for example, in the Molecular Cloning: A Laboratory Manual (3-Volume Set) Ed. Joseph Sambrook, David W. Russel, and Joe Sambrook, Cold Spring Harbor Laboratory; 3rd edition (Jan. 15, 2001), ISBN: 0879695773. Particularly useful protocol source for methods used in PCR amplification is PCR (Basics: From Background to Bench) by M. J. McPherson, S. G. Møller, R. Beynon, C. Howe, Springer Verlag; 1st edition (Oct. 15, 2000), ISBN: 0387916008.

Preferably, exons 19 and 21 of human EGFR are amplified by the polymerase chain reaction (PCR) using the following primers: Exon19 sense primer, 5'-GCAATATCA-GCCTTAGGTGCGGCTC-3' (SEQ ID NO: 505); Exon 19 antisense primer, 5'-CATAGAA AGTGAACATTTAGGAT-GTG-3' (SEQ ID NO: 506); Exon 21 sense primer, 5'-CTAACGTTCG CCAGCCATAAGTCC-3' (SEQ ID NO: 507); and Exon21 antisense primer, 5'-GCTGCGAGCT-CACCCAG AATGTCTGG-3' (SEQ ID NO: 508).

In an alternative embodiment, mutations in a EGFR gene from a sample cell can be identified by alterations in restriction enzyme cleavage patterns. For example, sample and control DNA is isolated, amplified (optionally), digested with one or more restriction endonucleases, and fragment length sizes are determined by gel electrophoresis and compared. Differences in fragment length sizes between sample and control DNA indicates mutations in the sample DNA. Moreover, the use of sequence specific ribozymes (see, e.g., U.S. Pat. No. 5,493,531) can be used to score for the presence of specific mutations by development or loss of a ribozyme cleavage site.

Other methods for detecting mutations in the EGFR gene include methods in which protection from cleavage agents is used to detect mismatched bases in RNA/RNA or RNA/DNA heteroduplexes. See, e.g., Myers, et al., 1985. Science 230: 1242. In general, the art technique of "mismatch cleavage" starts by providing heteroduplexes of formed by hybridizing (labeled) RNA or DNA containing the wild-type EGFR sequence with potentially mutant RNA or DNA obtained from a tissue sample. The double-stranded duplexes are treated with an agent that cleaves single-stranded regions of the duplex such as which will exist due to basepair mismatches between the control and sample strands. For instance, RNA/DNA duplexes can be treated with RNase and DNA/DNA hybrids treated with 51 nuclease to enzymatically digesting the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. See, e.g., Cotton, et al., 1988. Proc. Natl. Acad. Sci. USA 85: 4397; Saleeba, et al., 1992. Methods Enzymol. 217: 286-295. In an embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes) in defined systems for detecting and mapping point mutations in EGFR cDNAs obtained from samples of cells. For example, the mutY enzyme of E. coli cleaves A at G/A mismatches and the thymidine DNA glycosylase from HeLa cells cleaves T at G/T mismatches. See, e.g., Hsu, et al., 1994. Carcinogenesis 15: 1657-1662. According to an exemplary embodiment, a probe based on a mutant EGFR sequence, e.g., a DEL-1 through DEL-5, G719S, G857V, L883S or L858R EGFR sequence, is hybridized to a cDNA or other DNA product from a test cell(s). The duplex is treated with a DNA mismatch repair enzyme, and the cleavage products, if any, can be detected from electrophoresis protocols or the like. See, e.g., U.S. Pat. No. 5,459,039.

In other embodiments, alterations in electrophoretic mobility will be used to identify mutations in EGFR genes. For example, single strand conformation polymorphism (SSCP) may be used to detect differences in electrophoretic mobility between mutant and wild type nucleic acids. See, e.g., Orita, et al., 1989. Proc. Natl. Acad. Sci. USA: 86: 2766; Cotton, 1993. Mutat. Res. 285: 125-144; Hayashi, 1992. Genet. Anal. Tech. Appl. 9: 73-79. Single-stranded DNA fragments of sample and control EGFR nucleic acids will be denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In one embodiment, the subject method utilizes heteroduplex analysis to separate double stranded heteroduplex molecules on the basis of changes in electrophoretic mobility. See, e.g., Keen, et al., 1991. Trends Genet. 7: 5.

In yet another embodiment, the movement of mutant or wild-type fragments in polyacrylamide gels containing a gradient of denaturant is assayed using denaturing gradient gel electrophoresis (DGGE). See, e.g., Myers, et al., 1985. Nature 313: 495. When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA. See, e.g., Rosenbaum and Reissner, 1987. Biophys. Chem. 265: 12753.

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions that permit hybridization only if a perfect match is found. See, e.g., Saiki, et al., 1986. Nature 324: 163; Saiki, et al., 1989. Proc. Natl. Acad. Sci. USA 86: 6230. Such allele specific oligonucleotides are hybridized to PCR amplified target DNA or a number of different mutations when the oligonucleotides are attached to the hybridizing membrane and hybridized with labeled target DNA.

Alternatively, allele specific amplification technology that depends on selective PCR amplification may be used in conjunction with the instant invention. Oligonucleotides used as primers for specific amplification may carry the mutation of interest in the center of the molecule (so that amplification depends on differential hybridization; see, e.g., Gibbs, et al., 1989. Nucl. Acids Res. 17: 2437-2448) or at the extreme 3'-terminus of one primer where, under appropriate conditions, mismatch can prevent, or reduce polymerase extension (see, e.g., Prossner, 1993. Tibtech. 11: 238). In addition it may be desirable to introduce a novel restriction site in the region of the mutation to create cleavage-based detection. See, e.g., Gasparini, et al., 1992. Mol. Cell Probes 6: 1. It is anticipated that in certain embodiments amplification may also be performed using Taq ligase for amplification. See, e.g., Barany, 1991. Proc. Natl. Acad. Sci. USA 88: 189. In such cases, ligation will occur only if there is a perfect match at the 3'-terminus of the 5' sequence, making it possible to detect the presence of a known mutation at a specific site by looking for the presence or absence of amplification.

Solid Support and Probe

In an alternative embodiment, the detection of the presence or absence of the at least one nucleic acid variance involves contacting a nucleic acid sequence corresponding to the desired region of the erbB1 gene, identified above, with a probe. The probe is able to distinguish a particular form of the gene or the presence or a particular variance or variances, e.g., by differential binding or hybridization. Thus, exemplary probes include nucleic acid hybridization probes, peptide nucleic acid probes, nucleotide-containing probes which also contain at least one nucleotide analog, and antibodies, e.g., monoclonal antibodies, and other probes as discussed herein. Those skilled in the art are familiar with the preparation of probes with particular specificities. Those skilled in the art will recognize that a variety of variables can be adjusted to optimize the discrimination between two variant forms of a gene, including changes in salt concentration, temperature, pH and addition of various compounds that affect the differential affinity of GC vs. AT base pairs, such as tetramethyl ammonium chloride. (See Current Protocols in Molecular Biology by F. M. Ausubel, R. Brent, R. E. Kingston, D. D. Moore, J. G. Seidman, K. Struhl and V. B. Chanda (Editors), John Wiley & Sons.)

Thus, in preferred embodiments, the detection of the presence or absence of the at least one variance involves contacting a nucleic acid sequence which includes at least one variance site with a probe, preferably a nucleic acid probe, where the probe preferentially hybridizes with a form of the nucleic acid sequence containing a complementary base at the variance site as compared to hybridization to a form of the nucleic acid sequence having a noncomplementary base at the variance site, where the hybridization is carried out under selective hybridization conditions. Such a nucleic acid hybridization probe may span two or more variance sites. Unless otherwise specified, a nucleic acid probe can include one or more nucleic acid analogs, labels or other substituents or moieties so long as the base-pairing function is retained.

The probe may be designed to bind to, for example, at least three continuous nucleotides on both sides of the deleted region of SEQ ID NO: 495, SEQ ID NO: 497, or SEQ ID NO: 499. Such probes, when hybridized under the appropriate conditions, will bind to the variant form of EGFR, but will not bind to the wildtype EGFR.

Such hybridization probes are well known in the art (see, e.g., Sambrook et al., Eds., (most recent edition), Molecular Cloning: A Laboratory Manual, (third edition, 2001), Vol. 1-3, Cold Spring Harbor Laboratory, Cold Spring Harbor, N.Y.). Stringent hybridization conditions will typically include salt concentrations of less than about 1M, more usually less than about 500 mM and preferably less than about 200 mM. Hybridization temperatures can be as low as 5° C., but are typically greater than 22° C., more typically greater than about 30° C., and preferably in excess of about 37° C. Longer fragments may require higher hybridization temperatures for specific hybridization. Other factors may affect the stringency of hybridization, including base composition and length of the complementary strands, presence of organic solvents and extent of base mismatching; the combination of parameters used is more important than the absolute measure of any one alone. Other hybridization conditions which may be controlled include buffer type and concentration, solution pH, presence and concentration of blocking reagents (e.g., repeat sequences, Cot1 DNA, blocking protein solutions) to decrease background binding, detergent type(s) and concentrations, molecules such as polymers which increase the relative concentration of the polynucleotides, metal ion(s) and their concentration(s), chelator(s) and their concentrations, and other conditions known or discoverable in the art. Formulas may be used to predict the optimal melting temperature for a perfectly complementary sequence for a given probe, but true melting temperatures for a probe under a set of hybridization conditions must be determined empirically. Also, a probe may be tested against its exact complement to determine a precise melting temperature under a given set of condition as described in Sambrook et al, "Molecular Cloning," $3^{nd}$ edition, Cold Spring Harbor Laboratory Press, 2001. Hybridization temperatures can be systematically altered for a given hybridization solution using a support associated with target polynucleotides until a temperature range is identified which permits detection of binding of a detectable probe at the level of stringency desired, either at high stringency where only target polynucleotides with a high degree of complementarity hybridize, or at lower stringency where additional target polynucleotides having regions of complementarity with the probe detectably hybridize above the background level provided from nonspecific binding to noncomplementary target polynucleotides and to the support. When hybridization is performed with potential target polynucleotides on a support under a given set of conditions, the support is then washed under increasing conditions of stringency (typically lowered salt concentration and/or increased temperature, but other conditions may be altered) until background binding is lowered to the point where distinct positive signals may be seen. This can be monitored in progress using a Geiger counter where the probe is radiolabeled, radiographically, using a fluorescent imager, or by other means of detecting probe binding. The support is not allowed to dry during such procedures, or the probe may become irreversibly bound even to background locations. Where a probe produces undesirable background or false positives, blocking reagents are employed, or different regions of the probe or different probes are used until positive signals can be distinguished from background. Once conditions are found that provide satisfactory signal above background, the target polynucleotides providing a positive signal are isolated and further characterized. The isolated polynucleotides can be sequenced; the sequence can be compared to databank entries or known sequences; where necessary, full-length clones can be obtained by techniques known in the art; and the polynucleotides can be expressed using suitable vectors and hosts to determine if the polynucleotide identified encodes a protein having similar activity to that from which the probe polynucleotide was derived. The probes can be from 10-50 nucleotides. However, musch oarger probes can also be employed, e.g., 50-500 nucleotides or larger.

Solid Phase Support

The solid phase support of the present invention can be of any solid materials and structures suitable for supporting nucleotide hybridization and synthesis. Preferably, the solid phase support comprises at least one substantially rigid surface on which oligonucleotides or oligonucleotide primers can be immobilized. The solid phase support can be made of, for example, glass, synthetic polymer, plastic, hard non-mesh nylon or ceramic. Other suitable solid support materials are known and readily available to those of skill in the art. The size of the solid support can be any of the standard microarray sizes, useful for DNA microarray technology, and the size may be tailored to fit the particular machine being used to conduct a reaction of the invention. Methods and materials for derivatization of solid phase supports for the purpose of immobilizing oligonucleotides are known to those skill in the art and described in, for example, U.S. Pat. No. 5,919,523, the disclosure of which is incorporated herein by reference.

The solid support can be provided in or be part of a fluid containing vessel. For example, the solid support can be placed in a chamber with sides that create a seal along the edge of the solid support so as to contain the polymerase chain reaction (PCR) on the support. In a specific example the chamber can have walls on each side of a rectangular support to ensure that the PCR mixture remains on the support and also to make the entire surface useful for providing the primers.

The oligonucleotide or oligonucleotide primers of the invention are affixed, immobilized, provided, and/or applied to the surface of the solid support using any available means to fix, immobilize, provide and/or apply the oligonucleotides at a particular location on the solid support. For example, photolithography (Affymetrix, Santa Clara, Calif.) can be used to apply the oligonucleotide primers at particular position on a chip or solid support, as described in the U.S. Pat. Nos. 5,919,523, 5,837,832, 5,831,070, and 5,770,722, which are incorporated herein by reference. The oligonucleotide primers may also be applied to a solid support as described in Brown and Shalon, U.S. Pat. No. 5,807,522 (1998). Additionally, the primers may be applied to a solid support using a robotic system, such as one manufactured by Genetic MicroSystems (Woburn, Mass.), GeneMachines (San Carlos, Calif.) or Cartesian Technologies (Irvine, Calif.).

In one aspect of the invention, solid phase amplification of target polynucleotides from a biological sample is performed, wherein multiple groups of oligonucleotide primers are immobilized on a solid phase support. In a preferred embodiment, the primers within a group comprises at least a first set of primers that are identical in sequence and are complementary to a defined sequence of the target polynucleotide, capable of hybridizing to the target polynucleotide under appropriate conditions, and suitable as initial primers for nucleic acid synthesis (i.e., chain elongation or extension). Selected primers covering a particular region of the reference sequence are immobilized, as a group, onto a solid support at a discrete location. Preferably, the distance between groups is greater than the resolution of detection means to be used for detecting the amplified products. In a preferred embodiment, the primers are immobilized to form a microarray or chip that can be processed and analyzed via automated, processing. The immobilized primers are used for solid phase amplification of target polynucleotides under conditions suitable for a nucleic acid amplification means. In this manner, the presence or absence of a variety of potential variances in the kinase domain of the erbB1 gene can be determined in one assay.

A population of target polynucleotides isolated from a healthy individual can used as a control in determining whether a biological source has at least one kinase activity increasing variance in the kinase domain of the erb1 gene. Alternatively, target polynucleotides isolated from healthy tissue of the same individual may be used as a control as above.

An in situ-type PCR reactions on the microarrays can be conducted essentially as described in e.g. Embretson et al, Nature 362:359-362 (1993); Gosden et al, BioTechniques 15(1):78-80 (1993); Heniford et al Nuc. Acid Res. 21(14): 3159-3166 (1993); Long et al, Histochemistry 99:151-162 (1993); Nuovo et al, PCR Methods and Applications 2(4): 305-312 (1993); Patterson et al Science 260:976-979 (1993).

Alternatively, variances in the kinase domain of erbB1 can be determined by solid phase techniques without performing PCR on the support. A plurality of oligonucleotide probes, each containing a distinct variance in the kinase domain of erbB1, in duplicate, triplicate or quadruplicate, may be bound to the solid phase support. The presence or absence of variances in the test biological sample may be detected by selective hybridization techniques, known to those of skill in the art and described above.

Mass Spectrometry

In another embodiment, the presence or absence of kinase activity increasing nucleic acid variances in the kinase domain of the erbB1 gene are determined using mass spectrometry. To obtain an appropriate quantity of nucleic acid molecules on which to perform mass spectrometry, amplification may be necessary. Examples of appropriate amplification procedures for use in the invention include: cloning (Sambrook et al., Molecular Cloning: A Laboratory Manual, $3^{rd}$ Edition, Cold Spring Harbor Laboratory Press, 2001), polymerase chain reaction (PCR) (C. R. Newton and A. Graham, PCR, BIOS Publishers, 1994), ligase chain reaction (LCR) (Wiedmann, M., et al., (1994) PCR Methods Appl. Vol. 3, Pp. 57-64; F. Barnay Proc. Natl. Acad. Sci USA 88, 189-93 (1991), strand displacement amplification (SDA) (G. Terrance Walker et al., Nucleic Acids Res. 22, 2670-77 (1994)) and variations such as RT-PCR (Higuchi, et al., Bio/Technology 11:1026-1030 (1993)), allele-specific amplification (ASA) and transcription based processes.

To facilitate mass spectrometric analysis, a nucleic acid molecule containing a nucleic acid sequence to be detected can be immobilized to a solid support. Examples of appropriate solid supports include beads (e.g. silica gel, controlled pore glass, magnetic, Sephadex/Sepharose, cellulose), flat surfaces or chips (e.g. glass fiber filters, glass surfaces, metal surface (steel, gold, silver, aluminum, copper and silicon), capillaries, plastic (e.g. polyethylene, polypropylene, polyamide, polyvinylidenedifluoride membranes or microtiter plates)); or pins or combs made from similar materials comprising beads or flat surfaces or beads placed into pits in flat surfaces such as wafers (e.g. silicon wafers).

Immobilization can be accomplished, for example, based on hybridization between a capture nucleic acid sequence, which has already been immobilized to the support and a complementary nucleic acid sequence, which is also contained within the nucleic acid molecule containing the nucleic acid sequence to be detected. So that hybridization between the complementary nucleic acid molecules is not hindered by the support, the capture nucleic acid can include a spacer region of at least about five nucleotides in length between the solid support and the capture nucleic acid sequence. The duplex formed will be cleaved under the influence of the laser pulse and desorption can be initiated. The solid support-bound base sequence can be presented through natural oligoribo- or oligodeoxyribonucleotide as well as analogs (e.g. thio-modified phosphodiester or phosphotriester backbone) or employing oligonucleotide mimetics such as PNA analogs (see e.g. Nielsen et al., Science, 254, 1497 (1991)) which render the base sequence less susceptible to enzymatic degradation and hence increases overall stability of the solid support-bound capture base sequence.

Prior to mass spectrometric analysis, it may be useful to "condition" nucleic acid molecules, for example to decrease the laser energy required for volatilization and/or to minimize fragmentation. Conditioning is preferably performed while a target detection site is immobilized. An example of conditioning is modification of the phosphodiester backbone of the nucleic acid molecule (e.g. cation exchange), which can be useful for eliminating peak broadening due to a heterogeneity in the cations bound per nucleotide unit. Contacting a nucleic acid molecule with an alkylating agent such as alkyliodide, iodoacetamide, β-iodoethanol, 2,3-epoxy-1-propanol, the monothio phosphodiester bonds of a nucleic acid molecule can be transformed into a phosphotriester bond. Likewise, phosphodiester bonds may be transformed to uncharged derivatives employing trialkylsilyl chlorides. Further conditioning involves incorporating nucleotides which reduce sensitivity for depurination (fragmentation during MS) such as N7- or N9-deazapurine nucleotides, or RNA building blocks or using oligonucleotide triesters or incorporating phosphorothioate functions which are alkylated or employing oligonucleotide mimetics such as PNA.

For certain applications, it may be useful to simultaneously detect more than one (mutated) loci on a particular captured nucleic acid fragment (on one spot of an array) or it may be useful to perform parallel processing by using oligonucleotide or oligonucleotide mimetic arrays on various solid supports. "Multiplexing" can be achieved by several different methodologies. For example, several mutations can be simultaneously detected on one target sequence by employing corresponding detector (probe) molecules (e.g. oligonucleotides or oligonucleotide mimetics). However, the molecular weight differences between the detector oligonucleotides D1, D2 and D3 must be large enough so that simultaneous detection (multiplexing) is possible. This can be achieved either by the sequence itself (composition or length) or by the introduction of mass-modifying functionalities M1-M3 into the detector oligonucleotide.

Preferred mass spectrometer formats for use in the invention are matrix assisted laser desorption ionization (MALDI), electrospray (ES), ion cyclotron resonance (ICR) and Fourier Transform. Methods of performing mass spectrometry are known to those of skill in the art and are further described in Methods of Enzymology, Vol. 193: "Mass Spectrometry" (J. A. McCloskey, editor), 1990, Academic Press, New York.

Sequencing

In other preferred embodiments, determining the presence or absence of the at least one kinase activity increasing nucleic acid variance involves sequencing at least one nucleic acid sequence. The sequencing involves the sequencing of a portion or portions of the kinase domain of erbB1 which includes at least one variance site, and may include a plurality of such sites. Preferably, the portion is 500 nucleotides or less in length, more preferably 100 nucleotides or less, and most preferably 45 nucleotides or less in length. Such sequencing can be carried out by various methods recognized by those skilled in the art, including use of dideoxy termination methods (e.g., using dye-labeled dideoxy nucleotides), minisequencing, and the use of mass spectrometric methods.

Immunodetection

In one embodiment, determining the presence or absence of the at least one kinase activity increasing nucleic acid variance involves determining the activation state of downstream targets of EGFR.

The inventors of the present application have compared the phosphorylation status of the major downstream targets of EGFR. For example, the EGF-induced activation of Erk1 and Erk2, via Ras, of Akt via PLCγ/PI3K, and of STAT3 and STAT5 via JAK2, has been examined. Erk1 and Erk2, via Ras, Akt via PLCγ/PI3K, and STAT3 and STAT5 via JAK2 are essential downstream pathways mediating oncogenic effects of EGFR (R. N. Jorissen et al., *Exp. Cell Res.* 284, 31 (2003)).

The inventors of the present application have shown that EGF-induced Erk activation is indistinguishable among cells expressing wild-type EGFR or either of the two activating EGFR mutants.

In contrast, phosphorylation of both Akt and STAT5 was substantially elevated in cells expressing either of the mutant EGFRs. Increased phosphorylation of STAT3 was similarly observed in cells expressing mutant EGFRs. Thus, the selective EGF-induced autophosphorylation of C-terminal tyrosine residues within EGFR mutants is well correlated with the selective activation of downstream signaling pathways.

In one embodiment of the present application, the presence of EGFR mutations can be determined using immunological techniques well known in the art, e.g., antibody techniques such as immunohistochemistry, immunocytochemistry, FACS scanning, immunoblotting, radioimmunoassays, western blotting, immunoprecipitation, enzyme-linked immunosorbant assays (ELISA), and derivative techniques that make use of antibodies directed against activated downstream targets of EGFR. Examples of such targets include, for example, phosphorylated STAT3, phosphorylated STAT5, and phosphorylated Akt. Using phospho-specific antibodies, the activation status of STAT3, STAT5, and Akt can be determined. Activation of STAT3, STAT5, and Akt are useful as a diagnostic indicator of activating EGFR mutations.

In one embodiment of the present invention, the presence of activated (phosphorylated) STAT5, STAT3, or Akt indicates that an EGFR targeting treatment is likely to be effective.

The invention provides a method of screening for variants in the kinase domain of the erbB1 gene in a test biological sample by immunohistochemical or immunocytochemical methods.

Immunohistochemistry ("IHC") and immunocytochemistry ("ICC") techniques, for example, may be used. IHC is the application of immunochemistry to tissue sections, whereas ICC is the application of immunochemistry to cells or tissue imprints after they have undergone specific cytological preparations such as, for example, liquid-based preparations. Immunochemistry is a family of techniques based on the use of a specific antibody, wherein antibodies are used to specifically target molecules inside or on the surface of cells. The antibody typically contains a marker that will undergo a biochemical reaction, and thereby experience a change color, upon encountering the targeted molecules. In some instances, signal amplification may be integrated into the particular protocol, wherein a secondary antibody, that includes the marker stain, follows the application of a primary specific antibody.

Immunoshistochemical assays are known to those of skill in the art (e.g., see Jalkanen, et al., J. Cell. Biol. 101:976-985 (1985); Jalkanen, et al., J. Cell. Biol. 105:3087-3096 (1987).

Antibodies, polyclonal or monoclonal, can be purchased from a variety of commercial suppliers, or may be manufactured using well-known methods, e.g., as described in Harlow et al., Antibodies: A Laboratory Manual, 2nd Ed; Cold Spring Harbor Laboratory Press, Cold Spring Harbor, N.Y. (1988). In general, examples of antibodies useful in the present invention include anti-phospho-STAT3, anti-phospho-STAT5, and anti-phospho-Akt antibodies. Such antibodies can be purchased, for example, from Upstate Biotechnology (Lake Placid, N.Y.), New England Biolabs (Beverly, Mass.), NeoMarkers (Fremont, Calif.)

Typically, for immunohistochemistry, tissue sections are obtained from a patient and fixed by a suitable fixing agent such as alcohol, acetone, and paraformaldehyde, to which is reacted an antibody. Conventional methods for immunohistochemistry are described in Harlow and Lane (eds) (1988) In "Antibodies A Laboratory Manual", Cold Spring Harbor Press, Cold Spring Harbor, N.Y.; Ausbel et al (eds) (1987), in Current Protocols In Molecular Biology, John Wiley and Sons (New York, N.Y.). Biological samples appropriate for such detection assays include, but are not limited to, cells, tissue biopsy, whole blood, plasma, serum, sputum, cerebrospinal fluid, breast aspirates, pleural fluid, urine and the like.

For direct labeling techniques, a labeled antibody is utilized. For indirect labeling techniques, the sample is further reacted with a labeled substance.

Alternatively, immunocytochemistry may be utilized. In general, cells are obtained from a patient and fixed by a suitable fixing agent such as alcohol, acetone, and paraformaldehyde, to which is reacted an antibody. Methods of immunocytological staining of human samples is known to those of skill in the art and described, for example, in Brauer et al., 2001 (FASEB J, 15, 2689-2701), Smith-Swintosky et al., 1997.

Immunological methods of the present invention are advantageous because they require only small quantities of biological material. Such methods may be done at the cellular level and thereby necessitate a minimum of one cell. Preferably, several cells are obtained from a patient affected with or at risk for developing cancer and assayed according to the methods of the present invention.

Other Diagnostic Methods

An agent for detecting mutant EGFR protein is an antibody capable of binding to mutant EGFR protein, preferably an antibody with a detectable label. Antibodies can be polyclonal, or more preferably, monoclonal. An intact antibody, or a fragment thereof (e.g., $F_{ab}$ or $F_{(ab2)}$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently-labeled secondary antibody and end-labeling of a DNA probe with biotin such that it can be detected with fluorescently-labeled streptavidin. The term "biological sample" is intended to include tissues, cells and biological fluids isolated from a subject, as well as tissues, cells and fluids present within a subject. That is, the detection method of the invention can be used to detect mutant EGFR mRNA, protein, or genomic DNA in a biological sample in vitro as well as in vivo. For example, in vitro techniques for detection of mutant EGFR mRNA include Northern hybridizations and in situ hybridizations. In vitro techniques for detection of mutant EGFR protein include enzyme linked immunosorbent assays (ELISAs), Western blots, immunoprecipitations, and immunofluorescence. In vitro techniques for detection of mutant EGFR genomic DNA include Southern hybridizations. Furthermore, in vivo techniques for detection of mutant EGFR protein include introducing into a subject a labeled anti-mutant EGFR protein antibody. For example, the antibody can be labeled with a radioactive marker whose presence and location in a subject can be detected by standard imaging techniques.

In one embodiment, the biological sample contains protein molecules from the test subject. Alternatively, the biological sample can contain mRNA molecules from the test subject or genomic DNA molecules from the test subject.

In another embodiment, the methods further involve obtaining a control biological sample from a control subject, contacting the control sample with a compound or agent capable of detecting mutant EGFR protein, mRNA, or genomic DNA, such that the presence of mutant EGFR protein, mRNA or genomic DNA is detected in the biological sample, and comparing the presence of mutant EGFR protein, mRNA or genomic DNA in the control sample with the presence of mutant EGFR protein, mRNA or genomic DNA in the test sample.

In a different embodiment, the diagnostic assay is for mutant EGFR activity. In a specific embodiment, the mutant EGFR activity is a tyrosine kinase activity. One such diagnostic assay is for detecting EGFR-mediated phosphorylation of at least one EGFR substrate. Levels of EGFR activity can be assayed for, e.g., various mutant EGFR polypeptides, various tissues containing mutant EGFR, biopsies from cancer tissues suspected of having at least one mutant EGFR, and the like. Comparisons of the levels of EGFR activity in these various cells, tissues, or extracts of the same, can optionally be made. In one embodiment, high levels of EGFR activity in cancerous tissue is diagnostic for cancers that may be susceptible to treatments with one or more tyrosine kinase inhibitor. In related embodiments, EGFR activity levels can be determined between treated and untreated biopsy samples, cell lines, transgenic animals, or extracts from any of these, to determine the effect of a given treatment on mutant EGFR activity as compared to an untreated control.

Method of Treating a Patient

In one embodiment, the invention provides a method for selecting a treatment for a patient affected by or at risk for developing cancer by determining the presence or absence of at least one kinase activity increasing nucleic acid variance in the kinase domain of the erbB1 gene. In another embodiment, the variance is a plurality of variances, whereby a plurality may include variances from one, two, three or more gene loci.

In certain embodiments, the presence of the at least one variance is indicative that the treatment will be effective or otherwise beneficial (or more likely to be beneficial) in the patient. Stating that the treatment will be effective means that the probability of beneficial therapeutic effect is greater than in a person not having the appropriate presence of the particular kinase activity increasing nucleic acid variance(s) in the kinase domain of the erbB1 gene.

The treatment will involve the administration of a tyrosine kinase inhibitor. The treatment may involve a combination of treatments, including, but not limited to a tyrosine kinase inhibitor in combination with other tyrosine kinase inhibitors, chemotherapy, radiation, etc.

Thus, in connection with the administration of a tyrosine kinase inhibitor, a drug which is "effective against" a cancer indicates that administration in a clinically appropriate manner results in a beneficial effect for at least a statistically significant fraction of patients, such as a improvement of symptoms, a cure, a reduction in disease load, reduction in tumor mass or cell numbers, extension of life, improvement in quality of life, or other effect generally recognized as positive by medical doctors familiar with treating the particular type of disease or condition.

In a preferred embodiment, the compound is an anilinoquinazoline or synthetic anilinoquinazoline. European Patent Publication No. 0566226 discloses anilinoquinazolines which have activity against epidermal growth factor (EGF) receptor tyrosine kinase. It is also known from European Patent Applications Nos. 0520722 and 0566226 that certain 4-anilinoquinazoline derivatives are useful as inhibitors of receptor tyrosine kinases. The very tight structure-activity relationships shown by these compounds suggests a clearly-defined binding mode, where the quinazoline ring binds in the adenine pocket and the anilino ring binds in an adjacent, unique lipophilic pocket. Three 4-anilinoquinazoline analogues (two reversible and one irreversible inhibitor) have been evaluated clinically as anticancer drugs. Denny, Farmaco January-February 2001; 56(1-2):51-6. Alternatively, the compound is EKB-569, an inhibitor of EGF receptor kinase (Torrance et al., Nature Medicine, vol. 6, No. 9, September 2000, p. 1024). In a most preferred embodiment, the compound is gefitinib (IRESSA®) or erlotinib (TARCEVA®).

Treatment targeting cancer cells containing at least one mutant EGFR described herein may be administered alone or in combination with any other appropriate anti-cancer treatment and/or therapeutic agent known to one skilled in the art. In one embodiment, treatment of a pathology, such as a cancer, is provided comprising administering to a subject in need thereof therapeutically effective amounts of a compound that inhibits EGFR kinase activity, such as gefitinib, erlotinib, etc., administered alone or in combination with at least one other anti-cancer agent or therapy. Inhibition of activated protein kinases through the use of targeted small molecule drugs or antibody-based strategies has emerged as an effective approach to cancer therapy. See, e.g., G. D. Demetri et al., N. Engl. J. Med. 347, 472 (2002); B. J. Druker et al., N. Engl. J. Med. 344, 1038 (2001); D. J. Slamon et al., N. Engl. J. Med. 344, 783 (2001).

In one embodiment, the anti-cancer agent is at least one chemotherapeutic agent. In a related embodiment, the anti-cancer agent is at least one radiotherapy. In a variant embodiment, the anti-cancer therapy is an antiangiogenic therapy (e.g., endostatin, angiostatin, TNP-470, Caplostatin (Stachi-Fainaro et al., Cancer Cell 7(3), 251 (2005))

The therapeutic agents may be the same or different, and may be, for example, therapeutic radionuclides, drugs, hormones, hormone antagonists, receptor antagonists, enzymes or proenzymes activated by another agent, autocrines, cytokines or any suitable anti-cancer agent known to those skilled in the art. In one embodiment, the anti-cancer agent is Avastin, an anti-VEGF antibody proven successful in anti-angiogenic therapy of cancer against both solid cancers and hematological malignancies. See, e.g., Ribatti et al. 2003 J Hemathother Stem Cell Res. 12(1), 11-22. Toxins also can be used in the methods of the present invention. Other therapeutic agents useful in the present invention include anti-DNA, anti-RNA, radiolabeled oligonucleotides, such as antisense oligonucleotides, anti-protein and anti-chromatin cytotoxic or antimicrobial agents. Other therapeutic agents are known to those skilled in the art, and the use of such other therapeutic agents in accordance with the present invention is specifically contemplated.

The antitumor agent may be one of numerous chemotherapy agents such as an alkylating agent, an antimetabolite, a hormonal agent, an antibiotic, an antibody, an anti-cancer biological, gleevec, colchicine, a *vinca* alkaloid, L-asparaginase, procarbazine, hydroxyurea, mitotane, nitrosoureas or an imidazole carboxamide. Suitable agents are those agents that promote depolarization of tubulin or prohibit tumor cell proliferation. Chemotherapeutic agents contemplated as within the scope of the invention include, but are not limited to, anti-cancer agents listed in the Orange Book of Approved Drug Products With Therapeutic Equivalence Evaluations, as compiled by the Food and Drug Administration and the U.S. Department of Health and Human Services. Nonlimiting examples of chemotherapeutic agents include, e.g., carboplatin and paclitaxel. Treatments targeting EGFR kinase activity can also be administered together with radiation therapy treatment. Additional anti-cancer treatments known in the art are contemplated as being within the scope of the invention.

The therapeutic agent may be a chemotherapeutic agent. Chemotherapeutic agents are known in the art and include at least the taxanes, nitrogen mustards, ethylenimine derivatives, alkyl sulfonates, nitrosoureas, triazenes; folic acid analogs, pyrimidine analogs, purine analogs, *vinca* alkaloids, antibiotics, enzymes, platinum coordination complexes, substituted urea, methyl hydrazine derivatives, adrenocortical suppressants, or antagonists. More specifically, the chemotherapeutic agents may be one or more agents chosen from the nonlimiting group of steroids, progestins, estrogens, antiestrogens, or androgens. Even more specifically, the chemotherapy agents may be azaribine, bleomycin, bryostatin-1, busulfan, carmustine, chlorambucil, carboplatin, cisplatin, CPT-11, cyclophosphamide, cytarabine, dacarbazine, dactinomycin, daunorubicin, dexamethasone, diethylstilbestrol, doxorubicin, ethinyl estradiol, etoposide, fluorouracil, fluoxymesterone, gemcitabine, hydroxyprogesterone caproate, hydroxyurea, L-asparaginase, leucovorin, lomustine, mechlorethamine, medroprogesterone acetate, megestrol acetate, melphalan, mercaptopurine, methotrexate, methotrexate, mithramycin, mitomycin, mitotane, paclitaxel, phenyl butyrate, prednisone, procarbazine, semustine streptozocin, tamoxifen, taxanes, taxol, testosterone propionate, thalidomide, thioguanine, thiotepa, uracil mustard, vinblastine, or vincristine. The use of any combinations of chemotherapy agents is also contemplated. The administration of the chemotherapeutic agent may be before, during or after the administration of a treatment targeting EGFR activity.

Other suitable therapeutic agents are selected from the group consisting of radioisotope, boron addend, immunomodulator, toxin, photoactive agent or dye, cancer chemotherapeutic drug, antiviral drug, antifungal drug, antibacterial drug, antiprotozoal drug and chemosensitizing agent (See, U.S. Pat. Nos. 4,925,648 and 4,932,412). Suitable chemotherapeutic agents are described in REMINGTON'S PHARMACEUTICAL SCIENCES, 19th Ed. (Mack Publishing Co. 1995), and in Goodman and Gilman's The Pharmacological Basis of Therapeutics (Goodman et al., Eds. Macmillan Publishing Co., New York, 1980 and 2001 editions). Other suitable chemotherapeutic agents, such as experimental drugs, are known to those of skill in the art. Moreover a suitable therapeutic radioisotope is selected from the group consisting of α-emitters, β-emitters, γ-emitters, Auger electron emitters, neutron capturing agents that emit α-particles and radioisotopes that decay by electron capture. Preferably, the radioisotope is selected from the group consisting of 225Ac, 198Au, 32P, 125I, 131I, 90Y, 186Re, 188Re, 67Cu, 177Lu, 213Bi, 10B, and 211At.

Where more than one therapeutic agent is used, they may be the same or different. For example, the therapeutic agents may comprise different radionuclides, or a drug and a radionuclide. In a preferred embodiment, treatment targeting EGFR activity inhibits mutant EGFR kinase activity.

In another embodiment, different isotopes that are effective over different distances as a result of their individual energy emissions are used as first and second therapeutic agents. Such agents can be used to achieve more effective treatment of tumors, and are useful in patients presenting with multiple tumors of differing sizes, as in normal clinical circumstances.

Few of the available isotopes are useful for treating the very smallest tumor deposits and single cells. In these situations, a drug or toxin may be a more useful therapeutic agent. Accordingly, in preferred embodiments of the present invention, isotopes are used in combination with non-isotopic species such as drugs, toxins, and neutron capture agents. Many drugs and toxins are known which have cytotoxic effects on cells, and can be used in connection with the present invention. They are to be found in compendia of drugs and toxins, such as the Merck Index, Goodman and Gilman, and the like, and in the references cited above.

Drugs that interfere with intracellular protein synthesis can also be used in the methods of the present invention; such drugs are known to those skilled in the art and include puromycin, cycloheximide, and ribonuclease.

The therapeutic methods of the invention may be used for cancer therapy. It is well known that radioisotopes, drugs, and toxins can be conjugated to antibodies or antibody fragments which specifically bind to markers which are produced by or associated with cancer cells, and that such antibody conjugates can be used to target the radioisotopes, drugs or toxins to tumor sites to enhance their therapeutic efficacy and minimize side effects. Examples of these agents and methods are reviewed in Wawrzynczak and Thorpe (in Introduction to the Cellular and Molecular Biology of Cancer, L. M. Franks and N. M. Teich, eds, Chapter 18, pp. 378-410, Oxford University Press. Oxford, 1986), in Immunoconjugates: Antibody Conjugates in Radioimaging and Therapy of Cancer (C. W. Vogel, ed., 3-300, Oxford University Press, N.Y., 1987), in Dillman, R. O. (CRC Critical Reviews in Oncology/Hematology 1:357, CRC Press, Inc., 1984), in Pastan et al. (Cell 47:641, 1986). in Vitetta et al. (Science 238:1098-1104, 1987) and in Brady et al. (Int. J. Rad. Oncol. Biol. Phys. 13:1535-1544, 1987). Other examples of the use of immunoconjugates for cancer and other forms of therapy have been disclosed, inter alia, in U.S. Pat. Nos. 4,331,647, 4,348,376, 4,361,544, 4,468,457, 4,444,744, 4,460,459, 4,460,561 4,624,846, 4,818,709, 4,046,722, 4,671,958, 4,046,784, 5,332,567, 5,443,953, 5,541,297, 5,601,825, 5,635,603, 5,637,288, 5,677,427, 5,686,578, 5,698,178, 5,789,554, 5,922,302, 6,187,287, and 6,319,500.

Additionally, the treatment methods of the invention can be used in combination with other compounds or techniques for preventing, mitigating or reversing the side effects of certain cytotoxic agents. Examples of such combinations include, e.g., administration of IL-1 together with an antibody for rapid clearance, as described in e.g., U.S. Pat. No. 4,624,846. Such administration can be performed from 3 to 72 hours after administration of a primary therapeutic treatment targeting EGFR activity in combination with an anticancer agent (e.g., with a radioisotope, drug or toxin as the cytotoxic component). This can be used to enhance clearance of the conjugate, drug or toxin from the circulation and to mitigate or reverse myeloid and other hematopoietic toxicity caused by the therapeutic agent.

In another aspect of the invention, cancer therapy may involve a combination of more than one tumoricidal agent, e.g., a drug and a radioisotope, or a radioisotope and a Boron-10 agent for neutron-activated therapy, or a drug and a biological response modifier, or a fusion molecule conjugate and a biological response modifier. The cytokine can be integrated into such a therapeutic regimen to maximize the efficacy of each component thereof.

Similarly, certain antileukemic and antilymphoma antibodies conjugated with radioisotopes that are β or α emitters may induce myeloid and other hematopoietic side effects when these agents are not solely directed to the tumor cells. This is observed particularly when the tumor cells are in the circulation and in the blood-forming organs. Concomitant and/or subsequent administration of at least one hematopoietic cytokine (e.g., growth factors, such as colony stimulating factors, such as G-CSF and GM-CSF) is preferred to reduce or ameliorate the hematopoietic side effects, while augmenting the anticancer effects.

It is well known in the art that various methods of radionuclide therapy can be used for the treatment of cancer and other pathological conditions, as described, e.g., in Harbert, "Nuclear Medicine Therapy", New York, Thieme Medical Publishers, 1087, pp. 1-340. A clinician experienced in these procedures will readily be able to adapt the cytokine adjuvant therapy described herein to such procedures to mitigate any hematopoietic side effects thereof. Similarly, therapy with cytotoxic drugs, administered with treatment targeting EGFR activity, can be used, e.g., for treatment of cancer or other cell proliferative diseases. Such treatment is governed by analogous principles to radioisotope therapy with isotopes or radiolabeled antibodies. The ordinary skilled clinician will be able to adapt the administration of the additional anti-cancer therapy before, during and/or after the primary anti-cancer therapy.

Kits

The present invention therefore also provides predictive, diagnostic, and prognostic kits comprising degenerate primers to amplify a target nucleic acid in the kinase domain of the erbB1 gene and instructions comprising amplification protocol and analysis of the results. The kit may alternatively also comprise buffers, enzymes, and containers for performing the amplification and analysis of the amplification products. The kit may also be a component of a screening, diagnostic or prognostic kit comprising other tools such as DNA microarrays. Preferably, the kit also provides one or more control templates, such as nucleic acids isolated from normal tissue sample, and/or a series of samples representing different variances in the kinase domain of the erbB1 gene.

In one embodiment, the kit provides two or more primer pairs, each pair capable of amplifying a different region of the erbB1 gene (each region a site of potential variance) thereby providing a kit for analysis of expression of several gene variances in a biological sample in one reaction or several parallel reactions.

Primers in the kits may be labeled, for example fluorescently labeled, to facilitate detection of the amplification products and consequent analysis of the nucleic acid variances.

In one embodiment, more than one variance can be detected in one analysis. A combination kit will therefore comprise of primers capable of amplifying different segments of the kinase domain of the erbB1 gene. The primers may be differentially labeled, for example using different fluorescent labels, so as to differentiate between the variances.

The primers contained within the kit may include the following primers: Exon 19 sense primer, 5'-GCAATATCA-GCCTTAGGTGCGGCTC-3' (SEQ ID NO: 505); Exon 19 antisense primer, 5'-CATAGAA AGTGAACATTTAGGAT-GTG-3' (SEQ ID NO: 506); Exon 21 sense primer, 5'-CTAACGTTCG CCAGCCATAAGTCC-3' (SEQ ID NO: 507); and Exon 21 antisense primer, 5'-GCTGCGAGCT-CACCCAG AATGTCTGG-3' (SEQ ID NO: 508).

In a preferred embodiment, the primers are selected from the group consisting of SEQ ID NOS 646-673 (see Tables 5 and 6). These primers have SEQ ID NO 645 on the 5' end of the forward primer and SEQ ID NO 674 on the 5' end of the reverse primers.

Immunodetection Kits

In further embodiments, the invention provides immunological kits for use in detecting the activation levels of downstream EGFR targets (i.e. STAT3, STAT5, and Akt). Such kits will generally comprise one or more antibodies that have immunospecificity for the phosphorylated form of STAT3, STAT5, or Akt.

A kit comprising an antibody capable of immunospecifically binding a phosphorylated protein in a mammalian cell selected from the group consisting of phosphorylated Akt, STAT3, and STAT5 proteins and instructions for using the antibody to examine the mammalian cell for Akt, STAT3 or STAT5 pathway activation is provided in the present invention. In preferred methods, the kit comprises different antibodies, each of which is capable of immunospecifically binding phosphorylated proteins in a mammalian cell selected from the group consisting of phosphorylated Akt, STAT3 or STAT5 proteins.

The kit generally comprises, a) a pharmaceutically acceptable carrier; b) an antibody directed against phosphorylated STAT3, STAT5, or Akt, in a suitable container means; and c) an immunodetection reagent. Antibodies (monoclonal or polyclonal) are commercially available and may also be prepared by methods known to those of skill in the art, for example, in Current Protocols in Immunology, John Wiley & Sons, Edited by: John E. Coligan, Ada M. Kruisbeek, David H. Margulies, Ethan M. Shevach, Warren Strober, 2001.

In certain embodiments, the antigen or the antibody may be bound to a solid support, such as a column matrix or well of a microtitre plate. The immunodetection reagents of the kit may take any one of a variety of forms, including those detectable labels that are associated with, or linked to, the given antibody or antigen itself. Detectable labels that are associated with or attached to a secondary binding ligand are also contemplated. Exemplary secondary ligands are those secondary antibodies that have binding affinity for the first antibody or antigen.

Suitable assay labels are known in the art and include enzyme labels, such as, glucose oxidase; radioisotopes, such as iodine ($^{131}I$, $^{125}I$, $^{123}I$, $^{121}I$) carbon ($^{14}C$), sulfur ($^{35}S$), tritium ($^{3}H$), indium ($^{115m}In$, $^{113m}In$, $^{112}In$, $^{111}In$), and technetium ($^{99}Tc$, $^{99m}Tc$), thallium ($^{201}Ti$), gallium ($^{68}Ga$, $^{67}Ga$), palladium ($^{103}Pd$), molybdenum ($^{99}Mo$), xenon ($^{133}Xe$), fluorine ($^{18}F$), $^{153}Sm$, $^{177}Lu$, $^{159}Gd$, $^{149}Pm$, $^{140}La$, $^{175}Yb$, $^{166}Ho$, $^{90}Y$, $^{47}Sc$, $^{186}Re$, $^{188}Re$, $^{142}Pr$, $^{105}Rh$, $^{97}Ru$; luminescent labels, such as luminol; and fluorescent labels, such as fluorescein and rhodamine, and biotin.

Further suitable immunodetection reagents for use in the present kits include the two-component reagent that comprises a secondary antibody that has binding affinity for the first antibody or antigen, along with a third antibody that has binding affinity for the second antibody, wherein the third antibody is linked to a detectable label.

A number of exemplary labels are known in the art and all such labels may be employed in connection with the present invention. Radiolabels, nuclear magnetic spin-resonance isotopes, fluorescent labels and enzyme tags capable of generating a colored product upon contact with an appropriate substrate are suitable examples.

The kits may contain antibody-label conjugates either in fully conjugated form, in the form of intermediates, or as separate moieties to be conjugated by the user of the kit.

The kits may further comprise a suitably aliquoted composition of an antigen whether labeled or unlabeled, as may be used to prepare a standard curve for a detection assay or as a positive control.

The kits of the invention, regardless of type, will generally comprise one or more containers into which the biological agents are placed and, preferably, suitable aliquoted. The components of the kits may be packaged either in aqueous media or in lyophilized form.

The immunodetection kits of the invention may additionally contain one or more of a variety of other cancer marker antibodies or antigens, if so desired. Such kits could thus provide a panel of cancer markers, as may be better used in testing a variety of patients. By way of example, such additional markers could include, other tumor markers such as PSA, SeLe (X), HCG, as well as p53, cyclin D1, p16, tyrosinase, MAGE, BAGE, PAGE, MUC18, CEA, p27, [bgr]HCG or other markers known to those of skill in the art.

The container means of the kits will generally include at least one vial, test tube, flask, bottle, or even syringe or other container means, into which the antibody or antigen may be placed, and preferably, suitably aliquoted. Where a second or third binding ligand or additional component is provided, the kit will also generally contain a second, third or other additional container into which this ligand or component may be placed.

The kits of the present invention will also typically include a means for containing the antibody, antigen, and any other reagent containers in close confinement for commercial sale. Such containers may include injection or blow-molded plastic containers into which the desired vials are retained.

The methods of the present invention also encompass the identification of compounds that interfere with the kinase activity of a variant form of the EGFR. The variant EGFR comprises at least one variance in its kinase domain. Such compounds may, for example, be tyrosine kinase inhibitors. Methods for identifying compounds that interfere with the kinase activity of a receptor are generally known to those of skill in the art and are further described in, for example, for example, Dhanabal et al., Cancer Res. 59:189-197 (1999); Xin et al., J. Biol. Chem. 274:9116-9121 (1999); Sheu et al., Anticancer Res. 18:4435-4441; Ausprunk et al., Dev. Biol. 38:237-248 (1974); Gimbrone et al., J. Natl. Cancer Inst. 52:413-427; Nicosia et al., In vitro 18:538-549, incorporated herein by reference. In general, compounds are identified, using the methods disclosed herein, that interfere with the enhanced kinase activity characteristic of at least one variance in the kinase domain of the erbB1 gene.

Solid Support

In another embodiment, the invention provides a kit for practicing the methods of the invention. In one embodiment, a kit for the detection of variances in the kinase domain of erbB1 gene on a solid support is described. The kit can include, e.g. the materials and reagents for detecting a plurality of variances in one assay. The kit can include e.g. a solid support, oligonucleotide primers for a specific set of target polynucleotides, polymerase chain reaction reagents and components, e.g. enzymes for DNA synthesis, labeling materials, and other buffers and reagents for washing. The kit may also include instructions for use of the kit to amplify specific targets on a solid support. Where the kit contains a prepared solid support having a set of primers already fixed on the solid support, e.g. for amplifying a particular set of target polynucleotides, the design and construction of such a prepared solid support is described above. The kit also includes reagents necessary for conducting a PCR on a solid support, for example using an in situ-type or solid phase type PCR procedure where the support is capable of PCR amplification using an in situ-type PCR machine. The PCR reagents, included in the kit, include the usual PCR buffers, a thermostable polymerase (e.g. Taq DNA polymerase), nucleotides (e.g. dNTPs), and other components and labeling molecules (e.g. for direct or indirect labeling as described above). The kits can be assembled to support practice of the PCR amplification method using immobilized primers alone or, alternatively, together with solution phase primers.

Alternatively, the kit may include a solid support with affixed oligonucleotides specific to any number of EGFR variances, further defined in FIGS. 4A-4C and FIGS. 7 and 8. A test biological sample may be applied to the solid support, under selective hybridization conditions, for the determination of the presence or absence of variances in the kinase domain of erbB1.

The methods of the present invention also encompass the identification of compounds that interfere with the kinase activity of a variant form of the EGFR. The variant EGFR comprises at least one variance in its kinase domain. However, in an alternative embodiment, the variant EGFR comprises a secondary mutation that confers resistance to a first TKI e.g., gefitinib or erlotinib. Such compounds may, for example, be tyrosine kinase inhibitors. Methods for identifying compounds that interfere with the kinase activity of a receptor are generally known to those of skill in the art and are further described in, for example, for example, Dhanabal et al., Cancer Res. 59:189-197 (1999); Xin et al., J. Biol. Chem. 274:9116-9121 (1999); Sheu et al., Anticancer Res. 18:4435-4441; Ausprunk et al., Dev. Biol. 38:237-248 (1974); Gimbrone et al., J. Natl. Cancer Inst. 52:413-427; Nicosia et al., In vitro 18:538-549, incorporated herein by reference. In general, compounds are identified, using the methods disclosed herein, that interfere with the enhanced kinase activity characteristic of at least one variance in the kinase domain of the erbB1 gene. Such known variances are described in FIGS. 4, 7, 8 and Table 2.

Once identified, such compounds are administered to patients in need of EGFR targeted treatment, for example, patients affected with or at risk for developing cancer.

The route of administration may be intravenous (I.V.), intramuscular (I.M.), subcutaneous (S.C.), intradermal (I.D.), intraperitoneal (I.P.), intrathecal (I.T.), intrapleural, intrauterine, rectal, vaginal, topical, intratumor and the like. The compounds of the invention can be administered parenterally by injection or by gradual infusion over time and can be delivered by peristaltic means.

Administration may be by transmucosal or transdermal means. For transmucosal or transdermal administration, penetrants appropriate to the barrier to be permeated are used in the formulation. Such penetrants are generally known in the art, and include, for example, for transmucosal administration bile salts and fusidic acid derivatives. In addition, detergents may be used to facilitate permeation. Transmucosal administration may be through nasal sprays, for example, or using suppositories. For oral administration, the compounds of the invention are formulated into conventional oral administration forms such as capsules, tablets and tonics.

For topical administration, the pharmaceutical composition (inhibitor of kinase activity) is formulated into ointments, salves, gels, or creams, as is generally known in the art.

The therapeutic compositions of this invention are conventionally administered intravenously, as by injection of a unit dose, for example. The term "unit dose" when used in reference to a therapeutic composition of the present invention refers to physically discrete units suitable as unitary dosage for the subject, each unit containing a predetermined quantity of active material calculated to produce the desired therapeutic effect in association with the required diluent; i.e., carrier, or vehicle.

The compositions are administered in a manner compatible with the dosage formulation, and in a therapeutically effective amount. The quantity to be administered and timing depends on the subject to be treated, capacity of the subject's system to utilize the active ingredient, and degree of therapeutic effect desired. Precise amounts of active ingredient required to be administered depend on the judgment of the practitioner and are peculiar to each individual.

The tyrosine kinase inhibitors useful for practicing the methods of the present invention are described herein. Any formulation or drug delivery system containing the active ingredients, which is suitable for the intended use, as are generally known to those of skill in the art, can be used. Suitable pharmaceutically acceptable carriers for oral, rectal, topical or parenteral (including inhaled, subcutaneous, intraperitoneal, intramuscular and intravenous) administration are known to those of skill in the art. The carrier must be pharmaceutically acceptable in the sense of being compatible with the other ingredients of the formulation and not deleterious to the recipient thereof.

As used herein, the terms "pharmaceutically acceptable", "physiologically tolerable" and grammatical variations thereof, as they refer to compositions, carriers, diluents and reagents, are used interchangeably and represent that the materials are capable of administration to or upon a mammal without the production of undesirable physiological effects.

Formulations suitable for parenteral administration conveniently include sterile aqueous preparation of the active compound which is preferably isotonic with the blood of the recipient. Thus, such formulations may conveniently contain distilled water, 5% dextrose in distilled water or saline. Useful formulations also include concentrated solutions or solids containing the compound which upon dilution with an appropriate solvent give a solution suitable for parental administration above.

For enteral administration, a compound can be incorporated into an inert carrier in discrete units such as capsules, cachets, tablets or lozenges, each containing a predetermined amount of the active compound; as a powder or granules; or a suspension or solution in an aqueous liquid or non-aqueous liquid, e.g., a syrup, an elixir, an emulsion or a draught. Suitable carriers may be starches or sugars and include lubricants, flavorings, binders, and other materials of the same nature.

A tablet may be made by compression or molding, optionally with one or more accessory ingredients. Compressed tablets may be prepared by compressing in a suitable machine the active compound in a free-flowing form, e.g., a powder or granules, optionally mixed with accessory ingredients, e.g., binders, lubricants, inert diluents, surface active or dispersing agents. Molded tablets may be made by molding in a suitable machine, a mixture of the powdered active compound with any suitable carrier.

A syrup or suspension may be made by adding the active compound to a concentrated, aqueous solution of a sugar, e.g., sucrose, to which may also be added any accessory ingredients. Such accessory ingredients may include flavoring, an agent to retard crystallization of the sugar or an agent to increase the solubility of any other ingredient, e.g., as a polyhydric alcohol, for example, glycerol or sorbitol.

Formulations for rectal administration may be presented as a suppository with a conventional carrier, e.g., cocoa butter or Witepsol S55 (trademark of Dynamite Nobel Chemical, Germany), for a suppository base.

Formulations for oral administration may be presented with an enhancer. Orally-acceptable absorption enhancers include surfactants such as sodium lauryl sulfate, palmitoyl carnitine, Laureth-9, phosphatidylcholine, cyclodextrin and derivatives thereof; bile salts such as sodium deoxycholate, sodium taurocholate, sodium glycochlate, and sodium fusidate; chelating agents including EDTA, citric acid and salicylates; and fatty acids (e.g., oleic acid, lauric acid, acylcarnitines, mono- and diglycerides). Other oral absorption enhancers include benzalkonium chloride, benzethonium chloride, CHAPS (3-(3-cholamidopropyl)-dimethyl-ammonio-1-propanesulfonate), Big-CHAPS (N, N-bis(3-D-gluconamidopropyl)-cholamide), chlorobutanol, octoxynol-9, benzyl alcohol, phenols, cresols, and alkyl alcohols. An especially preferred oral absorption enhancer for the present invention is sodium lauryl sulfate.

Alternatively, the compound may be administered in liposomes or microspheres (or microparticles). Methods for preparing liposomes and microspheres for administration to a patient are well known to those of skill in the art. U.S. Pat. No. 4,789,734, the contents of which are hereby incorporated by reference, describes methods for encapsulating biological materials in liposomes. Essentially, the material is dissolved in an aqueous solution, the appropriate phospholipids and lipids added, along with surfactants if required, and the material dialyzed or sonicated, as necessary. A review of known methods is provided by G. Gregoriadis, Chapter 14, "Liposomes," Drug Carriers in Biology and Medicine, pp. 287-341 (Academic Press, 1979).

Microspheres formed of polymers or proteins are well known to those skilled in the art, and can be tailored for passage through the gastrointestinal tract directly into the blood stream. Alternatively, the compound can be incorporated and the microspheres, or composite of microspheres, implanted for slow release over a period of time ranging from days to months. See, for example, U.S. Pat. Nos. 4,906,474, 4,925,673 and 3,625,214, and Jein, TIPS 19:155-157 (1998), the contents of which are hereby incorporated by reference.

In one embodiment, the tyrosine kinase inhibitor of the present invention can be formulated into a liposome or microparticle which is suitably sized to lodge in capillary beds following intravenous administration. When the liposome or microparticle is lodged in the capillary beds surrounding ischemic tissue, the agents can be administered locally to the site at which they can be most effective. Suitable liposomes for targeting ischemic tissue are generally less than about 200 nanometers and are also typically unilamellar vesicles, as disclosed, for example, in U.S. Pat. No. 5,593,688 to Baldeschweiler, entitled "Liposomal targeting of ischemic tissue," the contents of which are hereby incorporated by reference.

Preferred microparticles are those prepared from biodegradable polymers, such as polyglycolide, polylactide and copolymers thereof. Those of skill in the art can readily determine an appropriate carrier system depending on various factors, including the desired rate of drug release and the desired dosage.

In one embodiment, the formulations are administered via catheter directly to the inside of blood vessels. The administration can occur, for example, through holes in the catheter. In those embodiments wherein the active compounds have a relatively long half life (on the order of 1 day to a week or more), the formulations can be included in biodegradable polymeric hydrogels, such as those disclosed in U.S. Pat. No. 5,410,016 to Hubbell et al. These polymeric hydrogels can be delivered to the inside of a tissue lumen and the active compounds released over time as the polymer degrades. If desirable, the polymeric hydrogels can have microparticles or liposomes which include the active compound dispersed therein, providing another mechanism for the controlled release of the active compounds.

The formulations may conveniently be presented in unit dosage form and may be prepared by any of the methods well known in the art of pharmacy. All methods include the step of bringing the active compound into association with a carrier which constitutes one or more accessory ingredients. In general, the formulations are prepared by uniformly and intimately bringing the active compound into association with a liquid carrier or a finely divided solid carrier and then, if necessary, shaping the product into desired unit dosage form.

The formulations may further include one or more optional accessory ingredient(s) utilized in the art of pharmaceutical formulations, e.g., diluents, buffers, flavoring agents, binders, surface active agents, thickeners, lubricants, suspending agents, preservatives (including antioxidants) and the like.

Compounds of the present methods may be presented for administration to the respiratory tract as a snuff or an aerosol or solution for a nebulizer, or as a microfine powder for insufflation, alone or in combination with an inert carrier such as lactose. In such a case the particles of active compound suitably have diameters of less than 50 microns, preferably less than 10 microns, more preferably between 2 and 5 microns.

Generally for nasal administration a mildly acid pH will be preferred. Preferably the compositions of the invention have a pH of from about 3 to 5, more preferably from about 3.5 to about 3.9 and most preferably 3.7. Adjustment of the pH is achieved by addition of an appropriate acid, such as hydrochloric acid.

The preparation of a pharmacological composition that contains active ingredients dissolved or dispersed therein is well understood in the art and need not be limited based on formulation. Typically such compositions are prepared as injectables either as liquid solutions or suspensions, however, solid forms suitable for solution, or suspensions, in liquid prior to use can also be prepared. The preparation can also be emulsified.

The active ingredient can be mixed with excipients which are pharmaceutically acceptable and compatible with the active ingredient and in amounts suitable for use in the therapeutic methods described herein. Suitable excipients are, for example, water, saline, dextrose, glycerol, ethanol or the like and combinations thereof. In addition, if desired, the composition can contain minor amounts of auxiliary substances such as wetting or emulsifying agents, pH buffering agents and the like which enhance the effectiveness of the active ingredient.

The kinase inhibitor of the present invention can include pharmaceutically acceptable salts of the components therein. Pharmaceutically acceptable salts include the acid addition salts (formed with the free amino groups of the polypeptide) that are formed with inorganic acids such as, for example, hydrochloric or phosphoric acids, or such organic acids as acetic, tartaric, mandelic and the like. Salts formed with the free carboxyl groups can also be derived from inorganic bases such as, for example, sodium, potassium, ammonium, calcium or ferric hydroxides, and such organic bases as isopropylamine, trimethylamine, 2-ethylamino ethanol, histidine, procaine and the like.

Physiologically tolerable carriers are well known in the art. Exemplary of liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, polyethylene glycol and other solutes.

Liquid compositions can also contain liquid phases in addition to and to the exclusion of water. Exemplary of such additional liquid phases are glycerin, vegetable oils such as cottonseed oil, and water-oil emulsions.

Predicting Mutations

In another embodiment, the present invention discloses a method to predict variances in the erbB1 gene following treatment with a tyrosine kinase inhibitor. It is generally known that response to cancer treatment with a tyrosine kinase inhibitor is often followed by resistance to that or other similar compounds. Such resistance is thought to arise through the acquisition of mutations in the drug target, for example in the EGFR. The ability to predict (and select) such mutations will allow for better treatment options and fewer relapses.

In one embodiment of the present invention, DNA encoding the EGFR kinase domain is isolated and sequenced from a tumor sample of cancer patients that have responded to gefitinib (or a similar EGFR targeting treatment) but have subsequently relapsed. The relapse in such patients is expected to involve the acquisition of secondary mutations within the EGFR kinase domain. Compounds that target, and inhibit the kinase activity of, these newly defined mutations are then identified using methods disclosed herein. Such compounds may be used alone, or in combination with other known EGFR targeting treatments, to treat cancer patients with primary or secondary (as above) mutations in the kinase domain of EGFR.

In one embodiment, predicting variances in the kinase (catalytic) domain of the EGFR (erbB1 gene) is done in vitro. In this method, cells, e.g. fibroblast cells, are stably transfected with cDNAs containing kinase domain mutations that have been identified in human cancer cell lines. For example, the cells may be transfected with an EGFR that bears a mutation such as SEQ ID NO:495, further described in FIG. 4A, or with any number of identified or as yet unidentified kinase domain-mutated EGFRs. The transfection of kinase domain-mutated EGFRs into cells will result in aberrant proliferation of the cells in culture. Methods of stable transfection are known to those of skill in the art and are further defined in Current Protocols in Molecular Biology by F. M. Ausubel, R. Brent, R. E. Kingston, D. D. Moore, J. G. Seidman, K. Struhl and V. B. Chanda (Editors), John Wiley & Sons., 2004, incorporated herein by reference. The transfected cells are then given an effective, yet sublethal, dose of a drug, preferably a tyrosine kinase inhibitor, predicted to inhibit cellular proliferation. In a preferred embodiment, the drug is an anilinoquinazoline, synthetic anilinoquinazoline, gefitinib or erlotinib. The cells are serially passaged in the presence of drug and subclones that survive are selected. Over many generations, cells that survive (i.e. are resistant to the compound), are selected and analyzed for variances in the erbB1 gene. Secondary variances can thus be predicted to occur following repeated treatment with a tyrosine kinase inhibitor in vivo.

Alternatively, cells are transfected with gefitinib-resistant mutant cDNA derived from human NSCLC cell lines, for example, NCI-1650 and NCI-1975. Each cell line has a heterozygous mutation with the kinase domain of EGFR, and is, therefore, expected to be sensitive to gefitinib. The EGFR mutation in NCI-1650 consists of an in-frame deletion of 15 nucleotides at position 2235-2249 (delLE746-A750) within exon 19, while NCI-1975 has a missense mutation within exon 21 that substitutes a G for T at nucleotide 2573 (L858R). As shown herein, the L858R mutation in NCI-H1975 is activating and confers increased sensitivity to gefitinib in vitro. Other cancer cell lines that harbor EGFR kinase domain mutations may be utilized. The cancer cell lines may include lung cancer as well as other cancers that are found to harbor such mutations.

The cells may be treated with a mutagen in order to increase the frequency with which cells acquire secondary mutations. A mutagen may induce mutations at different frequencies depending upon the dosage regimen, mode of delivery, and the developmental stage of the organism or cell upon mutagen administration, all parameters of which are disclosed in the prior art for different mutagens or mutagenesis techniques. The mutagen may be an alkylating agent, such as ethyl methanesulfonate (EMS), N-ethyl-N-nitrosourea (ENU) or N-methyl-N-nitrosourea (MNU). Alternatively, the mutagen may be, for example, phocarbaxine hydrochloride (Prc), methyl methanesulfonate (MeMS), chlorambucil (Chl), melphalan, porcarbazine hydrochloride, cyclophosphamide (Cp), diethyl sulfate ($Et_2SO_4$), acrylamide monomer (AA), triethylene melamin (TEM), nitrogen mustard, vincristine, dimethylnitrosamine, N-methyl-N'-nitro-Nitrosoguanidine (MNNG), 7,12 dimethylbenz(a)anthracene (DMBA), ethylene oxide, hexamethylphosphoramide, bisulfan, and ethyl methanesulforate (EtMs). Methods of treating cells with mutagens is described, for example, in U.S. Pat. No. 6,015,670, incorporated herein by reference. Following mutagenesis, cells (i.e. transfected with variant EGFR or human cancer cell line derived) can be cultured in gefitinib-supplemented medium to select for the outgrowth of resistant clones. Subcultivation of individual clones can be followed, for example, by nucleotide sequence determination of the EGFR gene following specific PCR-mediated amplification of genomic DNA corresponding to the EGFR kinase domain.

In another embodiment, cells (with an EGFR variance) are serially passaged in the presence of gradually increasing concentrations of gefitinib (or a similar tyrosine kinase inhibitor) over a course of several weeks or months in order to select for the spontaneous acquisition of mutations within the EGFR gene that confer resistance to gefitinib. Selected cells (that continue to proliferate at relatively high gefitinib concentration) can be isolated as colonies, and mutations will be identified as described above. Such variances can thus be predicted to occur following repeated treatment with a tyrosine kinase inhibitor in vivo. See, for example, Scappini et al., Cancer, Apr. 1, 2004, Vol. 100, pg. 1459, incorporated herein by reference.

In yet another embodiment, a variant form of the EGFR gene can be propagated in a DNA repair-deficient bacterial strain before re-introducing it into stably selected cell lines. Replication in such bacteria will enhance the frequency of mutagenesis. Alternatively, "error-prone" PCR can be utilized to enhance the frequency of mutations in the cloned EGFR DNA in vitro, using standard methods, known to those of skill in the art.

In another embodiment, predicting variances in the kinase domain of the erbB1 gene is done in vivo. For example, a kinase activity increasing variant form of the erbB1 gene is transfected into an animal, i.e. a mouse, generating a cancer model. The animal is then treated with an effective dose of a compound, preferably an anilinoquinazoline, synthetic anilinoquinazoline, gefitinib or erlotinib. Upon repeated exposure to the compound, the cancer is initially inhibited. As in humans treated with such compounds, tumor cells in the animal acquire mutations which make them resistant to such treatment. The methods of the present invention allow for the isolation and characterization of the erbB1 gene in such resistant tumors. Compounds that specifically target these newly characterized variances are useful in the treatment of patients suspected of carrying such a mutated erbB1 gene. Such patients include, for example, patients who initially respond to therapy with a tyrosine kinase inhibitor, but subsequently fail to respond to the same or similar compound.

Methods of creating an animal model are known to those of skill in the art and are further defined in e.g., Ohashi et al., Cell, 65:305-317 (1991); Adams et al., Nature, 325:223-228 (1987); and Roman et al., Cell, 61:383-396 (1990), incorporated herein by reference. In the case of fertilized oocytes, the preferred method of transgene introduction is by microinjection, see, e.g., Leder et al., U.S. Pat. Nos. 4,736,866 and 5,175,383, which are incorporated herein by reference, whereas in the case of embryonic stem (ES) cells, the preferred method is electroporation. However, other methods including viral delivery systems such as retroviral infection, or liposomal fusion can be used. The isolation and characterization of nucleic acid is described above and in the examples.

The above-identified kinase activity increasing variances in the erbB1 gene may be screened for in patients (diagnostically or prognostically), using the methods of the present invention. The presence or absence of such mutations may then be used as a criteria for determining ones sensitivity to treatment with an EGFR targeting compound, such as, for example, a tyrosine kinase inhibitor.

Compounds that specifically target these newly defined variances, whether detected in vivo or in vitro, can be selected using techniques known in the art and discussed herein. Candidate drug screening assays may be used to identify bioactive candidate agents that inhibit the activity of variant forms of EGFR. Of particular interest are screening assays for agents that have a low toxicity for human cells. A wide variety of assays may be used for this purpose, including labeled in vitro protein-protein binding assays, electrophoretic mobility shift assays, enzyme activity assays, immunoassays for protein binding, and the like. The purified mutant EGFR protein may also be used for determination of three-dimensional crystal structure, which can be used for modeling intermolecular interactions, transporter function, etc. Such compounds may be, for example, tyrosine kinase inhibitors, antibodies, aptamers, siRNAs, and vectors that inhibit the kinase activity of EGFR.

In another embodiment, compounds useful in the method of the present invention are antibodies which interfere with kinase signaling via the mutant EGFR, including monoclonal, chimeric humanized, and recombinant antibodies and fragment thereof which are characterized by their ability to inhibit the kinase activity of the EGFR and which have low toxicity.

Neutralizing antibodies are readily raised in animals such as rabbits or mice by immunization with an EGFR with at least one nucleic acid variance in its kinase domain. Immunized mice are particularly useful for providing sources of B cells for the manufacture of hybridomas, which in turn are cultured to produce large quantities of anti-EGFR monoclonal antibodies. Chimeric antibodies are immunoglobin molecules characterized by two or more segments or portions derived from different animal species. Generally, the variable region of the chimeric antibody is derived from a non-human mammalian antibody, such as murine monoclonal antibody, and the immunoglobin constant region is derived from a human immunoglobin molecule. Preferably, both regions and the combination have low immunogenicity as routinely determined. Humanized antibodies are immunoglobin molecules created by genetic engineering techniques in which the murine constant regions are replaced with human counterparts while retaining the murine antigen binding regions. The resulting mouse-human chimeric antibody should have reduced immunogenicity and improved pharmacokinetics in humans. Preferred examples of high affinity monoclonal antibodies and chimeric derivatives thereof, useful in the methods of the present invention, are described in the European Patent Application EP 186,833; PCT Patent Application WO 92/16553; and U.S. Pat. No. 6,090,923.

Existing or newly identified compounds as described above are useful in the treatment of patients carrying primary and/or secondary EGFR mutations.

In a preferred embodiment, the compound is an inhibitor of the tyrosine kinase activity of an EGFR with at least one variance in its kinase domain, particularly small molecule inhibitors having selective action on "mutated" EGFRs as compared to other tyrosine kinases. Inhibitors of EGFR include, but are not limited to, tyrosine kinase inhibitors such as quinazolines, such as PID 153035, 4-(3-chloroanilino) quinazoline, or CP-358,774, pyridopyrimidines, pyrimidopyrimidines, pyrrolopyrimidines, such as CGP 59326, CGP 60261 and CGP 62706, and pyrazolopyrimidines, 4-(phenylamino)-7H-pyrrolo[2,3-d] pyrimidines (Traxler et al., (1996) J. Med Chem 39:2285-2292), curcumin (diferuloyl methane) (Laxmin arayana, et al., (1995), Carcinogen 16:1741-1745), 4,5-bis (4-fluoroanilino) phthalimide (Buchdunger et al. (1995) Clin. Cancer Res. 1:813-821; Dinney et al. (1997) Clin. Cancer Res. 3:161-168); tyrphostins containing nitrothiophene moieties (Brunton et al. (1996) Anti Cancer Drug Design 11:265-295); the protein kinase inhibitor ZD-1 839 (AstraZeneca); CP-358774 (Pfizer, Inc.); PD-01 83805 (Warner-Lambert), EKB-569 (Torrance et al., Nature Medicine, Vol. 6, No. 9, September 2000, p. 1024), HKI-272 and HKI-357 (Wyeth); or as described in International patent application WO99/09016 (American Cyanamid); WO98/43960 (American Cyanamid); WO97/38983 (Warener Labert); WO99/06378 (Warner Lambert); WO99/06396 (Warner Lambert); WO96/30347 (Pfizer, Inc.); WO96/33978 (Zeneca); WO96/33977 (Zeneca); and WO96/33980) Zeneca; all herein incorporated by reference.

In another embodiment, an antisense strategy may be used to interfere with the kinase activity of a variant EGFR. This approach may, for instance, utilize antisense nucleic acids or ribozymes that block translation of a specific mRNA, either by masking that mRNA with an antisense nucleic acid or cleaving it with a ribozyme. For a general discussion of antisense technology, see, e.g., Antisense DNA and RNA, (Cold Spring Harbor Laboratory, D. Melton, ed., 1988).

Reversible short inhibition of variant EGFR gene transcription may also be useful. Such inhibition can be achieved by use of siRNAs. RNA interference (RNAi) technology prevents the expression of genes by using small RNA molecules such as small interfering RNAs (siRNAs). This technology in turn takes advantage of the fact that RNAi is a natural biological mechanism for silencing genes in most cells of many living organisms, from plants to insects to mammals (McManus et al., Nature Reviews Genetics, 2002, 3(10) p. 737). RNAi prevents a gene from producing a functional protein by ensuring that the molecule intermediate, the messenger RNA copy of the gene is destroyed. siRNAs can be used in a naked form and incorporated in a vector, as described below. One can further make use of aptamers to specifically inhibit variant EGFR gene transcription, see, for example, U.S. Pat. No. 6,699,843. Aptamers useful in the present invention may be identified using the SELEX process. The methods of SELEX have been described in, for example, U.S. Pat. Nos. 5,707,796, 5,763,177, 6,011,577, 5,580,737, 5,567,588, and 5,660,985.

An "antisense nucleic acid" or "antisense oligonucleotide" is a single stranded nucleic acid molecule, which, on hybridizing under cytoplasmic conditions with complementary bases in a RNA or DNA molecule, inhibits the latter's role. If the RNA is a messenger RNA transcript, the antisense nucleic acid is a countertranscript or mRNA-interfering complementary nucleic acid. As presently used, "antisense" broadly includes RNA-RNA interactions, RNA-DNA interactions, ribozymes, RNAi, aptamers and Rnase-H mediated arrest.

Ribozymes are RNA molecules possessing the ability to specifically cleave other single stranded RNA molecules in a manner somewhat analogous to DNA restriction endonucleases. Ribozymes were discovered from the observation that certain mRNAs have the ability to excise their own introns. By modifying the nucleotide sequence of these ribozymes, researchers have been able to engineer molecules that recognize specific nucleotide sequences in an RNA molecule and cleave it (Cech, 1989, Science 245 (4915) p. 276). Because they are sequence-specific, only mRNAs with particular sequences are inactivated.

Antisense nucleic acid molecules can be encoded by a recombinant gene for expression in a cell (e.g., U.S. Pat. Nos. 5,814,500; 5,811,234), or alternatively they can be prepared synthetically (e.g., U.S. Pat. No. 5,780,607).

The present invention further provides methods of treating patients with cancer. In particular, patients with at least one nucleic acid variance in the kinase domain of EGFR. The treatment method comprises administering an siRNA-containing composition to a patient within an appropriate time window. The siRNAs may be chemically synthesized, produced using in vitro transcription, etc. In addition, the siRNA molecule can be customized to individual patients in such a way as to correspond precisely to the mutation identified in their tumor. Since siRNA can discriminate between nucleotide sequences that differ by only a single nucleotide, it is possible to design siRNAs that uniquely target a mutant form of the EGFR gene that is associated with either a single nucleotide substitution or a small deletion of several nucleotides—both of which have been identified in tumors as described herein. SiRNAs have been described in Brummelkamp et al., Science 296; 550-553, 2002, Jaque et al., Nature 418; 435-438, 2002, Elbashir S. M. et al. (2001) Nature, 411: 494-498, McCaffrey et al. (2002), Nature, 418: 38-39; Xia H. et al. (2002), Nat. Biotech. 20: 1006-1010, Novina et al. (2002), Nat. Med. 8: 681-686, and U.S. Application No. 20030198627.

An important advantage of such a therapeutic strategy relative to the use of drugs such as gefitinib, which inhibit both the mutated receptor and the normal receptor, is that siRNA directed specifically against the mutated EGFR should not inhibit the wildtype EGFR. This is significant because it is generally believed that the "side effects" of gefitinib treatment, which include diarrhea and dermatitis, are a consequence of inhibition of EGFR in normal tissues that require its function.

The delivery of siRNA to tumors can potentially be achieved via any of several gene delivery "vehicles" that are currently available. These include viral vectors, such as adenovirus, lentivirus, herpes simplex virus, vaccinia virus, and retrovirus, as well as chemical-mediated gene delivery systems (for example, liposomes), or mechanical DNA delivery systems (DNA guns). The oligonucleotides to be expressed for such siRNA-mediated inhibition of gene expression would be between 18 and 28 nucleotides in length.

In another embodiment, the compounds are antisense molecules specific for human sequences coding for an EGFR having at least one variance in its kinase domain. The administered therapeutic agent may be an antisense oligonucleotides, particularly synthetic oligonucleotides; having chemical modifications from native nucleic acids, or nucleic acid constructs that express such anti-sense molecules as RNA. The antisense sequence is complementary to the mRNA of the targeted EGFR genes, and inhibits expression of the targeted gene products (see e.g. Nyce et al. (1997) Nature 385:720). Antisense molecules inhibit gene expression by reducing the amount of mRNA available for translation, through activation of RNAse H or steric hindrance. One or a combination of antisense molecules may be administered, where a combination may comprise multiple different sequences from a single targeted gene, or sequences that complement several different genes.

A preferred target gene is an EGFR with at least one nucleic acid variance in its kinase domain. The gene sequence is incorporated herein, such as, for example, in FIG. 5. Generally, the antisense sequence will have the same species of origin as the animal host.

Antisense molecules may be produced by expression of all or a part of the target gene sequence in an appropriate vector, where the vector is introduced and expressed in the targeted cells. The transcriptional initiation will be oriented such that the antisense strand is produced as an RNA molecule.

The anti-sense RNA hybridizes with the endogenous sense strand mRNA, thereby blocking expression of the targeted gene. The native transcriptional initiation region, or an exogenous transcriptional initiation region may be employed. The promoter may be introduced by recombinant methods in vitro, or as the result of homologous integration of the sequence into a chromosome. Many strong promoters that are active in muscle cells are known in the art, including the 0-actin promoter, SV40 early and late promoters, human cytomegalovirus promoter, retroviral LTRs, etc. Transcription vectors generally have convenient restriction sites located near the promoter sequence to provide for the insertion of nucleic acid sequences. Transcription cassettes maybe prepared comprising a transcription initiation region, the target gene or fragment thereof, and a transcriptional termination region. The transcription cassettes may be introduced into a variety of vectors, e.g. plasmid; retrovirus, e.g. lentivirus; adenovirus; and the like, where the vectors are able to transiently or stably be maintained in cells, usually for a period of at least about one day, more usually for a period of at least about several days.

Aptamers are also useful. Aptamers are a promising new class of therapeutic oligonucleotides or peptides and are selected in vitro to specifically bind to a given target with high affinity, such as for example ligand receptors. Their binding characteristics are likely a reflection of the ability of oligonucleotides to form three dimensional structures held together by intramolecular nucleobase pairing. Aptamers are synthetic DNA, RNA or peptide sequences which may be normal and modified (e.g. peptide nucleic acid (PNA), thiophophorylated DNA, etc) that interact with a target protein, ligand (lipid, carbohydrate, metabolite, etc). In a further embodiment, RNA aptamers specific for a variant EGFR can be introduced into or expressed in a cell as a therapeutic.

Peptide nucleic acids (PNAs) are compounds that in certain respects are similar to oligonucleotides and their analogs and thus may mimic DNA and RNA. In PNA, the deoxyribose backbone of oligonucleotides has been replaced by a pseudo-peptide backbone (Nielsen et al. 1991 Science 254, 1457-1500). Each subunit, or monomer, has a naturally occurring or non-naturally occurring nucleobase attached to this backbone. One such backbone is constructed of repeating units of N-(2-aminoethyl) glycine linked through amide bonds. PNA hybridises with complementary nucleic acids through Watson and Crick base pairing and helix formation. The Pseudo-peptide backbone provides superior hybridization properties (Egholm et al. Nature (1993) 365, 566-568), resistance to enzymatic degradation (Demidov et al. Biochem. Pharmacol. (1994) 48, 1310-1313) and access to a variety of chemical modifications (Nielsen and Haaima Chemical Society Reviews (1997) 73-78). PNAs specific for a variant EGFR can be introduced into or expressed in a cell as a therapeutic. PNAs have been described, for example, in U.S. Application No. 20040063906.

Patients to be treated with a compound which targets a variant EGFR include, for example, patients diagnosed with a primary or secondary mutation in their EGFR, patients who initially respond to therapy with a tyrosine kinase inhibitor, but subsequently fail to respond to the same or similar compound. Alternatively, compounds that target secondary EGFR mutations may be given to cancer patients in combination with compounds that target primary EGFR mutations, for example, gefitinib, as a combination therapy. By combining compounds that target both primary and secondary EGFR mutations, the likelihood of resistance will be reduced.

Additional EGFR mutations that confer resistance to currently known anti-cancer therapeutics, including but not limited to EGFR tyrosine kinase inhibitors gefitinib, erlotinib and the like, are within the scope of the invention. Resistant EGFR mutants are predicted to have mutants analogous to mutants identified in kinase domains of related tyrosine kinase domain containing proteins that have high homology in this kinase region. Papers describing mutations in analogous proteins include those known in the art for BCR-ABL. See, e.g., Bradford et al. Blood. 2003 Jul. 1; 102(1):276-83, Epub 2003 Mar. 6; Hochhaus et al., Leukemia. 2002 November; 16(11):2190-6; and Al-Ali et al., Hematol J. 2004; 5(1):55-60.

A mutant EGFR resistant to known EGFR tyrosine kinase inhibitors includes any one or more EGFR polypeptides, or a nucleotide encoding the same, with a non-wild type residue at one or more positions analogous to c-abl (BCR-ABL) residues that confirm an imatinib resistant phenotype. The residues that when mutated in EGFR confer drug resistance include especially those residues from the kinase domain, including but not limited to, e.g., the P-loop and the activation loop, wherein the mutated residues in the EGFR polypeptide are analogous to c-able residues. Contemplated resistant EGFR mutants have non-wild type residues at the amino acids positions that are analogous to at least positions Met 244, Leu 248, Gly 250, Gln 252, Tyr 253, Glu 255, Asp 276, Thr 315, Phe 317, Met 351, Glu 355, Phe 359, His 396, Ser 417, and Phe 486 of BCR-ABL, see, for example Table S3C and FIG. 9. These BCL-ABL residues correspond to residues Lys 714, Leu 718, Ser 720, Ala 722, Phe 723, Thr 725, Ala 750, Thr 790, Leu 792, Met 825, Glu 829, Leu 833, His 870, Thr 892, Phe 961, respectively, in EGFR. See, e.g., Table S3C, FIG. 9.

Prognostic Testing

The methods of the present invention are used as a prognostic indicator of the development of cancer. Alternatively, the methods are used to detect cancer that is present but has not yet been diagnosed or is at a stage that is undetectable. Patients at risk for developing cancer are screened, using the methods of the present invention, for the presence of kinase activity increasing nucleic acid variation in the erbB1 gene. The presence of a variance or variances in the kinase domain of the erbB1 gene indicate the presence or imminent presence of cancer. Thus, the presence of variances in the kinase domain of the erbB1 gene suggest that a patient would benefit from an EGFR targeted treatment. As described herein, an EGFR targeted treatment is preferably treatment with a tyrosine kinase inhibitor.

In a preferred embodiment of the present invention, a patient is screened for the presence or absence of nucleic acid variances in the kinase domain of the erbB1 gene by obtaining a biological sample. The sample may be any sample from the patient including tissue, e.g., from the tongue, mouth, cheek, trachea, bronchial tube, lungs, etc. or fluid, e.g., from sputum or lung aspirates. Methods of obtaining these biological specimens are well known to those of skill in the art.

Thus, the invention provides a method for identifying a disease or disorder associated with aberrant mutant EGFR expression or activity in which a test sample is obtained from a subject and mutant EGFR protein or nucleic acid (e.g., mRNA, genomic DNA) is detected, wherein the presence of mutant EGFR protein or nucleic acid is diagnostic for a subject having or at risk of developing a disease or disorder associated with aberrant mutant EGFR expression or activity. As used herein, a "test sample" refers to a biological sample obtained from a subject of interest. For example, a test sample can be a biological fluid (e.g., serum), cell sample, or tissue, especially a tissue biopsy sample.

Furthermore, the prognostic assays described herein can be used to determine whether a subject can be administered an agent (e.g., an agonist, antagonist, peptidomimetic, protein, peptide, nucleic acid, small molecule, or other drug candidate) to treat a disease or disorder associated with aberrant mutant EGFR expression or activity. For example, such methods can be used to determine whether a subject can be effectively treated with an agent for a disorder. Thus, the invention provides methods for determining whether a subject can be effectively treated with an agent for a disorder associated with aberrant mutant EGFR expression or activity in which a test sample is obtained and mutant EGFR protein or nucleic acid is detected (e.g., wherein the presence of mutant EGFR protein or nucleic acid is diagnostic for a subject that can be administered the agent to treat a disorder associated with mutant EGFR expression or activity).

EXAMPLES

Example 1

Nucleotide Sequence Analysis of Tumor Specimens

Tumor specimens from initial diagnostic or surgical procedures were collected from patients with NSCLC who were subsequently treated with Gefitinib, under an IRB-approved protocol. Frozen tumor specimens, along with matched normal tissue, were available for four cases, and paraffin-embedded material was used for the remaining specimens. In addition, 25 unselected cases of primary NSCLC (15 bronchioalveolar, 7 adenocarcinoma, and 3 large cell lung cancers), with matched normal tissues, were obtained from the Massachusetts General Hospital tumor bank. For mutational analysis of the entire EGFR coding sequence, DNA was extracted from specimens, followed by amplification of all 28 exons, automated sequencing of uncloned PCR fragments, and analysis of electropherograms in both sense and antisense direction for the presence of heterozygous mutations. All sequence variants were confirmed by multiple independent PCR amplifications. Primer sequences and amplification conditions are provided in Supplementary Material. EGFR mutations in exons 19 and 21 were also sought in primary tumors of the breast (15 cases), colon (20 cases), kidney (16 cases), and brain (4 cases), along with a panel of 78 cancer-derived cell lines representing diverse histologies (listed below).

Functional Analysis of Mutant EGFR Constructs

The L858R and delL747-P753insS mutations were introduced into the full length EGFR coding sequence using site-directed mutagenesis and inserted into a cytomegalovirus-driven expression construct (pUSE, Upstate). Cos-7 cells were transfected (Lipofectamine 2000, Invitrogen) using 1 µg of the expression constructs, followed after 18 hrs by replating at $5 \times 10^4$ cells/well (12-well plates, Costar) in DMEM lacking fetal calf serum. After 16 hrs of serum starvation, cells were stimulated with 10 ng/ml of EGF (SIGMA). To demonstrate Gefitinib inhibition, the drug was added to the culture medium 3 hrs prior to the addition of EGF (30 min stimulation with 100 ng/ml of EGF). Cell lysates were prepared in 100 µL of Laemmli lysis buffer, followed by resolution of proteins on 10% SDS-PAGE, transfer to PVDF membranes, and Western blot analysis using enhanced chemiluminescence reagent (Amersham). Autophosphorylation of EGFR was measured using antibody to phosphotyrosine Y-1068, and comparable protein expression was shown using anti-EGFR antibody (working concentration of 1:1000; Cell Signaling Technology).

Mutational Analysis

The polymerase chain reaction was used to amplify the 28 exons comprising the EGFR gene using DNA isolated from primary tumor tissue or tumor-derived cell-lines. Primer pairs used were:

```
Exon 1,
                                    (SEQ ID NO: 513)
CAGATTTGGCTCGACCTGGACATAG (sense)
and (SEQ ID NO: 514)
CAGCTGATCTCAAGGAAACAGG (antisense);

Exon 2,
                                    (SEQ ID NO: 515)
GTATTATCAGTCAC TAAAGCTCAC (sense)
and (SEQ ID NO: 516)
CACACTTCAAGTGGAATTCTGC;

Exon 3,
                                    (SEQ ID NO: 517)
CTCGTGTGCATTAGGGTTCAACTGG (sense)
and (SEQ ID NO: 518)
CCTTCTCCGAGGTGGAATTGAGTGAC (antisense);

Exon 4,
                                    (SEQ ID NO: 519)
GCTAATTGCGGGACTCTTGTTCGCAC (sense)
and (SEQ ID NO: 520)
TACATGC TTTTCTAGTGGTCAG (antisense);

Exon 5,
                                    (SEQ ID NO: 521)
GGTCTCAAGTGATTCTACAAACCAG (sense)
and (SEQ ID NO: 522)
CCTTCACCTACTGGTTCACATCTG (antisense);

Exon 6,
                                    (SEQ ID NO: 523)
CATGGT TTGACTTAGTTTGAATGTGG (sense)
and (SEQ ID NO: 524)
GGATACTAAAGATACTTTGTCAC CAGG(antisense);

Exon 7,
                                    (SEQ ID NO: 525)
GAACACTAGGCTGCAAAGACAGTAAC (sense)
and (SEQ ID NO: 526)
CCAAGCAAGGCAAACACATCCACC(antisense);

Exon 8,
                                    (SEQ ID NO: 527)
GGAGGATGGAGCC TTTCCATCAC (sense)
and (SEQ ID NO: 528)
GAAGAGGAAGATGTGTTCCTTTGG (antisense);

Exons 9 and 10,
                                    (SEQ ID NO: 529)
GAATGAAGGATGATGTGGCAGTGG (sense)
and (SEQ ID NO: 530)
CAAAACATCAGCC ATTAACGG (antisense);

Exon 11,
                                    (SEQ ID NO: 531)
CCACTTACTGTTCATATAATACAGAG (sense)
and (SEQ ID NO: 532)
CATGTGAGATAGCATTTGGGAATGC (antisense);
```

-continued

Exon 12,
(SEQ ID NO: 533)
CATGACCT ACCATCATTGGAAAGCAG (sense)
and (SEQ ID NO: 534)
GTAATTTCACAGTTAGGAATC (sense);

Exon 13,
(SEQ ID NO: 535)
GTCACCCAAGGTCATGGAGCACAGG (sense)
and (SEQ ID NO: 536)
CAGAATGC CTGTAAAGCTATAAC (antisense);

Exon 14,
(SEQ ID NO: 537)
GTCCTGGAGTCCCAACTCCTTGAC (sense)
and (SEQ ID NO: 538)
GGAAGTGGCTCTGA TGGCCGTCCTG (antisense);

Exon 15,
(SEQ ID NO: 539)
CCAC TCACACACACTAAATATTTTAAG (sense)
and (SEQ ID NO: 540)
GACCAAAACACCTTAAGTAA CTGACTC (antisense);

Exon 16,
(SEQ ID NO: 541)
CCAA TCCAACATCCAGACACATAG (sense)
and (SEQ ID NO: 542)
CCAGAGCCATAGAAACTTGATCAG (antisense);

Exon 17,
(SEQ ID NO: 543)
GTATGGACTATGGC ACTTCAATTGCATGG (sense)
and (SEQ ID NO: 544)
CCAGAGAACATGGCAACCAGCACAGGAC (antisense);

Exon 18,
(SEQ ID NO: 545)
CAAATGAGCTGGCAAGTGCCGTGTC (sense)
and (SEQ ID NO: 546)
GAGTTT CCCAAACACTCAGTGAAAC (antisense)
or (SEQ ID NO: 675)
CAAGTGCCGTGTCCTGGCACCCAAGC (sense)
and (SEQ ID NO: 676)
CCAAACACTCAGTGAAACAAAGAG (antisense);

Exon 19,
(SEQ ID NO: 547)
GCAATATCAGCC TTAGG TGCGGCTC (sense)
and (SEQ ID NO: 548)
CATAGAAAGTGAACATTTAGGATGTG (antisense);

Exon 20,
(SEQ ID NO: 549)
CCATGAGTACGTATTTTGAAACTC (sense)
and (SEQ ID NO: 550)
CATATCC CCATGGC AAACTCTTGC (antisense);

Exon 21,
(SEQ ID NO: 551)
CTAACGTTCGCCAG CCATAAGTCC (sense)
and (SEQ ID NO: 552)
GCTGCGAGCTCACCCAGAATGTCTGG (antisense);

Exon 22,
(SEQ ID NO: 553)
GACGGG TCCTGGGGTGATCTGGCTC (sense)
and (SEQ ID NO: 684)
CTCAGTACAATAGATAGACAGCAATG (antisense);

Exon 23,
(SEQ ID NO: 555)
CAGGACTACAGAAATGTAGGTTTC (sense)
and (SEQ ID NO: 556)
GTGCCTG CCTTAAGTAATGTGATGAC (antisense);

Exon 24,
(SEQ ID NO: 557)
GACTGG AAGTGTCGCA TCACCAATG (sense)
and (SEQ ID NO: 558)
GGTTTAATAATGCGATCTGGGACAC (antisense);

Exon 25,
(SEQ ID NO: 559)
GCAGCTATAATTTAGAGAACCAAGG (sense)
and (SEQ ID NO: 560)
GGTTAAAATTGACTTC ATTTCCATG (antisense);

Exon 26,
(SEQ ID NO: 561)
CCTAGTTGCTCTAAA ACTAACG (sense)
and (SEQ ID NO: 562)
CTGTGAGGCGTGACAGCCGTGCAG (antisense);

Exon 27,
(SEQ ID NO: 563)
CAACCTACTAATCAG AACCAGCATC (sense)
and (SEQ ID NO: 564)
CCTTCACTGTGTCTGC AAATCTGC (antisense);

Exon 28,
(SEQ ID NO: 565)
CCTGTCATAAGTCTCCTTGTTGAG (sense)
and (SEQ ID NO: 566)
CAGTCTGTGGGTCTAAG AGCTAATG (antisense).

Annealing temperatures were 58° C. (exons 1, 3, 4, 7-10, 12-25, 27, and 28), 56° C. (exons 2, 5, 6, and 26), or 52° C. (exon 11).

Nested PCR amplification of DNA extracted from archival tumor tissue was performed as follows. An initial PCR for exons 2, 5, 6, 7, 11, 12, 14, 16, 18, 19, 20, 21, 23, 24, 25, 26, and 27 was generated using primers and conditions described above. Subsequently, 2 µl of this reaction was amplified in a secondary PCR using the following internal primer pairs:

Exon 2,
(SEQ ID NO: 567)
CAGGAATGGGTGAGTCTCTGTGTG (sense)
and

-continued (SEQ ID NO: 568)
GTGGAATTCTGCCCAGGCCTTTC (antisense);

Exon 5,
(SEQ ID NO: 569)
GATTCTACAAACCA GCCAGCCAAAC (sense)
and (SEQ ID NO: 570)
CCTACTGGTTCACATCTGACCCTG (antisense);

Exon 6,
(SEQ ID NO: 571)
GTTTGAATGTGGTTTCGTTGGAAG (sense)
and (SEQ ID NO: 572)
CTTTGTCACCAGGCAGAGG GCAATATC (antisense);

Exon 7,
(SEQ ID NO: 573)
GACAGTAACTTGGGCTTTCTGAC (sense)
and (SEQ ID NO: 574)
CATCCACCCAAAGACTCTCCAAG (antisense);

Exon11,
(SEQ ID NO: 575)
CTGTTCATATAATAC AGAGTCCCTG (sense)
and (SEQ ID NO: 576)
GAGAGATGCAGGAGCTCTGTGC (antisense);

Exon12,
(SEQ ID NO: 577)
GCAGTTTGTAGTCAATCAAAGGTGG (sense)
and (SEQ ID NO: 578)
GTAATTTAAATGGGAAT AGCCC (antisense);

Exon14,
(SEQ ID NO: 579)
CAACTCCTTGACCATTACCTCAAG (sense)
and (SEQ ID NO: 580)
GATGGCCGTCCTGCCCACACAGG (antisense);

Exon16,
(SEQ ID NO: 581)
GAGTAGTTTAGCA TATATTGC (sense)
and (SEQ ID NO: 582)
GACAGTCAGAAATGCAGGAAAGC (antisense);

Exon18,
(SEQ ID NO: 583)
CAAGTGCCGTGTCCTGGCACCCAAGC (sense)
and (SEQ ID NO: 584)
CCAAACACTCAGTGAAACAAAGAG (antisense)
or (SEQ ID NO: 677)
GCACCCAAGCCCATGCCGTGGCTGC (sense)
and (SEQ ID NO: 678)
GAAACAAAGAGTAAAGTAGATGATGG (antisense);

Exon 19,
(SEQ ID NO: 585)
CCTTAGGTGCGGCTCCACAGC (sense)
and (SEQ ID NO: 586)
CATTTAGGATGTGGAGATGAGC (antisense);

Exon 20,
(SEQ ID NO: 587)
GAAACTCAAG ATCGCATTCATGC (sense)
and (SEQ ID NO: 588)
GCAAACTCTTGCTATCCCAGGAG (antisense);

Exon 21,
(SEQ ID NO: 589)
CAGCCATAAGTCCTCGACGTGG (sense)
and (SEQ ID NO: 590)
CATCCTCCCCTGCATGTGTTAAAC (antisense);

Exon 23,
(SEQ ID NO: 591)
GTAGGTTTCTAAACATCAAGAAAC (sense)
and (SEQ ID NO: 592)
GTGATGACATTTCTCCAGGGATGC (antisense);

Exon 24,
(SEQ ID NO: 593)
CATCACCAATGCCTTCTTTAAGC (sense)
and (SEQ ID NO: 594)
GCTGGAGGGTTTAATAATGCGATC (antisense);

Exon 25,
(SEQ ID NO: 595)
GCAAACACACAGGCACCTGCTGGC (sense)
and (SEQ ID NO: 596)
CATTTCCATGTGAGTTTCACTAGATGG (antisense);

Exon 26,
(SEQ ID NO: 679)
CACCTTCACAATATACCCTCCATG (sense)
and (SEQ ID NO: 680)
GACAGCCGTGCAGGGAAAAACC (antisense);

Exon 27,
(SEQ ID NO: 681)
GAACCAGCATCTCAAGGAGATCTC (sense)
and (SEQ ID NO: 682)
GAGCACCTGGCTTGGACACTGGAG (antisense).

Nested PCR amplifications for the remaining exons consisted of primary PCR using the following primers. Exon 1, GACCGGACGACAGGCCACCTCGTC (sense) (SEQ ID NO: 597) and GAAGAACGAAACGTCCCGTTCCTCC (antisense) (SEQ ID NO: 598); Exon 3, GTTGAGCACT CGTGTGCATTAGG (sense) (SEQ ID NO: 599) and CTCAGTGCACGTGTACTGGGTA (antisense) (SEQ ID NO: 600); Exon 4, GTTCACTGGGCTAATTGCGGGACTCTTGTTCGCAC (sense) (SEQ ID NO: 601) and GGTA AATACATGCTTTTCTAGTGGTCAG (antisense) (SEQ ID NO: 602); Exon 8, GGAGGATGGA GCCTTTCCATCAC (sense) (SEQ ID NO: 603) and GAAGAGGAAGATGTGTTCCTTTGG (antisense) (SEQ ID NO: 604); Exon 9, GAATGAAGGATGATGTGGCA-GTGG (sense) (SEQ ID NO: 605) and GTATGTGT-GAAGGAG TCACTGAAAC (antisense) (SEQ ID NO: 606); Exon 10, GGTGAGTCACAGGTTCAGTTGC (sense) (SEQ ID NO: 607) and CAAAACATCAGCCAT- TAACGG (antisense) (SEQ ID NO: 608); Exon 13, GTAGCCAGCATGTC TGTGTCAC (sense) (SEQ ID NO: 609) and CAGAATGCCTGTAAAGCTATAAC (antisense) (SEQ ID NO: 610); Exon 15, CATTTGGCTTTCCCCACT-CACAC (sense) (SEQ ID NO: 611) and GACCAAAACAC-CTTAA GTAACTGACTC (antisense) (SEQ ID NO: 612); Exon 17, GAAGCTACATAGTGTCTCACTTTCC (sense) (SEQ ID NO: 613) and CACAACTGCTAATGGCCCGT-TCTCG (antisense) (SEQ ID NO: 614); Exon 22, GAGCA-GCCCTGAACTCCGTCAGACTG (sense) (SEQ ID NO: 683) and CTCAGTACAATAGATAGACAGCAATG (antisense) (SEQ ID NO: 684); Exon 28a GCTCC TGCTCCCT-GTCATAAGTC (sense) (SEQ ID NO: 615) and GAAGTC-CTGCTGGTAGTCAGGGTTG (antisense) (SEQ ID NO: 616); Exon 28b, CTGCAGTGGGCAACCCCGAGTATC (sense) (SEQ ID NO: 617) and CAGTC TGTGGGTCTAAGAGCTAATG (antisense) (SEQ ID NO: 618). Secondary PCR amplification was carried out using primer pairs: Exon 1, GACAGGCCACCTCGTCGGCGTC (sense) (SEQ ID NO: 619) and CAGCTGATCT-CAAGGAAACAGG (antisense) (SEQ ID NO: 620); Exon 3, CTCGTG TGCATTA GGGTTCAACTGG (sense) (SEQ ID NO: 621) and CCTTCTCCGAGGTGGAATTGAGT-GAC (antisense) (SEQ ID NO: 622); Exon 4, GCTAATT-GCGGGACTCTTGTTCGCAC (sense) (SEQ ID NO: 623) and TACATGCTTT TCTAGTGGTCAG (antisense) (SEQ ID NO: 624); Exon 8, CCTTTCCATCACCCCT-CAAGAGG (sense) (SEQ ID NO: 625) and GATGTGTTC-CTTTGGAGGTGGCATG (antisense) (SEQ ID NO: 626); Exon 9, GATGTGG CAGTGGCGGTTCCGGTG (sense) (SEQ ID NO: 627) and GGAGTCACT-GAAACAAACAACAGG (antisense) (SEQ ID NO: 628); Exon 10, GGTTCAGTTGCTTGTATAAAG (sense) (SEQ ID NO: 629) and CCATTAACGGT AAAATTTCAGAAG (antisense) (SEQ ID NO: 630); Exon 13, CCAAGGTCATG-GAGCACAGG (sense) (SEQ ID NO: 631) and CTG-TAAAGCTATAACAACAACCTGG (antisense) (SEQ ID NO: 632); Exon 15, CCACTCACA CACACTAAATATTT-TAAG (sense) (SEQ ID NO: 633) and GTAACTGACT-CAAATACAAACCAC (antisense) (SEQ ID NO: 634); Exon 17, GAAGCTACATAGTGTCTCACTTTCC (sense) (SEQ ID NO: 635) and CACAA CTGCTAATGGCCCGT-TCTCG (antisense) (SEQ ID NO: 636); Exon 22, GACGGGTCCTGGGGTGATCTGGCTC (sense) (SEQ ID NO: 685) and CTCAGTACAATAGATAGACAGCAATG (antisense) (SEQ ID NO: 686); Exon 28a, CCTGTCATAAG TCTCCTTGTTGAG (sense) (SEQ ID NO: 637) and GGTAGTCAGGGTTGTCCAGG (antisense) (SEQ ID NO: 638); Exon 28b, CGAGTATCTCAACACTGTCCAGC (sense) (SEQ ID NO: 639) and CTAAGAGCTAAT-GCGGGC ATGGCTG (antisense) (SEQ ID NO: 640). Annealing temperature for exon 1 amplifications was 54°. Annealing temperatures for both primary and secondary amplifications were 58° C. (exons 3, 4, 7-10, 12-17, 19-25, 27, and 28), 56° C. (exons 2, 5, 6, and 26), or 52° C. (exons 11 and 18).

PCR amplicons were purified using exonuclease I (United States Biochemical, Cleveland, Ohio), and shrimp alkaline phosphatase (United States Biochemical, Cleveland, Ohio) prior to sequencing. Purified DNA was diluted and cycle-sequenced using the ABI BigDye Terminator kit v1.1 (ABI, Foster City, Calif.) according to manufacturer's instructions. Sequencing reactions were electrophoresed on an ABI3100 genetic analyzer. Electropherograms were analyzed in both sense and antisense direction for the presence of mutations, using Sequence Navigator software in combination with Factura to mark heterozygous positions. All sequence variants were confirmed in multiple independent PCR amplifications and sequencing reactions.

Cancer-Derived Cell Lines:

A panel of 14 lung cancer-derived cell lines was analyzed for EGFR mutations. These were derived from tumors of NSCLC (N=5), small cell lung cancer (N=6), adenosquamous (N=1), bronchial carcinoid (N=1), and unknown histology (N=1). Specific cell lines were: NCI-H460, NCI-522, HOP-92, NCIH841, NCIH734, NCIH2228, NCIH596, NCIH727, NCIH446, NCIH1781, NCIH209, NCIH510, NCIH82, NCIH865. In addition, 64 cancer-derived cell lines were screened for mutations in exons 19 and 21. These represented the following histologies: breast cancer (BT549, BT483, UACC893, HS467T, HS578T, MCF7, MCF7-ADR, MDA-MB-15, MDA-MB-175, MDA-MB-231, MDA-MB-415, MDA-MB-436, MDA-MB-453, MDA-MB-468, T47D), ovarian cancer (ES-2, IGROV-1, MDAH2774, OV1063, OVCAR3, OVCAR4, OVCAR5, SKOV3, SW626), CNS cancers (SF-295, SNB-19, U-251, CCF-STTG1, SW-1088, SW-1783, T98G, M059K, A172, SK-N-DZ, SK-N-MC), leukemia (CCRF-CEM, K562, MOLT-4, RPMI8226, SR), prostate cancer (DU-145, PC-3), colon cancer (COLO-205, HCT-116, HCT-15, HT-29, SW-620), renal cancer (786-O, ACHN, CAKI-1, SN-12C, UO-31), melanoma (LOX-IMVI, M14, SKMEL2, UACC-62), osteosarcoma (SAOS-2), and head and neck cancers (O11, O13, O19, O28, O22, O29, O12). The head and neck cancer cell-lines were provided by Dr. James Rocco, Massachusetts General Hospital/Massachusetts Eye and Ear Infirmary. All other cell-lines are available through the American Type Culture Collection (Manassas, Va.).

Genomic DNA was isolated from snap-frozen tumor specimens. Tumor specimens were first crushed to a fine powder using a pre-chilled and sterilized mortar and pestle. Tumor tissue was immediately transferred into a DNA extraction solution consisting of 100 mM sodium chloride, 10 mM Tris pH7.5, 25 mM EDTA (disodium ethylenediamine tetraacetate) pH8.0, and 0.5% (w/v) sodium dodecyle sulfate, and 100 µg/ml fresh proteinase K and incubated overnight at 37° C. or for 3 hours at 50° C. DNA was then extracted using standard phenol-chloroform methods, ethanol precipitated, washed with 70fi ethanol, air-dried and resuspended in TE buffer. The DNA concentration was determined spectrophotometrically. Exons 19 and 21 of human EGFR were amplified by the polymerase chain reaction using the following primer pairs: Exon19 sense primer, 5'-GCAATATCAGCCTTAGGTGCGGCTC-3' (SEQ ID NO: 505); Exon 19 antisense primer, 5'-CATA-GAA AGTGAACATTTAGGATGTG-3' (SEQ ID NO: 506); Exon 21 sense primer, 5'-CTAACGTTCG CCAGC-CATAAGTCC-3' (SEQ ID NO: 507); Exon21 antisense primer, 5'-GCTGCGAGCTCACCCAG AATGTCTGG-3' (SEQ ID NO: 508). For each sample, 20 ng of genomic DNA was amplified in a PCR reaction consisting of 1× Expand Long Template buffer 1 (Roche, Mannhein Germany), 50 µM sequencing grade dATP (Amersham Biosciences, Cleveland Ohio), 50 µM sequencing grade dCTP (Amersham Biosciences, Cleveland Ohio), 50 µM sequencing grade dGTP (Amersham Biosciences, Cleveland Ohio), 50 µM sequencing grade dTTP (Amersham Biosciences, Cleveland Ohio), 0.2 µM sense primer, 0.2 µM antisense primer, 1.25 units Expand Long Template enzyme mix (Taq DNA polymerase/Tgo DNA polymerase) (Roche, Mannhein Germany) that has been preincubated for 5 minutes on ice with ⅙ volume of TaqStart Antibody (1.1 µg/µl) (Clontech, Palo Alto, Calif.) and water to final volume of 25 µl. Each series of amplifications also includes a negative control for which the DNA template is omitted. PCR cycling conditions for both exons were 95° C. for 2 min followed by 40 cycles of 95° C. for 30 s, 58° C. for 30 s and 72° C. for 45 sec; and a final extension of 72° C. for 10 min followed by holding at 4° C. on an MJ-Research PTC-200 or PTC-225 thermalcycler (MJ-Research, Waltham Mass.).

PCR products were resolved by electrophoresis through a 0.8% agarose gel to ensure amplification from patient material and no amplification in the negative control. PCR products were purified prior to sequencing by mixing 10 µl each PCR amplicon with 0.5 µl exonuclease I (10 U/µl) (United States Biochemical, Cleveland, Ohio), and 1 µl shrimp alkaline phosphatase (1 U/µl) (United States Biochemical, Cleveland, Ohio) and incubating at 37° C. for 20 minutes followed by inactivation at 80° C. for 15 minutes on a thermal-cycler (MJ-Research, Waltham, Mass.). Purified DNA was diluted in water, according to the intensity of the amplicon, and cycle-sequencing was performed using the ABI BigDye Terminator kit v1.1 (Applied Biosystems, Foster City, Calif.) according to manufacturer's instructions. Cycle-sequencing was performed on an MJ-Research thermal-cycler using the following cycling conditions: Primers used for sequencing were: Exon19 sense primer, 5'-GCAATATCAGCCTTAGGTGCGGCTC-3' (SEQ ID NO: 505); Exon 19 antisense primer, 5'-CATAG AAAGTGAACATTTAGGATGTG-3' (SEQ ID NO: 506); Exon21 sense primer, 5'-CTAACGTTCGCCAG CCATAAGTCC-3' (SEQ ID NO: 507) or 5'-CGTGGAGAGGCTCAGAGC-CTGGCATG-3' (SEQ ID NO: 687); Exon 21 antisense primer, 5'-GCTGCGAGCTCACCCAGAATGTCTGG-3' (SEQ ID NO: 508). Sequencing reactions were electrophoresed on an ABI3100 genetic analyzer (Applied Biosystems, Foster City, Calif.). Factura and Sequence Navigator (Applied Biosystems, Foster City, Calif.) software programs were used to mark potential heterozygous positions and display them for evaluation. Nucleotide positions at which the height of the secondary peak was greater than, or equal to, 30% the height of the primary peak were marked as heterozygous and were confirmed by analysis of both sense and antisense reads. Samples with sequence indicative of the presence of a mutation were reamplified and sequenced for confirmation.

Position of Primers Used in Sequence Analysis Relative to Exons 19 and 21

Intronic primers are shown in lower case and underlined.

Intronic Sequence is Shown in Lowercase.

Exonic Sequence is Shown in Uppercase.

EGFR Exon 19 (5'-3')
(SEQ ID NO: 641)
gcaatatcagccttaggtgcggctccacagccccagtgtccctcaccttc ggggtgcatcgctggtaacatccacccagatcactgggcagcatgtggca ccatctcacaattgccagttaacgtcttccttctctctctgtcatagGGA

CTCTGGATCCCAGAAGGTGAGAAAGTTAAAATTCCCGTCGCTATCAAGGA

ATTAAGAGAAGCAACATCTCCGAAAGCCAACAAGGAAATCCTCGATgtga gtttctgctttgctgtgtgggggtccatggctctgaacctcaggcccacc ttttctcatgtctggcagctgctctgctctagaccctgctcatctccaca tcctaaatgttcactttctatg EGFR Exon 21 (5'-3')
(SEQ ID NO: 642) or (SEQ ID NO: 687)
ctaacgttcgccagccataagtcctcgacgtggagaggctcagagcctgg catgaacatgaccctgaattcggatgcagagcttcttcccatgatgatct gtccctcacagcagggtcttctctgtttcagGGCATGAACTACTTGGAGG

ACCGTCGCTTGGTGCACCGCGACCTGGCAGCCAGGAACGTACTGGTGAAA

ACACCGCAGCATGTCAAGATCACAGATTTTGGGCTGGCCAAACTGCTGGG

Figure 1A:
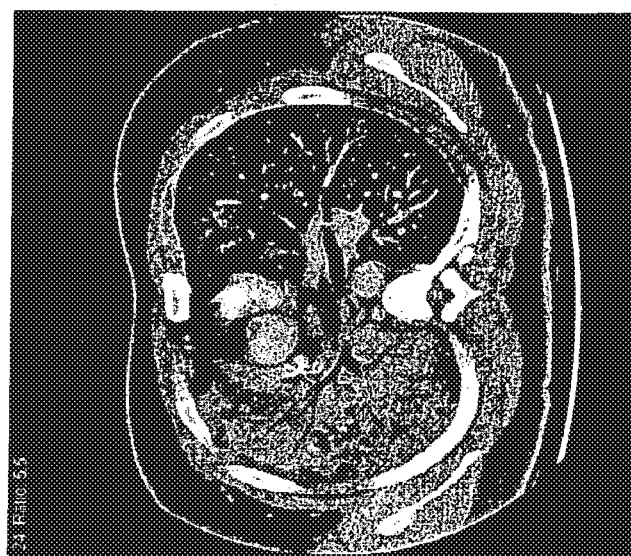
FIGS. 1A-1B show a representative illustration of Gefitinib response in refractory non-small cell lung cancer (NSCLC). Chest CT scan of case 6 (Table 1), demonstrating (FIG. 1A) a large mass in the right lung before treatment with gefitinib, and (FIG. 1B) marked improvement six weeks after Gefitinib was initiated.
Figure 1B:
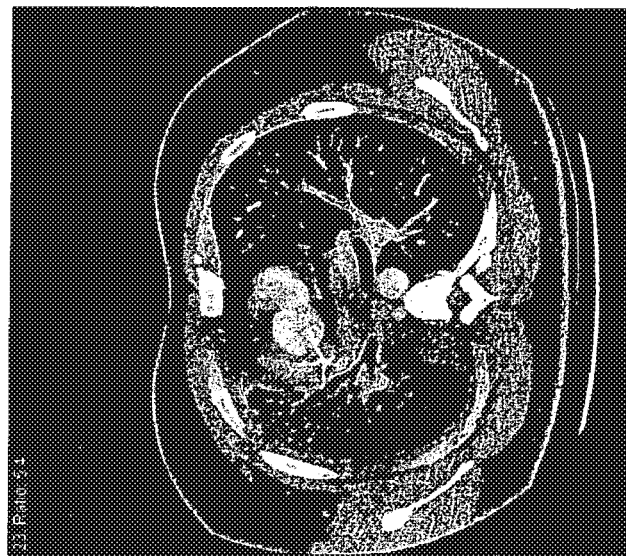

TGCGGAAGAGAAAGAATACCATGCAGAAGGAGGCAAAgtaaggaggtggc tttaggtcagccagcattttcctgacaccagggaccaggctgccttccca ctagctgtattgtttaacacatgcaggggaggatgctctccagacattct gggtgagctcgcagc Results Clinical Characteristics of Gefitinib Responders Patients with advanced, chemotherapy-refractory NSCLC have been treated with single agent Gefitinib since 2000 at Massachusetts General Hospital. A total of 275 patients were treated, both prior to its approval on May 2003 by the FDA, as part of a compassionate use expanded access program, and following that date using commercial supply. During this period, 25 patients were identified by clinicians as having significant clinical responses. A significant clinical response was defined either as a partial response using RECIST criteria for patients with measurable disease, or for patients whose tumor burden could not be quantified using these criteria, an evaluable response was assessed by two physicians. Table 1 shows clinical characteristics of 9 cases for whom tumor specimens obtained at the time of initial diagnosis were available. For the other Gefitinib-responders, tissue was not available, most commonly because diagnostic specimens were limited to cytology from needle aspirates. As a group, the 9 patients experienced substantial benefit from Gefitinib. The median survival from the start of drug treatment is in excess of 18 months, and the median duration of therapy is greater than 16 months. Consistent with previous reports, Gefitinib-responders have a high prevalence of female sex, absence of smoking history, and tumors with bronchioalveolar histology (11, 12). Case 6 is representative of the Gefitinib-responsive cohort. This patient is a 32 year-old man, without smoking history, who presented with multiple brain lesions and disease in the right lung diagnosed as bronchoalveolar carcinoma. He was treated with whole brain radiotherapy, followed by a series of chemotherapy regimens to which his tumor did not respond (carboplatin and gemcitabine; docetaxel; vinorelbine). With a declining functional status and progressive lung tumor burden, he started therapy with 250 mg per day of Gefitinib. His shortness of breath promptly improved and a lung CT scan 6 weeks after initiation of treatment revealed the dramatic improvement shown in FIG. 1.

EGFR Mutations in Gefitinib Responders

We hypothesized that cases of NSCLC with striking responses to Gefitinib might harbor somatic mutations in EGFR, indicating an essential role played by this growth factor signaling pathway in these tumors. To search for such mutations, we first tested for rearrangements within the extracellular domain of EGFR that are characteristic of gliomas (15): none were detected. We therefore sequenced the entire coding region of the gene using PCR-amplification of individual exons. Heterozygous mutations were observed in 8/9 cases, all of which were clustered within the kinase domain of EGFR (Table 2 and FIG. 2). Four tumors had in-frame deletions removing amino acids 746-750 (delE756-A750; case 1), 747 to 750 (delL747-T751insS; case 2), and 747 to 752 (delL747-P753insS; cases 3 and 4). The latter two deletions were associated with the insertion of a serine residue, resulting from the generation of a novel codon at the deletion breakpoint. Remarkably, these four deletions were overlapping, with the deletion of four amino acids (leucine, arginine, glutamic acid and alanine, at codons 747 to 750) within exon 19 shared by all cases (see FIG. 4a). Another three tumors had amino acid substitutions within exon 21: leucine to arginine at codon 858 (L858R; cases 5 and 6), and leucine to glutamine at codon 861 (L861Q; case 7). The L861Q mutation is of particular interest, since the same amino acid change in the mouse egfr gene is responsible for the Dark Skin (dsk5) trait, associated with altered EGFR signaling (18). A fourth missense mutation in the kinase domain resulted in a glycine to cysteine substitution at codon 719 within exon 18 (G719C; case 8). Matched normal tissue was available for cases 1, 4, 5 and 6, and showed only wild-type sequence, indicating that the mutations had arisen somatically, during tumor formation. No mutations were observed in seven cases of NSCLC that failed to respond to Gefitinib (P=0.0007; 2-sided Fisher's exact test).

Prevalence of Specific EGFR Mutations in NSCLC and Other Cancer Types

Unlike gliomas, in which rearrangements affecting the EGFR extracellular domain have been extensively studied (15), the frequency of EGFR mutations in NSCLC has not been defined. We therefore sequenced the entire coding region of the gene in 25 primary cases of NSCLC unrelated to the Gefitinib study, including 15 with bronchioalveolar histology, which has been associated with Gefitinib-responsiveness in previous clinical trials (11, 12). Heterozygous mutations were detected in two bronchoalveolar cancers. Both cases had in-frame deletions in the kinase domain identical to those found in Gefitinib responders, namely delL747-P753insS and delE746-A750 (Table 2). Given the apparent clustering of EGFR mutations, we sequenced exons 19 and 21 in a total of 55 primary tumors and 78 cancer-derived cell lines, representing diverse tumor types (see Supplementary Material). No mutations were detected, suggesting that these arise only in a subset of cancers, in which EGFR signaling may play a critical role in tumorigenesis.

Increase in EGF-Induced Activation and Gefitinib Inhibition of Mutant EGFR Proteins To study the functional properties encoded by these mutations, the L747-S752insS deletion and the L858R missense mutants were expressed in cultured cells. Transient transfection of wild-type and mutant constructs into Cos-7 cells demonstrated equivalent expression levels, indicating that the mutations do not affect protein stability. EGFR activation was quantified by measuring phosphorylation of the tyrosine$^{1068}$ residue, commonly used as a marker of receptor autophosphorylation (19). In the absence of serum and associated growth factors, neither wild-type nor mutant EGFR demonstrated autophosphorylation (FIG. 3a). However, addition of EGF led to a 2-3 fold increase in receptor activation for both the missense and deletion EGFR mutants, compared with the wild-type receptor. Moreover, whereas normal EGFR activation was downregulated after 15 min, consistent with receptor internalization, the two mutant receptors demonstrated continued activation for up to 3 hrs (FIG. 3a). Similar results were obtained with antibodies measuring total EGFR phosphorylation following addition of EGF (not shown).

Since 7/8 EGFR kinase mutations reside near the ATP cleft, which is targeted by Gefitinib, we determined whether the mutant proteins have altered sensitivity to the inhibitor. EGF-induced receptor autophosphorylation was measured in cells pretreated with variable concentrations of Gefitinib. Remarkably, both mutant receptors displayed increased sensitivity to inhibition by Gefitinib. Wild-type EGFR had an $IC_{50}$ of 0.1 µM and showed complete inhibition of autophosphorylation at 2 µM Gefitinib, whereas the two mutant proteins had an $IC_{50}$ of 0.015 µM and abrogation of autophosphorylation at 0.2 µM (FIG. 3b). This difference in drug sensitivity may be clinically relevant, since pharmacokinetic studies indicate that daily oral administration of 400-600 mg of Gefitinib results in a mean steady-state trough plasma concentration of 1.1-1.4 µM, while the currently recommended daily dose of 250 mg leads to a mean trough concentration of 0.4 µM (20).

Example 2

Tumor cells harboring mutations within the kinase domain of the EGFR, and are therefore sensitive to growth inhibition by gefitinib treatment, can undergo "second-site" mutations, also within the kinase domain, that confer resistance to gefitinib but are still "activating" in the sense that they exhibit increased EGFR signaling relative to wild-type EGFR. Such gefitinib-resistant mutants are generated from two sporadic human NSCLC cell lines namely NCI-1650 and NCI-1975. Each cell line contains a heterozygous mutation with the kinase domain of EGFR, and is, therefore, expected to be sensitive to gefitinib. The EGFR mutation in NCI-1650 consists of an in-frame deletion of 15 nucleotides at position 2235-2249 (delLE746-A750) within exon 19, while NCI-1975 has a missense mutation within exon 21 that substitutes a G for T at nucleotide 2573 (L858R). The L858R mutation in NCI-H1975 has been shown herein to be activating and to confer increased sensitivity to gefitinib in vitro.

Gefitinib-resistant cell lines, derived from both NCI-1650 and NCI-1975 are isolated, following random chemical mutagenesis using EMS (ethyl methanesulfonate) followed by culture in gefitinib-supplemented medium to select for the outgrowth of resistant clones. Subcultivation of individual clones is followed by nucleotide sequence determination of the EGFR gene following specific PCR-mediated amplification of genomic DNA corresponding to the EGFR kinase domain.

A variation of this strategy involves the serial passage of these two cell lines in the presence of gradually increasing concentrations of gefitinib over a course of several weeks or months in order to select for the spontaneous acquisition of mutations within the EGFR gene that confer resistance to gefitinib. Selected cells (that continue to proliferate at relatively high gefitinib concentration) are isolated as colonies, and mutations are identified as described above.

Example 3

To determine whether mutation of receptor tyrosine kinases plays a causal role in NSCLC, we searched for somatic genetic alterations in a set of 119 primary NSCLC tumors, consisting of 58 samples from Nagoya City University Hospital in Japan and 61 from the Brigham and Women's Hospital in Boston, Mass. The tumors included 70 lung adenocarcinomas and 49 other NSCLC tumors from 74 male and 45 female patients, none of whom had documented treatment with EGFR kinase inhibitors.

As an initial screen, we amplified and sequenced the exons encoding the activation loops of 47 of the 58 human receptor tyrosine kinase genes (*) (Table 51) from genomic DNA from a subset of 58 NSCLC samples including 41 lung adenocarcinomas. Three of the tumors, all lung adenocarcinomas, showed heterozygous missense mutations in EGFR not present in the DNA from normal lung tissue from the same patients (Table S2; S0361, S0388, S0389). No mutations were detected in amplicons from other receptor tyrosine kinase genes. All three tumors had the same EGFR mutation, predicted to change leucine ("L") at position 858 to arginine ("R") (FIG. 6A; CTG→CGG; "L858R"), wherein all numbering refers to human EGFR.

We next examined exons 2 through 25 of EGFR in the complete collection of 119 NSCLC tumors. Exon sequencing of genomic DNA revealed missense and deletion mutations of EGFR in a total of 16 tumors, all within exons 18 through 21 of the kinase domain. All sequence alterations in this group were heterozygous in the tumor DNA; in each case, paired normal lung tissue from the same patient showed wild-type sequence, confirming that the mutations are somatic in origin. The distribution of nucleotide and protein sequence alterations, and the patient characteristics associated with these abnormalities, are summarized in Table S2.

Substitution mutations G719S and L858R were detected in two and three tumors, respectively. The "G719S" mutation changes the glycine (G) at position 719 to serine (S) (FIG. 6B). These mutations are located in the GXGXXG motif (SEQ ID NO:490) of the nucleotide triphosphate binding domain or P-loop and adjacent to the highly conserved DFG motif in the activation loop (52), respectively. See, e.g., FIG. 7. The mutated residues are nearly invariant in all protein kinases and the analogous residues (G463 and L596) in the B-Raf protein serine-threonine kinase are somatically mutated in colorectal, ovarian and lung carcinomas (41, 53) (FIG. 6A, 6B).

We also detected multiple deletion mutations clustered in the region spanning codons 746 to 759 within the kinase domain of EGFR. Ten tumors carried one of two overlapping 15-nucleotide deletions eliminating EGFR codons 746 to 750, starting at either nucleotide 2235 or 2236 (Del-1; FIGS. 6C and 8C; Table S2). EGFR DNA from another tumor displayed a heterozygous 24-nucleotide gap leading to the deletion of codons 752 to 759 (Del-2; FIG. 6C). Representative chromatograms are shown in FIGS. 8A-8F.

The positions of the substitution mutations and the Del-1 deletion in the three-dimensional structure of the active form of the EGFR kinase domain (54) are shown in FIG. 7. Note that the sequence alterations cluster around the active site of the kinase, and that the substitution mutations lie in the activation loop and glycine-rich P-loop, structural elements known to be important for autoregulation in many protein kinases (52).

Two additional EGFR mutations in two different tumor types have been identified. Namely, we have identified the EGFR mutation G857V in Acute Myelogenous Leukemia (AML) and the EGFR mutation L883 S in a metastatic sarcoma. The "G857V" mutation has the glycine (G) at position 857 substituted with a valine (V), while the "L883S" mutation has the leucine (L) at position 883 substituted with a serine (S). These findings suggest that mutations in EGFR occur in several tumor types and, most importantly, that EGFR inhibitors would be efficacious in the treatment of patients harboring such mutations. This expands the use of kinase inhibitors such as, e.g., the tyrosine kinase inhibitors gefitinib (marketed as Iressa™), erlotinib (marketed as Tarceva™), and the like in treating tumor types other than NSCLC.

The EGFR mutations show a striking correlation with the differential patient characteristics described in Japanese and U.S. patient populations. As noted above, clinical trials reveal significant variability in the response to the tyrosine kinase inhibitor gefitinib (Iressa™) with higher responses seen in Japanese patients than in a predominantly European-derived population (27.5% vs. 10.4%, in a multi-institutional phase II trial) (48); and with partial responses seen more frequently in the U.S. in women, non-smokers, and patients with adenocarcinomas (49-51). We show that EGFR mutations were more frequent in adenocarcinomas (15/70 or 21%) than in other NSCLCs (1/49 or 2%); more frequent in women (9/45 or 20%) than in men (7/74 or 9%), and more frequent in the patients from Japan (15/58 or 26%, and 14/41 adenocarcinomas or 32%) than in those from the US (1/61 or 2%, and 1/29 adenocarcinomas or 3%). The highest fraction of EGFR mutations was observed in Japanese women with adenocarcinoma (8/14 or 57%). Notably, the patient characteristics that correlate with the presence of EGFR mutations appear to be those that correlate with clinical response to gefitinib treatment.

To investigate whether EGFR mutations might be a determinant of gefitinib sensitivity, pre-treatment NSCLC samples were obtained from 5 patients who responded and 4 patients who progressed during treatment with gefitinib, where these patients were identified out of more than 125 patients treated at the Dana-Farber Cancer Institute either on an expanded access program or after regulatory approval of gefitinib (49). Four of the patients had partial radiographic responses (≥50% tumor regression in a CT scan after 2 months of treatment) while the fifth patient experienced dramatic symptomatic improvement in less than two months. All of the patients were from the United States and were Caucasian.

While sequencing of the kinase domain (exons 18 through 24) revealed no mutations in tumors from the four patients whose tumors progressed on gefitinib, all five tumors from gefitinib-responsive patients harbored EGFR kinase domain mutations. The Chi-squared test revealed the difference in EGFR mutation frequency between gefitinib responders (5/5) and non-responders (0/4) to be statistically significant with p=0.0027, while the difference between the gefitinib-responders and unselected U.S. NSCLC patients (5/5 vs. 1/61) was also significant with $p<10^{-12}$ (*). The EGFR L858R mutation, previously observed in the unselected tumors, was identified in one gefitinib-sensitive lung adenocarcinoma (FIG. 6A; Table S3A, IR3T). Three gefitinib-sensitive tumors contained heterozygous in-frame deletions (FIG. 6C and Tables S3A and S3B, Del-3 in two cases and Del-4 in one) and one contained a homozygous in-frame deletion (FIG. 6C and Tables S3A and S3B, Del-5). Each of these deletions was within the codon 746 to 753 region of EGFR where deletions were also found in unselected tumors. Each of these three deletions is also associated with an amino acid substitution (Tables S3A-S3C). In all four samples where matched normal tissue was available, these mutations were confirmed as somatic.

Example 3A: Primer Design

The cDNA sequences of receptor tyrosine kinases were obtained from GenBank (accession numbers listed in Table S1), and were to the human genome assembly (http://genome.ucsc.edu) using the BLAT alignment to identify exon/intron boundaries. External gene specific primer pairs were designed to amplify exon sequences and at least 250 bp of flanking intronic sequence or adjacent exonic sequence on each side using the Primer3 program (http://frodo.wi.mit.edu/primer3/primer3_code.html). The resulting predicted amplicons were then used to design internal primers flanking the exon (generally greater than 50 bp from the exon/intron boundary) and containing appended M13 forward or reverse primer tails. These nested primer sets were tested for appropriate amplicon size and high-quality sequence from control DNA. Amplicons encompassing exons encoding the receptor tyrosine kinase activation loop of 47 tyrosine kinases were amplified and sequenced in a set of 58 primary lung cancer samples from Nagoya City University Medical School. In addition, amplicons covering the full length EGFR were also amplified.

Example 3B: PCR and Sequencing Methods for Genomic DNA

Tyrosine kinase exons and flanking intronic sequences were amplified using specific primers in a 384-well format nested PCR setup. Each PCR reaction contained 5 ng of DNA, 1× HotStar Buffer, 0.8 mM dNTPs, 1 mM MgCl2, 0.2 U HotStar Enzyme (Qiagen, Valencia, Calif.), and 0.2 µM forward and reverse primers in a 10 µL reaction volume. PCR cycling parameters were: one cycle of 95° C. for 15 min, 35 cycles of 95° C. for 20 s, 60° C. for 30 s and 72° C. for 1 min, followed by one cycle of 72° C. for 3 min.

The resulting PCR products were purified by solid phase reversible immobilization chemistry followed by bi-directional dye-terminator fluorescent sequencing with universal M13 primers. Sequencing fragments were detected via capillary electrophoresis using ABI Prism 3700 DNA Analyzer (Applied Biosystems, Foster City, Calif.). PCR and sequencing were performed by Agencourt Bioscience Corporation (Beverly, Mass.).

Example 3B: Sequence Analysis and Validation

Forward (F) and reverse (R) chromatograms were analyzed in batch by Mutation Surveyor 2.03 (SoftGenetics, State College, Pa.), followed by manual review. High quality sequence variations found in one or both directions were scored as candidate mutations. Exons harboring candidate mutations were reamplified from the original DNA sample and re-sequenced as above.

Example 3C: Patients

Lung tumor specimens were obtained from patients with non-small cell lung cancer treated at Nagoya City University Hospital and the Brigham and Womens's Hospital (unselected Japanese tumors and gefitinib-treated U.S. tumors, respectively) and from the Brigham and Women's Hospital anonymized tumor bank (unselected U.S. samples) under Institutional Review Board approved studies. Information on gender, age, and histology was available for most samples. Patient samples were also obtained from patients treated on an open-label clinical trial of gefitinib at Dana-Farber Cancer Institute (13). Responses to gefitinib were defined using standard criteria (See, e.g., A. B. Miller, B. Hoogstraten, M. Staquet, A. Winkler, 1981 Cancer 47, 207-14). IRB approval was obtained for these studies.

Of the gefitinib-responsive patients, there were two patients who had been previously treated with at least one cycle of chemotherapy, one patient previously treated with radiation therapy, one patient concurrently treated with chemotherapy, and one patient who received no other treatment. For gefitinib-insensitive patients, treatment failure was defined as the appearance of new tumor lesions or the growth of existing tumor lesions in a CT scan after 2 months of gefitinib treatment compared to a baseline CT scan.

Example 3D: cDNA Sequencing of Patient Samples

Total RNA is isolated from tissue samples using Trizol™ (Invitrogen, Carlsbad, Calif.) and is purified using an RNeasy™ mini-elute cleanup kit (Qiagen, Valencia, Calif.). cDNA is transcribed from 2 µg of total RNA with Superscript II Reverse Transcriptase (Invitrogen Life technologies, Carlsbad, Calif.), according to the manufacturer's recommendations. The cDNA is used as template for subsequent PCR amplifications of EGFR.

The components of the PCR are: 20 mM Tris-HCl (pH 8.4), 50 mM KCl, 1.5 mM MgCl2, 0.1 mM each of dATP, dCTP, dGTP, dTTP, 0.2 µM of each primer, and 0.05 units/µl Taq polymerase (Taq Platinum, GIBCO BRL, Gaithersburg, Md.). Amplification of fragment "a" requires addition of 4% DMSO to the reaction. The primer sequences are listed in Table S4. Forward and reverse primers are synthesized with 18 base pairs of an overhanging M13 forward and reverse sequences respectively. The thermocycling conditions are: 94° C., 4 min; followed by 11 cycles, with denaturing step at 94° C. for 20", extension step at 72° C. for 20", and with a 20" annealing step that decreased 1° C./cycle, from 60° C. at cycle one to 50° C. at cycle 11; cycle 11 was then repeated 25 times. A 6 minute incubation at 72° C. followed by a 4° C. soak completes the program.

An aliquot of the PCR reaction is diluted 1:50 with water. The diluted PCR product is sequenced using an M13 Forward Big Dye Primer kit (Perkin-Elmer/Applied Biosystems, Foster City, Calif.), according to the manufacturer's recommendations. The sequencing products are separated on a fluorescent sequencer (model 3100 from Applied Biosystems, Foster City, Calif.). Base calls are made by the instrument software, and reviewed by visual inspection. Each sequence is compared to the corresponding normal sequence using Sequencher 4.1 software (Gene Codes Corp.).

Example 3E: Tumor Types Expressing Mutant EGFR

Two additional mutations in EGFR were found in two different tumor types. An EGFR mutation that substitutes a glycine (G) for a valine (V) at position 857 ("G857V") was identified in Acute Myelogenous Leukemia (AML). An EGFR mutation that substitutes a leucine (L) with a serine (S) at position 883 ("L883S") in a metastatic sarcoma.

Example 3F: Cell Lines

The effects of gefitinib on NSCLC cell lines in vitro were examined. One cell line, H3255, was particularly sensitive to gefitinib, with an IC50 of 40 nM. Other cell lines had much higher IC50s. For example, a wild type cell line H1666 has an IC50 of 2 uM, which is 50 fold higher than for the mutant cell line When the EGFR from this cell line was sequenced, it contained the L858R missense mutation, while the other cell lines were wild type for EGFR. Much lower concentrations of gefitinib were required to turn off EGFR and also AKT and ERK phosphorylation by EGFR as compared to EGFR wild type cells, which required at least 100 times higher concentrations of gefitinib to achieve the same effect. These findings suggest that the mutant receptor is more sensitive to the effects of gefitinib. Also note here, Example 3G: Combination Therapies Tumor specimens were analyzed from patients with advanced NSCLC treated on the randomized trial of carboplatin/paclitaxel with or without erlotinib. The clinical portion of this trial demonstrated equivalent survival in the two treatment arms. Tumor specimens were available for sequencing from 228 of the 1076 patients. The preliminary clinical characteristics of these patients is not different from the group as a whole with respect to baseline demographics, response rate, median and overall survival.

Exons 18-21 of the tyrosine kinase domain were sequenced and 29 mutations, for a mutation frequency of 12.7 percent, were identified.

As a whole the patients with EGFR mutations have a better survival regardless of whether they received treatment with chemotherapy alone or in combination with erlotinib. These differences are statistically significant with a p value of less than 0.001. These findings raise the possibility the EGFR mutations, in addition to being predictors of response to gefitinib and erlotinib, may also be prognostic for an improved survival.

(*) Note that the frequency of EGFR mutation in the unselected US patients, 1 of 61, appears to be low when compared to the frequency of reported gefitinib response at 10.4%. This difference has a modest statistical significance (p=0.025 by the chi-squared test). Thus this result could still be due to chance, could be due to a fraction of responders who do not have EGFR mutations, or could be due to failure to detect EGFR mutations experimentally in this tumor collection. If the frequency of EGFR mutation in gefitinib-responsive US patients (5/5) is compared to the expected frequency of gefitinib response (10.4%), the chi-squared probability is again less than 10-12.

Example 4

Study Design:

We performed a retrospective cohort study of NSCLC patients referred for somatic EGFR kinase domain sequencing from August 2004 to January 2005 at Massachusetts General Hospital (MGH), Dana-Farber Cancer Institute (DFCI), and Brigham and Women's Hospital (BWH). These three institutions comprise Dana-Farber/Partners Cancer-Care (DF/PCC), an academic joint venture cancer center that cares for approximately 1,200 lung cancer patients per year. In August 2004, EGFR kinase domain sequencing was made available for clinical use at DF/PCC. Clinicians could select which patients to refer for testing, however patients needed to have sufficient and appropriate tumor specimens available. Tumor cells had to comprise at least 50% of the specimen based on histologic examination by MGH and BWH reference pathologists, and the specimen had to be from a resection, bronchoscopic biopsy, or core needle biopsy of a primary or metastatic tumor, or a cellblock from pleural fluid. In rare cases, fine needle aspirate samples were determined adequate. Samples could be either paraffin-embedded or frozen tissue. Due to the low incidence of EGFR mutations in squamous cell tumors (62) patients with this diagnosis were not eligible for testing.

We identified patients undergoing EGFR testing using the EGFR case log maintained at the Laboratory for Molecular Medicine (LMM), of the Harvard Medical School/Partners HealthCare Center for Genetics and Genomics (CLIA #22D1005307), the diagnostic testing facility where all sequencing was performed and interpreted. We included all patients referred for EGFR testing from DF/PCC with a diagnosis of NSCLC during the study period.

Patient age, gender, and race were collected from the electronic medical record system. Smoking status, cancer history, EGFR kinase domain sequencing results, and subsequent EGFR-TKI treatment plans were documented using structured physician chart review. Specifically, the smoking status and cancer history were obtained from physician and nursing notes. Former smokers were defined as patients who had quit smoking at least one year before their diagnosis of lung cancer and never-smokers were defined as patients who had smoked less than 100 cigarettes in their lifetime. Smokers who had quit within a year of their diagnosis or who were smoking at the time of diagnosis were classified as current smokers. Pack-years of smoking were calculated by multiplying the number of packs smoked per day by the number of years of smoking. Tumor histology and EGFR kinase domain sequencing results were obtained from pathology reports. All pathology specimens were centrally reviewed at either MGH or BWH and histology was categorized using the World Health Organization (WHO) classification system (63). Subsequent treatment plans were obtained from physician notes.

Complete data were available for age, gender, tumor histology, and EGFR mutation status. There were missing data for race (12%), tumor stage at time of testing (4%), smoking status (6%), prior treatments (5%), and subsequent EGFR-TKI treatment plans (11%). This study was approved by the Institutional Review Board at DF/PCC.

EGFR Gene Sequencing:

Serial sections of either frozen or formalin-fixed, paraffin-embedded (FFPE) tumor tissue were cut and placed on a glass slide. A region of tumor tissue consisting of at least 50% viable tumor cells was identified by a pathologist. FFPE samples were extracted with xylene and ethanol to remove paraffin. Both FFPE and frozen tissue samples were digested with proteinase K overnight. Genomic deoxyribonucleic acid (DNA) was extracted from tissue and peripheral whole blood using standard procedures. Genomic DNA was extracted from saliva samples using the DNA Genotek-Oragene™ saliva kit.

The kinase domain of EGFR (exons 18-24 and flanking intronic regions) was amplified in a set of individual nested polymerase chain reaction (PCR) reactions. The primers used in the nested PCR amplifications are described in Table S1A and B and SEQ ID 1-424 with the addition of universal sequences to the 5' ends of the primers (5' tgtaaaacgacggc-cagt) (SEQ ID NO. 645). The PCR products were directly sequenced bi-directionally by dye-terminator sequencing. PCR was performed in a 384-well plate in a volume of 15 µl containing 5 ng genomic DNA, 2 mM MgCl2, 0.75 µl DMSO, 1 M Betaine, 0.2 mM dNTPs, 20 pmol primers, 0.2 µl AmpliTaq Gold® (Applied Biosystems), 1× buffer (supplied with AmpliTaq Gold). Thermal cycling conditions were as follows: 95° C. for 10 minutes; 95° C. for 30 seconds, 60° C. for 30 seconds, 72° C. for 1 minute for 30 cycles; and 72° C. for 10 minutes. PCR products were purified with Ampure® Magnetic Beads (Agencourt).

Sequencing products were purified using Cleanseq™ Magnetic Beads (Agencourt) and separated by capillary electrophoresis on an ABI 3730 DNA Analyzer (Applied Biosystems). Sequence analysis was performed by Mutation Surveyor (SoftGenetics, State College, Pa.) and manually by two reviewers. Non-synonymous DNA sequence variants were confirmed by analysis of 3-5 independent PCR reactions of the original genomic DNA sample. Blood or saliva samples from individuals with non-synonymous DNA sequence variants were analyzed to determine whether the sequence changes were unique to tumor tissue.

Statistical Analysis:

We constructed logistic regression models to assess the univariate association between patient demographic and clinical characteristics and EGFR mutation status. To identify significant predictors of mutation positive status, we constructed a multivariable logistic regression model including independent variables identified in prior studies as predictive of mutations, specifically gender, race, histology, and smoking status. Six patients were excluded from these analyses due to missing EGFR mutation data as a result of PCR failure. All analyses were performed using SAS statistical software (version 8.02, SAS Institute, Cary, N.C.).

Results:

Patient Characteristics:

Among the 100 patients with NSCLC referred for somatic EGFR kinase domain sequencing as part of clinical cancer care during the study period, the mean age was 60.7 years and 63% were female (Table 4). The majority of patients were white (76%) or Asian (7%), and had metastatic disease at the time the test was ordered (67%). Nearly all patients (94%) tested for EGFR mutations had adenocarcinoma, adenocarcinoma with bronchioloalveolar carcinoma (BAC) features, or pure BAC. Approximately one third of the patients were never-smokers. Therapy administered prior to the referral for EGFR testing included surgery (50%), chest radiotherapy (22%), chemotherapy (47%), and EGFR directed targeted therapy (11%).

Mutations Identified:

The average length of time from referral for testing to result availability was 12 business days. The majority of specimens submitted were paraffin-embedded (74%). Six of the 74 (8%) paraffin-embedded specimens failed PCR amplification, while all of the 26 frozen specimens were successfully amplified. Among the 94 patients with interpretable results, 23 (24%) were found to have at least one mutation in the EGFR kinase domain, with two of these patients demonstrating two point mutations each, for a total of 25 mutations identified (Table 5). Among the 23 patients with mutations, 9 (39%) had one or more point mutations, 12 (52%) had in-frame overlapping deletions in exon 19 and two patients (9%) had duplications in exon 20. The point mutations were in exons 18 and 21, and included five 2573T>G (L858R), and one each of 2126A>T (E709V), 2155G>A (G719S), 2156G>C (G719A), 2327G>A (R776H), 2543C>T (P848L), and 2582T>A (L861Q). One of the point mutations (P848L) was detected in both the tumor specimen and in mononuclear cells obtained from a buccal swab. No mutations were detected in exons 22, 23, or 24.

Predictors of Mutations:

In our sample, there was no significant association between EGFR mutation status and age (p=0.61), female gender (p=0.92), Asian race (p=0.08), or metastatic disease at the time of referral (p=0.43, Table 4). None of the 6 patients with non-adenocarcinoma tumor histology were found to have mutations. Among the patients with adenocarcinoma, adenocarcinoma with BAC features and pure BAC, there was no association between BAC/BAC features and EGFR mutation status (p=0.35).

None of the 17 current smokers were found to have a mutation. Never-smokers were significantly more likely to have an EGFR mutation than former smokers (odds ratio [OR]=3.08, 95% confidence interval [CI] 1.09-8.76). The mean number of pack-years smoked was significantly lower among EGFR mutation-positive patients (0.7 pack-years) compared to EGFR mutation-negative patients (25.0 pack-years, p<0.001). For each additional pack-year smoked, there was a 4% decrease in the likelihood of having a mutation (OR=0.96, 95% CI 0.93-0.99).

The number of pack-years of smoking remained a significant predictor of mutation status after controlling for gender, race, and tumor histology (OR=0.96, 95% CI 0.93-0.99).

Subsequent Use of Test Information:

EGFR mutation-positive patients were significantly more likely to have documented plans to receive subsequent EGFR-TKI treatment (86%) than EGFR mutation-negative patients (11%, p<0.001). Clinicians documented that the EGFR results affected their prioritization of recommended therapies in 38% of cases. These cases included 14 (61%) of the 23 mutation-positive patients for whom EGFR-TKI therapy was recommended earlier than it would have been had the test been negative, and 24 (34%) of the 71 mutation-negative patients for whom EGFR-TKI therapy was not recommended, or was recommended later than it would have been had the test been positive.

EGFR mutation status was more likely to change prioritization of treatment options in patients with metastatic disease (54%) than in patients with local or locally advanced disease (19%, p=0.003). Given this finding, we further analyzed the decision-making process in metastatic patients (FIG. 10). Among the 31 patients with metastatic disease whose test results affected treatment recommendations, five mutation-positive patients were offered first-line EGFR-TKI treatment and six mutation-positive patients were offered second-line EGFR-TKI treatment in lieu of chemotherapy. Twenty mutation-negative patients were encouraged to defer EGFR-TKI treatment until third-line treatment or beyond based on their negative EGFR test results. Among the 26 patients with metastatic disease whose test results did not affect treatment recommendations, two mutation-negative patients received first-line EGFR-TKI treatment despite their negative results, nine patients including four mutation-positive patients received second or third-line EGFR-TKI treatment, and 15 patients including two mutation-positive patients did not receive a recommendation for an EGFR-TKI. Three of the patients with metastatic disease were participating in trials evaluating first-line EGFR-TKI therapy. Nine of the patients with metastatic disease had previously received or were receiving EGFR-TKIs at the time of EGFR testing.

Discussion:

We studied the first 100 patients with NSCLC to undergo screening for somatic EGFR mutations as part of clinical cancer care at our institution and found that testing was feasible and significantly impacted the treatment of NSCLC patients. Patients harboring EGFR mutations were significantly more likely to receive recommendations for EGFR-TKI therapy than patients without mutations. Physicians adjusted their treatment recommendations based on the test results in over one-third of the cases, and were more likely to do so in patients with metastatic disease. In our patient sample, physicians used positive EGFR test results to help make the decision to prioritize EGFR-TKIs over chemotherapy for some patients, especially for first or second-line treatment. However, negative EGFR test results did not prevent physicians from administering EGFR-TKIs to selected patients. Many of the patients in whom the test result did not impact clinical decision-making had early stage, resected disease or were already receiving an EGFR- TKI for metastatic disease at the time of testing. This is reasonable since the utility of EGFR-TKIs as adjuvant therapy is not known and there is a benefit to EGFR-TKI therapy in a small number of patients without an identified EGFR mutation (65, 66-70, 71).

Our study also provides evidence that molecular diagnostics can enhance the clinical ability to identify patients with EGFR mutations. Many oncologists currently use the clinical characteristics associated with EGFR mutations and response to EGFR-TKIs to guide the decision-making process for patients with NSCLC. Indeed, our population of patients referred for EGFR testing demonstrated an increased prevalence of such characteristics. For example, 95% of referred patients had adenocarcinoma or BAC tumor histology, compared to 45% in the general NSCLC population (72). While never-smokers comprised 29% of our population, the incidence of never-smokers in the general NSCLC population has been reported as 2-10%, and may be as high as 27% in women with NSCLC (73-75). Similarly, our population consisted of only 17% current smokers, compared to the 38-75% rate of current smoking among newly diagnosed NSCLC patients (75, 78-80). Our clinically selected population consequently had an EGFR mutation rate of 24%, which is substantially higher than rates documented by our and other U.S. groups that tested unselected available NSCLC tumor samples (65-66, 81). However, it is important to note that while clinicians appeared to be attempting to select patients for testing that had the clinical characteristics predictive of EGFR mutations, the mutation frequency was still only 24%, highlighting the fact that molecular diagnostics increase the information available to make clinical decisions.

Smoking status was the strongest predictor of EGFR mutation status in our patients, with an increase in smoking history associated with a significantly decreased likelihood of harboring an EGFR mutation, after controlling for previously described predictors of mutation status. Our results are consistent with other case series documenting the importance of smoking status in the likelihood of EGFR mutations (66, 69, 70, 81, 82). Just as the extremely low prevalence of EGFR mutations in squamous cell tumors (62) has shifted testing efforts towards adenocarcinoma tumors, it may be appropriate to focus future efforts on patients with a low or absent smoking history. However, reports of EGFR mutations in patients without typical clinical characteristics advise against strict testing limitations (83). When examining the other clinical characteristics thought to be associated with mutations, we found Asian race and BAC tumor histology to have non-significant trends towards predicting EGFR mutation status. The lack of statistical significance in these associations may be due to small sample size.

The test was feasible and fit into the time constraints of clinical cancer care. Nearly all of the tumors submitted for analysis produced interpretable results. The six specimens that failed PCR amplification were all paraffin-embedded, while none of the frozen specimens failed PCR amplification. When available, fresh frozen tissue is the preferable substrate for EGFR mutation testing.

There have been close to 2,500 NSCLC samples reported thus far that have undergone partial or complete EGFR sequence analysis. Our patients demonstrated mutations similar to previous reports, with overlapping exon 19 deletions of 9-23 base pairs and point mutations leading to single amino acid substitutions in exons 18 and 21. Five of the point mutations we found have been described above (E709V, G719S, G719A, L858R, and L861Q). One of the point mutations we found causes an amino acid substitution at a codon where a different amino acid substitution has been previously described (R776H). The E709V and R776H variants were each found in combination with a known gefitinib-sensitizing mutation involving codon 719. The P848L mutation in exon 21 was found in both the somatic and buccal samples, suggesting it may be a germline variant of uncertain significance. The patient was a never-smoking female with adenocarcinoma who had stable disease for 15 months on gefitinib treatment, prior to the EGFR mutation testing. When the P848L mutation was revealed, she had recently been found to have progressive disease and was started on erlotinib therapy. No information about response to erlotinib is available at this time.

The (2253_2276 del) deletion overlaps previously described exon 19 deletions. The deletions in our patients can be categorized into one of two groups: those spanning codons 747-749 at a minimum (amino acid sequence LRE), and those spanning codons 752-759 (FIG. 11). Analysis of all exon 19 deletions reported to date suggests that a wide variety of amino acids can be deleted from the TK region spanning codons 747-759. There does not appear to be a required common codon deleted; however, all of the deletions we detected maintained a lysine residue at position 745.

One of our two exon 20 mutations are in a never-smoking female with recurrent adenocarcinoma who was treated with erlotinib after EGFR testing was performed and has had stable disease for two months at this time. The other is a former-smoking male with metastatic adenocarcinoma who was treated with an EGFR-TKI, but could not tolerate it due to severe rash. The identification of clinically relevant EGFR mutations in exon 20 underscores the importance of comprehensive sequencing of the TK region of EGFR.

In conclusion, this study demonstrates the feasibility and utility of comprehensive screening of the TK region of the EGFR gene for somatic mutations in NSCLC patients as part of clinical cancer care. The result of the test provides useful information regarding clinical predictors of EGFR-TKI response. Current smokers are less likely to harbor a mutation, as are former smokers with a high number of pack-years of smoking history.

Example 5

EGFR Gene Test for Non-Small Cell Lung Cancer, a Standard Operating Procedure.

Clinical Indications:

This test is indicated for individuals with Non-Small Cell Lung Cancer.

Analytical Principle

The EGFR Gene Test is a genetic test that detects mutations in the kinase domain of EGFR. DNA is first obtained from a tumor biopsy. The DNA sequence of 7 exons (18, 19, 20, 21, 22, 23, 24) of EGFR is then determined by direct bi-directional gene sequencing. The sequence obtained is then compared to known EGFR sequence to identify DNA sequence changes. If a DNA sequence change is detected in tumor tissue, the test will be repeated on the original tissue sample. If the change has not previously been reported in a gefitinib- or erlotinib-responder, the test will also be conducted with a sample of the individual's blood to determine whether the mutation is constitutive (and therefore likely a normally occurring polymorphism) or occurred somatically in the tumor tissue.

Specimen Requirements:

A minimum of 100 ng of DNA is required from tissue sample. Note: Extremely small quantities of DNA may be extracted from tissue samples. The concentration of this DNA may not be accurately quantitated.

Quality Control:
Controls Used

Two negative controls (water) and a positive control (human DNA) for each exon are included in the PCR reactions. The negative control should proceed through the entire procedure to ensure that the sequence obtained is not the result of contamination. A pGEM positive control and an ABI array control are included in the sequencing step.

Control Preparation and Storage:

The positive control for PCR is either Clontech human DNA or human DNA from an anonymous blood sample and is stored at 4° C. The negative control for the PCR reaction is HyPure Molecular Biology Grade water stored at room temperature. The pGEM positive sequencing reaction control and the ABI array control are stored at −20° C.

Tolerance Limits and Steps to Take if Individual Control Fails:

If the positive PCR control fails but the negative controls and samples pass, the PCR results will be designated as pass and sequencing will be performed. If a negative control shows evidence of DNA amplification, the whole reaction will be repeated with a new aliquot of patient's DNA. If the pGEM control fails and the test reactions fail, the sequencing run will be repeated with a second aliquot of the PCR product. If the sequencing controls fail but the test reactions pass, the sequencing does not need to be repeated. NOTE: Due to the low yield of DNA extraction from paraffin embedded tissue samples, external PCR reactions often do not yield visible products. Internal PCR reactions should yield visible products. The size of the product detected on the gel should be compared to the anticipated sizes (see below) to ensure that the appropriate PCR product has been obtained. If an internal PCR product is not visible on the gel, exon-specific PCR failures should be repeated.

If PCR amplification for an individual sample fails, a new round of PCR should be attempted with a two-fold increase in input DNA template. If PCR amplification fails again, a new DNA sample for that patient should be acquired if available. If the sample was a paraffin-embedded tissue sample, additional slides should be scraped. If available, more slides than used to generate the original sample should be scraped and digestion in Proteinase K should be allowed to occur for three nights.

Equipment and Reagents (All reagents stable for one year unless otherwise noted.)

PCR and Sequencing (in general, PCR and sequencing equipment and reagents are known to those of skill in the art and may be used herein, also noted above).

Primers: (see Table 6 and 7 below)

TABLE 6

External PCR Primers:

| Exon | Forward Primer Sequence, (5'→3') | SEQ ID NOS | Reverse Primer Sequence, (5'→3') | SEQ ID NOS |
|---|---|---|---|---|
| 18 | TCAGAGCCTGTGTTTCTACCAA | 653 | TGGTCTCACAGGACCACTGATT | 646 |
| 19 | AAATAATCAGTGTGATTCGTGGAG | 654 | GAGGCCAGTGCTGTCTCTAAGG | 647 |
| 20 | ACTTCACAGCCCTGCGTAAAC | 655 | ATGGGACAGGCACTGATTTGT | 648 |
| 21 | GCAGCGGGTTACATCTTCTTTC | 656 | CAGCTCTGGCTCACACTACCAG | 649 |
| 22 | CCTGAACTCCGTCAGACTGAAA | 657 | GCAGCTGGACTCGATTTCCT | 650 |
| 23 | CCTTACAGCAATCCTGTGAAACA | 658 | TGCCCAATGAGTCAAGAAGTGT | 651 |
| 24 | ATGTACAGTGCTGGCATGGTCT | 659 | CACTCACGGATGCTGCTTAGTT | 652 |

TABLE 7

Internal PCR Primers:

| Exon | Forward Primer Sequence, (5'→3') | Reverse Primer Sequence, (5'→3') | Product Length (bp) |
|---|---|---|---|
| 18 | TCCAAATGAGCTGGCAAGTG (SEQ ID NO 660) | TCCCAAACACTCAGTGAAACAAA (SEQ ID NO 667) | 397 |
| 19 | GTGCATCGCTGGTAACATCC (SEQ ID NO 661) | TGTGGAGATGAGCAGGGTCT (SEQ ID NO 668) | 297 |
| 20 | ATCGCATTCATGCGTCTTCA (SEQ ID NO 662) | ATCCCCATGGCAAACTCTTG (SEQ ID NO 669) | 378 |
| 21 | GCTCAGAGCCTGGCATGAA (SEQ ID NO 663) | CATCCTCCCCTGCATGTGT (SEQ ID NO 670) | 348 |
| 22 | TGGCTCGTCTGTGTGTGTCA (SEQ ID NO 664) | CGAAAGAAAATACTTGCATGTCAGA (SEQ ID NO 671) | 287 |
| 23 | TGAAGCAAATTGCCCAAGAC (SEQ ID NO 665) | TGACATTTCTCCAGGGATGC (SEQ ID NO 672) | 383 |
| 24 | AAGTGTCGCATCACCAATGC (SEQ ID NO 666) | ATGCGATCTGGGACACAGG (SEQ ID NO 673) | 302 |

TABLE 7-continued

Internal PCR Primers:

| Exon | Forward Primer Sequence, (5'→3') | Reverse Primer Sequence, (5'→3') | Product Length (bp) |
|---|---|---|---|
| F primer linker | tgtaaaacgacggccagt (SEQ ID NO 645) | 5' end of all forward primers | 18 |
| R primer linker | aacagctatgaccatg (SEQ ID NO 674) | 5' end of all reverse primers | 16 |

Precautions

TABLE 8

| Task | | Instruction(s) | Risk |
|---|---|---|---|
| 1. | PCR Setup | Use PCR Hood Use dedicated pipets and filtered tips Only open reagents in the hood | Contamination of PCR reaction |
| 2. | Use of PCR Hood | Do not use any post-PCR samples or reagents in the hood | Contamination of PCR reaction |

Preparing PCR Reaction Mix for External PCR

All procedures performed in PCR hood for genomic DNA, not the clean hood.
1. Thaw out Taq Gold and dNTP on ice.
2. Prepare the master mix in a tube (eppendorf or 15 mL tubes) using the table below. Water, Betaine, 10× Buffer, MgCl2, DMSO, Taq Gold and dNTP should be added in the order listed. It is very important to mix the reagents by pipetting up-and-down gently while adding each reagent.
3. DNA should be added to the master mix before aliquoting. After making the large volume of master mix, aliquot 96 ul (enough for 8 rxns) to a separate tube for each patient or control. Add 8 ul of DNA at 5 ng/ul to the 96 ul of mastermix. 13 ul can then be added to the individual wells of the plate or put in strip tubes and pipetted with a multi-channel pipettor.
4. For a full 384-well plate of reactions, make enough master mix for about 415 reactions.
5. Spin the plate of master mix to get rid of air bubbles.
6. If using a large set of primers, it would help to have them in 96-well plates with forward primers and reverse primers in separate plates.
7. Add the primers using a multi-channel pipette. Make sure to mix by pipetting up-and-down gently.
8. Spin the plate to get rid of any air bubbles.
9. Use the cycle below to amplify.

Note: PCR is done in 384-well plates.

TABLE 9

| Reagent | Volume per reaction (μL) |
|---|---|
| Autoclaved ddH2O | 4.90 |
| 5M Betaine | 3.00 |
| 10X Buffer | 1.50 |
| Magnesium Chloride | 1.50 |
| DMSO | 0.75 |
| Taq | 0.20 |

TABLE 9-continued

| Reagent | Volume per reaction (μL) |
|---|---|
| dNTP | 0.15 |
| PCR Forward Primer1 (conc. 20 pmol/uL) | 1.00 |
| PCR Reverse Primer2 (conc. 20 pmol/uL) | 1.00 |
| DNA (conc. 5 ng/uL) | 1.00 |
| Total volume of PCR reaction | 15.00 |

TABLE 10

| PCR Amplification Cycle | | | |
|---|---|---|---|
| Activate Taq Gold | 10 minutes | 95° C. | |
| Denature | 30 seconds | 95° C. | 30 cycles |
| Anneal | 30 seconds | 60° C. | |
| | 1 minutes | 72° C. | |
| Extend | 10 minutes | 72° C. | |
| Hold | ∞ | 4° C. | |

Note: A cleanup is not necessary after performing the external PCR.

Preparing PCR Reaction Mix for Internal PCR

The internal PCR set up is almost the same as the external PCR with a few exceptions.
1. Make the large volume of master mix as described for external PCR in the PCR hood.
2. Aliquot MM to 7 strip tubes and multichannel pipette 12 ul into the 384-well plate.
3. Add 1 ul each of forward and reverse internal primers. Temporarily seal plate.
4. Remove from hood, spin down plate and proceed to post PCR set-up area. 5. Use dedicated pipettes to aliquot 1 ul of external PCR product into each reaction.
6. Heat seal and spin again.
7. Run same amplification cycle as external.

Run PCR products on a 1% gel before clean-up. Determine Pass/Failed exons for repeat PCR.

Clean-up Internal PCR Using Ampure Magnetic Bead Clean-Up

Cleanup
1. Vortex the plate of Ampure magnetic beads till there is no deposit of beads. 2. It is very important that the temperature of the Ampure beads is at room temperature.
3. Use the 384-well Ampure protocol on the Biomek and change the volume of reaction to 12 uL to accommodate reagents used for cleanup. If this is not done, an error will be generated.
4. After the program is complete, hydrate plate with 20 uL of autoclaved ddH2O per well. While adding water, make sure to mix by pipetting up-and-down gently.

5. Spin the plate to get rid of any air bubbles.
6. Place the plate on a magnet to separate out the beads. Now you should be able to take up 1 uL of the DNA to setup sequencing reactions. Save the rest at −20° C. for future use.

Sequencing Protocol

Preparing Sequencing Reaction Mix

1. Thaw out BigDye 3.1 in a dark place, on ice.
2. Prepare the master mix in a tube (eppendorf or 15 mL tubes) using the table below. Water, buffer, DMSO and BigDye should be added in the order listed. 3. It is very important to mix the reagents by pipetting up-and-down gently while adding each reagent.
4. When using a universal primer for sequencing, the primer can also be added to the master mix at this time. If the primer is unique it should be added individually after the master mix is in the 384-well plate.
5. Usually for a full 384-well plate of reactions, make enough master mix for about 415 reactions.
6. Once the master mix is setup divide the mix into 8 wells of strip tubes. (Do not use reservoirs to aliquot master mix. That would be a waste of reagents) 7. 7. Now a multi-channel pipette can be used to aliquot the master mix into the 384-well plate
8. Spin the plate of master mix to get rid of air bubbles.
9. Add the PCR product to be sequenced, using a multi-channel pipette. Make sure to mix by pipetting up-and-down.
10. Spin the plate to get rid of any air bubbles.
11. Use the cycle below to amplify.

TABLE 11

| Reagent | Volume per reaction (µL) |
|---|---|
| Autoclaved ddH2O | 4.38 |
| 5X ABI Buffer | 3.65 |
| DMSO | 0.50 |
| ABI BigDye 3.1 | 0.35 |
| Sequencing Primer concentration | 0.12 |
| DNA from Internal PCR reaction | 1.00 |
| Total Volume of reaction | 10.00 |

TABLE 12

| Amplification Cycle for Sequencing | | | |
|---|---|---|---|
| Denature | 10 seconds | 96° C. | 25 cycles |
| Anneal | 5 seconds | 50° C. | |
| Extend | 4 minutes | 60° C. | |
| Hold | ∞ | 4° C. | |

Clean-Up Via Cleanseq Magnetic Bead Clean-Up

1. Vortex the plate of Cleanseq magnetic beads till there is no deposit of beads.
2. Use the Cleanseq 384-well plate program on the Biomek to clean-up the samples.
3. Once the program is done, save the original plate at −20° C. The new plate with the clean samples is ready to go on the ABI 3730.

(Note: If the PCR products are shorter than 300 bps you might have to dilute the sample before putting it on the 3730)

Create Mutation Surveyor templates for the EGFR test and save them on LMM/Sequencing/Sequences-MS Review/EGFR.

Repeat Result Criteria

All positive results are repeated by amplifying and sequencing the specific exon(s) in which a DNA sequence change has been detected from a second aliquot of patient DNA derived from the original tissue sample. In addition, DNA extracted from a sample of the patient's blood should be run in parallel to compare with tumor tissue if the sequence change detected has not previously been detected in a gefitinib- or erlotinib-responder.

Any exon that did not produce clear sequence will be repeated either from extraction, PCR or sequencing, based on the specific technical problems.

Assay Parameters

Sensitivity of the Test—Somatic EGFR kinase domain mutations have been found in approximately 13% of individuals with NSCLC (Paez J G et al., 2004). In addition, somatic EGFR kinase domain mutations have been found in 13/14 (92.8%) individuals with NSCLC that were gefitinib-responsive (Paez J G et al., 2004, Lynch, et al., 2004). Validation of the technical sensitivity of the test demonstrated 100% sensitivity to known mutations and validation of the sequencing platform in our lab shows 100% sensitivity (see "Accuracy of the Technique" below). The sensitivity for mutation detection of mosaic samples has been determined to be 25% (ie, heterozygous mutations can be detected when present at 50% of a cell mixture). We have found that up to 20% of paraffin-embedded tissue do not yield high quality DNA. We are unable to obtain sequence information from these samples.

Specificity of the Test—To date, published literature indicates that no individuals with a somatic mutation in EGFR were not responsive to gefitinib (11/11). The chance of finding a mutation due to an artifact of bi-directional sequencing is close to 0% (see "Accuracy of the Technique" below). As such, the specificity of the test is approximately 100%.

Accuracy of the Technique—The technique of DNA sequencing is the gold standard in molecular diagnostics. This lab uses the ABI 3730 DNA Analyzer that has a reported accuracy of 98.5%. Combining this with bi-directional sequencing, automated chromatogram analysis with Mutation Surveyor, and manual analysis of false positives, we have achieved an accuracy rate of 100%. This is based upon an analysis of over 100,000 bases of raw sequence. For details of this assessment, see our Quality Assurance Program manual.

Note: We do not assume that these results guarantee 100% accuracy of this platform. It is known that sequencing errors can occur and, as such, we report our accuracy to be 99.99% that has been found by large scale sequencing projects (Hill et al. 2000).

Reproducibility of the Test—Due to the accuracy of the test, when results are achieved, they are reproducible equal to the accuracy of the test (99.99%). However, on occasion, the test can fail due to factors listed below (see Limitations of Method) or because of PCR or sequencing failure due to unexplained technical reasons. In these cases, no results are achieved and the assay is repeated until a result is achieved or the patient specimen is deemed unacceptable. Specific rates of failure of each assay step and of specimens can be found in the validation reports in our Quality Assurance Program manual.

Normal Range of the Results—The normal sequence of the EGFR gene can be found online using GenBank accessions: NT 033968.5 (genomic sequence) and NM 005228.3 (mRNA sequence).

Limitations of Method:

Large deletions spanning one or more exons will not be detected by the sequencing method, particularly if present in heterozygosity. Mutations in the EGFR gene outside of the kinase domain will not be detected by this assay. Inhibitors may be present in the DNA sample preventing amplification by PCR. Degraded DNA may not produce analyzable data and re-submission of the specimen may be required. Rare sequence variations or secondary structures of the targeted primer sequences could affect PCR amplification and therefore mutation(s) could be missed in that region of one allele.

Example 6

Gefitinib (Iressa) is a tyrosine kinase inhibitor that targets the epidermal growth factor receptor (EGFR), and induces dramatic clinical responses in non-small cell lung cancers (NSCLCs) with activating mutations within the EGFR kinase domain. We report that these mutant EGFRs selectively activate Akt and STAT signaling pathways, which promote cell survival, but have no effect on Erk/MAPK signaling, which induces proliferation. NSCLCs expressing mutant EGFRs underwent extensive apoptosis following siRNA-mediated knockdown of the mutant EGFR or treatment with pharmacological inhibitors of Akt and STAT signaling, and were relatively resistant to apoptosis induced by conventional chemotherapeutic drugs. Thus, mutant EGFRs selectively transduce survival signals on which NSCLCs become dependent; consequently, inhibition of those signals by Gefitinib may underlie striking clinical responses.

Receptor tyrosine kinases of the EGFR family regulate essential cellular functions including proliferation, survival, migration, and differentiation, and appear to play a central role in the etiology and progression of solid tumors (R. N. Jorissen et al., *Exp. Cell Res.* 284, 31 (2003), H. S. Earp, T. L. Dawson, X. Li, H. Yu, *Breast Cancer Res. Treat.* 35, 115 (1995)). EGFR is frequently overexpressed in breast, lung, colon, ovarian, and brain tumors, prompting the development of specific pharmacological inhibitors, such as Gefitinib, which disrupts EGFR kinase activity by binding the ATP pocket within the catalytic domain (A. E. Wakeling et al., *Cancer Res.* 62, 5749 (2002)). Gefitinib has induced dramatic clinical responses in approximately 10% of patients with chemotherapy-refractory NSCLC (J. Baselga et al., *J. Clin. Oncol.* 20, 4292 (2002), M. Fukuoka et al., *J. Clin. Oncol.* 21, 2237 (2003), G. Giaccone et al., *J Clin Oncol.* 22, 777 (2004), M. G. Kris et al., *JAMA* 290, 2149 (2003)). Virtually all Gefitinib-responsive lung cancers harbor somatic mutations within the EGFR kinase domain, whereas no mutations have been seen in non-responsive cases (T. J. Lynch et al., *N. Engl. J. Med.* 350, 2129 (2004), J. G. Paez et al., *Science* 304, 1497 (2004).) These heterozygous mutations include small in-frame deletions and missense substitutions clustered within the ATP-binding pocket.

Using transient transfections of mutant EGFRs, we showed previously that both types of mutations lead to increased EGF-dependent receptor activation, as measured by autophosphorylation of Y1068, one of the prominent C-terminal phosphorylation sites of EGFR. (T. J. Lynch et al., *N. Engl. J. Med.* 350, 2129 (2004).

To enable studies of qualitative differences in signaling by mutant EGFRs, we generated stable lines of non-transformed mouse mammary epithelial cells (NMuMg) expressing wild-type or mutant EGFRs, and analyzed EGF-mediated autophosphorylation of multiple tyrosine residues linked to activation of distinct downstream effectors (R. N. Jorissen et al., *Exp. Cell Res.* 284, 31 (2003)). Cell lines were generated that expressed either wild-type EGFR or one of two recurrent mutations detected in tumors from Gefitinib-responsive patients: the missense mutation L858R and the 18 bp in-frame deletion, delL747-P753insS. Significantly different tyrosine phosphorylation patterns were observed between wild-type and the two mutant EGFRs at several C-terminal sites. EGF-induced phosphorylation of Y1045 and Y1173 was virtually indistinguishable between wild-type and mutant EGFRs, whereas phosphorylation of Y992 and Y1068 was substantially increased in both mutants. Interestingly, Y845 was highly phosphorylated in the L858R missense mutant, but not in the wild-type or the deletion mutant, and hence appears to be unique in distinguishing between the two types of EGFR mutations. The differential EGF-induced tyrosine phosphorylation pattern seen with wild-type and mutant receptors was reproducible in transiently transfected COS7 cells, ensuring against potential cell type specific effects.

Thus, Gefitinib-sensitive mutant EGFRs transduce signals that are qualitatively distinct from those mediated by wild-type EGFR. These differences may result directly from structural alterations within the catalytic pocket affecting substrate specificity, or from altered interactions with accessory proteins that modulate EGFR signaling.

The establishment of cell lines stably transfected with mutant EGFRs made it possible to compare the phosphorylation status of the major downstream targets of EGFR in a shared cellular background. EGF-induced activation of Erk1 and Erk2, via Ras, of Akt via PLCγ/PI3K, and of STAT3 and STAT5 via JAK2, are essential downstream pathways mediating oncogenic effects of EGFR (R. N. Jorissen et al., *Exp. Cell Res.* 284, 31 (2003)). EGF-induced Erk activation was essentially indistinguishable among cells expressing wild-type EGFR or either of the two activating EGFR mutants. In contrast, phosphorylation of both Akt and STAT5 was substantially elevated in cells expressing either of the mutant EGFRs. Increased phosphorylation of STAT3 was similarly observed in cells expressing mutant EGFRs. The unaltered Erk activation by the mutant EGFRs is consistent with the absence of increased phosphorylation of Y1173, an important docking site for the Shc and Grb-2 adaptors that leads to Ras activation and subsequent Erk phosphorylation (R. N. Jorissen et al., *Exp. Cell Res.* 284, 31 (2003)). The increased Akt and STAT phosphorylation following activation of the mutant EGFRs is consistent with the increase in Y992 and Y1068 phosphorylation, both of which have been previously linked to Akt and STAT activation (R. N. Jorissen et al., *Exp. Cell Res.* 284, 31 (2003)). Thus, the selective EGF-induced autophosphorylation of C-terminal tyrosine residues within EGFR mutants is well correlated with the selective activation of downstream signaling pathways.

To extend these observations to lung cancer cells in which EGFR mutations appear to drive tumorigenesis, we studied lines derived from five NSCL tumors. NCI-H1975 carries the recurrent heterozygous missense mutation L858R and NCI-H1650 has the in-frame deletion delE746-A750, whereas NCI-358, NCI-H1666, and NCI-H1734 express wild-type EGFR. As in transfected cells, EGF-induced autophosphorylation of Y992 and Y1068 was markedly elevated in the two lines with endogenous EGFR mutations, as was phosphorylation of Akt and STAT5, but not Erk.

The oncogenic activity of EGFR reflects the activation of signals that promote both cell proliferation and cell survival (S. Grant, L. Qiao, P. Dent, *Front. Biosci.* 7, d376 (2002)). While these pathways exhibit overlap, Ras-mediated activation of the Erk kinases contributes substantially to the proliferative activity of EGFR, whereas activation of Akt and STATs is largely linked to an anti-apoptotic function (S. Grant, L. Qiao, P. Dent, *Front. Biosci.* 7, d376 (2002), F. Chang et al., *Leukemia* 17, 1263 (2003), F. Chang et al., *Leukemia* 17, 590 (2003), F. Chang et al., *Int. J. Oncol.* 22, 469 (2003), V. Calo et al., *J. Cell Physiol.* 197, 157 (2003), T. J. Ahonen et al., *J. Biol. Chem.* 278, 27287 (2003)). The two lung cancer cell lines harboring EGFR mutations exhibited a proliferative response to EGF at low serum concentrations that was not observed in cells with wild-type receptors. However, their proliferation rate and cell density at confluence were comparable at normal serum concentrations.

SiRNA

In contrast, apoptotic pathways were markedly different in lung cancer cells with mutant EGFRs: siRNA-mediated specific inactivation of mutant EGFR in these cell lines resulted in rapid and massive apoptosis. About 90% of NCI-H1975 cells transfected with L858R-specific siRNA died within 96 hours, as did NCI-H1650 cells transfected with delE746-A750-specific siRNA. SiRNA specific for either EGFR mutation had no effect on cells expressing the alternative mutation, and siRNA that targets both wild-type and mutant EGFR had minimal effect on the viability of cells expressing only wild-type receptor, but induced rapid cell death in lines expressing EGFR mutants. The ability of siRNAs to specifically target the corresponding EGFR alleles was confirmed in transfected COST cells by immunoblotting. Thus, expression of mutant EGFRs appears essential for suppression of pro-apoptotic signals in lung cancers harboring these mutations. The fact that lung cancer cells expressing only wild-type receptors do not display a similar dependence on EGFR expression may also account for the relative Gefitinib-insensitivity of human tumors that overexpress wild-type EGFR.

The effectiveness of Gefitinib in lung cancers harboring mutant EGFRs may reflect both its inhibition of critical anti-apoptotic pathways on which these cells have become strictly dependent, as well as altered biochemical properties of the mutant receptors. We previously reported that mutant EGFRs are more sensitive to Gefitinib inhibition of EGF-dependent autophosphorylation than wild-type receptors (T. J. Lynch et al., *N. Engl. J. Med.* 350, 2129 (2004)). This increased drug sensitivity by mutant receptors was also observed for both Erk and STAT5 activation. Thus, while EGF-induced signaling by mutant receptors demonstrates selective activation of downstream effectors via differential autophosphorylation events, their enhanced inhibition by Gefitinib is uniform, and may reflect altered drug binding to the mutant ATP pocket.

To establish the relevance of increased Akt and STAT signaling in EGFR-mediated NSCLC survival, we targeted these pathways with specific pharmacological inhibitors. Lung cancer cells harboring EGFR mutations were 100-fold more sensitive to Gefitinib than cells with wild-type receptor. Cells expressing mutant EGFRs were also more sensitive to pharmacological inhibition of Akt or STAT signaling than cells expressing only wild-type EGFR. While EGFR-mutant lung cancer cells exhibited increased sensitivity to disruption of Akt/STAT-mediated anti-apoptotic signals, they demonstrated markedly increased resistance to cell death signals induced by the commonly used chemotherapeutic agents doxorubicin and cisplatin, and the pro-apoptotic Fas-ligand.

Enhanced Akt/STAT signaling in cells with mutant EGFR might therefore provide an additional therapeutic target, while raising the possibility that conventional chemotherapy may be less effective against these tumors.

"Oncogene addiction" has been proposed to explain the apoptosis of cancer cells following suppression of a proliferative signal on which they have become dependent (I. B. Weinstein, *Science* 297, 63 (2002)). Interestingly, Imatinib (Gleevec) efficiently triggers cell death in chronic myeloid leukemias expressing the BCR-ABL translocation product and in gastrointestinal stromal tumors expressing activating c-Kit mutations, both of which exhibit frequently constitutive STAT activation that is effectively inhibited by the drug (T. Kindler et al., *Leukemia* 17, 999 (2003), G. P. Paner et al., *Anticancer Res.* 23, 2253 (2003)). Similarly, in lung cancer cells with EGFR kinase mutations, Gefitinib-responsiveness may result in large part from its effective inhibition of essential anti-apoptotic signals transduced by the mutant receptor.

Materials and Methods

Immunoblotting

Lysates from cultured cells were prepared in ice-cold RIPA lysis solution (1% Triton X-100, 0.1% SDS, 50 mM Tris-Hcl, pH 7.4, 150 mM NaCl, 1 mM EDTA, 1 mM EGTA, 10 mM β-glycerol-phosphate, 10 mM NaF, 1 mM Na-orthovanadate, containing protease inhibitors. Debris was removed by centrifugation in a microfuge at 12,000×g for 10 min at 4° C. Clarified lysates were boiled in gel loading buffer and separated by 10% SDS-PAGE. Proteins were electrotransferred to nitrocellulose and detected with specific antibodies followed by incubation with horseradish peroxidase-conjugated secondary goat antibody (Cell signaling (Beverly, Mass.; 1:2000) and development with enhanced chemiluminescence (DuPont NEN) followed by autoradiography. The phospho-EGFR Y845, Y992, Y1045, Y1068, phospho-STAT5 (tyr694), phospho-AKT (Ser473), phospho-ERK1/2(Thr202/Tyr204), AKT, STAT5, and ERK1/2 antibodies were obtained from New England Biolabs (Beverly, Mass.). The total EGFR Ab-20 antibody was obtained from NeoMarkers (Fremont, Calif.). The phospho-EGFR Y1173 antibody was from Upstate Biotechnology (Lake Placid, N.Y.) and the total phosphotyrosine antibody PY-20 was from Transduction Laboratories (Lexington, Ky.). All antibodies were used at a 1:1000 dilution.

EGFR Expression Vectors

Full-length EGFR expression constructs encoding the wild type, L858 or del L747-P753insS mutations were sub-cloned using standard methods into plasmid pUSEamp. All constructs were confirmed by DNA sequence analysis.

Cell Lines and Transfections

COS7 cells and NMuMg (normal mouse mammary epithelial) cells were grown in DMEM (Dulbecco's modified Eagle's media) with 10% fetal calf serum in the presence of 2 mM L-glutamine and 50 U/ml penicillin/streptomycin. The NCI-H358, NCI-H1650, NCI-H1734, NCI-H1666, and NCI-H1975 human lung cancer cell lines were obtained from the American Type Culture Collection collection and were grown in RPMI1640 with 10% fetal bovine serum, 2 mM L-glutamine, 50 U/ml penicillin/streptomycin and 1 mM sodium pyruvate. They are referred to in the text, in an abbreviated manner, as H358, H1650, H1734, H1666, and H1975, respectively. Transient transfection of COS7 cells was performed using Lipofectamine 2000 (Invitrogen; Carlsbad, Calif.). Plasmid (1 µg) was transfected into cells at 80% confluence on a 10 cm dish. After 12 hours, the cells were harvested and reseeded in 12-well plates in the absence of serum. The following day, cells were stimulated with 30 ng/ml of EGF. Stable NMuMg cell lines were prepared by co-transfecting the EGFR expression constructs with the drug-selectable plasmid pBABE puro, followed by selection in 3 ug/ml puromycin. Pools of drug-resistant cells were used for analysis. Expression of EGFR in stably transfected cells was confirmed by immunoblotting.

SiRNA-Mediated "Knockdown" of EGFR Expression

SiRNA for EGFR L858R was designed to target the nucleotide sequence CACAGATTTTGGGCGGGCCAA (SEQ ID NO.: 688), while the GCTATCAAAACATCTC-CGAAA (SEQ ID NO.: 689) sequence was used for the delE745-A750 (Qiagen; Valencia, Calif.). To target all forms of EGFR, commercially prepared siRNA corresponding to human wild-type EGFR was obtained from Dharmacon (Lafayette, Colo.). Transfection of siRNAs was performed with Lipofectamine 2000 (Invitrogen) as per the manufacturer's instructions. Cells were assayed for viability after 96 hours using the MTT assay.

Apoptosis Assay 10,000 cells were seeded into individual wells of a 96-well plate. After 6 hours, the medium was changed and the cells were maintained in the presence of increasing concentrations of doxorubicin (Sigma; St. Louis, Mo.), cisplatin (Sigma), Fas-ligand (human activating, clone CH11; Upstate Biotechnology), Ly294002 (Sigma), or AG490 (Calbiochem; La Jolla, Calif.). After 96 hours, the viability of cells was determined using the MTT assay. For caspase immunostaining, 10,000 cells were seeded onto 10 mm coverslips. The next day they were transfected with siRNA (see previous section for details). After 72 hours the cells were fixed in 4% paraformaldehyde at room temperature for 10 min. They were subsequently permeabilized for 5 min in 0.5% Triton X-100 and blocked for 1 hr in 5% normal goat serum (NGS). The coverslips were then incubated overnight at 4° C. in primary antibody (cleaved caspase-3 Asp175 5A1 from Cell Signaling) at a 1:100 dilution. The next day the coverslips were washed 3 times in PBS and incubated for 1 hour with secondary antibody (goat anti-rabbit Texas-red conjugated; from Jackson Immunoresearch; West Grove, Pa.) at a 1:250 dilution in 5% normal goat serum and 0.5 µg/ml of DAPI (4',6-Diamidino-2-phenylindole). After 3 washes in PBS the coverslips were mounted with ProLong Gold anti-fade reagent from Molecular Probes (Eugene, Oreg.).

Cell Viability Assay

10 µl of 5 mg/ml MTT (Thiazolyl blue; Sigma) solution was added to each well of a 96-well plate. After 2 hours of incubation at 37° C., the medium was removed and the MTT was solubilized by the addition of 100 µl of acidic isopropanol (0.1N HCL) to each well. The absorbance was determined spectophotometrically at 570 nm.

Growth Curve

Growth curves for H-358, H-1650, H-1734, and H-1975 cells were obtained by seeding 1000 cells in individual wells of 96-well plates. Each cell line was plated in 8 separate wells. On consecutive days, the cells were fixed in 4% formaldehyde and stained with 0.1% (w/v) crystal violet solution. The crystal violet was then solubilized in 100 µl of 10% acetic acid, and the absorbance was measured at 570 nm using a plate reader to determine the relative cell number.

Mutation Identification

To identify sporadic NSCLC cell lines harboring mutations within EGFR, we sequenced exons 19 and 21 within a panel of 15 NSCLC cell-lines, as described above. Cell lines were selected for analysis based on their derivation from tumors of bronchoalveolar histology irrespective of smoking history (NCI-H358, NCI-H650, NCI-H1650), or from adenocarcinomas arising within non-smokers (NCI-H1435, NCI-H1563, NCI-H1651, NCI-H1734, NCI-H1793, NCI-H1975, NCI-H2291, NCI-H2342, NCI-H2030, NCI-H1838, NCI-H2347, NCI-H2023). NCI-H1666 has been reported to harbor only wild type EGFR (see examples above). All cell lines are available from the American Type Culture Collection.

The references cited herein and throughout the specification are incorporated herein by reference in their entirety.

REFERENCES

1. Schiller J H, Harrington D, Belani C P, et al. Comparison of four chemotherapy regimens for advanced non-small cell lung cancer. N Engl J Med 2002; 346:92-98.
2. Druker B J, Talpaz M, Resta D J et al. Efficacy and safety of a specific inhibitor of the BCR-ABL tyrosine kinase in Chronic Myeloid Leukemia. N Engl J Med 2001; 344: 1031-1037.
3. Arteaga C L. ErbB-targeted therapeutic approaches in human cancer. Exp Cell Res. 2003; 284:122-30.
4. Jorissen R N, Walker F, Pouliot N, Garrett T P, Ward C W, Burgess A W. Epidermal growth factor receptor: mechanisms of activation and signaling. Exp Cell Res 2003; 284:31-53
5. Luetteke N C, Phillips H K, Qui T H, Copeland N G, Earp H S, Jenkins N A, Lee D C. The mouse waved-2 phenotype results from a point mutation in the EGF receptor tyrosine kinase. Genes Dev 1994; 8:399-413.
6. Nicholson R I, Gee J M W, Harper M E. EGFR and cancer prognosis. Eur J Cancer. 2001; 37:S9-15
7. Wong A J, Ruppert J M, Bigner S H, et al. Structural alterations of the epidermal growth factor receptor gene in human gliomas. Proc Natl Acad Sci. 1992; 89:2965-2969.
8. Ciesielski M J, Genstermaker R A. Oncogenic epidermal growth factor receptor mutants with tandem duplication: gene structure and effects on receptor function. Oncogene 2000; 19:810-820.
9. Frederick L, Wang W-Y, Eley G, James C D. Diversity and frequency of epidermal growth factor receptor mutations in human glioblastomas. Cancer Res 2000; 60:1383-1387.
10. Huang H-J S, Nagane M. Klingbeil C K, et al. The enhanced tumorigenic activity of a mutant epidermal growth factor receptor common in human cancers is mediated by threshold levels of constitutive tyrosine phophorylation and unattenuated signaling. J Biol Chem 1997; 272:2927-2935
11. Pegram M D, Konecny G, Slamon D J. The molecular and cellular biology of HER2/neu gene amplification/overexpression and the clinical development of herceptin (trastuzumab) therapy for breast cancer. Cancer Treat Res 2000; 103:57-75.
12. Ciardiello F, Tortora G. A novel approach in the treatment of cancer targeting the epidermal growth factor receptor. Clin Cancer Res. 2001; 7:2958-2970
13. Wakeling A E, Guy S P, Woodburn J R et al. ZD1839 (Iressa): An orally active inhibitor of Epidermal Growth Factor signaling with potential for cancer therapy. Cancer Res 2002; 62:5749-5754.
14. Moulder S L, Yakes F M, Muthuswamy S K, Bianco R, Simpson J F, Arteaga C L. Epidermal growth factor receptor (HER1) tyrosine kinase inhibitor ZD1839 (Iressa) inhibits HER2/neu (erbB2)-overexpressing breast cancer cells in vitro and in vivo. Cancer Res 2001; 61:8887-8895.
15. Moasser M M, Basso A, Averbuch S D, Rosen N. The tyrosine kinase inhibitor ZD1839 ("Iressa") inhibits HER2-driven signaling and suppresses the growth of HER-2 overexpressing tumor cells. Cancer Res 2001; 61:7184-7188.
16. Ranson M, Hammond L A, Ferry D, et al. ZD1839, a selective oral epidermal growth factor receptor-tyrosine kinase inhibitor, is well tolerated and active in patients with solid, malignant tumors: results of a phase I trial. J Clin Oncol. 2002; 20: 2240-2250.
17. Herbst R S, Maddox A-M, Rothernberg M L, et al. Selective oral epidermal growth factor receptor tyrosine kinase inhibitor ZD1839 is generally well tolerated and has activity in non-small cell lung cancer and other solid tumors: results of a phase I trial. J Clin Oncol. 2002; 20:3815-3825.
18. Baselga J, Rischin J B, Ranson M, et al. Phase I safety, pharmacokinetic and pharmacodynamic trial of ZD1839, a selective oral Epidermal Growth Factor Receptor tyrosine kinase inhibitor, in patients with five selected solid tumor types. J Clin Onc 2002; 20:4292-4302.
19. Albanell J, Rojo F, Averbuch S, et al. Pharmacodynamic studies of the epidermal growth factor receptor inhibitor ZD1839 in skin from cancer patients: histopathologic and molecular consequences of receptor inhibition. J Clin Oncol. 2001; 20:110-124.
20. Kris M G, Natale R B, Herbst R S, et al. Efficacy of Gefitinib, an inhibitor of the epidermal growth factor receptor tyrosine kinase, in symptomatic patients with non-small cell lung cancer: A randomized trial. JAMA 2003; 290:2149-2158.
21. Fukuoka M, Yano S, Giaccone G, et al. Multi-institutional randomized phase II trial of gefitinib for previously treated patients with advanced non-small-cell lung cancer. J Clin Oncol 2003; 21:2237-2246.
22. Giaccone G, Herbst R S, Manegold C, et al. Gefitinib in combination with gemcitabine and cisplatin in advanced non-small-cell lung cancer: A phase III trial-INTACT 1. J Clin Oncol 2004; 22:777-784.
23. Herbst R S, Giaccone G, Schiller J H, et al. Gefitinib in combination with paclitaxel and carboplatin in advanced non-small-cell lung cancer: A phase III trial—INTACT 2. J Clin Oncol 2004; 22:785-794.
24. Rich J N, Reardon D A, Peery T, et al. Phase II Trial of Gefitinib in recurrent glioblastoma. J Clin Oncol 2004; 22:133-142
25. Cohen M H, Williams G A, Sridhara R, et al. United States Food and Drug Administration Drug Approval Summary: Gefitinib (ZD1839; Iressa) Tablets. Clin Cancer Res. 2004; 10:1212-1218.
26. Cappuzzo F, Gregorc V, Rossi E, et al. Gefitinib in pretreated non-small-cell lung cancer (NSCLC): Analysis of efficacy and correlation with HER2 and epidermal growth factor receptor expression in locally advanced or Metastatic NSCLC. J Clin Oncol. 2003; 21:2658-2663.
27. Fitch K R, McGowan K A, van Raamsdonk C D, et al. Genetics of Dark Skin in mice. Genes & Dev 2003; 17:214-228.
28. Nielsen U B, Cardone M H, Sinskey A J, MacBeath G, Sorger P K. Profiling receptor tyrosine kinase activation by using Ab microarrays. Proc Natl Acad Sci USA 2003; 100:9330-5.
29. Burgess A W, Cho H, Eigenbrot C, et al. An open-and-shut case? Recent insights into the activation of EGF/ErbB receptors. Mol Cell 2003; 12:541-552.
30. Stamos J, Sliwkowski M X, Eigenbrot C. Structure of the epidermal growth factor receptor kinase domain alone and in complex with a 4-anilinoquinazoline inhibitor. J Biol Chem. 2002; 277:46265-46272.
31. Lorenzato A, Olivero M, Patrane S, et al. Novel somatic mutations of the MET oncogene in human carcinoma metastases activating cell motility and invasion. Cancer Res 2002; 62:7025-30.
32. Davies H, Bignell G R, Cox C, et al. Mutations of the BRAF gene in human cancer. Nature 2002; 417:906-7.
33. Bardelli A, Parsons D W, Silliman N, et al. Mutational analysis of the tyrosine kinome in colorectal cancers. Science 2003; 300:949.
34. Daley G Q, Van Etten R A, Baltimore D. Induction of chronic myelogenous leukemia in mice by the P210bcr/abl gene of the Philadelphia chromosome. Science 1990; 247:824-30.
35. Heinrich, M C, Corless C L, Demetri G D, et al. Kinase mutations and imatinib response in patients with metastatic gastrointestinal stromal tumor. J Clin Oncol 2003; 21:4342-4349.
36. Li B, Chang C, Yuan M, McKenna W G, Shu H G. Resistance to small molecule inhibitors of epidermal growth factor receptor in malignant gliomas. Cancer Res 2003; 63:7443-7450.
37. C. L. Sawyers, Genes Dev 17, 2998-3010 (2003).
38. G. D. Demetri et al., N Engl J Med 347, 472-80 (2002).
39. B. J. Druker et al., N Engl J Med 344, 1038-42. (2001).
40. D. J. Slamon et al., N Engl J Med 344, 783-92 (2001).
41. H. Davies et al., Nature 417, 949-54 (2002).
42. Bardelli et al., Science 300, 949 (2003).
43. Y. Samuels et al., Science (2004).
44. Jemal et al., CA Cancer J Clin 54, 8-29 (2004).
45. S. Breathnach et al., J Clin Oncol 19, 1734-1742 (2001).
46. V. Rusch et al., Cancer Res 53, 2379-85 (1993).
47. R. Bailey et al., Lung Cancer 41 S2, 71 (2003).
48. M. Fukuoka et al., J Clin Oncol 21, 2237-46 (2003).
49. P. A. Janne et al., Lung Cancer 44, 221-230 (2004).
50. M. G. Kris et al., Jama 290, 2149-58 (2003).
51. V. A. Miller et al., J Clin Oncol 22, 1103-9 (2004).
52. M. Huse, J. Kuriyan, Cell 109, 275-82 (2002).
53. K. Naoki, T. H. Chen, W. G. Richards, D. J. Sugarbaker, M. Meyerson, Cancer Res 62, 7001-3 (2002).
54. J. Stamos, M. X. Sliwkowski, C. Eigenbrot, J Biol Chem 277, 46265-72 (2002).
55. T. Fujishita et al., Oncology 64, 399-406 (2003).
56. M. Ono et al., Mol Cancer Ther 3, 465-472 (2004).
57. M. C. Heinrich et al., J Clin Oncol 21, 4342-9 (2003).
58. G. Giaccone et al., J Clin Oncol 22, 777-84 (2004).
59. R. S. Herbst et al., J Clin Oncol 22, 785-94 (2004).
60. H. Yamazaki et al., Mol Cell Biol 8, 1816-20 (1988).
61. M. E. Gorre et al., Science 293, 876-80 (2001).
62. Marchetti A, Martella C, Felicioni L, et al: EGFR mutations in non-small-cell lung cancer: analysis of a large series of cases and development of a rapid and sensitive method for diagnostic screening with potential implications on pharmacologic treatment. J Clin Oncol 23:857-65, 2005.
63. Franklin W A: Diagnosis of lung cancer: pathology of invasive and preinvasive neoplasia. Chest 117:80S-89S, 2000.
64. Paez J G, Janne P A, Lee J C, et al: EGFR mutations in lung cancer: correlation with clinical response to gefitinib therapy. Science 304:1497-500, 2004.
65. Lynch T J, Bell D W, Sordella R, et al: Activating mutations in the epidermal growth factor receptor underlying responsiveness of non-small-cell lung cancer to gefitinib. N Engl J Med 350:2129-39, 2004.
66. Pao W, Miller V, Zakowski M, et al: EGF receptor gene mutations are common in lung cancers from "never smokers" and are associated with sensitivity of tumors to gefitinib and erlotinib. Proc Natl Acad Sci USA 101: 13306-11, 2004
67. Huang S F, Liu H P, Li L H, et al: High frequency of epidermal growth factor receptor mutations with complex patterns in non-small cell lung cancers related to gefitinib responsiveness in Taiwan. Clin Cancer Res 10:8195-203, 2004.
68. Han S W, Kim T Y, Hwang P G, et al: Predictive and Prognostic Impact of Epidermal Growth Factor Receptor Mutation in Non-Small-Cell Lung Cancer Patients Treated With Gefitinib. J Clin Oncol, 2005.
69. Tokumo M, Toyooka S, Kiura K, et al: The relationship between epidermal growth factor receptor mutations and clinicopathologic features in non-small cell lung cancers. Clin Cancer Res 11:1167-73, 2005.
70. Mitsudomi T, Kosaka T, Endoh H, et al: Mutations of the Epidermal Growth Factor Receptor Gene Predict Prolonged Survival After Gefitinib Treatment in Patients with Non-Small-Cell Lung Cancer With Postoperative Recurrence. J Clin Oncol, 2005.
71. Pao W, Wang T Y, Riely G J, et al: KRAS Mutations and Primary Resistance of Lung Adenocarcinomas to Gefitinib or Erlotinib. PLoS Med 2:e17, 2005
72. Read W L, Page N C, Tierney R M, et al: The epidemiology of bronchioloalveolar carcinoma over the past two decades: analysis of the SEER database. Lung Cancer 45:137-42, 2004.
73. Sanderson Cox L, Sloan J A, Patten C A, et al: Smoking behavior of 226 patients with diagnosis of stage IIIA/IIIB non-small cell lung cancer. Psychooncology 11:472-8, 2002.
74. Radzikowska E, Glaz P, Roszkowski K: Lung cancer in women: age, smoking, histology, performance status, stage, initial treatment and survival. Population-based study of 20 561 cases. Ann Oncol 13:1087-93, 2002.
75. Tong L, Spitz M R, Fueger J J, et al: Lung carcinoma in former smokers. Cancer 78:1004-10, 1996.
76. de Perrot M, Licker M, Bouchardy C, et al: Sex differences in presentation, management, and prognosis of patients with non-small cell lung carcinoma. J Thorac Cardiovasc Surg 119:21-6, 2000
77. Capewell S, Sankaran R, Lamb D, et al: Lung cancer in lifelong non-smokers. Edinburgh Lung Cancer Group. Thorax 46:565-8, 1991
78. Gritz E R, Nisenbaum R, Elashoff R E, et al: Smoking behavior following diagnosis in patients with stage I non-small cell lung cancer. Cancer Causes Control 2:105-12, 1991
79. Sridhar K S, Raub W A, Jr.: Present and past smoking history and other predisposing factors in 100 lung cancer patients. Chest 101:19-25, 1992
80. Barbone F, Bovenzi M, Cavallieri F, et al: Cigarette smoking and histologic type of lung cancer in men. Chest 112:1474-9, 1997
81. Shigematsu H, Lin L, Takahashi T, et al: Clinical and biological features associated with epidermal growth factor receptor gene mutations in lung cancers. J Natl Cancer Inst 97:339-46, 2005
82. Kosaka T, Yatabe Y, Endoh H, et al: Mutations of the epidermal growth factor receptor gene in lung cancer: biological and clinical implications. Cancer Res 64:8919-23, 2004
83. Cho D, Kocher O, Tenen D G, et al: Unusual cases in multiple myeloma and a dramatic response in metastatic lung cancer: case 4. Mutation of the epidermal growth factor receptor in an elderly man with advanced, gefitinib-responsive, non-small-cell lung cancer. J Clin Oncol 23:235-7, 2005

TABLE 1

Characteristics of Nine Patients with Non-Small-Cell Lung Cancer and a Response to Gefitinib.

| Patient No. | Sex | Age at Beginning of Gefitinib Therapy | Pathological Type* | No. of Prior Regimens | Smoking-Status† | Duration of Therapy | Overall Survival‡ | EGFR Mutation§ | Response¶ |
|---|---|---|---|---|---|---|---|---|---|
| | | yr | | | | mo | | | |
| 1 | F | 70 | BAC | 3 | Never | 15.6 | 18.8 | Yes | Major; improved lung lesions |
| 2 | M | 66 | BAC | 0 | Never | >14.0 | >14.0 | Yes | Major; improved bilateral lung lesions |
| 3 | M | 64 | Adeno | 2 | Never | 9.6 | 12.9 | Yes | Partial; improved lung lesions and soft-tissue mass |
| 4 | F | 81 | Adeno | 1 | Former | >13.3 | >21.4 | Yes | Minor; improved pleural disease |
| 5 | F | 45 | Adeno | 2 | Never | >14.7 | >14.7 | Yes | Partial; improved liver lesions |
| 6 | M | 32 | BAC | 3 | Never | >7.8 | >7.8 | Yes | Major; improved lung lesions |
| 7 | F | 62 | Adeno | 1 | Former | >4.3 | >4.3 | Yes | Partial; improved liver and lung lesions |
| 8 | F | 58 | Adeno | 1 | Former | 11.7 | 17.9 | Yes | Partial; improved liver lesions |
| 9 | F | 42 | BAC | 2 | Never | >33.5 | >33.5 | No | Partial; improved lung nodules |

*Adenocarcinoma (Adeno) with any element of bronchoalveolar carcinoma (BAC) is listed as BAC.
†Smoking status was defined as former if the patient had not smoked any cigarettes within 12 months before entry and never if the patients had smoked less than 100 cigarettes in his or her lifetime.
‡Overall survival was measured from the beginning of gefitinib treatment to death.
§EGFR denotes the epidermal growth factor receptor gene.
¶A partial response was evaluated with the use of response evaluation criteria in solid tumors; major and minor responses were evaluated by two physicians in patients in whom the response could not be measured with the use of these criteria.

TABLE 2

Somatic Mutations in the Tyrosine Kinase Domain of EGFR in Patients with Non-Small Cell Lung Cancer

| Patient | Seq. Id. No. | Mutation | Effect of Mutation |
|---|---|---|---|
| *Patients with a response to gefitinib* | | | |
| Pateint 1 | 730 | Deletion of 15 nucleotides (2235-2249) | In-frame deletion (746-750) |
| Pateint 2 | 731 | Deletion of 12 nucleotides (2240-2251) | In-frame deletion (747-751) and insertion of a serine residue |
| Pateint 3 | 732 | Deletion of 18 nucleotides (2240-2257) | In-frame deletion (747-753) and insertion of a serine residue |
| Pateint 4 | 733 | Deletion of 18 nucleotides (2240-2257) | In-frame deletion (747-753) and insertion of a serine residue |
| Pateint 5 | 734 | Substitution of G for T at nucleotide 2573 | Amino acid substitution (L858R) |
| Pateint 6 | 735 | Substitution of G for T at nucleotide 2573 | Amino acid substitution (L858R) |
| Pateint 7 | 736 | Substitution of A for T at nucleotide 2582 | Amino acid substitution (L861Q) |
| Pateint 8 | 737 | Substitution of T for G at nucleotide 2155 | Amino acid substitution (G719C) |
| *Patients with no exposure to gefitinib** | | | |
| Patient A | 738 | Deletion of 18 nucleotides (2240-2257) | In frame deletion (747-753) and insertion of a serine residue |
| Patient B | 739 | Deletion of nucleotides (2253-2249) | In frame deletion (746-750) |

*Among the 25 patients with no exposure to gefitinib (15 with bronchoalveolar cancer, 7 with adenocarcinoma, and 3 with large-cell carcinoma), 2 (Patients A and B)-both of whom had bronchoalveolar cancer-had EGFR mutations. No mutations were found in 14 lung-cancer cell lines representing diverse histologic types: non-small-cell lung cancer (6 specimens), small-cell-lung cancer (6 specimens), bronchus carcinoid (3 specimen), and an unknown type (1 specimen). Polymorphic variants identified within EGFR included the following: the substitution of A for G at nucleotide 1562, the substitution for A for T at nucleotide 1887, and a germ-line variant of unknown functional significance, the substitution of A for G at nucleotide 2885, within the tyrosine kinase domain.

TABLE 4

Population Characteristics Among 100 Patients Tested for EGFR Mutations as Part of NSCLC Care

| Characteristic | Frequency |
|---|---|
| Mean age, years (standard deviation) | 60.7 (11.0) |
| Female | 63 |
| Race | |
| White | 76 |
| Asian | 7 |
| Other | 5 |
| Unknown | 12 |
| Stage at Time of Test | |
| I | 15 |
| II | 4 |
| III | 10 |
| IV | 67 |
| Unknown | 4 |
| Histology | |
| Pure BAC | 1 |
| Adenocarcinoma with BAC Features | 24 |
| Adenocarcinoma | 69 |
| NSCLC, all other subtypes | 6 |
| Smoking Status | |
| Current | 17 |
| Former | 48 |
| Never | 29 |
| Unknown | 6 |
| Mean amount smoked by current and former smokers, pack-years (standard deviation) | 39.0 (32.3) |
| Mean time from diagnosis to EGFR test, months (standard deviation) | 18.7 (78.4) |
| Prior Chemotherapy Treatment | 47 |
| Prior EGFR Targeted Treatment | 11 |

BAC = Bronchioloalveolar Carcinoma,
EGFR = Epidermal Growth Factor Receptor

TABLE 5

Epidermal Growth Factor Receptor Somatic Gene Mutations Identified

| Patient | Gender | Histology | Pack-Years Smoked | Exon | Nucleotide Change | Amino Acid Change | Seq. Id. No. |
|---|---|---|---|---|---|---|---|
| 1 | F | Adeno | 0 | 18 | 2126A>T | E709V | 740 |
|   |   |       |   | 18 | 2155G>A | G719S |     |
| 2 | F | A + BAC | 60 | 18 | 2156G>C | G719A | 741 |
|   |   |       |    | 20 | 2327G>A | R776H |     |
| 3 | F | A + BAC | 0 | 19 | 2235_2249 del | K745_A750 del ins K | 742 |
| 4 | M | A + BAC | 0 | 19 | 2235_2249 del | K745_A750 del ins K | 743 |

TABLE 5-continued

Epidermal Growth Factor Receptor Somatic Gene Mutations Identified

| Patient | Gender | Histology | Pack-Years Smoked | Exon | Nucleotide Change | Amino Acid Change | Seq. Id. No. |
|---|---|---|---|---|---|---|---|
| 5 | F | Adeno | 5 | 19 | 2235_2249 del | K745_A750 del ins K | 744 |
| 6 | M | Adeno | Unknown | 19 | 2235_2249 del | K745_A750 del ins K | 745 |
| 7 | F | Adeno | 0 | 19 | 2236_2250 del | E746_A750 del | 746 |
| 8 | M | Adeno | 45 | 19 | 2236_2250 del | E746_A750 del | 747 |
| 9 | F | Adeno | Unknown | 19 | 2236_2250 del | E746_A750 del | 748 |
| 10 | M | A + BAC | 12 | 19 | 2237_2255 del ins T | E746_S752 del ins V | 749 |
| 11 | M | Adeno | 1 | 19 | 2239_2248 del ins C | L747_A750 del ins P | 750 |
| 12 | M | A + BAC | 0 | 19 | 2239_2251 del ins C | L747_T751 del ins P | 751 |
| 13 | F | Adeno | 30 | 19 | 2253_2276 del | T751_I759 del ins T | 752 |
| 14 | F | Adeno | 0 | 19 | 2254_2277 del | S752_I759 del | 753 |
| 15 | F | Adeno | 0 | 20 | 2303_2311 dup | D770_N771 ins SVD | 754 |
| 16 | M | Adeno | 5 | 20 | 2313_2318 dup CCCCCA | P772_H773 dup | 755 |
| 17 | F | Adeno | 0 | 21 | 2543C>T | P848L* | 756 |
| 18 | M | BAC | 0 | 21 | 2573T>G | L858R | 757 |
| 19 | F | A + BAC | 0 | 21 | 2573T>G | L858R | 758 |
| 20 | M | A + BAC | 1 | 21 | 2573T>G | L858R | 759 |
| 21 | F | Adeno | 0 | 21 | 2573T>G | L858R | 760 |
| 22 | F | Adeno | 15 | 21 | 2573T>G | L858R | 761 |
| 23 | F | Adeno | 0 | 21 | 2582T>A | L861Q | 762 |

Adeno = Adenocarcinoma, Adeno + BAC = Adenocarcinoma with Bronchioloalveolar Carcinoma Features, BAC = Pure Bronchioloalveolar Carcinoma
* This mutation was identified as a germline variant

TABLE S1A

Primers for amplification of selected EGFR and receptor tyrosine kinase exons (SEQ ID NOS: 1-212)

| Gene | RefSeq | Exon | SEQ ID NO | F Nested | R Nested |
|---|---|---|---|---|---|
| ALK | NM_004304 | 24 | 1, 2 | GGAAATATAGGGAAGGGAAGGAA | TTGACAGGGTACCAGGAGATGA |
| ALK | NM_004304 | 25 | 3, 4 | CTGAACCGCCAAGGACTCAT | TTTTCCCTCCCTACTAACACACG |
| AXL | NM_021913 | 19 | 5, 6 | ACTGATGCCCTGACCCTGTT | CCCATGGTTCCCCACTCTT |
| CSF1R | NM_005211 | 18 | 7, 8 | AGGGACTCCAAAGCCATGTG | CTCTCTGGGGCCATCCACT |
| CSF1R | NM_005211 | 19 | 9, 10 | CATTGTCAAGGGCAATGTAAGTG | CTCTCACCAACCCTCGCTGT |
| DDR1 | NM_013994 | 15 | 11, 12 | ACATGGGGAGCCAGAGTGAC | TGCAACCCAGAGAAAGTGTG |
| DDR2 | NM_006182 | 16 | 13, 14 | TGAGCTTTCAACCCTAGTTTGTTG | GTTTGCCTCCTGCTGTCTCA |
| DKFZp761P1010 | NM_018423 | 8 | 15, 16 | TGTCCTTGTGTTTTTGAAGATTCC | TGCAGACAGATGACAAACATGAA |
| EGFR | NM_005228 | 2 | 17, 18 | TGGGTGAGTCTCTGTGTGGAG | CATTGCCATAGCAAAAATAAACACA |
| EGFR | NM_005228 | 3 | 19, 20 | GGTTCAACTGGGCGTCCTA | CCTTCTCCGAGGTGGAATTG |
| EGFR | NM_005228 | 4 | 21, 22 | CGCACCATGGCATCTCTTTA | AAAACGATCTCTATGTCCGTGGT |
| EGFR | NM_005228 | 5 | 23, 24 | CAGCCAGCCAAACAATCAGA | TCTTTGGAGTCTTCAGAGGGAAA |
| EGFR | NM_005228 | 6 | 25, 26 | TGTGGTTTCGTTGGAAGCAA | AATTGACAGCTCCCCCACAG |
| EGFR | NM_005228 | 7 | 27, 28 | GGCTTTCTGACGGGAGTCAA | CCACCCAAAGACTCTCCAAGA |
| EGFR | NM_005228 | 8 | 29, 30 | CCTTTCCATCACCCCTCAAG | AGTGCCTTCCCATTGCCTAA |
| EGFR | NM_005228 | 9 | 31, 32 | ACCGGAATTCCTTCCTGCTT | CACTGAAACAAACAACAGGGTGA |
| EGFR | NM_005228 | 10 | 33, 34 | AGGGGGTGAGTCACAGGTTC | TCAGAAGAAATGTTTTTATTCCAAGG |
| EGFR | NM_005228 | 11 | 35, 36 | GCAAATCCAATTTTCCCACTT | GCAGGAGCTCTGTGCCCTAT |
| EGFR | NM_005228 | 12 | 37, 38 | TCCCACAGCATGACCTACCA | TTTGCTTCTTAAGGAACTGAAAA |
| EGFR | NM_005228 | 13 | 39, 40 | TGTCACCCAAGGTCATGGAG | CAAAAGCCAAGGGCAAAGAA |
| EGFR | NM_005228 | 14 | 41, 42 | GGAGTCCCAACTCCTTGACC | GTCCTGCCCACACAGGATG |

TABLE S1A-continued

Primers for amplification of selected EGFR and receptor tyrosine kinase exons
(SEQ ID NOS: 1-212)

| Gene | RefSeq | Exon | SEQ ID NO | F Nested | R Nested |
|---|---|---|---|---|---|
| EGFR | NM_005228 | 15 | 43, 44 | GCTTTCCCCACTCACACACA | CAAACCTCGGCAATTTGTTG |
| EGFR | NM_005228 | 16 | 45, 46 | CCACCAATCCAACATCCAGA | TGGCCCAGAGCCATAGAAAC |
| EGFR | NM_005228 | 17 | 47, 48 | TTCCAAGATCATTCTACAAGATGTCA | GCACATTCAGAGATTCTTTCTGC |
| EGFR | NM_005228 | 18 | 49, 50 | TCCAAATGAGCTGGCAAGTG | TCCCAAACACTCAGTGAAACAAA |
| EGFR | NM_005228 | 19 | 51, 52 | GTGCATCGCTGGTAACATCC | TGTGGAGATGAGCAGGGTCT |
| EGFR | NM_005228 | 20 | 53, 54 | ATCGCATTCATGCGTCTTCA | ATCCCCATGGCAAACTCTTG |
| EGFR | NM_005228 | 21 | 55, 56 | GCTCAGAGCCTGGCATGAA | CATCCTCCCCTGCATGTGT |
| EGFR | NM_005228 | 22 | 57, 58 | TGGCTCGTCTGTGTGTCA | CGAAAGAAAATACTTGCATGTCAGA |
| EGFR | NM_005228 | 23 | 59, 60 | TGAAGCAAATTGCCCAAGAC | TGACATTTCTCCAGGGATGC |
| EGFR | NM_005228 | 24 | 61, 62 | AAGTGTCGCATCACCAATGC | ATGCGATCTGGGACACAGG |
| EGFR | NM_005228 | 25 | 63, 64 | GGCACCTGCTGGCAATAGAC | TGACTTCATATCCATGTGAGTTTCACT |
| EGFR | NM_005228 | 26 | 65, 66 | TATACCCTCCATGAGGCACA | GGGAAAAACCCACACAGGAA |
| EGFR | NM_005228 | 27 | 67, 68 | TCAGAACCAGCATCTCAAGGA | GATGCTGGAGGGAGCACCT |
| EGFR | NM_005228 | 28_1 | 69, 70 | CCTTGTTGAGGACATTCACAGG | ATGTGCCCGAGGTGGAAGTA |
| EPHA1 | NM_005232 | 14 | 71, 72 | GGAGGGCAGAGGACTAGCTG | GTGCCTGGCCAAGTCTTTGT |
| EPHA1 | NM_005232 | 15 | 73, 74 | CTGCAGCCTAGCAACAGAGC | AAGAACCAGAGGAGCCAGGA |
| EPHA2 | NM_004431 | 13 | 75, 76 | CGGGTAAGGATGTGGGTTGT | CAGGTGTTCTGCCTCCTGAA |
| EPHA2 | NM_004431 | 14 | 77, 78 | GCTTCAGGAGGCAGAACACC | GGAGCAAGCCTAAGAAGGTTCA |
| EPHA3 | NM_005233 | 10 | 79, 80 | GCCTTGTATCCATTTGCCACA | TGACAACACGTTTTGGGTCAT |
| EPHA3 | NM_005233 | 11 | 81, 82 | TGCATATTCCATTTCAGAACAGA | AAACAGTTTCATTGCTGCTAAAT |
| EPHA4 | NM_004438 | 13 | 83, 84 | CCGGATACAGATACCCAAAAGA | GGAGGCTTCAAGGGATGAGA |
| EPHA4 | NM_004438 | 14 | 85, 86 | GCTGTTGTCCTGCTTGGCTA | TGGTTGTAATGTTGAACTAGCTTGC |
| EPHA7 | NM_004440 | 13 | 87, 88 | TGGCTGTCAGCTAAATAAGCATGT | TCAATTTGCTTCATTTCTCCTGTT |
| EPHA7 | NM_004440 | 14 | 89, 90 | TGCTGCTGAACTACCAACCAA | TGTGGTAGTAATTGTGGAAAACTG |
| EPHA8 | NM_020526 | 13 | 91, 92 | CAAAGCACCGTCTCAACTCG | CCCGAAACTGCCAACTTCAT |
| EPHA8 | NM_020526 | 14 | 93, 94 | GGAAAACAGGACCCCAGTGT | CCCTCCTCCACAGAGCTGAT |
| EPHB1 | NM_004441 | 7 | 95, 96 | GACAGAAGCTGACAAGCAGCA | AGGTTCCATTCCCTCCCAGT |
| EPHB1 | NM_004441 | 8 | 97, 98 | TGGGAGTGAGAGTTTGGAAGAA | TATGAGGCCGTGAGCTGAAA |
| EPHB2 | NM_017449 | 11 | 99, 100 | AGGGCCCTGCTCTGGTTT | CCAATTGGGCGTTAGTGAAA |
| EPHB2 | NM_017449 | 12 | 101, | CTCATGAGATTGGGGCATCA | AGGCCCATGATCTCAGAAGC |
| EPHB3 | NM_004443 | 11 | 103, | GGTTGCAGGAGAGACGAGGT | AGGCCCTTCACCCTGTGAC |
| EPHB3 | NM_004443 | 12 | 105 | ATGACCCCTCCGATCCTACC | TAATCCTGCTCCACGGCATT |
| EPHB4 | NM_004444 | 14 | 107 | GGAAAAGCAGAGGCAGGTG | TGGTCTCAAGAACCCAGCAG |
| EPHB6 | NM_004445 | 16 | 109 | GACACCCTCCCCCTCTCAT | ACTATGCACCCCGGCTGAG |
| EPHB6 | NM_004445 | 17 | 111 | TGCTTGATGTAAAACCCTTGG | GCAATCCAACAGCCATGAGA |
| ERBB2 | NM_004448 | 21 | 113 | GGAGCAAACCCCTATGTCCA | TCCTCCAACTGTGTGTTGTGG |
| ERBB3 | NM_001982 | 21 | 115 | TGGGGACCACTGCTGAGAG | TGCAGCCTTCTCTCCTTGAA |
| FGFR1 | NM_000604 | 14 | 117 | GCAGAGCAGTGTGGCAGAAG | ACAGGTGGGAAGGGACTGG |

TABLE S1A-continued

Primers for amplification of selected EGFR and receptor tyrosine kinase exons
(SEQ ID NOS: 1-212)

| Gene | RefSeq | Exon | SEQ ID NO | F Nested | R Nested |
|---|---|---|---|---|---|
| FGFR1 | NM_000604 | 15 | 119 | AGTGGGGTGGGCTGAGAAC | TCTCTGGGGCAGAAAGAGGA |
| FGFR2 | NM_000141 | 14 | 121 | ACCCGGCCACACTGTATTTC | CATCCCACCCAGCTCTCAAC |
| FGFR2 | NM_000141 | 15 | 123 | AGGGCATAGCCCTATTGAGC | CCCAGGAAAAAGCCAGAGAA |
| FGFR3 | NM_000142 | 13 | 125 | CAGGTGTGGGTGGAGTAGGC | CTCAGGCGCCATCCACTT |
| FGFR3 | NM_000142 | 14 | 127 | AAGAAGACGACCAACGTGAGC | AGGAGCTCCAGGGCACAG |
| FGFR4 | NM_002011 | 14 | 129 | CCTCCTCTGTAAAGTGGGTGGA | AGAGGGCCTCAGTGCAGAGT |
| FGFR4 | NM_002011 | 15 | 131 | AGATGGGGCAGAACTGGATG | GGGTCCCAGACCAAATCTGA |
| FLT1 | NM_002019 | 23 | 133 | AGGTGCTCCCTTCACAGCAT | TTCAGGGACTACAGCTGAGGAA |
| FLT1 | NM_002019 | 24 | 135 | GCCGTATGTTATCTGGGAGGT | TGGGCCCATTACACTTTAAGA |
| FLT3 | NM_004119 | 20 | 137 | TTCCATCACCGGTACCTCCT | CCATAAATCAAAAATGCACCACA |
| FLT3 | NM_004119 | 21 | 139 | GAGTGGTCTTAGGAAGATGATGC | AAAGTCATGGGCTGCAATACAA |
| FLT4 | NM_002020 | 23 | 141 | ATGGTCCCCACTGCTTGG | AGGAGCTCACCTCACCCTGT |
| IGF1R | NM_000875 | 18 | 143 | CCTTGCGTCTCTCCACACAT | TGGCAACGGGTAACAATGAA |
| INSR | NM_000208 | 18 | 145 | GGCTGAGGTAAGCTGCTTCG | AAAAGAAGTATCTTGCCCCTTT |
| INSR | NM_000208 | 19 | 147 | AACCCCTCTTAGGGCTCTGTG | CAGGAGGATGGCAGGCTTC |
| KDR | NM_002253 | 24 | 149 | CGTAGAGAGCTTCAGGACCTGTG | TTCCGAGAAGTTTTGCCTGA |
| KIT | NM_000222 | 17 | 151 | TGTGAACATCATTCAAGGCGTA | AAAATGTGTGATATCCCTAGACAGG |
| KIT | NM_000222 | 18 | 153 | TCCACATTTCAGCAACAGCA | GGCTGCTTCCTGAGACACAGT |
| LTK | NM_002344 | 16 | 155 | TATCTACCGGTGCGGGACTT | AGGTGTAGCCTCCCCTCACA |
| MERTK | NM_006343 | 17 | 157 | AGGCTGGTGGTGTCTCTGTG | CAAGCTGCCAACCCTCAGTT |
| MET | NM_000245 | 19 | 159 | TGGATTTCAAATACTGAAGCCACT | TGGAATTGGTGGTGTTGAATTT |
| MUSK | NM_005592 | 15_1 | 161 | GGGCTTCATATGTTCTGACATGG | CAGAGGACCACGCCATAGG |
| MUSK | NM_005592 | 15_2 | 163 | CCGAGATTAGCCACCAGGA | CCTGGGAAGCAAACAACACA |
| NTRK1 | NM_002529 | 15 | 165 | AGGTCCCCAGTCTCCTCTCC | AGACCCATGCAGCCATCCTA |
| NTRK1 | NM_002529 | 16 | 167 | CGTGAACCACCGAGCTTGT | AGAGGGGCAGAAGGGGAAC |
| NTRK2 | NM_006180 | 15 | 169 | GGTGGGGGTGAGGAGCTTAG | TCGTTTAAGCCACCCAGTCA |
| NTRK2 | NM_006180 | 16 | 171 | TGCAAATAAGGAAAGCAAACA | TCCTGACATGGTCTTCCAACC |
| NTRK3 | NM_002530 | 17 | 173 | CAGCATCTTCACACACCTCTGA | GCTGGCTCTAAATCCCACCT |
| NTRK3 | NM_002530 | 18 | 175 | CTAATCCGGGAAGTTGTTGC | TTCTGTATCAGCAGCTTCTCTGTG |
| PDGFRA | NM_006206 | 18 | 177 | CAAGTGCCACCATGGATCA | GGCAGTGTACTGACCCCTTGA |
| PDGFRA | NM_006206 | 19 | 179 | GCACAAGTTATTAAGAGCCCAAGG | AGCATACTGGCCTCACACCA |
| PDGFRB | NM_002609 | 18 | 181 | GCACATGGGCAGTGTTGTATTT | GAGCCCCACACAGATTTCCT |
| PDGFRB | NM_002609 | 19 | 183 | ATGGGACGGAGAAGTGGTTG | TCCCTGTATCAGGGCTCGTC |
| PTK7 | NM_002821 | 18 | 185 | TTCCTACGCAGCACACCAAT | GCAGGCACTAAACCCTTTCC |
| PTK7 | NM_002821 | 19 | 187 | GCACGCATGTGACCAATTTC | AGCCCTGAGAGGGAGGTAGG |
| RET | NM_000323 | 15 | 189 | CACACACCACCCCTCTGCT | AAAGATTTGGGGTGAGGGCTA |
| RET | NM_000323 | 16 | 191 | CTGAAAGCTCAGGGATAGGG | CTGGCCAAGCTGCACAGA |

TABLE S1A-continued

Primers for amplification of selected EGFR and receptor tyrosine kinase exons (SEQ ID NOS: 1-212)

| Gene | RefSeq | Exon | SEQ ID NO | F Nested | R Nested |
|---|---|---|---|---|---|
| ROR1 | NM_005012 | 09_1 | 193 | TGCAGCCAACGATTTGAAAG | GGAAAGCCCCAAGTCTGAAA |
| ROR1 | NM_005012 | 09_2 | 195 | TCATCATGAGATCCCCACACT | GCATTTCCCCCTGAAGGAGT |
| ROR1 | NM_005012 | 09_3 | 197 | TGGATTCAGTAACCAGGAAGTGA | CCCATTCCACCAGGATGATT |
| ROR1 | NM_005012 | 09_4 | 199 | GTTTCCAGCTGCCCACTACC | GCTCGAAACCACATGTTCCA |
| RYK | NM_002958 | 13 | 201 | CTGGATTTGGGGTTCTCTGC | CGGGAACAGCTAGCAGATTTT |
| TEK | NM_000459 | 18 | 203 | GGGAATTTTGGAGGGGAACT | GCTTCAGTCACCACAGAGCA |
| TEK | NM_000459 | 19 | 205 | TGAGTCTACCCAGCAATCATTTG | TTCCCGAGAGCTACAGGACA |
| TIE | NM_005424 | 18 | 207 | GGTAACAAGGGTACCCACGAA | GTTTGAGGGGCTGAGTGTGG |
| TIE | NM_005424 | 19 | 209 | CCTCACCCTTAGGGCTTGTG | AGCCCAGGTCATGCCTTAGA |
| TYRO3 | NM_006293 | 18 | 211, 212 | GGGTAGCTTGGGAGCAAAGA | CCAAACCCCAGAGAGCAGAC |

TABLE S1B

Primers for amplification of selected EGFR and receptor tyrosine kinase exons (SEQ ID NOS: 213-424)

| Gene | RefSeq | Exon | SEQ ID NO | F External | R External |
|---|---|---|---|---|---|
| ALK | NM_004304 | 24 | 213, 214 | CATTTCCCCTAATCCTTTTCCA | GTGATCCCAGATTTAGGCCTTC |
| ALK | NM_004304 | 25 | 215 | GCCTCTCGTGGTTTGTTTTGTC | CCCAGGGTAGGGTCCAATAATC |
| AXL | NM_021913 | 19 | 217 | CTTCCTGGTGGAGGTGACTGAT | CAGGCATAGTGTGTGATGGTCA |
| CSF1R | NM_005211 | 18 | 219 | TCACGATACACATTCTCAGATCC | GAAGATCTCCCAGAGGAGGATG |
| CSF1R | NM_005211 | 19 | 221 | CGTAACGTGCTGTTGACCAAT | AAACGAGGGAAGAGCCAGAAG |
| DDR1 | NM_013994 | 15 | 223 | TGGGGAGCACAATAAAAGAAGA | ACTCTTGGCTCCTGGATTCTTG |
| DDR2 | NM_006182 | 16 | 225 | GGAAGTCAGTGTGCAGGGAATA | TTTTAGCAGAAATAGGCAAGCA |
| DKEZp761P1010 | NM_018423 | 8 | 227 | TGGTAATCCTAAACACAATGCAGA | CTGGGCAACACAGTGAGATCCT |
| EGFR | NM_005228 | 2 | 229 | TCACAAATTTCTTTGCTGTGTCC | CATGGAACTCCAGATTAGCCTGT |
| EGFR | NM_005228 | 3 | 231 | GATTGTTGCAGATCGTGGACAT | CGCTTAAATCTTCCCATTCCAG |
| EGFR | NM_005228 | 4 | 233 | CTCCATGGCACCATCATTAACA | CTCAGGACACAAGTGCTCTGCT |
| EGFR | NM_005228 | 5 | 235 | GCAGTTCATGGTTCATCTTCTTTT | CAAAATAGCCCACCCTGGATTA |
| EGFR | NM_005228 | 6 | 237 | CTTTCTGCATTGCCCAAGATG | CAAGGTCTCAGTGAGTGGTGGA |
| EGFR | NM_005228 | 7 | 239 | GAGAAGGGTCTTTCTGACTCTGC | CAGGTGTTTCTCCTGTGAGGTG |
| EGFR | NM_005228 | 8 | 241 | CACATTGCGGCCTAGAATGTTA | ACCCCGTCACAACCTTCAGT |
| EGFR | NM_005228 | 9 | 243 | GCCGTAGCCCCAAAGTGTACTA | TCAGCTCAAACCTGTGATTTCC |
| EGFR | NM_005228 | 10 | 245 | CTCACTCTCCATAAATGCTACGAA | GACTTAACGTGTCCCCTTTTGC |
| EGFR | NM_005228 | 11 | 247 | GCCTCTTCGGGGTAATCAGATA | GAAGTCTGTGGTTTAGCGGACA |
| EGFR | NM_005228 | 12 | 249 | ATCTTTTGCCTGGAGGAACTTT | CAGGGTAAATTCATCCCATTGA |
| EGFR | NM_005228 | 13 | 251 | CAGCAGCCAGCACAACTACTTT | TTGGCTAGATGAACCATTGATGA |
| EGFR | NM_005228 | 14 | 253 | TGAATGAAGCTCCTGTGTTTACTC | ATGTTCATCGCAGGCTAATGTG |
| EGFR | NM_005228 | 15 | 255 | AAAACAGGGAGAACTTCTAAGCAA | CATGGCAGAGTCATTCCCACT |
| EGFR | NM_005228 | 16 | 257 | CAATGCTAGAACAACGCCTGTC | TCCCTCCACTGAGGACAAAGTT |

TABLE S1B-continued

Primers for amplification of selected EGFR and receptor tyrosine kinase exons (SEQ ID NOS: 213-424)

| Gene | RefSeq | Exon | SEQ ID NO | F External | R External |
|---|---|---|---|---|---|
| EGFR | NM_005228 | 17 | 259 | GGGAGAGCTTGAGAAAGTTGGA | ATTTCCTCGGATGGATGTACCA |
| EGFR | NM_005228 | 18 | 261 | TCAGAGCCTGTGTTTCTACCAA | TGGTCTCACAGGACCACTGATT |
| EGFR | NM_005228 | 19 | 263 | AAATAATCAGTGTGATTCGTGGAG | GAGGCCAGTGCTGTCTCTAAGG |
| EGFR | NM_005228 | 20 | 265 | ACTTCACAGCCCTGCGTAAAC | ATGGGACAGGCACTGATTTGT |
| EGFR | NM_005228 | 21 | 267 | GCAGCGGGTTACATCTTCTTTC | CAGCTCTGGCTCACACTACCAG |
| EGFR | NM_005228 | 22 | 269 | CCTGAACTCCGTCAGACTGAAA | GCAGCTGGACTCGATTTCCT |
| EGFR | NM_005228 | 23 | 271 | CCTTACAGCAATCCTGTGAAACA | TGCCCAATGAGTCAAGAAGTGT |
| EGFR | NM_005228 | 24 | 273 | ATGTACAGTGCTGGCATGGTCT | CACTCACGGATGCTGCTTAGTT |
| EGFR | NM_005228 | 25 | 275 | TAAGGCACCCACATCATGTCA | TGGACCTAAAAGGCTTACAATCAA |
| EGFR | NM_005228 | 26 | 277 | GCCTTTTAGGTCCACTATGGAATG | CCAGGCGATGCTACTACTGGTC |
| EGFR | NM_005228 | 27 | 279 | TCATAGCACACCTCCCTCACTG | ACACAACAAAGAGCTTGTGCAG |
| EGFR | NM_005228 | 28_1 | 281 | CCATTACTTTGAGAAGGACAGGAA | TATTCTTGCTGGATGCGTTTCT |
| EPHA1 | NM_005232 | 14 | 283 | AGGAGGGCAGAGGACTAGCTG | GGCAATGTGAATGTGCACTG |
| EPHA1 | NM_005232 | 15 | 285 | CTTGAACCTGGGAGGTGGAG | ATCAGGGTGGGAGGAGTAAAGA |
| EPHA2 | NM_004431 | 13 | 287 | CCCACTTACCTCTCACCTGTGC | GTGAACTTCCGGTAGGAAATGG |
| EPHA2 | NM_004431 | 14 | 289 | AGGGGACCTCAAGGGAGAAG | AGATCATGCCAGTGAACTCCAG |
| EPHA3 | NM_005233 | 10 | 291 | GGACCAGGAAAGTCCTTGCTTT | GGTGGGGAACATTAAACTGAGG |
| EPHA3 | NM_005233 | 11 | 293 | GCTTCAGGTTGTTTTGTTGCAG | ACCCTTGCTTGAGGGAAATATG |
| EPHA4 | NM_004438 | 13 | 295 | CCCAGCTCCTAGGGTACAGTCT | CAGTCAGCTTCAAAATCCCTCTT |
| EPHA4 | NM_004438 | 14 | 297 | TCACTTCCCTGTGAGTAAAGAAAA | GGCCATTTAATTCTTGTCCTTGA |
| EPHA7 | NM_004440 | 13 | 299 | TGGACTTGTGCAAACTCAAACTG | TCCCAATATAGGGCAGTCATGTT |
| EPHA7 | NM_004440 | 14 | 301 | TCTCAATCAGTTGAGTTGCCTTG | AGCTGTGCAAGTGTGGAAACAT |
| EPHA8 | NM_020526 | 13 | 303 | GCTGTGAGGGTAAATGAGACCA | GTCTCCTGGTGAGTGACTGTGG |
| EPHA8 | NM_020526 | 14 | 305 | CCTTCCTTCGTCTCCACAGC | GTCCTTGTGCCAACAGTCGAG |
| EPHB1 | NM_004441 | 7 | 307 | GCTTGGCAAGGAGAAGAGAACA | GCTTGCTTTCTTGCTTGAACAAC |
| EPHB1 | NM_004441 | 8 | 309 | GCTGGTCACCTTGAGCTTCTCT | CCATGCTGGGCTCTTTGATTA |
| EPHB2 | NM_017449 | 11 | 311 | CACCACTCTGAAGTTGGCCTCT | ATGGCTCTGCACATTTGTTCC |
| EPHB2 | NM_017449 | 12 | 313 | CAGAGTGGGAAAAGGCACTTCA | CCAGAGTCCTGTGCAGACATTC |
| EPHB3 | NM_004443 | 11 | 315 | ATGGGGATTAACTGGGATGTTG | CGTAGCTCCAGACATCACTAGCA |
| EPHB3 | NM_004443 | 12 | 317 | GCAACCTGGTCTGCAAAGTCTC | ACCCAGCAGTCCAGCATGAG |
| EPHB4 | NM_004444 | 14 | 319 | GAGTTTCAGTGAGCCAAGATCG | TTACAGGCTTGAGCCACTAGGC |
| EPHB6 | NM_004445 | 16 | 321 | AAGCTTCCAGGAGACGAGGTC | GTCCCTGAAATCCCTCAAACC |
| EPHB6 | NM_004445 | 17 | 323 | TGCTCCATAAACGTGACTATTGC | GTAAGAGGGTGGGCTGGAATCT |
| ERBB2 | NM_004448 | 21 | 325 | CTTAGACCATGTCCGGGAAAAC | CACATCACTCTGGTGGGTGAAC |
| ERBB3 | NM_001982 | 21 | 327 | AAATTTCATCCCAAAACCAACC | CCAGTCCCAAGTTCTTGATCATT |
| FGFR1 | NM_000604 | 14 | 329 | ACAAGTCGGCTAGTTGCATGG | TCTCAGATGAAACCACCAGCAC |
| FGFR1 | NM_000604 | 15 | 331 | TTCATCTGAGAAGCAAGGAGTGG | CCAGGGAGAAAGCAGGACTCTA |

TABLE S1B-continued

Primers for amplification of selected EGFR and receptor tyrosine kinase exons (SEQ ID NOS: 213-424)

| Gene | RefSeq | Exon | SEQ ID NO | F External | R External |
|---|---|---|---|---|---|
| FGFR2 | NM_000141 | 14 | 333 | TTCTGGCGGTGTTTTGAAATTA | CTCAACATTGACGGCCTTTCTT |
| FGFR2 | NM_000141 | 15 | 335 | TCAGCTCTTAAACAGGGCATAGC | GAAATGCAGCAGCCACTAAAGA |
| FGFR3 | NM_000142 | 13 | 337 | CTCACCTTCAAGGACCTGGTGT | CAGGGAGGGGTAGAAACCACA |
| FGFR3 | NM_000142 | 14 | 339 | GGAGAGGTGGAGAGGCTTCAG | GAGACTCCCAGGACAGACACCT |
| FGFR4 | NM_002011 | 14 | 341 | CACTCGTTCCTCACCCTTCC | AGGACTCACACGTCACTCTGGT |
| FGFR4 | NM_002011 | 15 | 343 | GGACAATGTGATGAAGATTGCTG | ATAGCAGGATCCCAAAAGACCA |
| FLT1 | NM_002019 | 23 | 345 | GGCTTGGGGACCTGTATTTGTA | CAGTGGCCTTTCTGAGCCTTAC |
| FLT1 | NM_002019 | 24 | 347 | GCACTCTAGCTCCCTCTTTTAGC | TTTTACAGTAGAGGGCAGACATGC |
| FLT3 | NM_004119 | 20 | 349 | GCCACCATAGCTGCAGAATTAG | CCCAAGGACAGATGTGATGCTA |
| FLT3 | NM_004119 | 21 | 351 | GCCTTTGTTCGAGAGGAGTTGT | GTTCACGCTCTCAAGCAGGTTA |
| FLT4 | NM_002020 | 23 | 353 | ATTCCACAAGCTCTCTCCATGA | CTTGCCCCAAGATGCCTAAG |
| IGF1R | NM_000875 | 18 | 355 | TGCTTGGTATTTGCTCATCATGT | CCCTTAGCTAGCCCACTGACAA |
| INSR | NM_000208 | 18 | 357 | CTCCTGGGAGTGGTGTCCAA | CCTGGGCAACAGACAGAGTAAG |
| INSR | NM_000208 | 19 | 359 | CTTCACTTCCCCATGCGTACC | GGGTTCACAATGCCTACAGGA |
| KDR | NM_002253 | 24 | 361 | AAAATCTGTGACTTTGGCTTGG | GGGAGGAGACATTCTTTGATTTG |
| KIT | NM_000222 | 17 | 363 | GCAGTCCTGAGAAGAAAACAGC | CTTCACATGCCCCAAAATTACA |
| KIT | NM_000222 | 18 | 365 | TGAGCCATGTATTTCAGAGGTGA | TACATTTCAGCAGGTGCGTGTT |
| LTK | NM_002344 | 16 | 367 | TTGCCTACTCTGTAGGGATATTGC | ATAGGGCATGTAGCCCAGTGA |
| MERTK | NM_006343 | 17 | 369 | GCTCTGCTGTTGGTCCTCACT | TTGCAAAGCACACATCTTCTGA |
| MET | NM_000245 | 19 | 371 | TGGCAATGTCAATGTCAAGCAT | GTATGTTGCCCCACTCAACAA |
| MUSK | NM_005592 | 15_1 | 373 | TGCATTTCCTAGCTGAGACTCC | TGCCATCTCGCACGTAGTAAAT |
| MUSK | NM_005592 | 15_2 | 375 | CTCTCCTGTGCTGAGCAGCTTT | TGTTTCCAATCACTGGCTTTCA |
| NTRK1 | NM_002529 | 15 | 377 | GAACCATGGGCTGTCTCTGG | ATCTGGGATAGCGAAGGAGACA |
| NTRK1 | NM_002529 | 16 | 379 | ATTACAGGCCACACGCCATC | AAGGCAAGAATAAGGGAGGAAGA |
| NTRK2 | NM_006180 | 15 | 381 | GCTCTCAGGACTGCAGAAGTACA | GAGGAACCAATCCCACTCACAC |
| NTRK2 | NM_006180 | 16 | 383 | TCACTCTTTGCCTTCTGTCTCTG | GCACTGTGCTTTGCTTTCTCAG |
| NTRK3 | NM_002530 | 17 | 385 | TGTCTCCTTTATCGTAGGTCTCCA | CACCACATTTCCTACAGTTCCA |
| NTRK3 | NM_002530 | 18 | 387 | CACTGTGCACCAGACAGACAAA | TGTGGTTTTCTGTATCAGCAGCTT |
| PDGFRA | NM_006206 | 18 | 389 | CAGGGAGTCTGAAATCATCAGG | TCAAGTATCTAGCCCCAAATCCA |
| PDGFRA | NM_006206 | 19 | 391 | GGCAATATTGACCATTCATCATTC | AGGCCAGGAGTAAGACGCAAC |
| PDGFRB | NM_002609 | 18 | 393 | AAGAACGTACGTGTGGTGTTGG | CGCTATACTTGCTCCATGCACT |
| PDGFRB | NM_002609 | 19 | 395 | AGGAAACAGCCTCTGGTCCTC | GTCAATGCTCAGACAGGGAGAT |
| PTK7 | NM_002821 | 18 | 397 | CCCAGGAAGGCAGGTACTGTTA | TTTTACAACCACCAAGGGTGTG |
| PTK7 | NM_002821 | 19 | 399 | TCGTGTGGTTACCTCCAGATTTT | AAATTAGCCAGGGAGTGGAGGT |
| RET | NM_000323 | 15 | 401 | CATGCCATGCTATGGCTCAC | AGGCTGAGCGGAGTTCTAATTG |
| RET | NM_000323 | 16 | 403 | ATCTCAGCAATCCACAGGAGGT | ATTTGCCTCACGAACACATCAT |
| ROR1 | NM_005012 | 09_1 | 405 | TGGAAAGTTGTCTATGGCACCTC | ATGGGCAGCAAGGACTTACTCT |
| ROR1 | NM_005012 | 09_2 | 407 | CACCCCAATATTGTCTGCCTTC | GGCTCGGGAACATGTAATTAGG |

TABLE S1B-continued

Primers for amplification of selected EGFR and receptor tyrosine kinase exons (SEQ ID NOS: 213-424)

| Gene | RefSeq | Exon | SEQ ID NO | F External | R External |
| --- | --- | --- | --- | --- | --- |
| ROR1 | NM_005012 | 09_3 | 409 | CCATCATGTATGGCAAATTCTCTT | TGGCGTCTCCTAGTAAAGATGCT |
| ROR1 | NM_005012 | 09_4 | 411 | GCCAGATTGCTGGTTTCATTG | GGCTAAAACACAAAGCACCATT |
| RYK | NM_002958 | 13 | 413 | GGGAAGTCATCCACAAAGACCT | GGTCTGGGTCACAGCTCCTC |
| TEK | NM_000459 | 18 | 415 | TTCTTCTGCCAAGATGTGGTGT | TGCAGATGCTGCAATCATGTTA |
| TEK | NM_000459 | 19 | 417 | TGGACCCCGAAAGATAAATAGG | TTCTGCACTCCTCTGGAAACTG |
| TIE | NM_005424 | 18 | 419 | GGGTGAGAGCCAACACTGATCT | CTGTGCCCTCTCATCTCACACT |
| TIE | NM_005424 | 19 | 421 | AGAACCTAGCCTCCAAGATTGC | ACACCTTCCAAGACTCCTTCCA |
| TYRO3 | NM_006293 | 18 | 423, 424 | GACTCGAGGGTGGGAGACAG | GCTGTCACTAGGTGTCCTGAGC |

TABLE S2

EGFR mutation status in untreated lung cancer

| Sample | Histology | Source | Gender | Exon | Sequence alteration | SEQ ID NO | Nucleotide | Amino acid |
| --- | --- | --- | --- | --- | --- | --- | --- | --- |
| S0514 | adenocarcinoma | U.S. | F | 18 | Substitution | 425 | 2155G > A | G719S |
| S0377 | adenocarcinoma | Japan | F | 18 | Substitution | 426 | 2155G > A | G719S |
| S0418 | adenocarcinoma | Japan | F | 19 | Del-1a | 427 | 2235_2249delGGAATTAAGAGAAGC | E746_A750del |
| S0363 | large cell ca. | Japan | F | 19 | Del-1a | 428 | 2235_2249delGGAATTAAGAGAAGC | E746_A750del |
| S0380 | adenocarcinoma | Japan | M | 19 | Del-1a | 429 | 2235_2249delGGAATTAAGAGAAGC | E746_A750del |
| S0399 | adenocarcinoma | Japan | F | 19 | Del-1a | 430 | 2235_2249delGGAATTAAGAGAAGC | E746_A750del |
| S0353 | adenocarcinoma | Japan | F | 19 | Del-1a | 431 | 2235_2249delGGAATTAAGAGAAGC | E746_A750del |
| S0385 | adenocarcinoma | Japan | M | 19 | Del-1a | 432 | 2235_2249delGGAATTAAGAGAAGC | E746_A750del |
| S0301 | adenocarcinoma | Japan | M | 19 | Del-1a | 433 | 2235_2249delGGAATTAAGAGAAGC | E746_A750del |
| S0412 | adenocarcinoma | Japan | M | 19 | Del-1b | 434 | 2236_2250delGAATTAAGAGAAGCA | E746_A750del |
| S0335 | adenocarcinoma | Japan | M | 19 | Del-1b | 435 | 2236_2250delGAATTAAGAGAAGCA | E746_A750del |
| S0405 | adenocarcinoma | Japan | F | 19 | Del-1b | 436 | 2236_2250delGAATTAAGAGAAGCA | E746_A750del |
| S0439 | adenocarcinoma | Japan | M | 19 | Del-2 | 437 | 2254_2277delTCTCCGAAAGCCAACAAGGAAATC | S752_1759del |
| S0361 | adenocarcinoma | Japan | F | 21 | Substitution | 438 | 2573T > G | L858R |
| S0388 | adenocarcinoma | Japan | F | 21 | Substitution | 439 | 2573T > G | L858R |
| S0389 | adenocarcinoma | Japan | F | 21 | Substitution | 440 | 2573T > G | L858R |

| Gefitinib sensitivity | Sample | Histology | Source | Gender | Exons | Sequence alteration | SEQ ID NO | Nucleotide | Amino acid |
|---|---|---|---|---|---|---|---|---|---|
| Y | IR1T | adenocarcinoma | U.S. | M | 19 | Del-3 | 441 | 2239_2247delTTAAGAGAA, 2248G>C | L747_E749del, A750P |
| Y | P003 | adenocarcinoma | U.S. | M | 19 | Del-3 | 442 | 2239_2247delTTAAGAGAA, 2248G>C | L747_E749del, A750P |
| Y | IR4T | bronchioloalveolar carcinoma | U.S. | F | 19 | Del-4 | 443 | 2240_2257delTAAGAGAAG CAACATCTC | L747_S752del, P753S |
| Y | IR21 | adenocarcinoma | U.S. | F | 19 | Del-5 | 444 | 2238_2255delATTAAGAGA AGCAACATC, 2237A>T | L747_S752del, E746V |
| Y | IR3T | adenocarcinoma | U.S. | F | 21 | Substitution | 445 | 2573T>G | L858R |
| Y in vitro | IRG H3255 | adenocarcinoma | U.S. | F | 21 | Substitution | 446 | 2573T>G | L858R |
| N | IR5 | adenocarcinoma | U.S. | F | 18-24 | None detected | | n/a | n/a |
| N | IR6 | adenocarcinoma | U.S. | M | 18-24 | None detected | | n/a | n/a |
| N | IR8 | adenocarcinoma | U.S. | F | 18-24 | None detected | | n/a | n/a |
| N | IR9 | NSCLC | U.S. | F | 18-24 | None detected | | n/a | n/a |

TABLE S3B

EGFR mutations not shown in Table 2, Table S2, or Table S3A

| Sample | Tissue | Exon | Sequence alteration | Nucleotide | Amino acid | Seq. Id. No. |
|---|---|---|---|---|---|---|
| Tar4T | Lung adenocarcinoma | 19 | Deletion | 2239-2250delTTAAGAGAAGCA; 2251A > C | L747_A750del; T751T | 554 |
| AD355 | Lung adenocarcinoma | 19 | Deletion | 2240-2250delTAAGAGAAGCA | L747_T751del | 720 |
| IR TT | Lung adenocarcinoma | 19 | Deletion | 2257-2271delCCGAAAGCCAACAAG | P753_K757del | 721 |
| AD240 | Lung adenocarcinoma | 20 | Insertion | 2309-2310insCAACCCGG | D770_N771insNPG | 722 |
| AD261 | Lung adenocarcinoma | 20 | Insertion | 2311-2312insGCGTGGACA | D770_N771insSVD | 723 |
|  | Lung adenocarcinoma | 20 | Insertion | 2316-2317insGGT | P772_H773insV | 724 |
| AD356 | Lung adenocarcinoma | 20 | Substitution | 2334-2335GG > AA | G779S | 725 |
| SP02-23 | Acute myeloid leukemia | 21 | Substitution | 2570G > T | G857V | 726 |
| SP08-94 | Glioma | 21 | Substitution | 2582T > A | L861Q | 727 |
| SP06-45 | Sarcoma | 21 | Substitution | 2648T > C | L883S | 728 |
| AD241 | Colon adenocarcinoma | 22 | Substitution | 2686G > T | D896Y | 729 |

TABLE S3C

Position of BCR-ABL mutants resistant to imatinib and analogous positions in EGFR

| Abl1 residue subject to resistance mutation | Analogous EGFR residue | Identical/similar/non-conserved |
|---|---|---|
| Met-244 | Lys-714 | Non-conserved |
| Leu-248 | Leu-718 | Identical |
| Gly-250 | Ser-720 | Non-conserved |
| Gln-252 | Ala-722 | Non-conserved |
| Tyr-253 | Phe-723 | Similar |
| Glu-255 | Thr-725 | Non-conserved |
| Asp-276 | Ala-750 | Non-conservd |
| Thr-315 | Thr-790 | Identical |
| Phe-317 | Leu-792 | Similar |
| Met-351 | Met-825 | Identical |
| Glu-355 | Glu-829 | Identical |
| Phe-359 | Leu-833 | Similar |
| His-396 | His-870 | Identical |
| Ser-417 | Thr-892 | Similar |
| Phe-486 | Phe-961 | Identical |

TABLE S4

Primers used for cDNA sequencing

| Primer name | SEQ ID NO | Primer sequence 5' to 3' |
|---|---|---|
| cDNA EGFR_aF | 447 | TGTAAAACGACGGCCAGTCGCCCAGACCGGACGACA |
| cDNA EGFR_aR | 448 | CAGGAAACAGCTATGACCAGGGCAATGAGGACATAACCA |
| cDNA EGFR_bF | 449 | TGTAAAACGACGGCCAGTGGTGGTCCTTGGGAATTTGG |
| cDNA EGFR_bR | 450 | CAGGAAACAGCTATGACCCCATCGACATGTTGCTGAGAAA |
| cDNA EGFR_cF | 451 | TGTAAAACGACGGCCAGTGAAGGAGCTGCCCATGAGAA |
| cDNA EGFR_cR | 452 | CAGGAAACAGCTATGACCCGTGGCTTCGTCTCGGAATT |
| cDNA EGFR_dF | 453 | TGTAAAACGACGGCCAGTGAAACTGACCAAAATCATCTGT |
| cDNA EGFR_dR | 454 | CAGGAAACAGCTATGACCTACCTATTCCGTTACACACTTT |

TABLE S4-continued

Primers used for cDNA sequencing

| Primer name | SEQ ID NO | Primer sequence 5' to 3' |
|---|---|---|
| cDNA EGFR_eF | 455 | TGTAAAACGACGGCCAGTCCGTAATTATGTGGTGACAGAT |
| cDNA EGFR_eR | 456 | CAGGAAACAGCTATGACCGCGTATGATTTCTAGGTTCTCA |
| cDNA EGFR_fF | 457 | TGTAAAACGACGGCCAGTCTGAAAACCGTAAAGGAAATCAC |
| cDNA EGFR_fR | 458 | CAGGAAACAGCTATGACCCCTGCCTCGGCTGACATTC |
| cDNA EGFR_gF | 459 | TGTAAAACGACGGCCAGTTAAGCAACAGAGGTGAAAACAG |
| cDNA EGFR_gR | 460 | CAGGAAACAGCTATGACCGGTGTTGTTTTCTCCCATGACT |
| cDNA EGFR_hF | 461 | TGTAAAACGACGGCCAGTGGACCAGACAACTGTATCCA |
| cDNA EGFR_hR | 462 | CAGGAAACAGCTATGACCTTCCTTCAAGATCCTCAAGAGA |
| cDNA EGFR_iF | 463 | TGTAAAACGACGGCCAGTGATCGGCCTCTTCATGCGAA |
| cDNA EGFR_iR | 464 | CAGGAAACAGCTATGACCACGGTGGAGGTGAGGCAGAT |
| cDNA EGFR_jF | 465 | TGTAAAACGACGGCCAGTCGAAAGCCAACAAGGAAATCC |
| cDNA EGFR_jR | 466 | CAGGAAACAGCTATGACCATTCCAATGCCATCCACTTGAT |
| cDNA EGFR_kF | 467 | TGTAAAACGACGGCCAGTAACACCGCAGCATGTCAAGAT |
| cDNA EGFR_kR | 468 | CAGGAAACAGCTATGACCCTCGGGCCATTTTGGAGAATT |
| cDNA EGFR_lF | 469 | TGTAAAACGACGGCCAGTTCAGCCACCCATATGTACCAT |
| cDNA EGFR_lR | 470 | CAGGAAACAGCTATGACCGCTTTGCAGCCCATTTCTATC |
| cDNA EGFR_mF | 471 | TGTAAAACGACGGCCAGTACAGCAGGGCTTCTTCAGCA |
| cDNA EGFR_mR | 472 | CAGGAAACAGCTATGACCTGACACAGGTGGGCTGGACA |
| cDNA EGFR_nF | 473 | TGTAAAACGACGGCCAGTGAATCCTGTCTATCACAATCAG |
| cDNA EGFR_nR | 474 | CAGGAAACAGCTATGACCGGTATCGAAAGAGTCTGGATTT |
| cDNA EGFR_oF | 475 | TGTAAAACGACGGCCAGTGCTCCACAGCTGAAAATGCA |
| cDNA EGFR_oR | 476 | CAGGAAACAGCTATGACCACGTTGCAAAACCAGTCTGTG |

What is claimed is:

1. An assay comprising:
  (a) adding primers specific for at least one of the following nucleotide variances in an epidermal growth factor receptor (EGFR) gene, where the nucleotide variance is selected from:
    i. a mutation in exon 18 that results in a substitution of cysteine for glycine at position 719 (G719C) or in a substitution of serine for glycine at position 719 (G719S) of SEQ ID NO: 512;
    ii. an in-frame deletion in exon 19 that results in a deletion of at least amino acids leucine, arginine, glutamic acid and alanine at codons 747, 748, 749, and 750 of SEQ ID NO: 512; and
    iii. a mutation in exon 21 that results in an amino acid substitution of arginine for leucine at position 858 (L858R) or of glutamine for leucine at position 861 (L861Q) of SEQ ID NO: 512;
      to a biological sample obtained from the blood of a human patient afflicted with non-small cell lung cancer;
  (b) performing an amplification step by polymerase chain reaction (PCR) wherein the PCR is allele-specific amplification for at least one of the nucleotide variances; and
  (c) detecting whether at least one of the above-described variances is present.

2. The assay of claim 1, wherein the blood is further processed to produce plasma.

3. The assay of claim 1, wherein the nucleotide variance is a mutation in exon 18 that results in a substitution of cysteine for glycine at position 719 (G719C).

4. The assay of claim 1, wherein the nucleotide variance is a mutation in exon 18 that results in a substitution of serine for glycine at position 719 (G719S) of SEQ ID NO: 512.

5. The assay of claim 1, wherein the nucleotide variance is an in-frame deletion in exon 19 that results in a deletion of at least amino acids leucine, arginine, glutamic acid and alanine at codons 747, 748, 749, and 750 of SEQ ID NO: 512.

6. The assay of claim 1, wherein the nucleotide variance is a mutation in exon 21 that results in an amino acid substitution of arginine for leucine at position 858 (L858R).

7. The assay of claim 1, wherein the nucleotide variance is a mutation in exon 21 that results in an amino acid substitution of glutamine for leucine at position 861 (L861Q) of SEQ ID NO: 512.

8. The assay of claim 3, wherein the allele-specific amplification is performed using at least one primer pair designed to anneal to an EGFR nucleic acid, wherein one primer of the pair comprises a sequence that selectively hybridizes to the nucleotide variance under high stringency conditions and amplifies the nucleotide variance sequence but does not amplify a corresponding wild type EGFR sequence.

9. The assay of claim 4, wherein the allele-specific amplification is performed using at least one primer pair designed to anneal to an EGFR nucleic acid, wherein one primer of the pair comprises a sequence that selectively hybridizes to the nucleotide variance under high stringency conditions and amplifies the nucleotide variance sequence but does not amplify a corresponding wild type EGFR sequence.

10. The assay of claim 5, wherein the allele-specific amplification is performed using at least one primer pair designed to anneal to an EGFR nucleic acid, wherein one primer of the pair comprises a sequence that selectively hybridizes to the nucleotide variance under high stringency conditions and amplifies the nucleotide variance sequence but does not amplify a corresponding wild type EGFR sequence.

11. The assay of claim 6, wherein the allele-specific amplification is performed using at least one primer pair designed to anneal to an EGFR nucleic acid, wherein one primer of the pair comprises a sequence that selectively hybridizes to the nucleotide variance under high stringency conditions and amplifies the nucleotide variance sequence but does not amplify a corresponding wild type EGFR sequence.

12. An assay comprising:
(a) adding primers specific for at least one of the following nucleotide variances in an epidermal growth factor receptor (EGFR) gene, where the nucleotide variance is selected from:
  i. a mutation in exon 18 that results in a substitution of cysteine for glycine at position 719 (G719C) or in a substitution of serine for glycine at position 719 (G719S) of SEQ ID NO: 512;
  ii. an in-frame deletion in exon 19 that results in a deletion of at least amino acids leucine, arginine, glutamic acid and alanine at codons 747, 748, 749, and 750 of SEQ ID NO: 512; and
  iii. a mutation in exon 21 that results in an amino acid substitution of arginine for leucine at position 858 (L858R) or of glutamine for leucine at position 861 (L861Q) of SEQ ID NO: 512;
    to a biological sample obtained from the blood of a human patient afflicted with non-small cell lung cancer;
(b) performing an amplification step by polymerase chain reaction (PCR) to amplify part of exon 18, 19, or 21 of the EGFR gene; and
(c) detecting whether at least one of the above-described nucleotide variances is present by hybridizing at least one allele-specific nucleic acid probe specific for the nucleotide variance to the EGFR gene.

13. The assay of claim 12, wherein the nucleic acid probe comprises a label.

* * * * *

UNITED STATES PATENT AND TRADEMARK OFFICE
CERTIFICATE OF CORRECTION

PATENT NO. : 10,669,589 B2
APPLICATION NO. : 15/981514
DATED : June 2, 2020
INVENTOR(S) : Daphne Winifred Bell et al.

Page 1 of 1

It is certified that error appears in the above-identified patent and that said Letters Patent is hereby corrected as shown below:

In the Specification

At Column 1, Lines 34-38, delete:
"This invention was made with government support under Grant Nos. RO1 CA 092824, P50 CA 090578, PO1 95281, and 1K12CA87723-01 awarded by The National Institutes for Health. The government has certain rights in the invention."

And insert the following:
--This invention was made with government support under grant numbers CA114465, RO1 CA092824, P50 CA090578, PO1 CA095281, and K12 CA087723 awarded by The National Institutes of Health. The government has certain rights in the invention.--

Signed and Sealed this
Twenty-seventh Day of December, 2022

Katherine Kelly Vidal
*Director of the United States Patent and Trademark Office*